(12) United States Patent
Eickmeier et al.

(10) Patent No.: US 7,713,961 B2
(45) Date of Patent: May 11, 2010

(54) SUBSTITUTED 1,2-ETHYLENEDIAMINES, METHODS FOR PREPARING THEM AND USES THEREOF

(75) Inventors: Christian Eickmeier, Mittelbiberach (DE); Stefan Peters, Biberach (DE); Klaus Fuchs, Mittelbiberach (DE); Niklas Heine, Biberach (DE); Sandra Handschuh, Warthausen (DE); Cornelia Dorner-Ciossek, Ravensburg (DE); Klaus Klinder, Oggelshausen (DE); Marcus Kostka, Biberach (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 392 days.

(21) Appl. No.: 11/278,059

(22) Filed: Mar. 30, 2006

(65) Prior Publication Data

US 2006/0223759 A1 Oct. 5, 2006

(30) Foreign Application Priority Data

Mar. 30, 2005 (EP) .................................. 05006939

(51) Int. Cl.
*A61K 31/54* (2006.01)
*A61K 31/505* (2006.01)
*A61K 31/535* (2006.01)
*C07D 295/00* (2006.01)
*C07C 239/00* (2006.01)
*A61K 31/16* (2006.01)
*C07D 285/16* (2006.01)
*C07D 279/00* (2006.01)

(52) U.S. Cl. ................ 514/222.5; 544/8; 544/316; 544/160; 544/3; 514/357; 514/616; 514/238.2; 514/269; 549/77; 564/153

(58) Field of Classification Search ................ 564/84, 564/153; 546/337, 293; 549/77, 567; 514/577, 514/357, 438, 428, 351, 238.2, 616, 269, 514/222.5; 544/3, 160, 316, 8
See application file for complete search history.

(56) References Cited

U.S. PATENT DOCUMENTS

| | | | |
|---|---|---|---|
| 7,166,599 B2 | 1/2007 | Bornemann | |
| 7,238,774 B2 | 7/2007 | Peters | |
| 2005/0090449 A1 | 4/2005 | Fuchs | |
| 2005/0130941 A1 | 6/2005 | Schostarez et al. | |
| 2005/0277635 A1 | 12/2005 | Bornemann | |
| 2006/0025345 A1 | 2/2006 | Peters | |
| 2006/0040928 A1 | 2/2006 | Bornemann | |
| 2006/0160747 A1 | 7/2006 | Peters | |
| 2008/0293680 A1 | 11/2008 | Peters | |
| 2009/0042867 A1 | 2/2009 | Fuchs | |

FOREIGN PATENT DOCUMENTS

| | | | |
|---|---|---|---|
| EP | 0 652 009 A1 | 5/1995 | |
| WO | WO 00/69262 A1 | 11/2000 | |
| WO | WO 01/00663 A2 | 1/2001 | |
| WO | WO 01/00665 A2 | 1/2001 | |
| WO | WO 02/100410 A1 | 12/2002 | |
| WO | WO 03/057721 A2 | 7/2003 | |
| WO | WO 2004/043916 A1 | 5/2004 | |
| WO | WO 2005/004802 A2 | 1/2005 | |
| WO | WO 2005004802 | * | 1/2005 |

OTHER PUBLICATIONS

U.S. Appl. No. 12/063,270, filed Feb. 8, 2008, Eickmeier.
U.S. Appl. No. 12/063,317, filed May 29, 2008, Heine.
U.S. Appl. No. 12/063,356, filed May 16, 2008, Fuchs.

* cited by examiner

*Primary Examiner*—Janet L Andres
*Assistant Examiner*—Binta M Robinson
(74) *Attorney, Agent, or Firm*—Michael P. Morris; Wendy Petka; Edward S. Lazer

(57) ABSTRACT

The present invention relates to substituted 1,2-ethylenediamines of general formula (I)

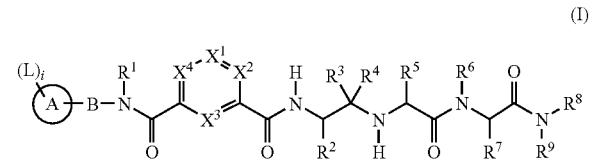

wherein the groups $R^1$ to $R^{15}$, A, B, L, i as well as $X^1$—$X^4$ are defined as in the specification and claims and the use thereof for the treatment of Alzheimer's disease (AD) and similar diseases.

27 Claims, No Drawings

SUBSTITUTED 1,2-ETHYLENEDIAMINES, METHODS FOR PREPARING THEM AND USES THEREOF

RELATED APPLICATIONS

This application claims priority to European Patent Application No. 05 006 939.2, filed Mar. 30, 2005, the content of which is incorporated herein by reference in its entirety.

FIELD OF THE INVENTION

The present invention relates to substituted 1,2-ethylenediamines of general formula (I)

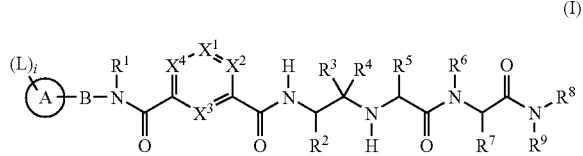

(I)

wherein the groups $R^1$ to $R^{15}$, A, B, L, i and $X^1$—$X^4$ are defined below, including the tautomers, the stereoisomers, the mixtures thereof and the salts thereof. A further object of this invention relates to pharmaceutical compositions containing a compound of formula (I) according to the invention and the use of a compound according to the invention for preparing a pharmaceutical composition for the treatment and/or prevention of Alzheimer's disease (AD) and other diseases associated with abnormal processing of Amyloid Precursor Protein (APP) or aggregation of the Abeta peptide, as well as diseases which can be treated or prevented by the inhibition of β-secretase. Such diseases include MCI ("mild cognitive impairment"), trisomy 21 (Down's syndrome), cerebral amyloid angiopathy, degenerative dementias, hereditary cerebral hemorrhage with amyloidosis, Dutch type (HCHWA-D), Alzheimer's dementia with Lewy bodies, trauma, stroke, pancreatitis, Inclusion Body Myositis (IBM), and other peripheral amyloidoses, diabetes and arteriosclerosis.

The compounds according to the invention also inhibit the aspartylprotease cathepsin D and are therefore suitable for suppressing the metastasisation of tumour cells.

The invention further relates to processes for preparing a pharmaceutical composition and a compound according to the invention.

BACKGROUND OF THE INVENTION

EP 652 009 A1 describes inhibitors of aspartate protease which inhibit the production of beta-amyloid peptides in cell culture and in vivo.

WO 00/69262 discloses a beta-secretase and the use thereof in assays for finding potential active substances for the treatment of AD.

WO 01/00663 discloses memapsin 2 (human beta-secretase) as well as a recombinant catalytically active enzyme. Methods of identifying inhibitors of memapsin 2 are also described.

WO 01/00665 discloses inhibitors of memapsin 2 for the treatment of AD.

WO 03/057721 discloses substituted aminocarboxamides for the treatment of AD.

At present there are no effective treatment methods capable of preventing, stopping or reversing AD.

The objective of the present invention is therefore to provide new substituted 1,2-ethylenediamines which inhibit the cleaving of APP (Amyloid Precursor Protein) mediated by β-secretase.

A further objective of the present invention is to provide physiologically acceptable salts of the compounds according to the invention with inorganic or organic acids.

Another objective of the present invention is to provide pharmaceutical compositions containing at least one compound according to the invention or a physiologically acceptable salt according to the invention, optionally together with one or more inert carriers and/or diluents.

The present invention further relates to pharmaceutical compositions containing one or more, preferably one active substance, which is selected from the compounds according to the invention and/or the corresponding salts, as well as one or more, preferably one additional active substance optionally together with one or more inert carriers and/or diluents.

This invention further relates to the use of at least one of the compounds according to the invention for inhibiting β-secretase.

The invention also sets out to provide new pharmaceutical compositions which are suitable for the treatment or prevention of diseases or conditions associated with the abnormal processing of Amyloid Precursor Protein (APP) or aggregation of Abeta peptide.

The invention also sets out to provide new pharmaceutical compositions which are suitable for the treatment or prevention of diseases or conditions which can be influenced by inhibiting the β-secretase activity.

The invention also sets out to provide new pharmaceutical compositions which are suitable for the treatment and/or prevention of Alzheimer's disease (AD) and other diseases which are associated with the abnormal processing of APP or aggregation of Abeta peptide, as well as diseases which can be treated or prevented by the inhibition of β-secretase, particularly AD.

The invention also relates to a method of inhibiting β-secretase activity.

Further objectives of the present invention will be apparent to the skilled man immediately from the foregoing remarks and those made hereinafter.

SUMMARY OF THE INVENTION

In a first aspect the present invention relates to substituted 1,2-ethylenediamines of general formula (I)

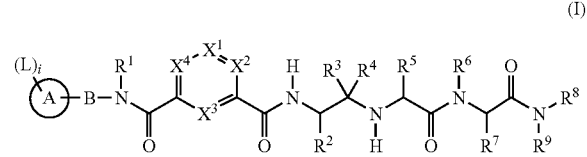

(I)

wherein

A denotes aryl or heteroaryl, wherein the group A in addition to the groups L may optionally be substituted by one or more fluorine atoms, L denotes in each case independently of one another hydrogen, fluorine, chlorine, bromine, iodine, hydroxy, carboxy, formyl, cyano, nitro, $F_3C$, $HF_2C$, $FH_2C$, $C_{1-6}$-alkyl, $C_{2-6}$-alkenyl, $C_{2-6}$-alkynyl, $C_{1-6}$-alkyl-S, $C_{1-6}$-alkyl-S—$C_{1-3}$-alkyl, $C_{3-7}$-cycloalkyl, $C_{3-7}$-cycloalkenyl, $C_{3-7}$-cycloalkyl-$C_{1-6}$-alkyl, $C_{3-7}$- cycloalkyl-$C_{2-6}$-alkenyl, $C_{3-7}$-cycloalkyl-$C_{2-6}$-alkynyl, $C_{3-7}$-cycloalkenyl-$C_{1-6}$-alkyl, $C_{3-7}$-cycloalkenyl-$C_{2-6}$-alkenyl, $C_{3-7}$-cycloalkenyl-$C_{2-6}$-alkynyl, aryl, aryl-$C_{1-6}$-alkyl, aryl-$C_{2-6}$-alkenyl, aryl-$C_{2-6}$-alkynyl, heterocyclyl, heterocyclyl-$C_{1-6}$-alkyl, heterocyclyl-$C_{2-6}$-alkenyl, heterocyclyl-$C_{2-6}$-alkynyl, heteroaryl, heteroaryl-$C_{1-6}$-alkyl, heteroaryl-$C_{2-6}$-alkenyl, heteroaryl-$C_{2-6}$-alkynyl, $R^{15}$—O, $R^{15}$—O—$C_{1-3}$-alkyl, $(R^{14})_2$N, $(R^{14})_2$N—CO, $R^{14}$—CO—$(R^{14})$N, $(R^{14})_2$N—CO—$(R^{14})$N, $R^{14}$—$SO_2$—$(R^{14})$N, $(R^{14})_2$N—$SO_2$ or $R^{14}$—$SO_2$ wherein the above-mentioned groups may optionally be substituted independently of one another by one or more groups selected from among fluorine, chlorine, bromine, iodine, hydroxy, oxo, carboxy, formyl, cyano, nitro, $F_3C$, $HF_2C$, $FH_2C$, hydroxy-$C_{1-6}$-alkyl, $C_{1-3}$-alkyl, $C_{1-6}$-alkoxy, $(R^{14})_2$N, $(R^{14})_2$N—$C_{1-3}$-alkyl, $(R^{14})_2$N—CO and $HOSO_2$—, i denotes 0, 1, 2 or 3, B denotes a $C_{1-4}$-alkylene bridge, wherein in the case of a $C_{3-4}$-alkylene bridge the $CH_2$ group of the $C_{3-4}$-alkylene bridge, which is bound to the group A, may be replaced by —O—, and the $C_{1-4}$-alkylene bridge may optionally be substituted by one or more groups selected from among fluorine, chlorine, bromine, iodine, hydroxy, oxo, carboxy, cyano, nitro, $F_3C$, $HF_2C$, $FH_2C$, $C_{1-4}$-alkyl, $C_{1-6}$-alkyl-S—$C_{1-3}$-alkyl, $C_{3-7}$-cycloalkyl, $C_{3-7}$-cycloalkyl-$C_{1-3}$-alkyl, heterocyclyl, heterocyclyl-$C_{1-3}$-alkyl, aryl, aryl-$C_{1-3}$-alkyl, heteroaryl, heteroaryl-$C_{1-3}$-alkyl, $R^{15}$—O, $(R^{14})_2$N—$SO_2$, $(R^{14})_2$N, $(R^{14})_2$N—$C_{1-3}$-alkyl, $(R^{14})_2$N—CO, $R^{14}$—$SO_2$, $R^{14}$—CO—$(R^{14})$N, $R^{14}$—$SO_2(R^{14})$N, $(R^{14})_2$N—$SO_2$, $R^{14}$—CO— and $R^{14}$—SO—, and two $C_{1-4}$-alkyl groups bound to the same carbon atom of the $C_{1-4}$-alkylene bridge may be joined together forming a $C_{3-7}$-cycloalkyl group, and the above-mentioned groups and the $C_{3-7}$-cycloalkyl group formed from the $C_{1-4}$-alkyl groups may optionally be substituted independently of one another by one or more groups selected from among fluorine, chlorine, bromine, iodine, hydroxy, oxo, carboxy, formyl, cyano, nitro, $F_3C$, $HF_2C$, $FH_2C$, $C_{1-3}$-alkyl, $C_{1-3}$-alkoxy, $R^{15}$—O—$C_{1-3}$-alkyl, $R^{14}$—$CO(R^{14})$N, $R^{14}$—$SO_2(R^{14})$N, $(R^{14})_2$N, $(R^{14})_2$N—$C_{1-3}$-alkyl, $(R^{14})_2$N—CO, $(R^{14})_2$N—$SO_2$— and $HOSO_2$—, $R^1$ denotes hydrogen, $C_{1-6}$-alkyl, $C_{2-6}$-alkenyl, $C_{2-6}$-alkynyl, $C_{3-7}$-cycloalkyl, $C_{3-7}$-cycloalkyl-$C_{1-6}$-alkyl, $C_{3-7}$-cycloalkyl-$C_{2-6}$-alkenyl, $C_{3-7}$-cycloalkyl-$C_{2-6}$-alkynyl, $C_{3-7}$-cycloalkenyl, $C_{3-7}$-cycloalkenyl-$C_{1-6}$-alkyl, $C_{3-7}$-cycloalkenyl-$C_{2-6}$-alkenyl, $C_{3-7}$-cycloalkenyl-$C_{2-6}$-alkynyl, aryl, aryl-$C_{1-6}$-alkyl, aryl-$C_{2-6}$-alkenyl, aryl-$C_{2-6}$-alkynyl, heterocyclyl, heterocyclyl-$C_{1-6}$-alkyl, heterocyclyl-$C_{2-6}$-alkenyl, heterocyclyl-$C_{2-6}$-alkynyl, heteroaryl, heteroaryl-$C_{1-6}$-alkyl, heteroaryl-$C_{2-6}$-alkenyl or heteroaryl-$C_{2-6}$-alkynyl, wherein the above-mentioned groups may optionally be substituted independently of one another by one or more groups selected from among fluorine, chlorine, bromine, iodine, hydroxy, oxo, carboxy, formyl, cyano, nitro, $F_3C$, $HF_2C$, $FH_2C$, $C_{1-3}$-alkyl, $C_{1-3}$-alkoxy, hydroxy-$C_{1-6}$-alkyl, $(R^{14})_2$N, $(R^{14})_2$N—$C_{1-3}$-alkyl, $(R^{14})_2$N—CO— $(R^{14})_2$N—$SO_2$, $R^{14}$—CO—$(R^{14})$N, $R^{14}$—$SO_2$—$(R^{14})$N and $HOSO_2$—, $X^1$, denotes nitrogen or $C(R^{10})$, $X^2$, $X^3$, $X^4$ each independently of one another denote nitrogen or $C(R^{11})$ with the proviso that 0, 1, 2 or 3 of the groups $X^1$, $X^2$, $X^3$ and $X^4$ may be nitrogen, $R^2$ denotes $C_{1-6}$-alkyl, $C_{2-6}$-alkenyl, $C_{2-6}$-alkynyl, $R^{15}$—O—$C_{1-3}$-alkyl, $C_{1-6}$-alkyl-S—$C_{1-3}$-alkyl, $C_{3-7}$-cycloalkyl, $C_{3-7}$-cycloalkyl-$C_{2-6}$-alkynyl, $C_{3-7}$-cycloalkenyl, $C_{3-7}$-cycloalkenyl-$C_{1-6}$-alkyl, $C_{3-7}$-cycloalkenyl-$C_{2-6}$-alkenyl, $C_{3-7}$-cycloalkenyl-$C_{2-6}$-alkynyl, heterocyclyl, $C_{3-7}$-cycloalkyl-$C_{1-3}$-alkyl, heterocyclyl-$C_{1-3}$-alkyl, $C_{3-7}$-cycloalkyl-$C_{2-3}$-alkenyl, heterocyclyl-$C_{2-3}$-alkenyl, heterocyclyl-$C_{2-3}$-alkynyl, aryl, heteroaryl, aryl-$C_{1-3}$-alkyl, heteroaryl-$C_{1-3}$-alkyl, aryl-$C_{2-3}$-alkenyl, aryl-$C_{2-3}$-alkynyl, heteroaryl-$C_{2-3}$-alkenyl or heteroaryl-$C_{2-3}$-alkynyl, wherein the above-mentioned groups may optionally be substituted independently of one another by one or more groups selected from among fluorine, chlorine, bromine, iodine, $F_3C$, $HF_2C$, $FH_2C$, hydroxy, oxo, carboxy, formyl, cyano, nitro, $(R^{14})_2$N, $HOSO_2$—, $C_{1-3}$-alkyl, $C_{1-6}$-alkyl-S—$C_{1-3}$-alkyl, $(R^{14})_2$N—$SO_2$—, $R^{14}$—CO—$(R^{14})$N, $R^{14}$—$SO_2$—$(R^{14})$N, $(R^{14})_2$N—$C_{1-3}$-alkyl, $(R^{14})_2$N—CO, $R^{15}$—O and $R^{15}$—O—$C_{1-3}$-alkyl, $R^3$, $R^4$ each independently of one another denote hydrogen, $C_{1-6}$-alkyl, fluorine, $F_3C$, $HF_2C$ or $FH_2C$, $R^5$, $R^7$ each independently of one another denote hydrogen, $C_{1-6}$-alkyl, $C_{2-6}$-alkenyl, $C_{2-6}$-alkynyl, $C_{3-7}$-cycloalkyl, heterocyclyl, $C_{3-7}$-cycloalkyl-$C_{1-3}$-alkyl, $C_{3-7}$-cycloalkyl-$C_{2-6}$-alkynyl, heterocyclyl-$C_{1-3}$-alkyl, $C_{3-7}$-cycloalkyl-$C_{2-4}$-alkenyl, heterocyclyl-$C_{2-4}$-alkenyl, heterocyclyl-$C_{2-4}$-alkynyl, $C_{3-7}$-cycloalkenyl, $C_{3-7}$-cycloalkenyl-$C_{1-6}$-alkyl, $C_{3-7}$-cycloalkenyl-$C_{2-6}$-alkenyl, $C_{3-7}$-cycloalkenyl-$C_{2-6}$-alkynyl, aryl, heteroaryl, aryl-$C_{1-3}$-alkyl, heteroaryl-$C_{1-3}$-alkyl, aryl-$C_{2-3}$-alkenyl, heteroaryl-$C_{2-3}$-alkenyl, aryl-$C_{2-3}$-alkynyl or heteroaryl-$C_{2-3}$-alkynyl, wherein the above-mentioned groups may optionally be substituted independently of one another by one or more groups selected from among fluorine, chlorine, bromine, iodine, hydroxy, oxo, carboxy, formyl, cyano, nitro, $C_{1-3}$-alkyl, $R^{15}$—O, $C_{1-3}$-alkyl-S, aryl, heteroaryl, heteroaryl-$C_{1-3}$-alkyl, aryl-$C_{1-6}$-alkyl, $R^{14}$—CO—$(R^{14})$N, $R^{14}$—$SO_2$—$(R^{14})$N, $(R^{14})_2$N—$SO_2$—, $(R^{14})_2$N, $(R^{14})_2$N—$C_{1-3}$-alkyl, $(R^{14})_2$N—CO and $HOSO_2$—, $R^6$, $R^9$ each independently of one another denote hydrogen, $C_{1-6}$-alkyl, $C_{1-6}$-alkoxy-$C_{1-3}$-alkyl, $C_{3-7}$-cycloalkyl, $C_{3-7}$-cycloalkyl-$C_{1-3}$-alkyl, $C_{2-6}$-alkenyl, heterocyclyl-$C_{1-3}$-alkyl, heteroaryl, heteroaryl-$C_{1-3}$-alkyl or $C_{2-6}$-alkynyl, wherein the above-mentioned groups may optionally be substituted independently of one another by one or more groups selected from among fluorine, chlorine, bromine, iodine, cyano, $C_{1-3}$-alkyl, $C_{1-6}$-alkoxy- and $(R^{14})_2$N, $R^8$ denotes hydrogen, $C_{1-6}$-alkyl, $C_{2-6}$-alkenyl, $C_{2-6}$-alkynyl, $C_{3-7}$-cycloalkyl, $C_{3-7}$-cycloalkyl-$C_{1-3}$-alkyl, $C_{3-7}$-cycloalkyl-$C_{2-4}$-alkenyl, $C_{3-7}$-cycloalkyl-$C_{2-4}$-alkynyl, $C_{3-7}$-cycloalkenyl, $C_{3-7}$-cycloalkenyl-$C_{1-6}$-alkyl, $C_{3-7}$-cycloalkenyl-$C_{2-6}$-alkenyl, $C_{3-7}$-cycloalkenyl-$C_{2-6}$-alkynyl, heterocyclyl, heterocyclyl-$C_{1-3}$-alkyl, heterocyclyl-$C_{2-4}$-alkenyl, heterocyclyl-$C_{2-4}$-alkynyl, aryl, aryl-$C_{1-3}$-alkyl, aryl-$C_{2-4}$-alkenyl, aryl-$C_{2-4}$-alkynyl, heteroaryl, heteroaryl-$C_{1-3}$-alkyl, heteroaryl-$C_{2-4}$-alkenyl or heteroaryl-$C_{2-4}$-alkynyl, wherein the above-mentioned groups may optionally be substituted independently of one another by one or more groups selected from among fluorine, chlorine, bromine, iodine, hydroxy, oxo, carboxy, formyl, cyano, nitro, $C_{1-3}$-alkyl, heterocyclyl, heterocyclyl- $C_{1-3}$-alkyl, $R^{15}$—O, $R^{15}$—O—$C_{1-3}$-alkyl, $R^{15}$—S, $R^{15}$—S—$C_{1-3}$-alkyl, aryl, heteroaryl, heteroaryl-$C_{1-3}$-alkyl, aryl-$C_{1-6}$-alkyl, $(R^{14})_2$N, $(R^{14})_2$N—$C_{1-3}$-alkyl, $(R^{14})_2$N—CO, $(R^{14})_2$N—CO—N$(R^{14})$—, $(R^{14})_2$N—SO$_2$— and HOSO$_2$—, $R^{10}$ denotes hydrogen, fluorine, chlorine, bromine, iodine, cyano, $C_{1-6}$-alkyl, $C_{2-6}$-alkenyl, $C_{2-6}$-alkynyl, $C_{3-7}$-cycloalkyl, $C_{3-7}$-cycloalkyl-$C_{1-6}$-alkyl, $C_{3-7}$-cycloalkyl-$C_{2-6}$-alkynyl, heterocyclyl, heterocyclyl-$C_{1-6}$-alkyl, heterocyclyl-$C_{2-6}$-alkenyl, heterocyclyl-$C_{2-6}$-alkynyl, $C_{3-7}$-cycloalkyl-$C_{2-6}$-alkenyl, heterocyclyl-$C_{2-4}$-alkenyl, $C_{3-7}$-cycloalkenyl, $C_{3-7}$-cycloalkenyl-$C_{1-6}$-alkyl, $C_{3-7}$-cycloalkenyl-$C_{2-6}$-alkenyl, $C_{3-7}$-cycloalkenyl-$C_{2-6}$-alkynyl, aryl, aryl-$C_{1-6}$-alkyl, heteroaryl, heteroaryl-$C_{1-6}$-alkyl, aryl-$C_{2-6}$-alkenyl, heteroaryl-$C_{2-6}$-alkenyl, aryl-$C_{2-6}$-alkynyl or heteroaryl-$C_{2-6}$-alkynyl, $R^{15}$—O, $R^{15}$—O—$C_{1-3}$-alkyl, $R^{12}$—SO$_2$—$(R^{13})$N or $R^{12}$—CO—$(R^{13})$N, wherein the above-mentioned groups may optionally be substituted independently of one another by one or more groups selected from among fluorine, chlorine, bromine, iodine, hydroxy, oxo, carboxy, formyl, cyano, nitro, $C_{1-6}$-alkyl, $C_{2-6}$-alkenyl, $C_{2-6}$-alkynyl, $C_{1-6}$-alkyl-S, $C_{1-6}$-alkyl-S—$C_{1-3}$-alkyl, $C_{3-7}$-cycloalkyl, $C_{3-7}$-cycloalkyl-$C_{1-6}$-alkyl, aryl, aryl-$C_{1-6}$-alkyl, heterocyclyl, heterocyclyl-$C_{1-6}$-alkyl, heteroaryl, heteroaryl-$C_{1-6}$-alkyl, $R^{15}$—O, $R^{15}$—O—CO, $R^{15}$—CO, $R^{15}$—O—CO—$(R^{14})$N, $(R^{14})_2$N—CO—O, $R^{15}$—O—$C_{1-3}$-alkyl, $(R^{14})_2$N, $(R^{14})_2$N—CO, $R^{14}$—CO—$(R^{14})$N, $(R^{14})_2$N—CO—$(R^{14})$N, $(R^{14})_2$N—SO$_2$—, $(R^{14})_2$N—SO$_2$—$(R^{14})$N, $R^{14}$—SO$_2$—, F$_3$C, HF$_2$C, FH$_2$C, F$_3$C—O, HF$_2$C—O, FH$_2$C—O and $R^{14}$—SO$_2$—$(R^{14})$N, $R^{11}$ each independently of one another denote hydrogen, fluorine, chlorine, bromine, iodine, $R^{15}$—O, $(R^{14})_2$N or $C_{1-3}$-alkyl, wherein the $C_{1-3}$-alkyl group may optionally be substituted by one or more fluorine atoms, $R^{12}$ denotes $C_{1-6}$-alkyl, $C_{2-6}$-alkenyl, $C_{2-6}$-alkynyl, $C_{3-7}$-cycloalkyl-$C_{2-6}$-alkenyl, aryl-$C_{2-3}$-alkenyl, heteroaryl-$C_{2-4}$-alkenyl, heterocyclyl-$C_{2-4}$-alkenyl, aryl-$C_{2-3}$-alkynyl, $C_{3-7}$-cycloalkyl-$C_{2-4}$-alkynyl, heterocyclyl-$C_{2-4}$-alkynyl-heteroaryl-$C_{2-3}$-alkynyl, $C_{3-7}$-cycloalkyl, $C_{3-7}$-cycloalkyl-$C_{1-6}$-alkyl, heterocyclyl, heterocyclyl-$C_{1-4}$-alkyl, $C_{3-7}$-cycloalkenyl, $C_{3-7}$-cycloalkenyl-$C_{1-6}$-alkyl, $C_{3-7}$-cycloalkenyl-$C_{2-6}$-alkenyl, $C_{3-7}$-cycloalkenyl-$C_{2-6}$-alkynyl, aryl, aryl-$C_{1-4}$-alkyl, heteroaryl, heteroaryl-$C_{1-3}$-alkyl or $(R^{14})_2$N, wherein the above-mentioned groups may optionally be substituted independently of one another by one or more groups selected from among fluorine, chlorine, bromine, hydroxy, oxo, carboxy, formyl, cyano, nitro, $C_{1-3}$-alkyl, heterocyclyl, heterocyclyl-$C_{1-3}$-alkyl, $R^{15}$—O, $R^{15}$—O—$C_{1-3}$-alkyl, $R^{14}$—CO$(R^{14})$N, $R^{14}$—SO$_2(R^{14})$N, $(R^{14})_2$N—SO$_2$—, $R^{14}$—SO$_2$—, $R^{14}$—SO, $R^{14}$—S, $(R^{14})_2$N, $(R^{14})_2$N—$C_{1-3}$-alkyl and $(R^{14})_2$N—CO, $R^{13}$ denotes hydrogen, $C_{1-6}$-alkyl, $C_{2-6}$-alkenyl, $C_{2-6}$-alkynyl, $C_{3-7}$-cycloalkyl, $C_{3-7}$-cycloalkyl-$C_{1-3}$-alkyl, aryl, aryl-$C_{1-3}$-alkyl, heterocyclyl, heterocyclyl-$C_{1-3}$-alkyl, heterocyclyl-$C_{2-3}$-alkenyl, heterocyclyl-$C_{2-3}$-alkynyl, heteroaryl, heteroaryl-$C_{2-3}$-alkenyl, heteroaryl-$C_{2-3}$-alkynyl or heteroaryl-$C_{1-3}$-alkyl, wherein the above-mentioned groups may optionally be substituted independently of one another by one or more groups selected from among fluorine, chlorine, bromine, hydroxy, carboxy, formyl, cyano, nitro, $C_{1-3}$-alkyl, heterocyclyl, heterocyclyl-$C_{1-3}$-alkyl, $R^{15}$—O, $R^{15}$—O—$C_{1-3}$-alkyl, $(R^{14})_2$N, $(R^{14})_2$N—$C_{1-3}$-alkyl and $R^{14}$CO, or $R^{12}$ and $R^{13}$ together form a $C_{2-6}$-alkylene bridge, so that with the inclusion of the nitrogen atom linked to $R^{13}$ and the SO$_2$— or CO group linked to $R^{12}$ a heterocyclic ring is formed, wherein one or two CH$_2$ groups of the $C_{2-6}$-alkylene bridge may be replaced independently of one another by O, S, SO, SO$_2$ or N$(R^{14})$ in such a way that in each case two O or S atoms or an O and an S atom are not joined together directly, and the C atoms of the above-mentioned $C_{2-6}$-alkylene bridge may optionally be substituted by one or more groups selected from among fluorine, chlorine, bromine, hydroxy, carboxy, formyl, cyano, F$_3$C, HF$_2$C, FH$_2$C, $C_{1-6}$-alkyl, $C_{1-6}$-alkoxy, oxo and nitro, $R^{14}$ each independently of one another denote hydrogen, $C_{1-6}$-alkyl, $C_{1-6}$-alkoxy-$C_{1-3}$-alkyl, $C_{3-6}$-cyclyoalkyl, $C_{3-6}$-cyclyoalkyl-$C_{1-3}$-alkyl, aryl or aryl-$C_{1-3}$-alkyl, heterocyclyl, heterocyclyl-$C_{1-3}$-alkyl, heteroaryl or heteroaryl-$C_{1-3}$-alkyl, wherein two $C_{1-6}$-alkyl groups bound to the same nitrogen atom together may form a $C_{2-6}$-alkylene bridge, so that with the inclusion of the nitrogen atom bound to the groups $R^{14}$ a heterocyclic ring is formed, wherein a CH$_2$ group of the $C_{2-6}$-alkylene bridge may be replaced by O, S or N$(R^{14})$, and the above-mentioned groups and the heterocyclic ring may optionally be substituted independently of one another by one or more groups selected from among fluorine, chlorine, bromine, iodine, hydroxy, oxo, carboxy, formyl, cyano, nitro, $C_{1-3}$-alkyl, hydroxy-$C_{1-3}$-alkyl, $C_{1-3}$-alkoxy, $(R^{15})_2$N—CO— and $(R^{15})_2$N—, and $R^{15}$ each independently of one another denote hydrogen, $C_{1-6}$-alkyl, $C_{2-6}$-alkenyl, $C_{2-6}$-alkynyl, $C_{3-7}$-cycloalkyl, $C_{3-7}$-cyclyoalkyl-$C_{1-3}$-alkyl, aryl, aryl-$C_{1-3}$-alkyl, heterocyclyl, heterocyclyl-$C_{1-3}$-alkyl, heteroaryl or heteroaryl-$C_{1-3}$-alkyl, wherein the above-mentioned groups may optionally be substituted independently of one another by one or more groups selected from among fluorine, chlorine, bromine, iodine, hydroxy, oxo, carboxy, formyl, cyano, nitro, $C_{1-3}$-alkyl- and $C_{1-3}$-alkoxy, the tautomers, the stereoisomers, the mixtures thereof and the salts thereof, particularly the physiologically acceptable salts thereof.

The compounds according to the invention of general formula (I) and the physiologically acceptable salts thereof have valuable pharmacological properties, particularly an inhibiting effect on β-secretase activity, particularly the β-secretase mediated cleaving of APP. In addition, the compounds of the present invention are characterised by a surprisingly good cellular activity.

In view of the inhibitory properties of the compounds according to the invention on cathepsin D activity, the compounds are also suitable for suppressing the metastasisation of tumour cells. The present invention also relates to the physiologically acceptable salts of the compounds according to the invention with inorganic or organic acids.

The invention therefore also relates to the use of the compounds according to the invention, including the physiologically acceptable salts, as medicaments.

The invention further relates to pharmaceutical compositions containing at least one compound according to the invention or a physiologically acceptable salt according to the invention optionally together with one or more inert carriers and/or diluents.

This invention further relates to pharmaceutical compositions containing one or more, preferably one active substance, which is selected from the compounds according to the invention and/or the corresponding salts, as well as one or more, preferably one active substance, selected for example from among the beta-secretase inhibitors; gamma-secretase inhibitors; amyloid aggregation inhibitors such as e.g. alzhemed; directly or indirectly acting neuroprotective substances; antioxidants, such as e.g. vitamin E or ginkolide; anti-inflammatory substances, such as e.g. Cox inhibitors, NSAIDs additionally or exclusively having Aβ lowering properties; HMG-CoA reductase inhibitors (statins); acetylcholinesterase inhibitors, such as donepezil, rivastigmine, tacrine, galantamine; NMDA receptor antagonists such as e.g. memantine; AMPA agonists; substances modulating the concentration or release of neurotransmitters such as NS-2330; substances inducing the secretion of growth hormone such as ibutamoren mesylate and capromorelin; CB-1 receptor antagonists or inverse agonists; antibiotics such as minocyclin or rifampicin; PDE-IV and PDE-IX inhibitors, $GABA_A$ inverse agonists, nicotinic agonists, histamine H3 antagonists, 5 HAT-4 agonists or partial agonists, 5HT-6 antagonists, a2-adrenoreceptor antagonists, muscarinic M1 agonists, muscarinic M2 antagonists, metabotropic glutamate-receptor 5 positive modulators, and other substances that modulate receptors or enzymes in a manner such that the efficacy and/or safety of the compounds according to the invention is increased and/or unwanted side effects are reduced, optionally together with one or more inert carriers and/or diluents.

This invention further relates to pharmaceutical compositions containing one or more, preferably one active substance, which is selected from the compounds according to the invention and/or the corresponding salts, as well as one or more, preferably one active substance selected from among alzhemed, vitamin E, ginkolide, donepezil, rivastigmine, tacrine, galantamine, memantine, NS-2330, ibutamoren mesylate, capromorelin, minocyclin and/or rifampicin, optionally together with one or more inert carriers and/or diluents.

This invention further relates to the use of at least one of the compounds according to the invention for inhibiting β-secretase.

This invention also relates to the use of at least one compound according to the invention or a physiologically acceptable salt of such a compound for preparing a pharmaceutical composition, which is suitable for the treatment or prophylaxis of diseases or conditions associated with the abnormal processing of Amyloid Precursor Protein (APP) or aggregation of the Abeta peptide.

This invention also relates to the use of at least one compound according to the invention or a physiologically acceptable salt of such a compound for preparing a pharmaceutical composition which is suitable for the treatment or prophylaxis of diseases or conditions which can be influenced by inhibiting the β-secretase activity.

This invention also relates to the use of at least one compound according to the invention or a pharmaceutical composition according to the invention for preparing a medicament which is suitable for the treatment and/or prevention of Alzheimer's disease (AD) and other diseases which are associated with the abnormal processing of APP or aggregation of Abeta peptide, as well as diseases which can be treated or prevented by the inhibition of β-secretase, particularly AD. Such diseases include MCI ("mild cognitive impairment"), trisomy 21 (Down's syndrome), cerebral amyloid angiopathy, degenerative dementias, hereditary cerebral haemorrhage with amyloidosis, Dutch type (HCHWA-D), Alzheimer's dementia with Lewy bodies, trauma, stroke, pancreatitis, Inclusion Body Myositis (IBM), and other peripheral amyloidoses, diabetes and arteriosclerosis.

This invention further relates to a method of inhibiting β-secretase activity, characterised in that β-secretase is brought into contact with an inhibitory amount of one of the compounds according to the invention.

DETAILED DESCRIPTION OF THE INVENTION

Unless otherwise stated the groups, residues and substituents $R^1$ to $R^{15}$, A, B, L, i and $X^1$—$X^4$ have the meanings given hereinbefore and below.

If residues, substituents or groups occur more than once in a compound, they may have the same or different meanings.

In a preferred embodiment of the compounds of the present invention the group

denotes a phenyl, biphenyl, naphthyl or a 5-, 6-, 7-, 8-, 9- or 10-membered aromatic mono- or bicyclic heteroaryl group which contains 1-4 heteroatoms selected from N, O and S.

In another preferred embodiment of the compounds of the present invention the group

denotes a phenyl ring or a 5- or 6-membered aromatic heteroaryl group which contains 1 or 2 heteroatoms selected from N, O and S, wherein a maximum of one O or S atom may be present.

In another preferred embodiment the group

has the following meanings:

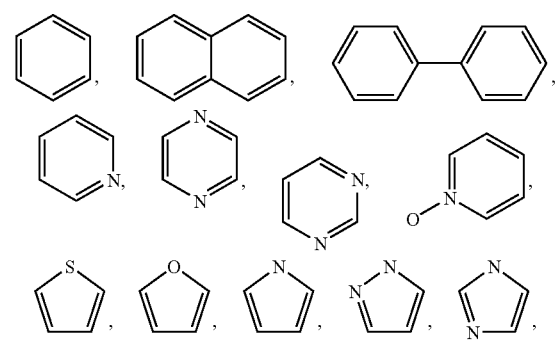

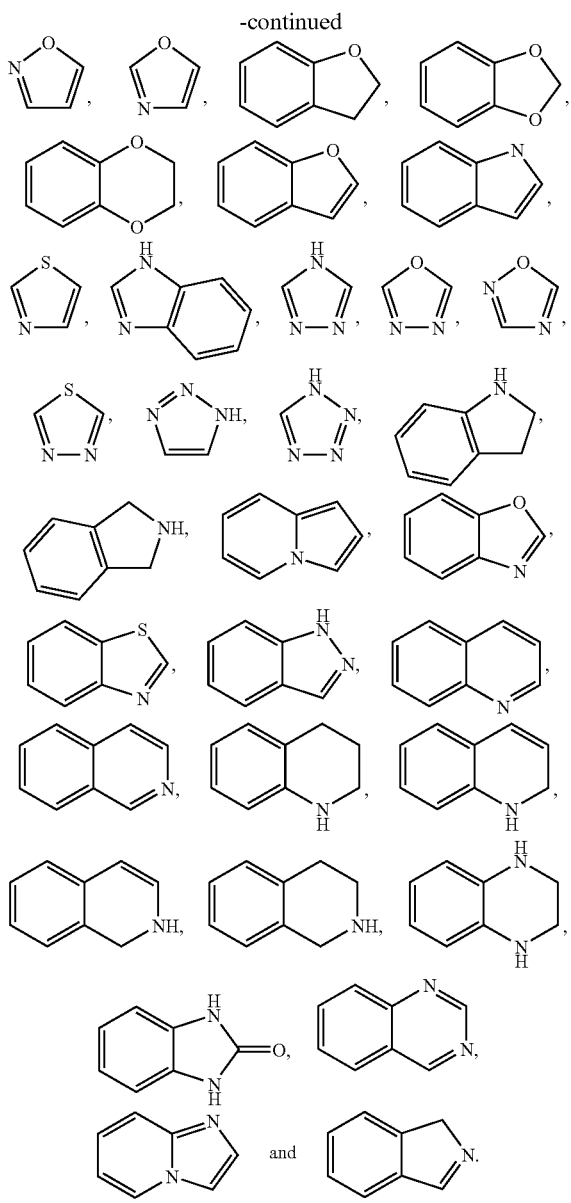

In a particularly preferred embodiment the group (A)

denotes a phenyl, thienyl, thiazolyl, particularly 2-thiazolyl, or a pyridyl group, wherein the phenyl, the thienyl, particularly the 3-thienyl, and the pyridyl group, particularly the 2-pyridyl group, are deemed to be particularly preferred.

Preferably the substituent L denotes independently of one another in each case hydrogen, fluorine, chlorine, bromine, iodine, hydroxy, carboxy, cyano, nitro, $F_3C$, $HF_2C$, $FH_2C$, $C_{1-6}$-alkyl, $C_{2-6}$-alkenyl, $C_{2-6}$-alkynyl, $C_{3-7}$-cycloalkyl, $C_{3-7}$-cycloalkyl-$C_{1-3}$-alkyl, aryl, aryl-$C_{1-3}$-alkyl, heterocyclyl, heterocyclyl-$C_{1-3}$-alkyl, heteroaryl, heteroaryl-$C_{1-3}$-alkyl, $R^{15}$—O, $R^{15}$—O—$C_{1-3}$-alkyl, $(R^{14})_2N$, $(R^{14})_2N$—CO, $R^{14}$—CO—$(R^{14})N$, $(R^{14})_2N$—CO—$(R^{14})N$, $(R^{14})_2N$—$SO_2$—, $R^{14}$—$SO_2$—$(R^{14})N$ or $C_{1-3}$-alkyl-$SO_2$—, wherein the above-mentioned groups may optionally be substituted independently of one another by one or more groups selected from among fluorine, chlorine, bromine, hydroxy, oxo, carboxy, cyano, nitro, $F_3C$, $HF_2C$, $FH_2C$, hydroxy-$C_{1-3}$-alkyl, $C_{1-3}$-alkyl, $C_{1-3}$-alkoxy, $(R^{14})_2N$, $(R^{14})_2N$—$C_{1-3}$-alkyl and $(R^{14})_2N$—CO.

Particularly preferably the substituent L denotes independently of one another in each case hydrogen, fluorine, chlorine, bromine, iodine, cyano, hydroxy, $C_{1-6}$-alkyl, $C_{1-6}$-alkoxy, $C_{3-7}$-cycloalkyl, $C_{3-7}$-cycloalkyl-$C_{1-3}$-alkyl, phenyl, $(R^{14})_2N$, $(R^{14})_2N$—CO, $R^{14}$—CO—$(R^{14})N$, $(R^{14})_2N$—CO—$(R^{14})N$, $R^{14}$—$SO_2$—$(R^{14})N$ or $(R^{14})_2N$—$SO_2$—, wherein the above-mentioned groups may optionally be substituted by one or more fluorine atoms.

Most particularly preferred meanings for the substituent L, independently of one another in each case, are hydrogen, fluorine, chlorine, bromine, hydroxy, $C_{1-4}$-alkyl or $C_{1-4}$-alkoxy, wherein the above-mentioned groups may optionally be substituted by one or more fluorine atoms.

Particularly preferred meanings for the substituent L, independently of one another in each case, are hydrogen, fluorine, chlorine, trifluoromethyl, trifluoromethoxy, methyl and methoxy.

Preferably the index i may assume the values 0, 1 or 2. In particularly preferred embodiments the value of the index i is 0 or 1.

In a preferred embodiment of the compounds according to the invention the group B represents a $C_{1-4}$-alkylene bridge which may optionally be substituted independently of one another by one or more groups selected from among fluorine, chlorine, bromine, iodine, hydroxy, oxo, carboxy, cyano, nitro, $F_3C$, $HF_2C$, $FH_2C$, $C_{1-4}$-alkyl, $C_{1-6}$-alkyl-S—$C_{1-3}$-alkyl, $C_{3-7}$-cycloalkyl, $C_{3-7}$-cycloalkyl-$C_{1-3}$-alkyl, heterocyclyl, heterocyclyl-$C_{1-3}$-alkyl, aryl, aryl-$C_{1-3}$-alkyl, heteroaryl, heteroaryl-$C_{1-3}$-alkyl, $R^{15}$—O, $(R^{14})_2N$—$SO_2$—, $(R^{14})_2N$, $(R^{14})_2N$—$C_{1-3}$-alkyl, $(R^{14})_2N$—CO, $R^{14}$—$SO_2$—, $R^{14}$—CO—$(R^{14})N$, $R^{14}$—$SO_2(R^{14})N$, $(R^{14})_2N$—$SO_2$—, $R^{14}$—CO and $R^{14}$—SO, and wherein two $C_{1-4}$-alkyl groups bound to the same carbon atom of the $C_{1-4}$-alkylene bridge may be joined together forming a $C_{3-7}$-cycloalkyl group, and the above-mentioned groups and the $C_{3-7}$-cycloalkyl group formed from the $C_{1-4}$-alkyl groups may optionally be substituted independently of one another by one or more groups selected from among fluorine, chlorine, bromine, iodine, hydroxy, oxo, carboxy, formyl, cyano, nitro, $F_3C$, $HF_2C$, $FH_2C$, $C_{1-3}$-alkyl, $C_{1-3}$-alkoxy, $R^{15}$—O—$C_{1-3}$-alkyl, $R^{14}$—CO($R^{14})N$, $R^{14}$—$SO_2(R^{14})N$, $(R^{14})_2N$, $(R^{14})_2N$—$C_{1-3}$-alkyl, $(R^{14})_2N$—CO, $(R^{14})_2N$—$SO_2$— and $HOSO_2$—.

In another preferred embodiment of the compounds according to the invention the group B represents a $C_{1-4}$-alkylene bridge, which may optionally be substituted independently of one another by one or more groups selected from among fluorine, hydroxy, carboxy, cyano, nitro, $F_3C$, $HF_2C$, $FH_2C$, $C_{1-4}$-alkyl, $C_{3-7}$-cycloalkyl, $C_{3-7}$-cycloalkyl-$C_{1-3}$-alkyl, heterocyclyl, heterocyclyl-$C_{1-3}$-alkyl, aryl, aryl-$C_{1-3}$-alkyl, heteroaryl, heteroaryl-$C_{1-3}$-alkyl, $R^{15}$—O, $(R^{14})_2N$—$SO_2$— and $(R^{14})_2N$, and two $C_{1-4}$-alkyl groups bound to the same carbon atom of the $C_{1-4}$-alkylene bridge may be joined together forming a $C_{3-7}$-cycloalkyl group, and the above-mentioned groups and the $C_{3-7}$-cycloalkyl group formed from the $C_{1-4}$-alkyl groups may optionally be substituted independently of one another by one or more groups selected from among fluorine, chlorine, bromine, hydroxy, carboxy, cyano, $F_3C$, $HF_2C$, $FH_2C$, $C_{1-3}$-alkyl, $C_{1-3}$-alkoxy-and $R^{15}$—O—$C_{1-3}$-alkyl.

Particularly preferably the group B denotes a $C_{1-4}$-alkylene bridge, wherein the $C_{1-4}$-alkylene bridge may optionally be substituted independently of one another by one or more groups selected from among $C_{1-4}$-alkyl, phenyl- and benzyl, and two $C_{1-4}$-alkyl groups bound to the same carbon atom of the $C_{1-4}$-alkylene bridge may be joined together forming a $C_{3-6}$-cycloalkyl group, and the above-mentioned groups and the $C_{3-7}$-cycloalkyl group formed from the $C_{1-4}$-alkyl groups may optionally be substituted independently of one another by one or more groups selected from among fluorine, hydroxy and $C_{1-3}$-alkoxy.

Most particularly preferred are the compounds according to the invention wherein the group B is selected from among

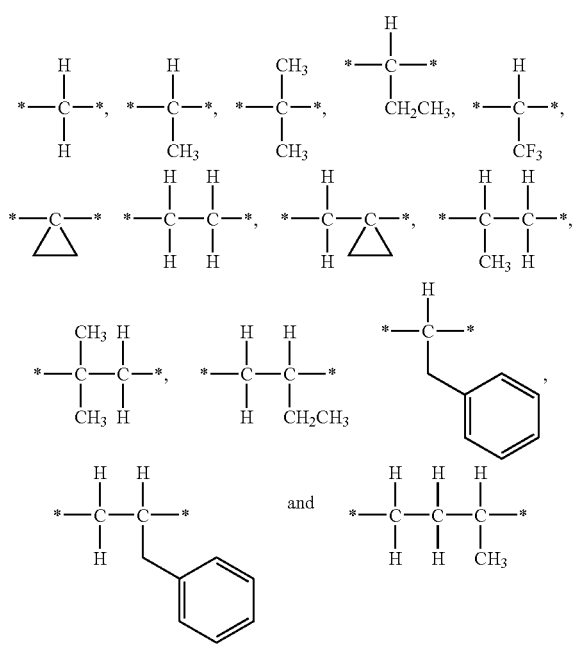

wherein one or more hydrogen atoms may optionally be replaced by fluorine.

In another most particularly preferred embodiment B is a $C_{1-2}$-alkylene bridge which may optionally be substituted by one or more $C_{1-4}$-alkyl groups, and wherein two $C_{1-4}$-alkyl groups bound to the same carbon atom of the $C_{1-2}$-alkylene bridge may be joined together forming a cyclopropyl group, and one or more hydrogen atoms of the above-mentioned $C_{1-2}$-alkylene bridge and/or the $C_{1-4}$-alkyl groups and/or the cyclopropyl group formed therefrom may optionally be replaced by one or more fluorine atoms.

Particularly preferred are those compounds according to the invention wherein the group B is selected from among

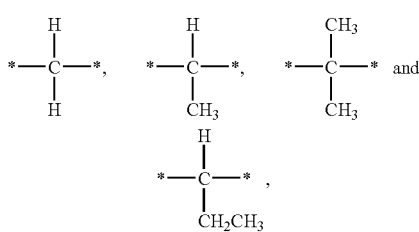

wherein one or more hydrogen atoms may optionally be replaced by fluorine.

Another preferred embodiment comprises those compounds according to the invention wherein the partial formula (II)

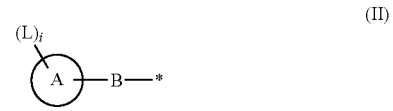

is selected from among

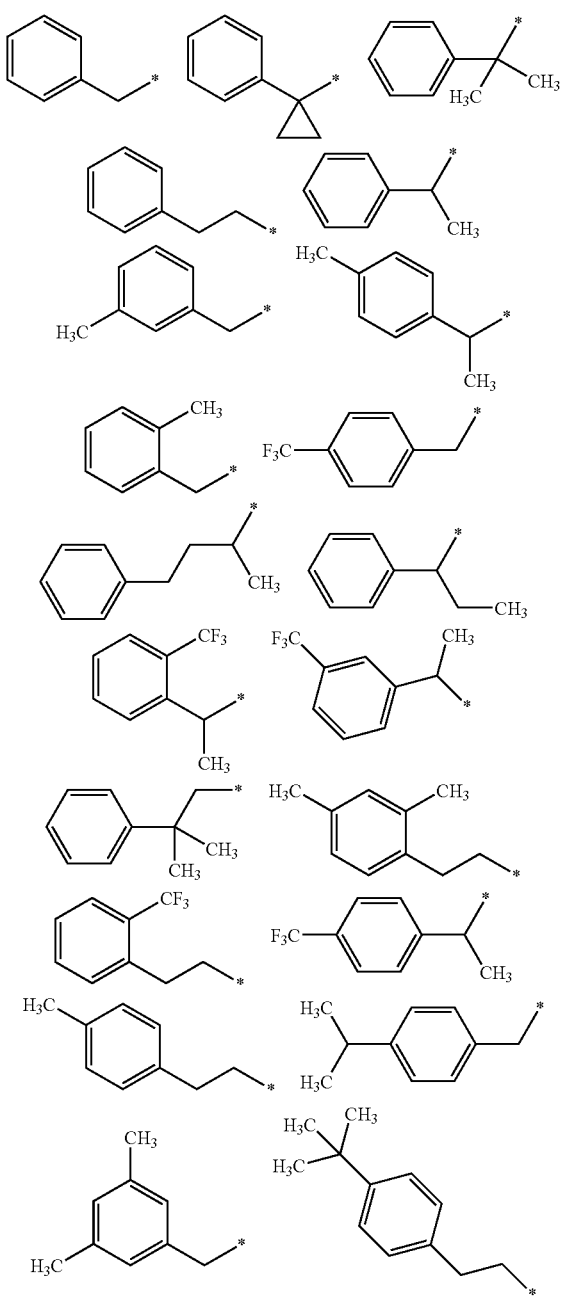

-continued
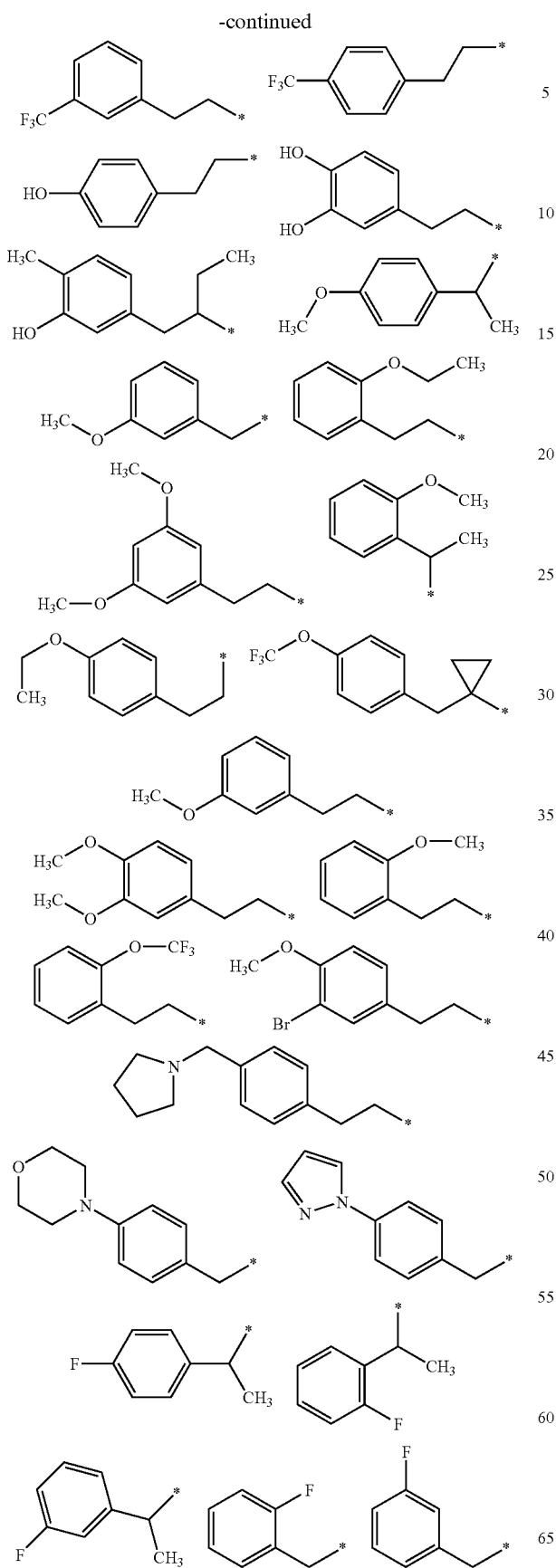
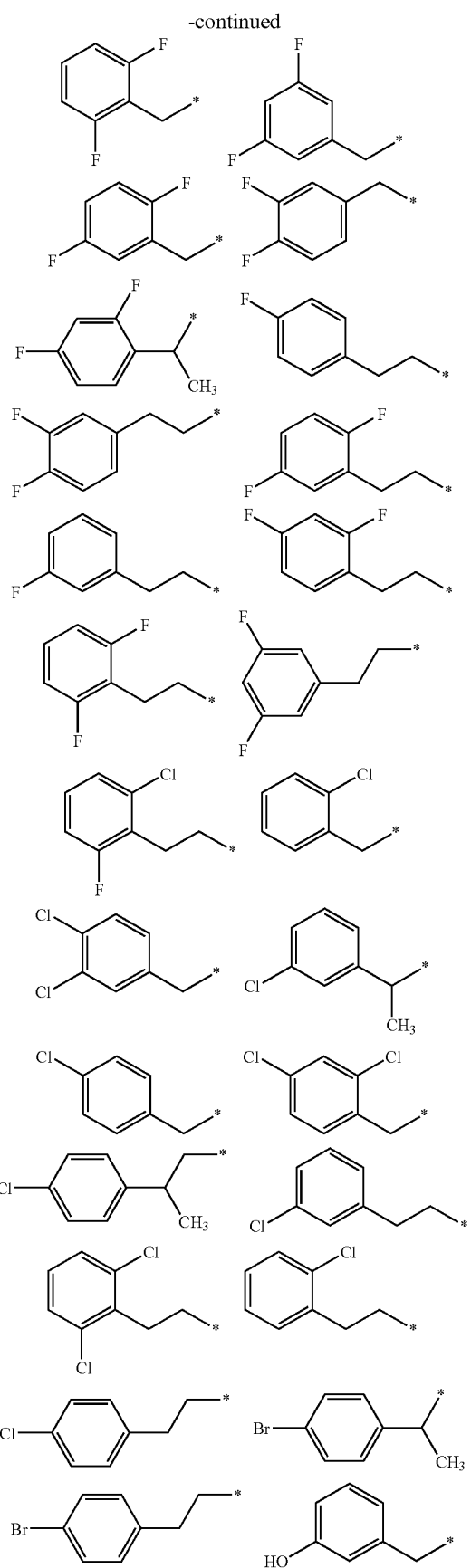

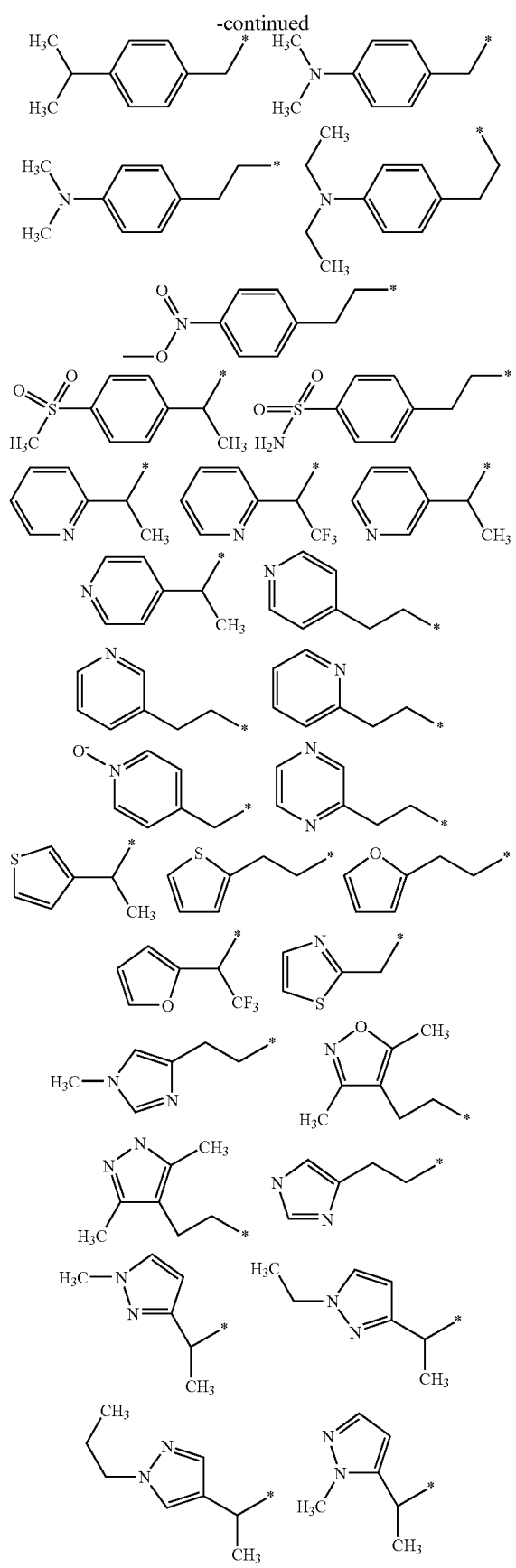
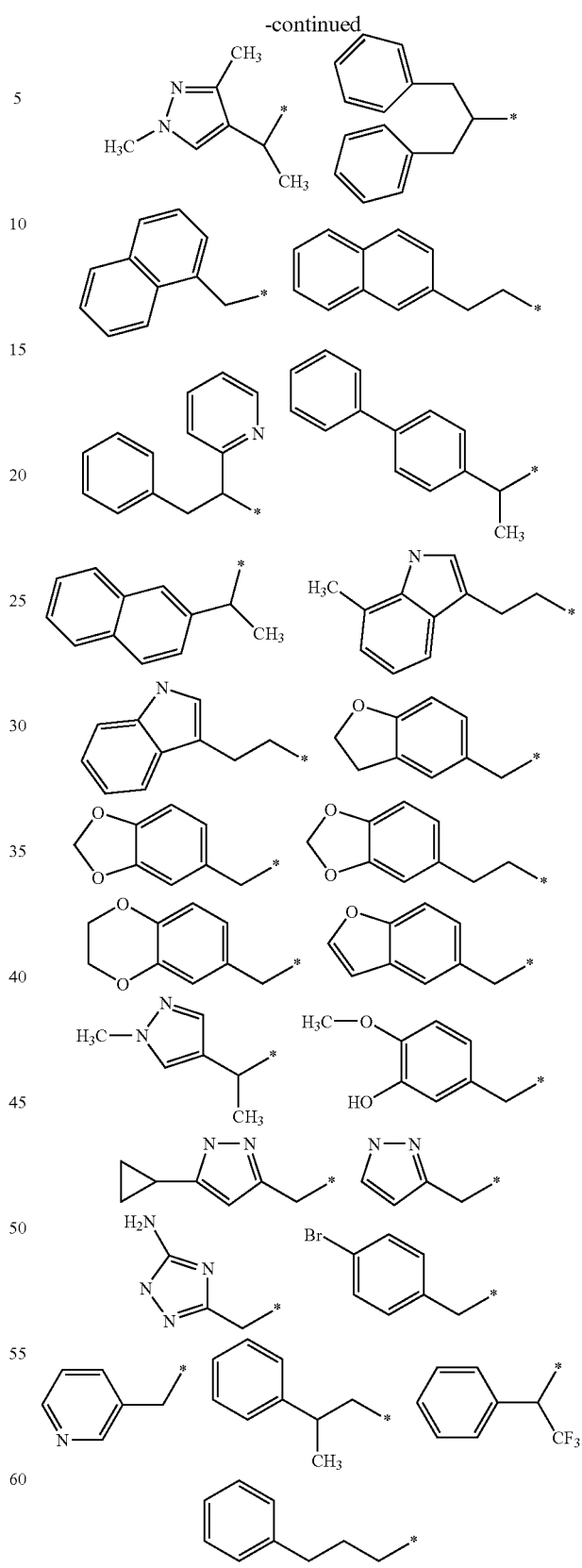
Preferably the group $R^1$ is selected from among hydrogen, $C_{1-6}$-alkyl, $C_{2-6}$-alkenyl, $C_{2-6}$-alkynyl, $C_{3-7}$-cycloalkyl, $C_{3-7}$- cycloalkyl-$C_{1-3}$-alkyl, heterocyclyl, heterocyclyl-$C_{1-3}$-alkyl, aryl, aryl-$C_{1-3}$-alkyl, heteroaryl and heteroaryl-$C_{1-3}$-alkyl, wherein the above-mentioned groups may optionally be substituted independently of one another by one or more groups selected from among fluorine, chlorine, bromine, hydroxy, carboxy, cyano, nitro, $F_3C$, $HF_2C$, $FH_2C$, $C_{1-3}$-alkyl, $C_{1-3}$-alkoxy and hydroxy-$C_{1-3}$-alkyl.

Particularly preferred are those groups $R^1$ selected from among hydrogen, $C_{1-4}$-alkyl, $C_{3-4}$-alkenyl, $C_{3-6}$-cycloalkyl- and $C_{3-6}$-cycloalkyl-$C_{1-3}$-alkyl, wherein the above-mentioned groups may optionally be substituted independently of one another by one or more groups selected from among fluorine, hydroxy and $C_{1-3}$-alkoxy.

Most particularly preferred are the groups $R^1$ selected from among hydrogen and $C_{1-4}$-alkyl, wherein the $C_{1-4}$-alkyl group may be substituted by one or more fluorine atoms.

Particularly preferred are those compounds according to the invention wherein $R^1$ is hydrogen.

In a preferred embodiment $X^1$ is $C(R^{10})$ and $X^2$, $X^3$, $X^4$ each independently of one another denote $C(R^{11})$, wherein the groups $R^{11}$ may each be selected independently of one another from the definitions given for $R^{11}$ hereinbefore and below.

In a particularly preferred embodiment $X^1$ is $C(R^{10})$ and $X^2$, $X^3$, $X^4$ in each case denote a=CH-group.

Preferred groups $R^2$ are groups selected from among $C_{1-6}$-alkyl, $C_{2-6}$-alkenyl, $C_{2-6}$-alkynyl, $C_{1-6}$-alkoxy-$C_{1-3}$-alkyl, $C_{1-6}$-alkyl-S—$C_{1-3}$-alkyl, $C_{3-7}$-cycloalkyl, $C_{3-7}$-cycloalkenyl-$C_{1-3}$-alkyl, $C_{3-7}$-cycloalkyl-$C_{1-3}$-alkyl, heterocyclyl, heterocyclyl-$C_{1-3}$-alkyl, aryl, aryl-$C_{1-3}$-alkyl, heteroaryl and heteroaryl-$C_{1-3}$-alkyl, wherein the above-mentioned groups may optionally be substituted independently of one another by one or more groups selected from among fluorine, chlorine, bromine, iodine, $F_3C$, $HF_2C$, $FH_2C$, hydroxy, carboxy, cyano, nitro, $C_{1-3}$-alkyl, $(R^{14})_2N$—$SO_2$—, $(R^{14})_2N$, $R^{14}$—CO—$(R^{14})N$, $R^{14}$—$SO_2(R^{14})N$, $(R^{14})_2N$—$C_{1-3}$-alkyl, $(R^{14})_2N$—CO, $R^{15}$—O and $R^{15}$—O—$C_{1-3}$-alkyl.

Particularly preferred groups $R^2$ are groups selected from among $C_{1-6}$-alkyl, $C_{2-6}$-alkynyl, $C_{3-6}$-cycloalkyl-$C_{1-3}$-alkyl, heterocyclyl-$C_{1-3}$-alkyl, phenyl, phenyl-$C_{1-3}$-alkyl, heteroaryl and heteroaryl-$C_{1-3}$-alkyl, wherein by the above-mentioned heteroaryl groups are meant 5- or 6-membered aromatic heteroaryl groups, which contain 1, 2 or 3 heteroatoms selected from N, O and S, and wherein the above-mentioned groups may optionally be substituted independently of one another by one or more groups selected from among fluorine, chlorine, bromine, iodine, cyano, hydroxy, $C_{1-3}$-alkyl, $F_3C$, $HF_2C$, $FH_2C$, $C_{1-3}$-alkoxy and $(R^{14})_2N$.

Other particularly preferred groups $R^2$ are groups selected from among $C_{1-6}$-alkyl, $C_{2-6}$-alkynyl, $C_{3-6}$-cycloalkyl-$C_{1-3}$-alkyl, heterocyclyl-$C_{1-3}$-alkyl, phenyl, phenyl-$C_{1-3}$-alkyl, heteroaryl and heteroaryl-$C_{1-3}$-alkyl, wherein by the above-mentioned heteroaryl groups are meant 5- or 6-membered aromatic heteroaryl groups, which contain 1 or 2 heteroatoms selected from N, O and S, wherein a maximum of one O or S atom may be present, and wherein the above-mentioned groups may optionally be substituted independently of one another by one or more groups selected from among fluorine, chlorine, bromine, iodine, cyano, hydroxy, $C_{1-3}$-alkyl, $F_3C$, $HF_2C$, $FH_2C$, $C_{1-3}$-alkoxy and $(R^{14})_2N$.

Most particularly preferred are those groups $R^2$ which are selected from among n-propyl, n-butyl, 2-propynyl, 2-butynyl, benzyl, 2-phenylethyl, pyridylmethyl, particularly 3-pyridylmethyl, furanylmethyl, thienylmethyl and thiazolylmethyl, wherein the above-mentioned propyl, butyl, propynyl and butynyl groups may optionally be substituted by one or more fluorine atoms and the benzyl, 2-phenylethyl, furanylmethyl, thienylmethyl or thiazolylmethyl groups may optionally be substituted independently of one another by one or more groups selected from among fluorine, chlorine, bromine, methyl, $F_3C$, $HF_2C$, $FH_2C$ and $H_2N$.

Also most particularly preferred are those groups $R^2$ which are selected from among n-butyl, benzyl, 2-phenylethyl, pyridylmethyl, particularly 3-pyridylmethyl, thienylmethyl and thiazolylmethyl, wherein the above-mentioned phenyl groups of the benzyl and 2-phenylethyl groups may optionally be substituted by one or more fluorine atoms.

Particularly preferred are those groups $R^2$ which are selected from among benzyl, 3,5-difluorobenzyl, thienylmethyl, particularly 3-thienylmethyl- and n-butyl, the benzyl group being the most preferred group.

Preferably the group $R^3$ denotes hydrogen, $C_{1-6}$-alkyl, fluorine, $F_3C$, $HF_2C$ or $FH_2C$— and particularly preferably $R^3$ is hydrogen.

The group $R^4$ is preferably hydrogen.

In a particularly preferred embodiment of the compounds according to the invention the group $R^3$ is selected from among hydrogen, $C_{1-6}$-alkyl, fluorine, $F_3C$, $HF_2C$ or $FH_2C$ and the group $R^4$ is hydrogen.

In a most particularly preferred embodiment of the compounds according to the invention the groups $R^3$ and $R^4$ are hydrogen.

Preferred groups $R^8$ are groups selected from among hydrogen, $C_{1-6}$-alkyl, $C_{2-6}$-alkenyl, $C_{2-6}$-alkynyl, $C_{3-7}$-cycloalkyl, $C_{3-7}$-cycloalkyl-$C_{1-3}$-alkyl, $C_{3-7}$-cycloalkenyl, $C_{3-7}$-cycloalkenyl-$C_{1-3}$-alkyl, heterocyclyl, heterocyclyl-$C_{1-3}$-alkyl, aryl, aryl-$C_{1-3}$-alkyl, heteroaryl and heteroaryl-$C_{1-3}$-alkyl, wherein the above-mentioned groups may optionally be substituted independently of one another by one or more groups selected from among fluorine, chlorine, bromine, iodine, hydroxy, carboxy, cyano, nitro, $C_{1-3}$-alkyl, heterocyclyl, heterocyclyl-$C_{1-3}$-alkyl, aryl, aryl-$C_{1-3}$-alkyl, heteroaryl, heteroaryl-$C_{1-3}$-alkyl, $(R^{14})_2N$, $(R^{14})_2N$—$C_{1-3}$-alkyl, $(R^{14})_2N$—CO, $(R^{14})_2N$—CO—$N(R^{14})$—, $(R^{14})_2N$—$SO_2$, $R^{15}$—O, $R^{15}$—O—$C_{1-3}$-alkyl, $R^{15}$—S and $R^{15}$—S—$C_{1-3}$-alkyl.

Particularly preferred groups $R^8$ are groups selected from among hydrogen, $C_{1-6}$-alkyl, $C_{2-6}$-alkenyl, $C_{2-6}$-alkynyl, $C_{3-6}$-cycloalkyl, $C_{3-6}$-cycloalkyl-$C_{1-3}$-alkyl, heterocyclyl, heterocyclyl-$C_{1-3}$-alkyl, phenyl, phenyl-$C_{1-3}$-alkyl, heteroaryl and heteroaryl-$C_{1-3}$-alkyl, wherein by the above-mentioned heteroaryl groups are meant 5- or 6-membered aromatic heteroaryl groups which contain 1, 2 or 3 heteroatoms selected from N, O and S, and wherein the above-mentioned groups may optionally be substituted independently of one another by one or more groups selected from among fluorine, chlorine, bromine, carboxy, hydroxy, cyano, $C_{1-3}$-alkyl, $C_{1-3}$-alkoxy, $C_{1-3}$-alkoxy-$C_{1-3}$-alkyl, $C_{1-3}$-alkyl-S, $C_{1-3}$-alkyl-S—$C_{1-3}$-alkyl, hydroxy-$C_{1-3}$-alkyl, heterocyclyl, heterocyclyl-$C_{1-3}$-alkyl, $(R^{14})_2N$, $(R^{14})_2N$—$C_{1-3}$-alkyl, $(R^{14})_2N$—CO—$N(R^{14})$— and $(R^{14})_2N$—$SO_2$—.

Other particularly preferred groups $R^8$ are groups selected from among hydrogen, $C_{1-6}$-alkyl, $C_{2-6}$-alkenyl, $C_{2-6}$-alkynyl, $C_{3-6}$-cycloalkyl, $C_{3-6}$-cycloalkyl-$C_{1-3}$-alkyl, heterocyclyl, heterocyclyl-$C_{1-3}$-alkyl, phenyl, phenyl-$C_{1-3}$-alkyl, heteroaryl and heteroaryl-$C_{1-3}$-alkyl, wherein by the above-mentioned heteroaryl groups are meant 5- or 6-membered aromatic heteroaryl groups which contain 1 or 2 heteroatoms selected from N, O and S, wherein a maximum of one O or S atom may be present, and wherein the above-mentioned groups may optionally be substituted independently of one another by one or more groups selected from among fluorine, chlorine, bromine, carboxy, hydroxy, cyano, $C_{1-3}$-alkyl, $C_{1-3}$-alkoxy, $C_{1-3}$-alkoxy-$C_{1-3}$-alkyl, $C_{1-3}$-alkyl-S, $C_{1-3}$-alkyl-S—$C_{1-3}$-alkyl, hydroxy-$C_{1-3}$-alkyl, heterocyclyl, heterocyclyl-$C_{1-3}$-alkyl, $(R^{14})_2N$, $(R^{14})_2N$—$C_{1-3}$-alkyl, $(R^{14})_2N$—CO—N($R^{14}$)— and $(R^{14})_2N$—$SO_2$—.

Most particularly preferred are those groups $R^8$ which are selected from among hydrogen, $C_{1-6}$-alkyl, $C_{3-6}$-cycloalkyl, $C_{3-6}$-cycloalkyl-$C_{1-3}$-alkyl, phenyl-$C_{1-3}$-alkyl or tetrahydropyranyl-$C_{1-3}$-alkyl, particularly 4-tetrahydropyranyl-$C_{1-3}$-alkyl, wherein the above-mentioned groups may optionally be substituted independently of one another by one or more groups selected from among fluorine, chlorine, bromine, pyrrolidin-1-ylmethyl, hydroxy, cyano, $C_{1-3}$-alkyl, $C_{1-3}$-alkoxy, $C_{1-3}$-alkyl-S, hydroxy-$C_{1-3}$-alkyl, $(R^{14})_2N$, $(R^{14})_2N$—$C_{1-3}$-alkyl, $(R^{14})_2N$—CO—N($R^{14}$)— and $(R^{14})_2N$—$SO_2$—.

Particularly preferred as the group $R^8$ is $C_{1-6}$-alkyl, particularly $C_{1-4}$-alkyl, $C_{3-5}$-cycloalkyl-$C_{1-2}$-alkyl, wherein $R^8$ in its most preferred embodiment denotes a methyl or ethyl group.

Preferred groups $R^5$ and $R^7$ are each selected independently of one another from among hydrogen, $C_{1-6}$-alkyl, $C_{2-6}$-alkenyl, $C_{2-6}$-alkynyl, $C_{3-7}$-cycloalkyl, heterocyclyl, $C_{3-7}$-cycloalkyl-$C_{1-3}$-alkyl, heterocyclyl-$C_{1-3}$-alkyl, $C_{3-7}$-cycloalkenyl, $C_{3-7}$-cycloalkenyl-$C_{1-3}$-alkyl, aryl, heteroaryl, aryl-$C_{1-3}$-alkyl- and heteroaryl-$C_{1-3}$-alkyl, wherein the above-mentioned groups may optionally be substituted independently of one another by one or more groups selected from among fluorine, chlorine, bromine, iodine, hydroxy, carboxy, cyano, nitro, $C_{1-3}$-alkyl, $C_{1-3}$-alkoxy, $C_{1-3}$-alkyl-S, aryl, heteroaryl, heteroaryl-$C_{1-3}$-alkyl, aryl-$C_{1-3}$-alkyl, $(R^{14})_2N$—$SO_2$—, $(R^{14})_2N$, $(R^{14})_2N$—$C_{1-3}$-alkyl and $(R^{14})_2N$—CO.

Particularly preferred groups $R^5$ are selected from among $C_{1-6}$-alkyl, cyclopropyl, $C_{3-6}$-cycloalkyl-$C_{1-3}$-alkyl and phenyl-$C_{1-3}$-alkyl, wherein the above-mentioned groups may optionally be substituted independently of one another by one or more groups selected from among fluorine, chlorine, bromine, iodine, cyano, hydroxy, carboxy, $C_{1-3}$-alkyl, $C_{1-3}$-alkoxy and $(R^{14})_2N$.

Particularly preferred groups $R^7$ are selected from among $C_{1-6}$-alkyl, $C_{3-6}$-cycloalkyl, $C_{3-6}$-cycloalkyl-$C_{1-3}$-alkyl, phenyl and phenyl-$C_{1-3}$-alkyl, wherein the above-mentioned groups may optionally be substituted independently of one another by one or more groups selected from among fluorine, chlorine, bromine, iodine, cyano, hydroxy, carboxy, $C_{1-3}$-alkyl, $C_{1-3}$-alkoxy and $(R^{14})_2N$.

In a most particularly preferred embodiment of the compounds according to the invention $R^5$ is selected from among $C_{1-6}$-alkyl, cyclopropyl, $C_{3-6}$-cycloalkyl-$C_{1-3}$-alkyl and phenyl-$C_{1-3}$-alkyl, wherein the above-mentioned groups may optionally be substituted independently of one another by one or more groups selected from among fluorine, chlorine, bromine, iodine, cyano, hydroxy, carboxy, $C_{1-3}$-alkyl, $C_{1-3}$-alkoxy and $(R^{14})_2N$, and $R^7$ is selected from among $C_{1-6}$-alkyl, $C_{3-6}$-cycloalkyl, $C_{3-6}$-cycloalkyl-$C_{1-3}$-alkyl, phenyl and phenyl-$C_{1-3}$-alkyl, wherein the above-mentioned groups may optionally be substituted independently of one another by one or more groups selected from among fluorine, chlorine, bromine, iodine, cyano, hydroxy, carboxy, $C_{1-3}$-alkyl, $C_{1-3}$-alkoxy and $(R^{14})_2N$.

Particularly preferred compounds are those wherein $R^5$ and $R^7$ each independently of one another denote $C_{1-4}$-alkyl or cyclopropyl groups, wherein one or more hydrogen atoms of the above-mentioned groups may optionally be replaced by fluorine atoms.

Particularly preferred compounds are those wherein $R^5$ and $R^7$ each independently of one another denote $C_{1-4}$-alkyl groups, wherein one or more hydrogen atoms of the $C_{1-4}$-alkyl groups may optionally be replaced by fluorine atoms, wherein $R^5$ is most preferably a methyl group and $R^7$ is most preferably an ethyl or isopropyl group.

Preferred groups $R^6$ and $R^9$ are in each case selected independently of one another from among hydrogen, $C_{1-6}$-alkyl, $C_{3-7}$-cycloalkyl-$C_{1-3}$-alkyl, $C_{2-6}$-alkenyl and $C_{2-6}$-alkynyl, wherein one or more hydrogen atoms of the above-mentioned groups may be replaced by fluorine.

In a particularly preferred embodiment of the compounds according to the invention $R^6$ is hydrogen and $R^9$ is selected from among hydrogen and $C_{1-4}$-alkyl, wherein one or more hydrogen atoms of the $C_{1-4}$-alkyl group may be replaced by fluorine.

In a most particularly preferred embodiment of the compounds according to the invention the groups $R^6$ and $R^9$ are hydrogen.

Preferred groups $R^{10}$ are groups selected from among hydrogen, fluorine, chlorine, bromine, cyano, $C_{1-6}$-alkyl, $C_{2-6}$-alkenyl, $C_{2-6}$-alkynyl, $C_{3-7}$-cycloalkyl, $C_{3-7}$-cycloalkyl-$C_{1-6}$-alkyl, heterocyclyl, heterocyclyl-$C_{1-6}$-alkyl, $C_{3-7}$-cycloalkenyl, aryl, aryl-$C_{1-6}$-alkyl, heteroaryl, heteroaryl-$C_{1-6}$-alkyl, $R^{15}$—O, $R^{15}$—O—$C_{1-3}$-alkyl, $R^{12}$—$SO_2$—$(R^{13})N$ and $R^{12}$—CO—$(R^{13})N$, wherein the above-mentioned groups may optionally be substituted independently of one another by one or more groups selected from among fluorine, chlorine, bromine, iodine, hydroxy, oxo, carboxy, formyl, cyano, nitro, $C_{3-7}$-cycloalkyl, heterocyclyl, $(R^{14})_2N$, $(R^{14})_2N$—CO, $R^{15}$—CO, $R^{15}$—O—CO, $R^{14}$—CO—$(R^{14})N$, $(R^{14})_2N$—CO—$(R^{14})N$, $(R^{14})_2N$—$SO_2$—, $(R^{14})_2N$—$SO_2$—$(R^{14})N$, $R^{14}$—$SO_2$—, $C_{1-4}$-alkyl, $R^{15}$—O, $C_{1-4}$-alkyl-S, $F_3C$, $HF_2C$, $FH_2C$, $F_3C$—O, $HF_2C$—O, $FH_2C$—O and $R^{14}$—$SO_2$—$(R^{14})N$.

Particularly preferred groups $R^{10}$ are groups selected from among hydrogen, fluorine, chlorine, bromine, cyano, $C_{1-4}$-alkyl, $C_{1-4}$-alkoxy, $C_{3-6}$-cycloalkyl, $C_{3-6}$-cycloalkyl-oxy, $C_{3-6}$-cycloalkyl-$C_{1-3}$-alkoxy, 1,3-diazacyclohexan-2-on-1-yl, 2-oxo-1,3-oxazinan-3-yl, 3-oxomorpholino, 1,1-dioxo-[1,2,6]thiadiazinan-2-yl, phenyl, pyridyl, thienyl, furyl, $R^{12}$—CO—$(R^{13})N$ and $R^{12}$—$SO_2$—$(R^{13})N$, wherein the above-mentioned groups may optionally be substituted independently of one another by one or more groups selected from among fluorine, chlorine, bromine, carboxy, cyano, $C_{1-4}$-alkyl, $C_{1-4}$-alkoxy, $C_{1-4}$-alkyl-S, $R^{15}$—CO, $R^{15}$—O—CO, $R^{14}$—$SO_2$—, $F_3C$, $HF_2C$, $FH_2C$, $F_3C$—O, $HF_2C$—O, $FH_2C$—O and $(R^{14})_2N$—CO.

Other particularly preferred groups $R^{10}$ are groups selected from among $R^{12}$—CO—$(R^{13})N$, $R^{12}$—$SO_2$—$(R^{13})N$, cyanophenyl, particularly o-cyanophenyl, and cyanothienyl, particularly o-cyanothienyl, wherein the above-mentioned cyanophenyl and cyanothienyl groups may optionally be substituted independently of one another by one or more groups selected from among fluorine, chlorine, bromine, $C_{1-4}$-alkyl, $C_{1-4}$-alkoxy, $F_3C$, $HF_2C$, $FH_2C$, $F_3C$—O, $HF_2C$—O and $FH_2C$—O.

In another most particularly preferred embodiment of the compounds according to the invention the group $R^{10}$ denotes $R^{12}$—$SO_2$—$(R^{13})N$ or o-cyanophenyl, wherein the o-cyanophenyl group may optionally be substituted by a $C_{1-4}$-alkyl or $C_{1-4}$-alkoxy group.

Preferred groups $R^{11}$ are in each case selected independently of one another from among hydrogen, fluorine, chlorine, bromine, iodine, methyl and $F_3C$, wherein the groups hydrogen, fluorine, chlorine and bromine are particularly preferred, and the group hydrogen is most preferred.

Also preferred according to the invention are those compounds wherein $R^{10}$ denotes hydrogen, fluorine, chlorine, bromine, cyano, $C_{1-6}$-alkyl, $C_{2-6}$-alkenyl, $C_{2-6}$-alkynyl, $C_{3-7}$- cycloalkyl, $C_{3-7}$-cycloalkyl-$C_{1-6}$-alkyl, heterocyclyl, heterocyclyl-$C_{1-6}$-alkyl, $C_{3-7}$-cycloalkenyl, aryl, aryl-$C_{1-6}$-alkyl, heteroaryl, heteroaryl-$C_{1-6}$-alkyl, $R^{15}$—O, $R^{15}$—O—$C_{1-3}$-alkyl, $R^{12}$—$SO_2$—($R^{13}$)N or $R^{12}$—CO—($R^{13}$)N, wherein the above-mentioned groups may optionally be substituted independently of one another by one or more groups selected from among fluorine, chlorine, bromine, iodine, hydroxy, oxo, carboxy, formyl, cyano, nitro, $C_{3-7}$-cycloalkyl, heterocyclyl, $(R^{14})_2N$, $(R^{14})_2N$—CO, $R^{15}$—CO, $R^{15}$—O—CO, $R^{14}$—CO—$(R^{14})N$, $(R^{14})_2N$—CO—$(R^{14})N$, $(R^{14})_2N$—$SO_2$—, $(R^{14})_2N$—$SO_2$—$(R^{14})N$, $R^{14}$—$SO_2$—, $C_{1-4}$-alkyl, $R^{15}$—O, $C_{1-4}$-alkyl-S, $F_3C$, $HF_2C$, $FH_2C$, $F_3C$—O, $HF_2C$—O, $FH_2C$—O and $R^{14}$—$SO_2$—$(R^{14})N$, and $R^{11}$ each independently of one another denote hydrogen, fluorine, chlorine, bromine, iodine, methyl or $F_3C$.

Particularly preferred are those compounds according to the invention wherein $R^{10}$ denotes hydrogen, fluorine, chlorine, bromine, cyano, $C_{1-4}$-alkyl, $C_{1-4}$-alkoxy, $C_{3-6}$-cycloalkyl, $C_{3-6}$-cycloalkyl-oxy, $C_{3-6}$-cycloalkyl-$C_{1-3}$-alkoxy, 1,3-diazacyclohexan-2-on-1-yl, 2-oxo-1,3-oxazinan-3-yl, 3-oxomorpholino, 1,1-dioxo-[1,2,6]thiadiazinan-2-yl, phenyl, pyridyl, thienyl, furyl, $R^{12}$—CO—$(R^{13})N$ or $R^{12}$—$SO_2$—$(R^{13})N$, wherein the above-mentioned groups may optionally be substituted independently of one another by one or more groups selected from among fluorine, chlorine, bromine, carboxy, cyano, $C_{1-4}$-alkyl, $C_{1-4}$-alkoxy, $C_{1-4}$-alkyl-S, $R^{15}$—CO, $R^{15}$—O—CO, $R^{14}$—$SO_2$—, $F_3C$, $HF_2C$, $FH_2C$, $F_3C$—O, $HF_2C$—O, $FH_2C$—O and $(R^{14})_2N$—CO, and $R^{11}$ each independently of one another denote hydrogen, fluorine, chlorine or bromine.

Most particularly preferred are those compounds according to the invention wherein $R^{10}$ denotes the group $R^{12}$—CO—$(R^{13})N$, $R^{12}$—$SO_2$—$(R^{13})N$, cyanophenyl, particularly o-cyanophenyl, or cyanothienyl, particularly o-cyanothienyl, wherein the above-mentioned cyanophenyl and cyanothienyl groups may optionally be substituted independently of one another by one or more groups selected from among fluorine, chlorine, bromine, $C_{1-4}$-alkyl, $C_{1-4}$-alkoxy, $F_3C$, $HF_2C$, $FH_2C$, $F_3C$—O, $HF_2C$—O and $FH_2C$—O, and $R^{11}$ each independently of one another denote hydrogen, fluorine, chlorine or bromine, particularly hydrogen.

Most particularly preferred are those compounds according to the invention wherein $R^{10}$ denotes the group $R^{12}$—$SO_2$—$(R^{13})N$ or o-cyanophenyl, wherein the o-cyanophenyl group may optionally be substituted by a $C_{1-4}$-alkyl or $C_{1-4}$-alkoxy group, and $R^{11}$ each independently of one another denote hydrogen, fluorine, chlorine or bromine, particularly hydrogen.

Preferred groups $R^{12}$ are groups selected from among $C_{1-6}$-alkyl, $C_{2-6}$-alkenyl, $C_{2-6}$-alkynyl, $C_{3-7}$-cycloalkyl, $C_{3-7}$-cycloalkyl-$C_{1-3}$-alkyl, heterocyclyl, heterocyclyl-$C_{1-3}$-alkyl, $C_{3-7}$-cycloalkenyl, $C_{3-7}$-cycloalkenyl-$C_{1-3}$-alkyl, aryl, aryl-$C_{1-3}$-alkyl, heteroaryl, heteroaryl-$C_{1-3}$-alkyl and $(R^{14})_2N$, wherein the above-mentioned groups may optionally be substituted independently of one another by one or more groups selected from among fluorine, chlorine, bromine, hydroxy, carboxy, cyano, nitro, $C_{1-3}$-alkyl, heterocyclyl, heterocyclyl-$C_{1-3}$-alkyl, $C_{1-3}$-alkoxy, hydroxy-$C_{1-3}$-alkyl, $R^{14}$—CO($R^{14}$)N, $R^{14}$—$SO_2(R^{14})N$, $(R^{14})_2N$—$SO_2$—, $R^{14}$—$SO_2$—, $R^{14}$—SO, $R^{14}$—S, $(R^{14})_2N$, $(R^{14})_2N$—$C_{1-3}$-alkyl and $(R^{14})_2N$—CO.

Particularly preferred groups $R^{12}$ are groups selected from among $C_{1-6}$-alkyl, heterocyclyl, phenyl, phenyl-$C_{1-3}$-alkyl, heteroaryl, heteroaryl-$C_{1-3}$-alkyl- and $(R^{14})_2N$, wherein by the above-mentioned heteroaryl groups are meant 5- or 6-membered aromatic heteroaryl groups which contain 1 or 2 heteroatoms selected from N, O and S, wherein a maximum of one O or S atom may be present, and wherein the above-mentioned groups may optionally be substituted independently of one another by one or more groups selected from among fluorine, chlorine, bromine, hydroxy, cyano, $C_{1-3}$-alkyl, $C_{1-3}$-alkoxy, heterocyclyl, heterocyclyl-$C_{1-3}$-alkyl, hydroxy-$C_{1-3}$-alkyl, $(R^{14})_2N$ and $(R^{14})_2N$—$C_{1-3}$-alkyl.

Most particularly preferred groups $R^{12}$ are groups selected from among $C_{1-4}$-alkyl, particularly methyl or ethyl, morpholinyl, phenyl, benzyl, pyridyl, particularly 3-pyridyl, and $(CH_3)_2N$, wherein the above-mentioned groups may optionally be substituted independently of one another by one or more groups selected from among fluorine, chlorine and bromine.

Preferred groups $R^{13}$ are groups selected from among hydrogen, $C_{1-6}$-alkyl, $C_{2-6}$-alkenyl, $C_{2-6}$-alkynyl, $C_{3-7}$-cycloalkyl, $C_{3-7}$-cycloalkyl-$C_{1-3}$-alkyl, aryl, aryl-$C_{1-3}$-alkyl, heterocyclyl, heterocyclyl-$C_{1-3}$-alkyl, heteroaryl and heteroaryl-$C_{1-3}$-alkyl, wherein the above-mentioned groups may optionally be substituted independently of one another by one or more groups selected from among fluorine, chlorine, bromine, hydroxy, cyano, $C_{1-3}$-alkyl, $C_{1-3}$-alkoxy, hydroxy-$C_{1-3}$-alkyl, heterocyclyl, heterocyclyl-$C_{1-3}$-alkyl, $(R^{14})_2N$ and $(R^{14})_2N$—$C_{1-3}$-alkyl.

Particularly preferred groups $R^{13}$ are groups selected from among hydrogen, $C_{1-6}$-alkyl, heterocyclyl, heterocyclyl-$C_{1-3}$-alkyl, $C_{3-6}$-cycloalkyl, $C_{3-6}$-cycloalkyl-$C_{1-3}$-alkyl, phenyl, phenyl-$C_{1-3}$-alkyl, heteroaryl and heteroaryl-$C_{1-3}$-alkyl, wherein by the above-mentioned heteroaryl groups are meant 5- or 6-membered aromatic heteroaryl groups which contain 1 or 2 heteroatoms selected from N, O and S, wherein a maximum of one O or S atom may be present, and wherein the above-mentioned groups may optionally be substituted independently of one another by one or more groups selected from among fluorine, chlorine, bromine, hydroxy, cyano, $C_{1-3}$-alkyl, $C_{1-3}$-alkoxy, hydroxy-$C_{1-3}$-alkyl, heterocyclyl, heterocyclyl-$C_{1-3}$-alkyl, $(R^{14})_2N$ and $(R^{14})_2N$—$C_{1-3}$-alkyl.

Most particularly preferred groups $R^{13}$ are groups selected from among hydrogen, methyl, ethyl, phenyl and 4-fluorophenyl, wherein the above-mentioned groups may optionally be substituted independently of one another by one or more groups selected from among fluorine, chlorine and bromine.

Also preferred according to the invention are those compounds wherein $R^{12}$ is selected from among $C_{1-6}$-alkyl, $C_{2-6}$-alkenyl, $C_{2-6}$-alkynyl, $C_{3-7}$-cycloalkyl, $C_{3-7}$-cycloalkyl-$C_{1-3}$-alkyl, heterocyclyl, heterocyclyl-$C_{1-3}$-alkyl, $C_{3-7}$-cycloalkenyl, $C_{3-7}$-cycloalkenyl-$C_{1-3}$-alkyl, aryl, aryl-$C_{1-3}$-alkyl, heteroaryl, heteroaryl-$C_{1-3}$-alkyl and $(R^{14})_2N$, wherein the above-mentioned groups may optionally be substituted independently of one another by one or more groups selected from among fluorine, chlorine, bromine, hydroxy, carboxy, cyano, nitro, $C_{1-3}$-alkyl, heterocyclyl, heterocyclyl-$C_{1-3}$-alkyl, $C_{1-3}$-alkoxy, hydroxy-$C_{1-3}$-alkyl, $R^{14}$—CO($R^{14}$)N, $R^{14}$—$SO_2(R^{14})N$, $(R^{14})_2N$—$SO_2$—, $R^{14}$—$SO_2$—, $R^{14}$—SO, $R^{14}$—S, $(R^{14})_2N$, $(R^{14})_2N$—$C_{1-3}$-alkyl and $(R^{14})_2N$—CO, and $R^{13}$ is selected from among hydrogen, $C_{1-6}$-alkyl, $C_{2-6}$-alkenyl, $C_{2-6}$-alkynyl, $C_{3-7}$-cycloalkyl, $C_{3-7}$-cycloalkyl-$C_{1-3}$-alkyl, aryl, aryl-$C_{1-3}$-alkyl, heterocyclyl, heterocyclyl-$C_{1-3}$-alkyl, heteroaryl and heteroaryl-$C_{1-3}$-alkyl, wherein the above-mentioned groups may optionally be substituted independently of one another by one or more groups selected from among fluorine, chlorine, bromine, hydroxy, cyano, $C_{1-3}$-alkyl, $C_{1-3}$-alkoxy, hydroxy-$C_{1-3}$-alkyl, heterocyclyl, heterocyclyl-$C_{1-3}$-alkyl, $(R^{14})_2N$ and $(R^{14})_2N$—$C_{1-3}$-alkyl.

Also particularly preferred are those compounds wherein $R^{12}$ is selected from among $C_{1-6}$-alkyl, heterocyclyl, phenyl, phenyl-$C_{1-3}$-alkyl, heteroaryl, heteroaryl-$C_{1-3}$-alkyl- and $(R^{14})_2N$, wherein by the above-mentioned heteroaryl groups are meant 5- or 6-membered aromatic heteroaryl groups which contain 1 or 2 heteroatoms selected from N, O and S, wherein a maximum of one O or S atom may be present, and wherein the above-mentioned groups may optionally be substituted independently of one another by one or more groups selected from among fluorine, chlorine, bromine, hydroxy, cyano, $C_{1-3}$-alkyl, $C_{1-3}$-alkoxy, heterocyclyl, heterocyclyl-$C_{1-3}$-alkyl, hydroxy-$C_{1-3}$-alkyl, $(R^{14})_2N$ and $(R^{14})_2N$—$C_{1-3}$-alkyl, and $R^{13}$ is selected from among hydrogen, $C_{1-6}$-alkyl, heterocyclyl, heterocyclyl-$C_{1-3}$-alkyl, $C_{3-6}$-cycloalkyl, $C_{3-6}$-cycloalkyl-$C_{1-3}$-alkyl, phenyl, phenyl-$C_{1-3}$-alkyl, heteroaryl and heteroaryl-$C_{1-3}$-alkyl, wherein by the above-mentioned heteroaryl groups are meant 5- or 6-membered aromatic heteroaryl groups, which contain 1 or 2 heteroatoms selected from N, O and S, wherein a maximum of one O or S atom may be present, and wherein the above-mentioned groups may optionally be substituted independently of one another by one or more groups selected from among fluorine, chlorine, bromine, hydroxy, cyano, $C_{1-3}$-alkyl, $C_{1-3}$-alkoxy, hydroxy-$C_{1-3}$-alkyl, heterocyclyl, heterocyclyl-$C_{1-3}$-alkyl, $(R^{14})_2N$ and $(R^{14})_2N$—$C_{1-3}$-alkyl.

Also particularly preferred are those compounds according to claim 1 wherein $R^{12}$ denotes $C_{1-4}$-alkyl, particularly methyl or ethyl, morpholinyl, phenyl, benzyl, pyridyl, particularly 3-pyridyl, and $(CH_3)_2N$, wherein the above-mentioned groups may optionally be substituted independently of one another by one or more groups selected from among fluorine, chlorine and bromine, and $R^{13}$ denotes hydrogen, methyl, ethyl, phenyl and 4-fluorophenyl, wherein the above-mentioned groups may optionally be substituted independently of one another by one or more groups selected from among fluorine, chlorine and bromine.

If $R^{12}$ and $R^{13}$ together form an alkylene bridge, a $C_{2-6}$-alkylene bridge is preferred, so that with the inclusion of the nitrogen atom linked to $R^{13}$ and the $SO_2$ or CO group linked to $R^{12}$ a heterocyclic ring is formed, wherein one or two $CH_2$ groups of the $C_{2-6}$-alkylene bridge may be replaced independently of one another by O, S, SO, $SO_2$ or $N(R^{14})$ in such a way that in each case two O or S atoms or an O atom and an S atom are not directly joined together, and wherein the C atoms of the above-mentioned $C_{2-6}$-alkylene bridge may optionally be substituted independently of one another by one or more groups selected from among fluorine, hydroxy, carboxy, $F_3C$, $HF_2C$, $FH_2C$, $C_{1-3}$-alkyl and $C_{1-3}$-alkoxy.

If $R^{12}$ and $R^{13}$ together form an alkylene bridge, a $C_{2-4}$-alkylene bridge is particularly preferred, so that with the inclusion of the nitrogen atom linked to $R^{13}$ and the $SO_2$ or CO group linked to $R^{12}$ a heterocyclic ring is formed, wherein one or two $CH_2$ groups of the $C_{2-4}$-alkylene bridge may be replaced independently of one another by O, S or $N(R^{14})$ in such a way that in each case two O, S or N atoms or an O and an S atom are not joined together directly, and wherein the C atoms of the above-mentioned $C_{2-4}$-alkylene bridge may optionally be substituted by one or more fluorine atoms. Particularly preferred are those compounds wherein $R^{12}$ and $R^{13}$ together form the heterocyclic rings of formulae (IIa), (IIb), (IIc) or (IId)

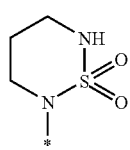
(IIa)

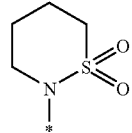
(IIb)

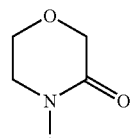
(IIc)

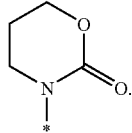
(IId)

Preferred groups $R^{14}$ are groups which are in each case selected independently from among hydrogen, $C_{1-6}$-alkyl, $C_{3-6}$-cyclyoalkyl, $C_{3-6}$-cyclyoalkyl-$C_{1-3}$-alkyl, aryl, aryl-$C_{1-3}$-alkyl, heterocyclyl, heterocyclyl-$C_{1-3}$-alkyl, heteroaryl and heteroaryl-$C_{1-3}$-alkyl, wherein the above-mentioned groups may optionally be substituted independently of one another by one or more groups selected from among fluorine, chlorine, bromine, hydroxy, carboxy, cyano, nitro, $C_{1-3}$-alkyl, hydroxy-$C_{1-3}$-alkyl and $C_{1-3}$-alkoxy.

Also preferred are those compounds of general formula (I) wherein two groups $R^{14}$ bound to the same nitrogen atom each denote a $C_{1-6}$-alkyl group which together form a $C_{2-6}$-alkylene bridge, so that with the inclusion of the nitrogen atom linked to the groups $R^{14}$ a heterocyclic ring is formed, wherein a $CH_2$ group of the $C_{2-6}$-alkylene bridge independently of one another may be replaced by O, S or $N(R^{14})$, and the heterocyclic ring may optionally be substituted independently of one another by one or more groups selected from among fluorine, chlorine, bromine, hydroxy, carboxy, cyano, nitro, $C_{1-3}$-alkyl, hydroxy-$C_{1-3}$-alkyl and $C_{1-3}$-alkoxy.

Particularly preferred groups $R^{14}$ independently of one another are hydrogen or $C_{1-6}$-alkyl groups, particularly hydrogen or a methyl group, wherein one or more hydrogen atoms of the $C_{1-6}$-alkyl group may be replaced by fluorine.

Preferably in each case $R^{15}$ is selected independently of one another from among hydrogen, $C_{1-6}$-alkyl, $C_{2-6}$-alkenyl, $C_{2-6}$-alkynyl, $C_{3-7}$-cycloalkyl, $C_{3-7}$-cyclyoalkyl-$C_{1-3}$-alkyl, aryl, aryl-$C_{1-3}$-alkyl, heterocyclyl, heterocyclyl-$C_{1-3}$-alkyl, heteroaryl and heteroaryl-$C_{1-3}$-alkyl, wherein the above-mentioned groups may optionally be substituted independently of one another by one or more groups selected from among fluorine, chlorine, bromine, hydroxy, carboxy, cyano, nitro, $C_{1-3}$-alkyl and $C_{1-3}$-alkoxy.

Particularly preferred groups $R^{15}$ independently of one another are hydrogen or $C_{1-3}$-alkyl groups, particularly hydrogen or a methyl group.

Particularly preferred compounds according to the invention are listed in the following group of formulae (Ia), (Ib), (Ic), (Id) and (Ie):

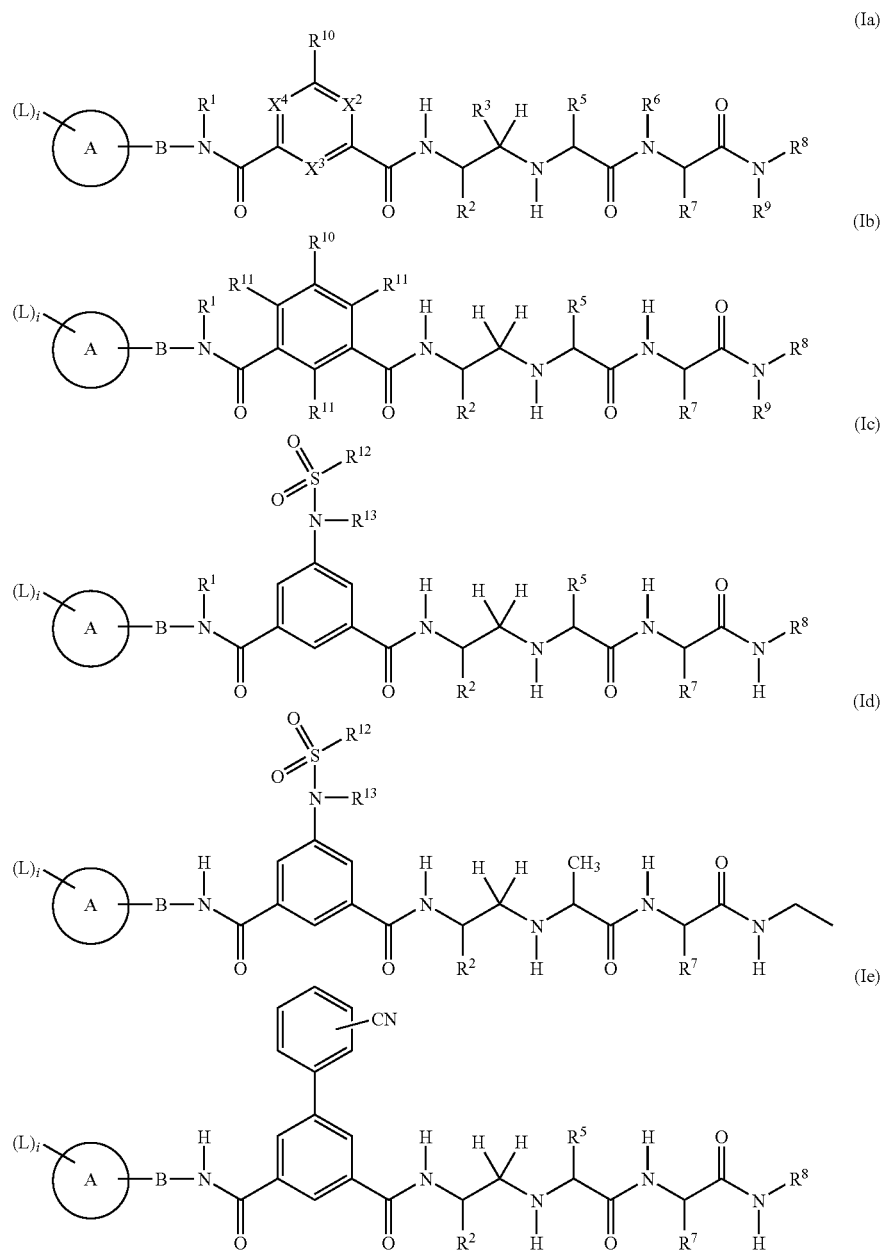

wherein

A, B, L, $X^2$, $X^3$, $X^4$, i, $R^1$, $R^2$, $R^3$, $R^5$, $R^6$, $R^7$, $R^8$, $R^9$, $R^{10}$, $R^{11}$, $R^{12}$, $R^{13}$, $R^{14}$ and $R^{15}$ have the meanings given hereinbefore.

Particularly preferred are compounds of formula (Ia) according to the invention, (Ia)

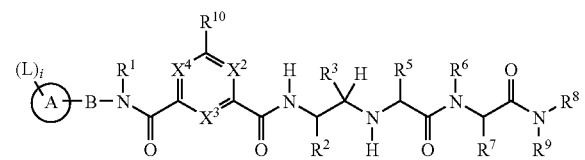

wherein

A denotes aryl or heteroaryl, wherein the group A in addition to the groups L may optionally be substituted by one or more fluorine atoms, L denotes in each case independently of one another hydrogen, fluorine, chlorine, bromine, iodine, hydroxy, carboxy, cyano, nitro, $F_3C$, $HF_2C$, $FH_2C$, $C_{1-6}$-alkyl, $C_{2-6}$-alkenyl, $C_{2-6}$-alkynyl, $C_{3-7}$-cycloalkyl, $C_{3-7}$-cycloalkyl-$C_{1-3}$-alkyl, aryl, aryl-$C_{1-3}$-alkyl, heterocyclyl, heterocyclyl-$C_{1-3}$-alkyl, heteroaryl, heteroaryl-$C_{1-3}$-alkyl, $R^{15}$-O, $R^{15}$—O—$C_{1-3}$-alkyl, $(R^{14})_2N$, $(R^{14})_2N$—CO, $R^{14}$—CO—$(R^{14})N$, $(R^{14})_2N$—CO—$(R^{14})N$, $(R^{14})_2N$—$SO_2$—, $R^{14}$—$SO_2$—$(R^{14})N$ or $C_{1-3}$-alkyl-$SO_2$— wherein the above-mentioned groups may optionally be substituted independently of one another by one or more groups selected from among fluorine, chlorine, bromine, hydroxy, oxo, carboxy, cyano, nitro, $F_3C$, $HF_2C$, $FH_2C$, hydroxy-$C_{1-3}$-alkyl, $C_{1-3}$-alkyl, $C_{1-3}$-alkoxy, $(R^{14})_2N$, $(R^{14})_2N$—$C_{1-3}$-alkyl and $(R^{14})_2N$—CO, and i denotes 0, 1 or 2, B denotes a $C_{1-4}$-alkylene bridge, wherein the $C_{1-4}$-alkylene bridge may optionally be substituted by one or more groups selected from among fluorine, chlorine, bromine, iodine, hydroxy, oxo, carboxy, cyano, nitro, $F_3C$, $HF_2C$, $FH_2C$, $C_{1-4}$-alkyl, $C_{1-6}$-alkyl-S—$C_{1-3}$-alkyl, $C_{3-7}$-cycloalkyl, $C_{3-7}$-cycloalkyl-$C_{1-3}$-alkyl, heterocyclyl, heterocyclyl-$C_{1-3}$-alkyl, aryl, aryl-$C_{1-3}$-alkyl, heteroaryl, heteroaryl-$C_{1-3}$-alkyl, $R^{15}$—O, $(R^{14})_2N$—$SO_2$—, $(R^{14})_2N$, $(R^{14})_2N$—$C_{1-3}$-alkyl, $(R^{14})_2N$—CO, $R^{14}$—$SO_2$—, $R^{14}$—CO—$(R^{14})N$, $R^{14}$—$SO_2(R^{14})N$, $(R^{14})_2N$—$SO_2$—, $R^{14}$—CO and $R^{14}$—SO, and wherein two $C_{1-4}$-alkyl groups bound to the same carbon atom of the $C_{1-4}$-alkylene bridge may be joined together forming a $C_{3-7}$-cycloalkyl group, and wherein the above-mentioned groups and the $C_{3-7}$-cycloalkyl group formed from the $C_{1-4}$-alkyl groups may optionally be substituted independently of one another by one or more groups selected from among fluorine, chlorine, bromine, iodine, hydroxy, oxo, carboxy, formyl, cyano, nitro, $F_3C$, $HF_2C$, $FH_2C$, $C_{1-3}$-alkyl, $C_{1-3}$-alkoxy, $R^{15}$—O—$C_{1-3}$-alkyl, $R^{14}$—CO$(R^{14})N$, $R^{14}$—$SO_2(R^{14})N$, $(R^{14})_2N$, $(R^{14})_2N$—$C_{1-3}$-alkyl, $(R^{14})_2N$—CO, $(R^{14})_2N$—$SO_2$— and $HOSO_2$—, $R^1$ denotes hydrogen, $C_{1-6}$-alkyl, $C_{2-6}$-alkenyl, $C_{2-6}$-alkynyl, $C_{3-7}$-cycloalkyl, $C_{3-7}$-cycloalkyl-$C_{1-3}$-alkyl, heterocyclyl, heterocyclyl-$C_{1-3}$-alkyl, aryl, aryl-$C_{1-3}$-alkyl, heteroaryl or heteroaryl-$C_{1-3}$-alkyl, wherein the above-mentioned groups may optionally be substituted independently of one another by one or more groups selected from among fluorine, chlorine, bromine, hydroxy, carboxy, cyano, nitro, $F_3C$, $HF_2C$, $FH_2C$, $C_{1-3}$-alkyl, $C_{1-3}$-alkoxy and hydroxy-$C_{1-3}$-alkyl, $X^2$, $X^3$, $X^4$ may each independently of one another be nitrogen or $C(R^{11})$, preferably $C(R^{11})$, $R^2$ denotes $C_{1-6}$-alkyl, $C_{2-6}$-alkenyl, $C_{2-6}$-alkynyl, $C_{1-6}$-alkoxy-$C_{1-3}$-alkyl, $C_{1-6}$-alkyl-S—$C_{1-3}$-alkyl, $C_{3-7}$-cycloalkyl, $C_{3-7}$-cycloalkenyl-$C_{1-3}$-alkyl, $C_{3-7}$-cycloalkyl-$C_{1-3}$-alkyl, heterocyclyl, heterocyclyl-$C_{1-3}$-alkyl, aryl, aryl-$C_{1-3}$-alkyl, heteroaryl or heteroaryl-$C_{1-3}$-alkyl, wherein the above-mentioned groups may optionally be substituted independently of one another by one or more groups selected from among fluorine, chlorine, bromine, iodine, $F_3C$, $HF_2C$, $FH_2C$, hydroxy, carboxy, cyano, nitro, $C_{1-3}$-alkyl, $(R^{14})_2N$—$SO_2$—, $(R^{14})_2N$, $R^{14}$—CO—$(R^{14})N$, $R^{14}$—$SO_2(R^{14})N$, $(R^{14})_2N$—$C_{1-3}$-alkyl, $(R^{14})_2N$—CO, $R^{15}$—O and $R^{15}$—O—$C_{1-3}$-alkyl, $R^3$ denotes hydrogen, $C_{1-6}$-alkyl, fluorine, $F_3C$, $HF_2C$ or $FH_2C$, $R^8$ denotes hydrogen, $C_{1-6}$-alkyl, $C_{2-6}$-alkenyl, $C_{2-6}$-alkynyl, $C_{3-7}$-cycloalkyl, $C_{3-7}$-cycloalkyl-$C_{1-3}$-alkyl, $C_{3-7}$-cycloalkenyl, $C_{3-7}$-cycloalkenyl-$C_{1-3}$-alkyl, heterocyclyl, heterocyclyl-$C_{1-3}$-alkyl, aryl, aryl-$C_{1-3}$-alkyl, heteroaryl and heteroaryl-$C_{1-3}$-alkyl, wherein the above-mentioned groups may optionally be substituted independently of one another by one or more groups selected from among fluorine, chlorine, bromine, iodine, hydroxy, carboxy, cyano, nitro, $C_{1-3}$-alkyl, heterocyclyl, heterocyclyl-$C_{1-3}$-alkyl, aryl, aryl-$C_{1-3}$-alkyl, heteroaryl, heteroaryl-$C_{1-3}$-alkyl, $(R^{14})_2N$, $(R^{14})_2N$—$C_{1-3}$-alkyl, $(R^{14})_2N$—CO, $(R^{14})_2N$—CO—$N(R^{14})$, $(R^{14})_2N$—$SO_2$—, $R^{15}$—O, $R^{15}$—O—$C_{1-3}$-alkyl, $R^{15}$—S and $R^{15}$—S—$C_{1-3}$-alkyl, $R^5$, $R^7$ each independently of one another denote hydrogen, $C_{1-6}$-alkyl, $C_{2-6}$-alkenyl, $C_{2-6}$-alkynyl, $C_{3-7}$-cycloalkyl, heterocyclyl, $C_{3-7}$-cycloalkyl-$C_{1-3}$-alkyl, heterocyclyl-$C_{1-3}$-alkyl, $C_{3-7}$-cycloalkenyl, $C_{3-7}$-cycloalkenyl-$C_{1-3}$-alkyl, aryl, heteroaryl, aryl-$C_{1-3}$-alkyl or heteroaryl-$C_{1-3}$-alkyl, wherein the above-mentioned groups may optionally be substituted independently of one another by one or more groups selected from among fluorine, chlorine, bromine, iodine, hydroxy, carboxy, cyano, nitro, $C_{1-3}$-alkyl, $C_{1-3}$-alkoxy, $C_{1-3}$-alkyl-S, aryl, heteroaryl, heteroaryl-$C_{1-3}$-alkyl, aryl-$C_{1-3}$-alkyl, $(R^{14})_2N$—$SO_2$—, $(R^{14})_2N$, $(R^{14})_2N$—$C_{1-3}$-alkyl and $(R^{14})_2N$—CO, $R^6$, $R^9$ each independently of one another denote hydrogen, $C_{1-6}$-alkyl, $C_{3-7}$-cycloalkyl-$C_{1-3}$-alkyl, $C_{2-6}$-alkenyl or $C_{2-6}$-alkynyl, wherein one or more hydrogen atoms of the above-mentioned groups may be replaced by fluorine, $R^{10}$ denotes hydrogen, fluorine, chlorine, bromine, cyano, $C_{1-6}$-alkyl, $C_{2-6}$-alkenyl, $C_{2-6}$-alkynyl, $C_{3-7}$-cycloalkyl, $C_{3-7}$-cycloalkyl-$C_{1-6}$-alkyl, heterocyclyl, heterocyclyl-$C_{1-6}$-alkyl, $C_{3-7}$-cycloalkenyl, aryl, aryl-$C_{1-6}$-alkyl, heteroaryl, heteroaryl-$C_{1-6}$-alkyl, $R^{15}$—O, $R^{15}$—O—$C_{1-3}$-alkyl, $R^{12}$—$SO_2$—$(R^{13})N$ or $R^{12}$—CO—$(R^{13})N$, wherein the above-mentioned groups may optionally be substituted independently of one another by one or more groups selected from among fluorine, chlorine, bromine, iodine, hydroxy, oxo, carboxy, formyl, cyano, nitro, $C_{3-7}$-cycloalkyl, heterocyclyl, $(R^{14})_2N$, $(R^{14})_2N$—CO, $R^{15}$—CO, $R^{15}$—O—CO, $R^{14}$—CO—$(R^{14})N$, $(R^{14})_2N$—CO—$(R^{14})N$, $(R^{14})_2N$—$SO_2$—, $(R^{14})_2N$—$SO_2$—$(R^{14})N$, $R^{14}$—$SO_2$—, $C_{1-4}$-alkyl, $R^{15}$—O, $C_{1-4}$-alkyl-S, $F_3C$, $HF_2C$, $FH_2C$, $F_3C$—O, $HF_2C$—O, $FH_2C$—O and $R^{14}$—$SO_2$—$(R^{14})N$, and $R^{11}$ each independently of one another denote hydrogen, fluorine, chlorine, bromine, iodine, methyl or $F_3C$, $R^{12}$ denotes $C_{1-6}$-alkyl, $C_{2-6}$-alkenyl, $C_{2-6}$-alkynyl, $C_{3-7}$-cycloalkyl, $C_{3-7}$-cycloalkyl-$C_{1-3}$-alkyl, heterocyclyl, heterocyclyl-$C_{1-3}$-alkyl, $C_{3-7}$-cycloalkenyl, $C_{3-7}$-cycloalkenyl-$C_{1-3}$-alkyl, aryl, aryl-$C_{1-3}$-alkyl, heteroaryl, heteroaryl-$C_{1-3}$-alkyl or $(R^{14})_2N$, wherein the above-mentioned groups may optionally be substituted independently of one another by one or more groups selected from among fluorine, chlorine, bromine, hydroxy, carboxy, cyano, nitro, $C_{1-3}$-alkyl, heterocyclyl, heterocyclyl-$C_{1-3}$-alkyl, $C_{1-3}$-alkoxy, hydroxy-$C_{1-3}$-alkyl, $R^{14}$—CO$(R^{14})N$, $R^{14}$—$SO_2$ $(R^{14})N$, $(R^{14})_2N$—$SO_2$—, $R^{14}$—$SO_2$—, $R^{14}$—SO, $R^{14}$—S, $(R^{14})_2N$, $(R^{14})_2N$—$C_{1-3}$-alkyl and $(R^{14})_2N$—CO, and $R^{13}$ denotes hydrogen, $C_{1-6}$-alkyl, $C_{2-6}$-alkenyl, $C_{2-6}$-alkynyl, $C_{3-7}$-cycloalkyl, $C_{3-7}$-cycloalkyl-$C_{1-3}$-alkyl, aryl, aryl-$C_{1-3}$-alkyl, heterocyclyl, heterocyclyl-$C_{1-3}$-alkyl, heteroaryl or heteroaryl-$C_{1-3}$-alkyl, wherein the above-mentioned groups may optionally be substituted independently of one another by one or more groups selected from among fluorine, chlorine, bromine, hydroxy, cyano, $C_{1-3}$-alkyl, $C_{1-3}$-alkoxy, hydroxy-$C_{1-3}$-alkyl, heterocyclyl, heterocyclyl-$C_{1-3}$-alkyl, $(R^{14})_2N$ and $(R^{14})_2N$—$C_{1-3}$-alkyl, or $R^{12}$ and $R^{13}$ together form a $C_{2-6}$-alkylene bridge, so that with the inclusion of the nitrogen atom linked to $R^{13}$ and the $SO_2$— or CO group linked to $R^{12}$ a heterocyclic ring is formed,
  wherein one or two $CH_2$ groups of the $C_{2-6}$-alkylene bridge may be replaced independently of one another by O, S, SO, $SO_2$ or $N(R^{14})$ in such a way that in each case two O or S atoms or an O atom and an S atom are not directly joined together, and
  wherein the C atoms of the above-mentioned $C_{2-6}$-alkylene bridge may optionally be substituted independently of one another by one or more groups selected from among fluorine, hydroxy, carboxy, $F_3C$, $HF_2C$, $FH_2C$, $C_{1-3}$-alkyl and $C_{1-3}$-alkoxy,
$R^{14}$ each independently of one another denote hydrogen, $C_{1-6}$-alkyl, $C_{3-6}$-cyclyoalkyl, $C_{3-6}$-cyclyoalkyl-$C_{1-3}$-alkyl, aryl, aryl-$C_{1-3}$-alkyl, heterocyclyl, heterocyclyl-$C_{1-3}$-alkyl, heteroaryl or heteroaryl-$C_{1-3}$-alkyl, or two $C_{1-6}$-alkyl groups bound to the same nitrogen atom may together form a $C_{2-6}$-alkylene bridge, so that with the inclusion of the nitrogen atom bound to the groups $R^{14}$ a heterocyclic ring is formed,
  wherein a $CH_2$ group of the $C_{2-6}$-alkylene bridge may be replaced independently of one another by O, S or $N(R^{14})$, and
  wherein the above-mentioned groups and the heterocyclic ring may optionally be substituted independently of one another by one or more groups selected from among fluorine, chlorine, bromine, hydroxy, carboxy, cyano, $C_{1-3}$-alkyl, hydroxy-$C_{1-3}$-alkyl and $C_{1-3}$-alkoxy, and
$R^{15}$ each independently of one another denote hydrogen, $C_{1-6}$-alkyl, $C_{2-6}$-alkenyl, $C_{2-6}$-alkynyl, $C_{3-7}$-cycloalkyl, $C_{3-7}$-cyclyoalkyl-$C_{1-3}$-alkyl, aryl, aryl-$C_{1-3}$-alkyl, heterocyclyl, heterocyclyl-$C_{1-3}$-alkyl, heteroaryl or heteroaryl-$C_{1-3}$-alkyl, wherein the above-mentioned groups may optionally be substituted independently of one another by one or more groups selected from among fluorine, chlorine, bromine, hydroxy, carboxy, cyano, nitro, $C_{1-3}$-alkyl and $C_{1-3}$-alkoxy.

Also particularly preferred are those compounds of formula (Ib) according to the invention,

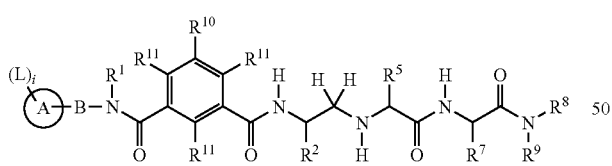

(Ib)

wherein
  A denotes phenyl, biphenyl, naphthyl or a 5-, 6-, 7-, 8-, 9- or 10-membered aromatic mono- or bicyclic heteroaryl group which contains 1-4 heteroatoms selected from N, O and S, or
    phenyl or a 5- or 6-membered aromatic heteroaryl group which contains 1 or 2 heteroatoms selected from N, O and S, wherein a maximum of one O or S atom may be present,
  L denotes in each case independently of one another hydrogen, fluorine, chlorine, bromine, iodine, cyano, hydroxy, $C_{1-6}$-alkyl, $C_{1-6}$-alkoxy, $C_{3-7}$-cycloalkyl, $C_{3-7}$-cycloalkyl-$C_{1-3}$-alkyl, phenyl, $(R^{14})_2N$, $(R^{14})_2N$—CO, $R^{14}$—CO—$(R^{14})N$, $(R^{14})_2N$—CO—$(R^{14})N$, $R^{14}$—$SO_2$—$(R^{14})N$ or $(R^{14})_2N$—$SO_2$—, wherein the above-mentioned groups may optionally be substituted by one or more fluorine atoms, and
  i denotes 0, 1 or 2,
  B denotes a $C_{1-4}$-alkylene bridge,
    wherein the $C_{1-4}$-alkylene bridge may optionally be substituted independently of one another by one or more groups selected from among fluorine, hydroxy, carboxy, cyano, nitro, $F_3C$, $HF_2C$, $FH_2C$, $C_{1-4}$-alkyl, $C_{3-7}$-cycloalkyl, $C_{3-7}$-cycloalkyl-$C_{1-3}$-alkyl, heterocyclyl, heterocyclyl-$C_{1-3}$-alkyl, aryl, aryl-$C_{1-3}$-alkyl, heteroaryl, heteroaryl-$C_{1-3}$-alkyl, $R^{15}$-O, $(R^{14})_2N$—$SO_2$— and $(R^{14})_2N$, and
    wherein two $C_{1-4}$-alkyl groups bound to the same carbon atom of the $C_{1-4}$-alkylene bridge may be joined together forming a $C_{3-7}$-cycloalkyl group, and
    wherein the above-mentioned groups and the $C_{3-7}$-cycloalkyl group formed from the $C_{1-4}$-alkyl groups may optionally be substituted independently of one another by one or more groups selected from among fluorine, chlorine, bromine, hydroxy, carboxy, cyano, $F_3C$, $HF_2C$, $FH_2C$, $C_{1-3}$-alkyl, $C_{1-3}$-alkoxy- and $R^{15}$—O—$C_{1-3}$-alkyl,
$R^1$ denotes hydrogen, $C_{1-4}$-alkyl, $C_{3-4}$-alkenyl, $C_{3-6}$-cycloalkyl or $C_{3-6}$-cycloalkyl-$C_{1-3}$-alkyl,
  wherein the above-mentioned groups may optionally be substituted independently of one another by one or more groups selected from among fluorine, hydroxy and $C_{1-3}$-alkoxy,
$R^2$ denotes $C_{1-6}$-alkyl, $C_{2-6}$-alkynyl, $C_{3-6}$-cycloalkyl-$C_{1-3}$-alkyl, heterocyclyl-$C_{1-3}$-alkyl, phenyl, phenyl-$C_{1-3}$-alkyl, heteroaryl or heteroaryl-$C_{1-3}$-alkyl,
  wherein by the above-mentioned heteroaryl groups are meant 5- or 6-membered aromatic heteroaryl groups, which contain 1, 2 or 3 heteroatoms selected from N, O and S, and
  wherein the above-mentioned groups may optionally be substituted independently of one another by one or more groups selected from among fluorine, chlorine, bromine, iodine, cyano, hydroxy, $C_{1-3}$-alkyl, $F_3C$, $HF_2C$, $FH_2C$, $C_{1-3}$-alkoxy and $(R^{14})_2N$,
$R^8$ denotes hydrogen, $C_{1-6}$-alkyl, $C_{2-6}$-alkenyl, $C_{2-6}$-alkynyl, $C_{3-6}$-cycloalkyl, $C_{3-6}$-cycloalkyl-$C_{1-3}$-alkyl, heterocyclyl, heterocyclyl-$C_{1-3}$-alkyl, phenyl, phenyl-$C_{1-3}$-alkyl, heteroaryl and heteroaryl-$C_{1-3}$-alkyl, wherein by the above-mentioned heteroaryl groups are meant 5- or 6-membered aromatic heteroaryl groups, which contain 1, 2 or 3 heteroatoms selected from N, O and S, and
  wherein the above-mentioned groups may optionally be substituted independently of one another by one or more groups selected from among fluorine, chlorine, bromine, carboxy, hydroxy, cyano, $C_{1-3}$-alkyl, $C_{1-3}$-alkoxy, $C_{1-3}$-alkoxy-$C_{1-3}$-alkyl, $C_{1-3}$-alkyl-S, $C_{1-3}$-alkyl-S—$C_{1-3}$-alkyl, hydroxy-$C_{1-3}$-alkyl, heterocyclyl, heterocyclyl-$C_{1-3}$-alkyl, $(R^{14})_2N$, $(R^{14})_2N$—$C_{1-3}$-alkyl, $(R^{14})_2N$—CO—$N(R^{14})$— and $(R^{14})_2N$—$SO_2$—,
$R^5$ denotes $C_{1-6}$-alkyl, cyclopropyl, $C_{3-6}$-cycloalkyl-$C_{1-3}$-alkyl or phenyl-$C_{1-3}$-alkyl, wherein the above-mentioned groups may optionally be substituted independently of one another by one or more groups selected from among fluorine, chlorine, bromine, iodine, cyano, hydroxy, carboxy, $C_{1-3}$-alkyl, $C_{1-3}$-alkoxy and $(R^{14})_2N$, and
$R^7$ denotes $C_{1-6}$-alkyl, $C_{3-6}$-cycloalkyl, $C_{3-6}$-cycloalkyl-$C_{1-3}$-alkyl, phenyl and phenyl-$C_{1-3}$-alkyl, wherein the above-mentioned groups may optionally be substituted independently of one another by one or more groups selected from among fluorine, chlorine, bromine, iodine, cyano, hydroxy, carboxy, $C_{1-3}$-alkyl, $C_{1-3}$-alkoxy and $(R^{14})_2N$, $R^9$ denotes hydrogen or $C_{1-4}$-alkyl,
wherein one or more hydrogen atoms of the $C_{1-4}$-alkyl group may be replaced by fluorine, $R^{10}$ denotes hydrogen, fluorine, chlorine, bromine, cyano, $C_{1-4}$-alkyl, $C_{1-4}$-alkoxy, $C_{3-6}$-cycloalkyl, $C_{3-6}$-cycloalkyl-oxy, $C_{3-6}$-cycloalkyl-$C_{1-3}$-alkoxy, 1,3-diazacyclohexan-2-on-1-yl, 2-oxo-1,3-oxazinan-3-yl, 3-oxomorpholino, 1,1-dioxo-[1,2,6]thiadiazinan-2-yl, phenyl, pyridyl, thienyl, furyl, $R^{12}$—CO—$(R^{13})N$ or $R^{12}$—$SO_2$—$(R^{13})N$,
wherein the above-mentioned groups may optionally be substituted independently of one another by one or more groups selected from among fluorine, chlorine, bromine, carboxy, cyano, $C_{1-4}$-alkyl, $C_{1-4}$-alkoxy, $C_{1-4}$-alkyl-S, $R^{15}$—CO, $R^{15}$—O—CO, $R^{14}$—$SO_2$—, $F_3C$, $HF_2C$, $FH_2C$, $F_3C$—O, $HF_2C$—O, $FH_2C$—O and $(R^{14})_2N$—CO, $R^{11}$ each independently of one another denote hydrogen, fluorine, chlorine or bromine $R^{12}$ denotes $C_{1-6}$-alkyl, heterocyclyl, phenyl, phenyl-$C_{1-3}$-alkyl, heteroaryl, heteroaryl-$C_{1-3}$-alkyl or $(R^{14})_2N$,
wherein by the above-mentioned heteroaryl groups are meant 5- or 6-membered aromatic heteroaryl groups which contain 1 or 2 heteroatoms selected from N, O and S, wherein a maximum of one O or S atom may be present, and
wherein the above-mentioned groups may optionally be substituted independently of one another by one or more groups selected from among fluorine, chlorine, bromine, hydroxy, cyano, $C_{1-3}$-alkyl, $C_{1-3}$-alkoxy, heterocyclyl, heterocyclyl-$C_{1-3}$-alkyl, hydroxy-$C_{1-3}$-alkyl, $(R^{14})_2N$ and $(R^{14})_2N$—$C_{1-3}$-alkyl, $R^{13}$ denotes hydrogen, $C_{1-6}$-alkyl, heterocyclyl, heterocyclyl-$C_{1-3}$-alkyl, $C_{3-6}$-cycloalkyl, $C_{3-6}$-cycloalkyl-$C_{1-3}$-alkyl, phenyl, phenyl-$C_{1-3}$-alkyl, heteroaryl and heteroaryl-$C_{1-3}$-alkyl,
wherein by the above-mentioned heteroaryl groups are meant 5- or 6-membered aromatic heteroaryl groups which contain 1 or 2 heteroatoms selected from N, O and S, wherein a maximum of one O or S atom may be present, and
wherein the above-mentioned groups may optionally be substituted independently of one another by one or more groups selected from among fluorine, chlorine, bromine, hydroxy, cyano, $C_{1-3}$-alkyl, $C_{1-3}$-alkoxy, hydroxy-$C_{1-3}$-alkyl, heterocyclyl, heterocyclyl-$C_{1-3}$-alkyl, $(R^{14})_2N$ and $(R^{14})_2N$—$C_{1-3}$-alkyl, or $R^{12}$ and $R^{13}$ together form a $C_{2-4}$-alkylene bridge, so that with the inclusion of the nitrogen atom linked to $R^{13}$ and the $SO_2$ or CO group linked to $R^{12}$ a heterocyclic ring is formed,
wherein one or two $CH_2$ groups of the $C_{2-4}$-alkylene bridge may be replaced independently of one another by O, S or $N(R^{14})$ in such a way that in each case two O, S or N atoms or an O and an S atom are not joined together directly, and
wherein the C atoms of the above-mentioned $C_{2-4}$-alkylene bridge may optionally be substituted by one or more fluorine atoms, and $R^{14}$ denotes hydrogen or $C_{1-6}$-alkyl,
wherein one or more hydrogen atoms of the $C_{1-6}$-alkyl group may be replaced by fluorine.

Also particularly preferred are those compounds according to the invention of formula (Ic),

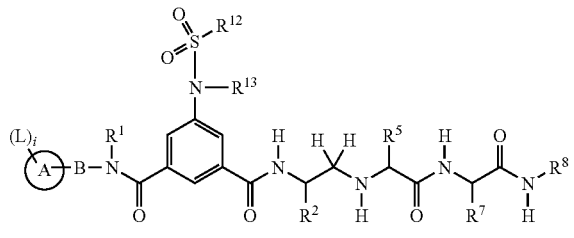

(Ic)

wherein
A denotes phenyl, thienyl, thiazolyl or pyridyl,
L denotes in each case independently of one another hydrogen, fluorine, chlorine, bromine, hydroxy, $C_{1-4}$-alkyl or $C_{1-4}$-alkoxy, wherein the above-mentioned groups may optionally be substituted by one or more fluorine atoms, and
i denotes 0, 1 or 2,
B denotes a $C_{1-2}$-alkylene bridge,
wherein the $C_{1-2}$-alkylene bridge may optionally be substituted by one or more $C_{1-4}$-alkyl groups, and
wherein two $C_{1-4}$-alkyl groups bound to the same carbon atom of the $C_{1-2}$-alkylene bridge may be joined together forming a cyclopropyl group, and
wherein one or more hydrogen atoms of the above-mentioned $C_{1-2}$-alkylene bridge or of the $C_{1-4}$-alkyl groups or of the cyclopropyl group formed therefrom may optionally be replaced by one or more fluorine atoms, $R^1$ denotes hydrogen or $C_{1-4}$-alkyl,
wherein the $C_{1-4}$-alkyl group may optionally be substituted by one or more fluorine atoms, $R^2$ denotes n-propyl, n-butyl, 2-propynyl, 2-butynyl, benzyl, 2-phenylethyl, pyridylmethyl, particularly 3-pyridylmethyl, furanylmethyl, thienylmethyl, particularly 3-thienylmethyl, or thiazolylmethyl, particularly 4-thiazolylmethyl, wherein thiazolylmethyl and 4-thiazolylmethyl are most particularly preferred, and
wherein the above-mentioned propyl, butyl, propynyl and butynyl groups may optionally be substituted by one or more fluorine atoms and the benzyl, 2-phenylethyl, furanylmethyl, thienylmethyl or thiazolylmethyl groups may optionally be substituted independently of one another by one or more groups selected from among fluorine, chlorine, bromine, methyl, $F_3C$, $HF_2C$, $FH_2C$ and $H_2N$, $R^8$ denotes hydrogen, $C_{1-6}$-alkyl, $C_{3-6}$-cycloalkyl, $C_{3-6}$-cycloalkyl-$C_{1-3}$-alkyl, phenyl-$C_{1-3}$-alkyl and tetrahydropyranyl-$C_{1-3}$-alkyl, preferably 4-tetrahydropyranylmethyl,
wherein the above-mentioned groups may optionally be substituted independently of one another by one or more groups selected from among fluorine, chlorine, bromine, pyrrolidin-1-ylmethyl, hydroxy, cyano, $C_{1-3}$-alkyl, $C_{1-3}$-alkoxy, $C_{1-3}$-alkyl-S, hydroxy-$C_{1-3}$-alkyl, $(R^{14})_2N$, $(R^{14})_2N$—$C_{1-3}$-alkyl, $(R^{14})_2N$—CO—$N(R^{14})$— and $(R^{14})_2N$—$SO_2$—, $R^5$, $R^7$ each independently of one another denote $C_{1-4}$-alkyl or cyclopropyl, wherein one or more hydrogen atoms of the above-mentioned groups may optionally be replaced by fluorine atoms, $R^{12}$ denotes $C_{1-4}$-alkyl, particularly methyl or ethyl, morpholinyl, phenyl, benzyl, pyridyl, particularly 3-pyridyl or $(CH_3)_2N$, wherein the above-mentioned groups may optionally be substituted independently of one another by one or more groups selected from among fluorine, chlorine and bromine, $R^{13}$ denotes hydrogen, methyl, ethyl, phenyl or 4-fluorophenyl, wherein the above-mentioned groups may optionally be substituted independently of one another by one or more groups selected from among fluorine, chlorine and bromine, or $R^{12}$ and $R^{13}$ together form, with the inclusion of the nitrogen atom linked to $R^{13}$ and the $SO_2$ or CO group linked to $R^{12}$, a heterocyclic ring of formulae (IIa), (IIb), (IIc) or (IId)

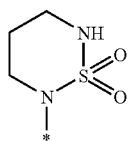
(IIa)

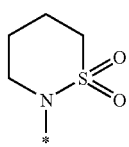
(IIb)

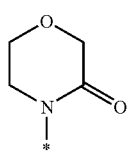
(IIc)

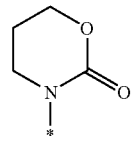
(IId)

and $R^{14}$ denotes hydrogen or $C_{1-6}$-alkyl, wherein one or more hydrogen atoms of the $C_{1-6}$-alkyl group may be replaced by fluorine.

Also particularly preferred are those compounds according to the invention of formulae (Id) or (Ie),

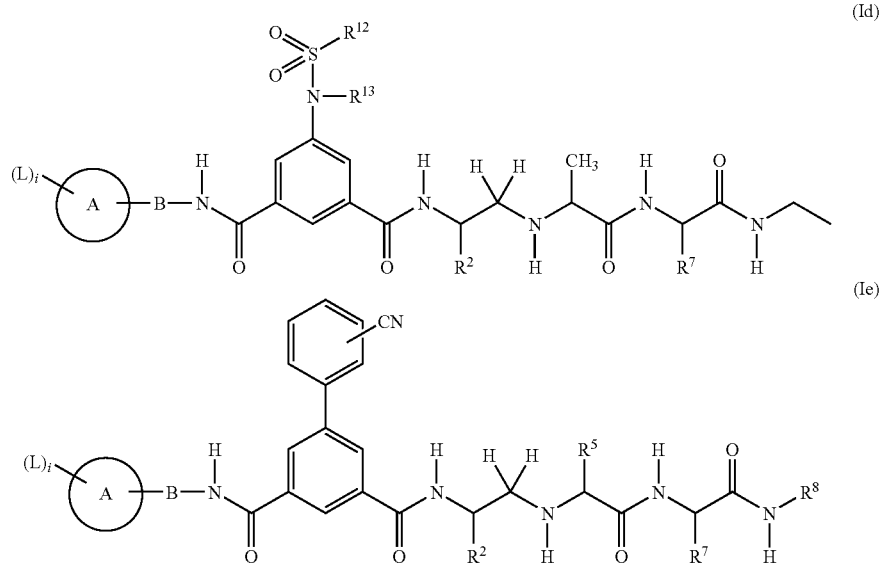

wherein, where applicable

A denotes phenyl, thienyl, preferably 3-thienyl, thiazolyl, particularly 2-thiazolyl, or pyridyl, preferably 2-pyridyl, L denotes hydrogen, fluorine, chlorine, trifluoromethyl, trifluoromethoxy, methyl and methoxy, i denotes 0 or 1, B is selected from among

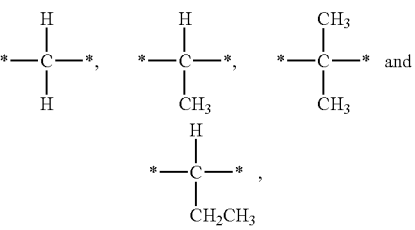

wherein one or more hydrogen atoms may optionally be replaced by fluorine, $R^2$ denotes n-propyl, n-butyl, 2-propynyl, 2-butynyl, benzyl, 3,5-difluorobenzyl, 2-phenylethyl, pyridylmethyl, particularly 3-pyridylmethyl, furanylmethyl, thienylmethyl, particularly 3-thienylmethyl, or thiazolylmethyl, particularly 4-thiazolylmethyl, wherein thiazolylmethyl or 4-thiazolylmethyl is most particularly preferred, wherein the above-mentioned propyl, butyl, propynyl and butynyl groups may optionally be substituted by one or more fluorine atoms and the benzyl, 2-phenylethyl, furanylmethyl, thienylmethyl or thiazolylmethyl groups may optionally be substituted independently of one another by one or more groups selected from among fluorine, chlorine, bromine, methyl, $F_3C$, $HF_2C$, $FH_2C$ and $H_2N$, $R^8$ denotes hydrogen, $C_{1-6}$-alkyl, $C_{3-6}$-cycloalkyl, $C_{3-6}$-cycloalkyl-$C_{1-3}$-alkyl, phenyl-$C_{1-3}$-alkyl and tetrahydropyranyl-$C_{1-3}$-alkyl, preferably 4-tetrahydropyranylmethyl, wherein the above-mentioned groups may optionally be substituted independently of one another by one or more groups selected from among fluorine, chlorine, bromine, pyrrolidin-1-ylmethyl, hydroxy, cyano, $C_{1-3}$-alkyl, $C_{1-3}$-alkoxy, $C_{1-3}$-alkyl-S, hydroxy-$C_{1-3}$-alkyl, $(R^{14})_2N$, $(R^{14})_2N$—$C_{1-3}$-alkyl, $(R^{14})_2N$—CO—$N(R^{14})$— and $(R^{14})_2N$—$SO_2$—, $R^5$ denotes $C_{1-4}$-alkyl or cyclopropyl,
wherein one or more hydrogen atoms of the above-mentioned groups may optionally be replaced by fluorine atoms, $R^7$ denotes $C_{1-4}$-alkyl, preferably ethyl or isopropyl, or cyclopropyl,
wherein one or more hydrogen atoms of the above-mentioned groups may optionally be replaced by fluorine atoms, $R^{12}$ denotes $C_{1-4}$-alkyl, particularly methyl or ethyl, morpholinyl, phenyl, benzyl, pyridyl, particularly 3-pyridyl or $(CH_3)_2N$,
wherein the above-mentioned groups may optionally be substituted independently of one another by one or more groups selected from among fluorine, chlorine and bromine, $R^{13}$ denotes hydrogen, methyl, ethyl, phenyl or 4-fluorophenyl,
wherein the above-mentioned groups may optionally be substituted independently of one another by one or more groups selected from among fluorine, chlorine and bromine, or $R^{12}$ and $R^{13}$ together form, with the inclusion of the nitrogen atom bound to $R^{13}$ and the $SO_2$ or CO group bound to $R^{12}$, a heterocyclic ring of formulae (IIa), (IIb), (IIc) or (IId)

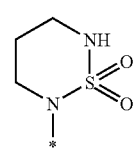

(IIa)

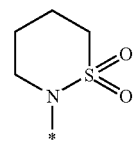

(IIb)

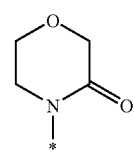

(IIc)

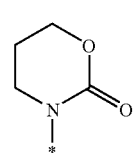

(IId)

Particularly preferred individual compounds are selected from among:

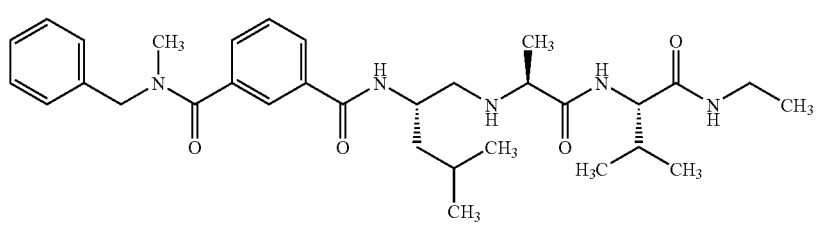

(1)

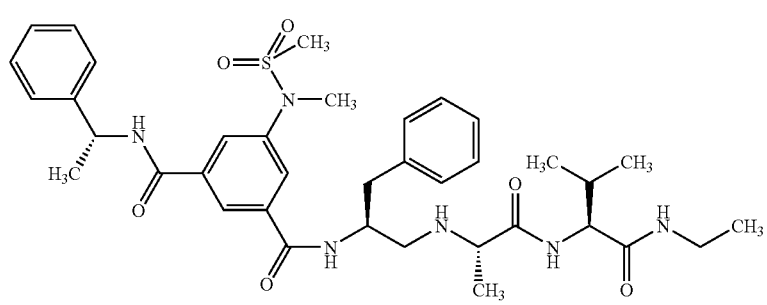

(2)

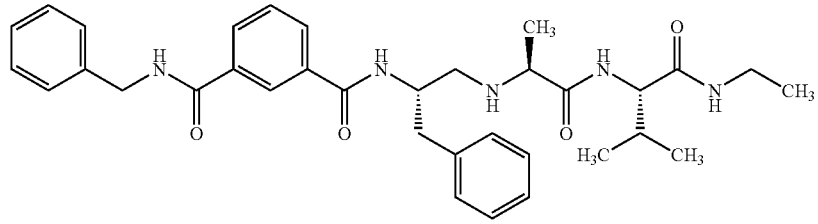
(3)
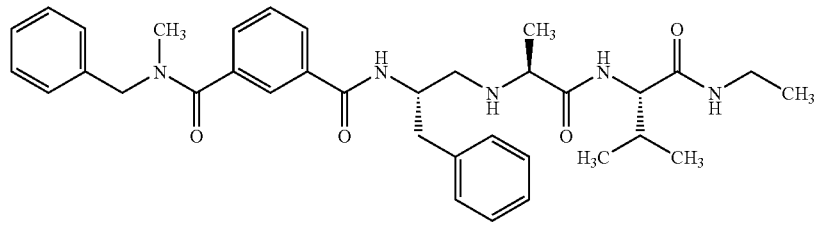
(4)
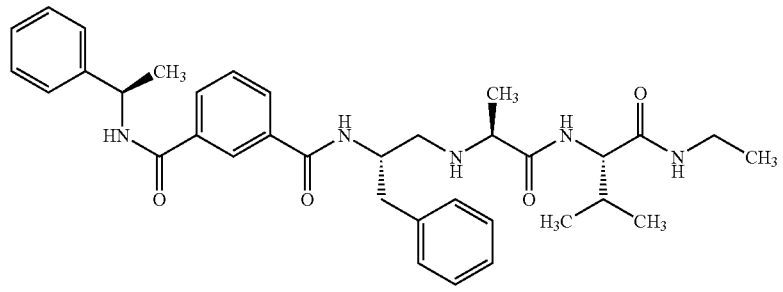
(5)
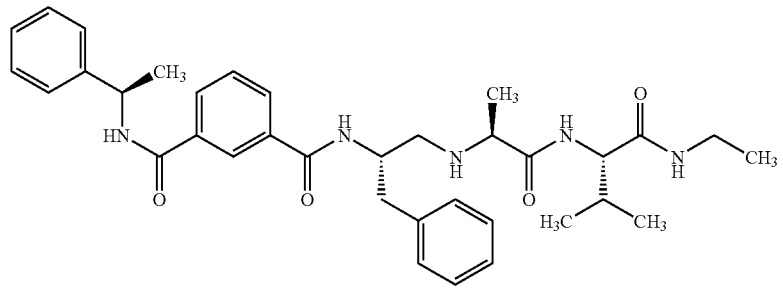
(6)
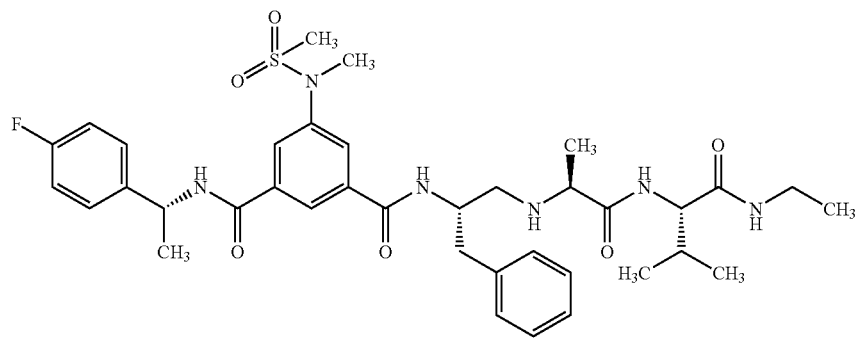
(7)

-continued
(8)
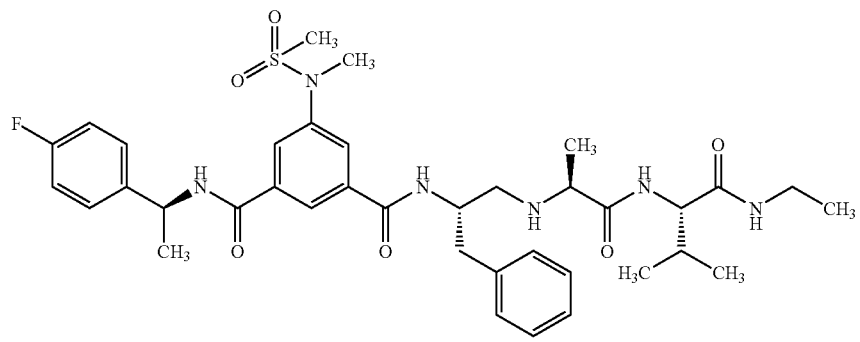
(9)
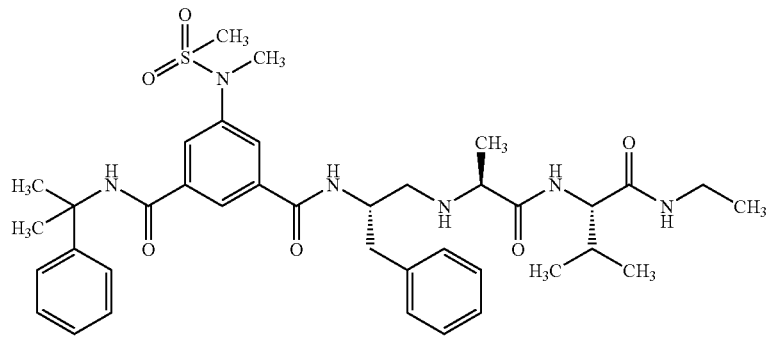
(10)
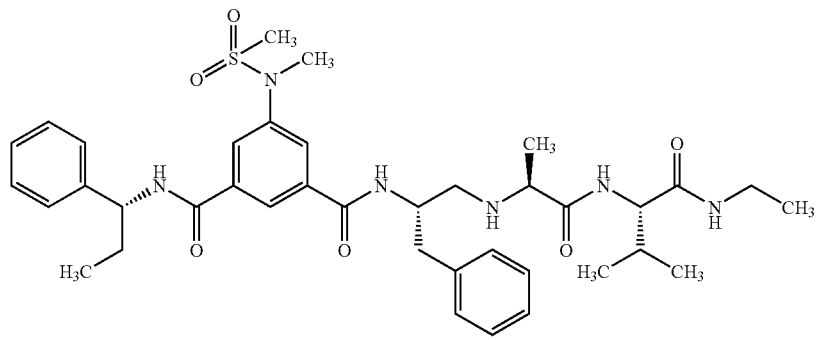
(11)
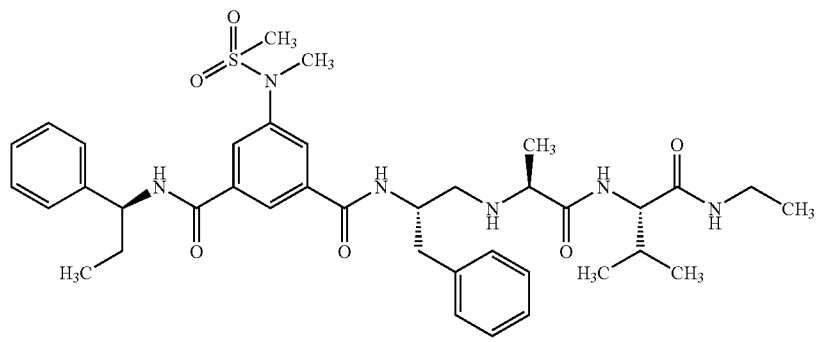

-continued
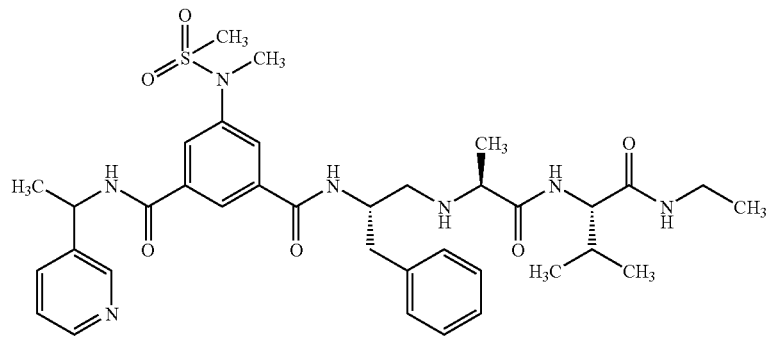
(12)
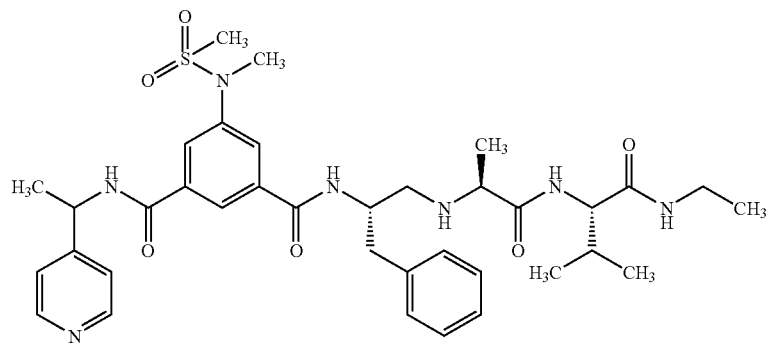
(13)
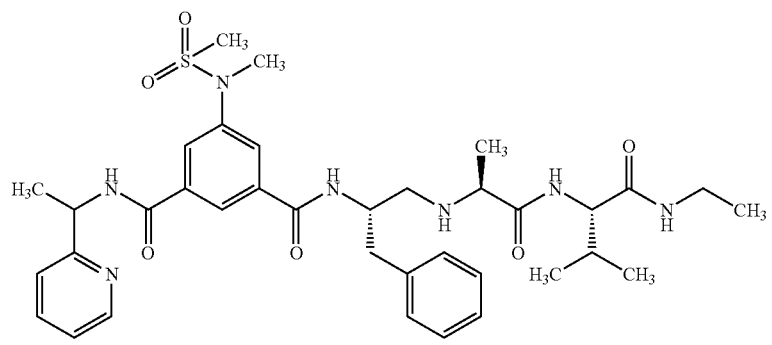
(14)
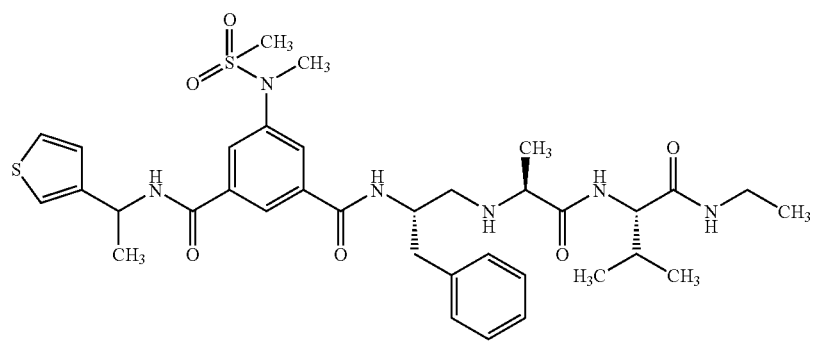
(15)

-continued
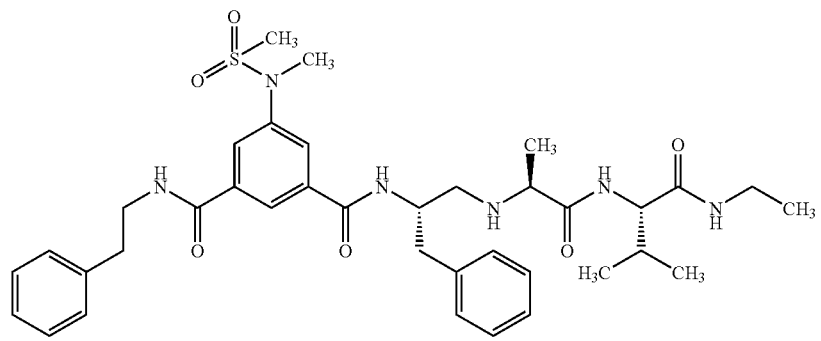
(16)
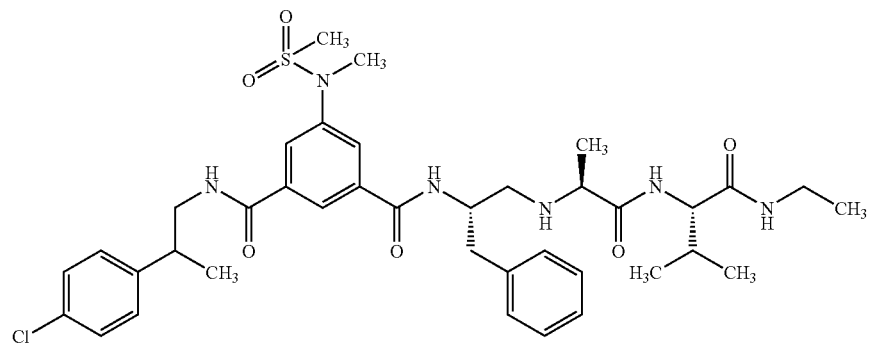
(17)
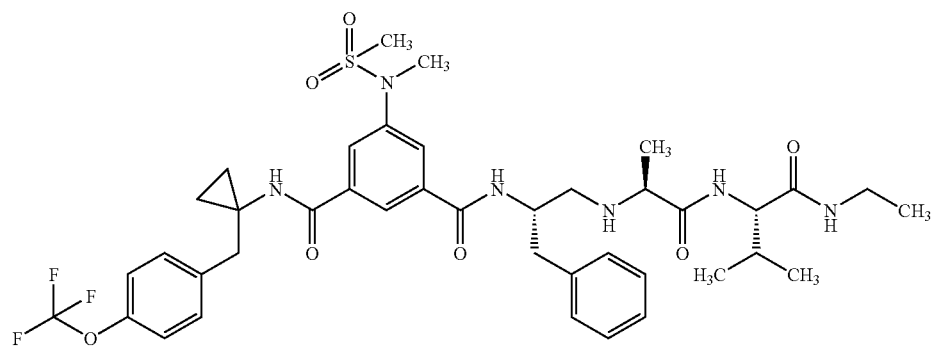
(18)
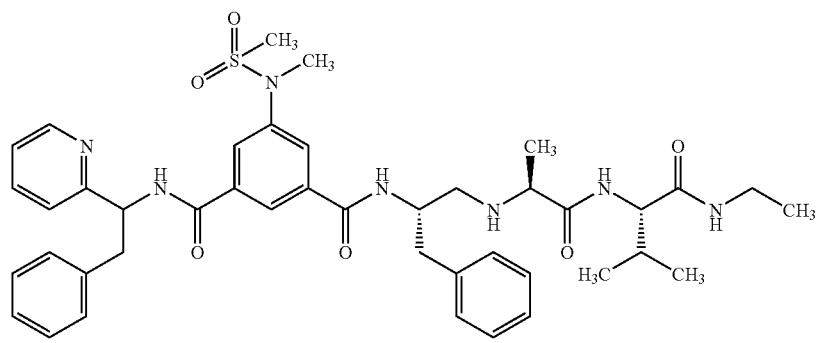
(19)

-continued
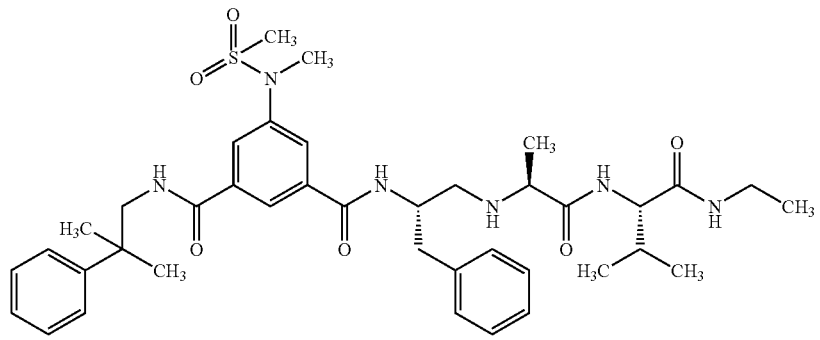
(20)
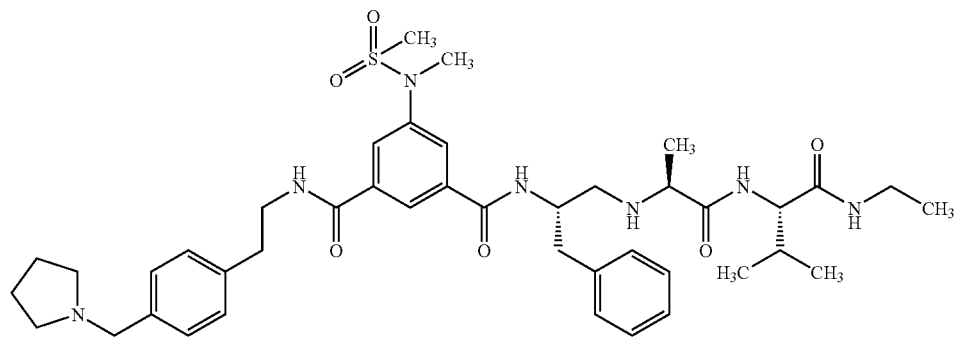
(21)
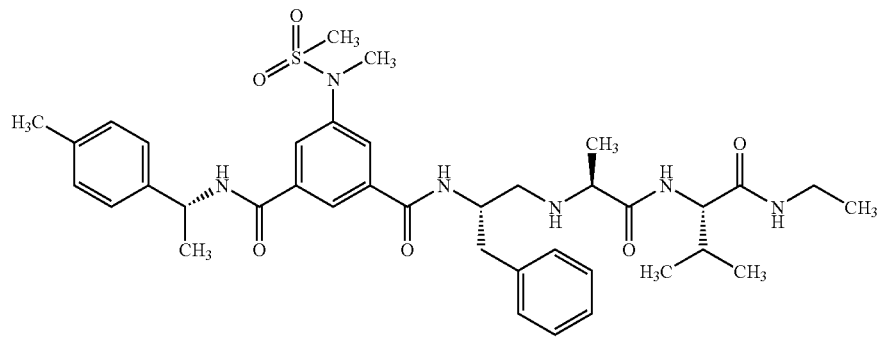
(22)
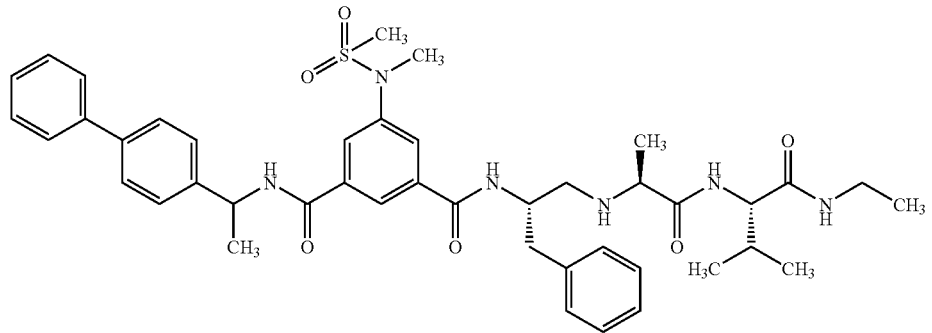
(23)

(24)
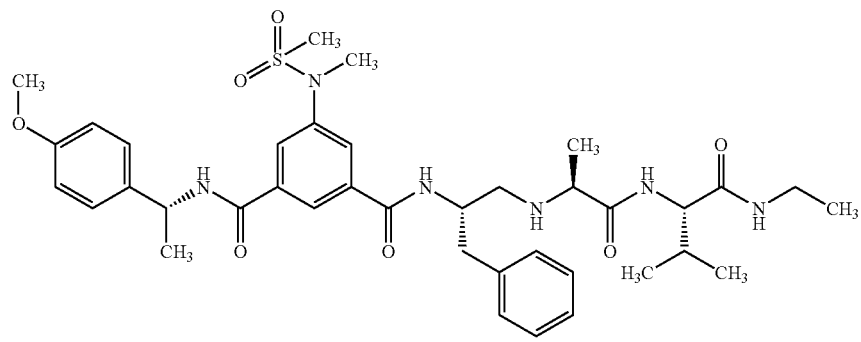
(25)
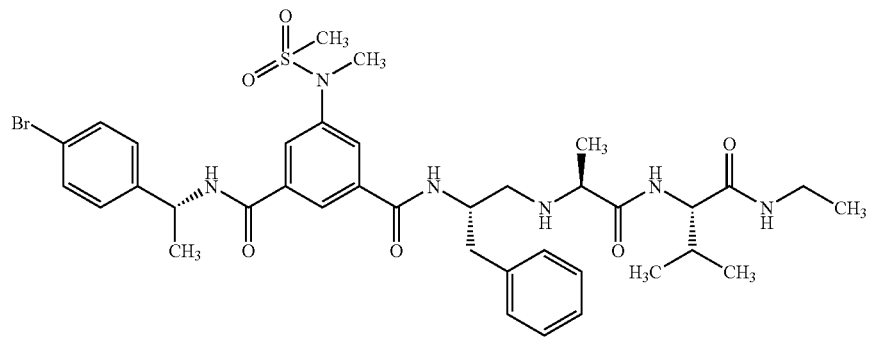
(26)
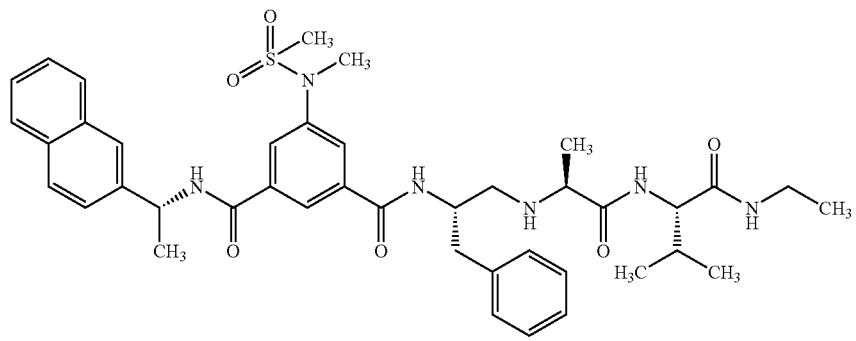
(27)
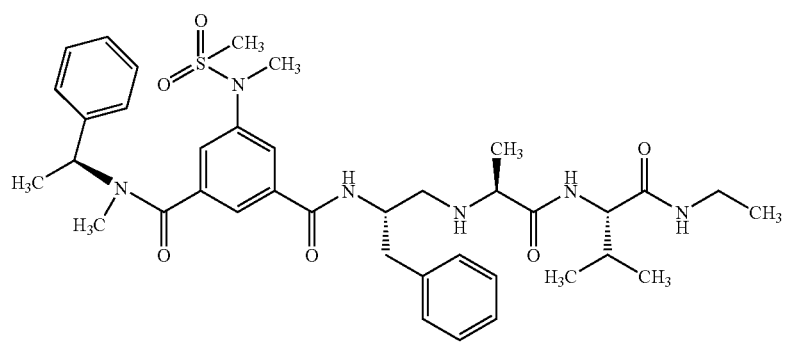

(28)
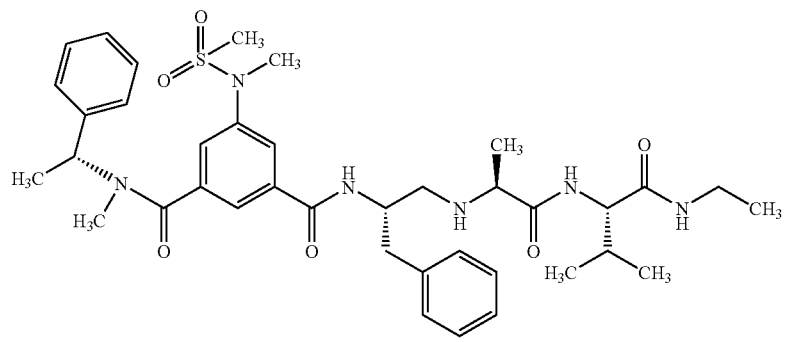
(29)
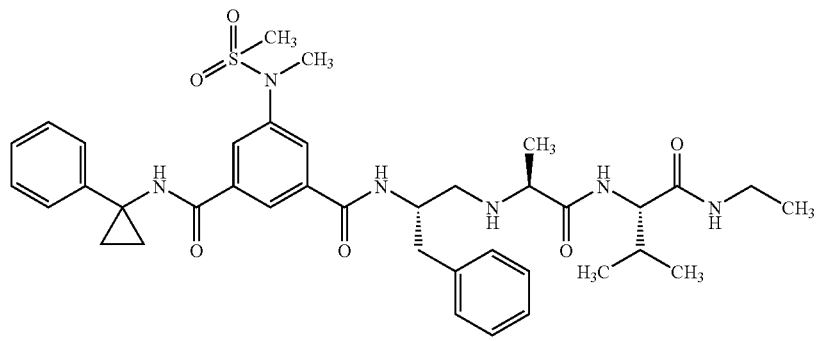
(30)
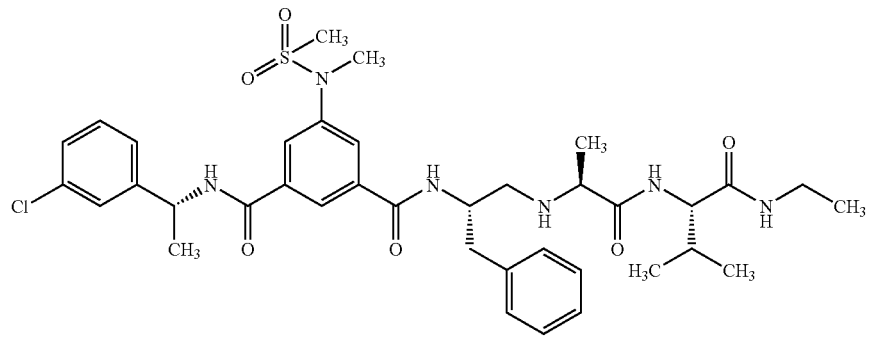
(31)
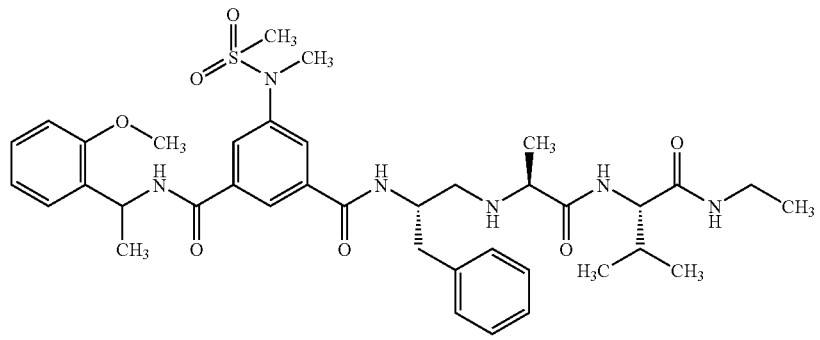

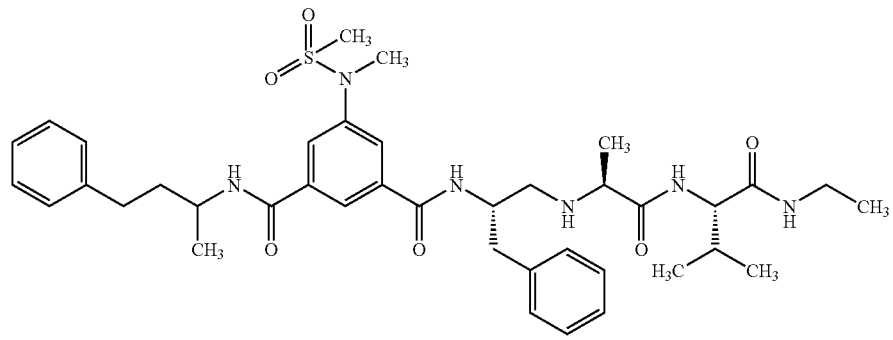
(32)
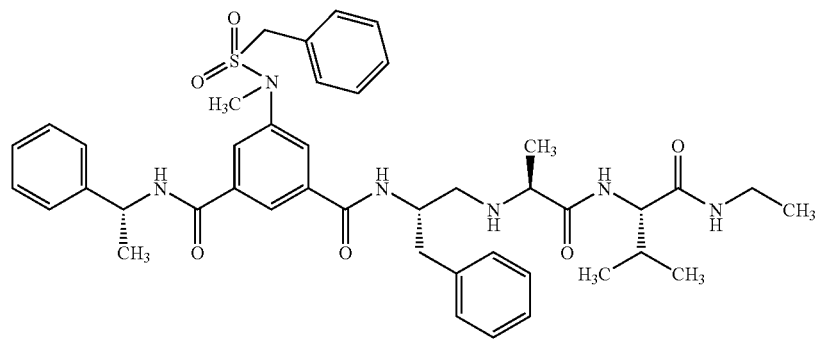
(33)
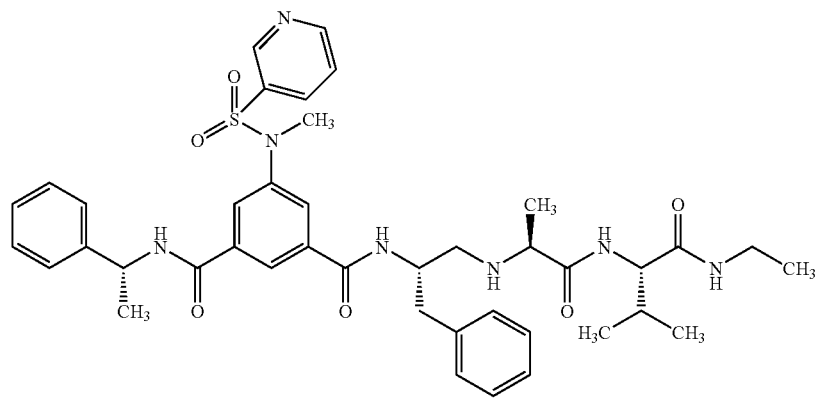
(34)
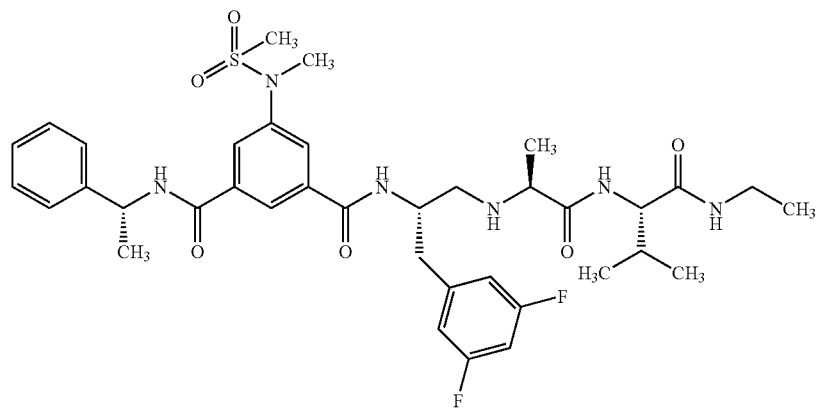
(35)

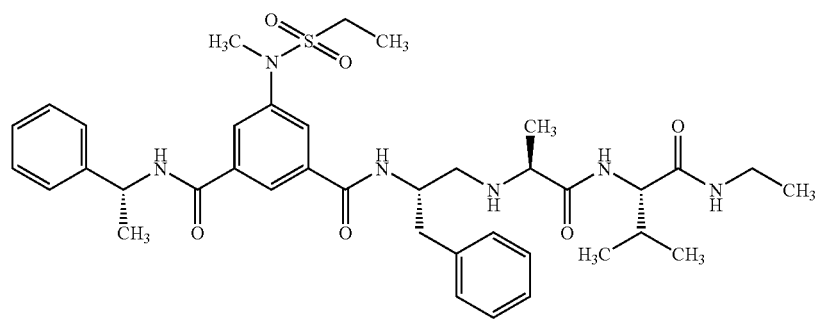
(36)
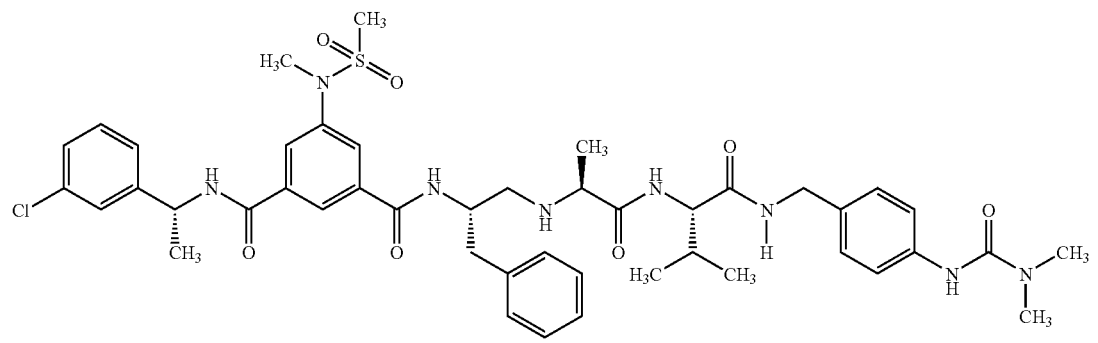
(37)
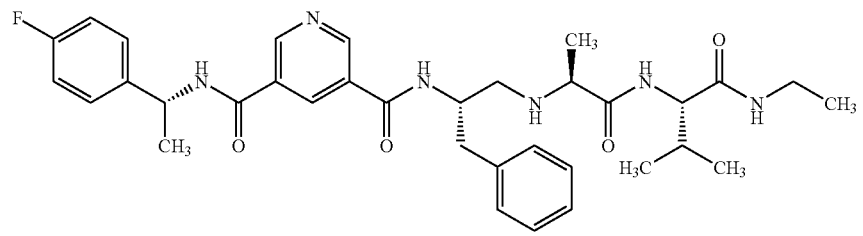
(38)
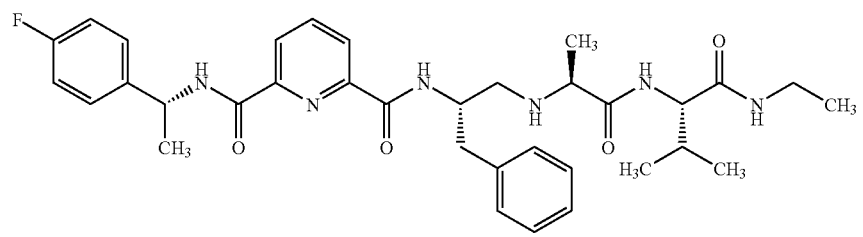
(39)
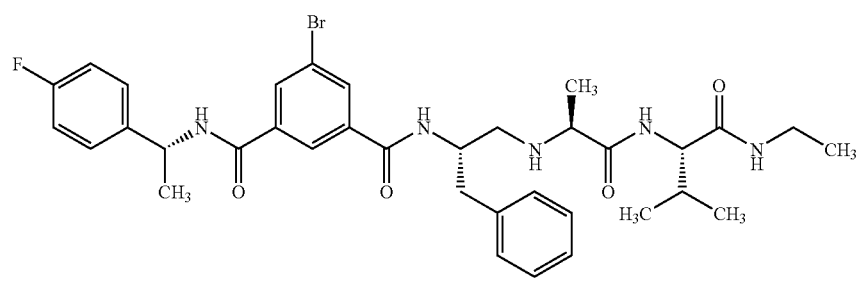
(40)

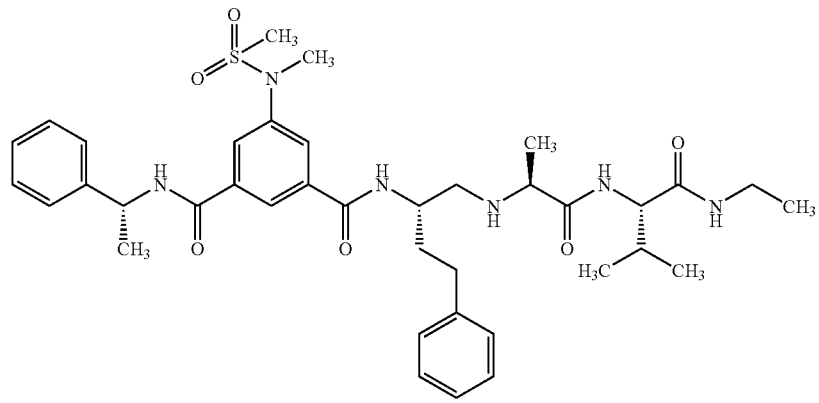
(41)
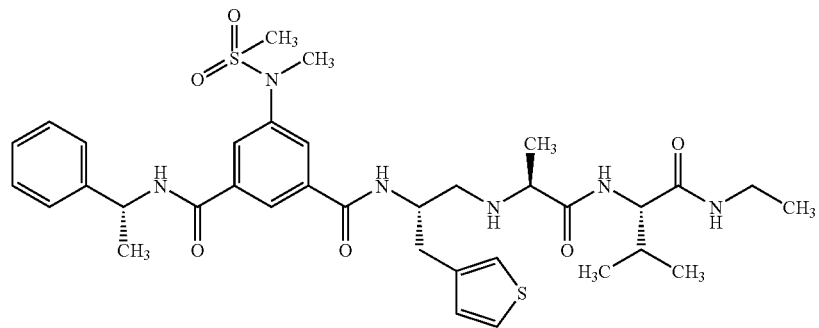
(42)
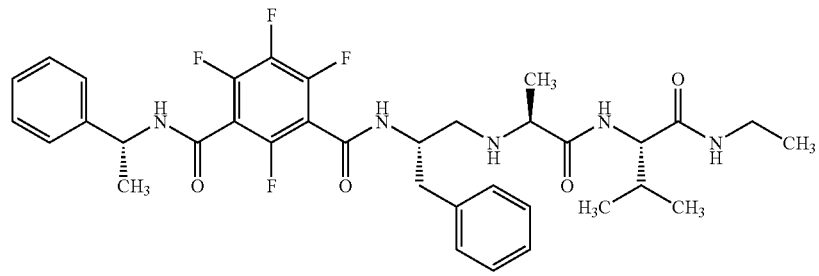
(43)
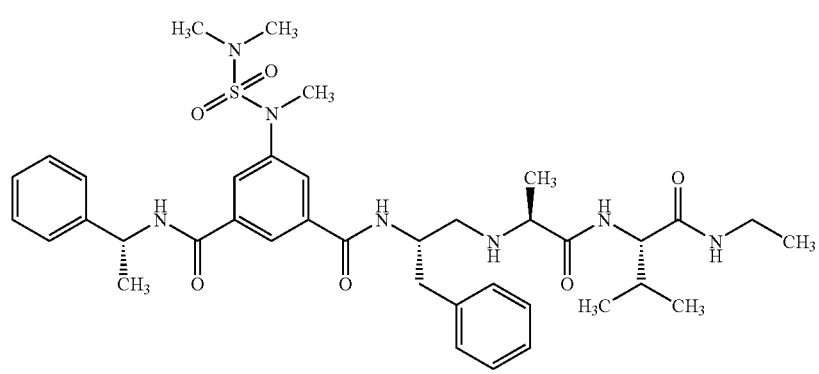
(44)

-continued
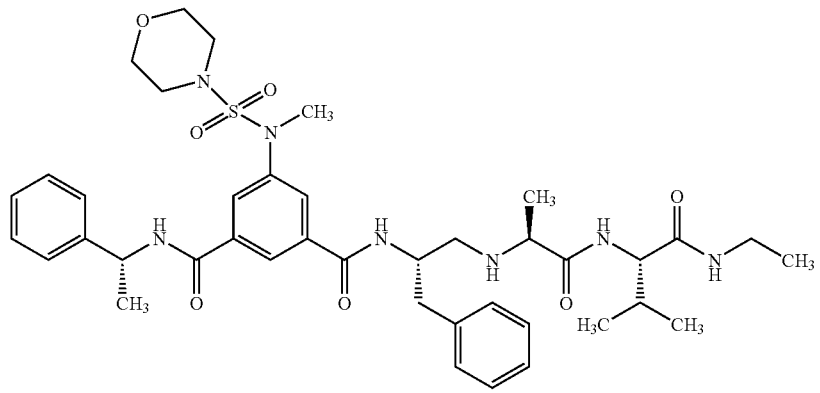
(45)
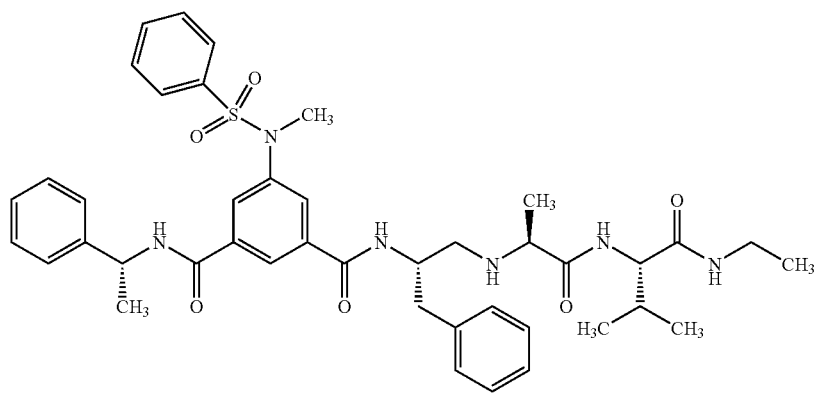
(46)
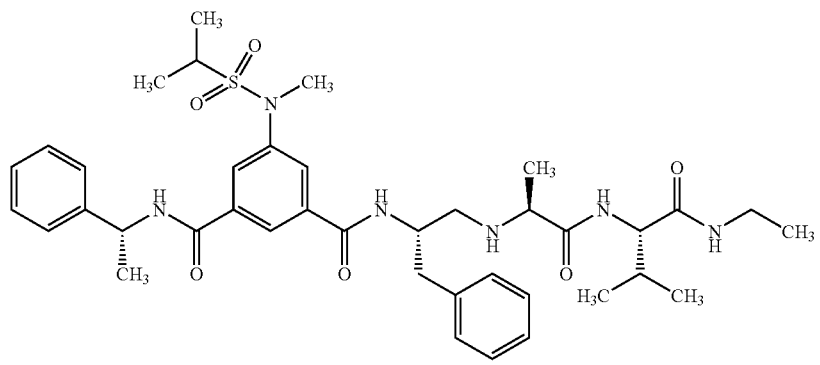
(47)
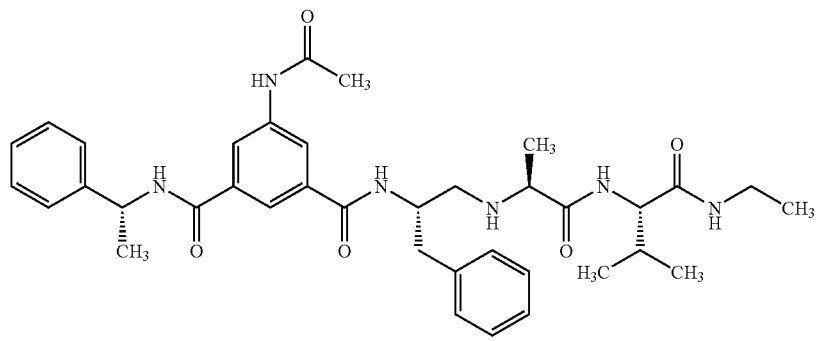
(48)

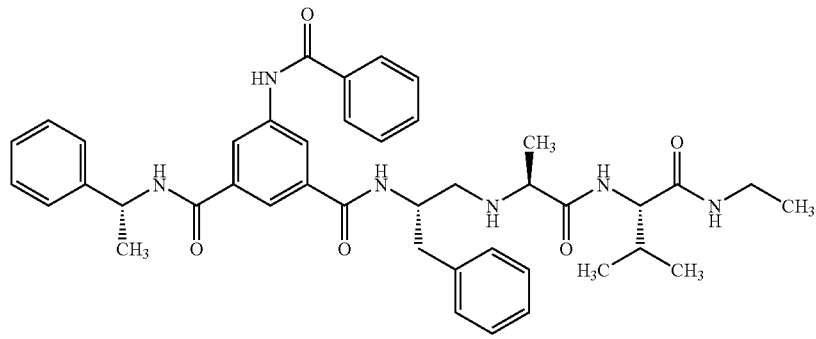
(49)
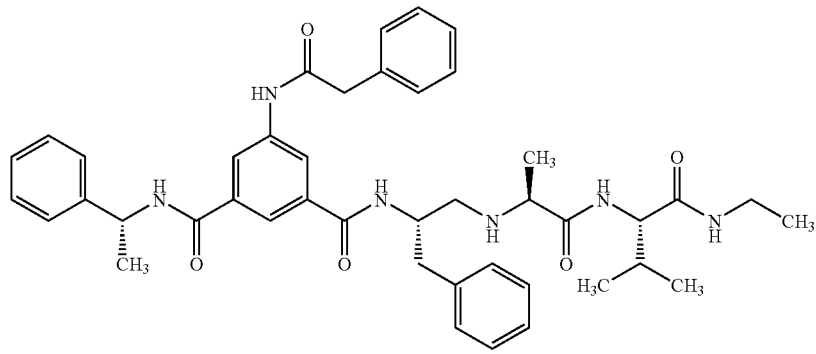
(50)
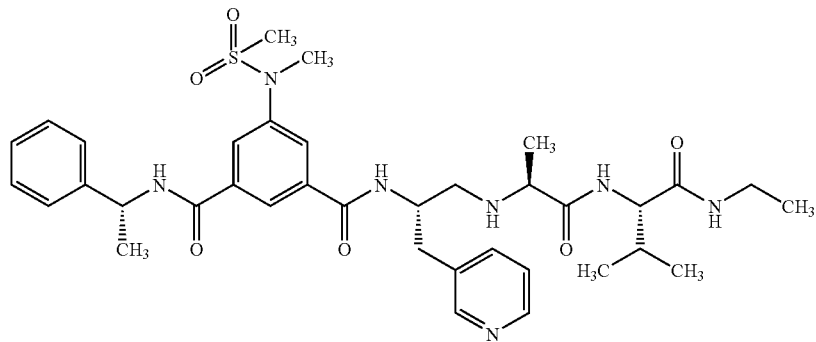
(51)
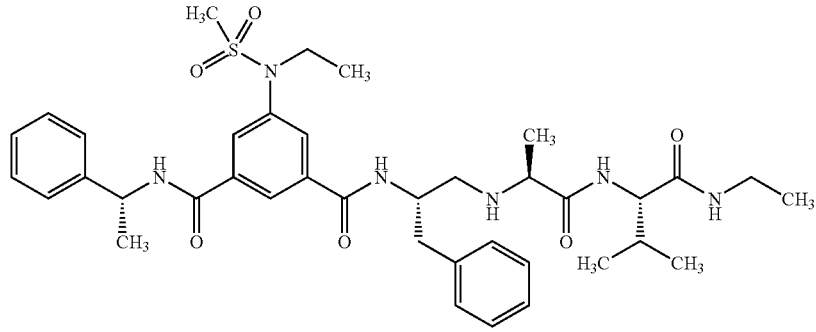
(52)

(53)
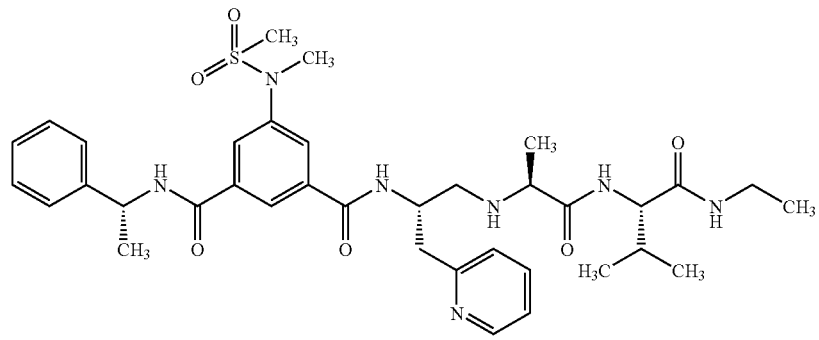
(54)
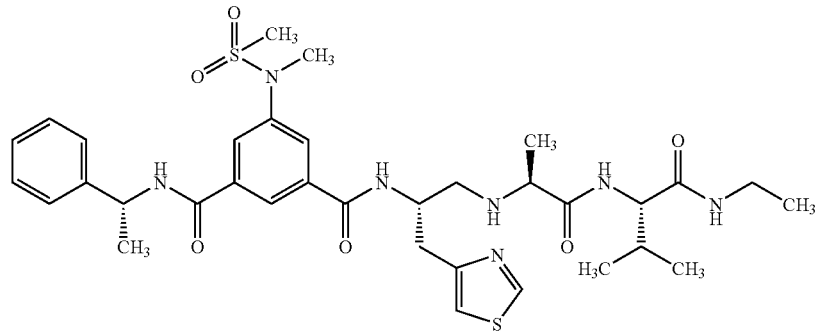
(55)
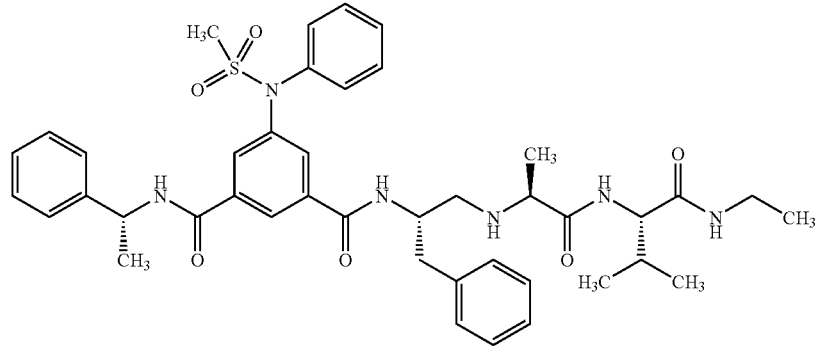
(56)
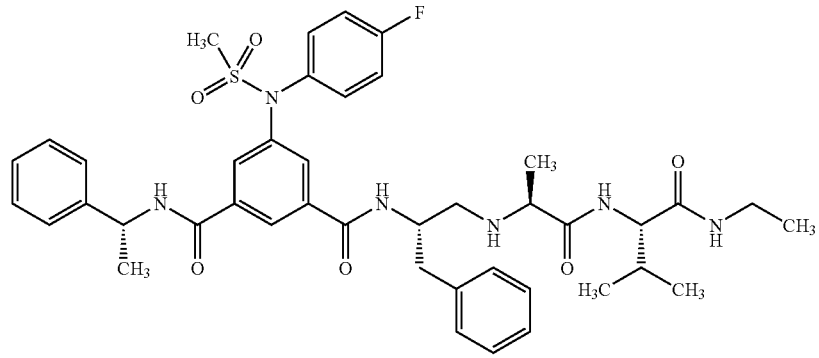

(57)
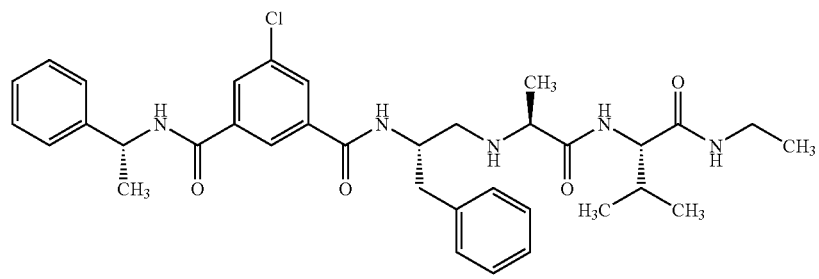
(58)
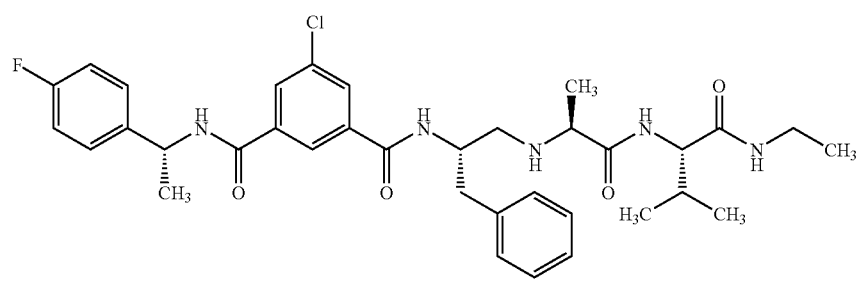
(59)
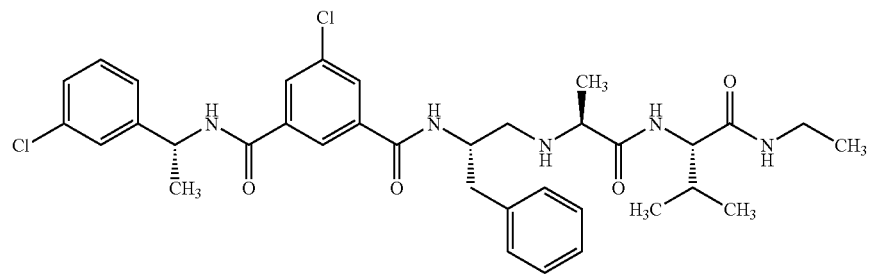
(60)
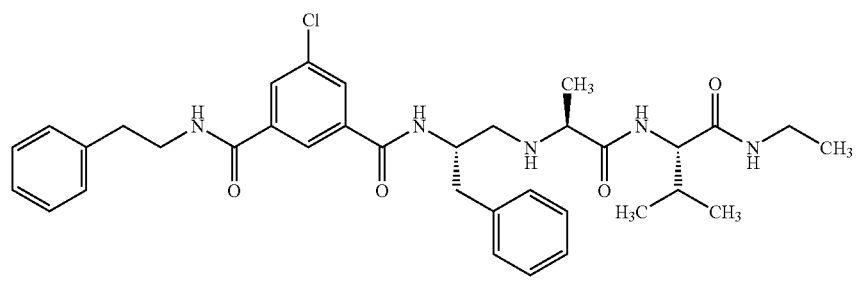
(61)
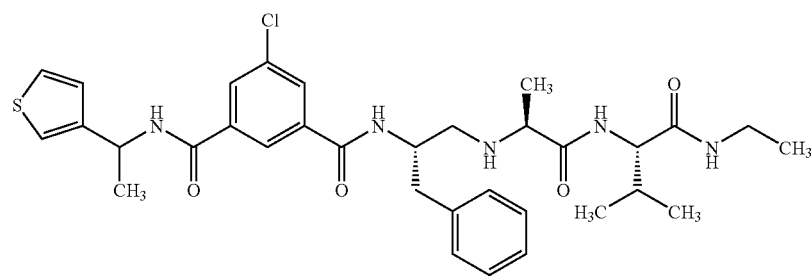

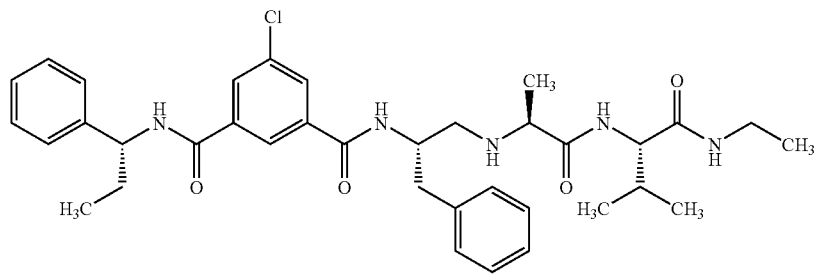
(62)
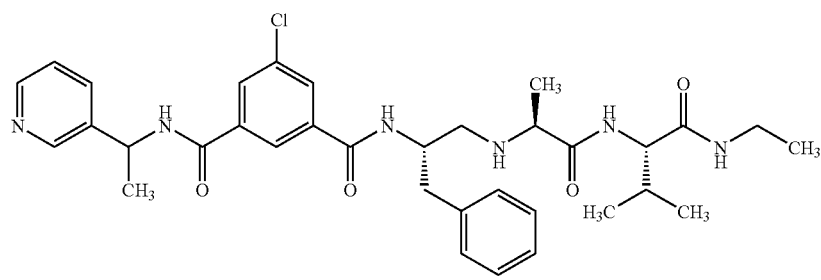
(63)
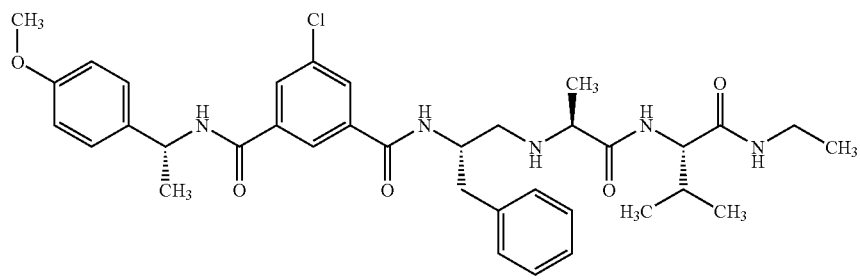
(64)
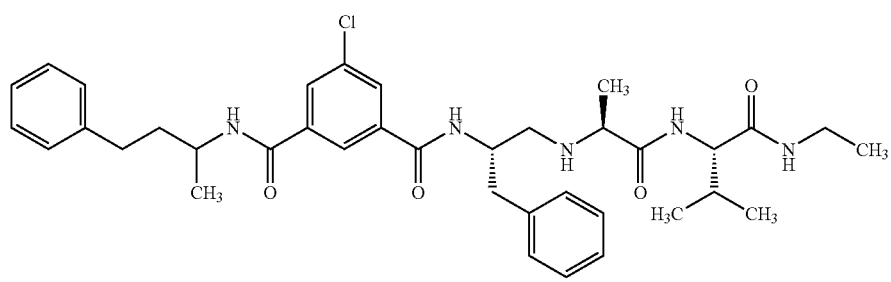
(65)
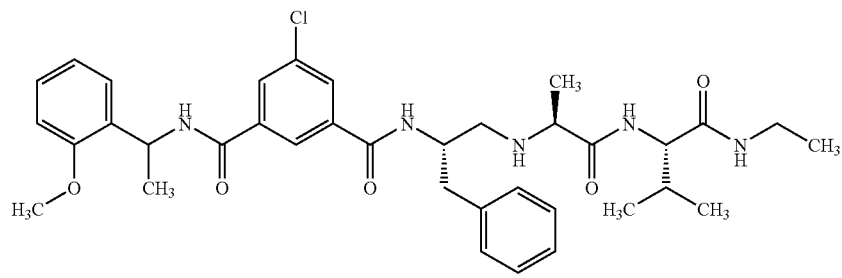
(66)

(67)
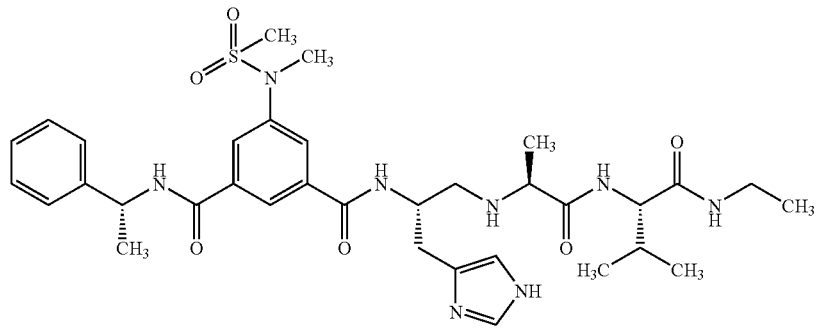
(68)
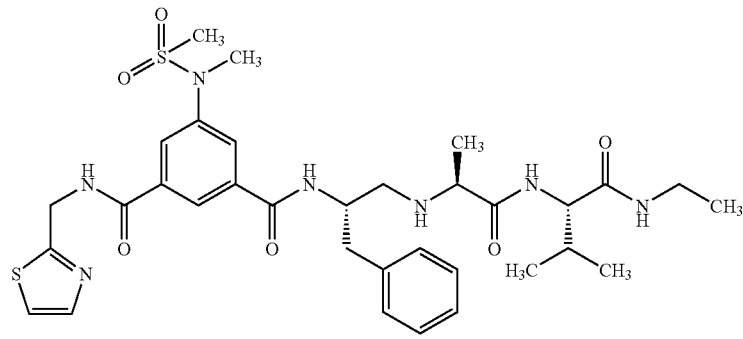
(69)
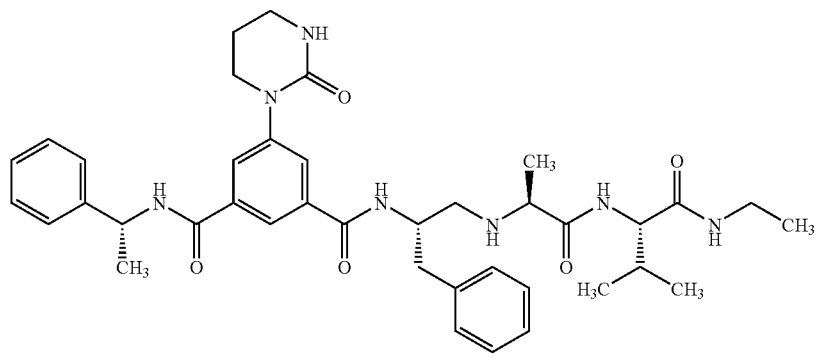
(70)
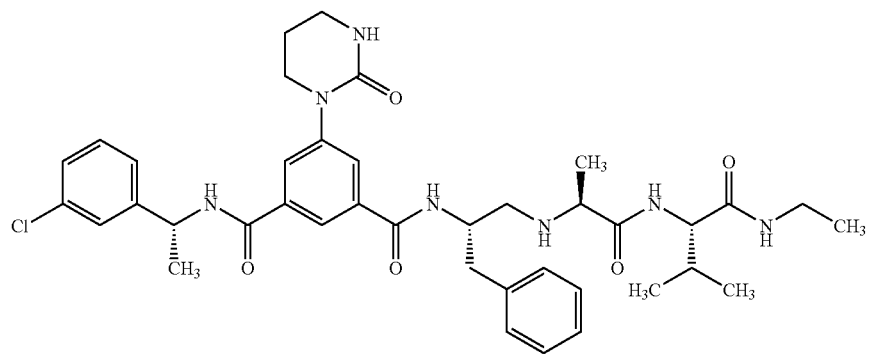

-continued
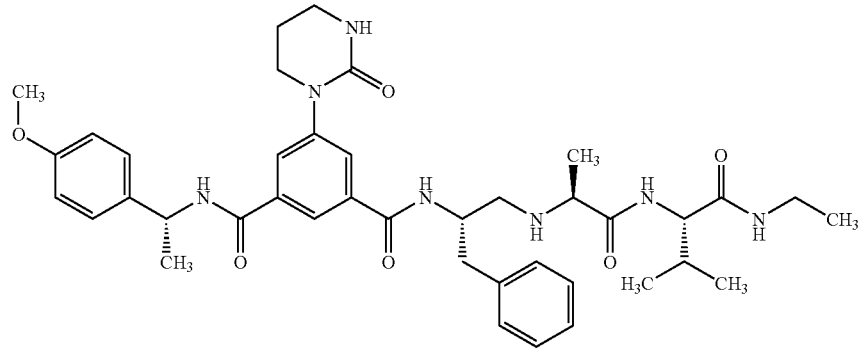
(71)
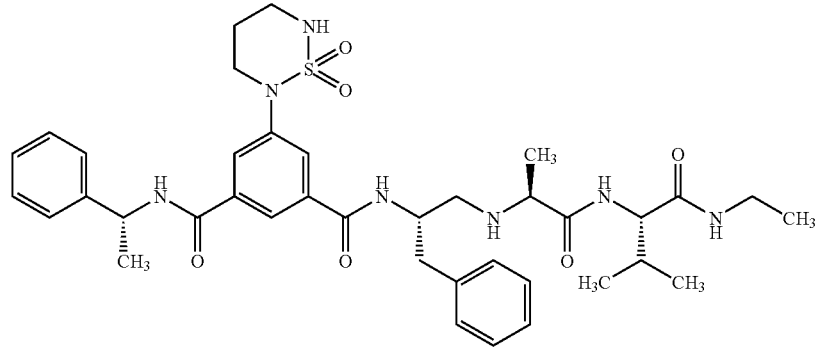
(72)
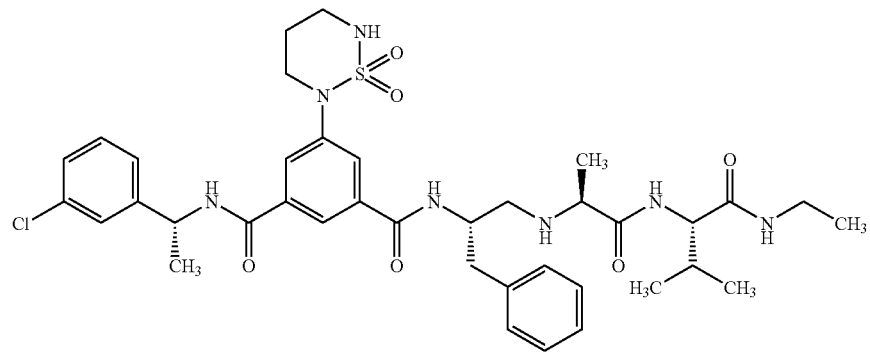
(73)
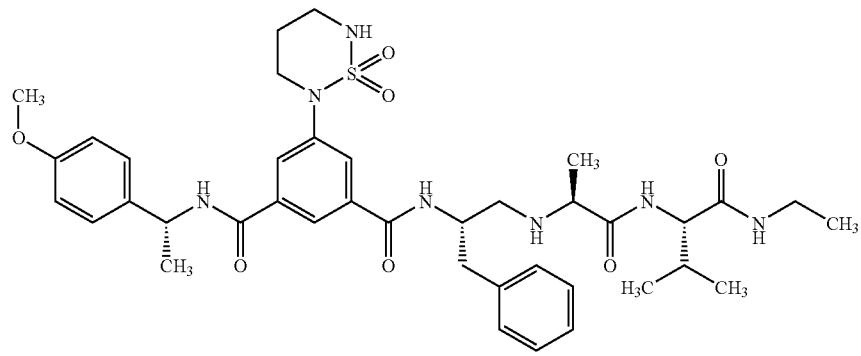
(74)

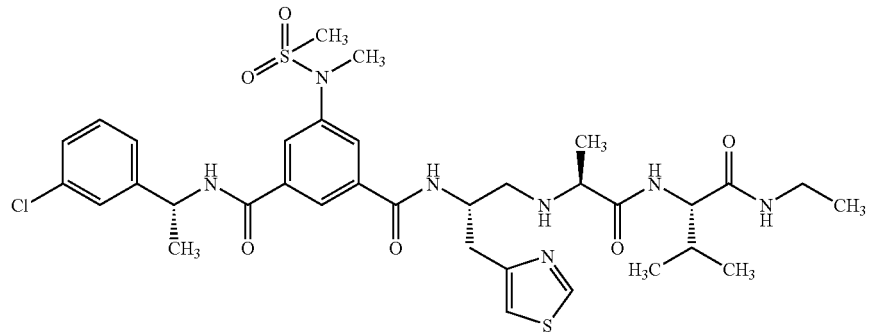
(75)
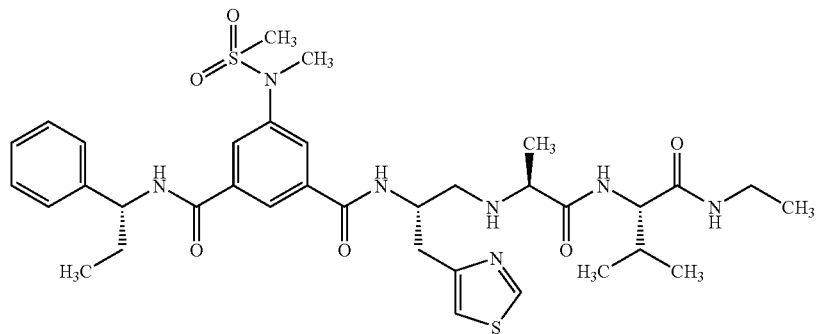
(76)
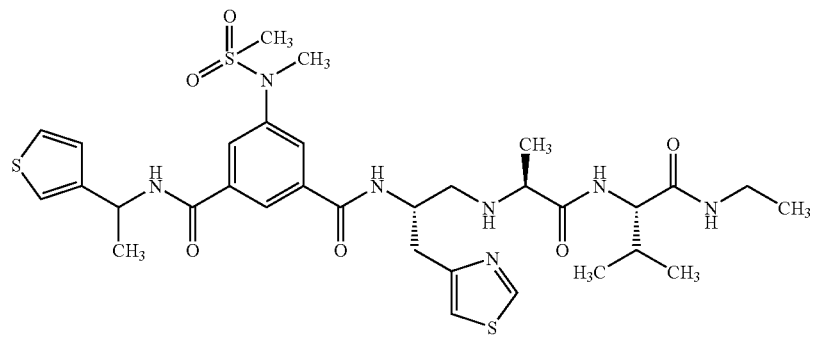
(77)
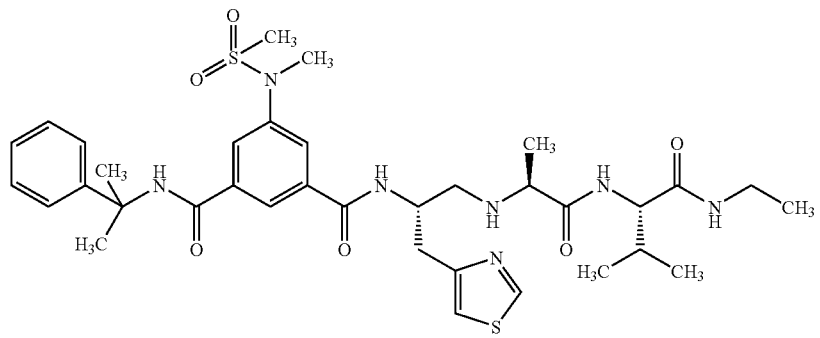
(78)

-continued
(79)
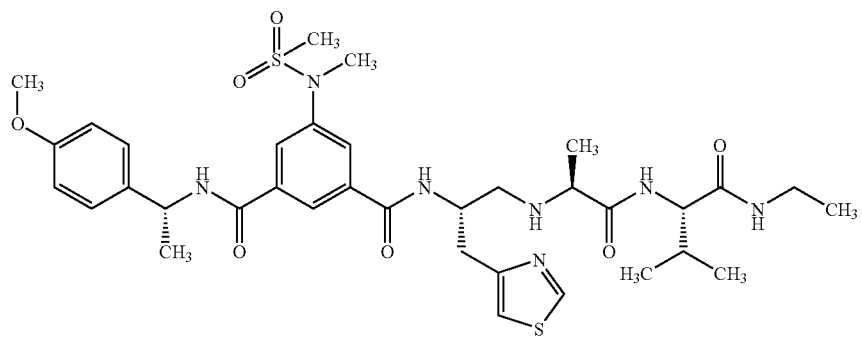
(80)
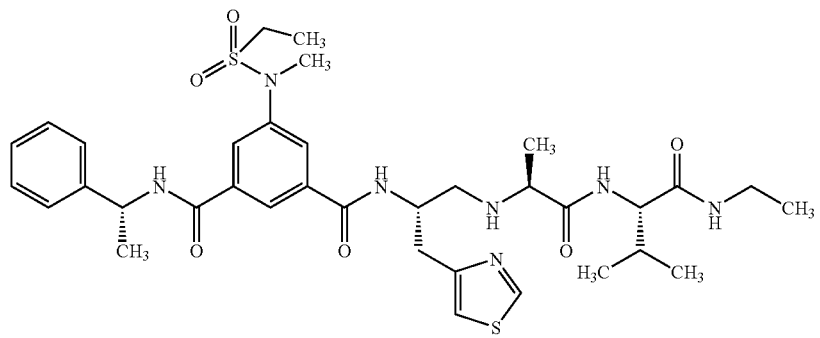
(81)
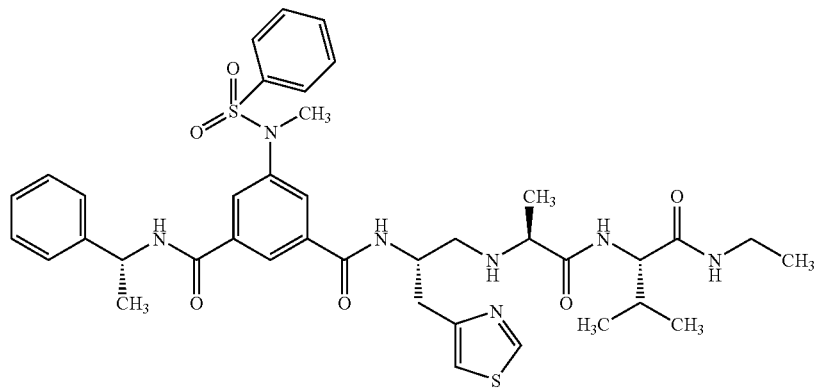
(82)
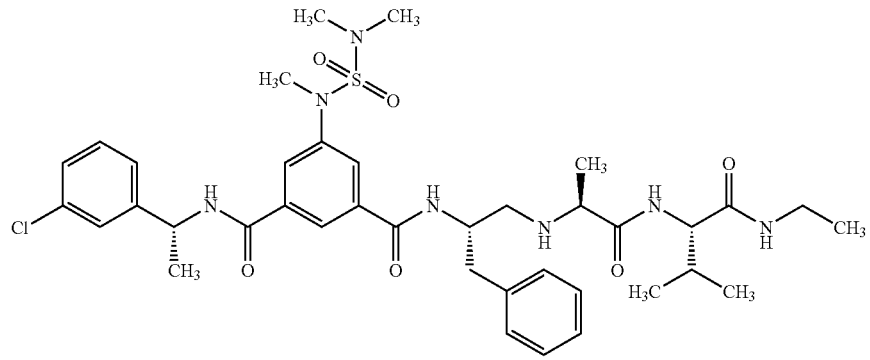

-continued
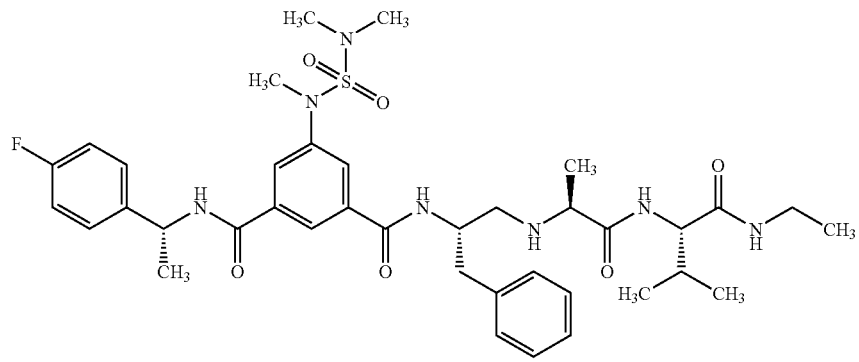
(83)
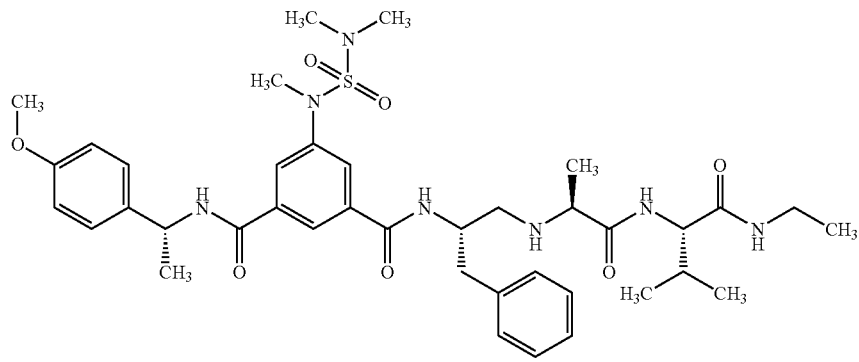
(84)
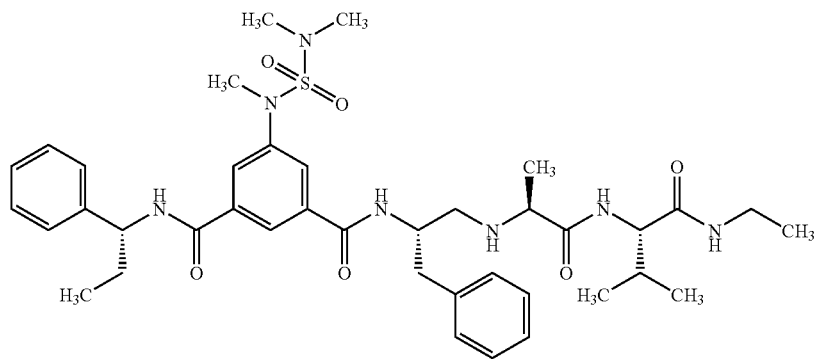
(85)
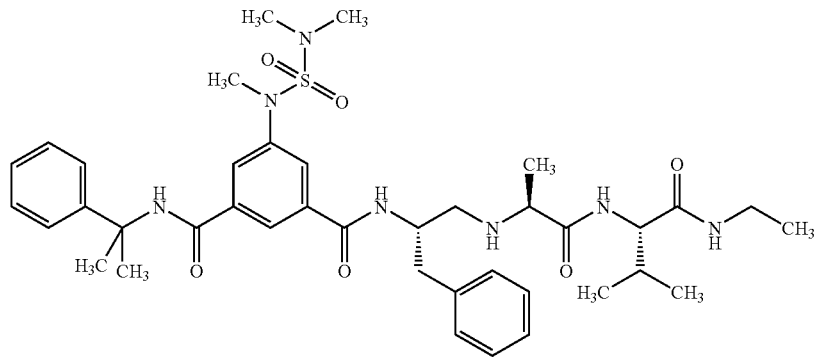
(86)

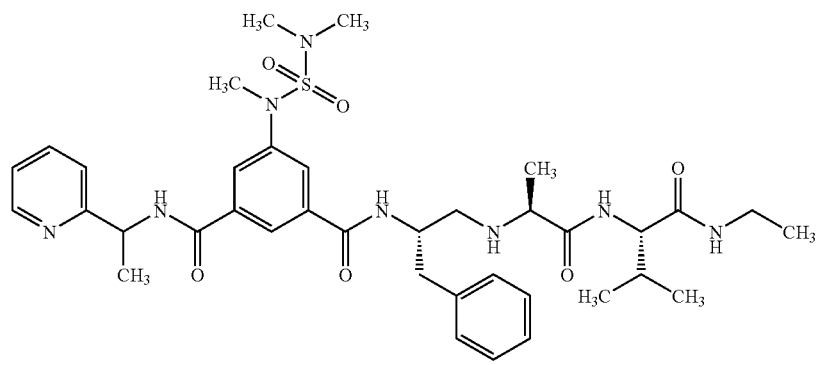
(87)
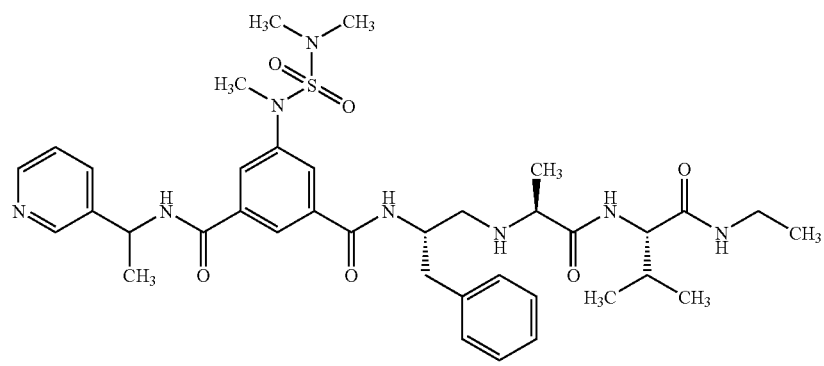
(88)
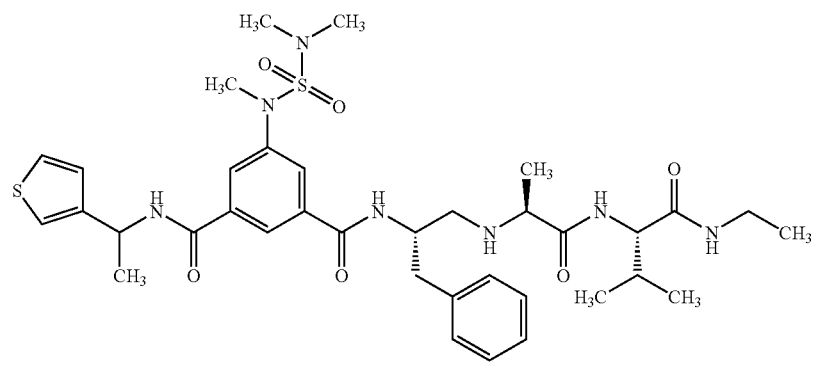
(89)
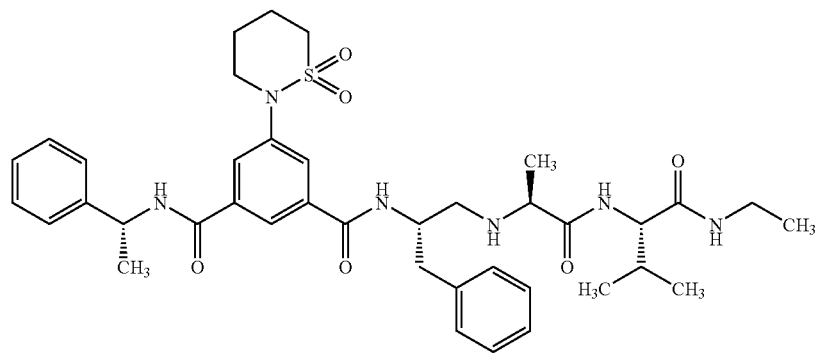
(90)

-continued
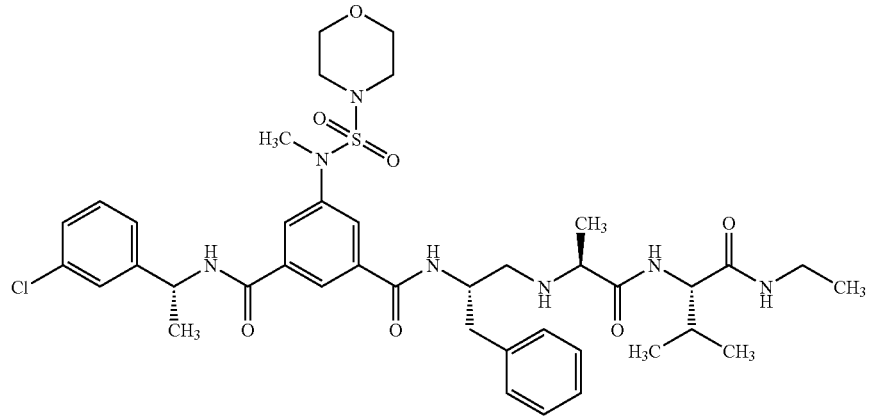
(91)
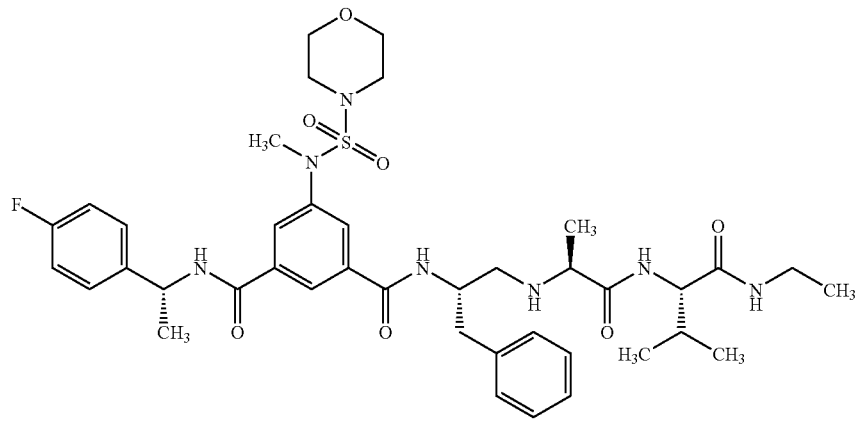
(92)
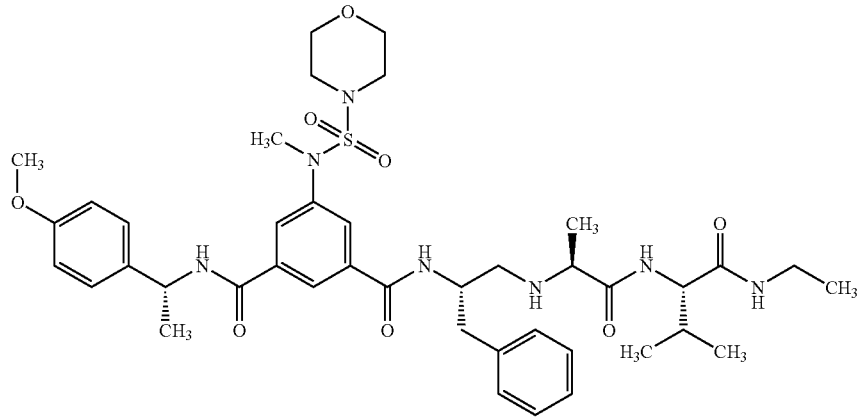
(93)

(94)
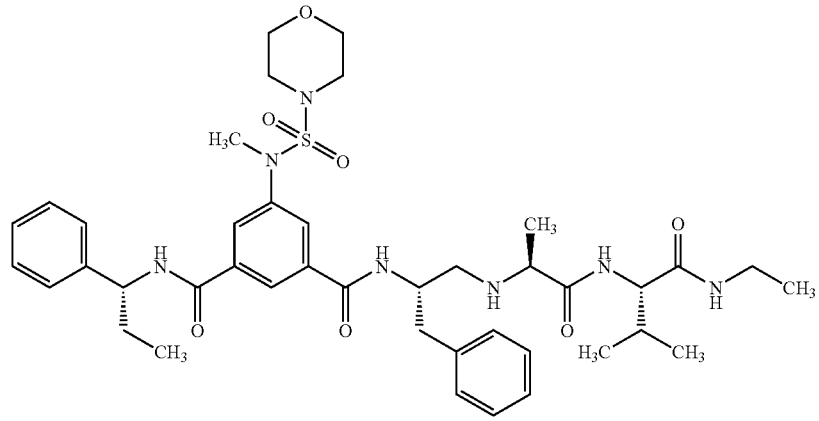
(95)
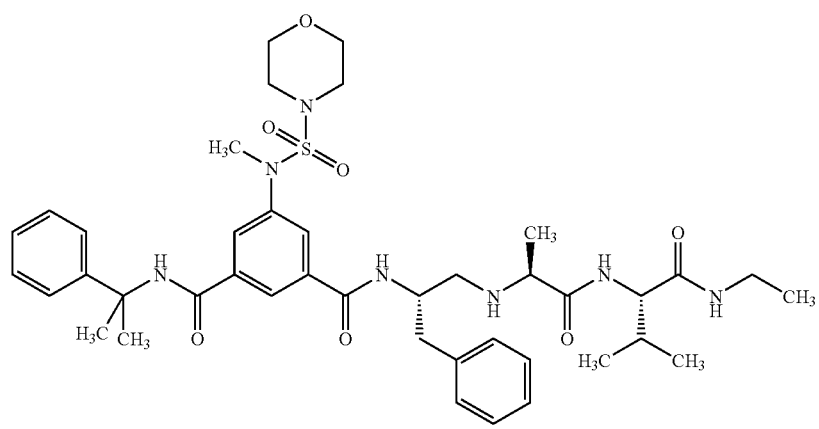
(96)
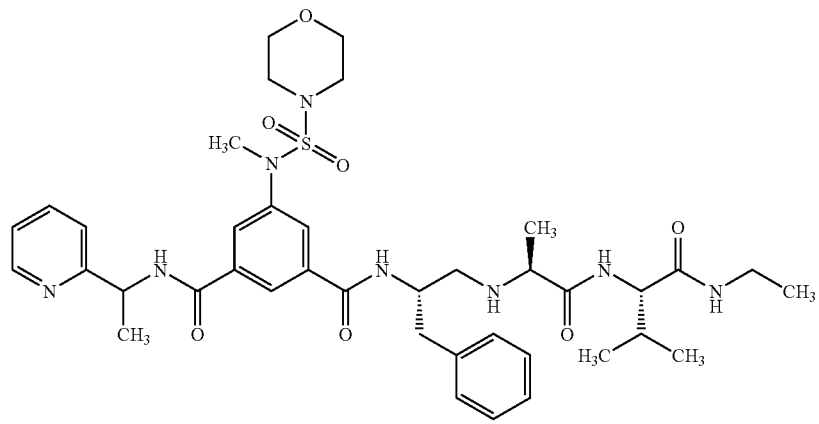

(97)
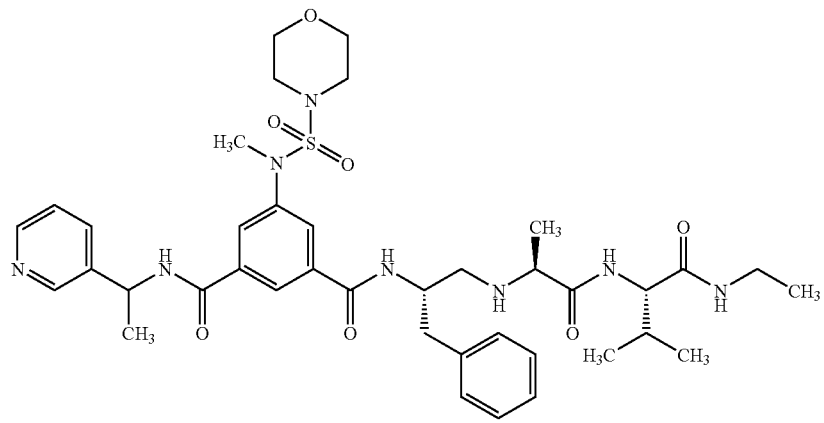
(98)
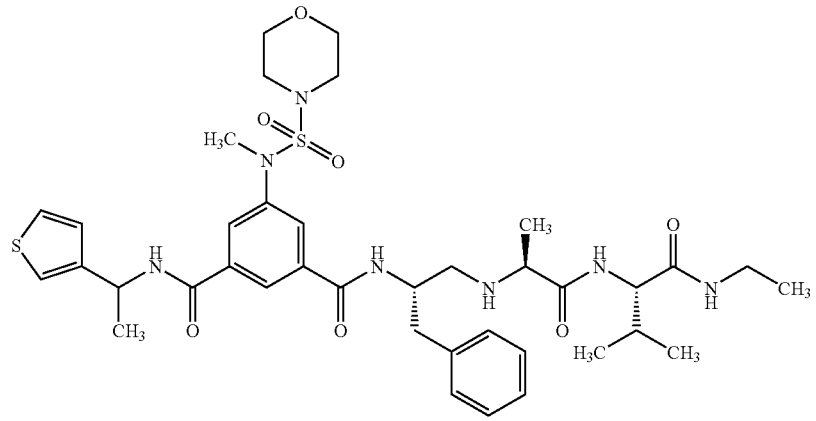
(99)
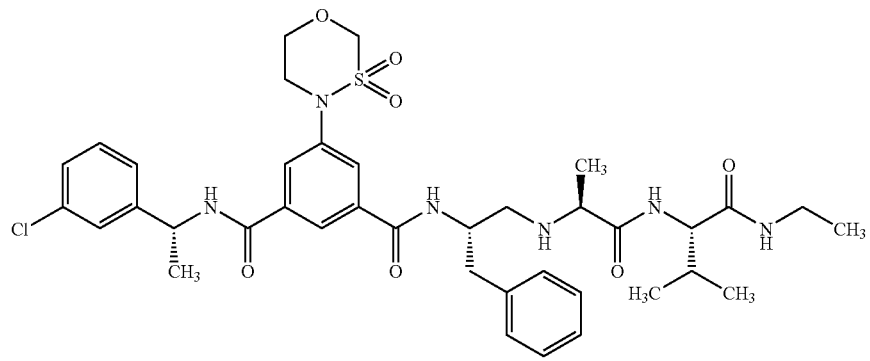
(100)
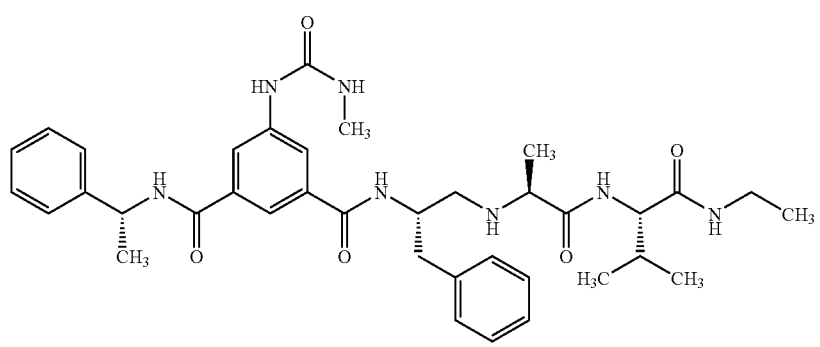

(101)
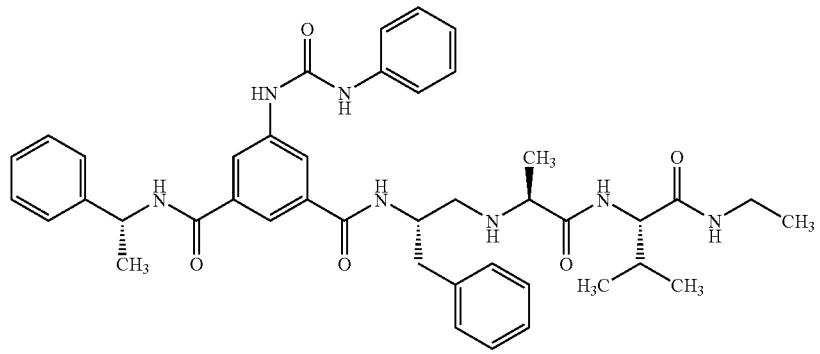
(102)
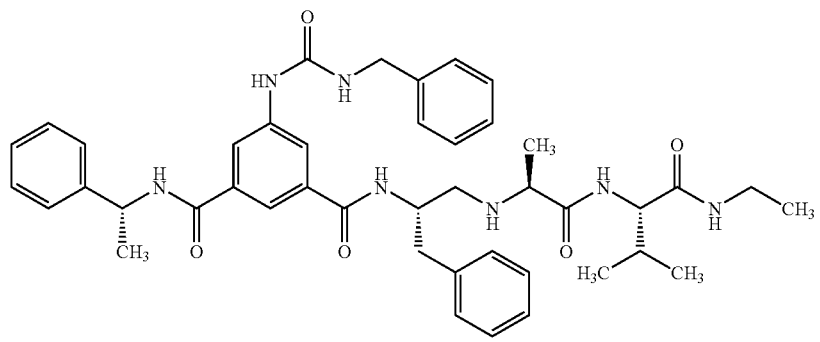
(103)
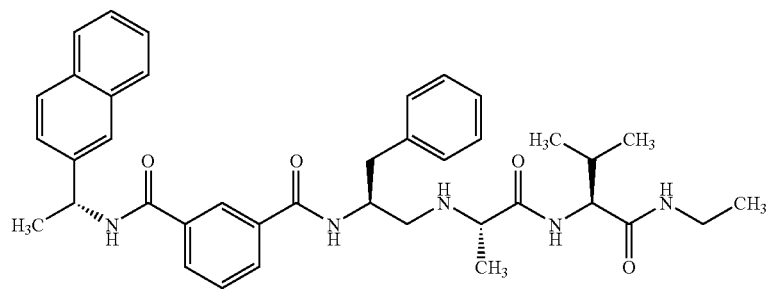
(104)
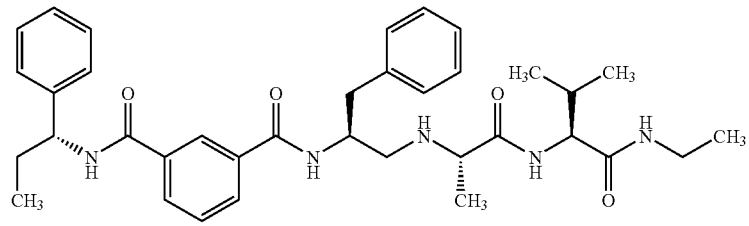
(105)
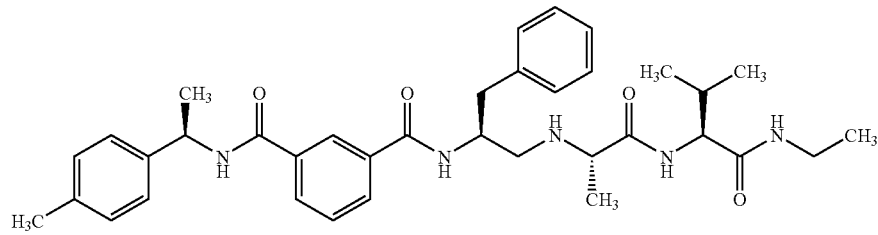

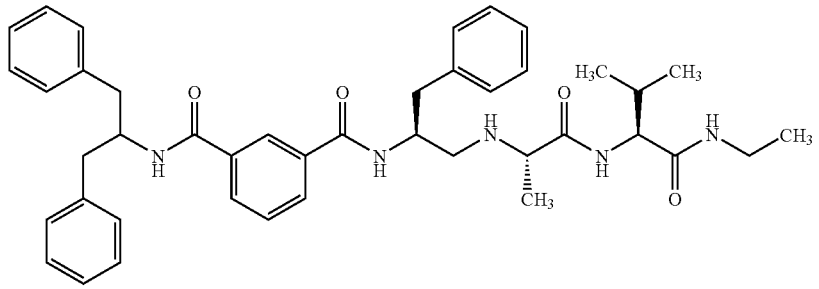
(106)
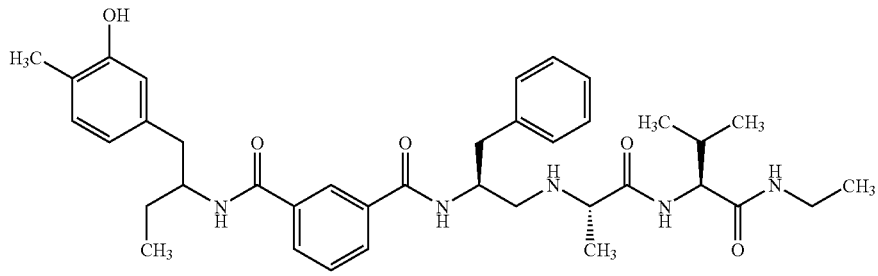
(107)
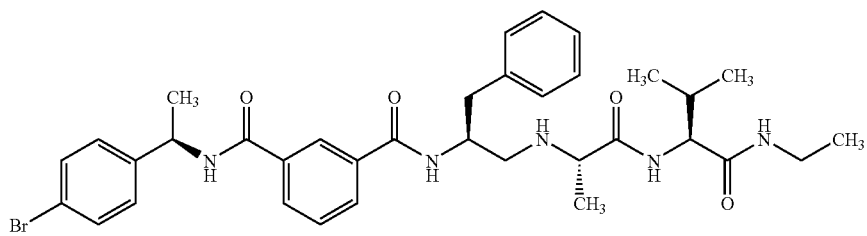
(108)
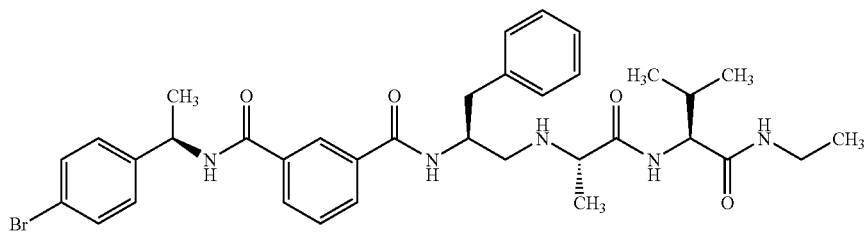
(109)
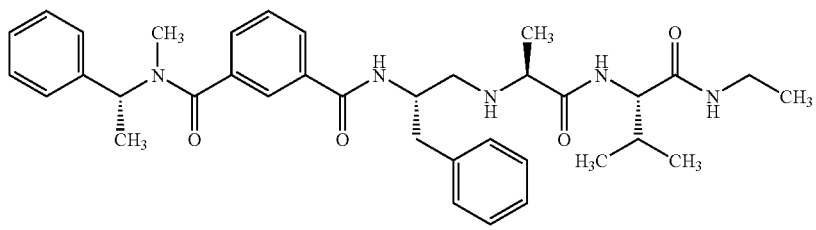
(110)
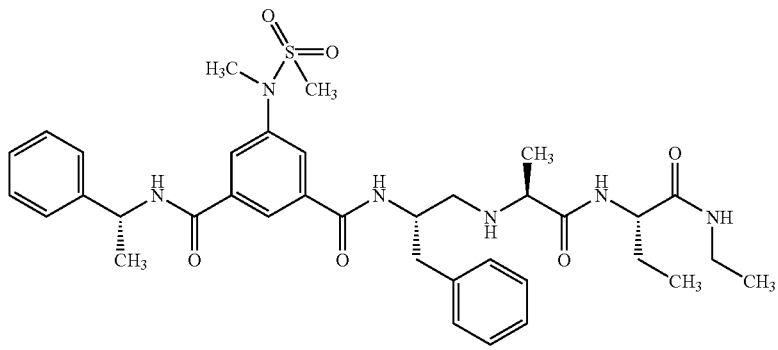
(111)

-continued
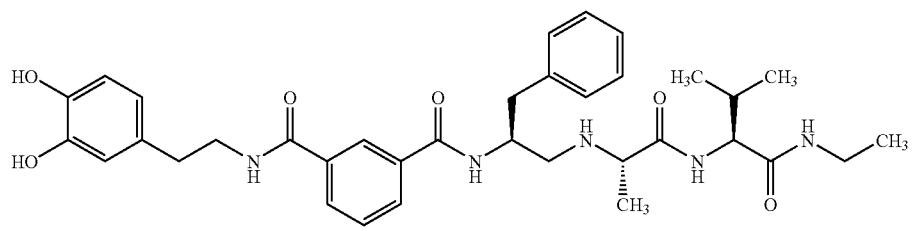
(112)
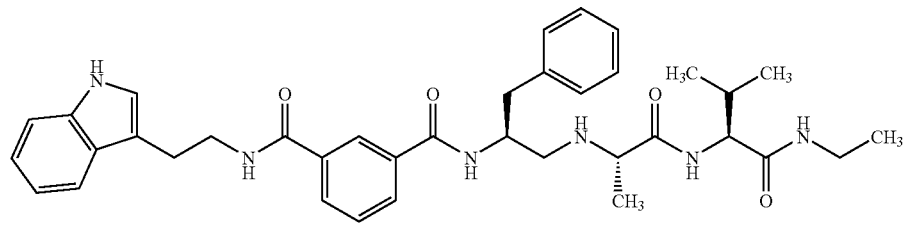
(113)
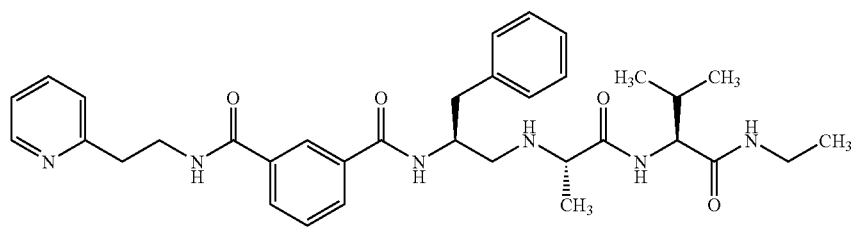
(114)
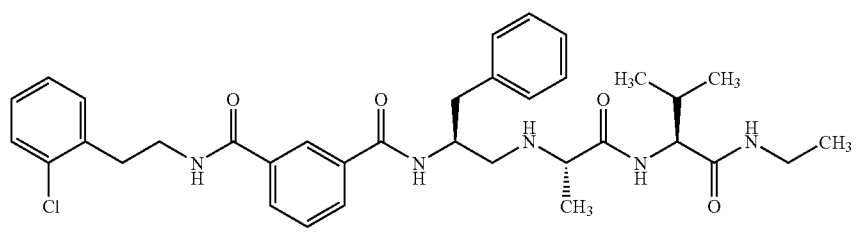
(115)
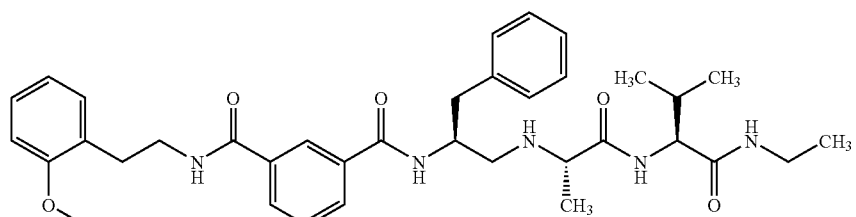
(116)
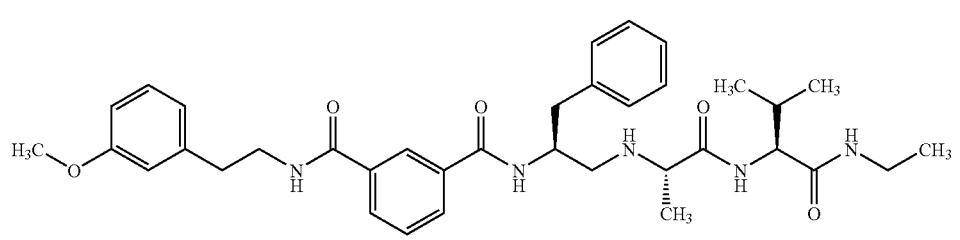
(117)
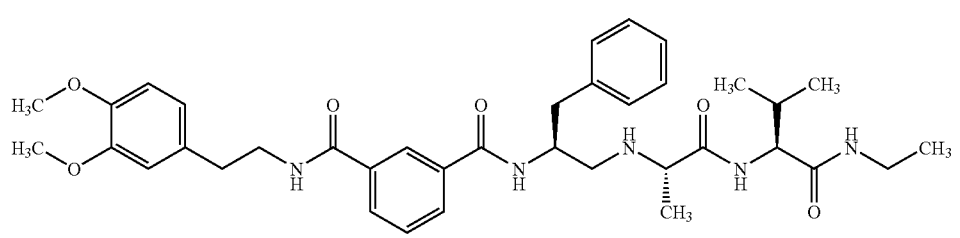
(118)

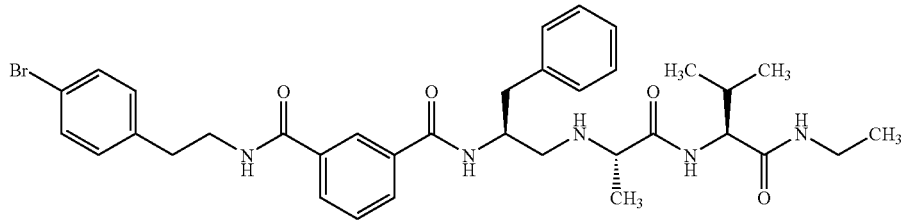
(119)
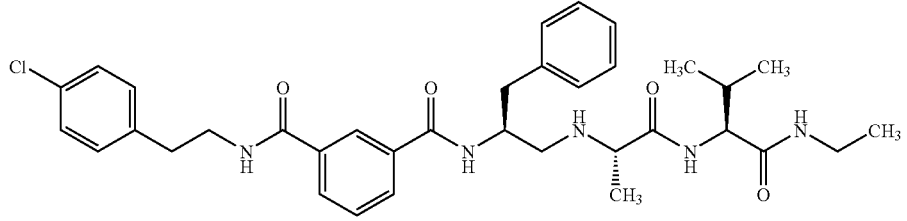
(120)
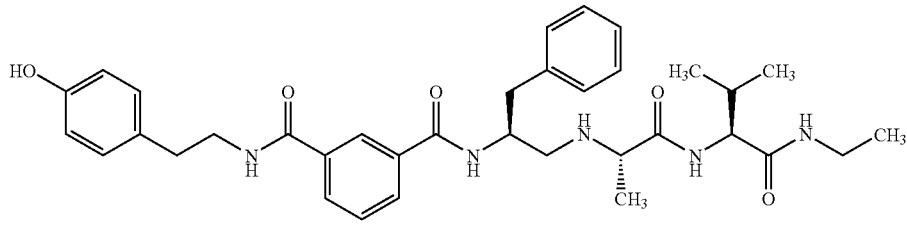
(121)
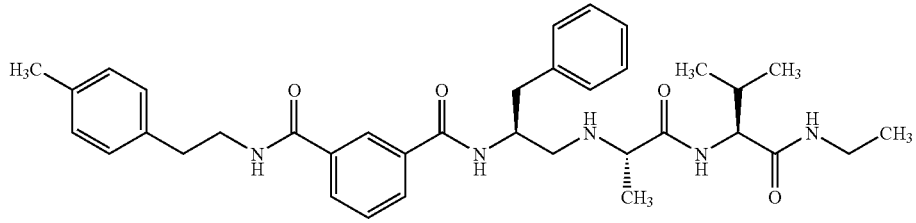
(122)
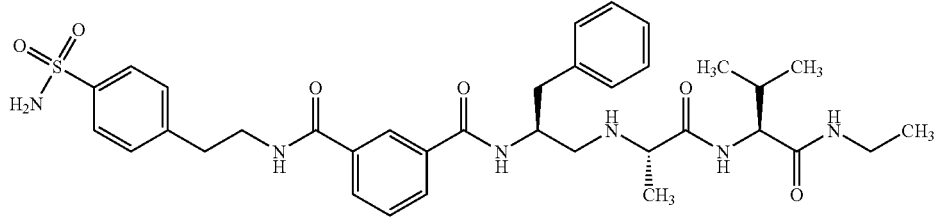
(123)
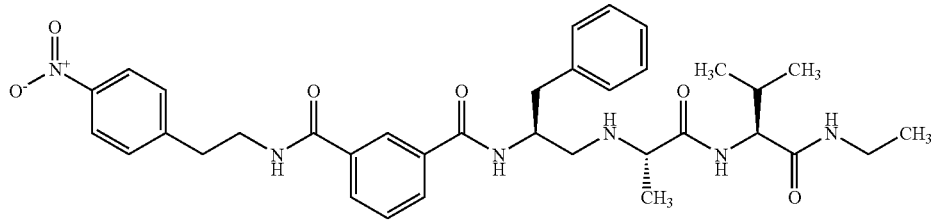
(124)
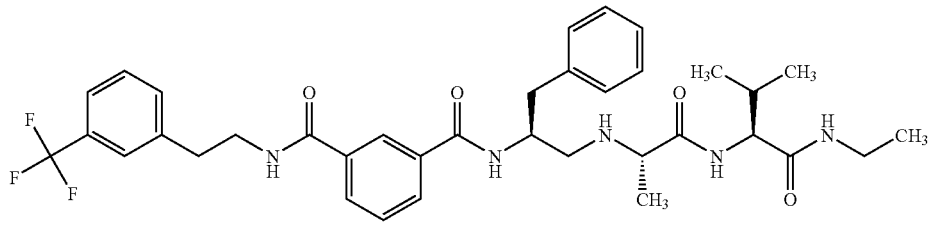
(125)

-continued
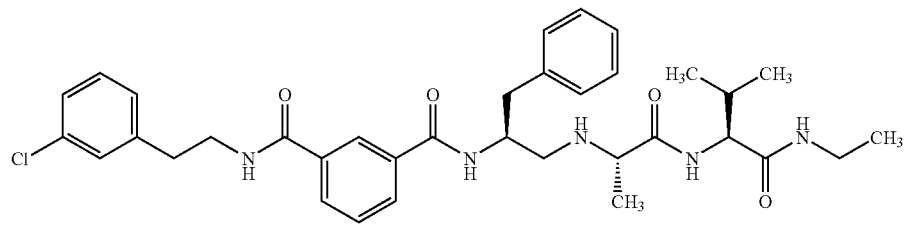
(126)
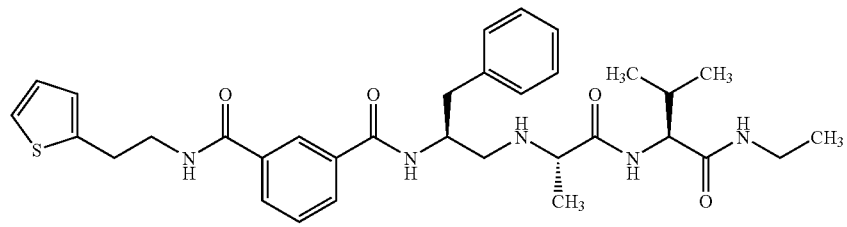
(127)
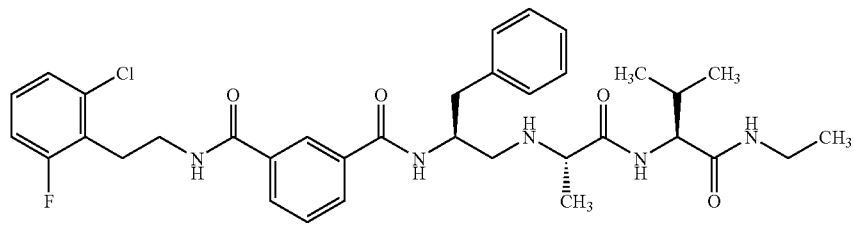
(128)
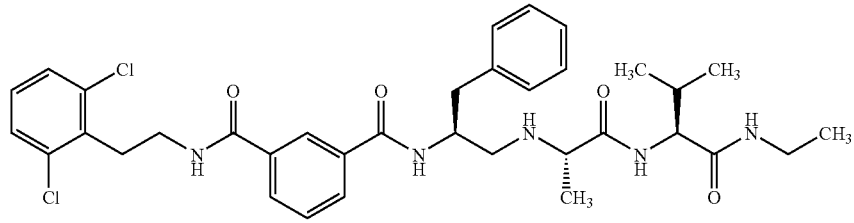
(129)
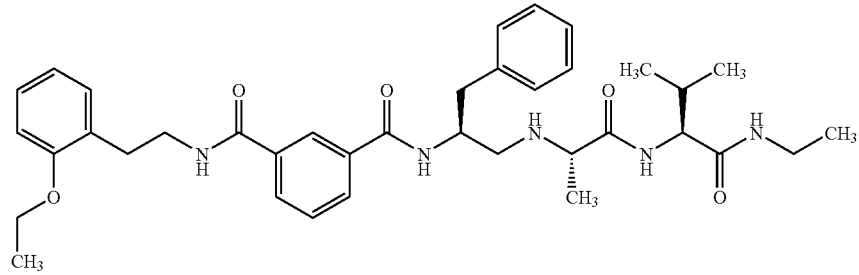
(130)
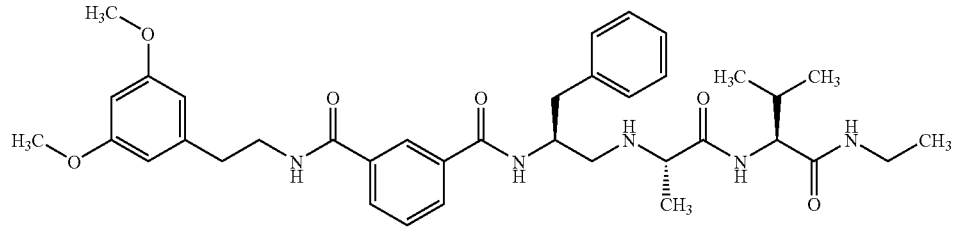
(131)

(132)
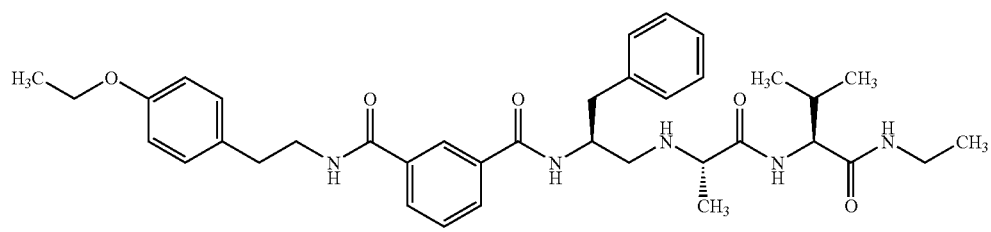
(133)
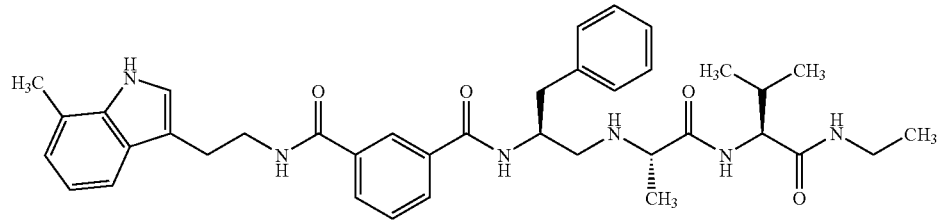
(134)
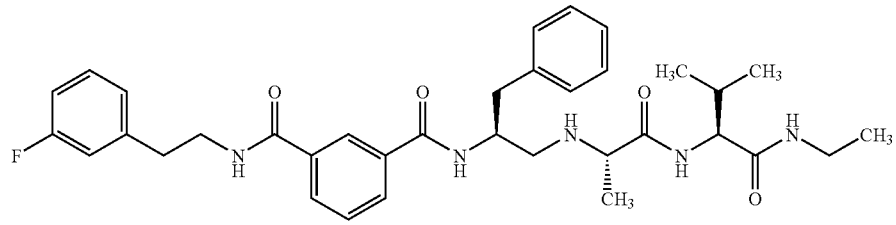
(135)
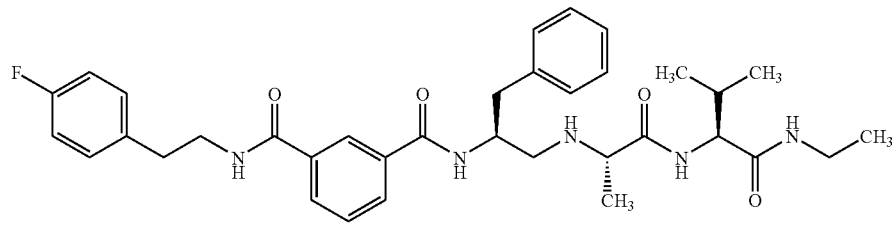
(136)
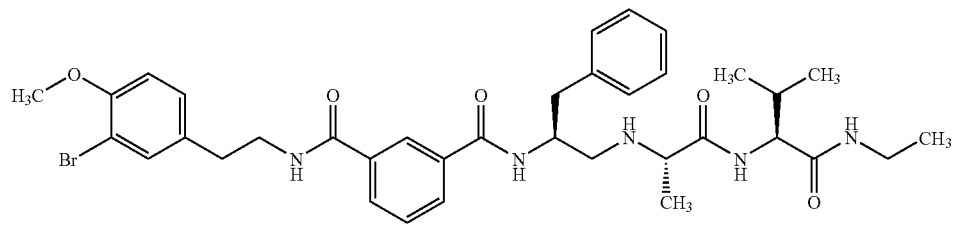
(137)
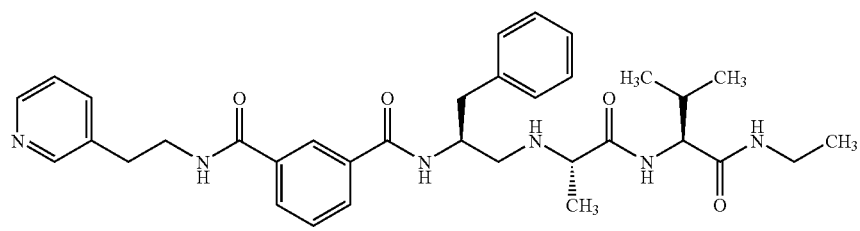
(138)
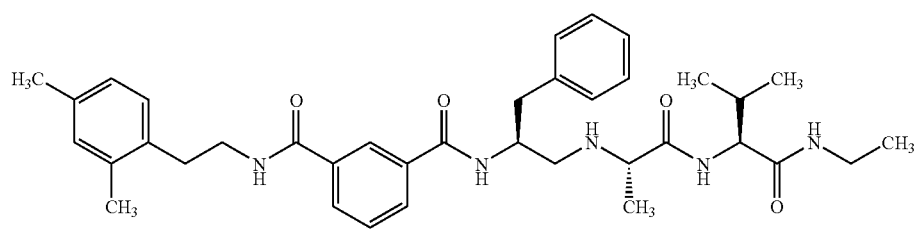

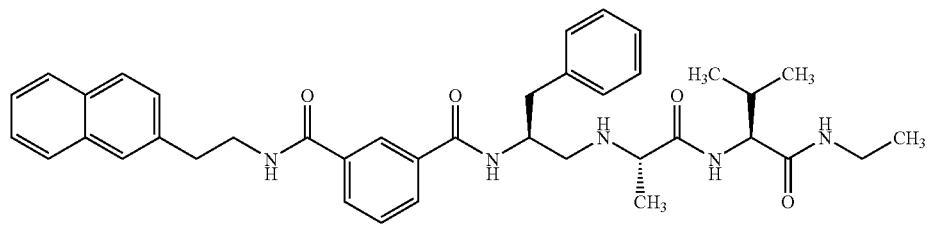
(139)
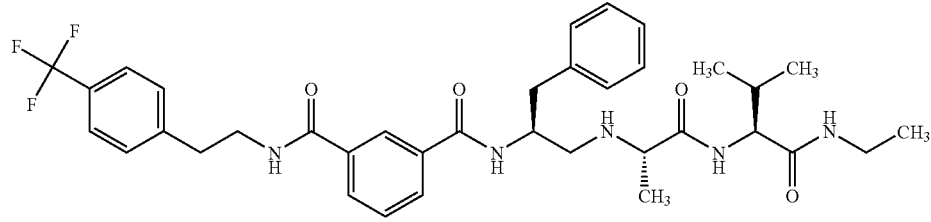
(140)
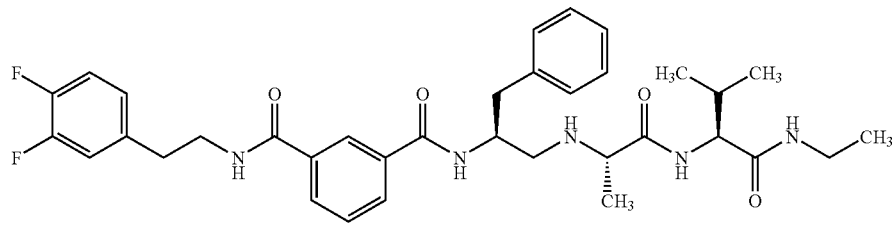
(141)
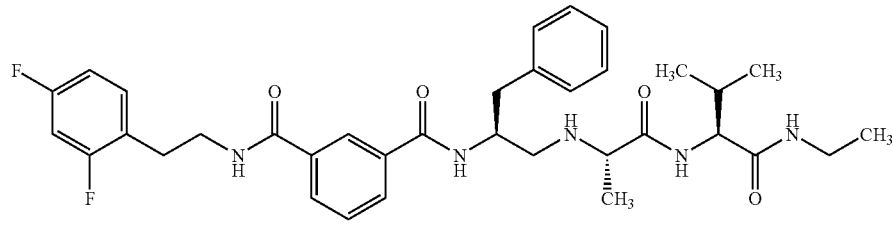
(142)
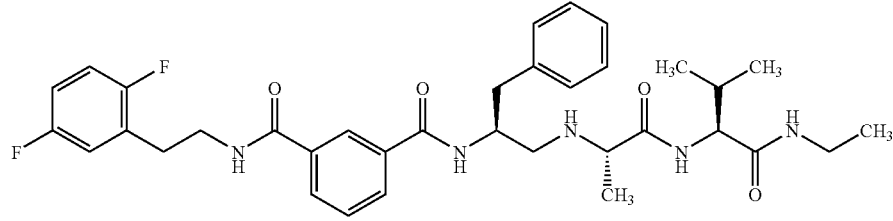
(143)
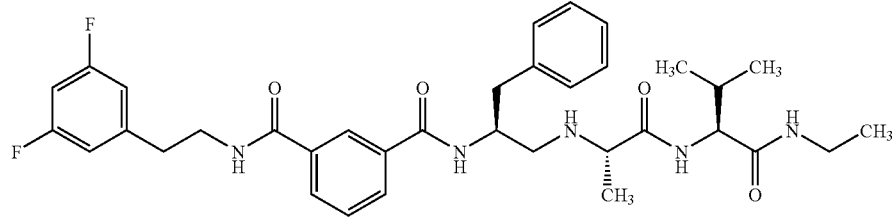
(144)
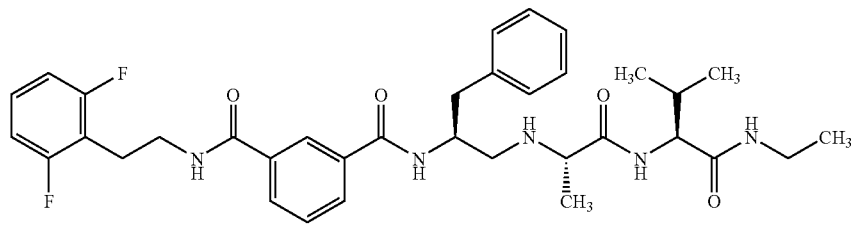
(145)

-continued
(146)
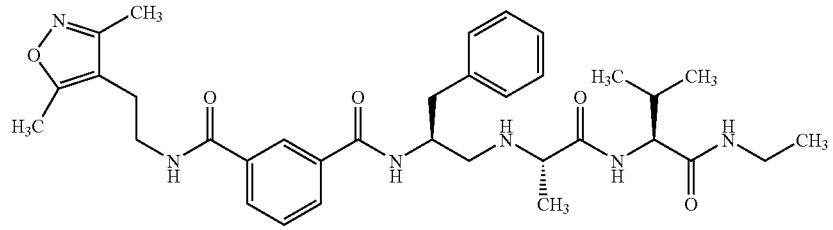
(147)
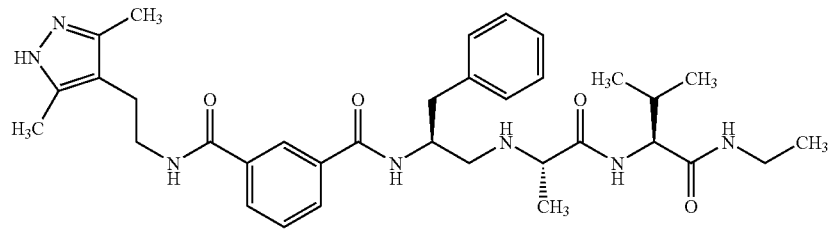
(148)
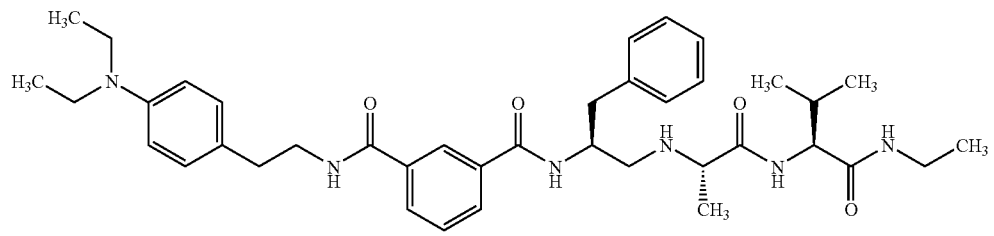
(149)
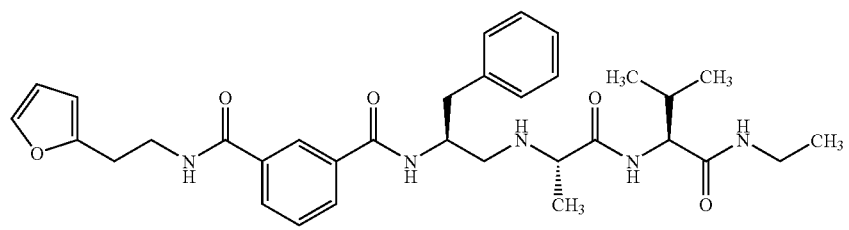
(150)
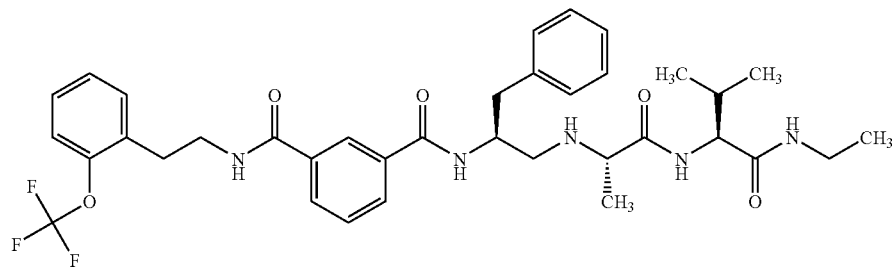
(151)
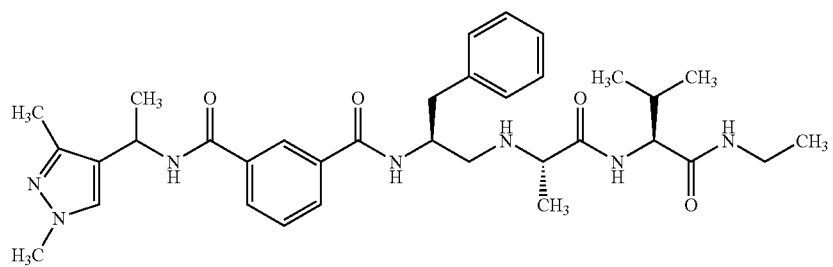

-continued
(152)
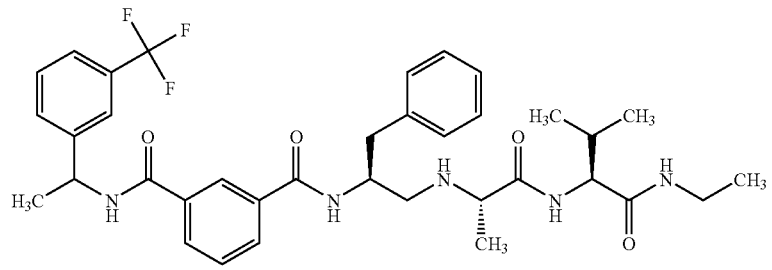
(153)
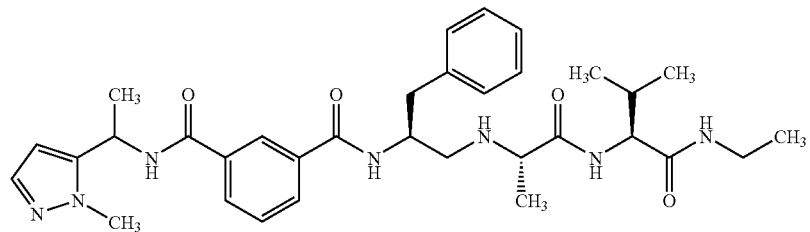
(154)
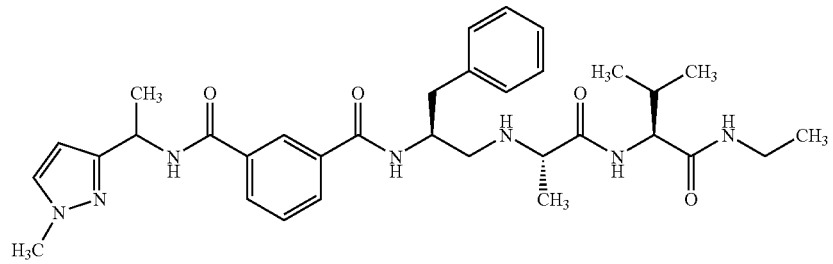
(155)
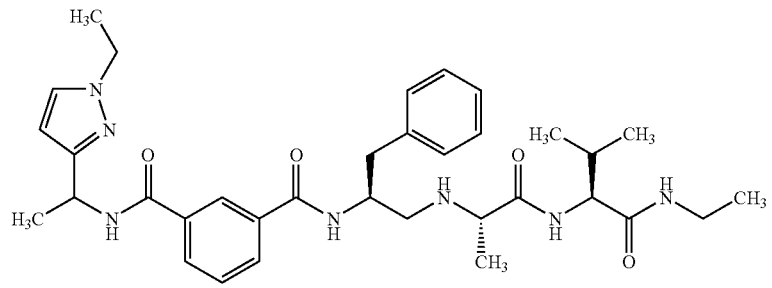
(156)
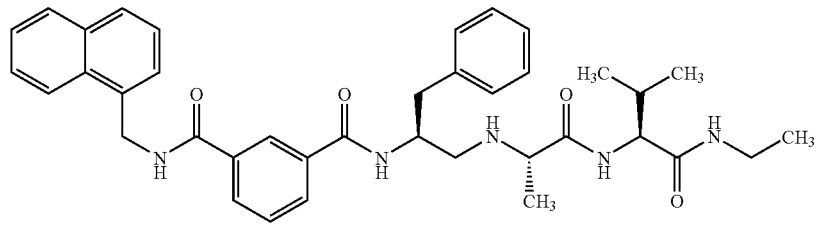
(157)
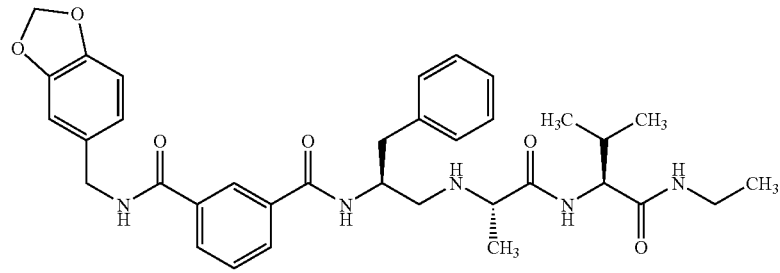

-continued
(158)
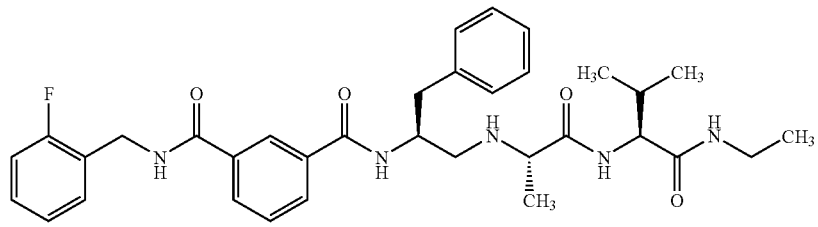
(159)
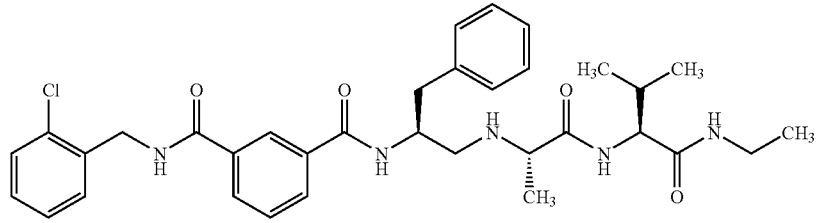
(160)
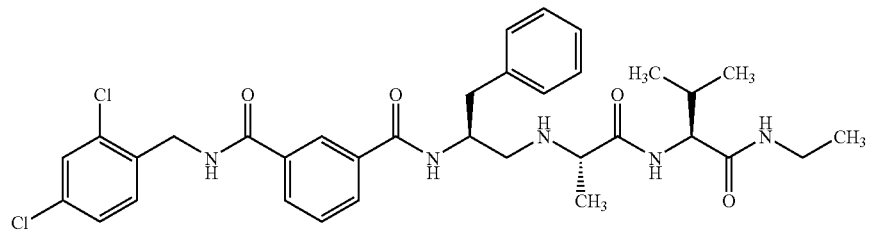
(161)
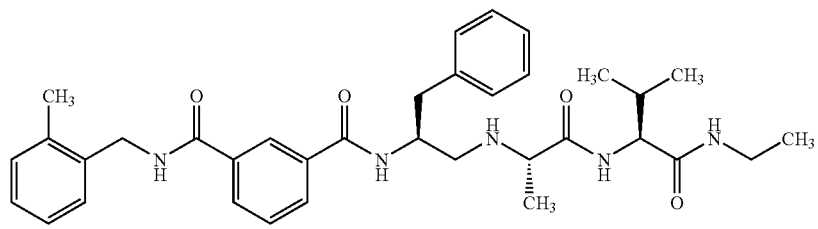
(162)
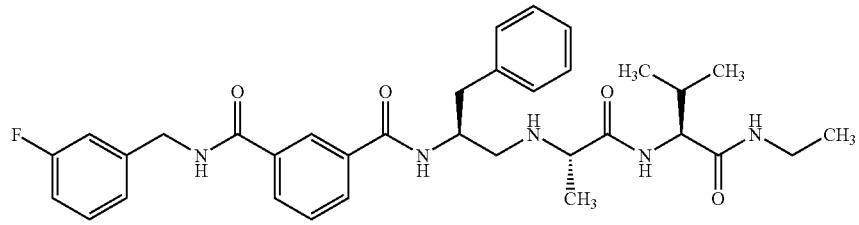
(163)
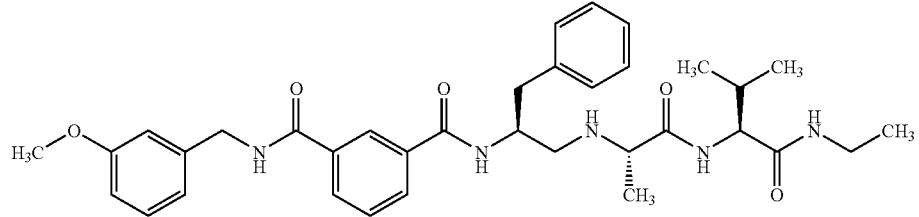
(164)
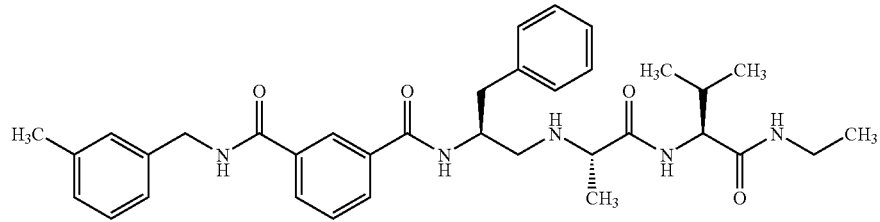

(165)
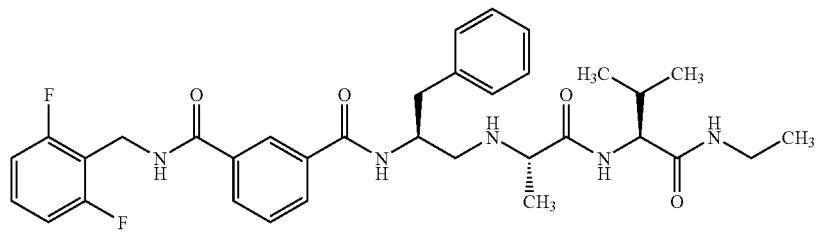
(166)
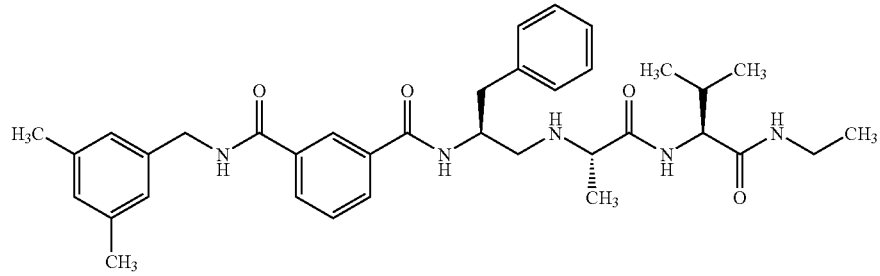
(167)
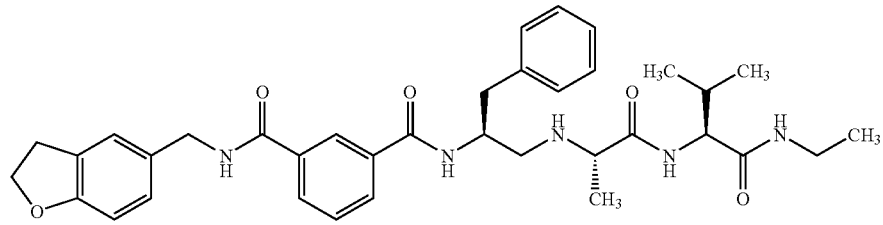
(168)
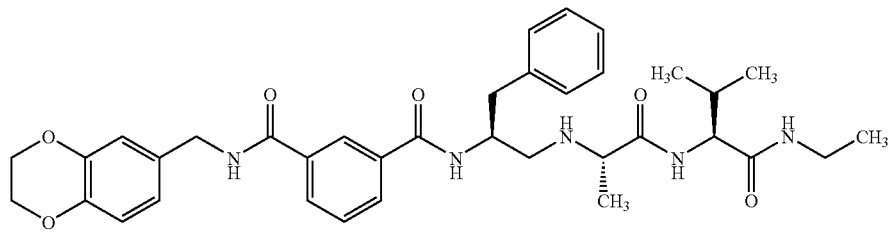
(169)
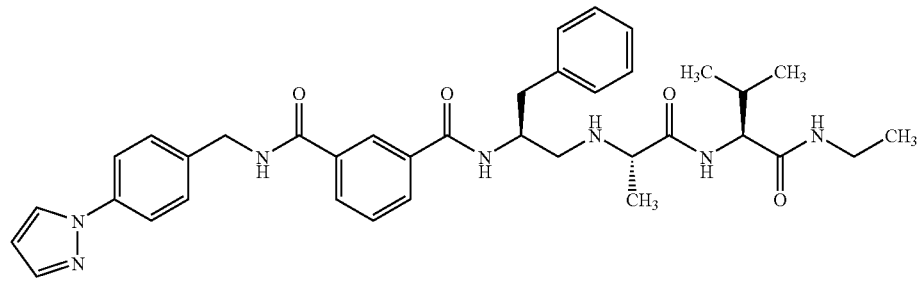
(170)
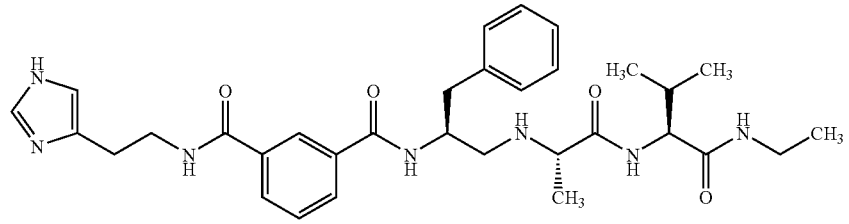

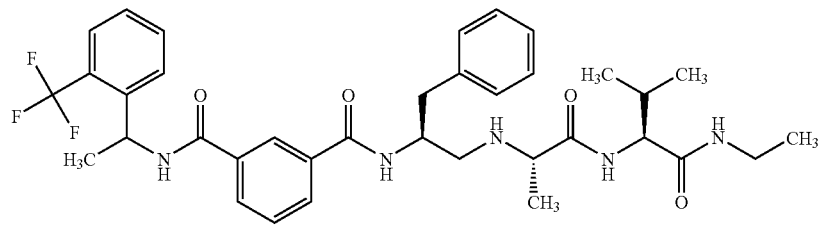
(171)
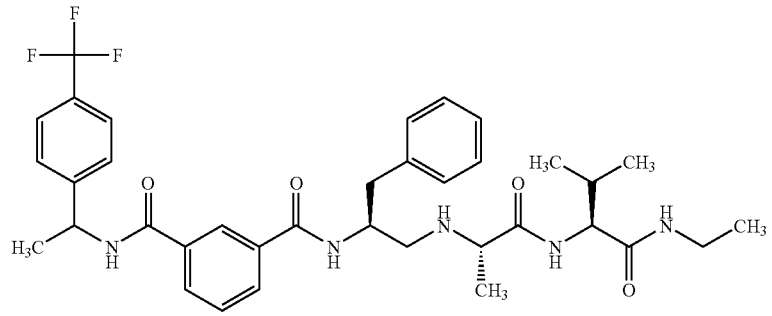
(172)
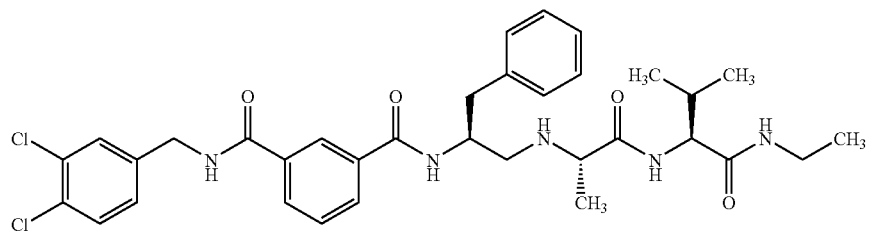
(173)
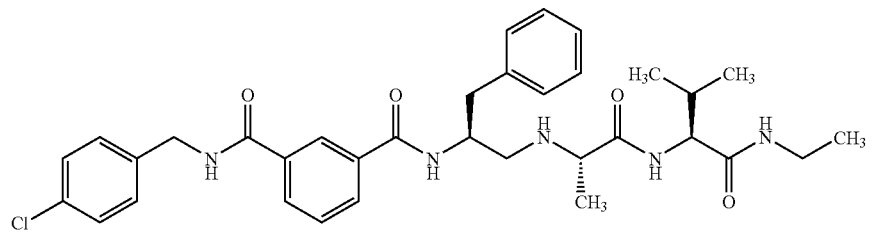
(174)
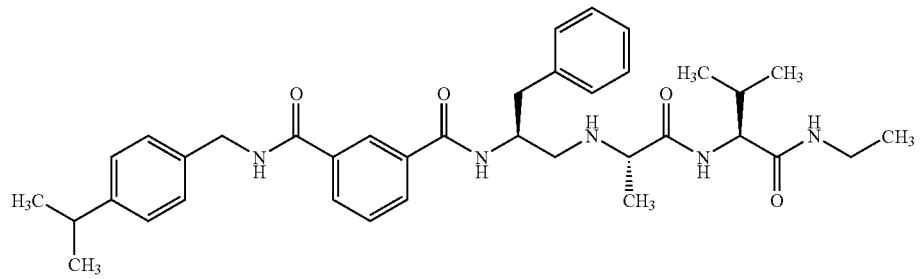
(175)
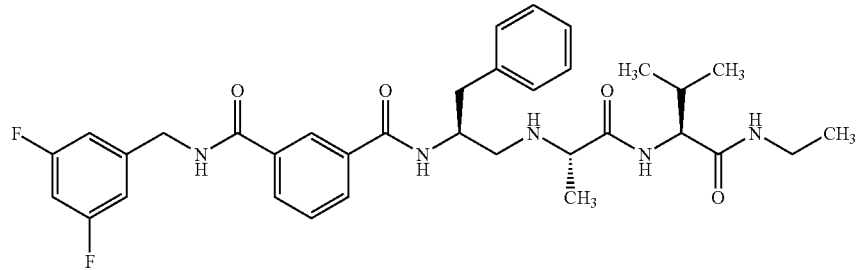
(176)

(177)
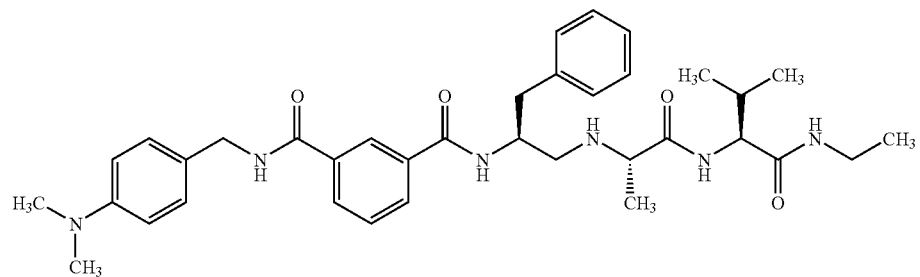
(178)
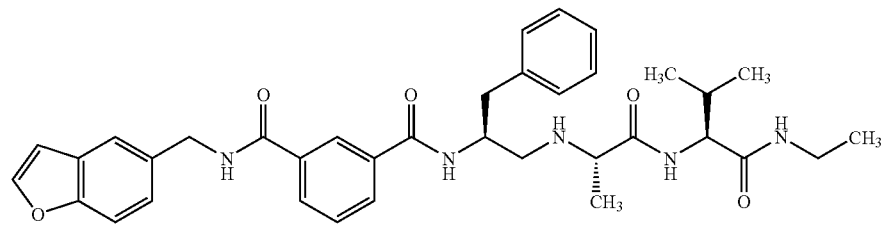
(179)
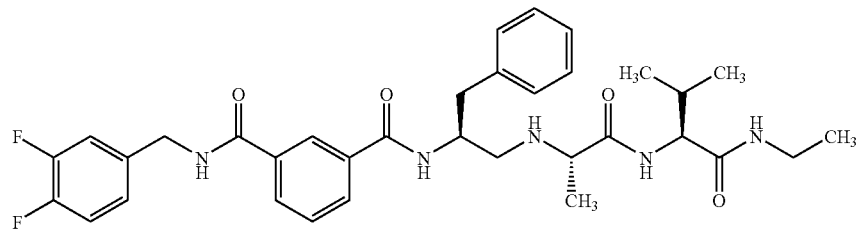
(180)
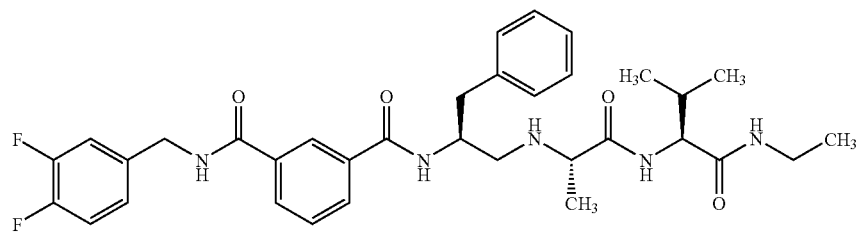
(181)
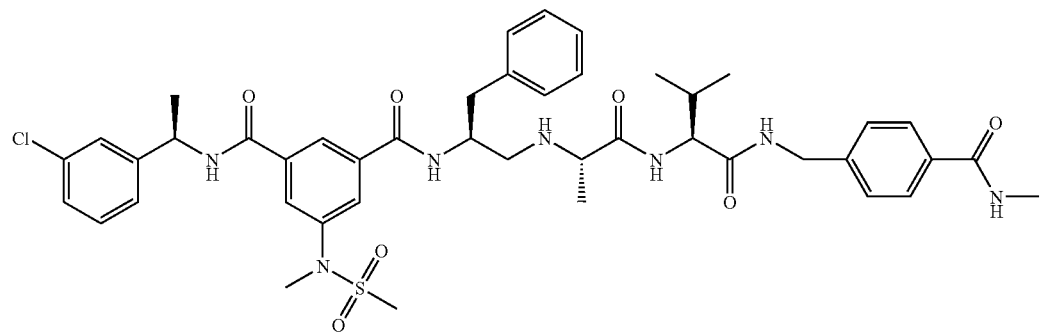

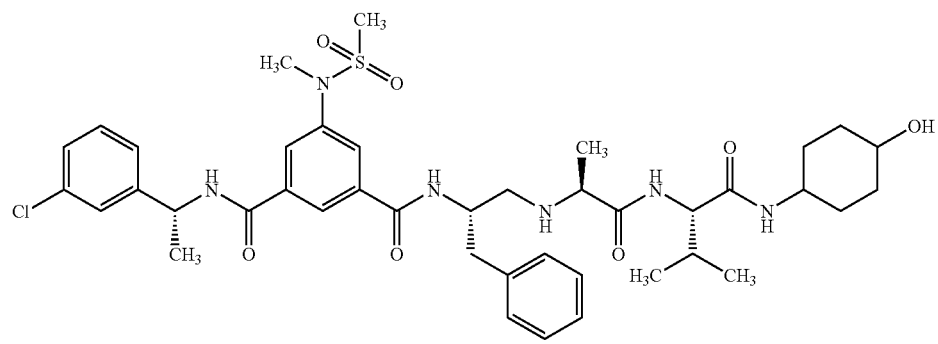
(182)
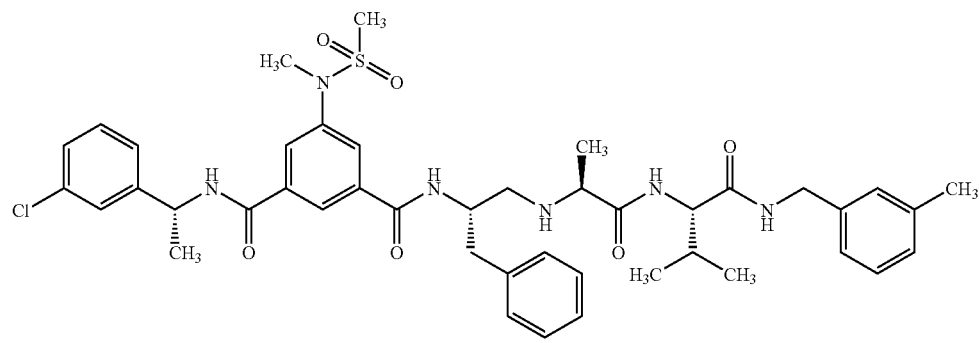
(183)
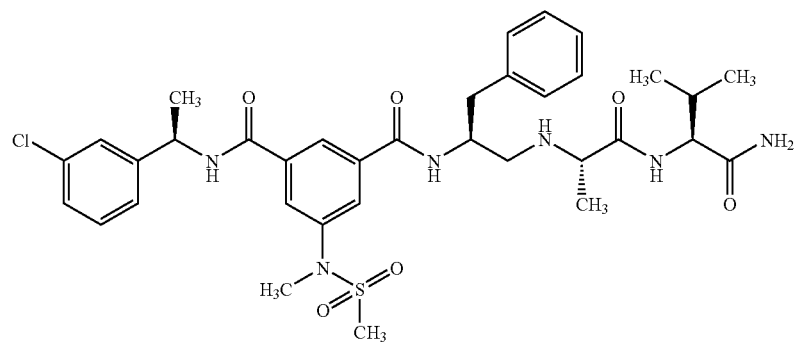
(184)
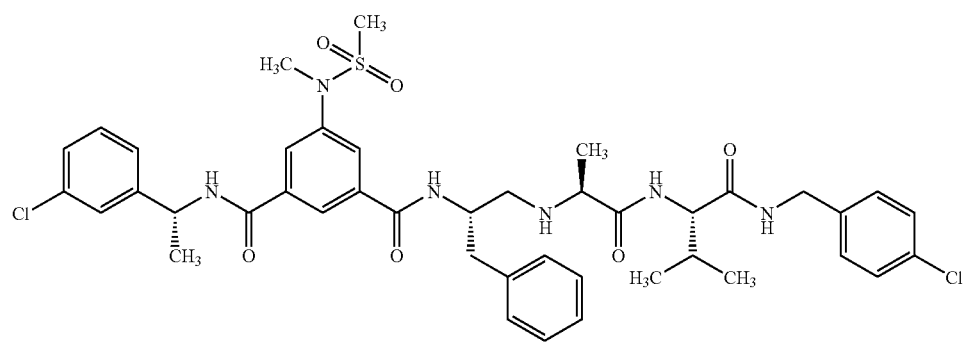
(185)

(186)
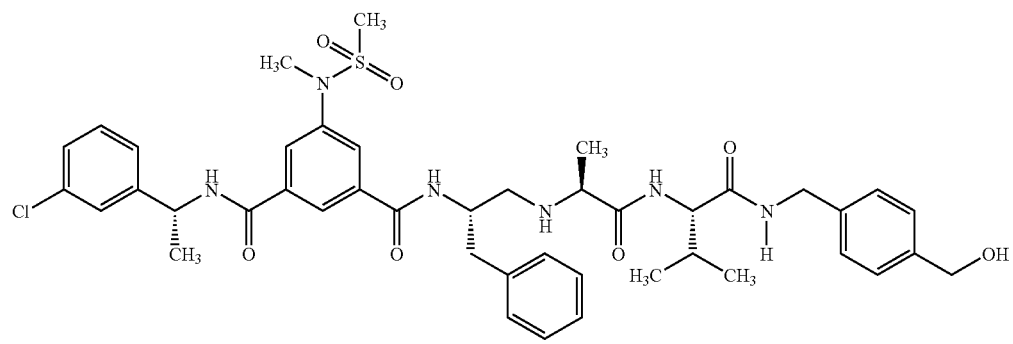
(187)
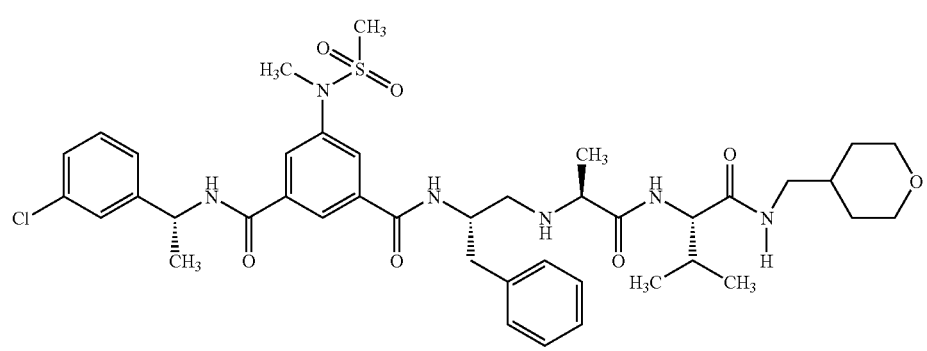
(188)
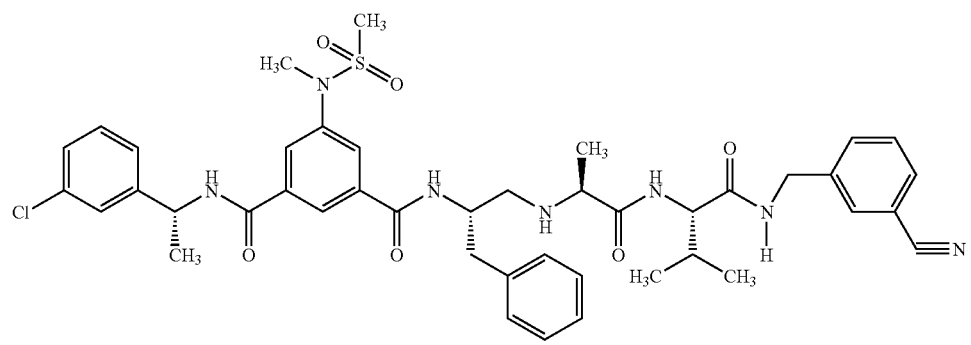
(189)
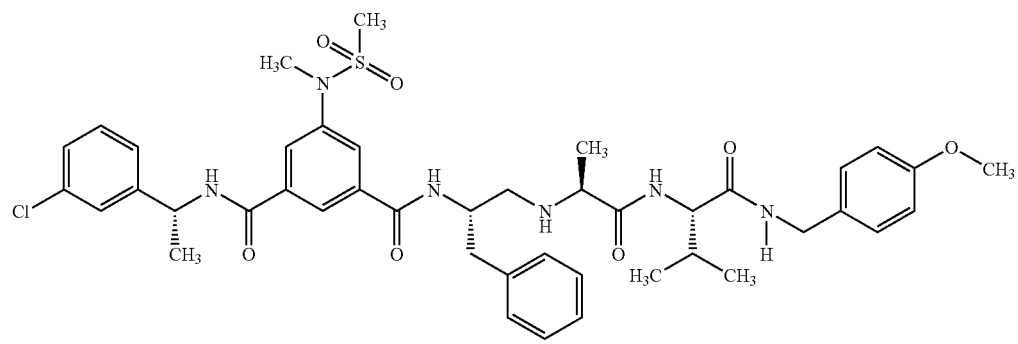

-continued
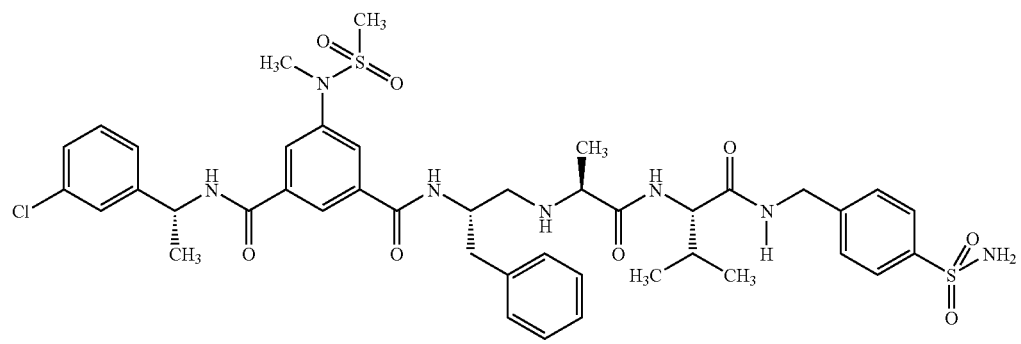
(190)
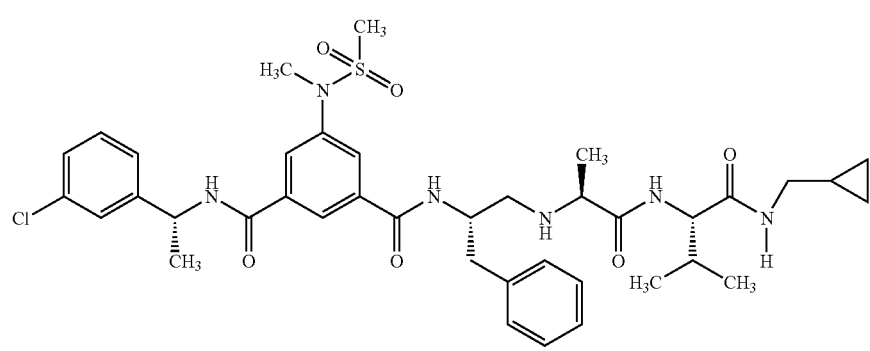
(191)
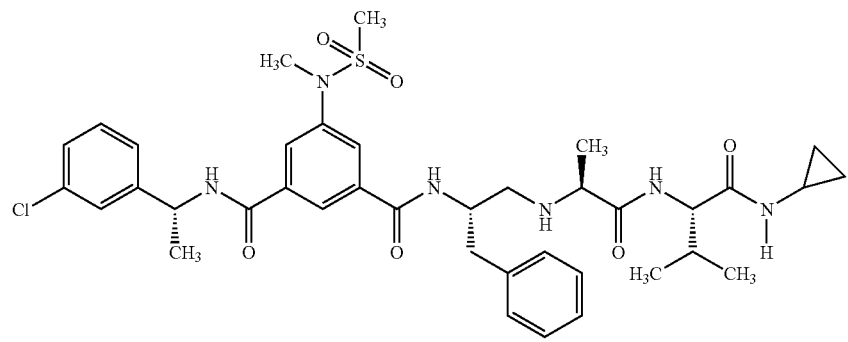
(192)
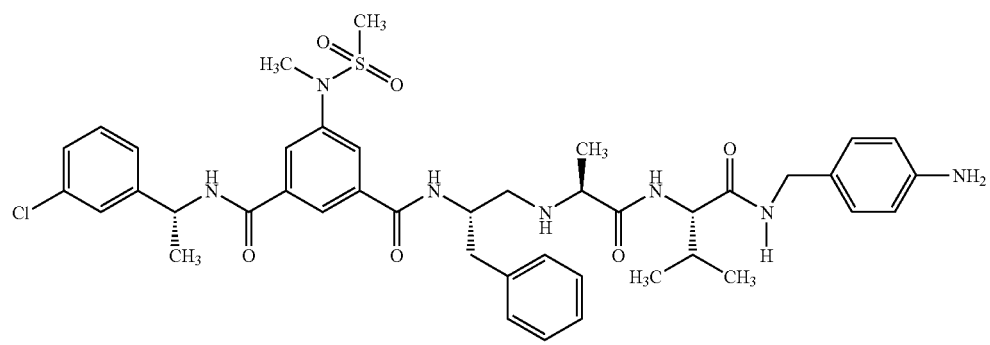
(193)

-continued
(194)
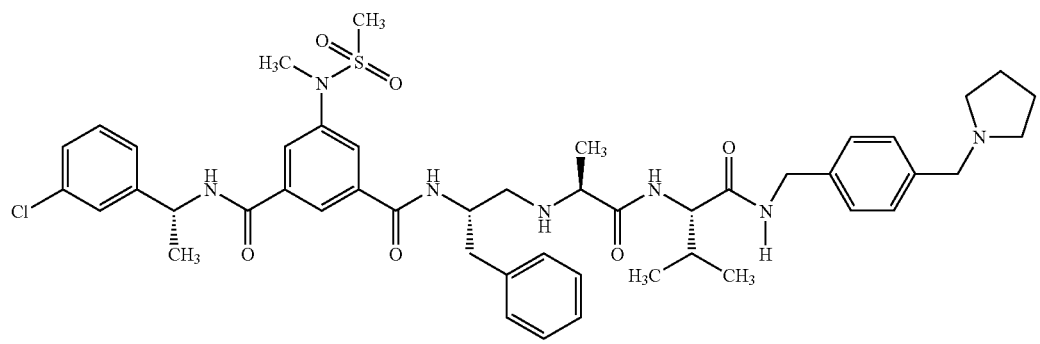
(195)
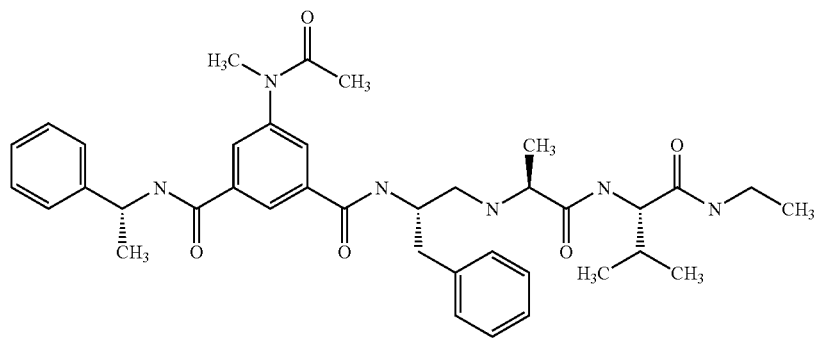
(196)
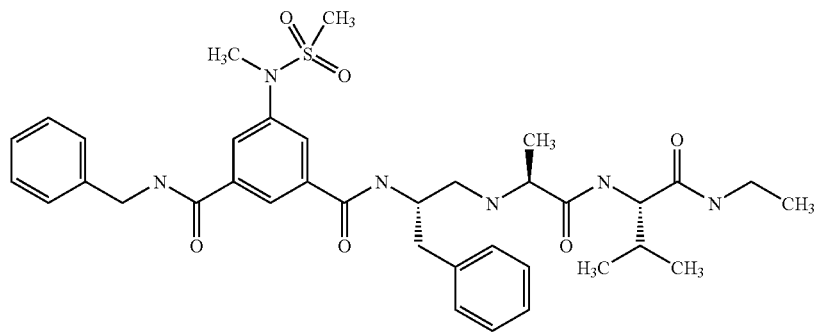
(197)
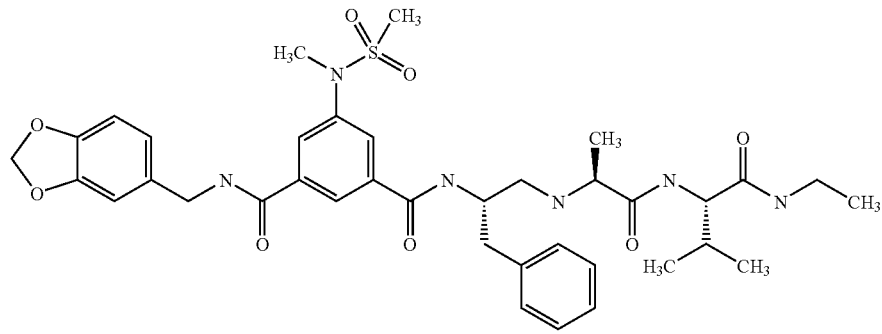

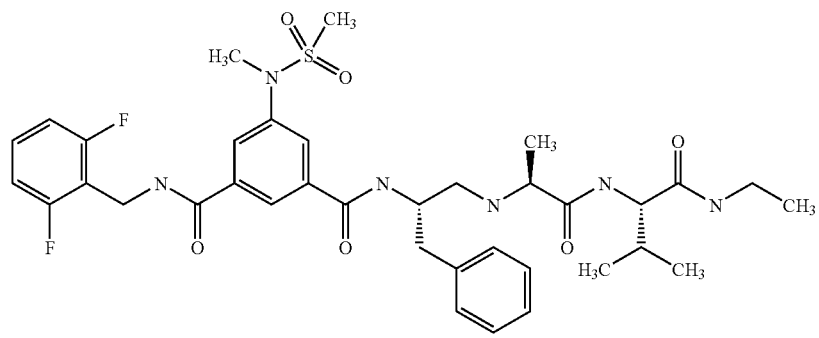
(198)
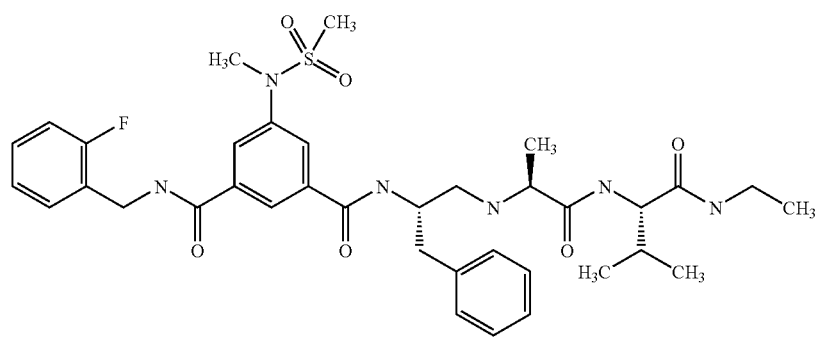
(199)
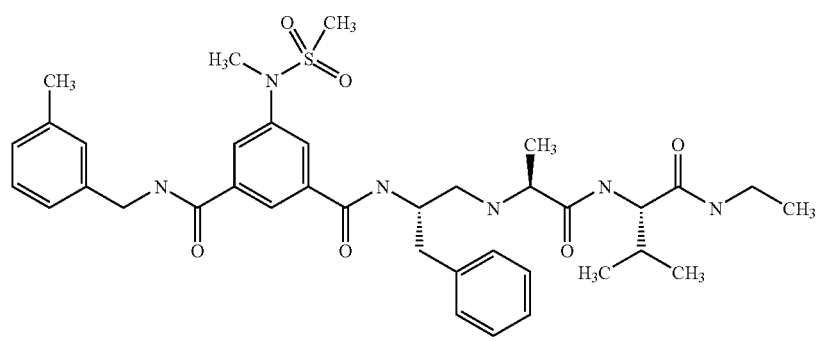
(200)
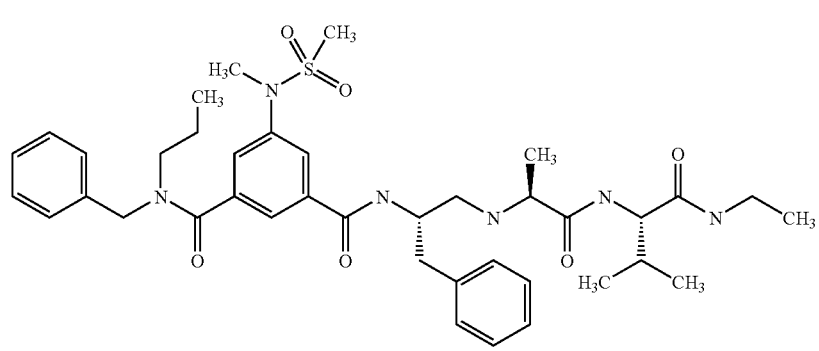
(201)

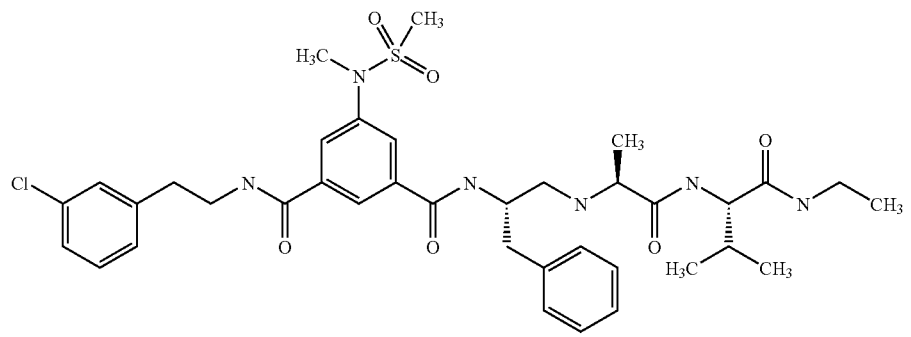
(202)
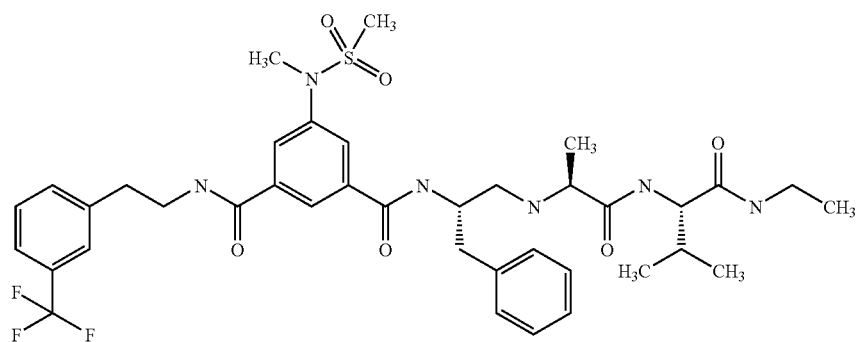
(203)
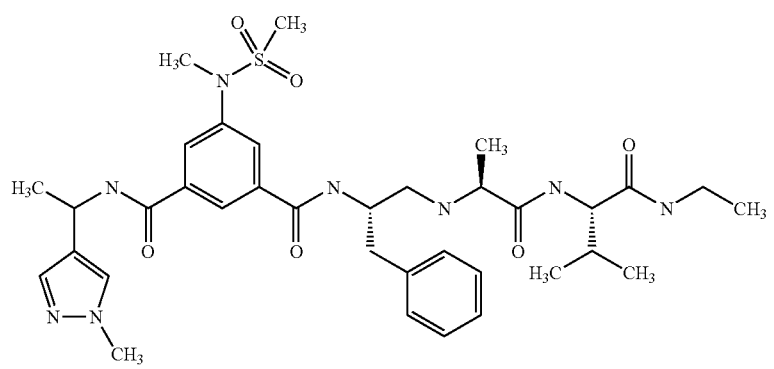
(204)
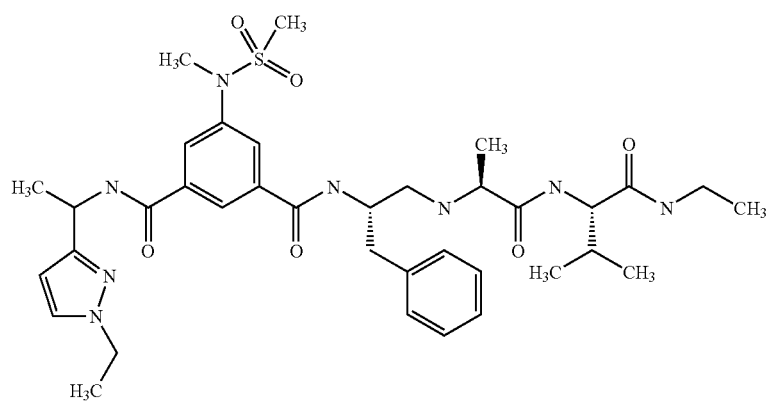
(205)

(206)
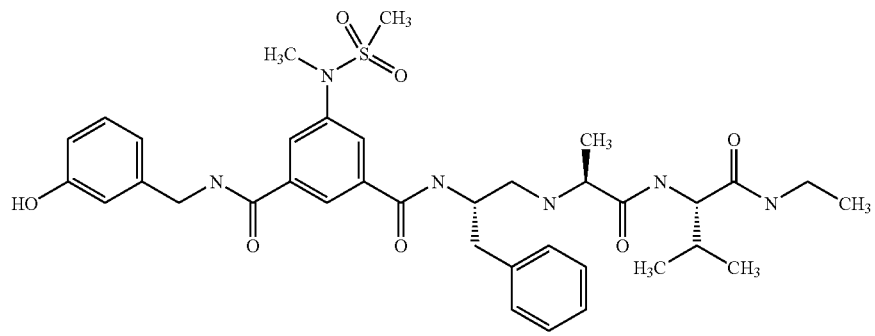
(207)
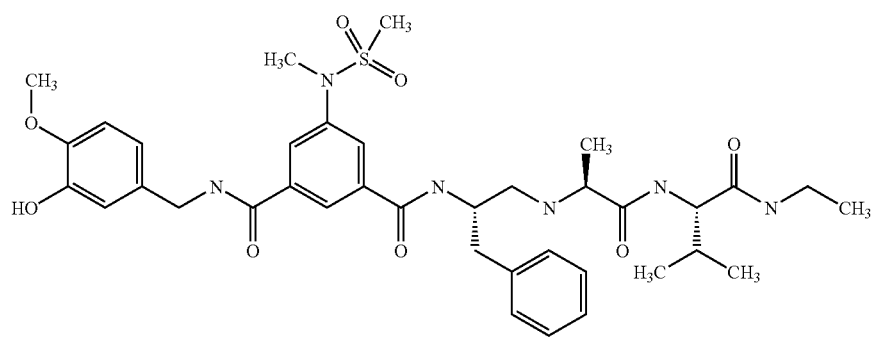
(208)
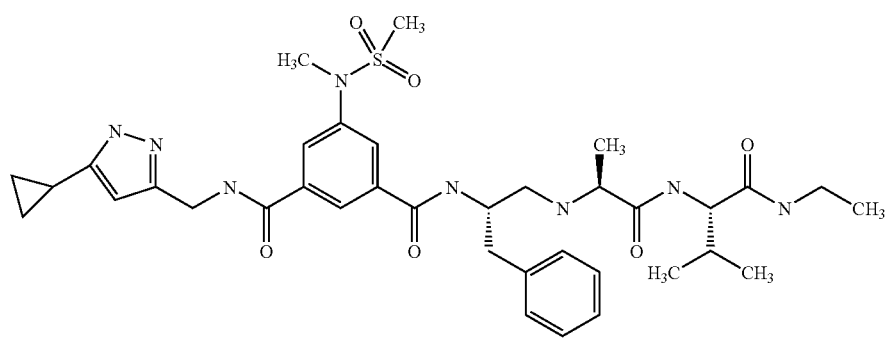
(209)
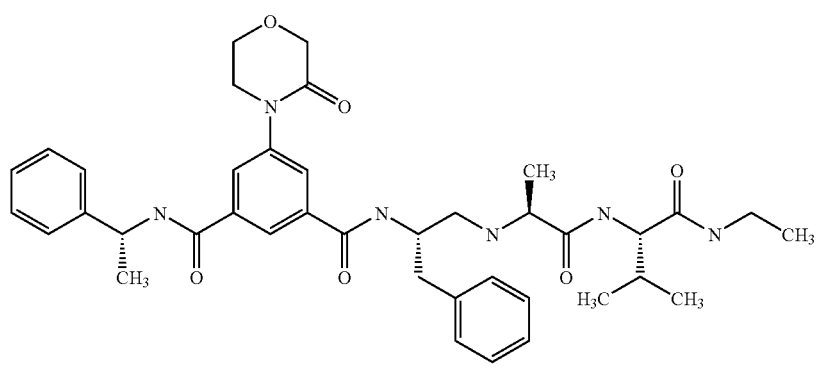

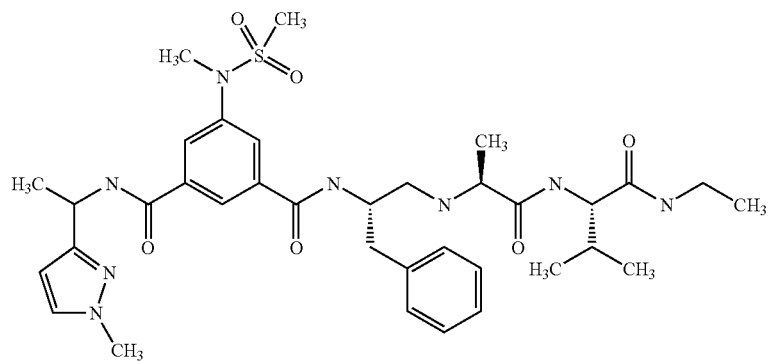
(210)
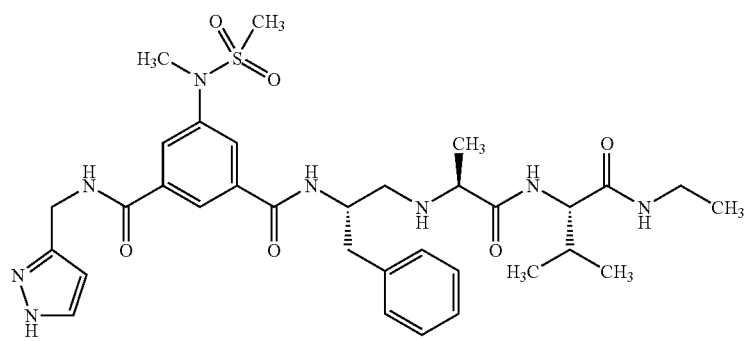
(211)
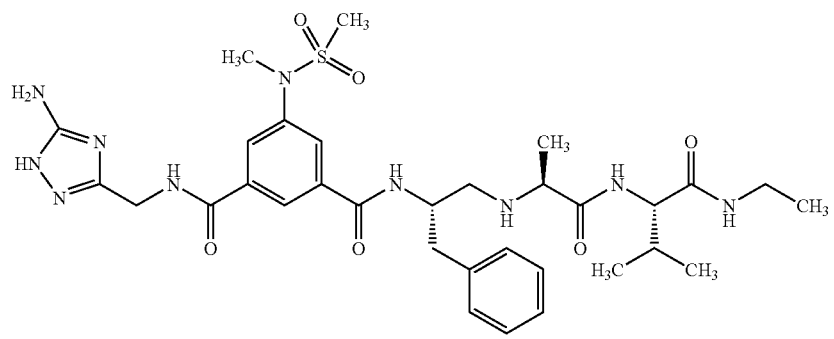
(212)
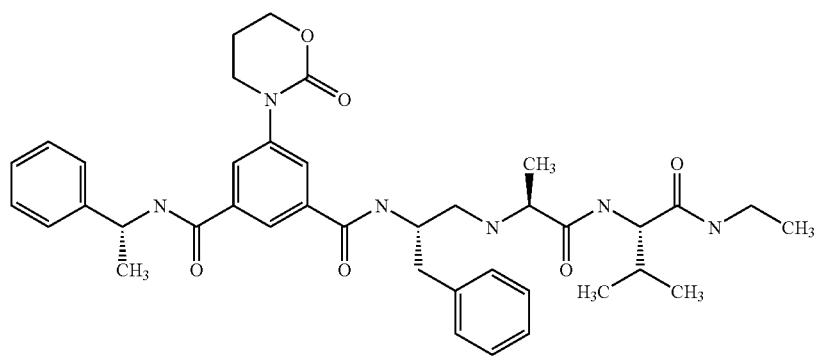
(213)

-continued
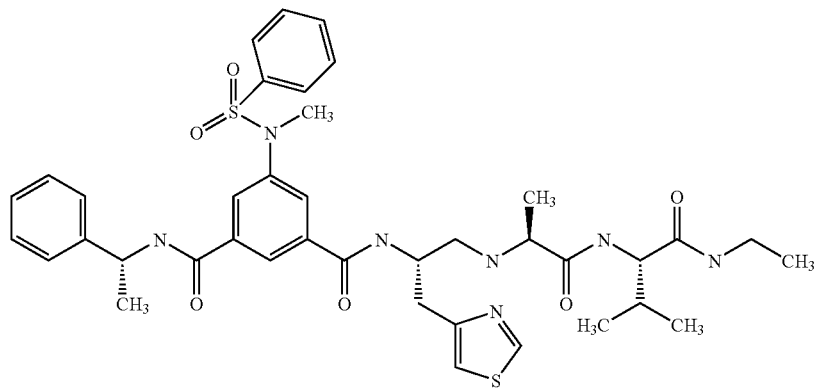
(214)
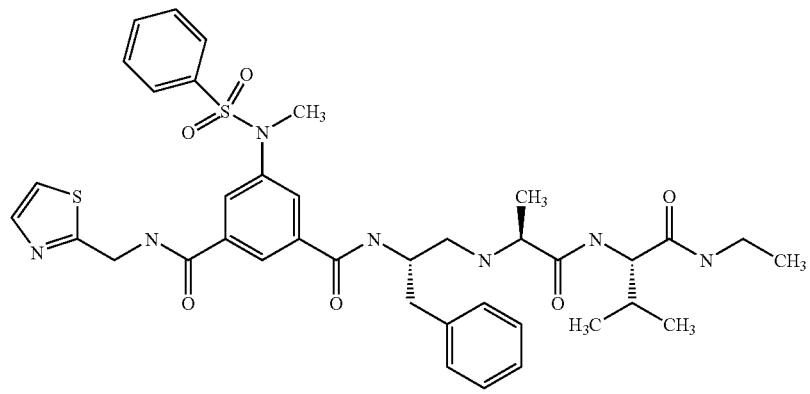
(215)
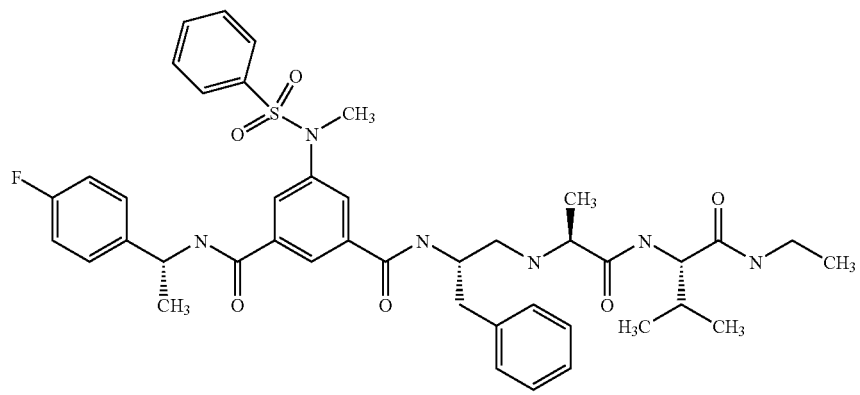
(216)
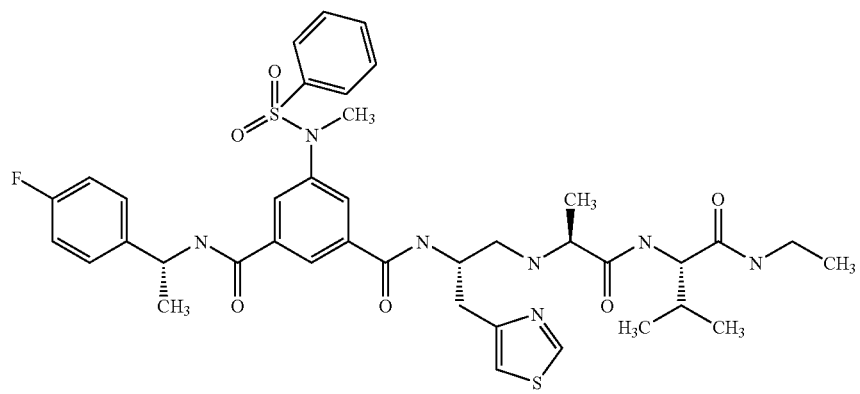
(217)

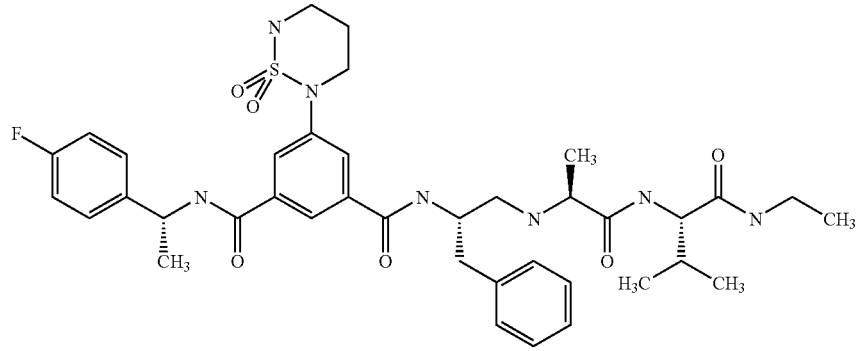
(218)
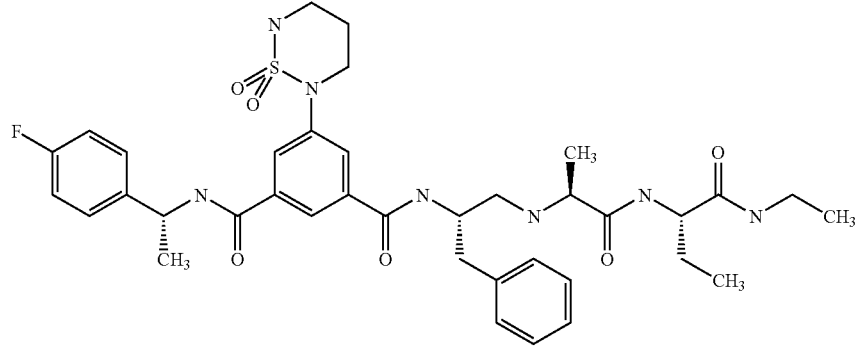
(219)
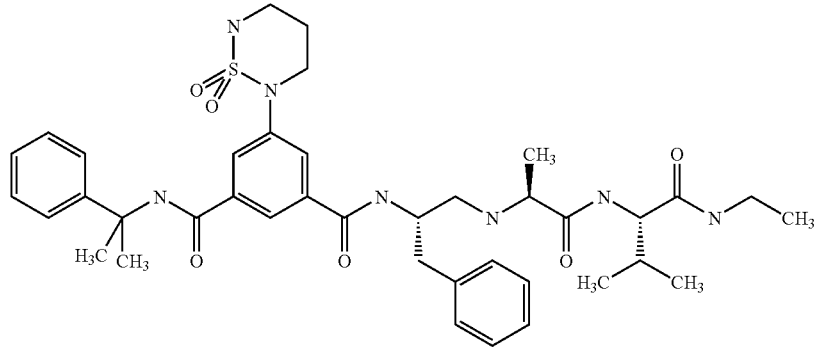
(220)
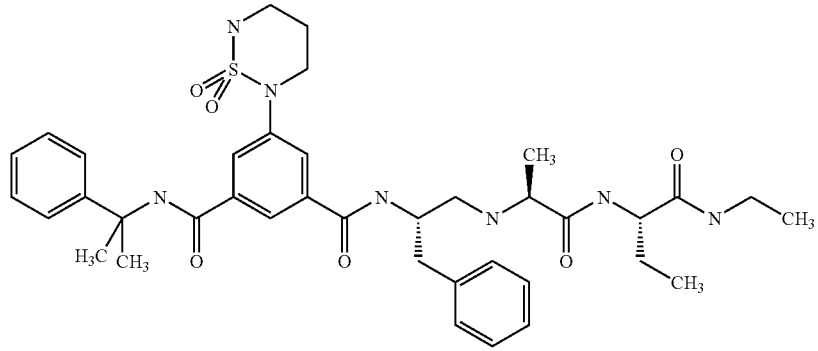
(221)

(222)
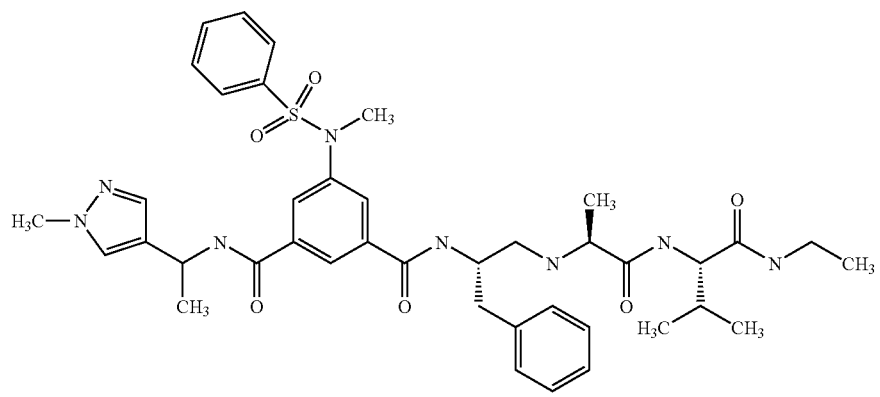
(223)
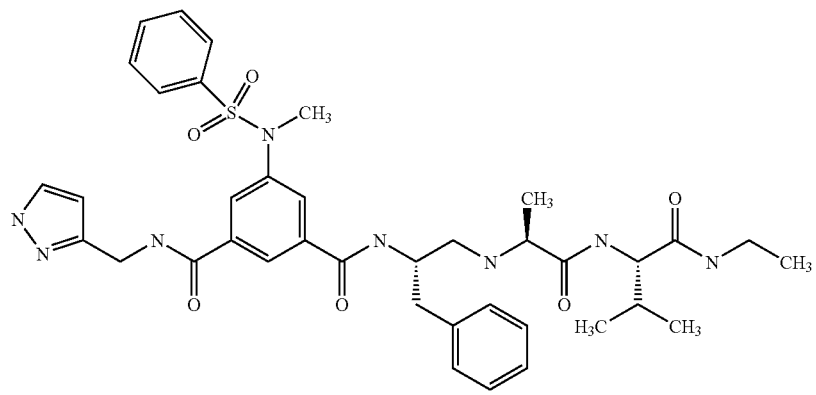
(224)
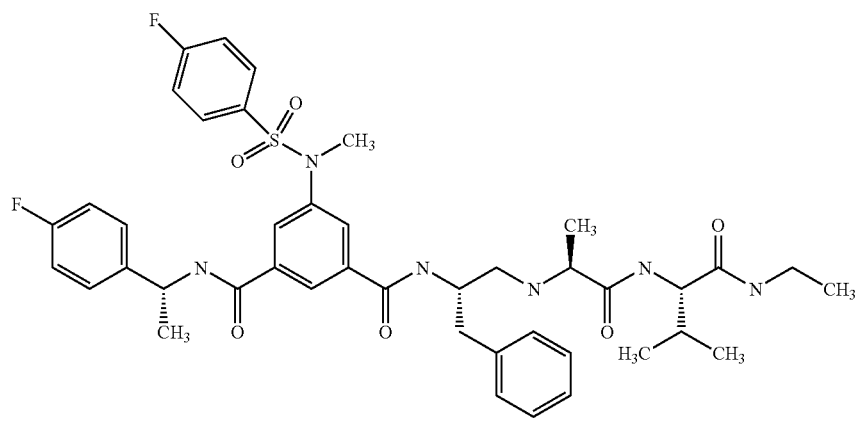
(225)
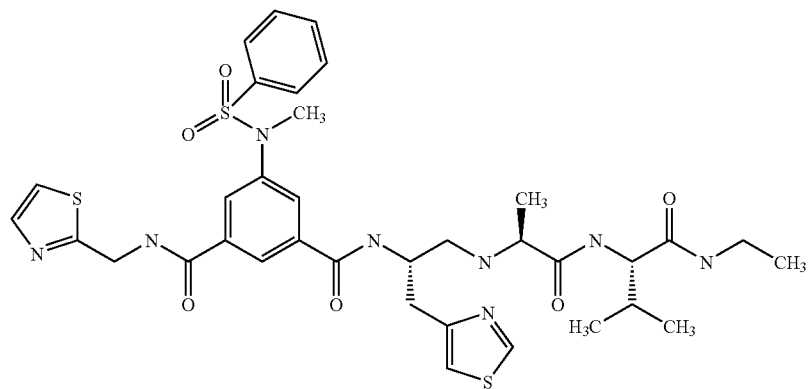

(226)
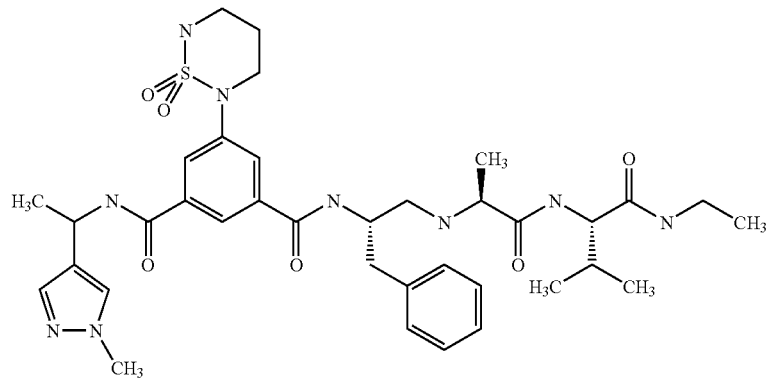
(227)
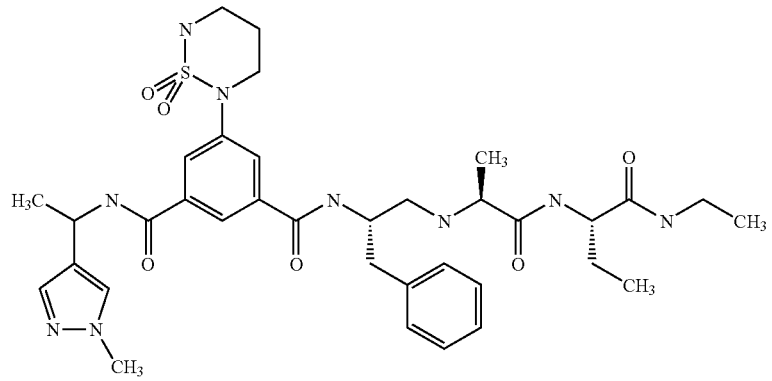
(228)
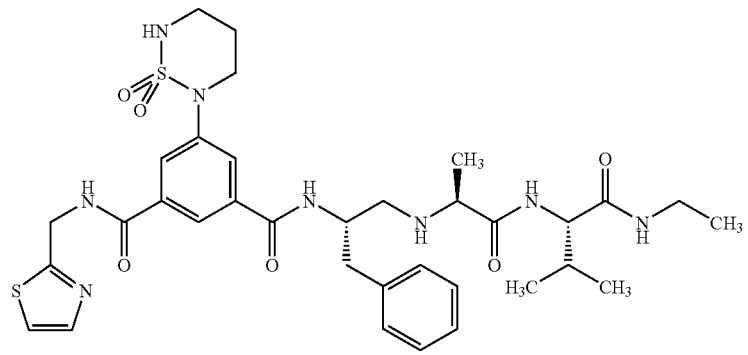
(229)
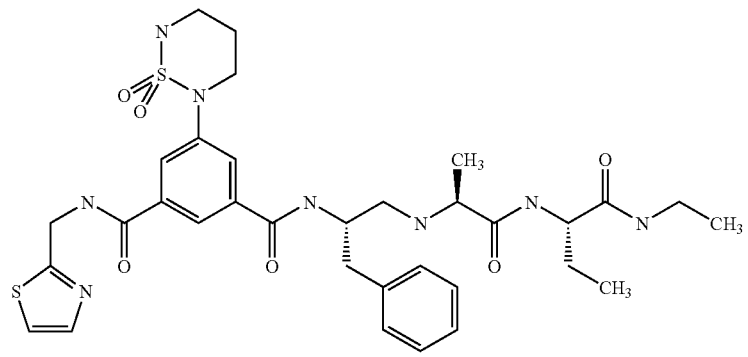

-continued
(230)
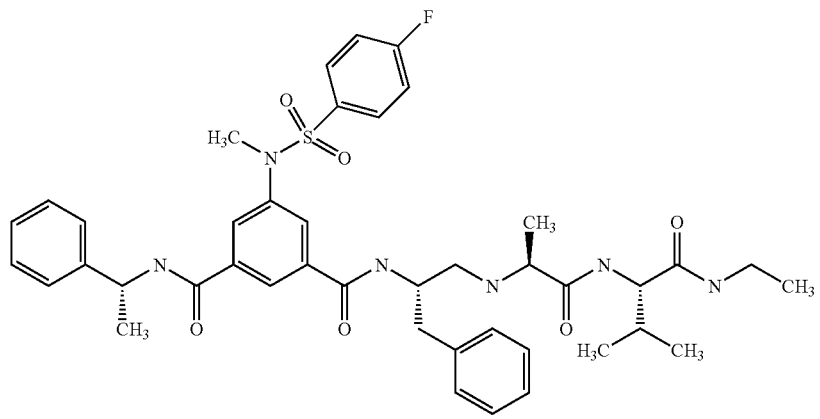
(231)
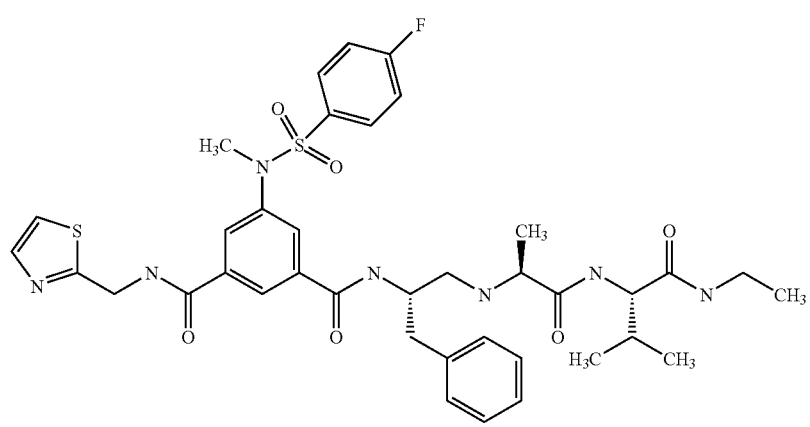
(232)
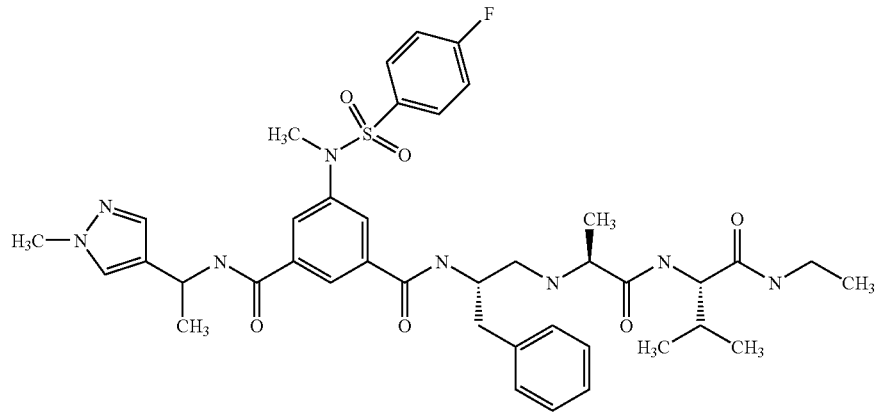

-continued
(233)
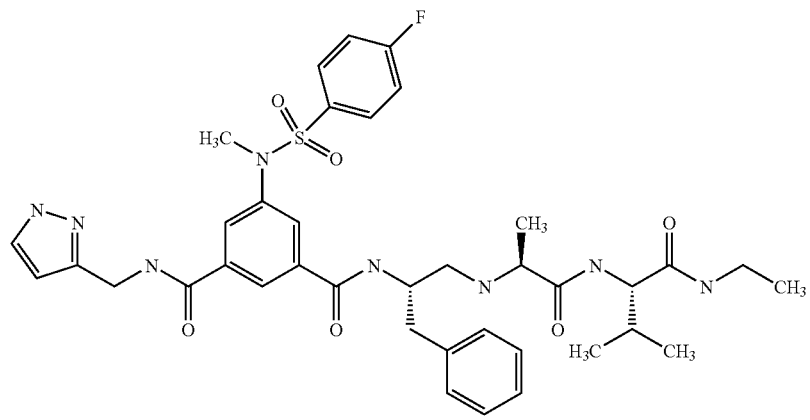
(234)
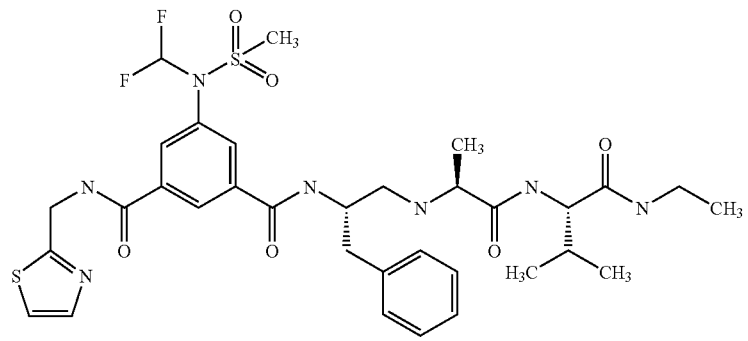
(235)
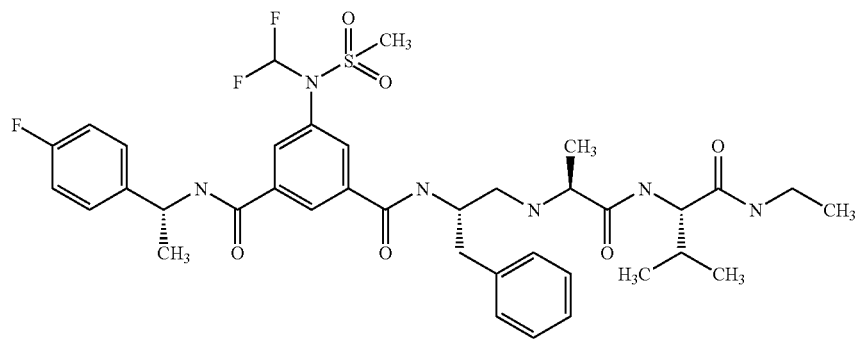
(236)
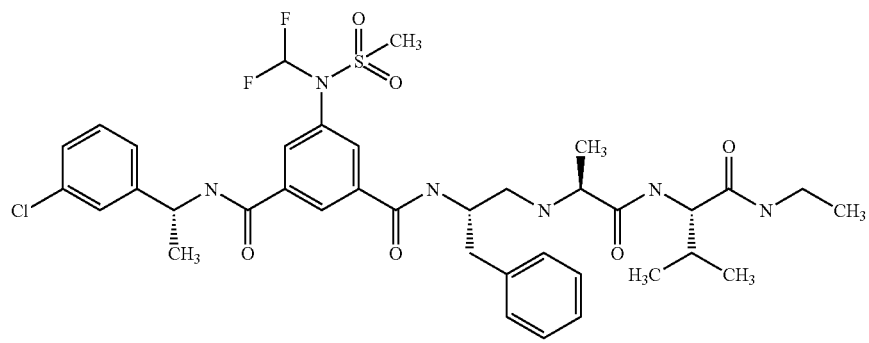

-continued
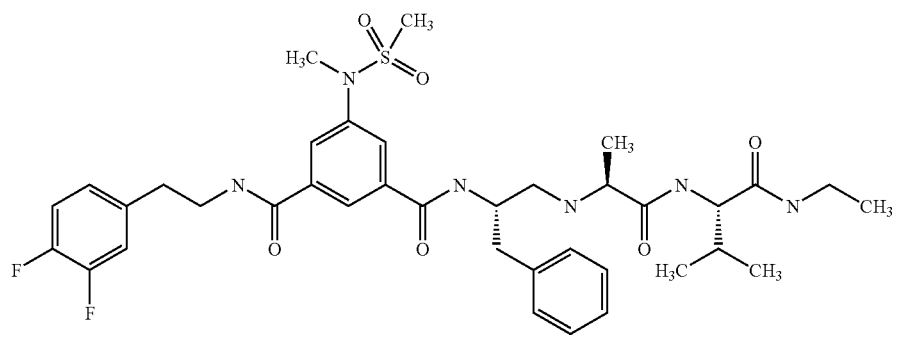
(237)
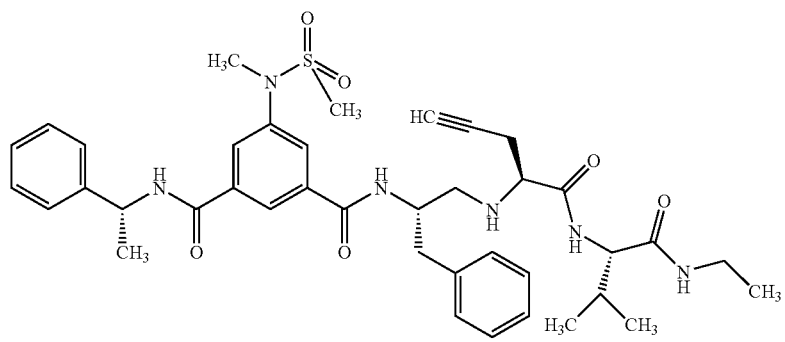
(238)
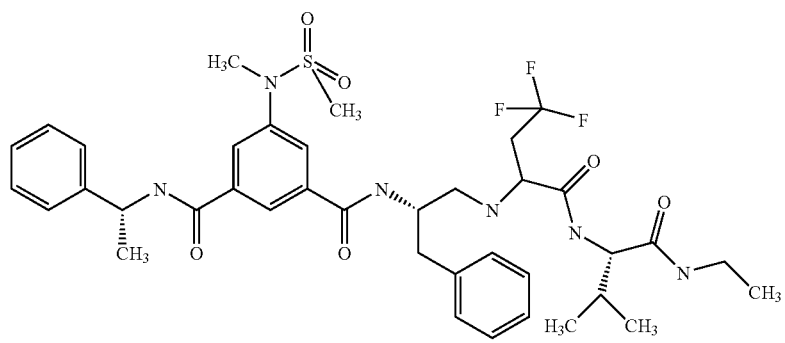
(239)
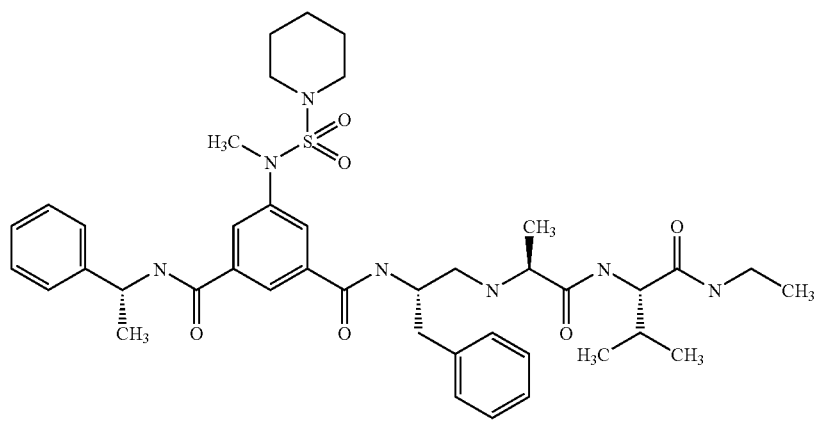
(240)

(241)
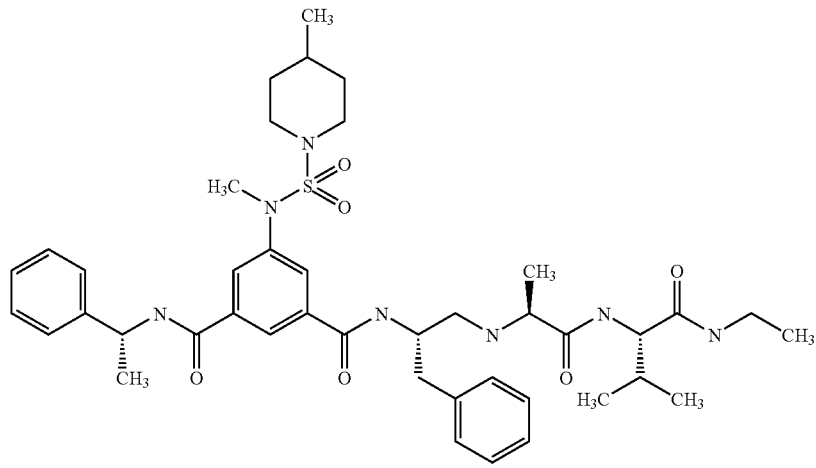
(242)
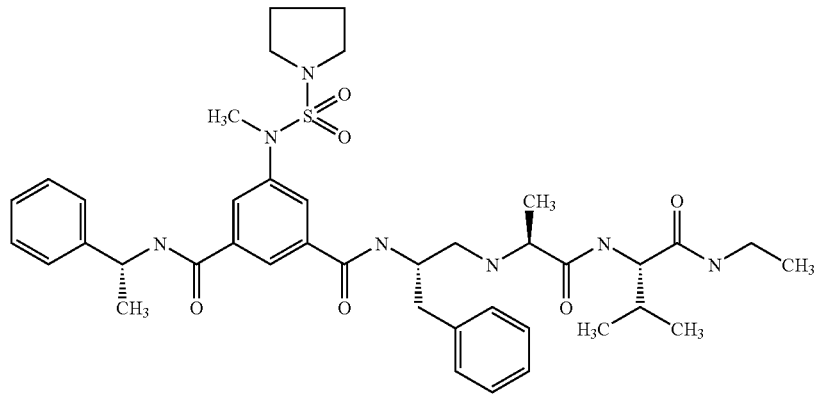
(243)
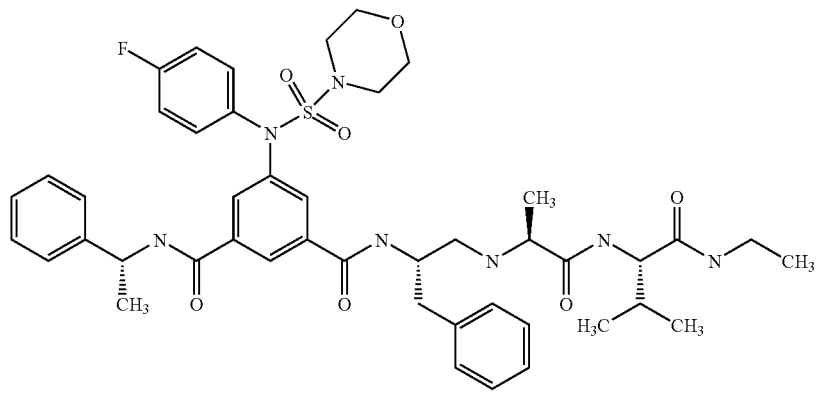
(244)
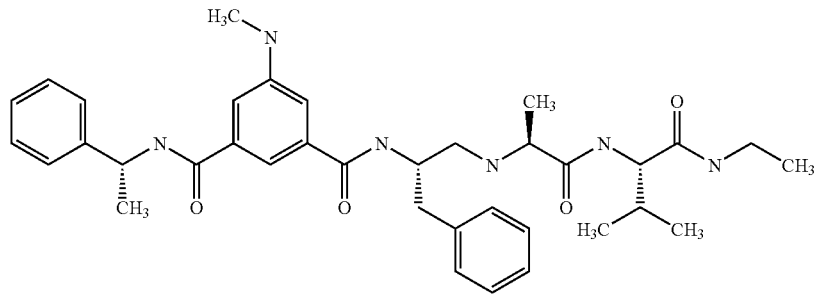

(245)
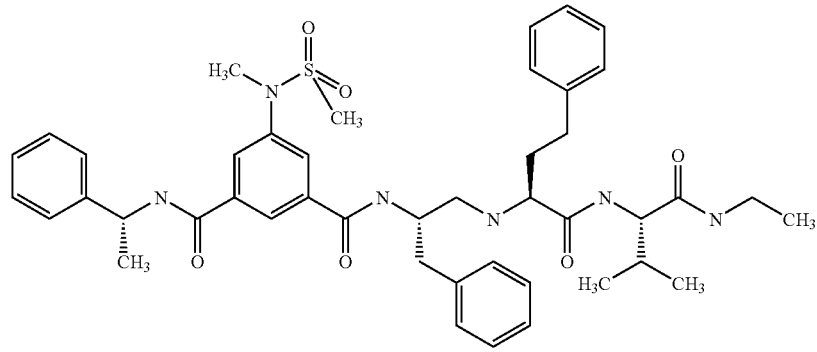
(246)
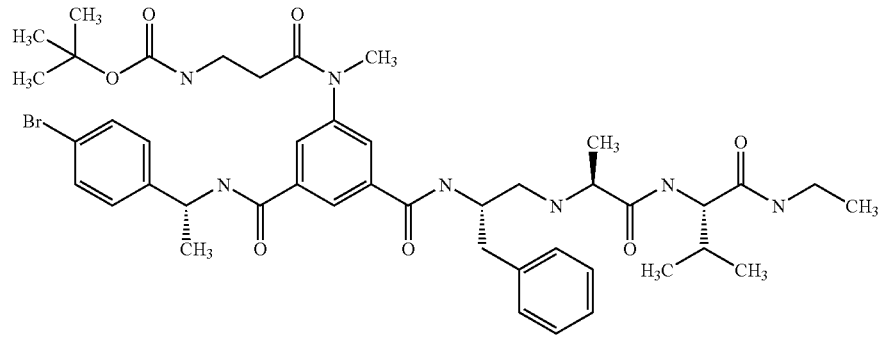
(247)
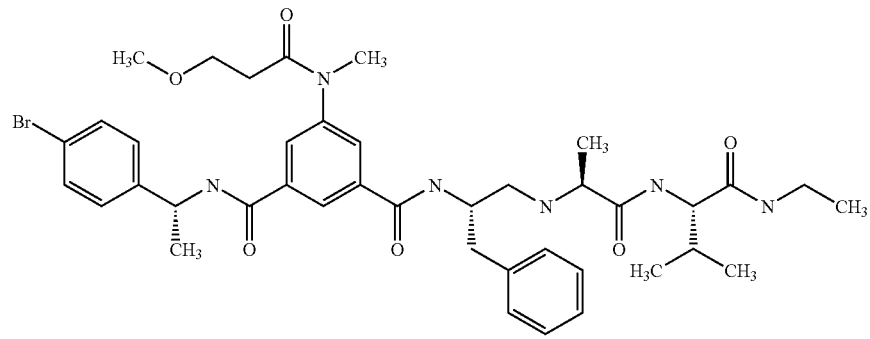
(248)
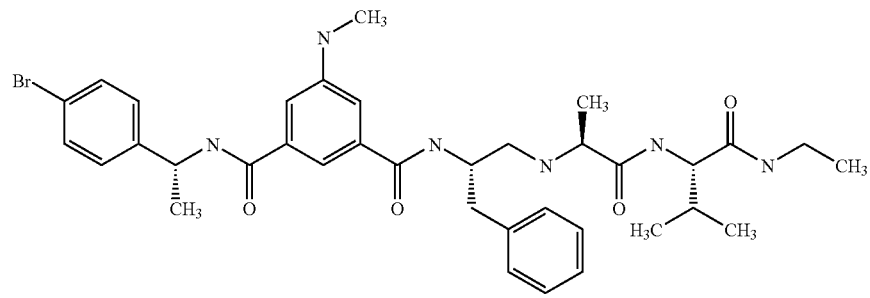

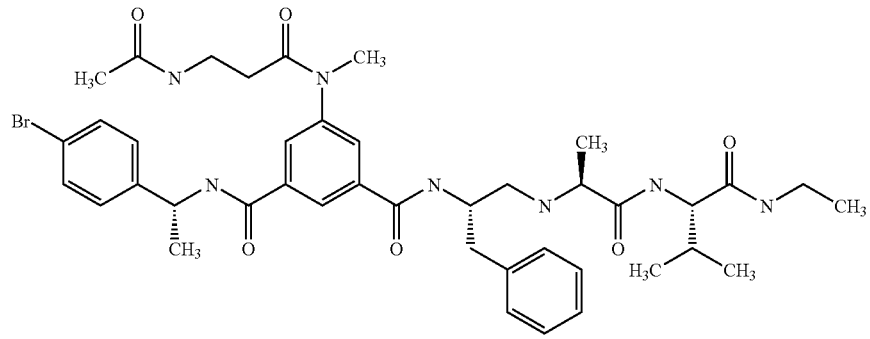
(249)
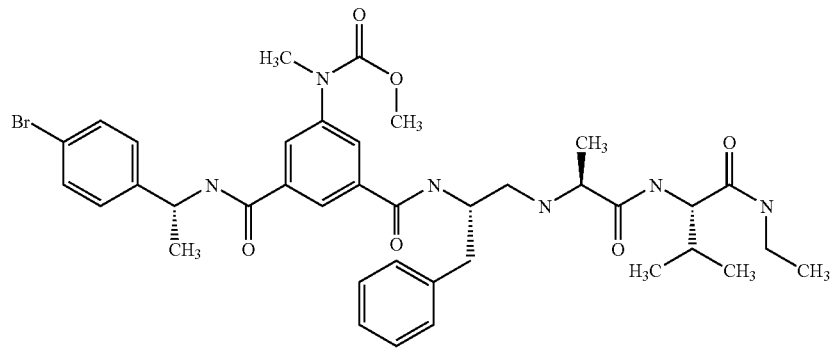
(250)
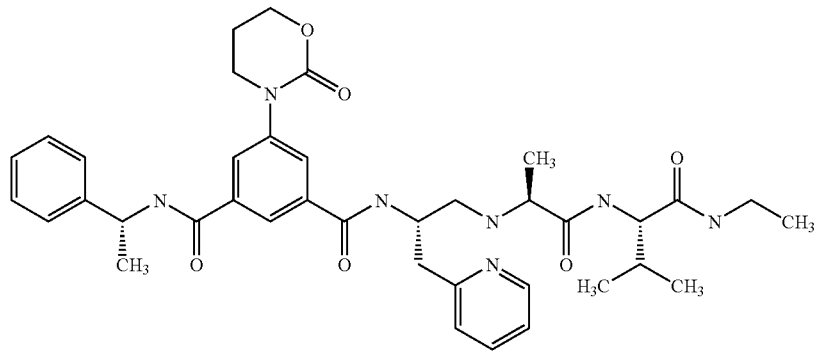
(251)
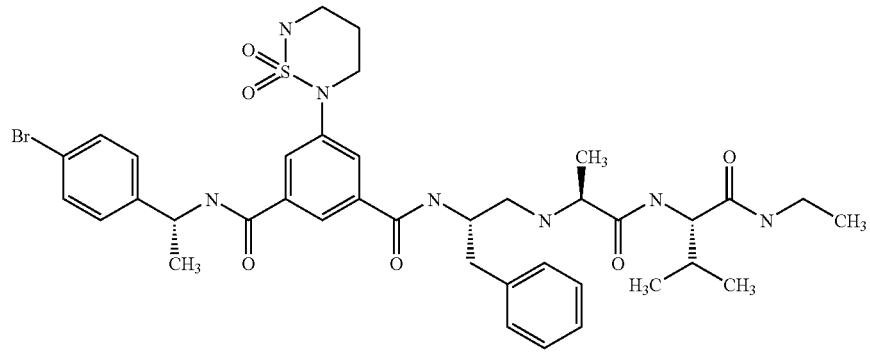
(252)

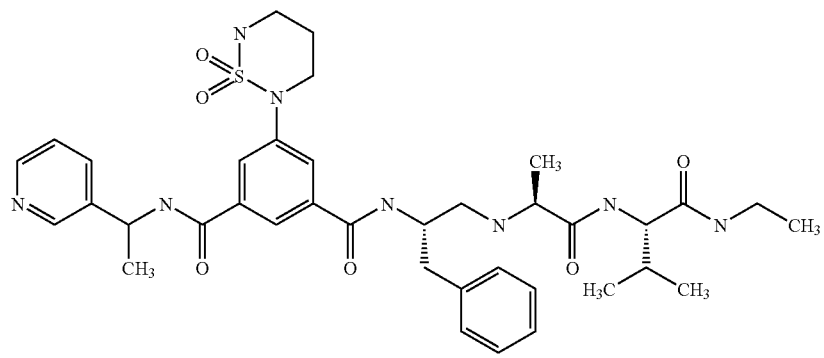
(253)
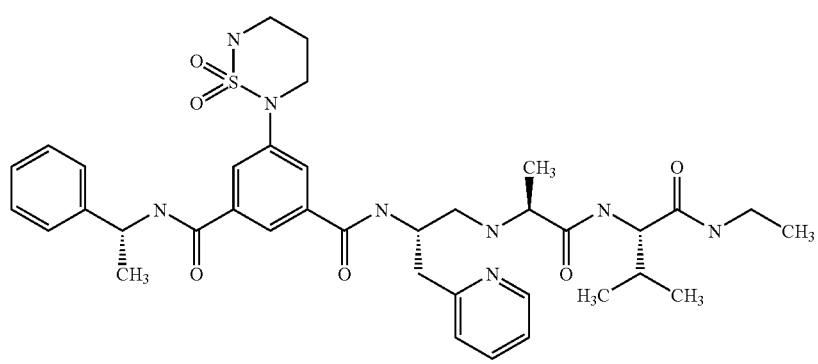
(254)
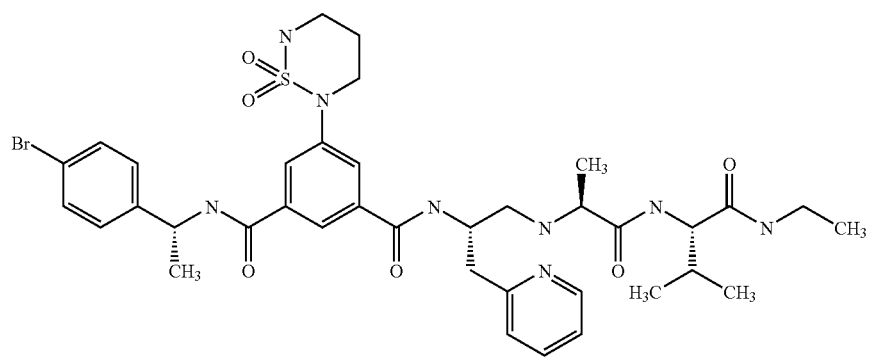
(255)
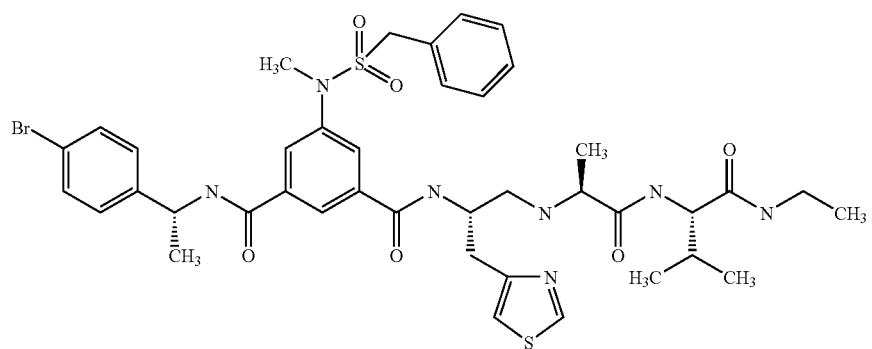
(256)

-continued
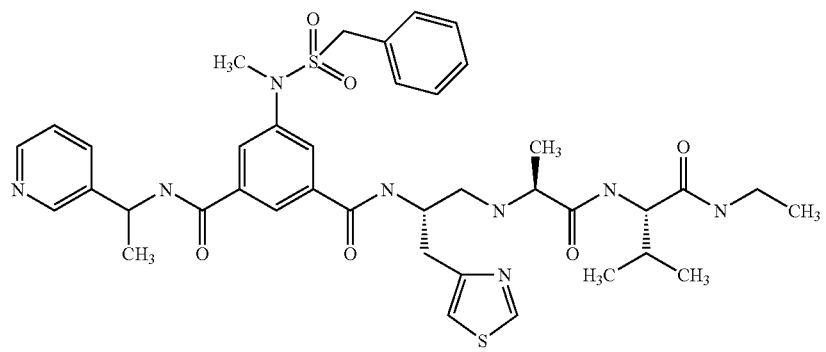
(257)
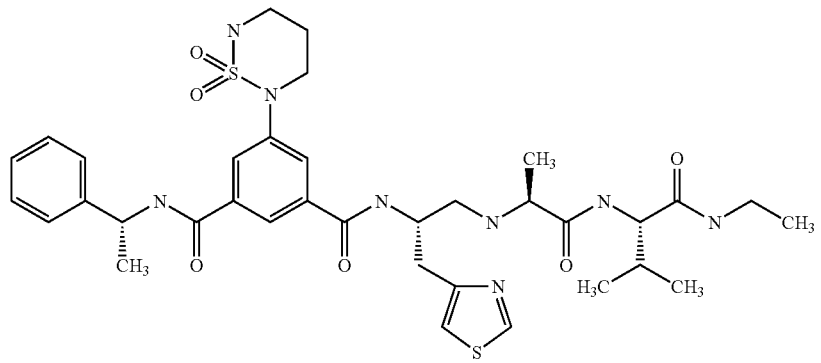
(258)
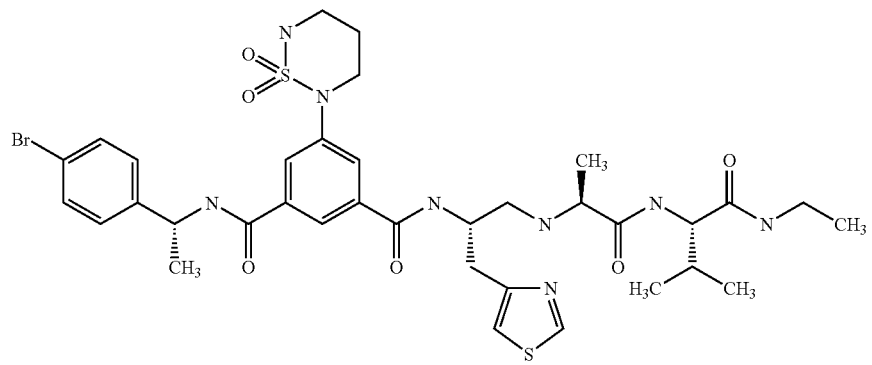
(259)
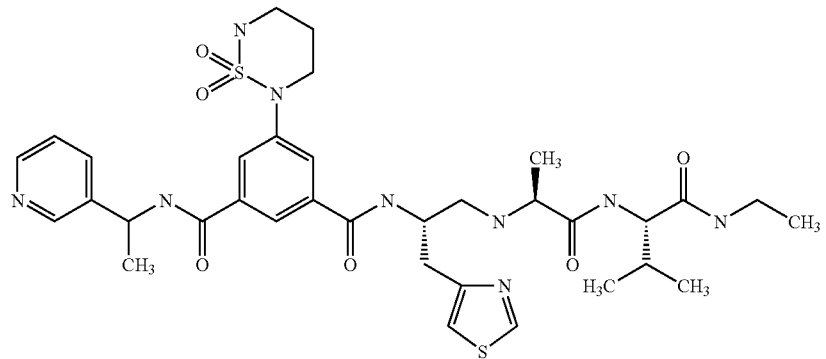
(260)

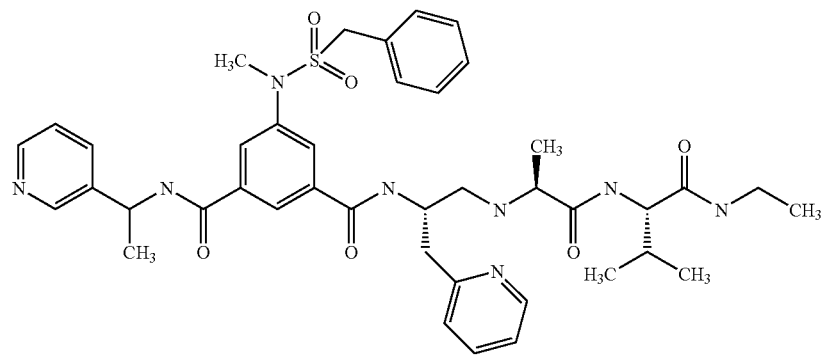
(261)
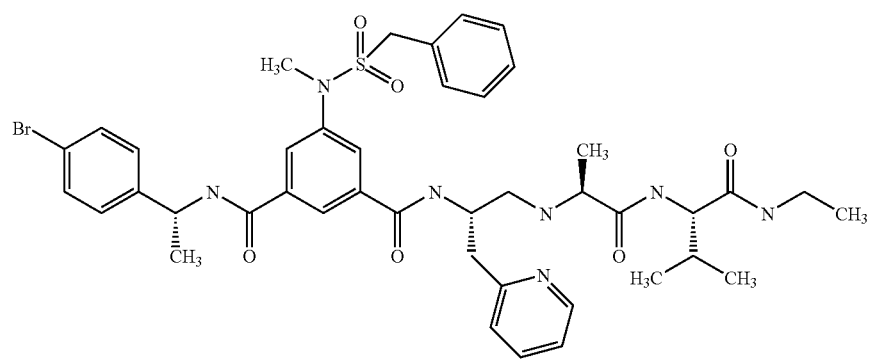
(262)
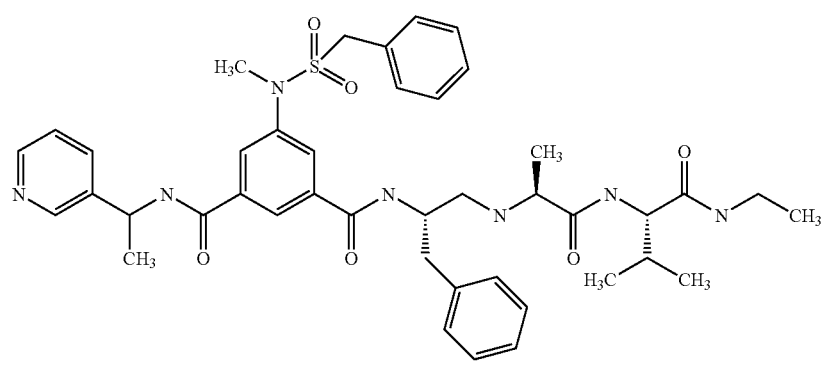
(263)
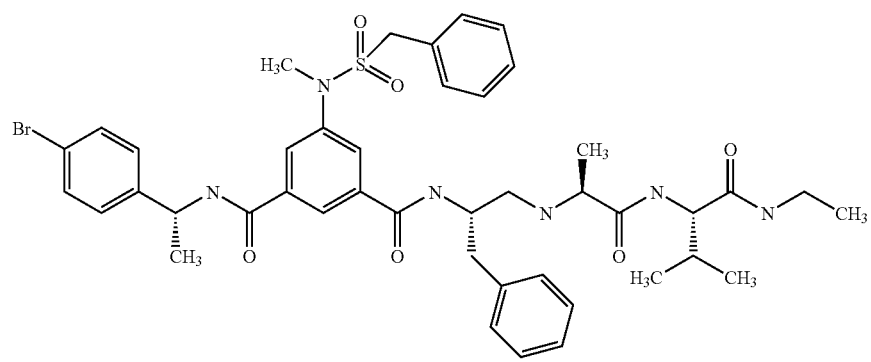
(264)

(265)
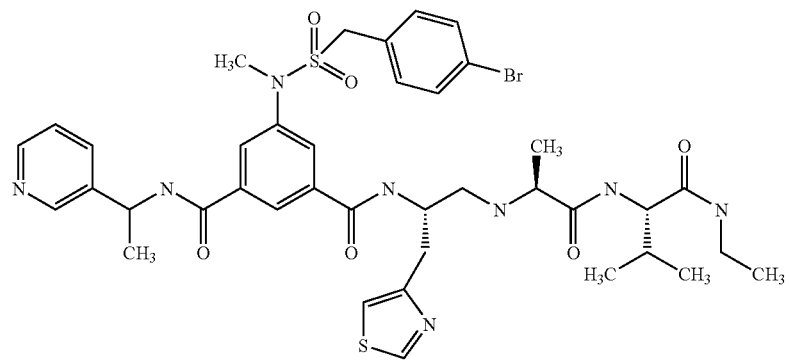
(266)
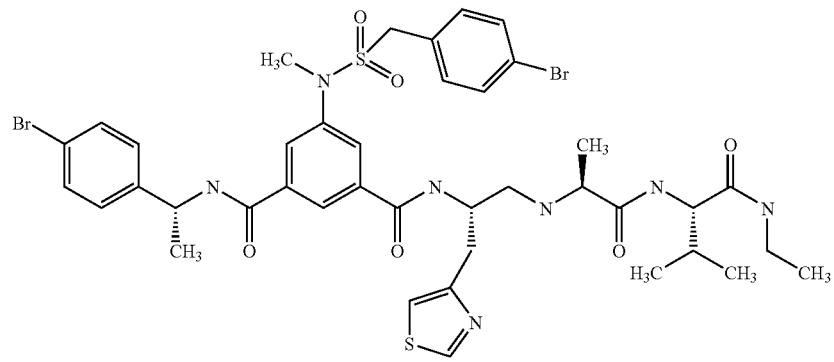
(267)
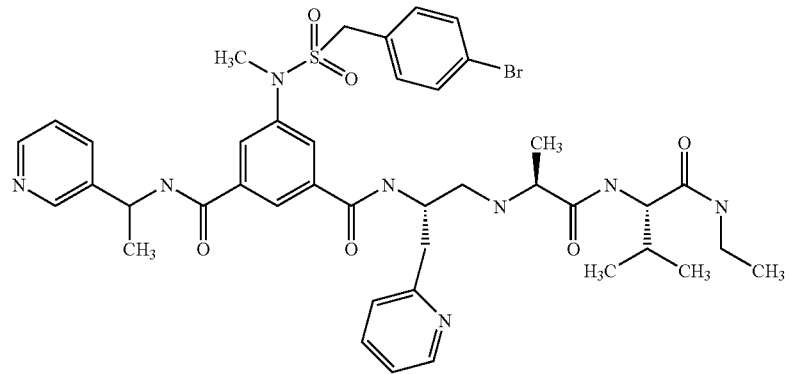
(268)
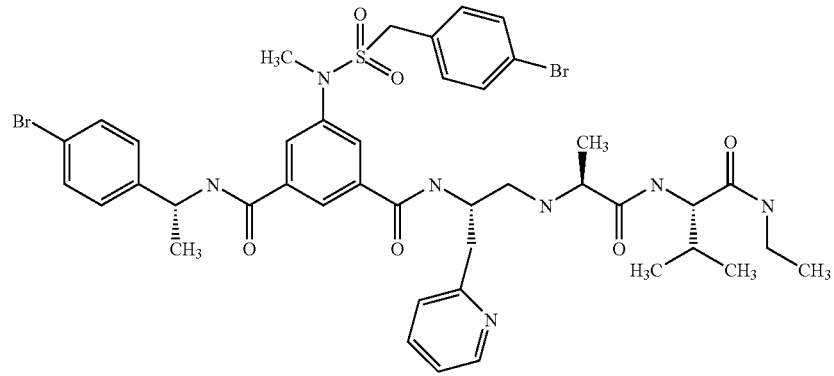

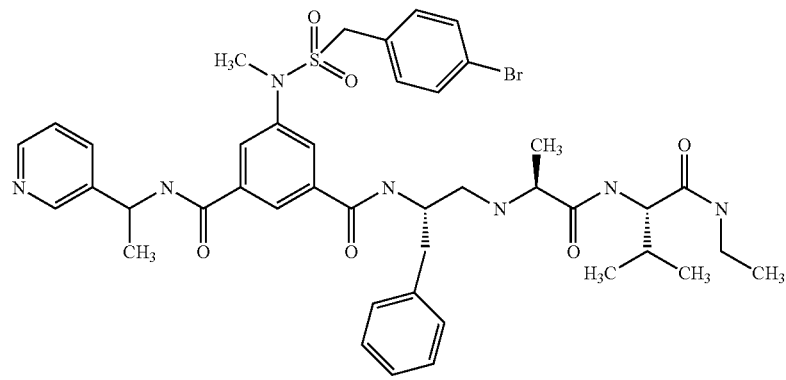
(269)
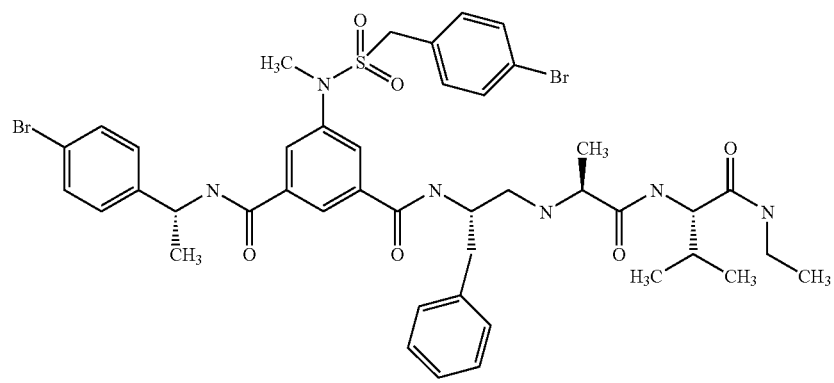
(270)
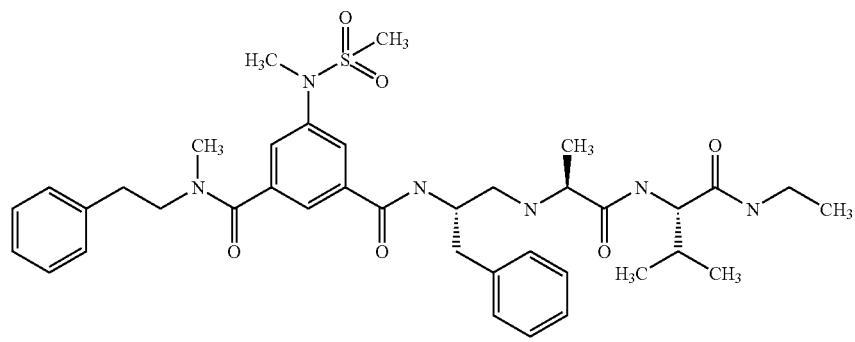
(271)
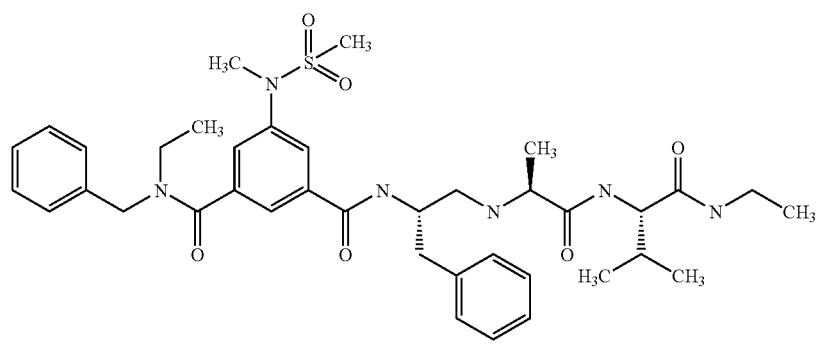
(272)

-continued
(273)
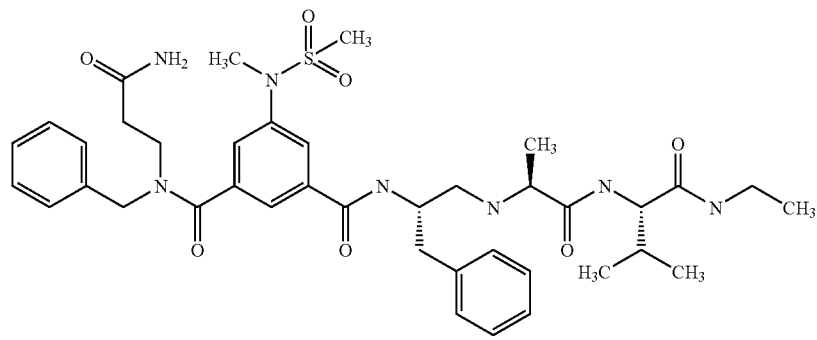
(274)
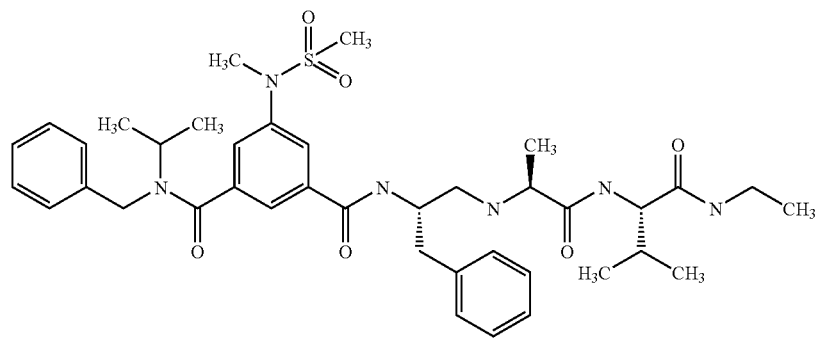
(275)
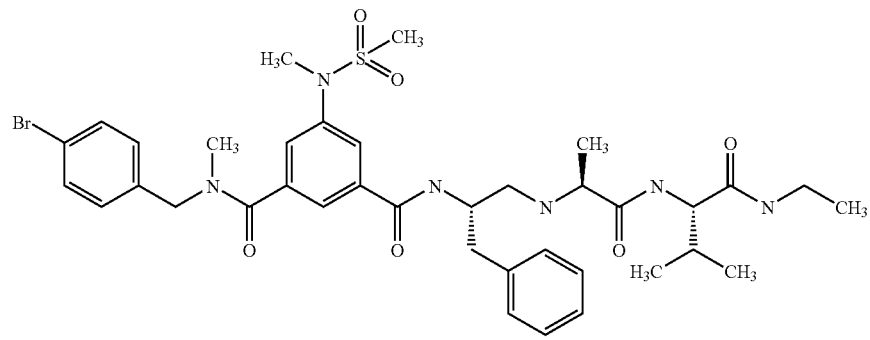
(276)
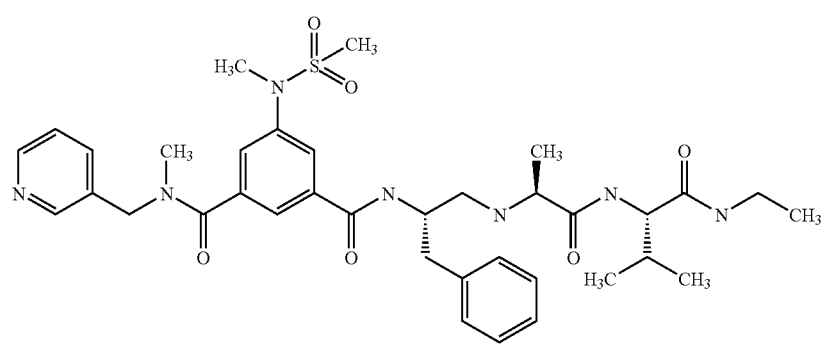

-continued
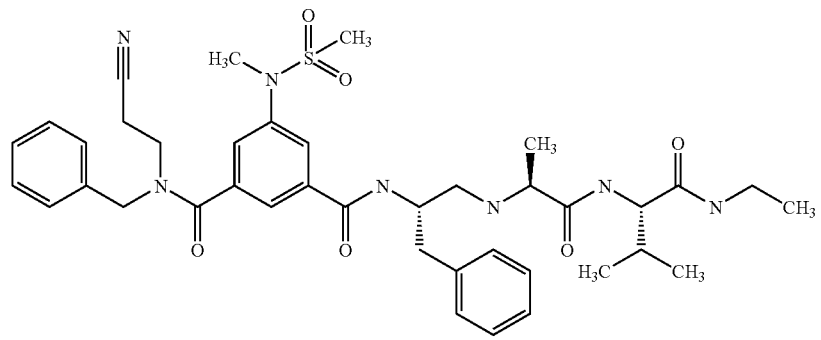
(277)
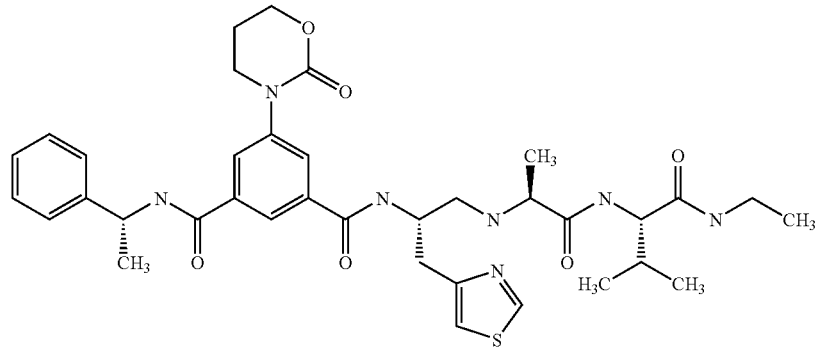
(278)
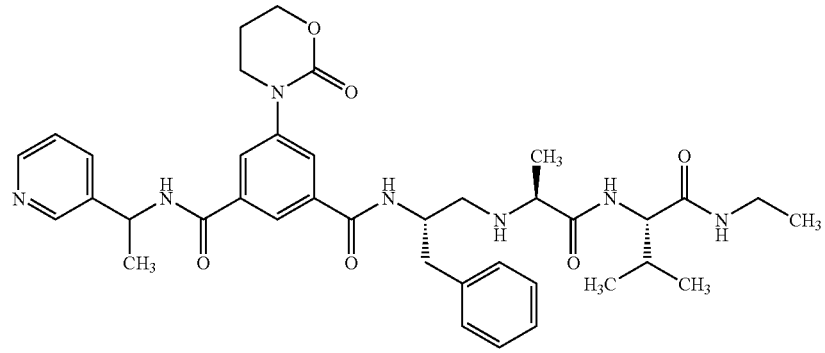
(279)
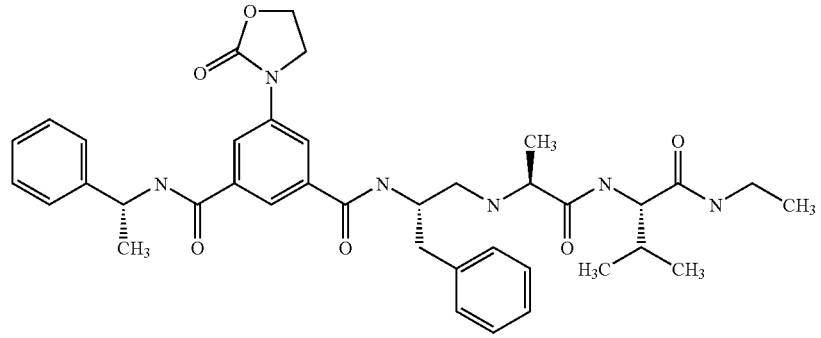
(280)

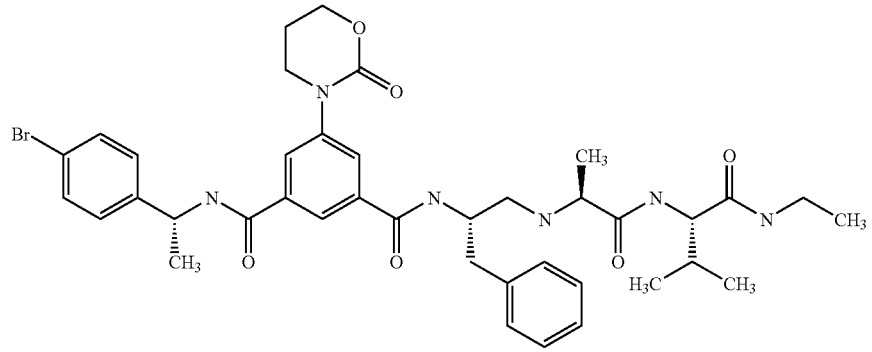
(281)
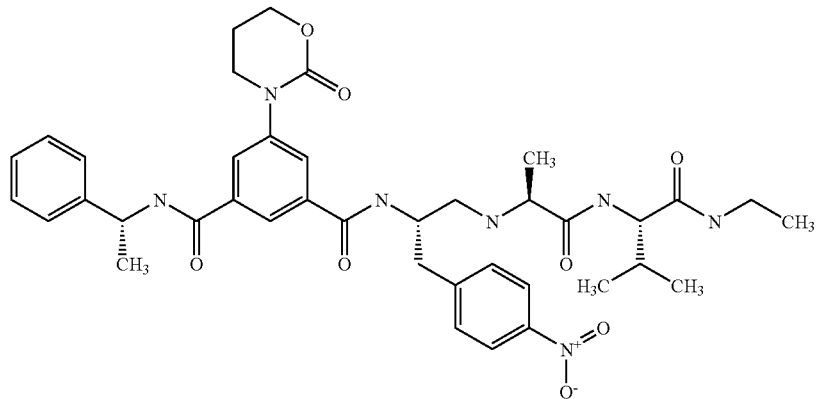
(282)
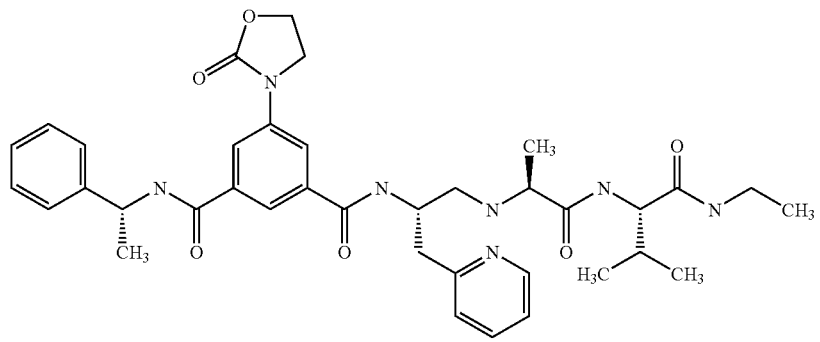
(283)
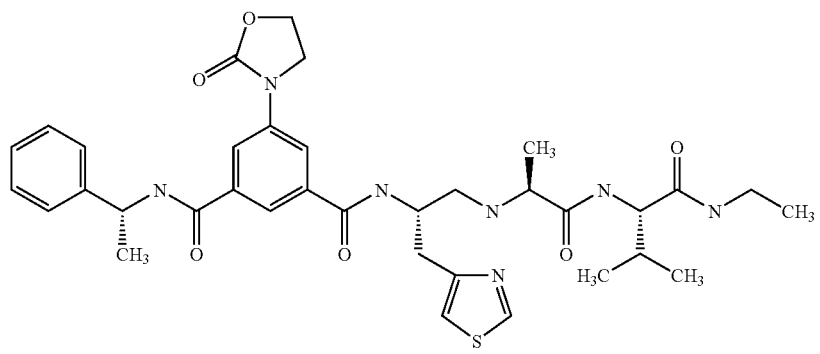
(284)

(285)
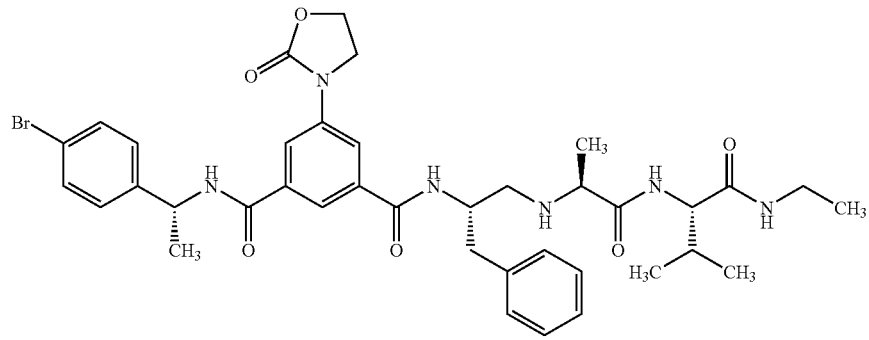
(286)
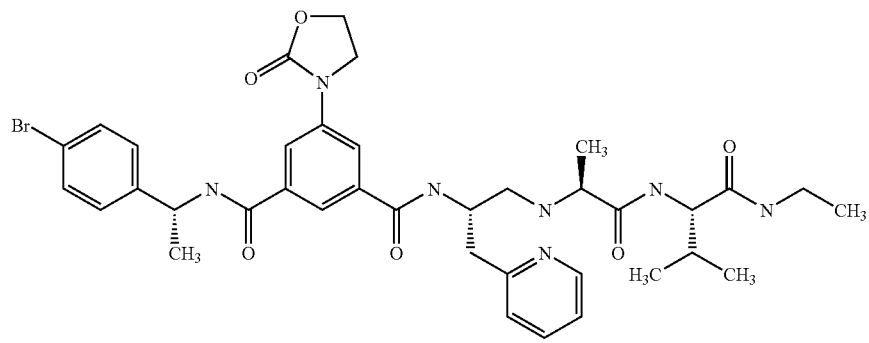
(287)
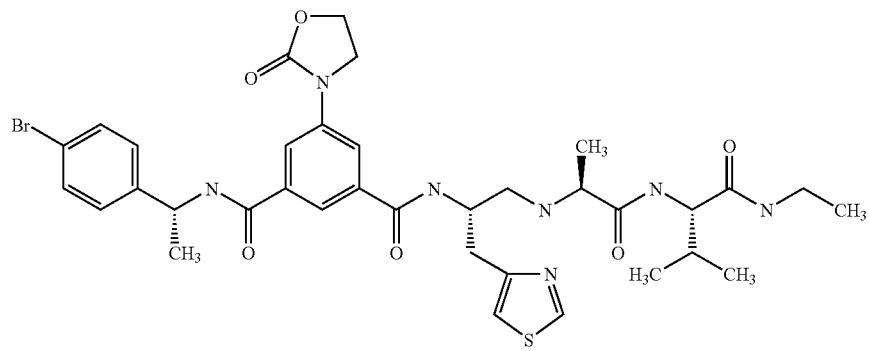
(288)
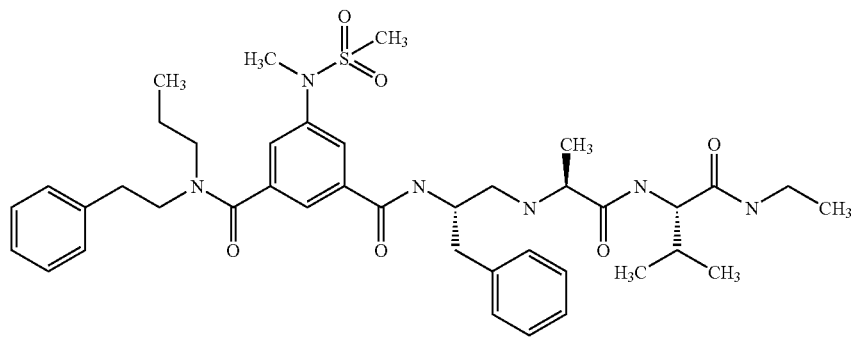

(289)
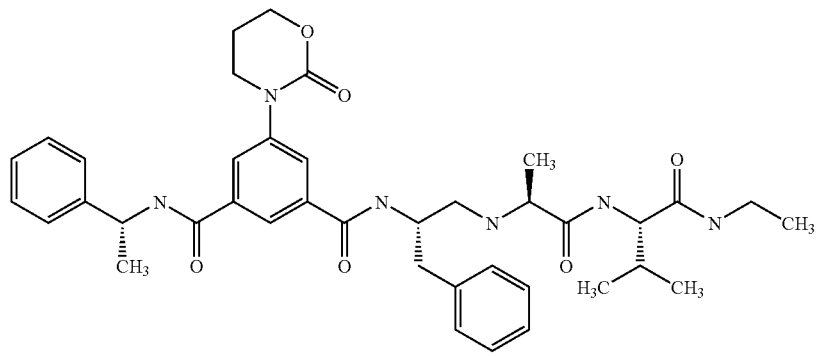
(290)
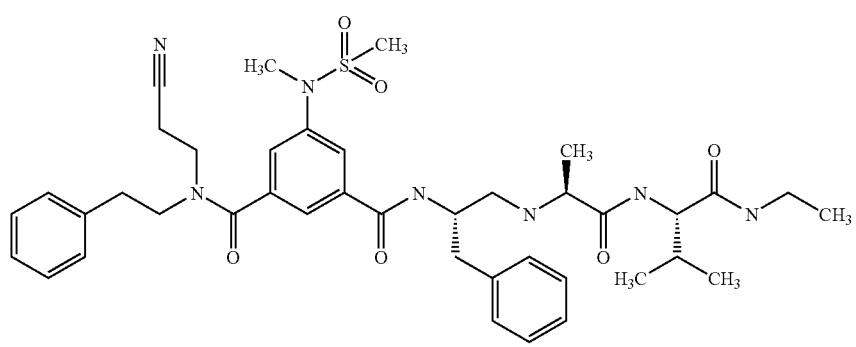
(291)
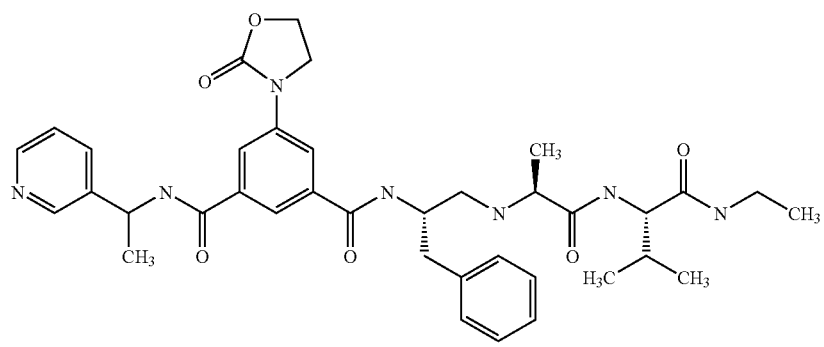
(292)
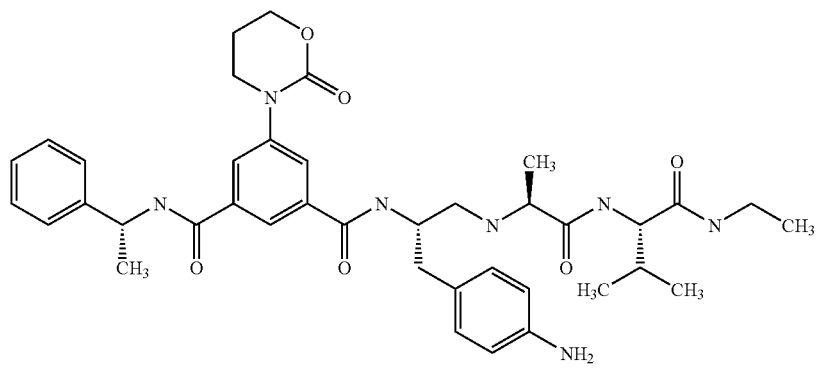

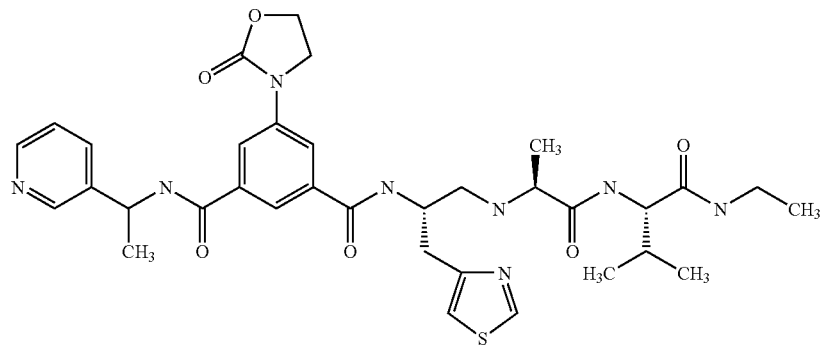
(293)
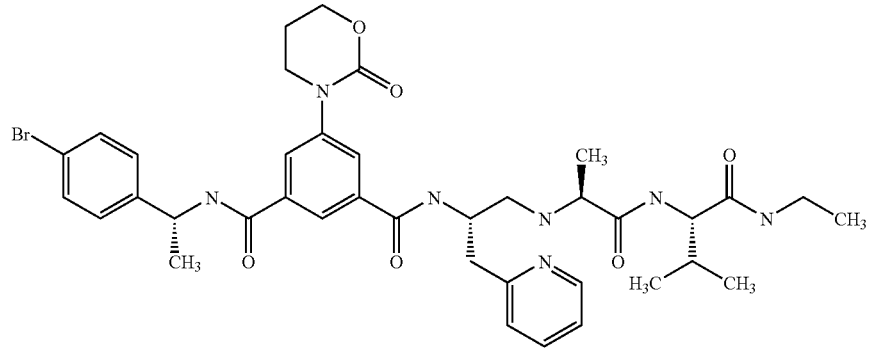
(294)
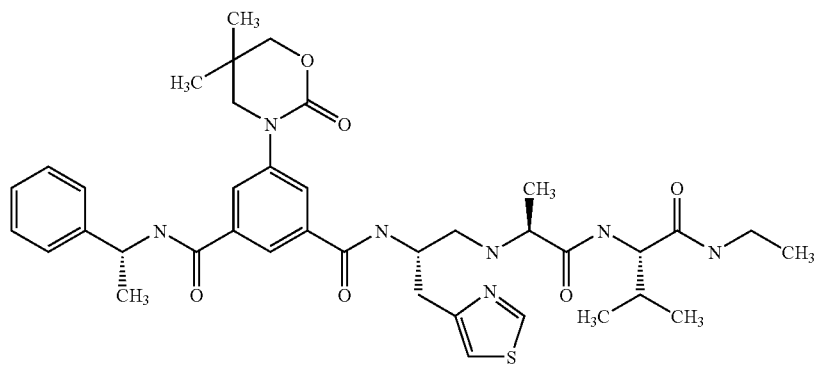
(295)
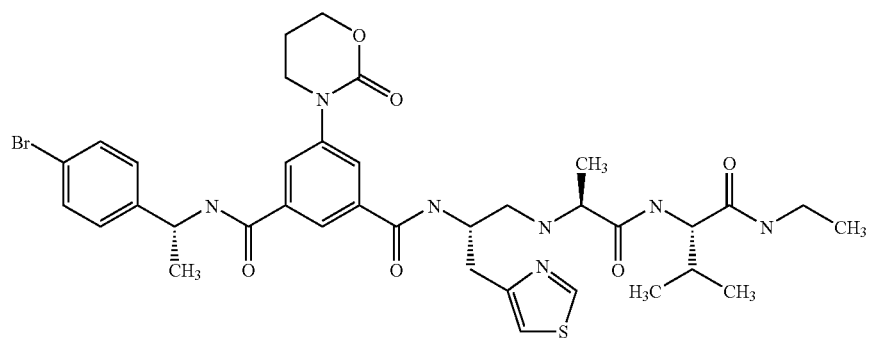
(296)

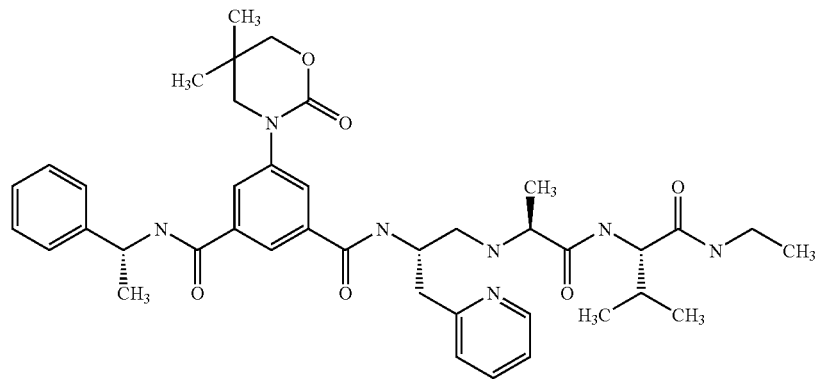
(297)
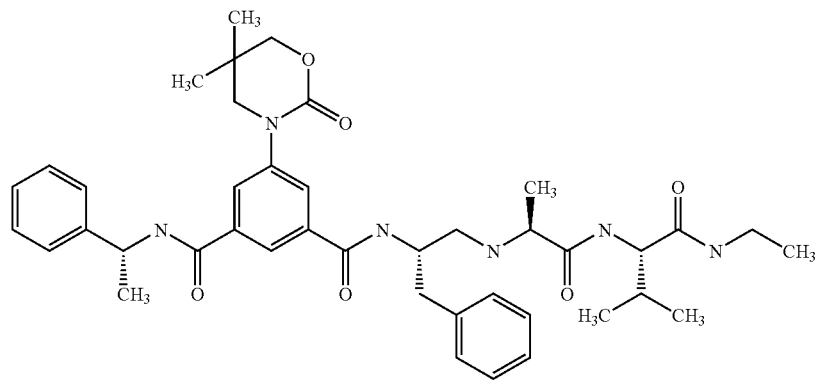
(298)
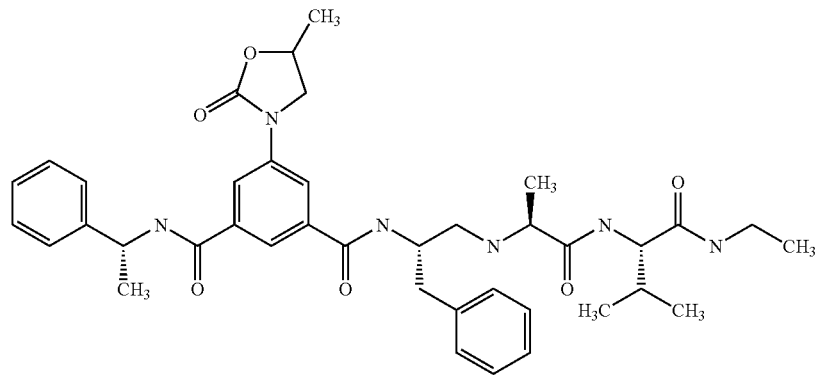
(299)
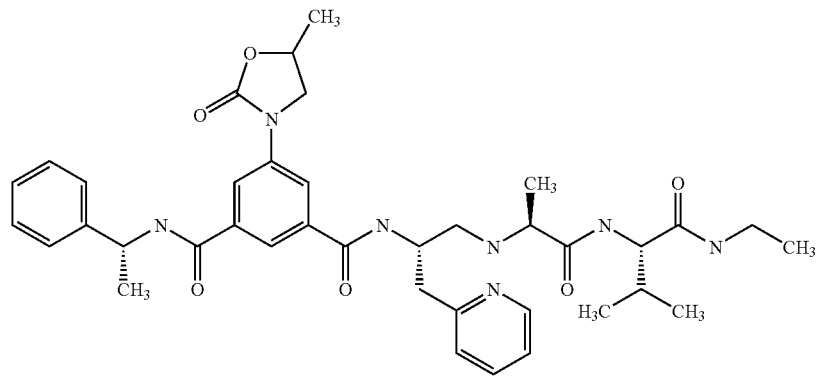
(300)

(301)
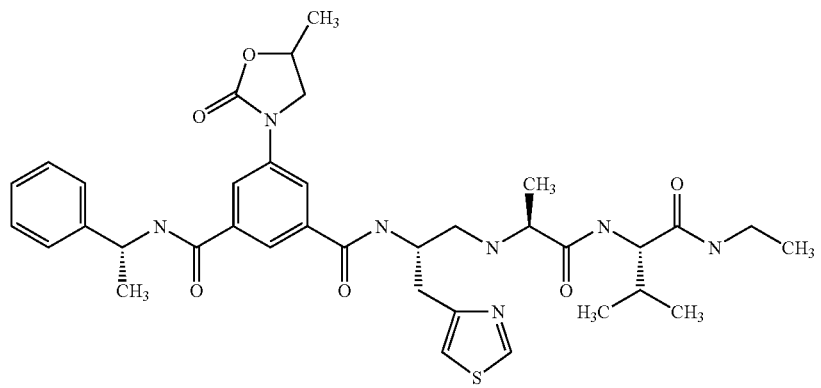
(302)
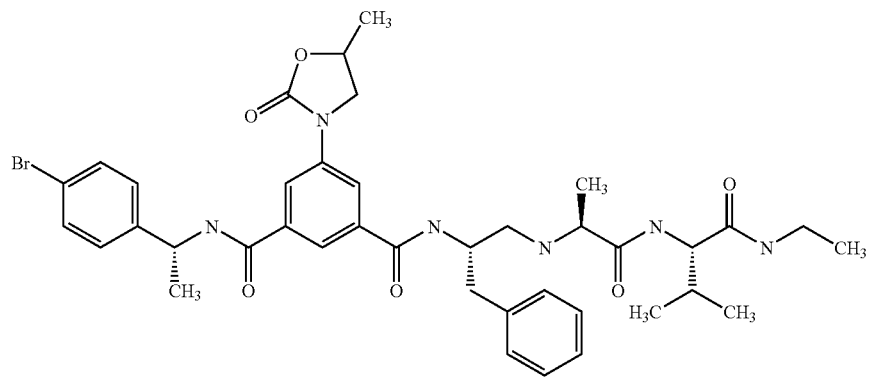
(303)
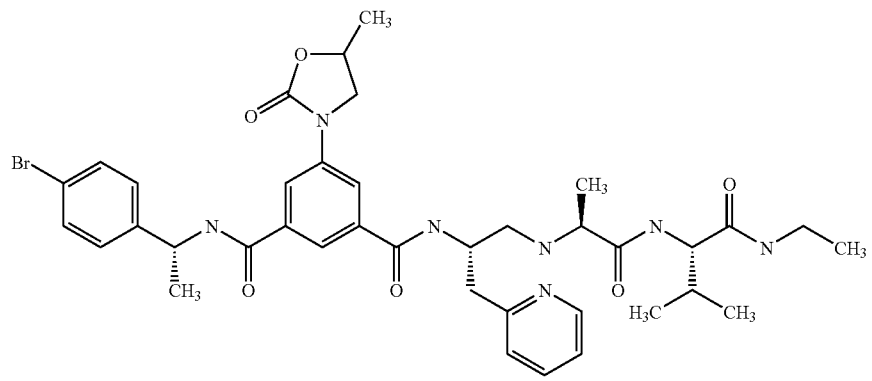
(304)
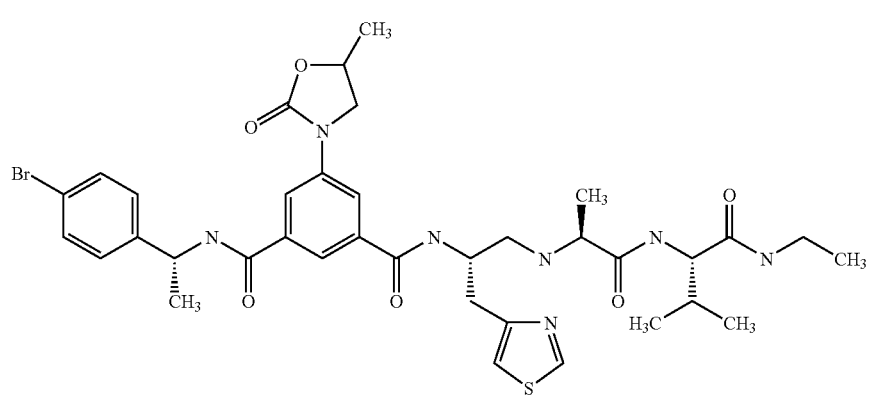

(305)
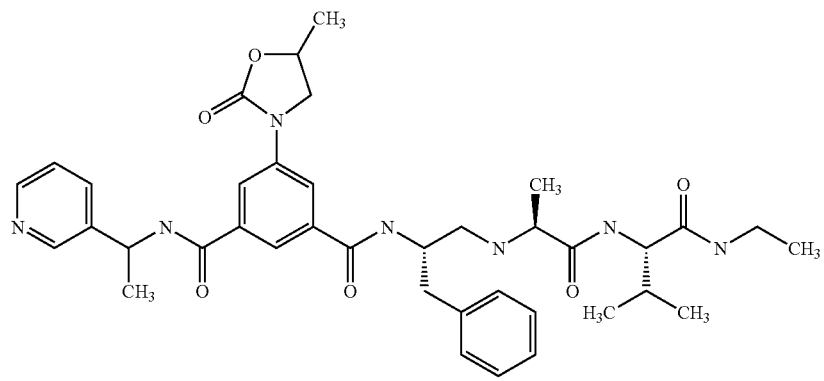
(306)
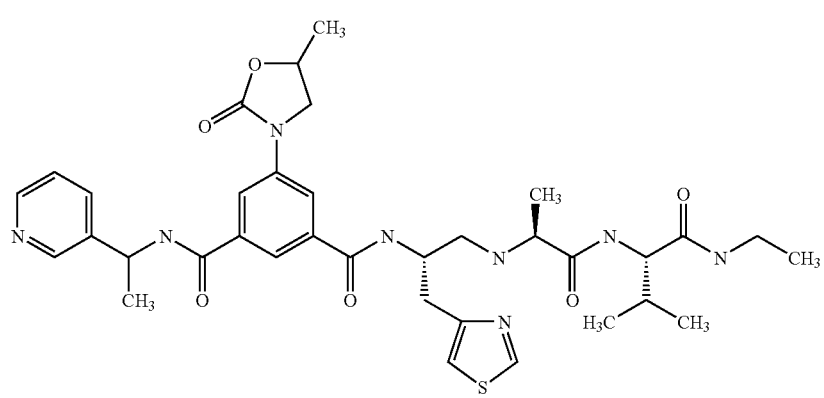
(307)
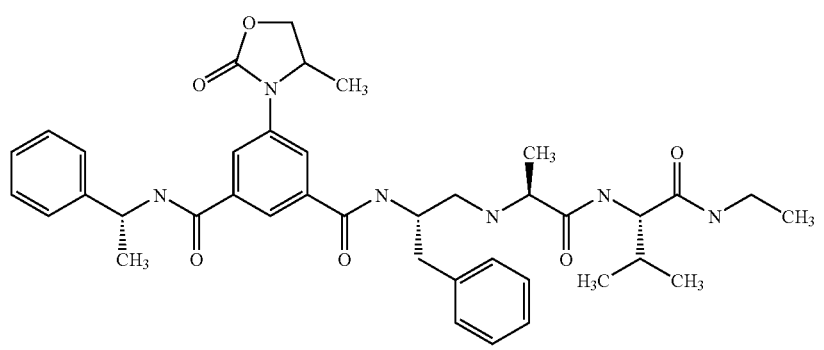
(308)
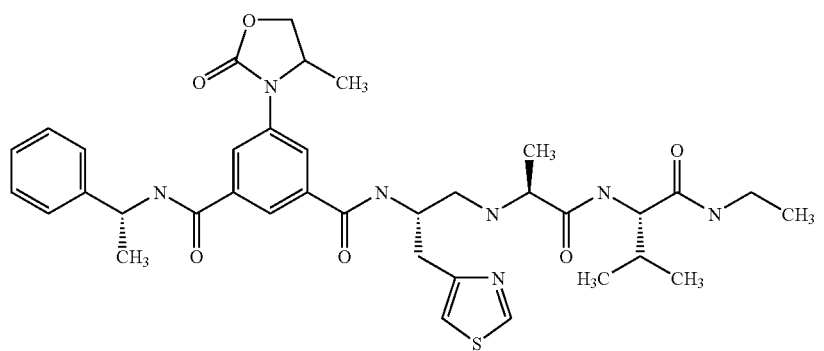

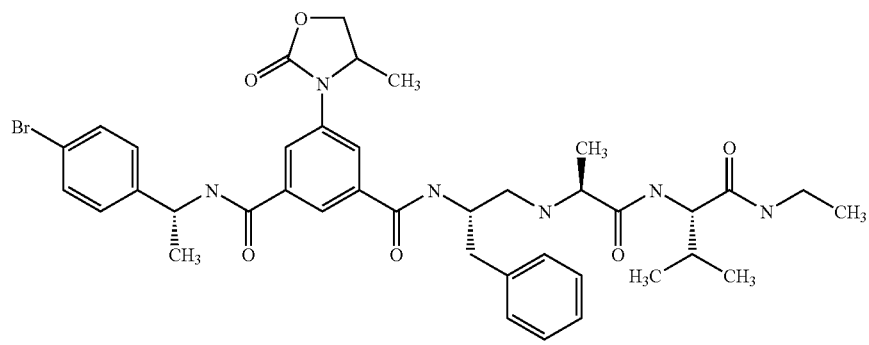
(309)
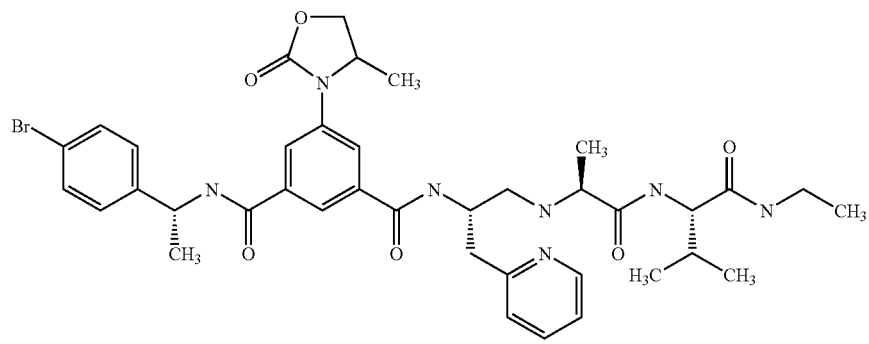
(310)
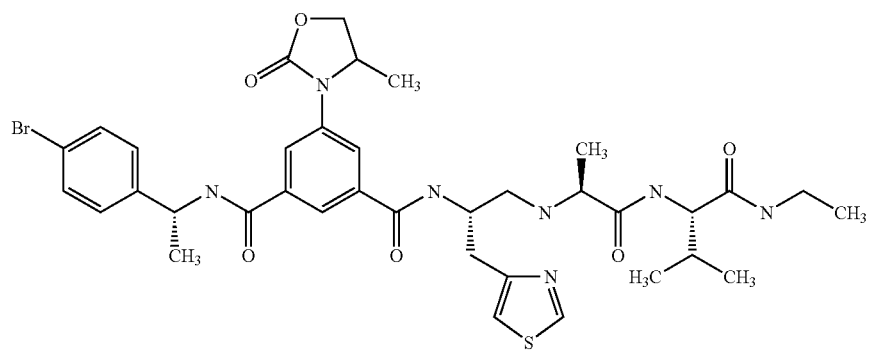
(311)
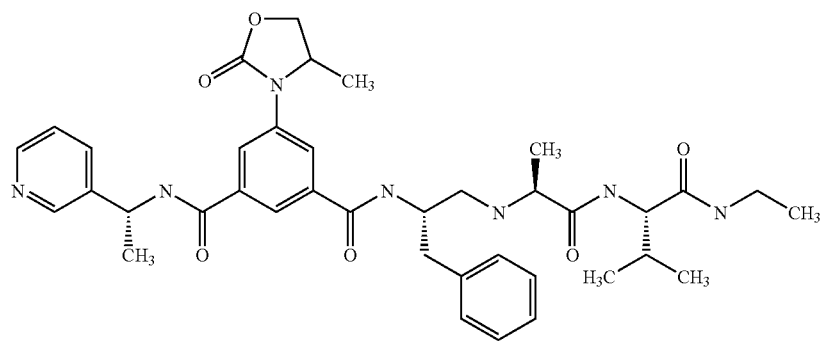
(312)

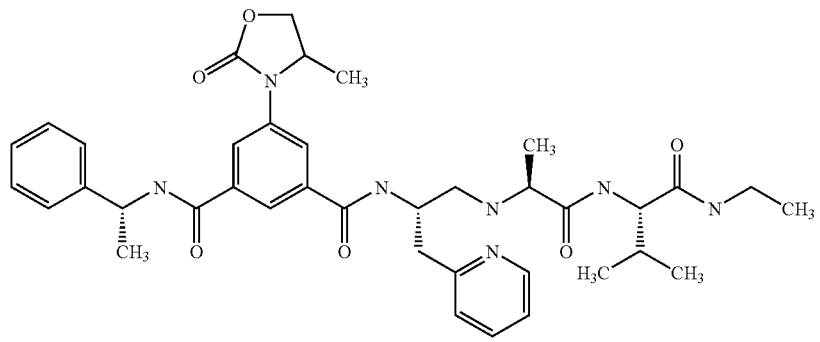
(313)
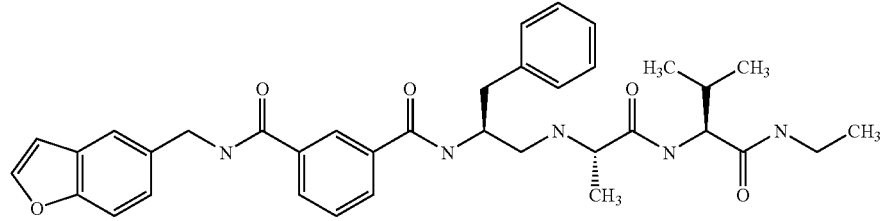
(314)
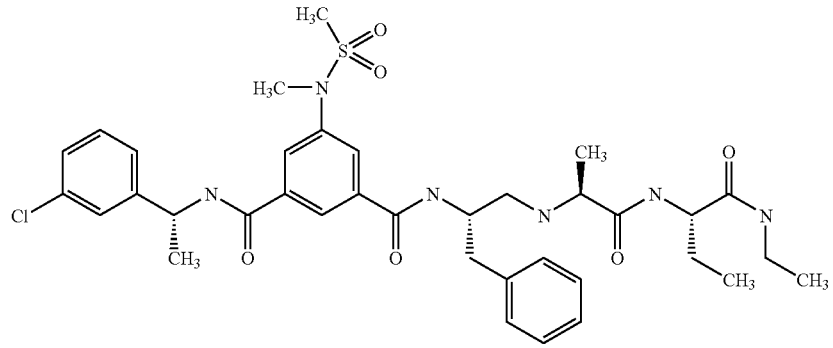
(315)
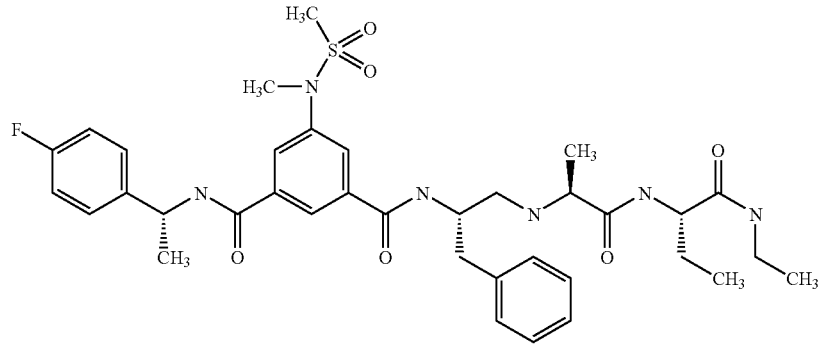
(316)
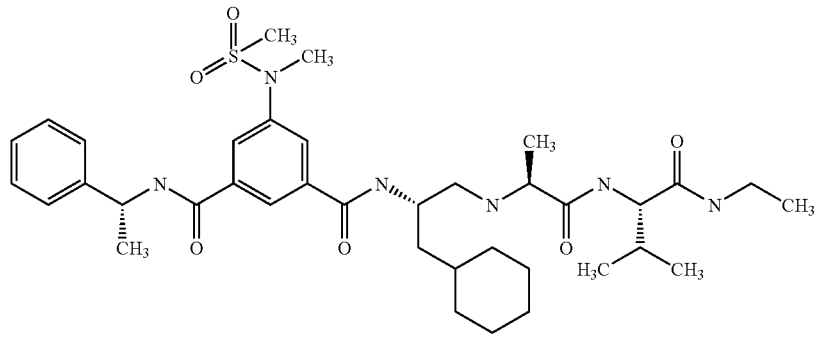
(317)

(318)
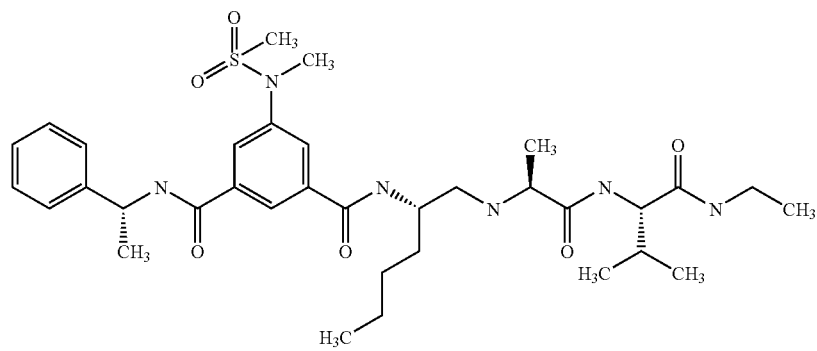
(319)
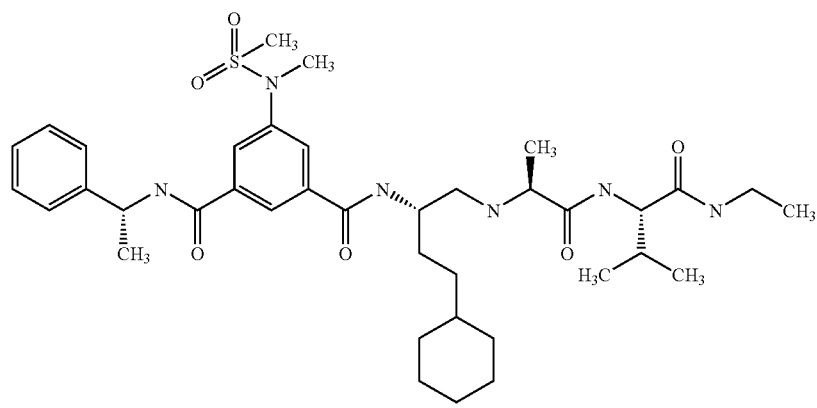
(320)
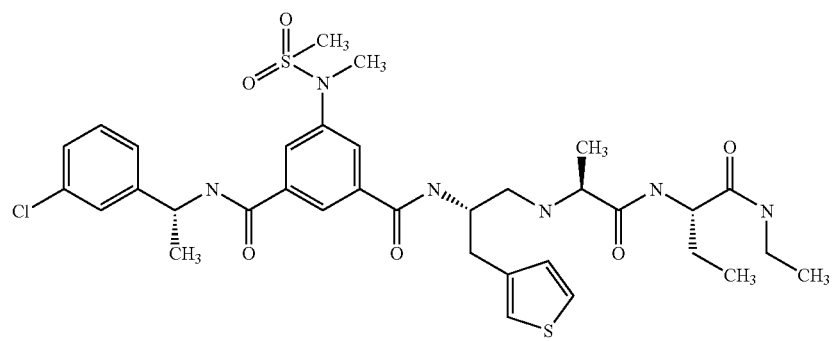
(321)
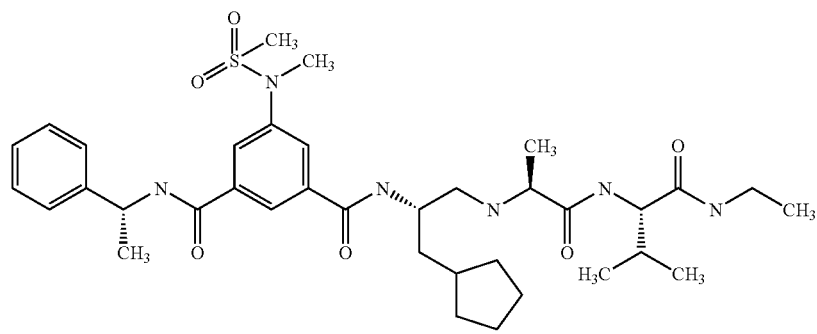

(322)
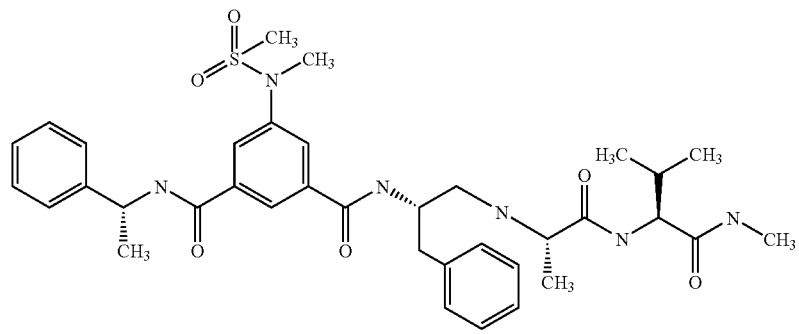
(323)
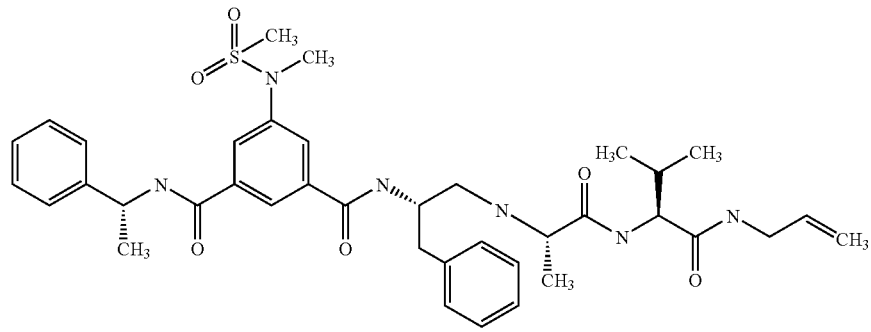
(324)
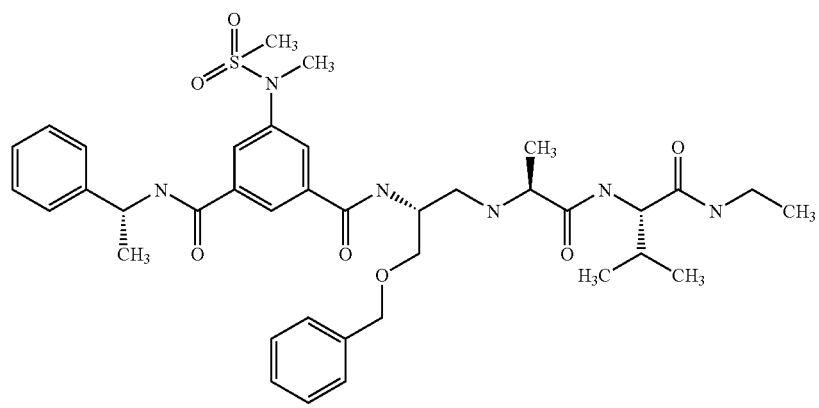
(325)
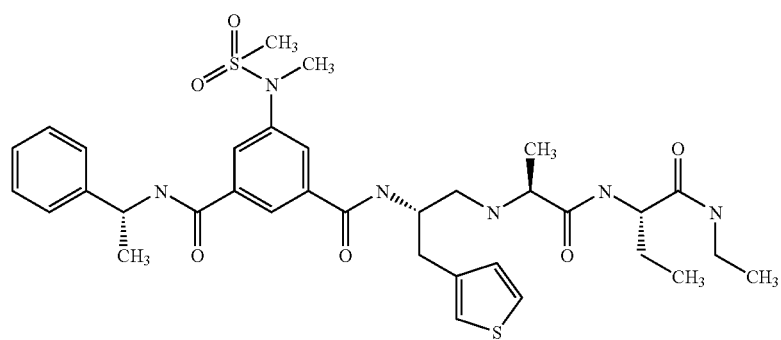

(326)
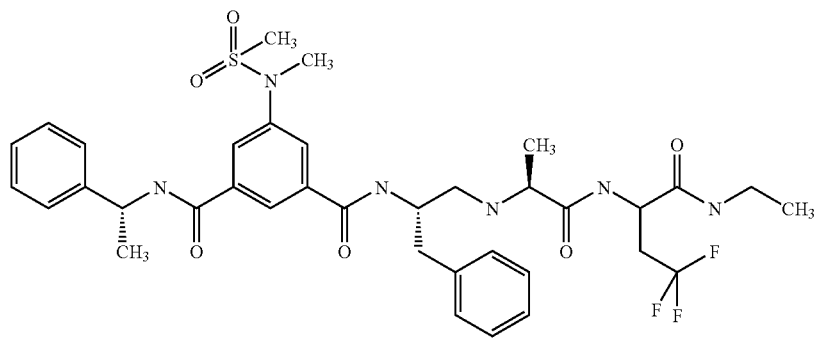
(327)
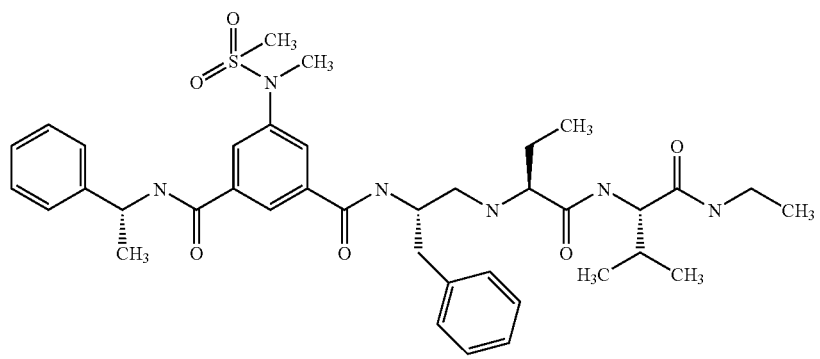
(328)
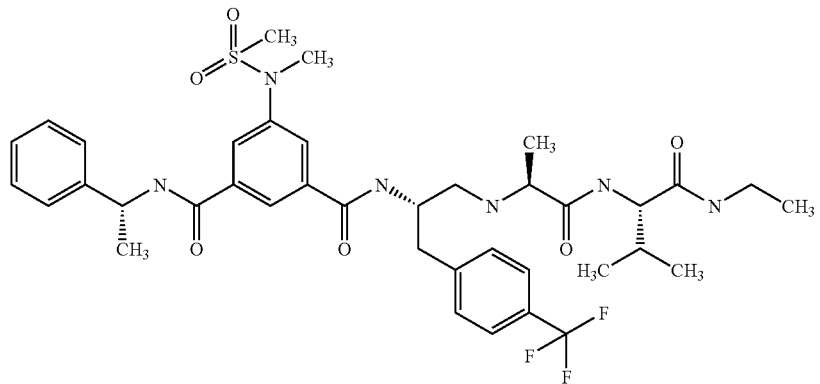
(329)
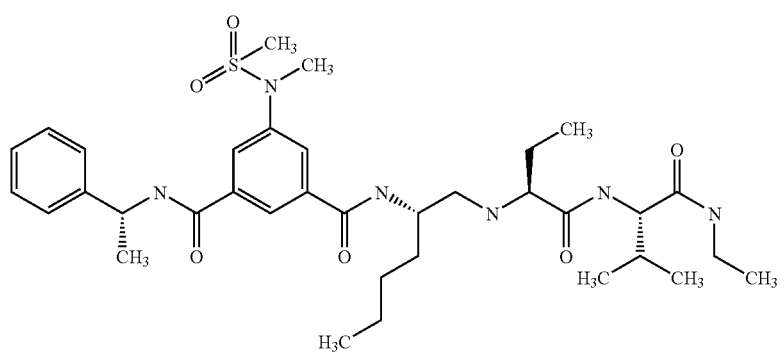

(330)
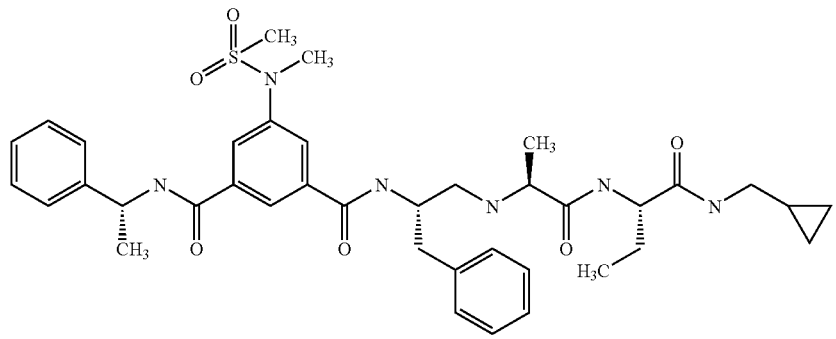
(331)
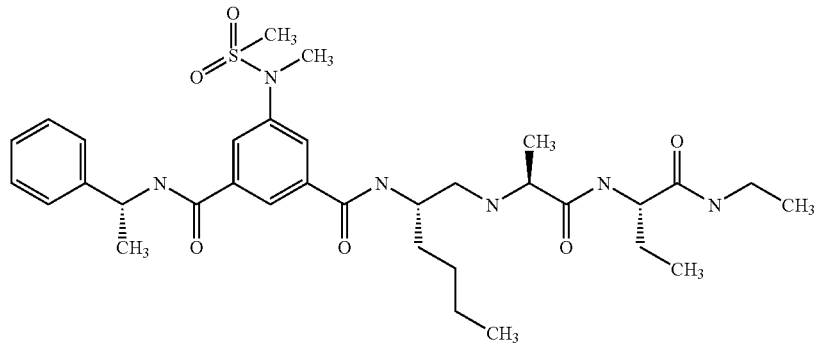
(332)
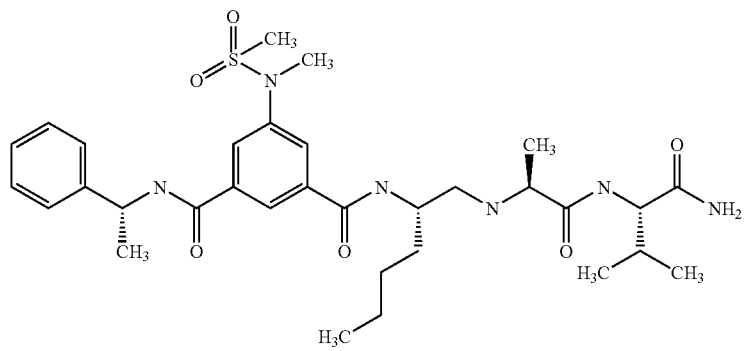
(333)
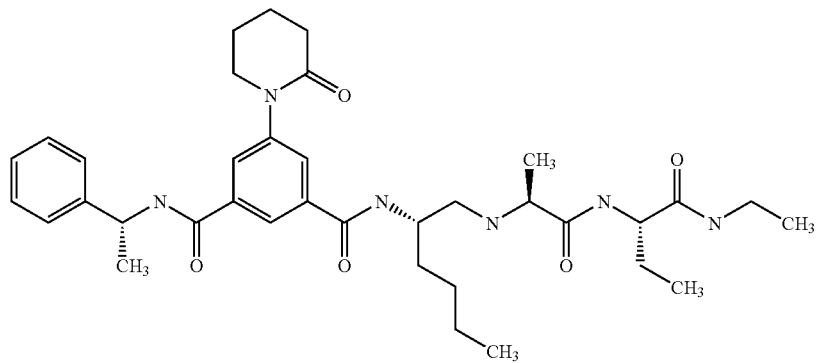

(334)
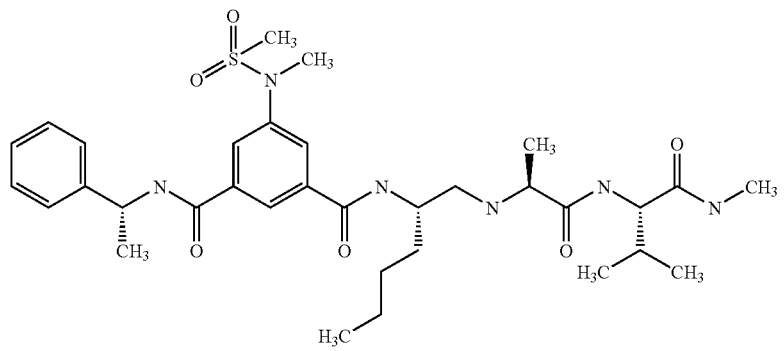
(335)
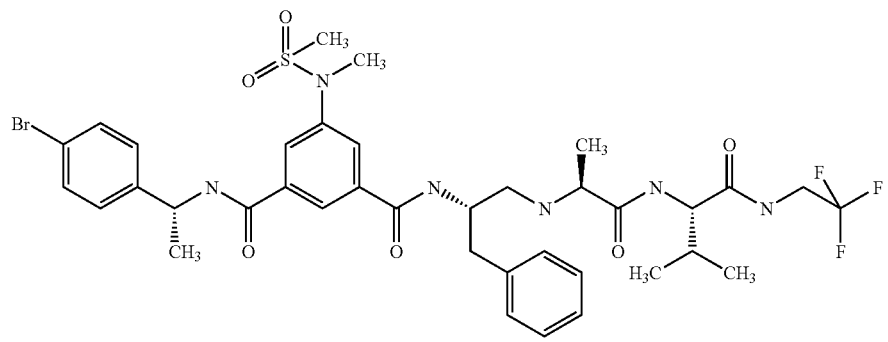
(336)
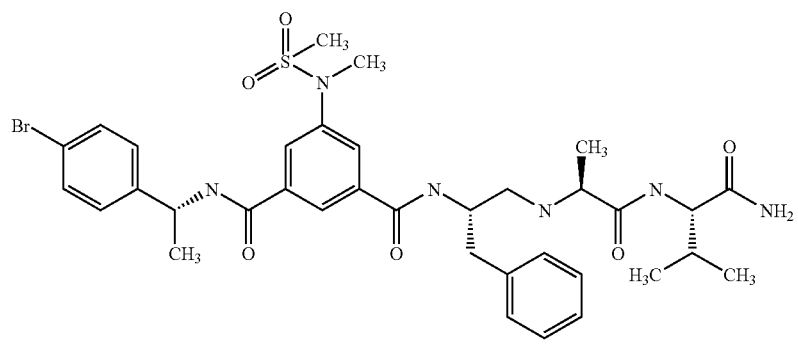
(337)
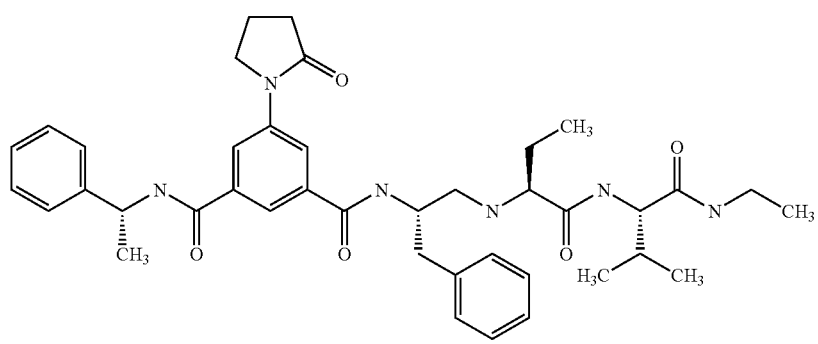

(338)
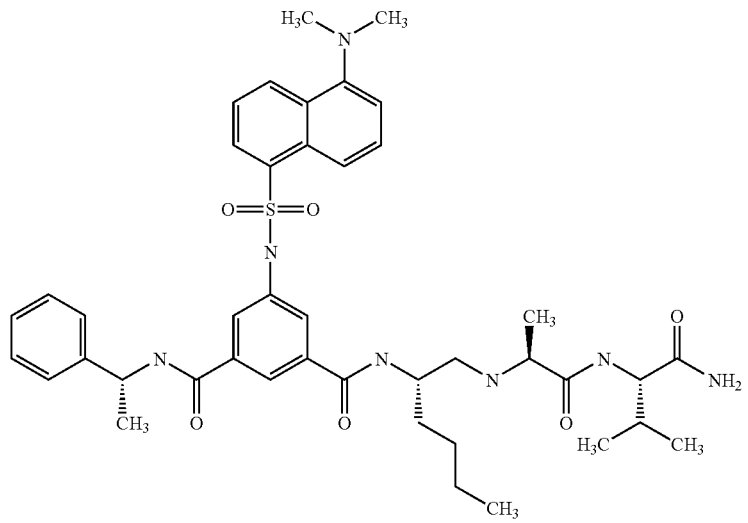
(339)
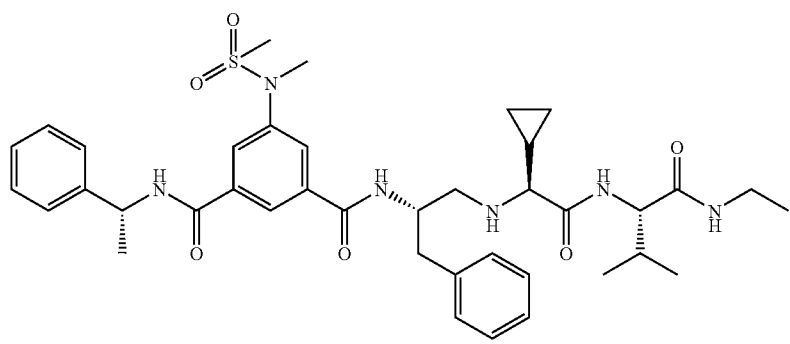
(340)
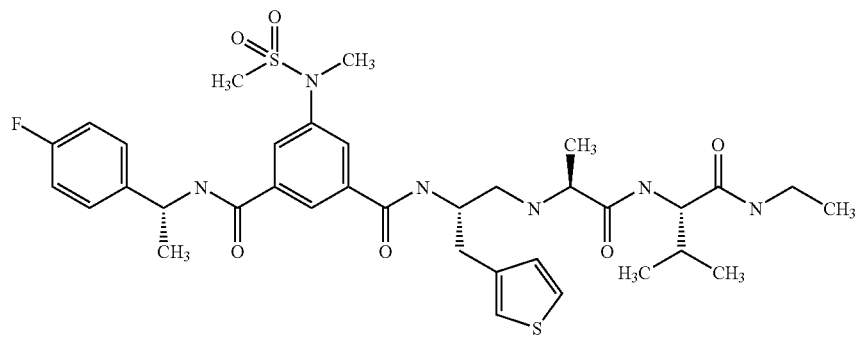
(341)
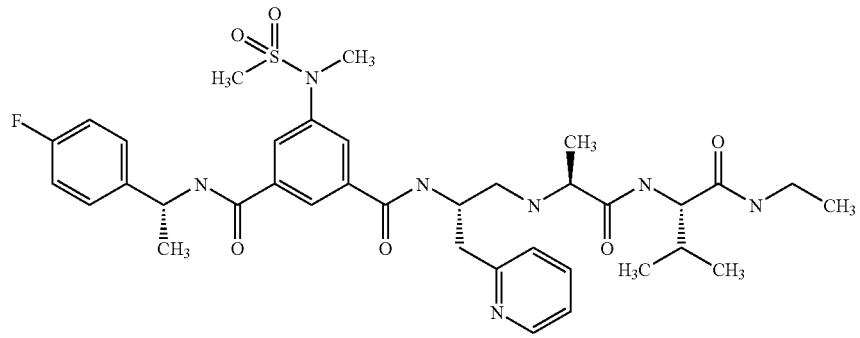

(342)
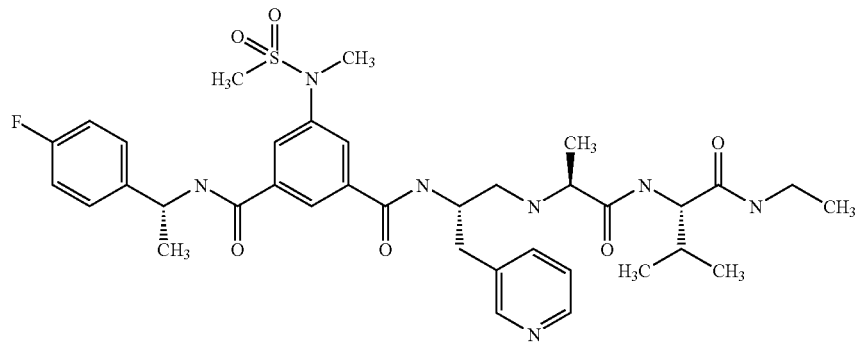
(343)
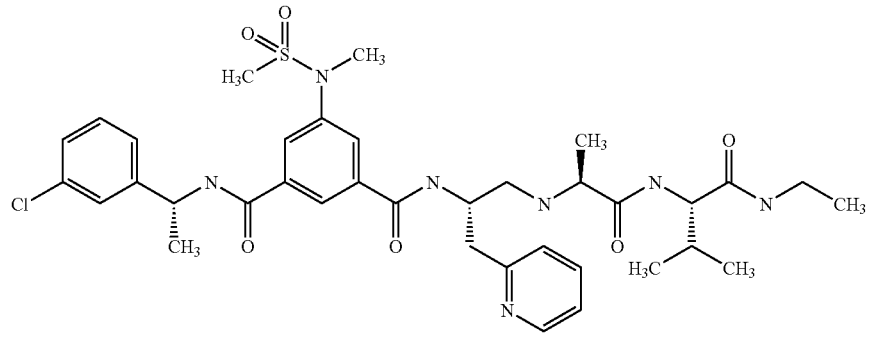
(344)
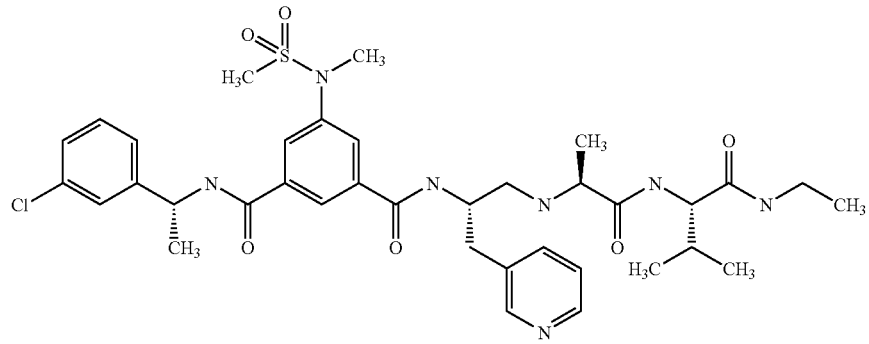
(345)
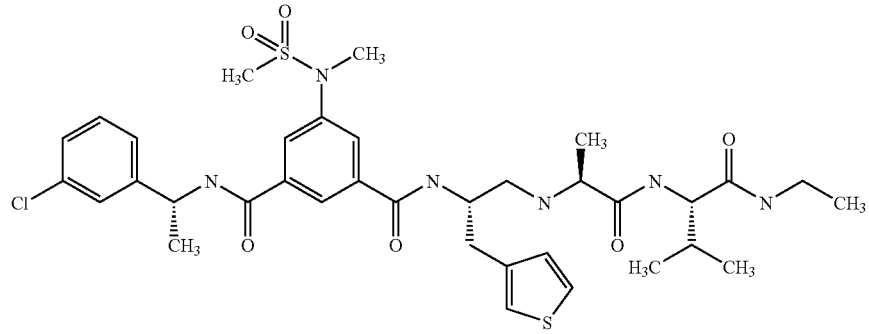

(346)
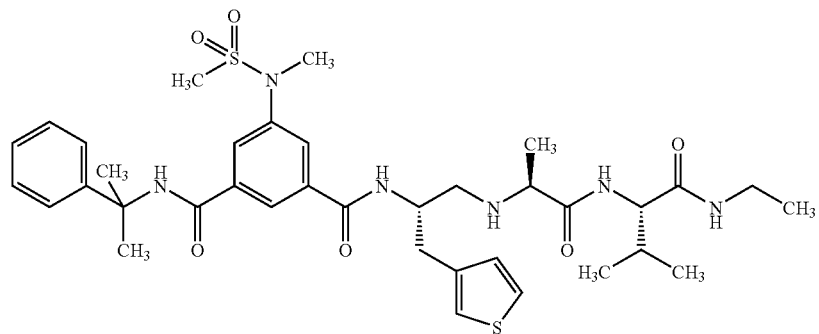
(347)
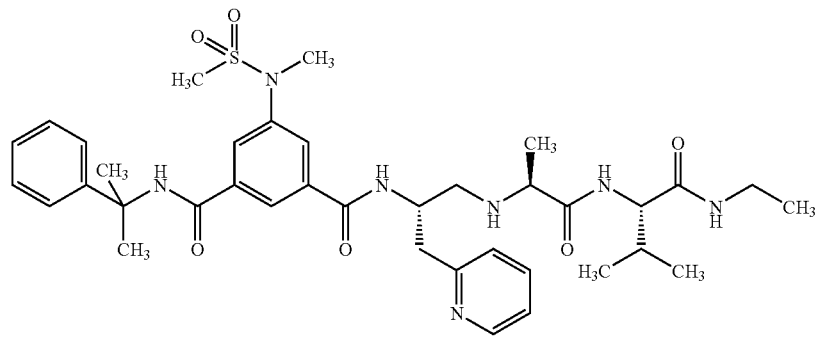
(348)
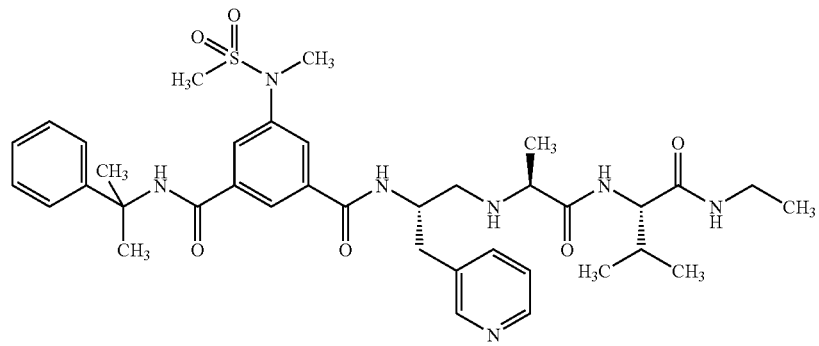
(349)
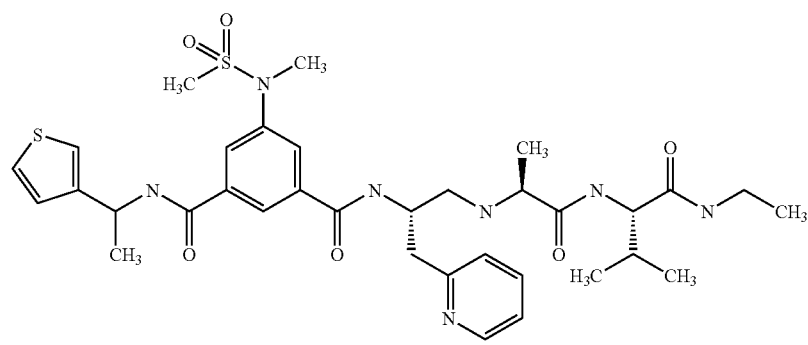

(350)
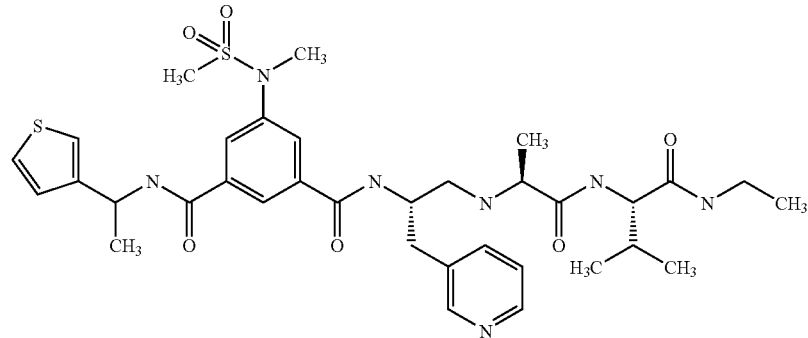
(351)
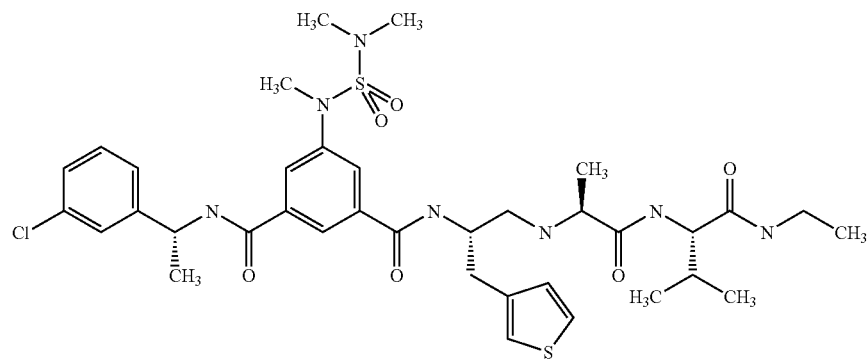
(352)
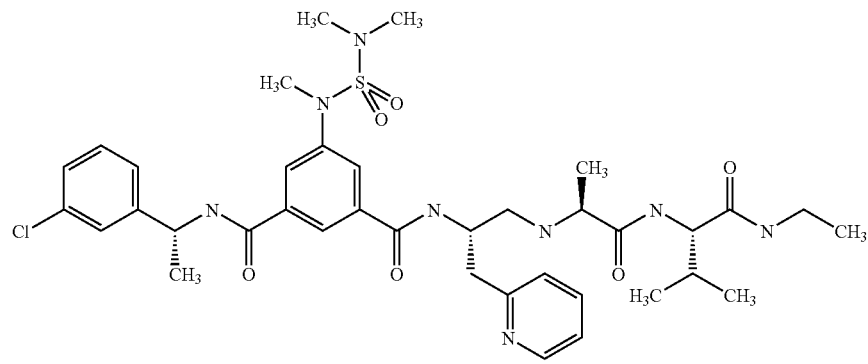
(353)
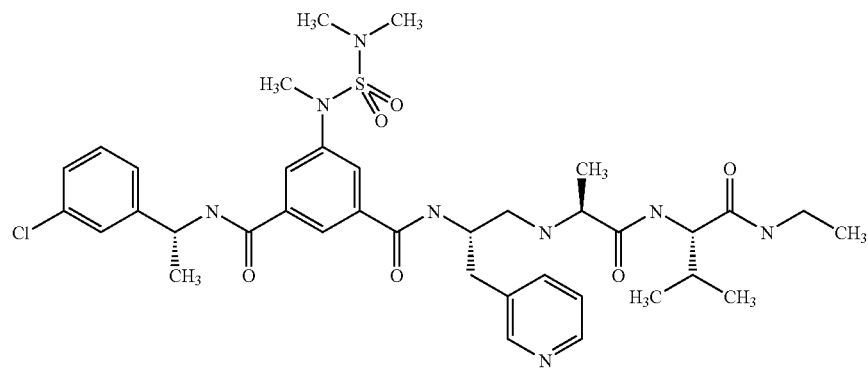

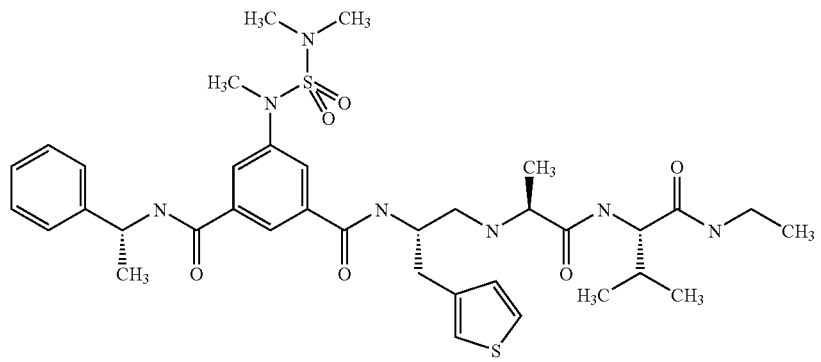
(354)
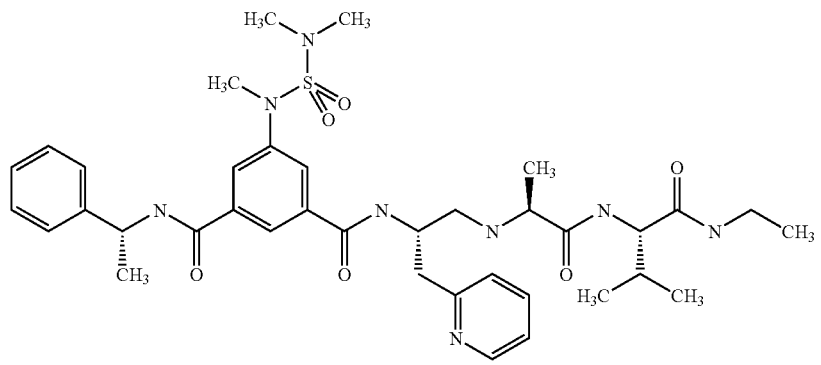
(355)
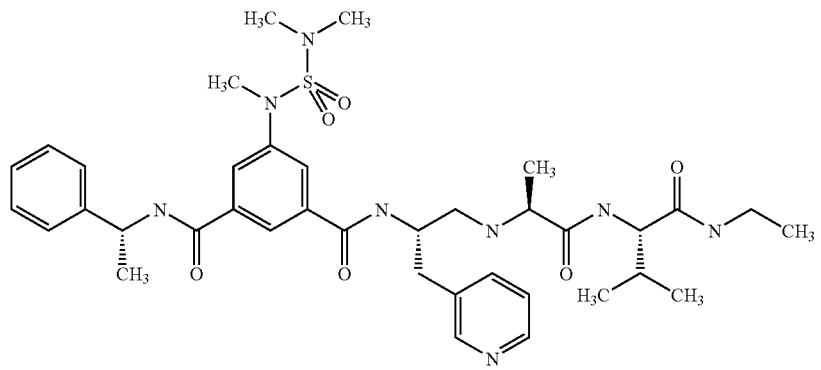
(356)
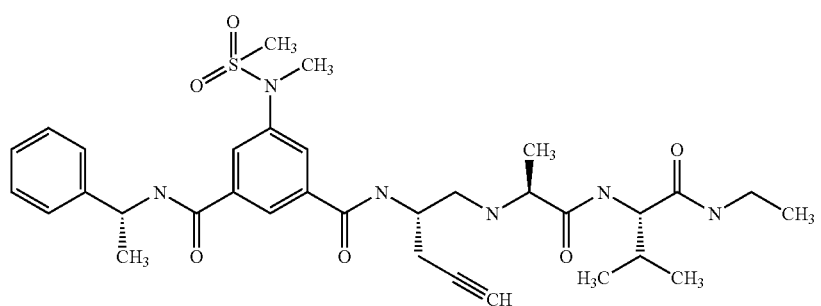
(357)

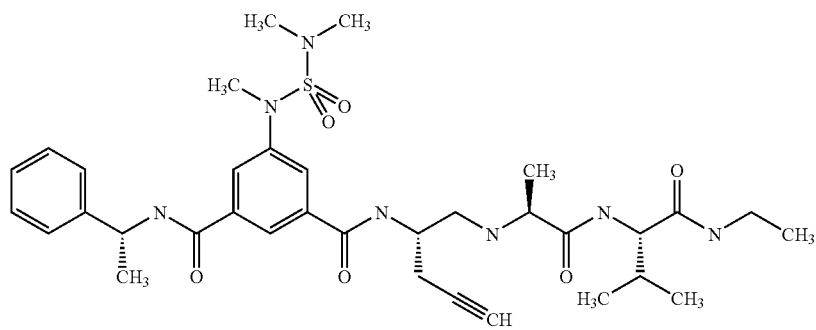
(358)
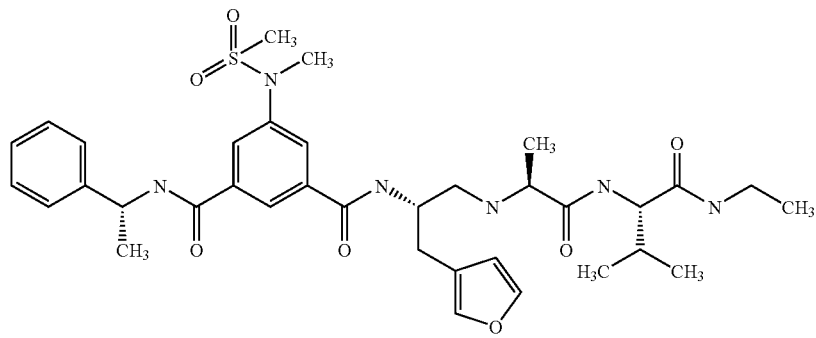
(359)
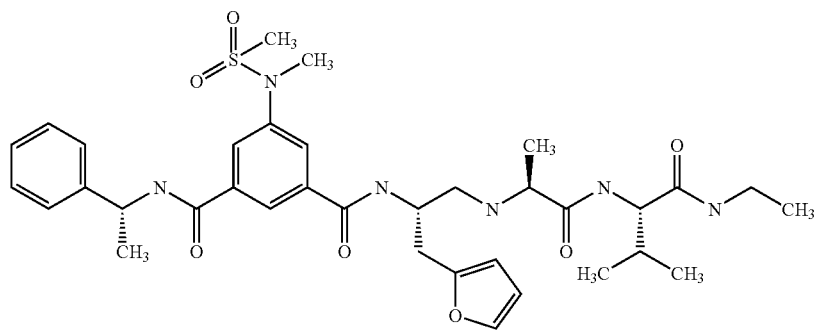
(360)
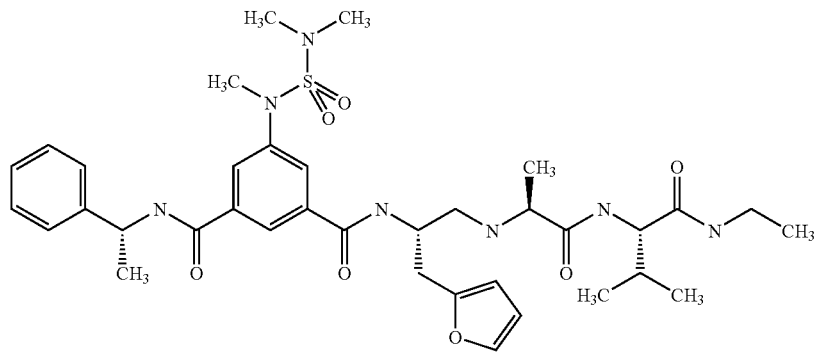
(361)

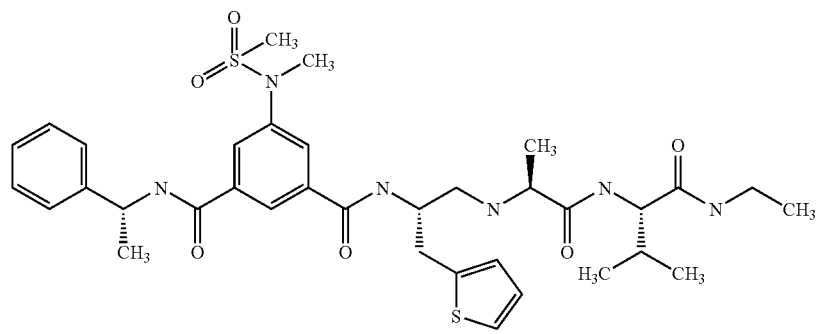
(362)
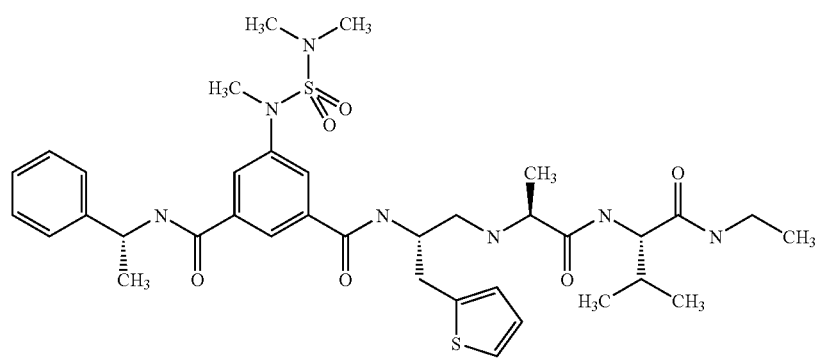
(363)
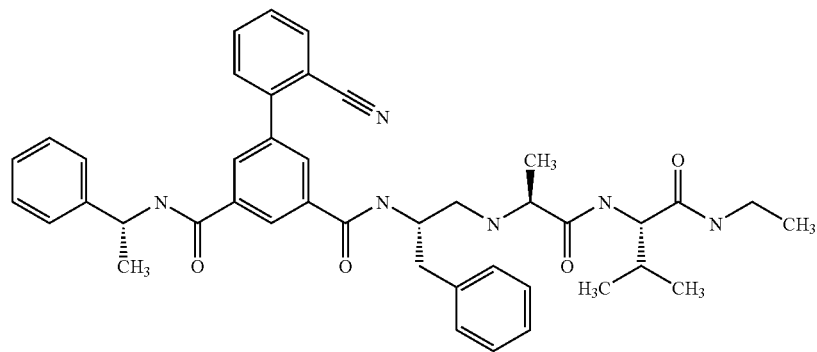
(364)
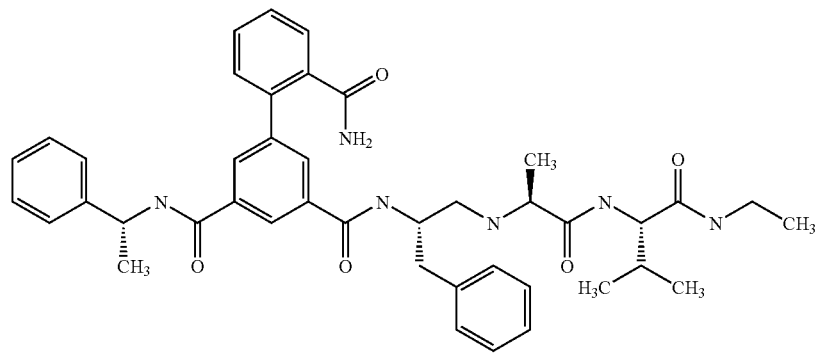
(365)

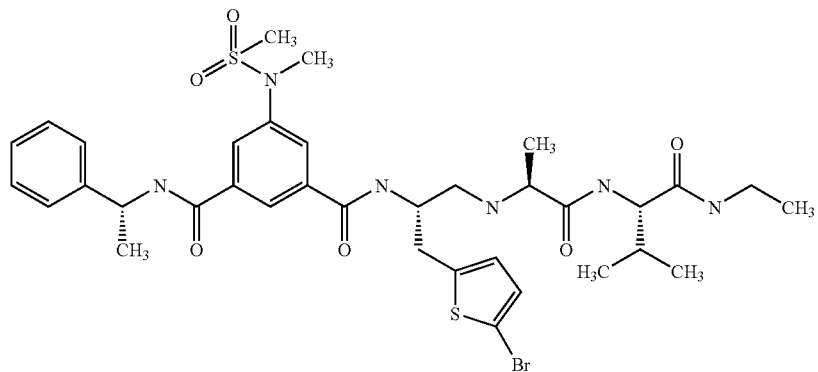
(366)
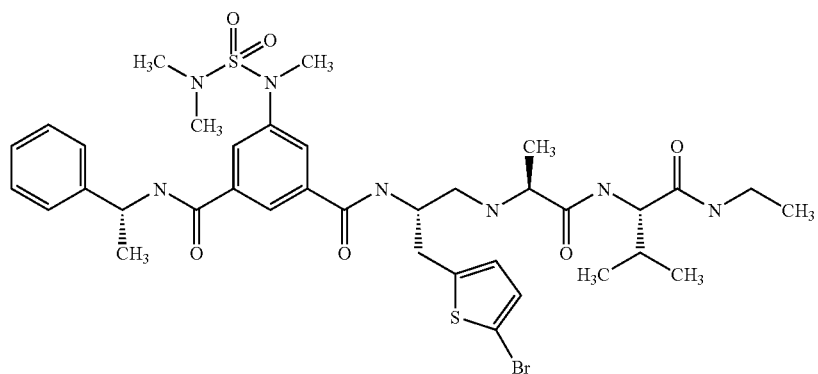
(367)
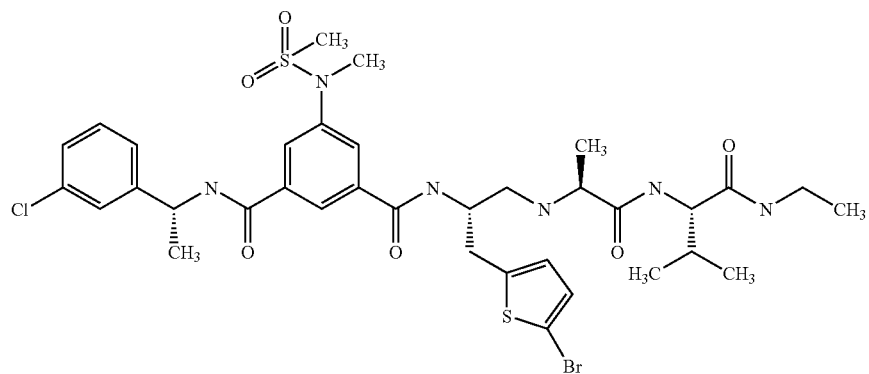
(368)
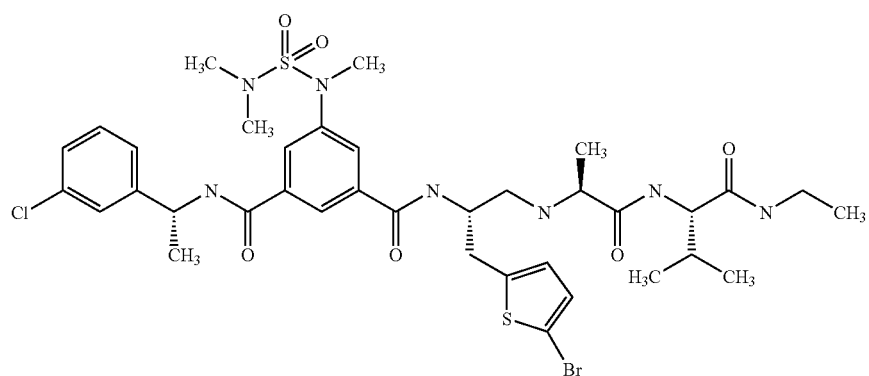
(369)

(370)
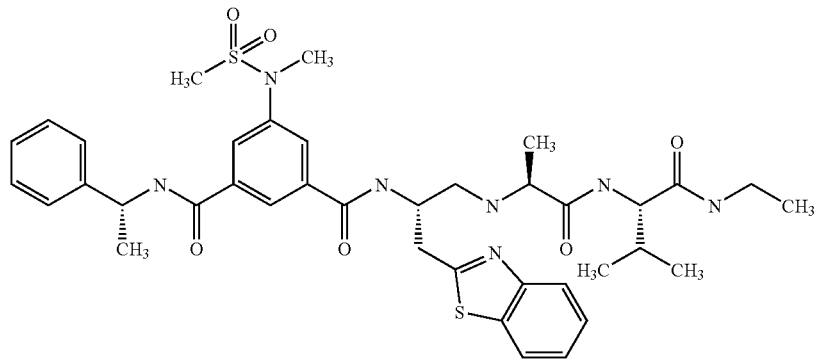
(371)
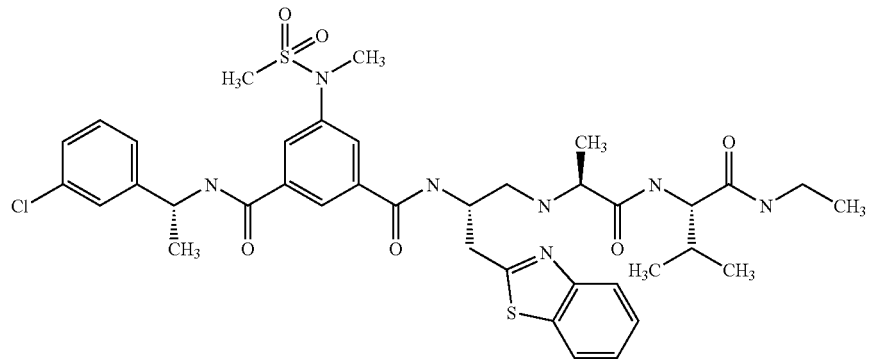
(372)
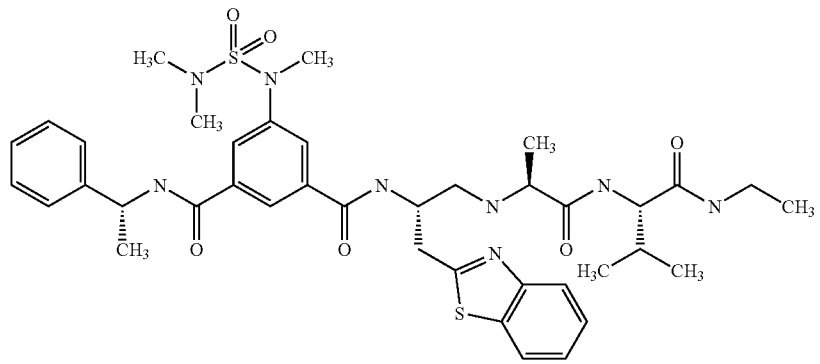
(373)
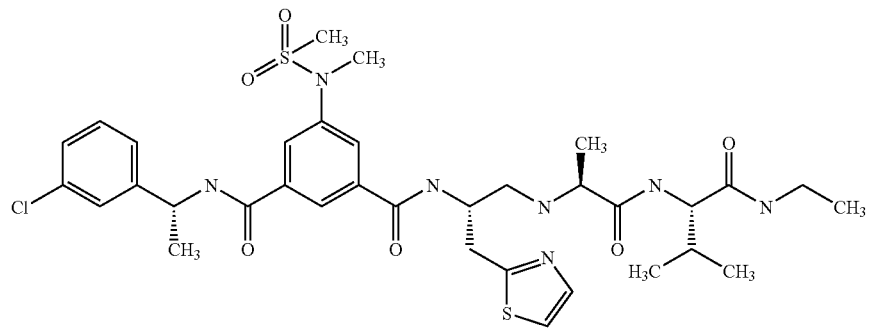

(374)
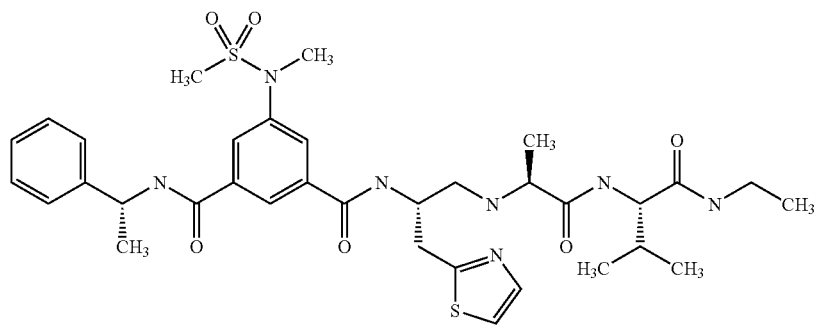
(375)
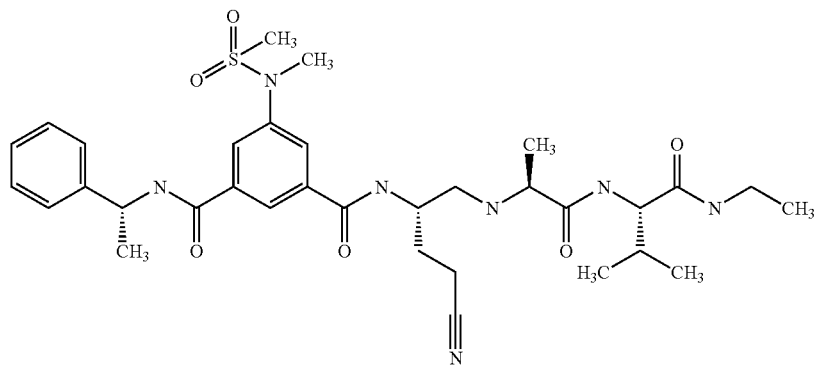
(376)
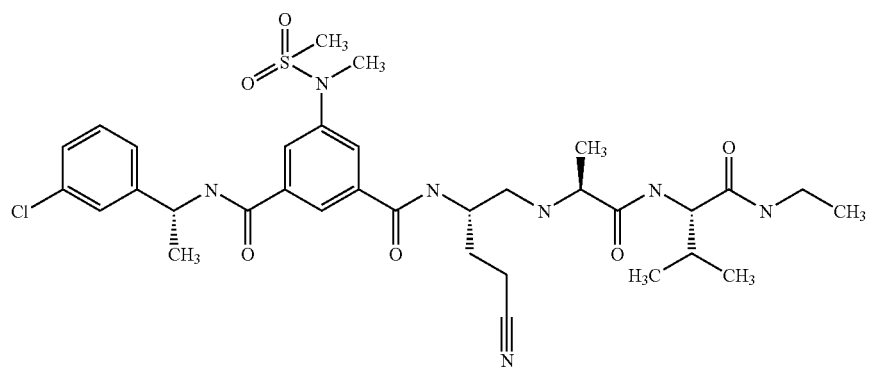
(377)
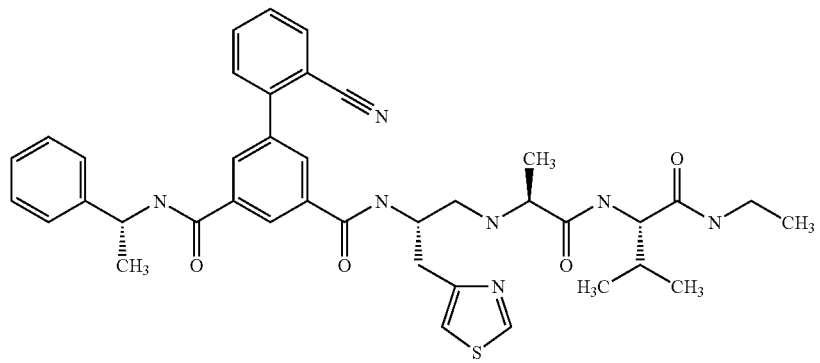

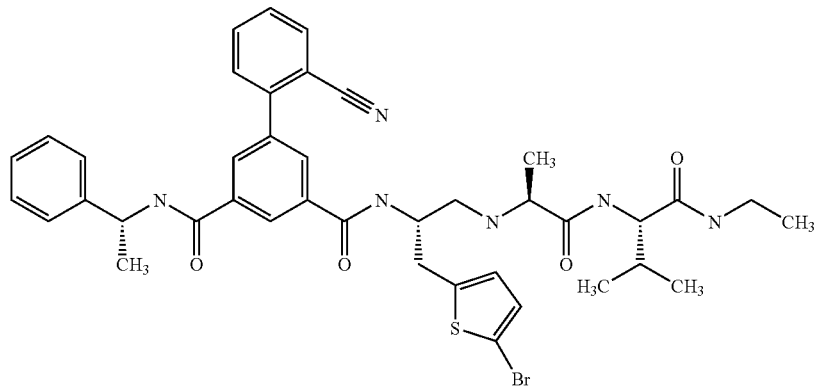
(378)
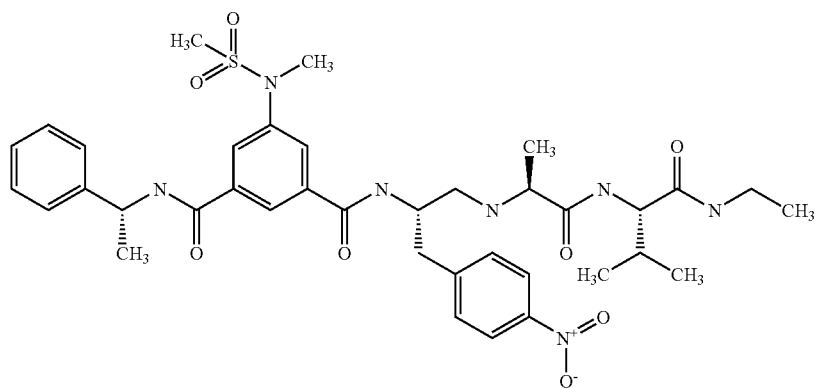
(379)
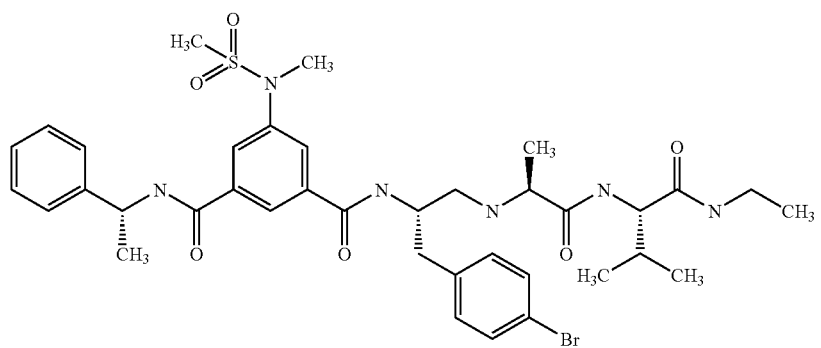
(380)
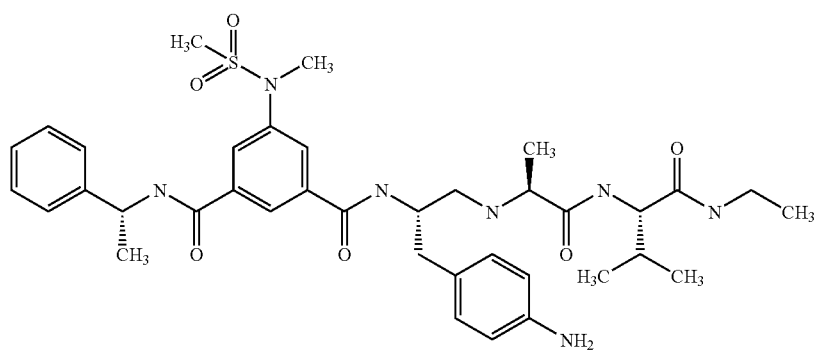
(381)

(382)
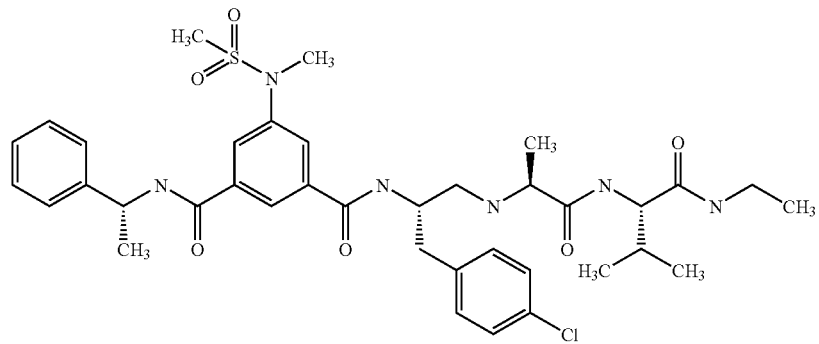
(383)
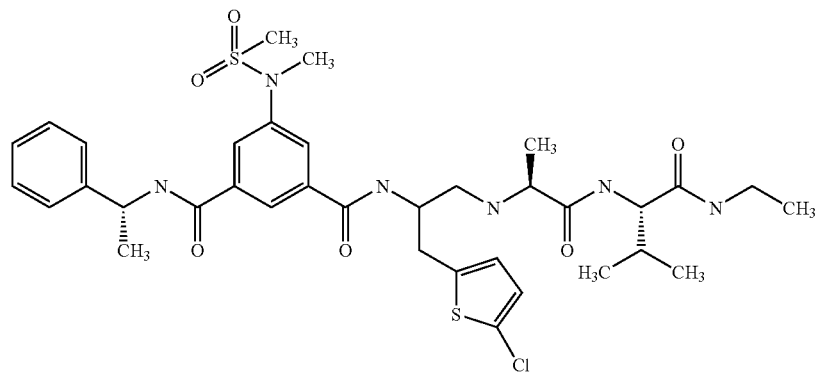
(384)
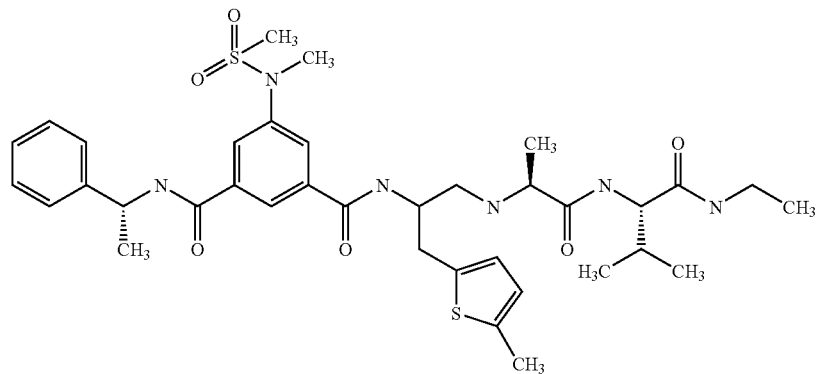
(385)
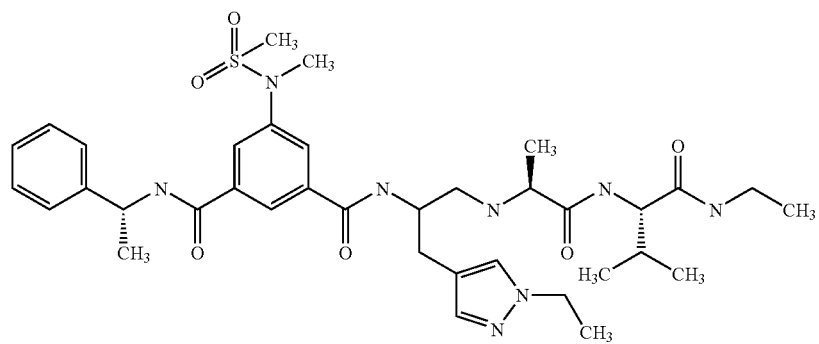

-continued
(386)
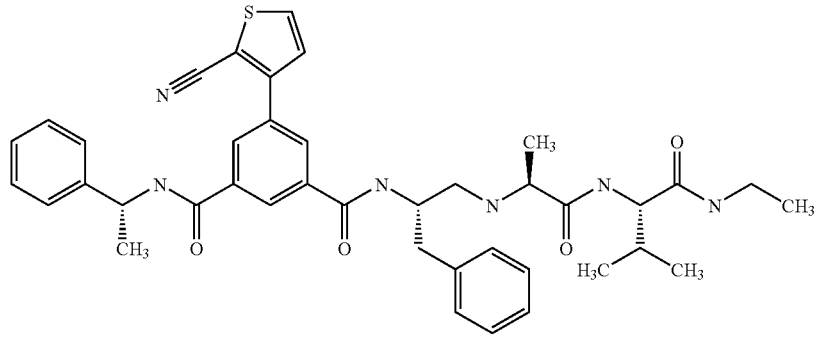
(387)
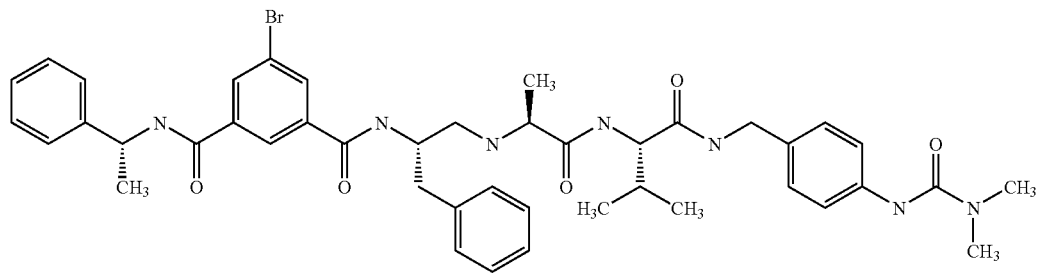
(388)
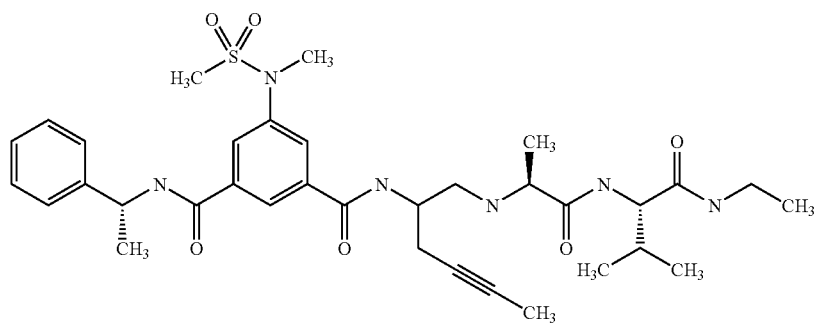
(389)
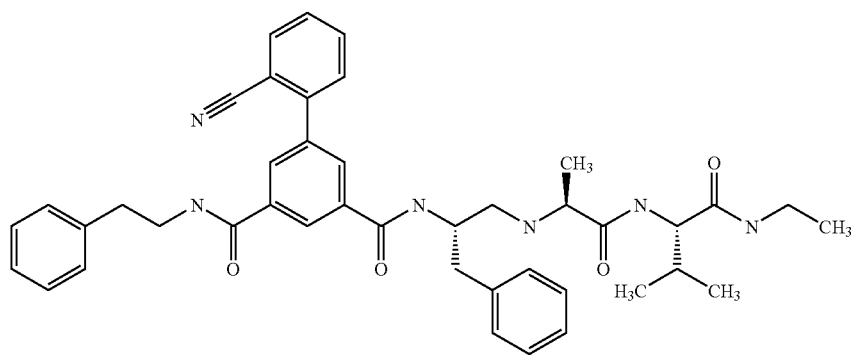

-continued
(390)
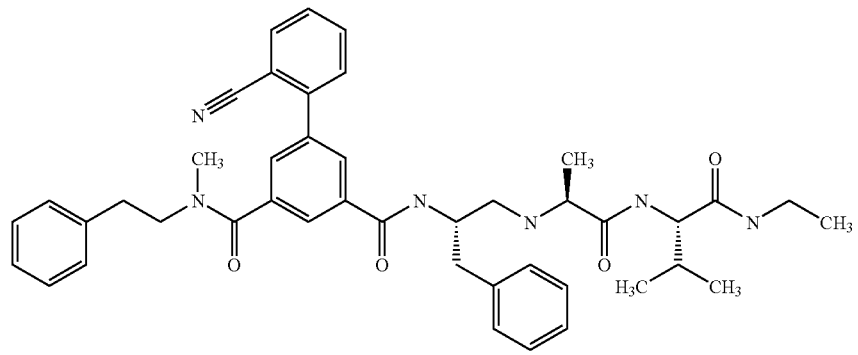
(391)
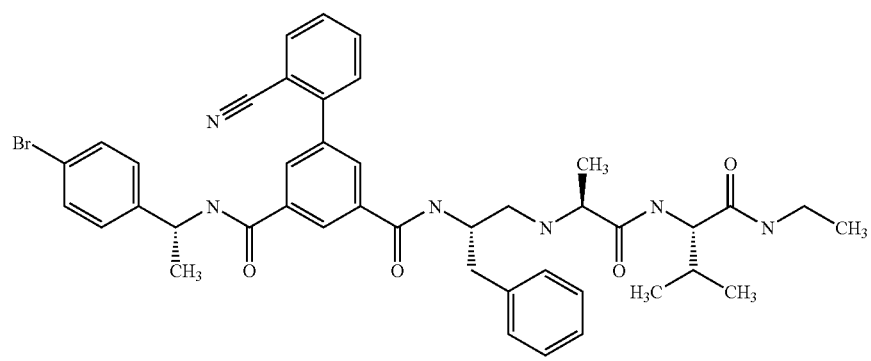
(392)
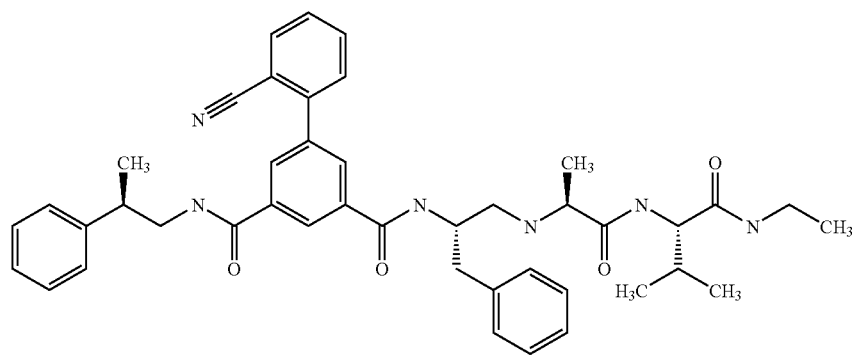
(393)
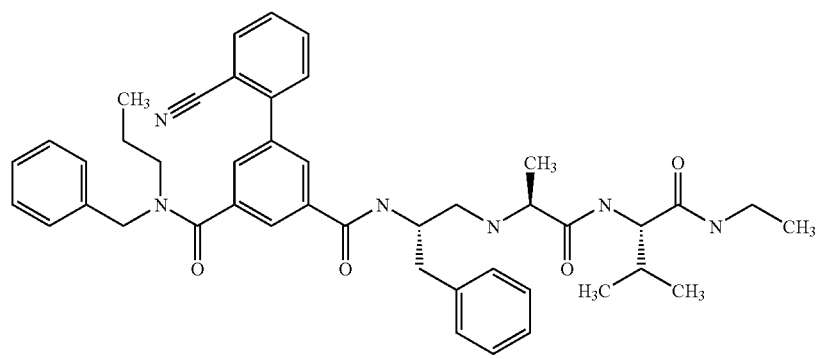

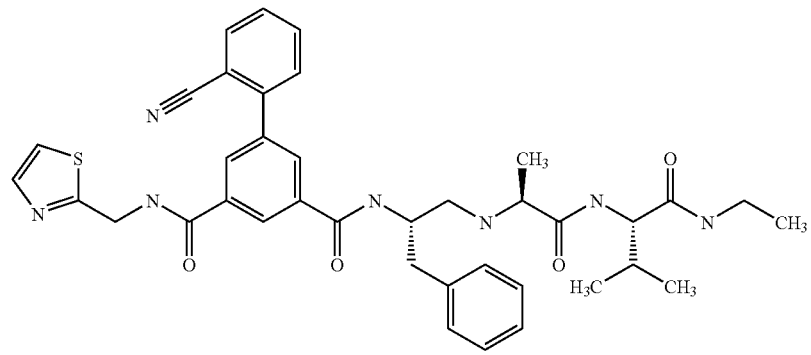
(394)
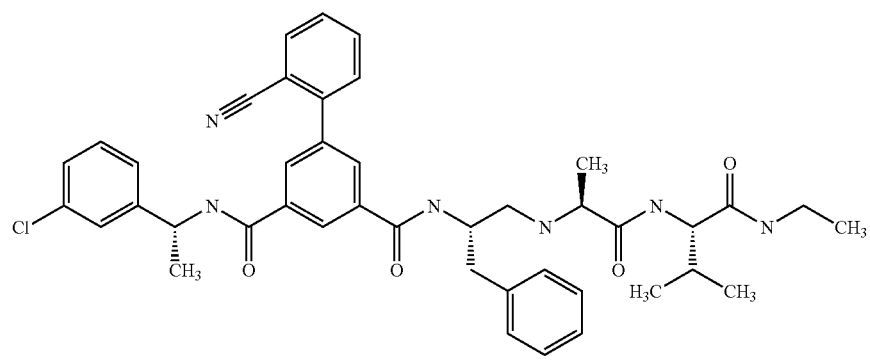
(395)
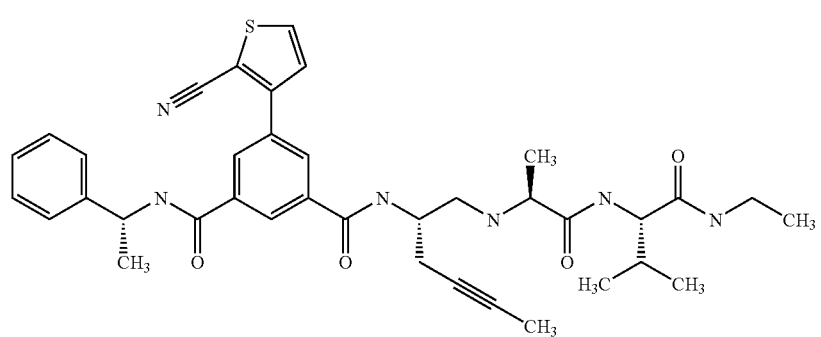
(396)
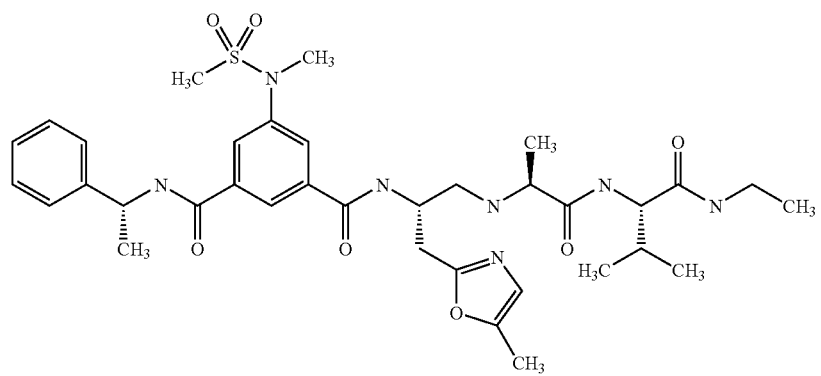
(397)

-continued
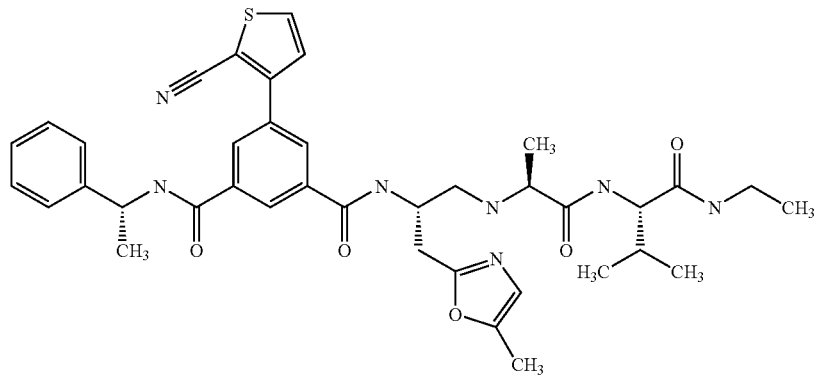
(398)
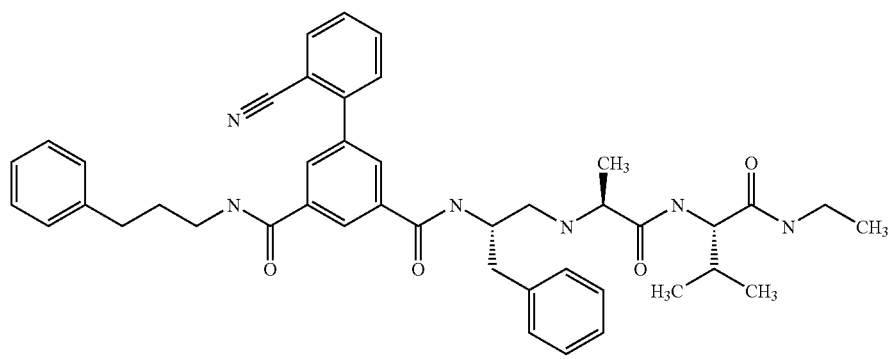
(399)
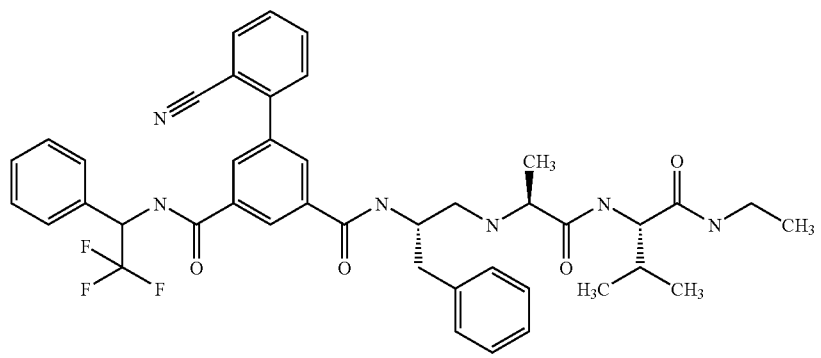
(400)
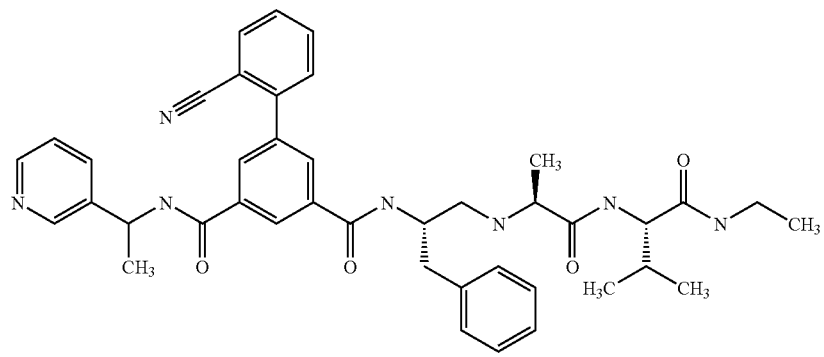
(401)

-continued
(402)
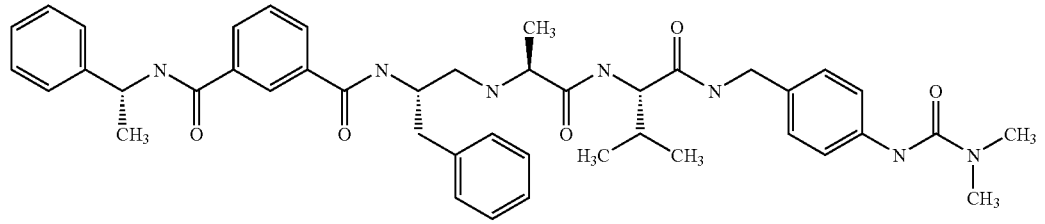
(403)
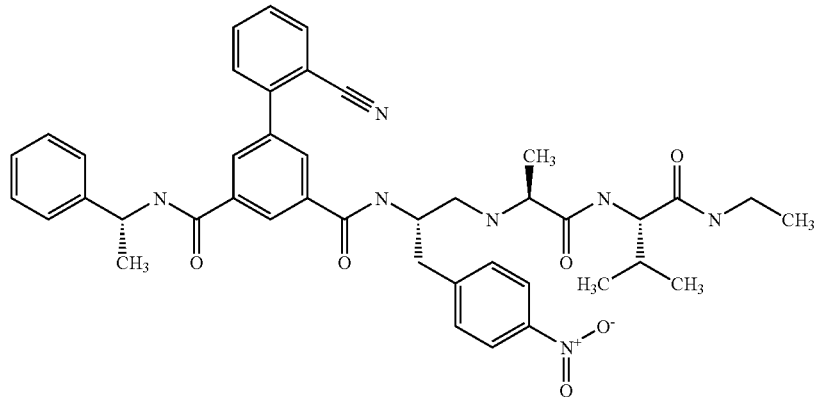
(404)
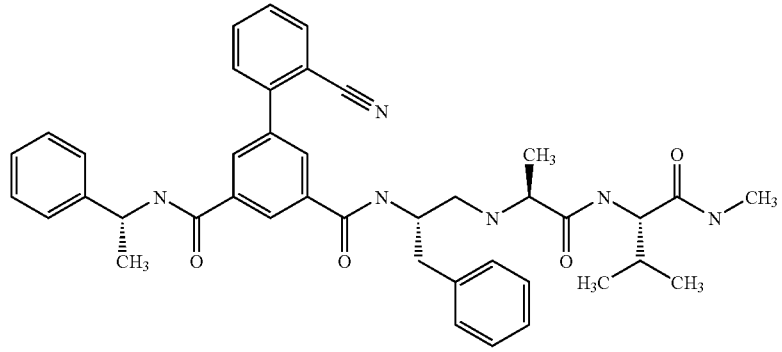
(405)
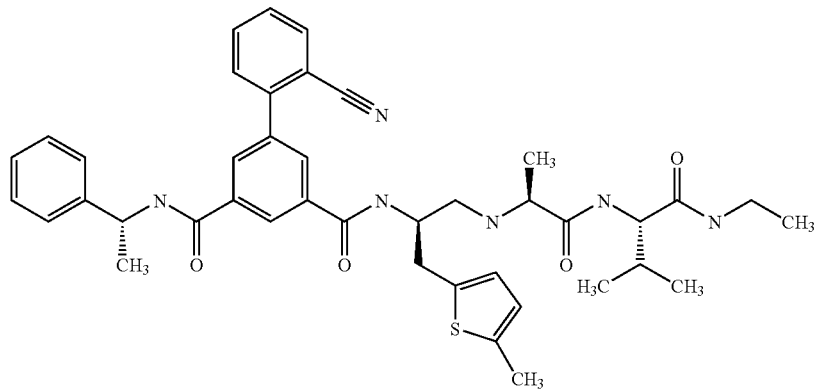

-continued
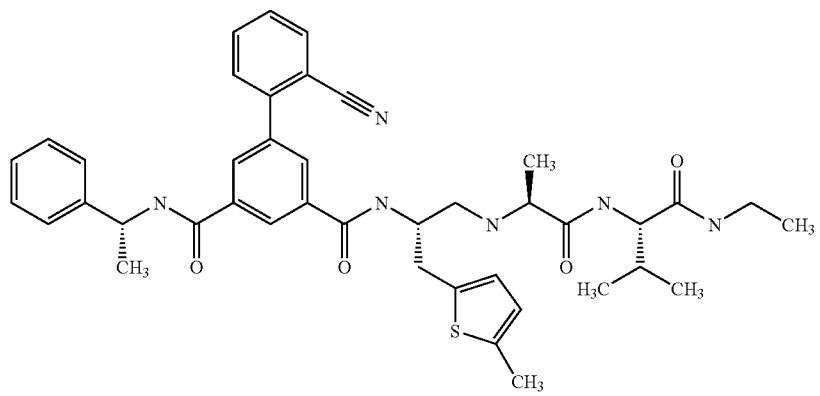
(406)
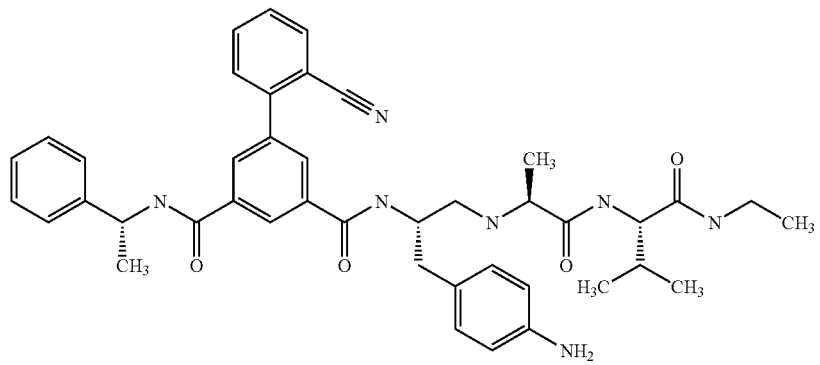
(407)
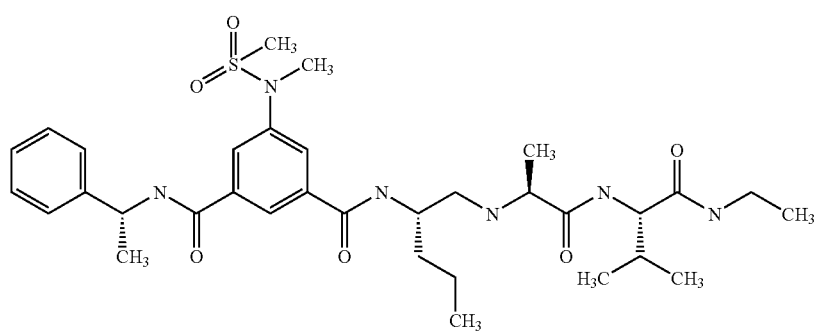
(408)
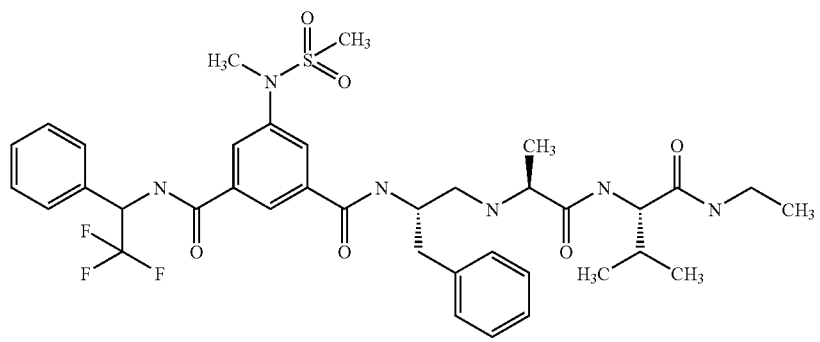
(409)

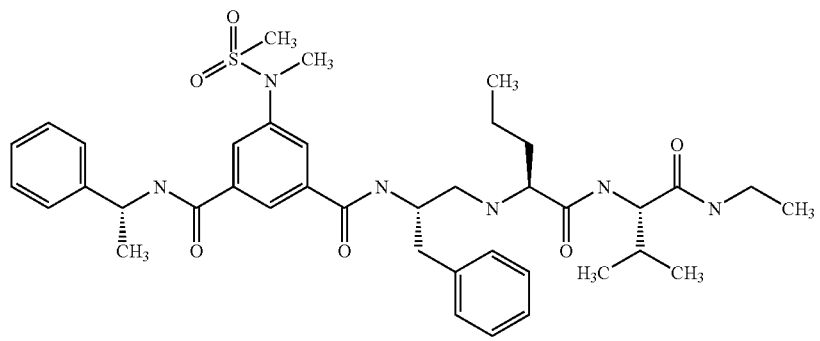
(410)
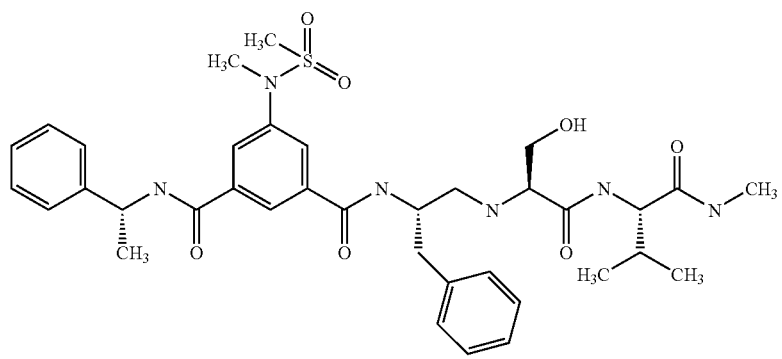
(411)
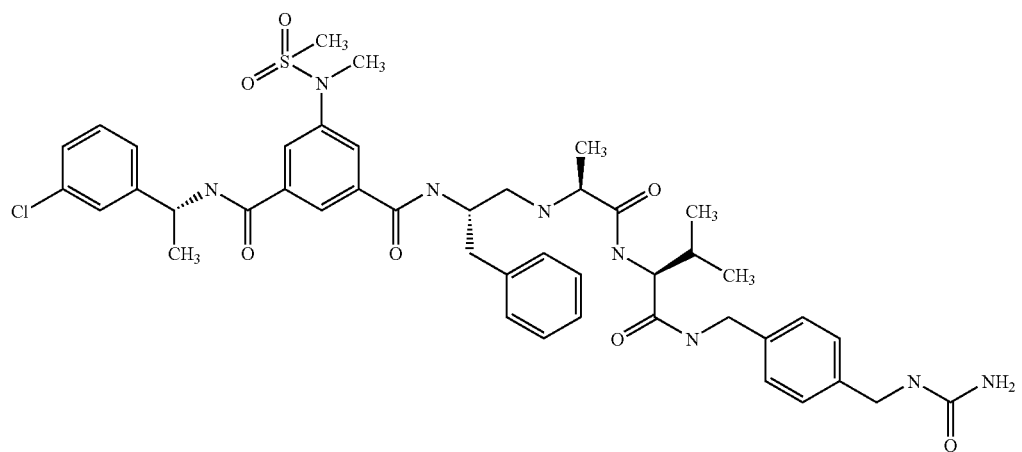
(412)
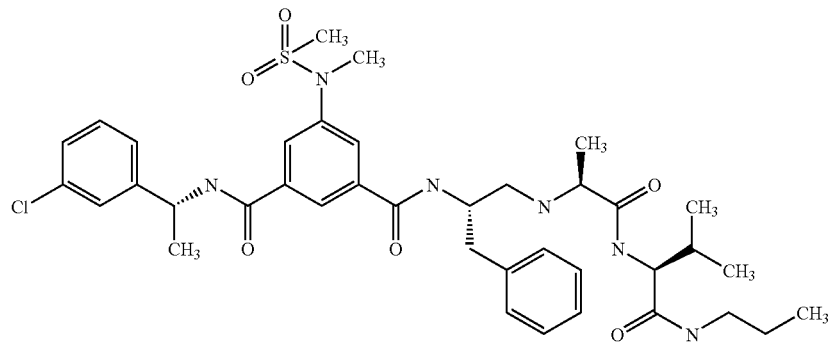
(413)

(414)
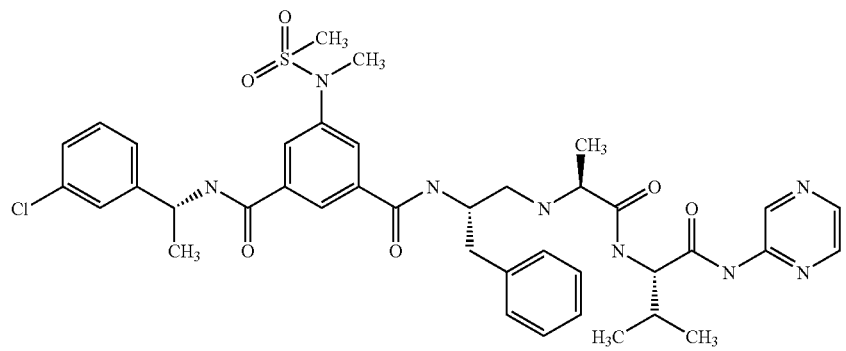
(415)
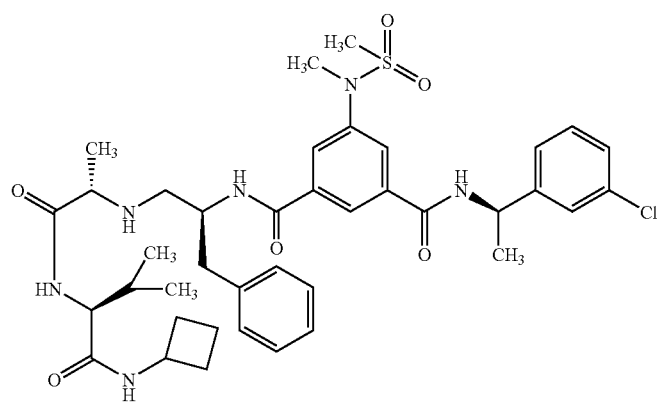
(416)
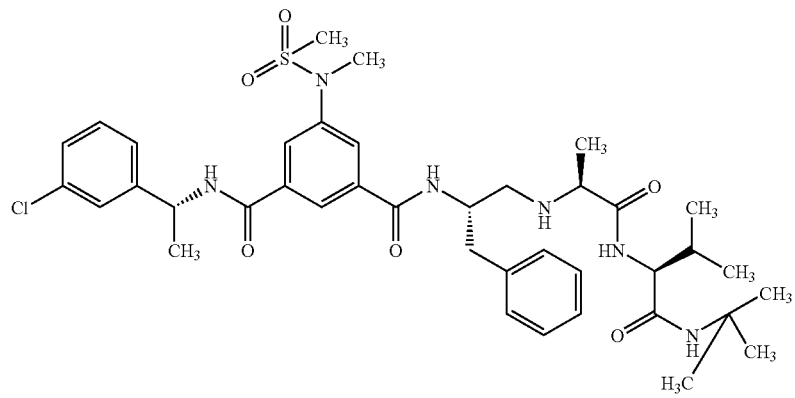
(417)
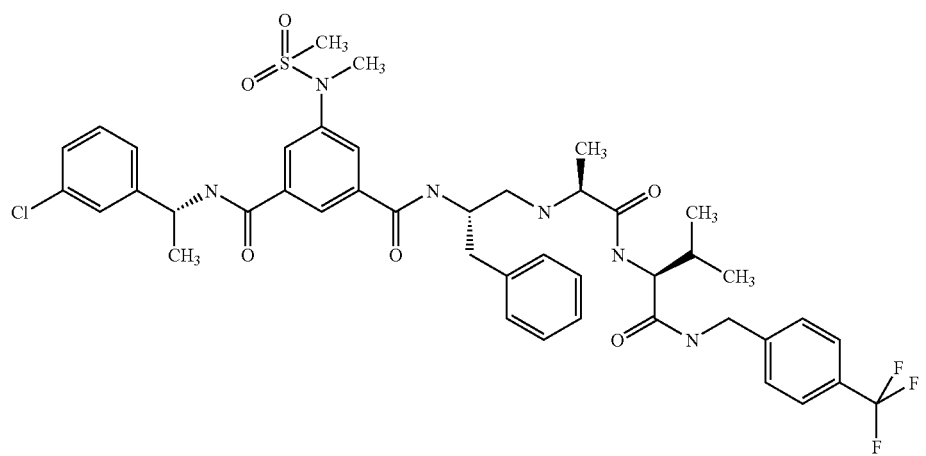

(418)
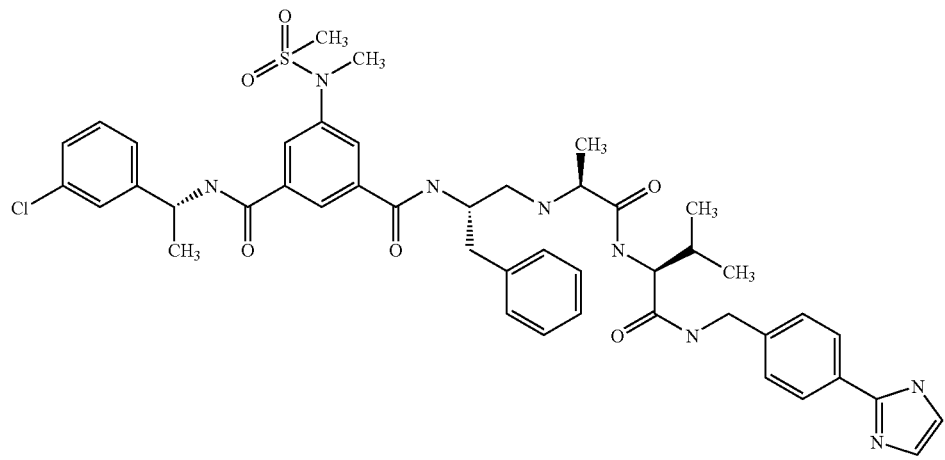
(419)
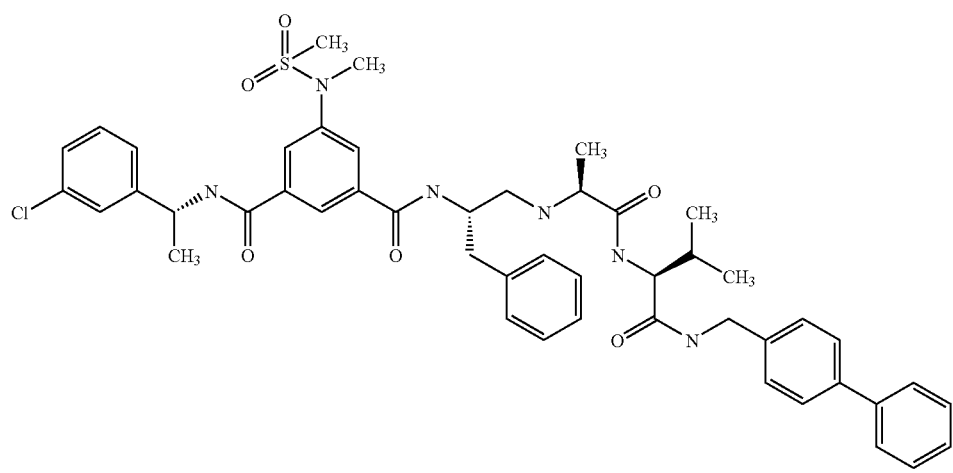
(420)
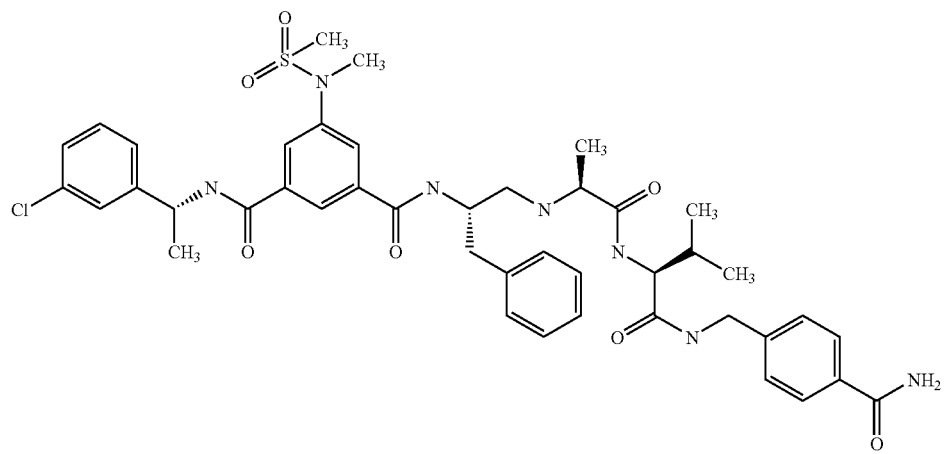

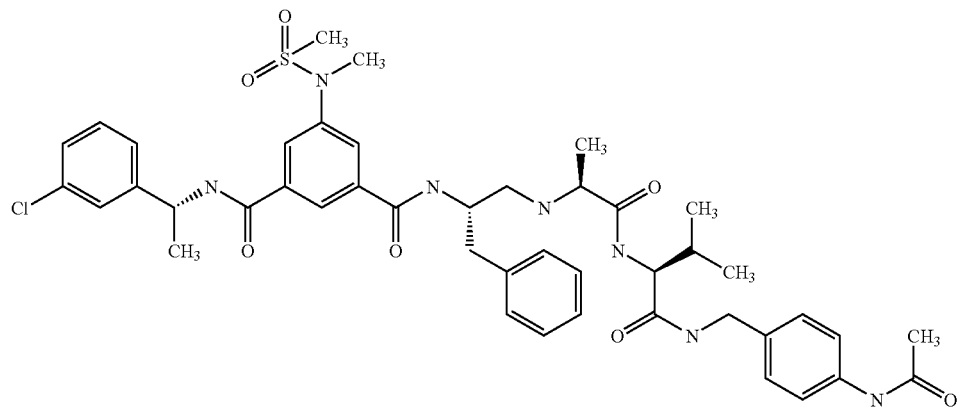
(421)
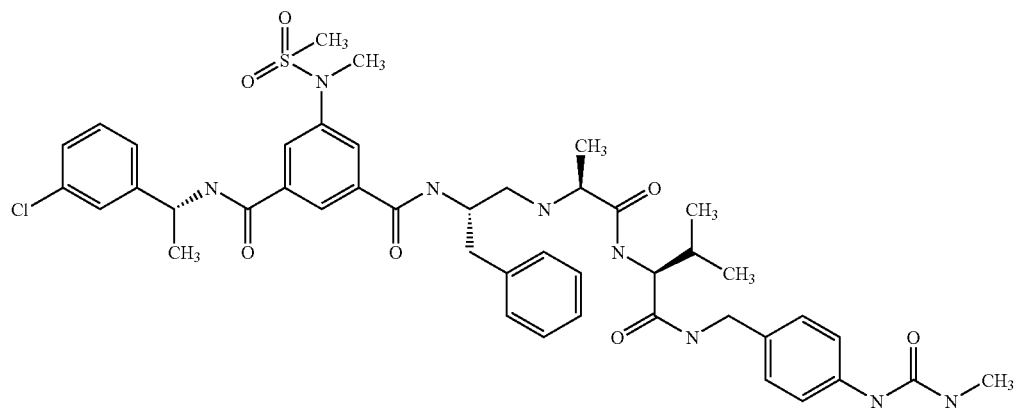
(422)
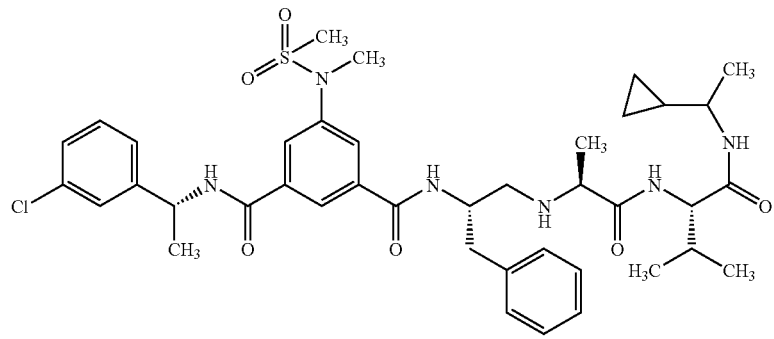
(423)
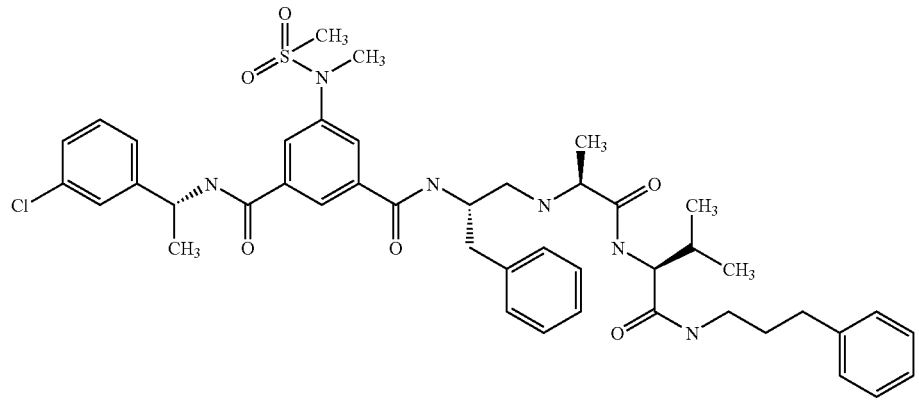
(424)

(425)
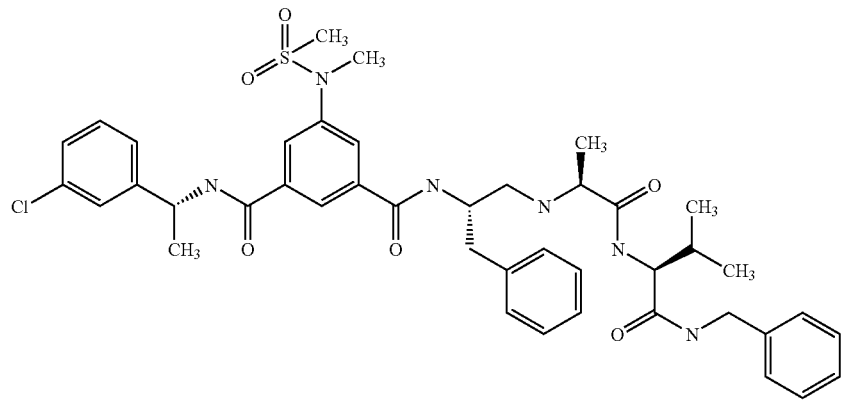
(426)
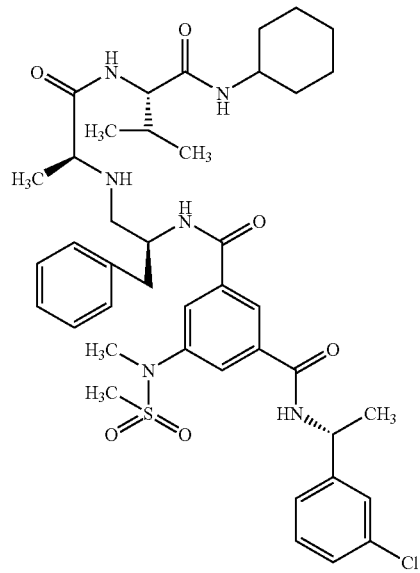
(427)
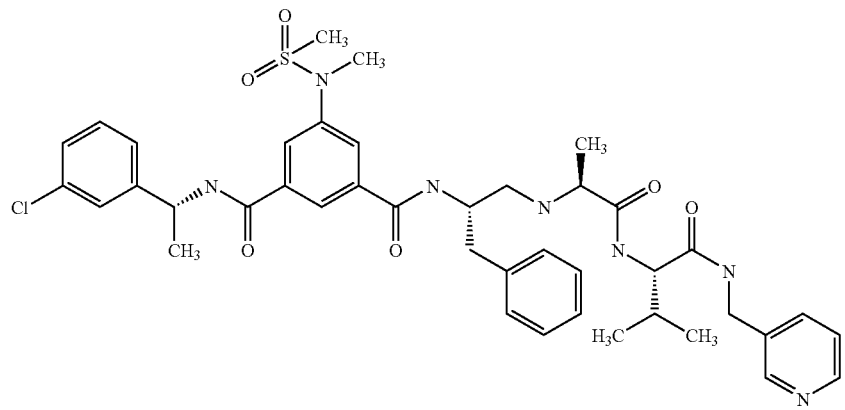

(428)
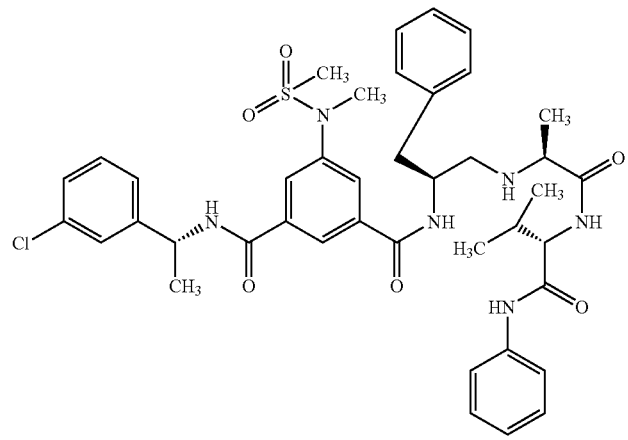
(429)
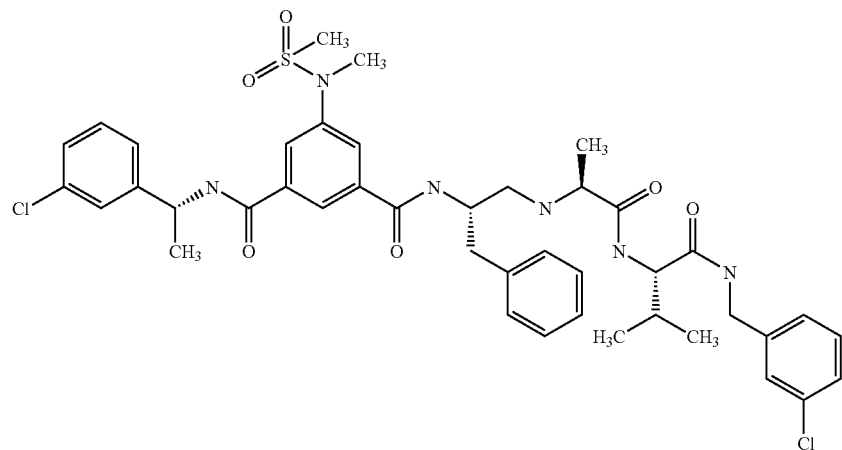
(430)
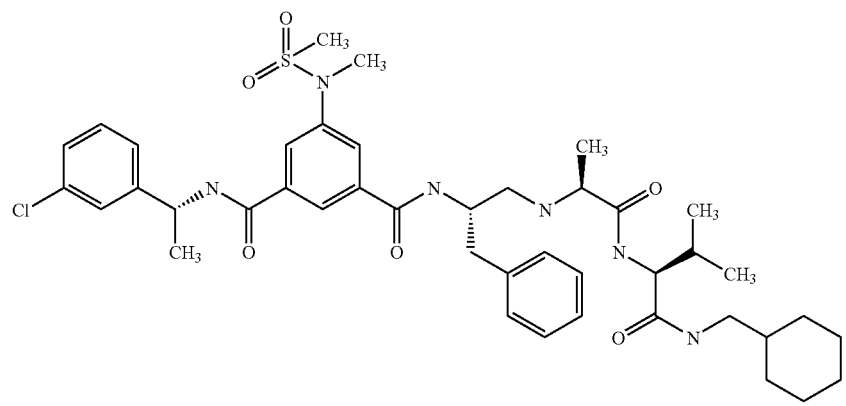

(431)
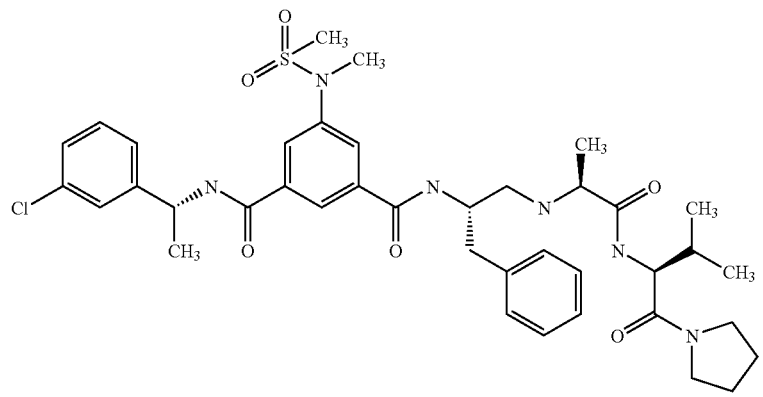
(432)
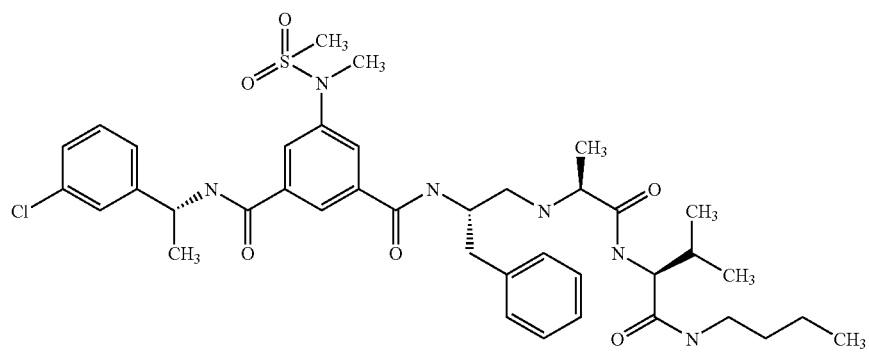
(433)
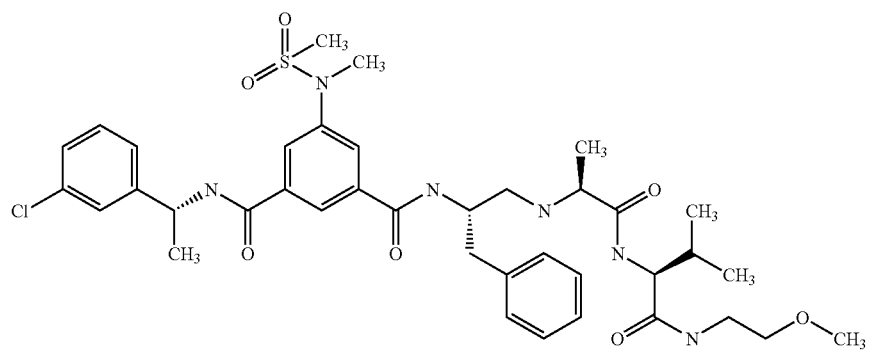
(434)
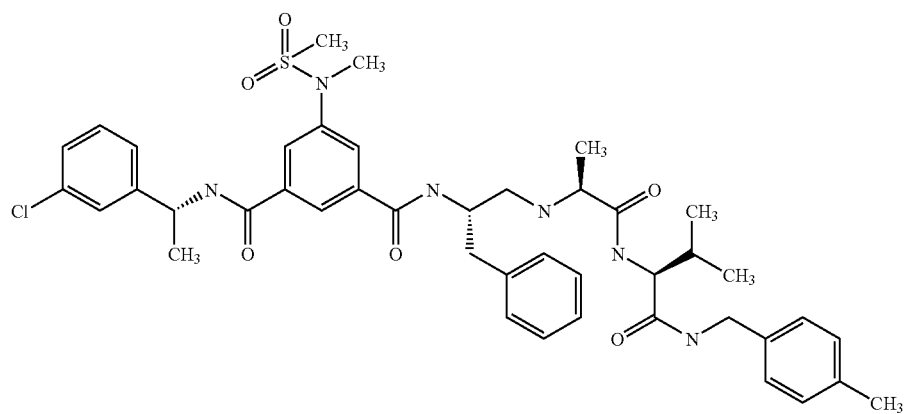

(435)
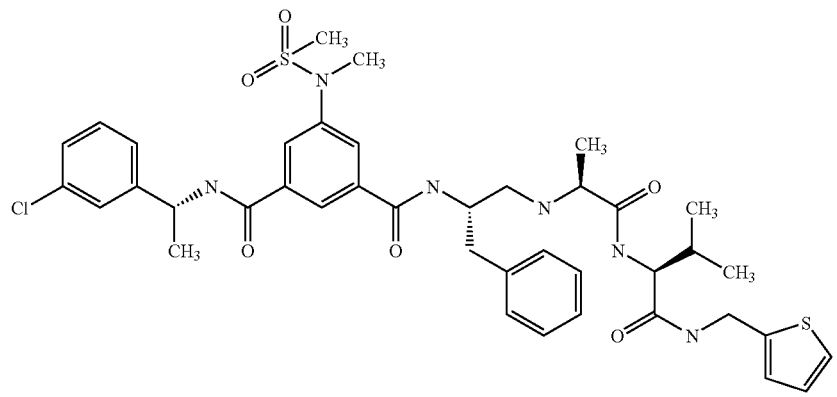
(436)
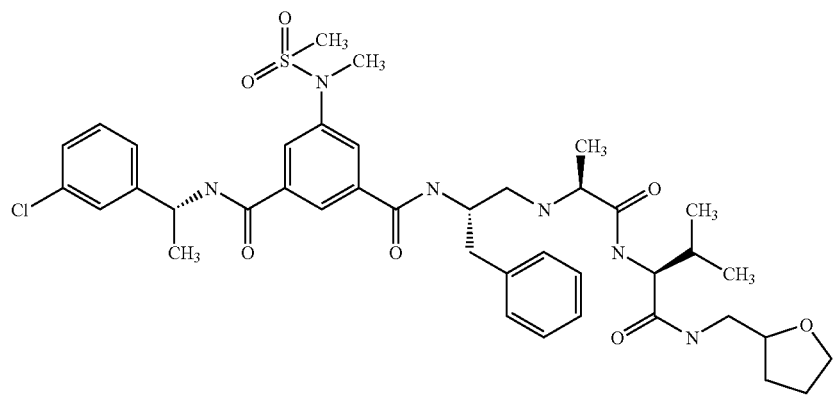
(437)
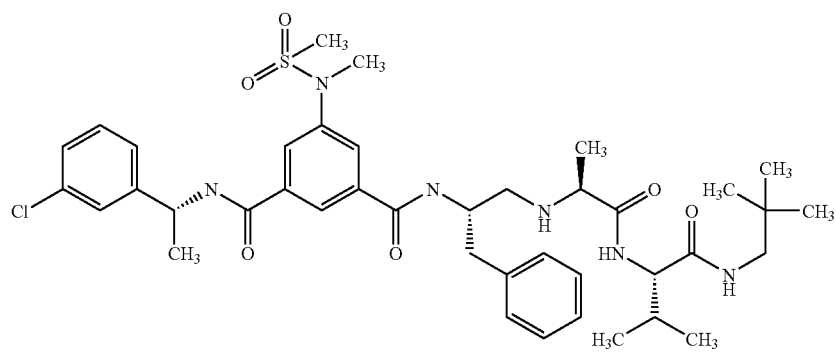
(438)
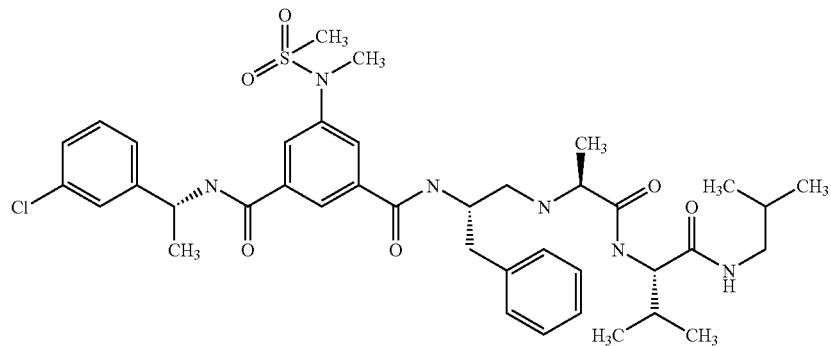

-continued
(439)
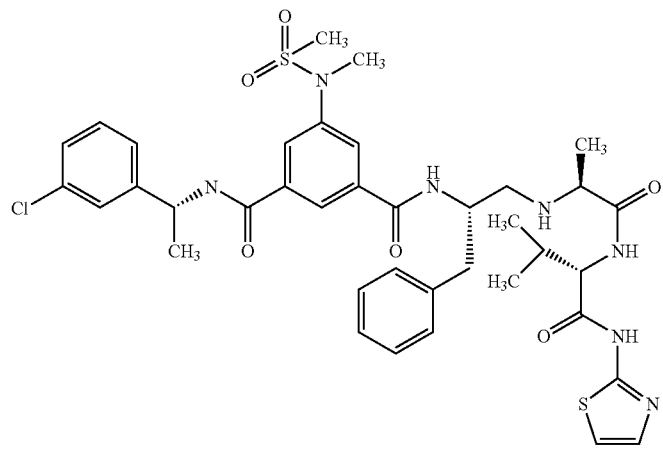
(440)
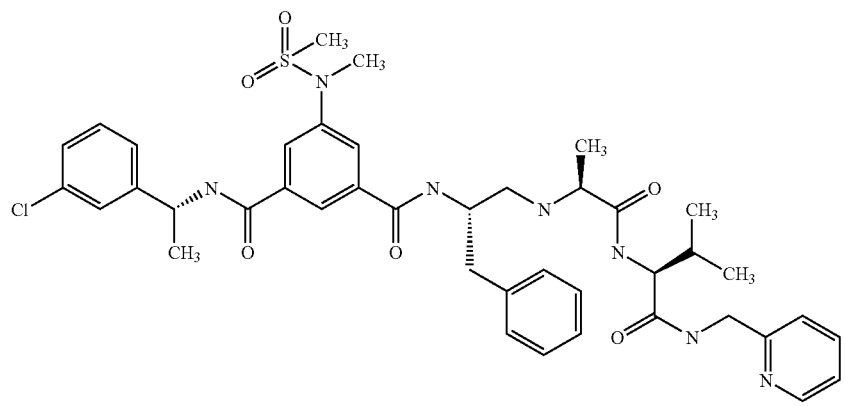
(441)
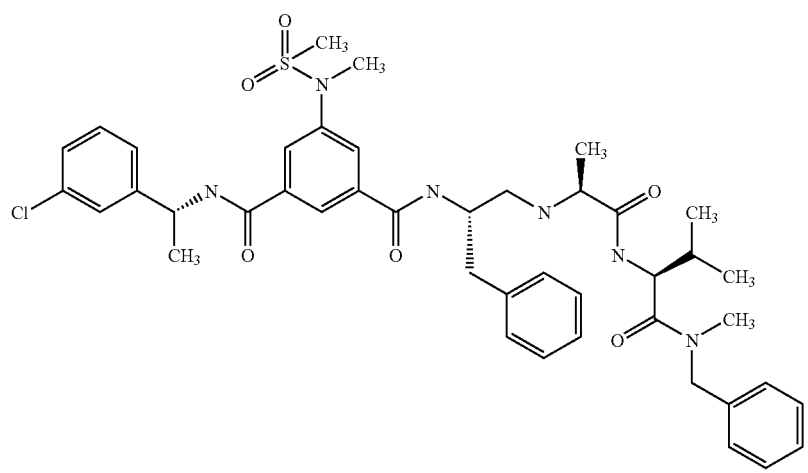

(442)
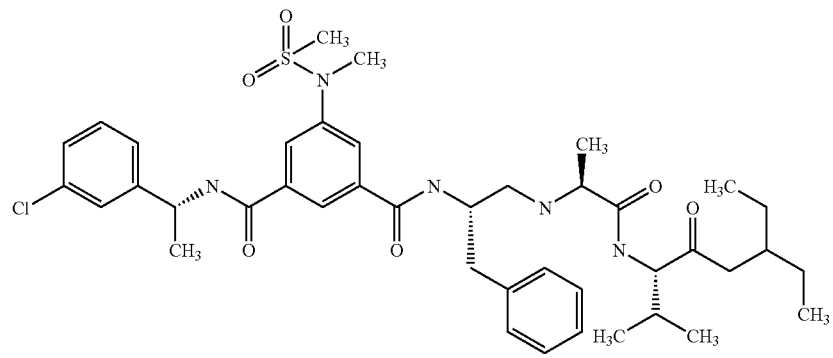
(443)
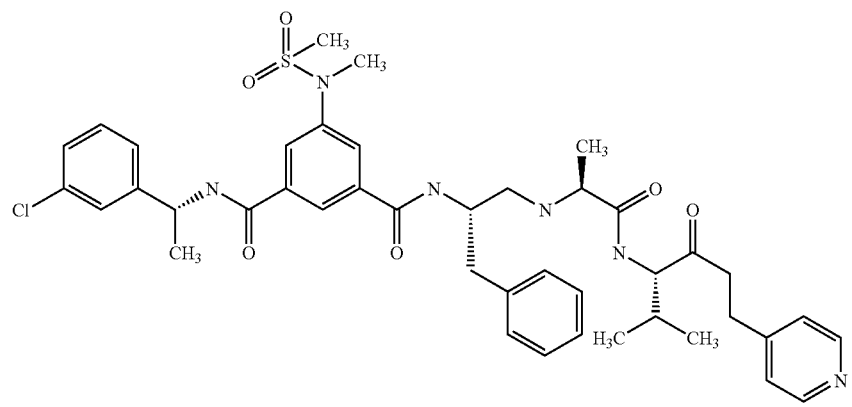
(444)
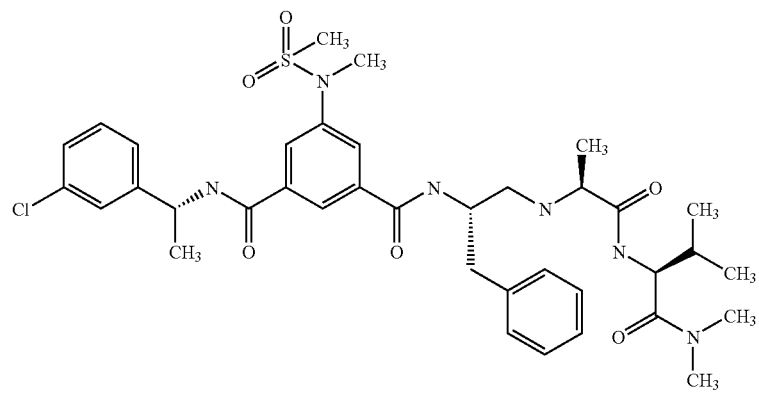
(445)
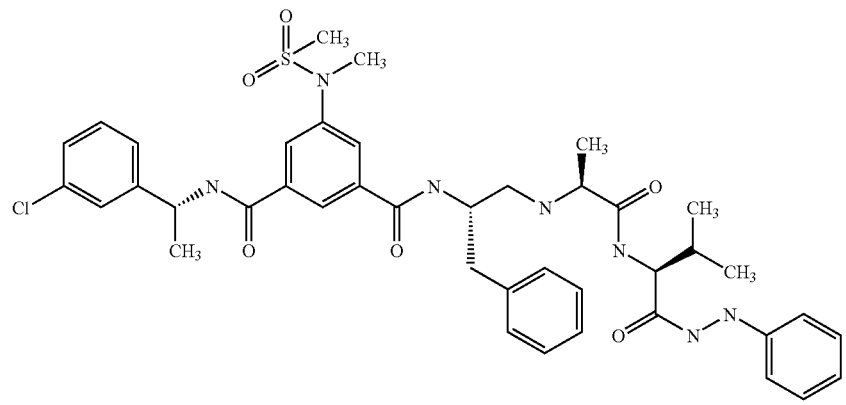

(446)
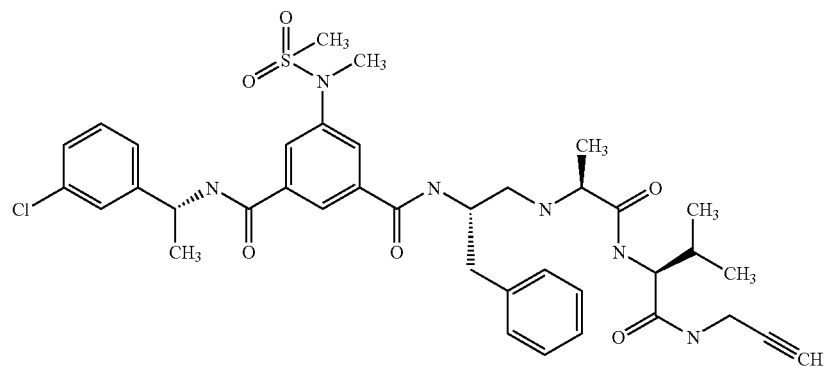
(447)
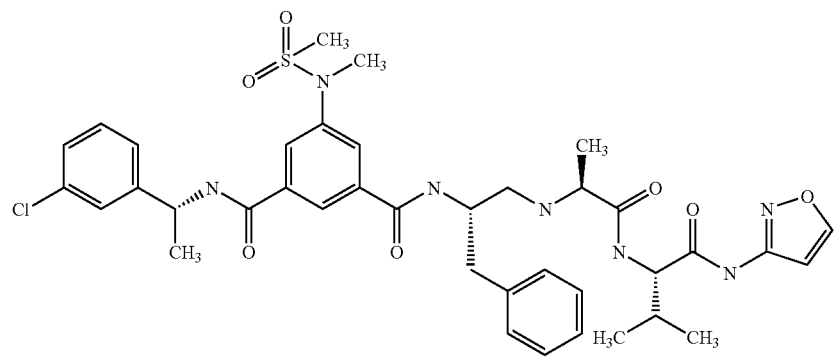
(448)
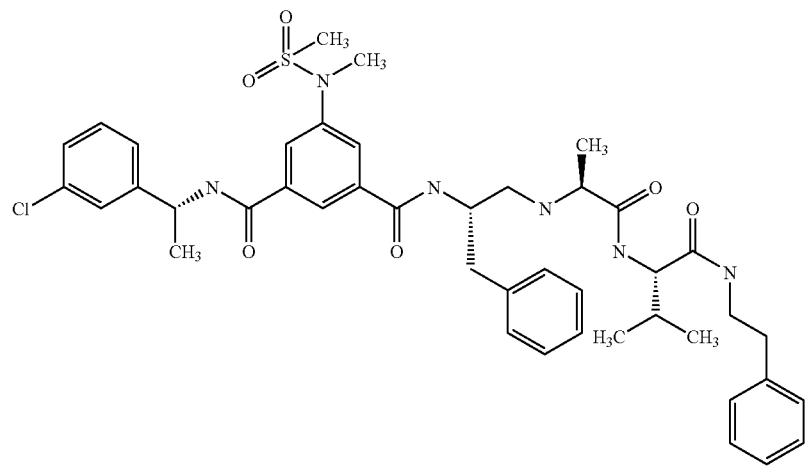
(449)
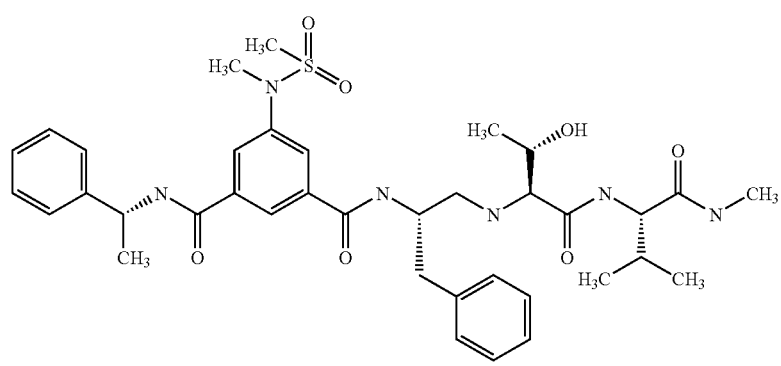

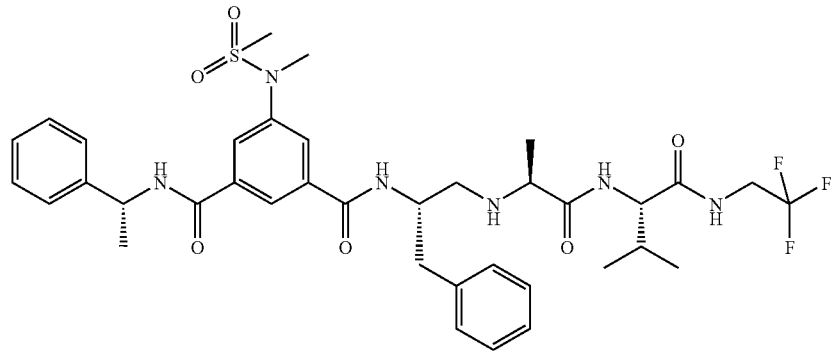
(450)
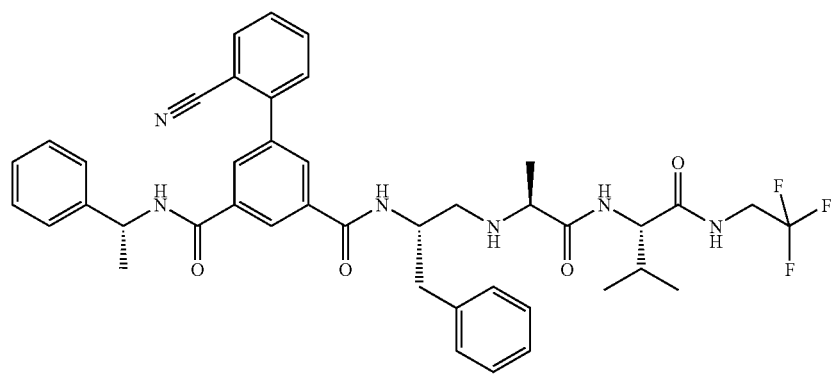
(451)
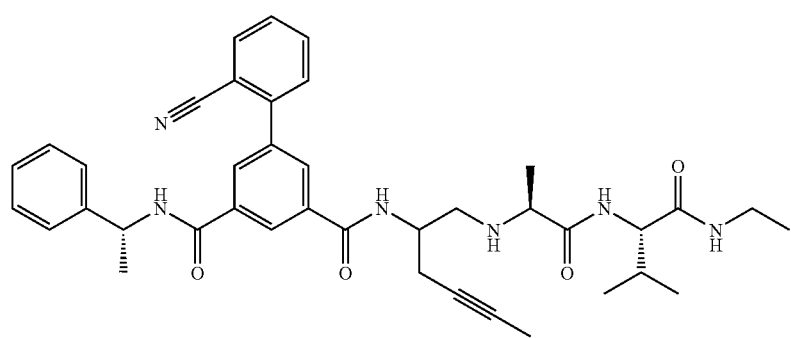
(452)
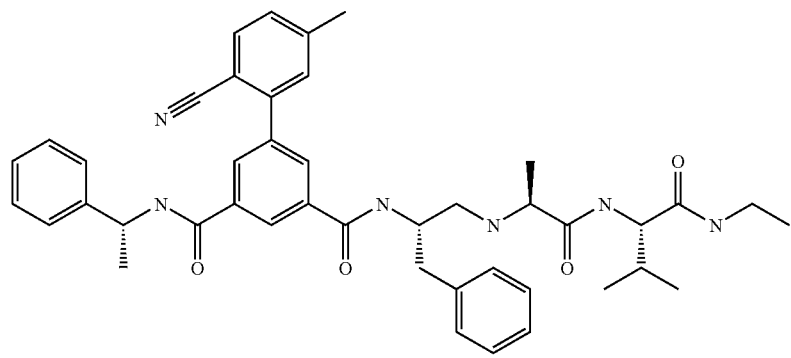
(453)

-continued
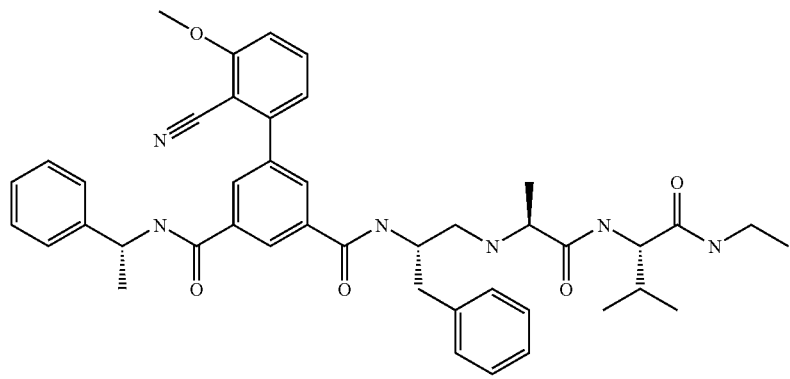
(454)
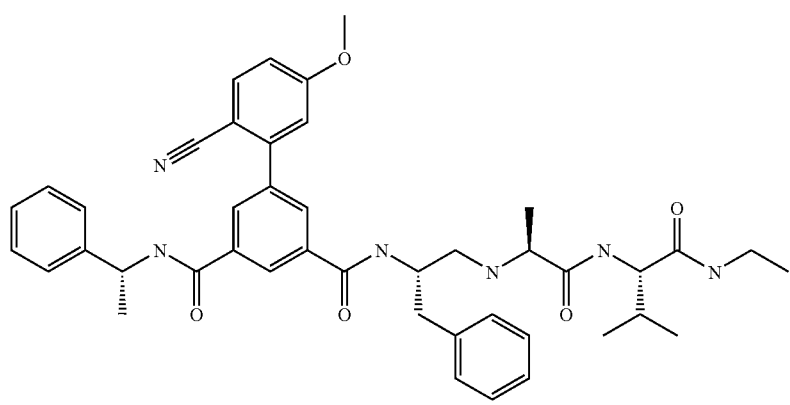
(455)
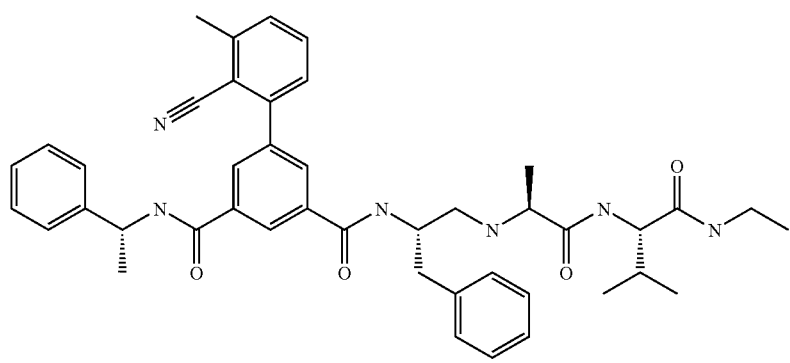
(456)
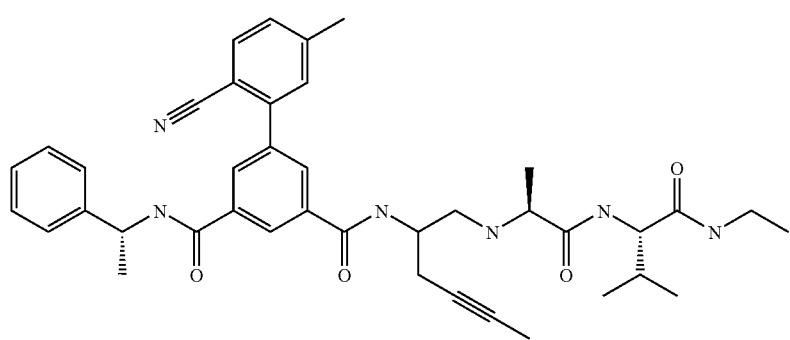
(457)

(458)

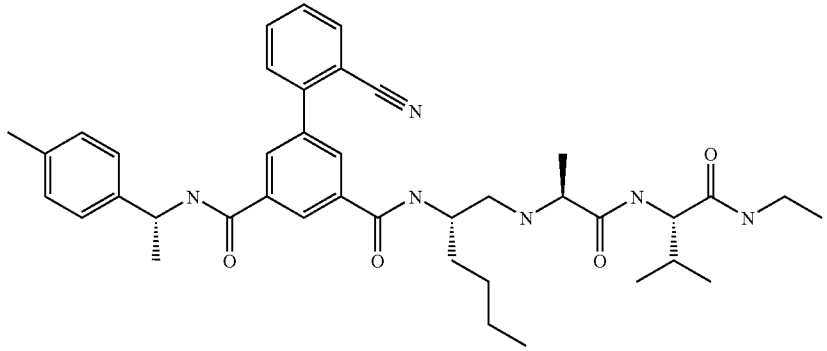

Some terms which are used hereinbefore and hereinafter to describe the compounds according to the invention will now be defined in more detail.

The term halogen denotes an atom selected from among F, Cl, Br and I.

The term $C_{1-n}$-alkyl, wherein n may have a value from 1 to 10, denotes a saturated, branched or unbranched hydrocarbon group with 1 to n C atoms. Examples of such groups include methyl, ethyl, n-propyl, iso-propyl, butyl, iso-butyl, sec-butyl, tert-butyl, n-pentyl, iso-pentyl, neo-pentyl, tert-pentyl, n-hexyl, iso-hexyl etc.

The term $C_{2-n}$-alkenyl, wherein n has a value of 3 to 6, denotes a branched or unbranched hydrocarbon group with 2 to n C atoms and a C=C double bond. Examples of such groups include ethenyl, 1-propenyl, 2-propenyl, iso-propenyl, 1-butenyl, 2-butenyl, 3-butenyl, 2-methyl-1-propenyl, 1-pentenyl, 2-pentenyl, 3-pentenyl, 4-pentenyl, 3-methyl-2-butenyl, 1-hexenyl, 2-hexenyl, 3-hexenyl, 4-hexenyl, 5-hexenyl etc.

The term $C_{2-n}$-alkynyl, wherein n has a value of 3 to 6, denotes a branched or unbranched hydrocarbon group with 2 to n C atoms and a C≡C triple bond. Examples of such groups include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl etc.

The term $C_{1-n}$-alkoxy or $C_{1-n}$-alkyloxy denotes a $C_{1-n}$-alkyl-O group, wherein $C_{1-n}$-alkyl is defined as above. Examples of such groups include methoxy, ethoxy, n-propoxy, iso-propoxy, n-butoxy, iso-butoxy, sec-butoxy, tert-butoxy, n-pentoxy, iso-pentoxy, neo-pentoxy, tert-pentoxy, n-hexoxy, iso-hexoxy etc.

The term $C_{3-n}$-cycloalkyl denotes a saturated monocyclic group with 3 to n C atoms. Examples of such groups include cyclopropyl, cyclobutyl, cyclopentyl, cyclohexyl, cycloheptyl etc.

The term $C_{3-n}$-cycloalkyloxy denotes a $C_{3-n}$-cycloalkyl-O group wherein $C_{3-n}$-cycloalkyl is defined as above. Examples of such groups include cyclopropyloxy, cyclobutyloxy, cyclopentyloxy, cyclohexyloxy, cycloheptyloxy etc.

The term $C_{3-n}$-cycloalkyl-$C_{1-n}$-alkoxy denotes a $C_{3-n}$-cycloalkyl group wherein $C_{3-n}$-cycloalkyl is defined as above and which is linked to a $C_{1-n}$-alkoxy group through a carbon atom of the $C_{1-n}$-alkoxy group. Examples of such groups include cyclopropylmethyloxy, cyclobutylethyloxy, cyclopentylmethyloxy, cyclohexylmethyloxy, cyclohexylethyloxy etc.

The term $C_{3-n}$-cycloalkenyl denotes a $C_{3-n}$-cycloalkyl group which is defined as above and additionally has at least one C=C double bond, but is not aromatic by nature.

The term heterocyclyl used in this application denotes a saturated five-, six- or seven-membered ring system or a 5-12 membered bicyclic ring system which includes one, two, three or four heteroatoms, selected from N, O and/or S, such as for example a morpholinyl, piperidinyl, piperazinyl, thiomorpholinyl, oxathianyl, dithianyl, dioxanyl, pyrrolidinyl, tetrahydrofuranyl, dioxolanyl, oxathiolanyl, imidazolidinyl, tetrahydropyranyl, pyrrolinyl, tetrahydrothienyl, oxazolidinyl, homopiperazinyl, homopiperidinyl, homomorpholinyl, homothiomorpholinyl, azetidinyl, 1,3-diazacyclohexanyl or pyrazolidinyl group.

The term aryl used in this application denotes a phenyl, biphenyl, indanyl, indenyl, 6,7,8,9-tetrahydrobenzocycloheptenyl, 1,2,3,4-tetrahydronaphthyl or naphthyl group.

The term heteroaryl used in this application denotes a heterocyclic, mono- or bicyclic aromatic ring system which includes in addition to at least one C atom one or more heteroatoms selected from N, O and/or S, wherein the term heteroaryl also includes the partially hydrogenated heterocyclic, aromatic ring systems. Examples of such groups are pyrrolyl, furanyl, thienyl, pyridyl-N-oxide, thiazolyl, imidazolyl, oxazolyl, triazinyl, triazolyl, 1,2,4-oxadiazoyl, 1,3,4-oxadiazoyl, 1,2,5-oxadiazoyl, isothiazolyl, isoxazolyl, 1,2,4-thiadiazolyl, 1,3,4-thiadiazolyl, 1,2,5-thiadiazolyl, pyrazolyl, pyrimidyl, pyridazinyl, pyrazinyl, tetrazolyl, pyridyl, indolyl, isoindoyl, indolizinyl, imidazopyridinyl, imidazo[1,2-a]pyridinyl, pyrrolopyrimidinyl, purinyl, pyridopyrimidinyl, pteridinyl, pyrimidopyrimidinyl, benzofuranyl, benzothienyl, quinolinyl, isoquinolinyl, quinazolinyl, quinoxalinyl, cinnolinyl, phthalazinyl, isobenzofuranyl, isobenzothienyl, thieno[3,2-b]thiophenyl, thieno[3,2-b]pyrrolyl, thieno[2,3-d]imidazolyl, naphthyridinyl, indazolyl, pyrrolopyridinyl, oxazolopyridinyl, benzimidazolyl, benzoxazolyl, benzisoxazolyl, benzothiazolyl, benzoisothiazolyl, benzoxadiazolyl, benzothiadiazolyl, 1,3-benzodioxolyl, 2,3-dihydrobenzofuranyl, 1,3-dihydroisobenzofuranyl, 2,3-dihydrobenzo[1,4]dioxinyl, 3,4-dihydrobenzo[1,4]oxazinyl, benzo[1,4]-oxazinyl, 2,3-dihydroindolyl, 2,3-dihydroisoindolyl, 1,2,3,4-tetrahydroquinolinyl, 1,2,3,4-tetrahydroisoquinolinyl, 2-oxo-2,3-dihydrobenzimidazolyl, 2-oxo-2,3-dihydroindolyl, pyrazolo[1,5-a]pyridinyl, pyrazolo[1,5-a]pyrimidinyl, chromanyl, chromenyl, chromonyl, isochromenyl, isochromanyl, dihydroquinolin-4-onyl, dihydroquinolin-2-onyl, quinolin-4-onyl, isoquinolin-2-onyl, imidazo[1,2-a]pyrazinyl, 1-oxoindanyl, benzoxazol-2-onyl, imidazo[4,5-d]thiazolyl or 6,7-dihydropyrrolizinyl groups.

Preferred heteroaryl groups are furanyl, thienyl, thiazolyl, imidazolyl, isoxazolyl, pyrazolyl, pyridyl, indolyl, benzofuranyl, 1,3-benzodioxolyl, 2,3-dihydrobenzofuranyl and 2,3-dihydrobenzo[1,4]dioxinyl.

The definition pyrazole includes the isomers 1H-, 3H- and 4H-pyrazole. Preferably pyrazolyl denotes 1H-pyrazolyl.

The definition imidazole includes the isomers 1H-, 2H- and 4H-imidazole. A preferred definition of imidazolyl is 1H-imidazolyl.

The definition triazole includes the isomers 1H-, 3H- and 4H-[1,2,4]-triazole as well as 1H-, 2H- and 4H-[1,2,3]-triazole. The definition triazolyl therefore includes 1H-[1,2,4]-triazol-1-, -3- and -5-yl, 3H-[1,2,4]-triazol-3- and -5-yl, 4H-[1,2,4]-triazol-3-, -4- and -5-yl, 1H-[1,2,3]-triazol-1-, -4- and -5-yl, 2H-[1,2,3]-triazol-2-, -4- and -5-yl as well as 4H-[1,2,3]-triazol-4- and -5-yl.

The term tetrazole includes the isomers 1H-, 2H- and 5H-tetrazole. The definition tetrazolyl therefore includes 1H-tetrazol-1- and -5-yl, 2H-tetrazol-2- and -5-yl and 5H-tetrazol-5-yl.

The definition indole includes the isomers 1H- and 3H-indole. The term indolyl preferably denotes 1H-indol-1-yl.

The term isoindole includes the isomers 1H— and 2H-isoindole.

In general, the bond to one of the above-mentioned heterocyclic or heteroaromatic groups may be effected via a C atom or optionally an N atom.

Within the scope of this application, in the definition of possible substituents, these may also be represented in the form of a structural formula. An asterisk (*) in the structural formula of the substituent is to be understood as being the linking point to the rest of the molecule. Thus, for example, the groups N-piperidinyl (a), 4-piperidinyl (b), 2-tolyl (c), 3-tolyl (d) and 4-tolyl (e) are represented as follows:

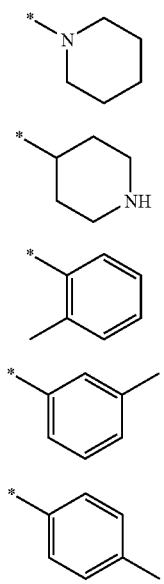

If there is no asterisk (*) in the structural formula of the substituent each hydrogen atom may be removed from the substituent and the valency thus freed may be used as a bonding point to the rest of a molecule. Thus, for example, (f)

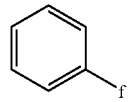

may denote 2-tolyl, 3-tolyl, 4-tolyl and benzyl.

The style of writing used in which in the group

a bond of a substituent is shown towards the centre of the group A denotes, unless stated otherwise, that this substituent may be bound to every free position of the group A carrying an H atom.

The term "optionally substituted" used in this application denotes that the group thus referred to is either unsubstituted or mono- or polysubstituted by the substituents specified. If the group in question is polysubstituted, the substituents may be identical or different.

The groups and substituents described hereinbefore may be mono- or polysubstituted by fluorine in the manner described. Preferred fluorinated alkyl groups are fluoromethyl, difluoromethyl and trifluoromethyl. Preferred fluorinated alkoxy groups are fluoromethoxy, difluoromethoxy and trifluoromethoxy. Preferred fluorinated alkylsulphinyl and alkylsulphonyl groups are trifluoromethylsulphinyl and trifluoromethylsulphonyl.

The compounds of general formula (I) according to the invention may have acid groups, chiefly carboxyl groups, and/or basic groups such as e.g. amino functions. Compounds of general formula (I) may therefore be present as internal salts, as salts with pharmaceutically useable inorganic acids such as hydrochloric acid, sulphuric acid, phosphoric acid, sulphonic acid or organic acids (such as for example maleic acid, fumaric acid, citric acid, tartaric acid or acetic acid) or as salts with pharmaceutically useable bases such as alkali or alkaline earth metal hydroxides or carbonates, zinc or ammonium hydroxides or organic amines such as e.g. diethylamine, triethylamine, triethanolamine, inter alia.

The compounds according to the invention may be obtained using the methods of synthesis known in principle from starting compounds known to the skilled man (cf. for example: Houben Weyl—Methods of Organic Chemistry, Vol. E22, Synthesis of Peptides and Peptidomimetics, M. Goodman, A. Felix, L. Moroder, C. Toniolo Eds., Georg Thieme Verlag Stuttgart, New York). The skilled man knowing the structure of the compounds according to the invention will be able to synthesise them from known starting materials without any further information. Thus, the compounds may be obtained by the methods of preparation described hereinafter.

Diagram A:
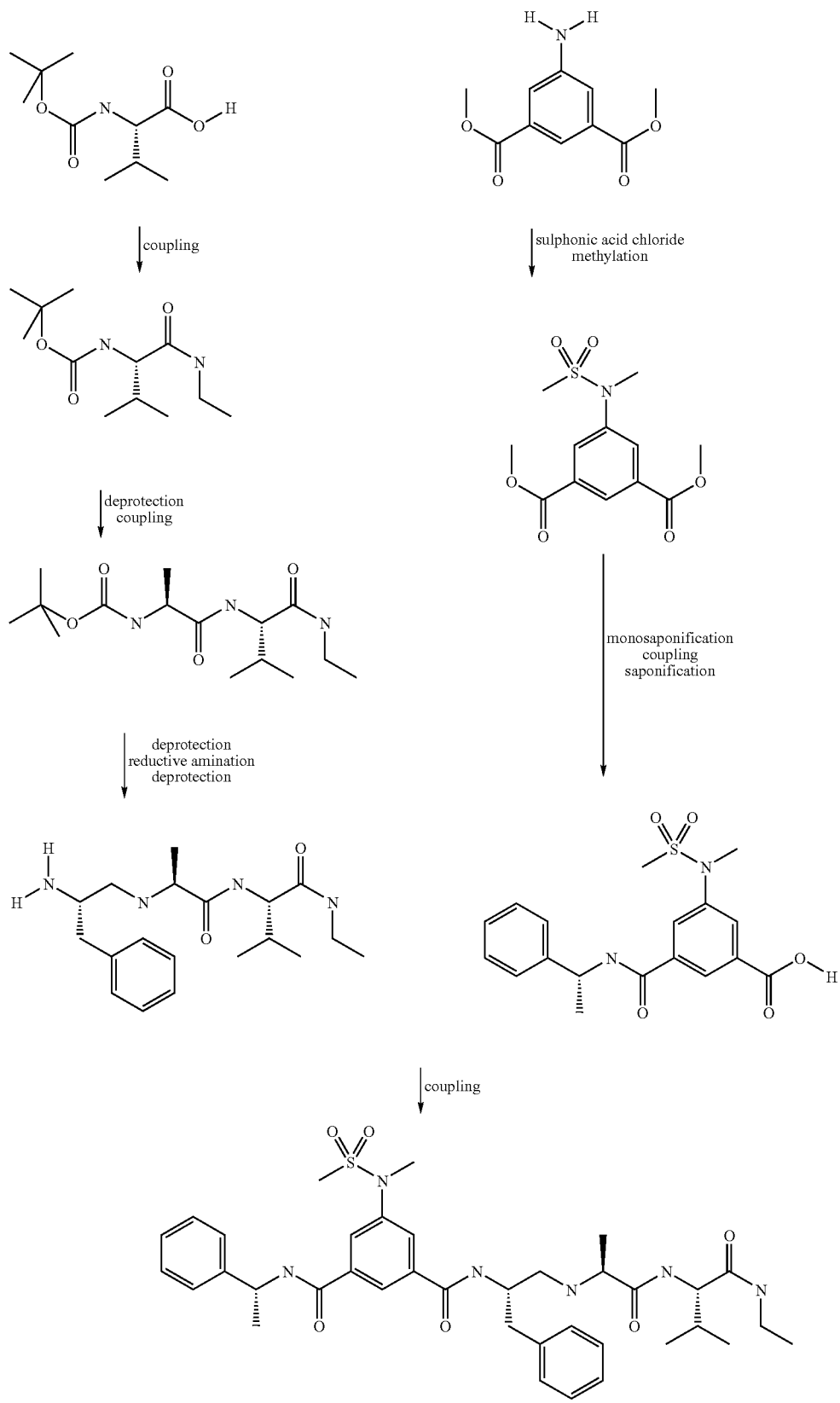

Diagram A illustrates by way of example the synthesis of the compounds according to the invention. Starting from a Boc-protected amino acid an amide is prepared by standard coupling methods. After deprotection coupling is carried out with another Boc-protected amino acid. The amine obtained after repeated deprotection is reductively aminated with a Boc-protected aminoaldehyde. The amine obtained after repeated deprotection is coupled with an isophthalic acid monoamide component to yield the end product.

Diagram B:

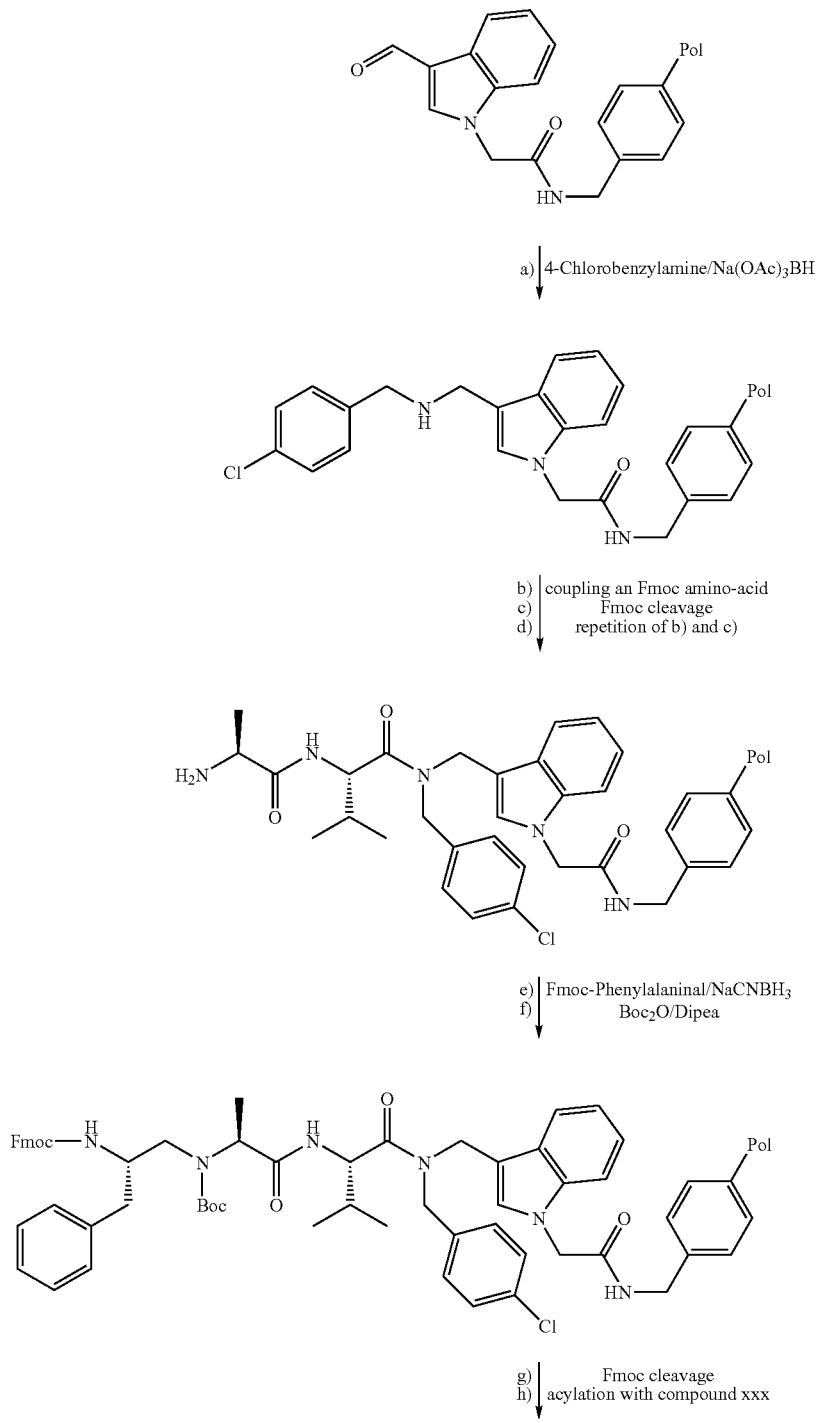

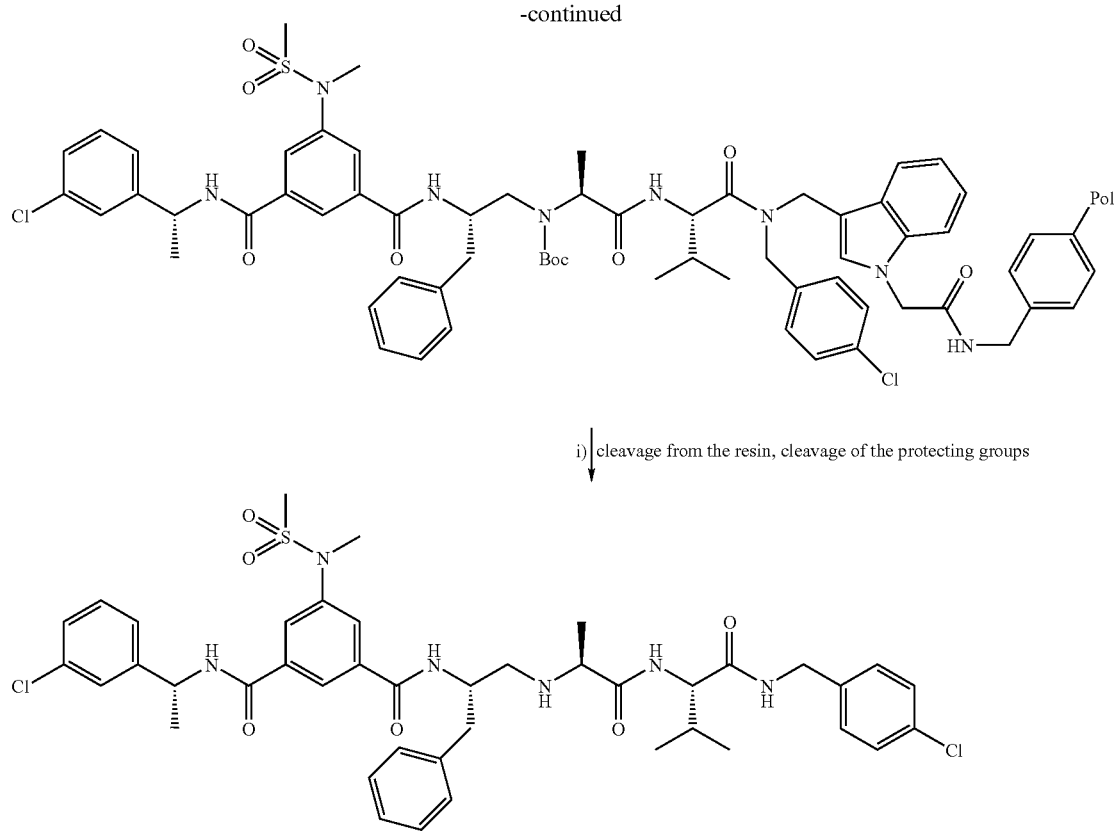

i) cleavage from the resin, cleavage of the protecting groups

Diagram B illustrates by way of example the solid phase synthesis of compounds of formula 19. The synthesis is carried out according to normal standard methods described in the literature (Houben-Weyl—Methods of Organic Chemistry, Vol. E22, Synthesis of Peptides and Peptidomimetics, M. Goodman, A. Felix, L. Moroder, C. Toniolo Eds., Georg Thieme Verlag Stuttgart, New York).

For the solid phase synthesis a commercially obtainable (formylindolyl)acetamido-methylpolystyrene resin is used. In the first reaction reductive alkylation is carried out between the aldehyde group and 4-chloro-benzylamine. The secondary amine formed is then acylated with the first amino acid (Fmoc-Val). The acylation is carried out according to standard methods of peptide chemistry, e.g. with HATU as coupling reagent. After the cleaving of the Fmoc group with piperidine in DMF the second Fmoc amino acid (Fmoc-Ala) is coupled in the presence of TBTU/HOBt as coupling reagent. After a repeat cleaving of the Fmoc group the second reductive alkylation is carried out with an Fmoc amino acid aldehyde, in this case Fmoc-phenylalaninal. The resulting secondary amine is then protected with Boc-anhydride. After cleaving of the Fmoc group the acylation is carried out with the isophthalic acid in the presence of TBTU/HOBt and Dipea. The cleaving of the product from the solid phase is carried out under acidic conditions with trifluoroacetic acid.

Diagram C:

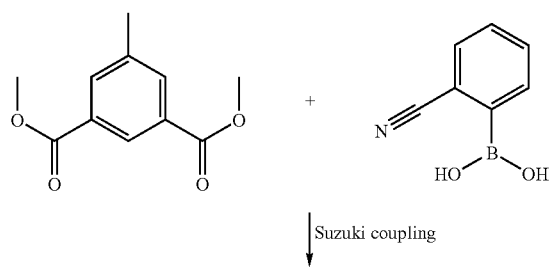

Suzuki coupling

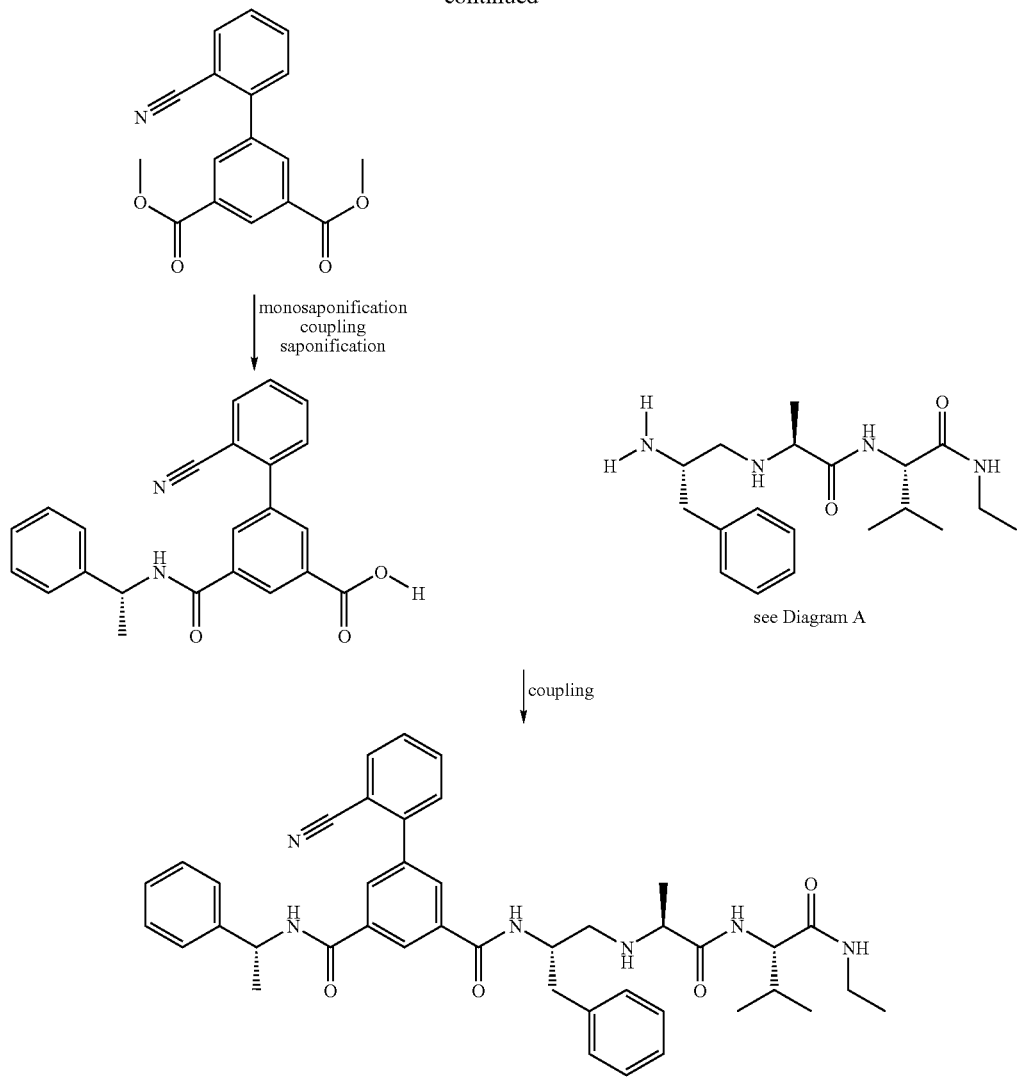

Diagram C illustrates by way of example the synthesis of the compounds according to the invention based on aryl-substituted isophthalic acids. The aryl-substituted isophthalic acid monoamide needed is obtained by Suzuki coupling, followed by monosaponification, amide coupling and a repeat saponification. It is coupled with an amine component (cf Diagram A) to yield the end product.

As stated previously, the compounds of formula (I) may be converted into the salts thereof, particularly for pharmaceutical use into the physiologically and pharmacologically acceptable salts thereof. On the one hand these salts may be present as physiologically and pharmacologically acceptable acid addition salts of the compounds of formula (I) with inorganic or organic acids. On the other hand, in the case of acidically bound hydrogen, the compound of formula (I) may also be converted by reaction with inorganic bases into physiologically and pharmacologically acceptable salts with alkali or alkaline earth metal cations as counter-ion. Acids which may be used to prepare the acid addition salts include for example hydrochloric acid, hydrobromic acid, sulphuric acid, phosphoric acid, methanesulphonic acid, acetic acid, fumaric acid, succinic acid, lactic acid, citric acid, tartaric acid or maleic acid. Mixtures of the above acids may also be used. For preparing the alkali and alkaline earth metal salts of the compound of formula (I) with acidically bound hydrogen it is preferable to use the alkali or alkaline earth metal hydroxides and hydrides, of which the hydroxides and hydrides of the alkali metals, particularly of sodium and potassium, are preferred, and sodium and potassium hydroxide are particularly preferred.

The compounds according to the invention of general formula (I) and the corresponding pharmaceutically acceptable salts thereof are chiefly suitable for the treatment and/or prevention of all those conditions or ailments which are characterised by a pathological form of the β-amyloid peptide, such as for example β-amyloid plaques, or which can be influenced by inhibition of β-secretase. For example the compounds according to the invention are particularly suitable for the prevention, treatment or slowing down of the progress of diseases such as Alzheimer's disease (AD) and other diseases associated with abnormal processing of Amyloid Precursor Protein (APP) or aggregation of the Abeta peptide, as well as diseases which can be treated or prevented by the inhibition of β-secretase or cathepsin D. Such diseases include MCI ("mild cognitive impairment"), trisomy 21 (Down's syndrome), cerebral amyloid angiopathy, degenerative dementias, hereditary cerebral hemorrhage with amyloidosis, Dutch type (HCHWA-D), Alzheimer's dementia with Lewy bodies, trauma, stroke, pancreatitis, Inclusion Body Myositis (IBM), and other peripheral amyloidoses, diabetes and arteriosclerosis.

The compounds are preferably suitable for the prevention and treatment of Alzheimer's disease. The compounds according to the invention may be used as a monotherapy and also in combination with other compounds which may be administered for the treatment of the above-mentioned diseases.

The compounds according to the invention are particularly suitable for administration to mammals, preferably primates, particularly preferably humans, for the treatment and/or prevention of the above-mentioned conditions and diseases.

The compounds according to the invention may be administered by oral, parenteral (intravenous, intramuscular etc.), intranasal, sublingual, inhalative, intrathecal, topical or rectal route.

When administered orally, as is preferred, the compounds according to the invention may be formulated such that the compounds according to the invention do not come into contact with the acidic gastric juices. Suitable oral formulations may for example have gastric juice-resistant coatings which only release the active substances on reaching the small intestine. Such tablet coats are known in the art.

Suitable pharmaceutical formulations for administering the compounds according to the invention are for example tablets, pellets, coated tablets, capsules, powders, suppositories, solutions, elixirs, active substance plasters, aerosols and suspensions.

Approximately 0.1 to 1000 mg of one of the compounds according to the invention or of a mixture of several of these compounds is formulated on its own or together with pharmaceutically conventional excipients such as carriers, diluents, binders, stabilisers, preservatives, dispersants etc. to form a dosage unit in a manner known to the skilled man.

A dosage unit (e.g. a tablet) preferably contains between 2 and 250 mg, particularly preferably between 10 and 100 mg of the compounds according to the invention.

Preferably, the pharmaceutical formulations are administered 1, 2, 3 or 4 times, particularly preferably 1-2 times, most preferably once a day.

The dosage required to achieve a corresponding effect with the treatment or prevention usually depends on the compound which is to be administered, the patient, the nature and gravity of the disease or condition and the method and frequency of administration and is for the doctor prescribing the treatment to decide.

Expediently, the amount of the compounds according to the invention administered is in the range from 0.1 to 1000 mg/day, preferably 2 to 250 mg/day, particularly preferably 5 to 100 mg/day, when administered orally. For this purpose, the compounds of formula (I) prepared according to the invention, optionally in combination with other active substances, may be formulated together with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethyleneglycol, propyleneglycol, cetylstearylalcohol, carboxymethylcellulose or fatty substances such as hard fat or suitable mixtures thereof into conventional galenic preparations such as tablets, pellets, coated tablets, capsules, powders, suppositories, solutions, elixirs, active substance plasters, aerosols and suspensions.

The compounds according to the invention may also be used in combination with other active substances, particularly for the treatment and/or prevention of the diseases and conditions mentioned hereinbefore. Other active substances which may be used for such combinations include in particular those which, for example, potentiate the therapeutic effect of a compound according to the invention in respect of one of the indications mentioned and/or enable the dosage of a compound according to the invention to be reduced. Therapeutic agents suitable for such a combination include, for example, beta-secretase inhibitors; gamma-secretase inhibitors; amyloid aggregation inhibitors such as e.g. alzhemed; directly or indirectly acting neuroprotective substances; anti-oxidants, such as e.g. vitamin E or ginkolide; anti-inflammatory substances, such as e.g. Cox inhibitors, NSAIDs additionally or exclusively having Aβ lowering properties; HMG-CoA reductase inhibitors (statins); acetylcholinesterase inhibitors, such as donepezil, rivastigmine, tacrine, galantamine; NMDA receptor antagonists such as e.g. memantine; AMPA agonists; substances modulating the concentration or release of neurotransmitters such as NS-2330; substances inducing the secretion of growth hormone such as ibutamoren mesylate and capromorelin; CB-1 receptor antagonists or inverse agonists; antibiotics such as minocyclin or rifampicin; PDE-IV and PDE-IX inhibitors, $GABA_A$ inverse agonists, nicotinic agonists, histamine H3 antagonists, 5 HAT-4 agonists or partial agonists, 5HT-6 antagonists, a2-adrenoreceptor antagonists, muscarinic M1 agonists, muscarinic M2 antagonists, metabotropic glutamate-receptor 5 positive modulators, and other substances that modulate receptors or enzymes in a manner such that the efficacy and/or safety of the compounds according to the invention is increased and/or unwanted side effects are reduced.

Preferred are those combinations which consist of one or more of the compounds according to the invention with one or more of the following substances selected from among alzhemed, vitamin E, ginkolide, donepezil, rivastigmine, tacrine, galantamine, memantine, NS-2330, ibutamoren mesylate, capromorelin, minocyclin and/or rifampicin.

The compounds according to the invention, or the physiologically acceptable salts thereof, and the other active substances to be combined with them may be contained together in a dosage unit, for example a tablet or capsule, or separately in two identical or different dosage units, for example as a so-called kit-of-parts.

The compounds according to the invention may also be used in combination with immunotherapies such as e.g. active immunisation with Abeta or parts thereof or passive immunisation with humanised anti-Abeta antibodies for the treatment of the above-mentioned diseases and conditions.

The dosage for the above-mentioned combination partners is expediently 1/5 of the normally recommended lowest dose up to 1/1 of the normally recommended dose.

Therefore in another aspect the invention relates to the use of a compound according to the invention or a physiologically acceptable salt of such a compound combined with at least one of the active substances described above as combination partners for preparing a pharmaceutical composition which is suitable for the treatment or prevention of diseases or conditions which can be influenced by the inhibition of β-secretase.

The compound according to the invention, or a physiologically acceptable salt thereof, in combination with another active substance may be used simultaneously or at staggered times, but particularly close together in time. If administered simultaneously, the two active substances are given to the patient together; if administered at staggered times the two active substances are given to the patient successively within a period of less than or equal to 12, particularly less than or equal to 6 hours.

Consequently, in another aspect, the invention relates to a pharmaceutical composition which contains a compound according to the invention or a physiologically acceptable salt of such a compound and at least one of the active substances described hereinbefore as combination partners, optionally together with one or more inert carriers and/or diluents.

Thus, for example, a pharmaceutical composition according to the invention contains a combination of a compound according to the invention of formula (I) or a physiologically acceptable salt of such a compound as well as at least one other of the above-mentioned active substances optionally together with one or more inert carriers and/or diluents.

The compounds according to the invention inhibit the proteolysis of the APP protein between the amino acids Met595 and Asp596 (the numbering relates to the APP695 isoform) or the proteolysis of other APP isoforms such as APP751 and APP770 or mutated APP at the corresponding site, which is also referred to as the β-secretase cleavage site. The inhibition of the β-secretase should therefore lead to a reduced production of the β-amyloid peptide (Aβ).

The activity of the β-secretase may be investigated in assays based on different detection techniques. In the test set-up a catalytically active form of β-secretase is incubated with a potential substrate in a suitable buffer. The reduction in the substrate concentration or the increase in the product concentration may be monitored using various technologies as a function of the substrate used: HPLS-MS analysis, fluorescence assays, fluorescence-quenching assays, luminescence assays are a non-representative selection of the various possibilities. Assay systems in which the effectiveness of a compound can be demonstrated are described e.g. in U.S. Patents U.S. Pat. Nos. 5,942,400 and 5,744,346 and hereinafter. An alternative assay format comprises displacing a known β-secretase ligand with a test substance (US 2003/0125257).

As the substrate, either the APP protein or parts thereof or any amino acid sequence which can be hydrolysed by β-secretase may be used. A selection of such sequences can be found for example in Tomasselli et al. 2003 in J. Neurochem 84: 1006. A peptide sequence of this kind may be coupled to suitable dyes which make it possible to detect proteolysis indirectly. The enzyme source used may be the total β-secretase enzyme or mutants with a catalytic activity or just parts of the β-secretase which still contain the catalytically active domain. Various forms of β-secretase are known and available and may be used as the enzyme source in a corresponding test set-up. This includes the native enzyme as well as the recombinant or synthetic enzyme. Human β-secretase is known by the name Beta Site APP Cleaving Enzyme (BACE), Asp2 and memapsin 2 and is described e.g. in U.S. Pat. No. 5,744,346 and in Patent Applications WO 98/22597, WO 00/03819, WO 01/23533, and WO 00/17369, as well as in the scientific literature (Hussain et. al., 1999, Mol. Cell. Neurosci. 14: 419-427; Vassar et. al., 1999, Science 286: 735-741; Yan et. al., 1999, Nature 402: 533-537; Sinha et. al., 1999, Nature 40: 537-540; and Lin et. al., 2000, PNAS USA 97: 1456-1460). Synthetic forms of the enzyme have also been described (W0 98/22597 and WO 00/17369). β-secretase may be extracted and purified for example from human brain tissue or produced recombinantly in mammalian cell cultures, insect cell cultures, yeasts or bacteria.

To calculate the IC50 value of a substance different amounts of substance are incubated with the β-secretase in an assay. The IC50 value of a compound is defined as the concentration of substance at which a 50% reduction in the detected signal is measured, compared with the mixture without the test compound. Substances are evaluated as inhibiting β-secretase if under these conditions their IC50 value is less than 50 µM, preferably less than 10 µM, particularly preferably less than 1 µM and most particularly preferably less than 100 nM.

In detail, an assay for detecting β-secretase activity may be as follows: The ectodomain of BACE (amino acids 1-454) fused to the recognition sequence for an anti-Myc antibody and a poly-histidine is secreted overnight by HEK293/APP/BACE$_{ect}$ cells in OptiMEM® (Invitrogen). A 10 µl aliquot of this cell culture supernatant is used as the enzyme source. The enzyme is stable over more than 3 months' storage at 4° C. or –20° C. in OptiMEM®. The substrate used is a peptide with the amino acid sequence SEVNLDAEFK, to which the Cy3 fluorophore (Amersham) is coupled N-terminally and the Cy5Q fluorophore (Amersham) is coupled C-terminally. The substrate is dissolved in DMSO in a concentration of 1 mg/ml and used in the experiment in a concentration of 1 µM. The test mixture also contains 20 mM NaOAc, pH 4.4 and a maximum of 1% DMSO. The test is carried out in a 96-well plate in a total volume of 200 µl for 30 minutes at 30° C. The cleaving of the substrate is recorded kinetically in a fluorimeter (ex: 530 nm, em: 590 nm). The assay is started by adding the substrate.

Mixtures without enzyme or without inhibitor are included in each plate as controls. The IC$_{50}$ value for the test compound is calculated using standard software (e.g. GraphPad Prism®) from the percentage inhibition of the substance at different test concentrations. The relative inhibition is calculated from the reduction in signal intensity in the presence of the substance, compared with the signal intensity without the substance.

The compounds (1)-(458) listed in the preceding Table have IC$_{50}$ values of less than 30 µM, measured using the test described hereinbefore.

The activity of the β-secretase may also be investigated in cellular systems. As APP is a substrate for β-secretase and Aβ is secreted by the cells after processing of APP by β-secretase has taken place, cellular test systems for detecting β-secretase activity are based on the detection of the amount of Aβ formed over a defined period.

A selection of suitable cells includes, but is not restricted to, human embryonic kidney fibroblasts 293 (HEK293), Chinese Hamster Ovary cells (CHO), human H4 neuroglioma cells, human U373 MG astrocytoma glioblastoma cells, murine neuroblastoma N2a cells, which stably or transiently express APP or mutated forms of APP, such as e.g. the Swedish or London or Indiana mutation. The transfection of the cells is carried out e.g. by cloning the cDNA from human APP into an expression vector such as e.g. pcDNA3 (Invitrogen) and adding it to the cells with a transfection reagent such as e.g. lipofectamine (Invitrogen) in accordance with the manufacturer's instructions.

The secretion of Aβ may also be measured from cells without genetic modification with a suitably sensitive Aβ detection assay such as e.g. ELISA or HTRF. Cells which may be used for this may be for example human IMR32 neuroblastoma cells, besides various other cells.

The secretion of Aβ may also be investigated in cells obtained from the brains of embryos or the young of APP transgenic mice, e.g. in those of Hsiao et al 1996 Science 274: 99-102, or from other organisms such as e.g. guinea pigs or rats. Substances are evaluated as inhibiting β-secretase if under these conditions their IC$_{50}$ value is less than 50 µM, preferably less than 10 µM, particularly preferably less than 1 µM and most preferably less than 100 nM.

An example of the method used to carry out a cell assay is described below: U373-MG cells which stably express APP (isoform 751) are cultivated in a culture medium such as DMEM+glucose, sodium pyruvate, glutamine and 10% FCS at 37° C. in a steam-saturated atmosphere with 5% $CO_2$. In order to investigate the β-secretase inhibiting activity of substances the cells are incubated with different concentrations of the compound between 50 µM and 50 µM for 12-24 h. The substance is dissolved in DMSO and diluted for the assay in culture medium such that the DMSO concentration does not exceed 0.5%. The production of Aβ during this period is determined using an ELISA which uses the antibodies 6E10 (Senentek) and SGY3160 (C. Eckman, Mayo Clinic, Jacksonville, Fla., USA) as capturing antibodies which are bound to the microtitre plate and Aβ40 and Aβ42-specific antibodies (Nanotools, Germany), coupled to alkaline phosphatase as detection antibodies. Non-specific binding of proteins to the microtitre plate is prevented by blocking with Block Ace (Serotec) before the addition of the Aβ-containing culture supernatant. The amounts of Aβ contained in the cell supernatant are quantified by adding the substrate for alkaline phosphatase CSPD/Sapphire II (Applied Biosystems) in accordance with the manufacturer's instructions. Possible non-specific effects of the test compound on the vitality of the cell are ruled out by determining this by AlamarBlue (Resazurin) reduction over a period of 60 minutes.

The potency of non-toxic substances is determined by calculating the concentration which results in a 50% reduction in the amount of Aβ secreted by comparison with untreated cells.

In addition, various animal models may be used to investigate the β-secretase activity and/or the APP processing and the release of Aβ. Thus, for example, transgenic animals which express APP and/or β-secretase are used to test the inhibitory activity of compounds of this invention. Corresponding transgenic animals are described e.g. in U.S. Pat. Nos. 5,877,399, 5,612,486, 5,387,742, 5,720,936, 5,850,003, 5,877,015 and 5,811,633, and in Games et. al., 1995, Nature 373: 523. It is preferable to use animal models which exhibit some of the characteristics of AD pathology. The addition of β-secretase inhibitors according to this invention and subsequent investigation of the pathology of the animals is another alternative for demonstrating the β-secretase inhibition by the compounds. The compounds are administered in such a way that they are able to reach their site of activity in a pharmaceutically effective form and amount.

The test for detecting cathepsin D (EC: 3.4.23.5) inhibition was carried out as follows: 20 mU of recombinant cathepsin D (Calbiochem, Cat.No. 219401) in 20 mM sodium acetate buffer pH 4.5 with 5 µM substrate peptide and various concentrations of the test substance are incubated at 37° C. in a 96-well dish and the conversion is recorded over 60 minutes in a fluorescence measuring device (emission: 535 nm, extinction: 340 nm). The peptide substrate used has the following sequence: $NH_2$-Arg-Glu(Edans)-Glu-Val-Asn-Leu-Asp-Ala-Glu-Phe-Lys(Dabcyl)-Arg-COOH (Bachem). However, it is also possible to use a peptide or protein substrate with a sequence that can be cleaved proteolytically by cathepsin D. The test substances are dissolved in DMSO and used in the assay after being diluted to a maximum 1% DMSO.

The assay is started by adding the substrate.

Mixtures without enzyme or without inhibitor are included in each plate as controls. The $IC_{50}$ value for the test compound is calculated using standard software (e.g. GraphPad Prism®) from the percentage inhibition of the substance at different test concentrations. The relative inhibition is calculated from the reduction in signal intensity in the presence of the substance, compared with the signal intensity without the substance.

The compounds (1)-(458) listed in the Table hereinbefore had an inhibitory effect on cathepsin D in the test described here.

The Examples that follow are intended to illustrate the invention, without restricting it thereto.

EXAMPLES

The following abbreviations are used in the test descriptions:

| | |
|---|---|
| BOC | tert.-butoxycarbonyl |
| DIPEA | N-ethyl-diisopropylamine |
| DMF | dimethylformamide |
| ES-MS | electrospray mass spectrometry |
| HPLC | high pressure liquid chromatography |
| HPLC-MS | high pressure liquid chromatography with mass detection |
| sat. | saturated |
| HOBt | 1-hydroxy-benzotriazole-hydrate |
| i. vac. | in vacuo |
| conc. | concentrated |
| MPLC | medium pressure liquid chromatography |
| RF | retention factor |
| RT | retention time |
| TBTU | O-(benzotriazol-1-yl)-N,N,N',N'-tetramethyluronium tetrafluoroborate |
| TEA | triethylamine |
| TFA | trifluoroacetic acid |
| THF | tetrahydrofuran |
| →* | indicates the binding site of a group |
| —* | indicates the binding site of a group |

The HPLC 1-data were produced under the following conditions:

Waters Alliance 2695 HPLC, Waters 2700 Autosampler, Waters 2996 diode array detector The mobile phase used is:

A: water with 0.13% TFA

B: acetonitrile with 0.10% TFA

| time in min | % A | % B | flow rate in ml/min |
|---|---|---|---|
| 0.0 | 95 | 5 | 1.00 |
| 0.7 | 95 | 5 | 1.00 |
| 5.2 | 2 | 98 | 1.00 |
| 5.7 | 2 | 98 | 1.00 |
| 6.0 | 95 | 5 | 1.00 |
| 6.5 | 95 | 5 | 1.00 |

The stationary phase used was a Varian column, Microsorb 100 $C_{18}$ 3 µm, 4.6 mm×50 mm, batch no. 2231108 (column temperature: constant at 25° C.).

The diode array detection took place at a wavelength range of 210-300 nm.

The HPLC 2-data were produced under the following conditions:

The mobile phase used is:

A: water

B: acetonitrile

| time in min | % A | % B | flow rate in ml/min |
|---|---|---|---|
| 0.0 | 95 | 5 | 1.50 |
| 5.0 | 0 | 100 | 1.50 |
| 6.0 | 0 | 100 | 1.50 |
| 6.2 | 95 | 5 | 1.50 |

The stationary phase used was a Develosil RPAq. column 4.6 mm×50 mm,

The detection took place at wavelengths of 254 nm.

The HPLC 3- data were produced under the following conditions:

Waters Alliance 2795 HPLC with integrated Autosampler, Waters 2996 PDA, Waters ZQ mass spectrometer The mobile phase used is:
A: water with 0.10% TFA
B: acetonitrile with 0.08% TFA

| time in min | % A | % B | flow rate in ml/min |
|---|---|---|---|
| 0.00 | 95 | 5 | 0.80 |
| 2.75 | 2 | 98 | 0.80 |
| 3.50 | 2 | 98 | 0.80 |
| 3.80 | 95 | 5 | 0.80 |
| 5.00 | 95 | 5 | 0.80 |
| 6.5 | 95 | 5 | 1.00 |

The stationary phase used was a Waters column, Xterra MS $C_{18}$, 3.5 μm, 2.1 mm×50 mm (column temperature: constant at 40° C.).

The diode array detection took place at a wavelength range of 210-500 nm.

The HPLC 4-data were produced under the following conditions:

Abimed Gilson, Autoinjector 231 XL, Fraction collector 202 C, Detector 118 UV/Vis, The mobile phase used is:
A: water with 0.10% TFA
B: acetonitrile with 0.10% TFA

| time in min | % A | % B | flow rate in ml/min |
|---|---|---|---|
| 0 | 90 | 10 | 20.00 |
| 5 | 90 | 10 | 20.00 |
| 16 | 50 | 50 | 20.00 |
| 25 | 50 | 50 | 20.00 |
| 31 | 0 | 100 | 20.00 |
| 32 | 90 | 10 | 20.00 |
| 37 | 90 | 10 | 20.00 |

The stationary phase used was a Varian column, Microsorb $C_{18}$ 8 μm, 21.2 mm×250 mm; the diode array detection took place at a wavelength range of 210-300 nm.

The HPLC 5-data were produced under the following conditions:

column: Waters Xterra MS. C18. 4.6×50 mm. 3.5 μm.
column temperature. 40° C.
flow rate 1 ml/min.
buffer A: water+0.1% TFA.
buffer B: MeCN+0.08% TFA.
gradient: from 95% A to 2% A in 4.50 min The HPLC 6 data were produced under the following conditions:

Waters ZQ2000 mass spectrometer, HP1100 HPLC+DAD, Gilson 215

The mobile phase used is:
A: water with 0.10% TFA
B: acetonitrile with 0.10% TFA

| time in min | % A | % B | flow rate in ml/min |
|---|---|---|---|
| 0.0 | 95 | 5 | 1.00 |
| 0.4 | 95 | 5 | 1.00 |
| 4.0 | 2 | 98 | 1.00 |
| 4.35 | 2 | 98 | 1.00 |
| 4.50 | 95 | 5 | 1.00 |

The stationary phase used was a column X-Terra MS C18, 3.5 μm, 4.6 mm×50 mm, (column temperature: constant at 40° C.).

The diode array detection took place at a wavelength range of 210-500 nm.

The HPLC-MS-data were produced under the following conditions:

Waters ZMD, Waters Alliance 2690 HPLC, Waters 2700 Autosampler, Waters 996 diode array detector The mobile phase used is:
A: water with 0.13% TFA
B: acetonitrile with 0.10% TFA

| time in min | % A | % B | flow rate in ml/min |
|---|---|---|---|
| 0.0 | 95 | 5 | 1.00 |
| 0.1 | 95 | 5 | 1.00 |
| 3.1 | 2 | 98 | 1.00 |
| 4.5 | 2 | 98 | 1.00 |
| 5.0 | 95 | 5 | 1.00 |

The stationary phase used was a Waters column, Xterra MS $C_{18}$ 2.5 μm, 4.6 mm×30 mm, (column temperature: constant at 25° C.).

The diode array detection took place at a wavelength range of 210-500 nm.

Example 1

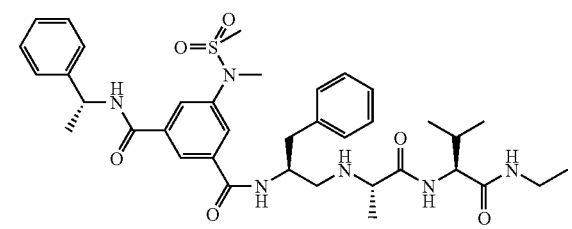

a) Preparation of 1-a:

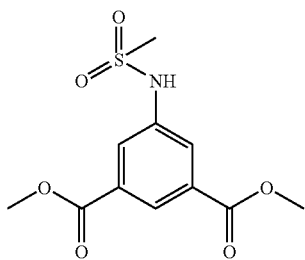

1-a 2.0 g (9.6 mmol) dimethyl 5-amino-isophthalate were dissolved in 19 ml dichloromethane and combined with 1.5 ml (19.1 mmol) pyridine. The reaction solution was cooled to 0° C., at this temperature 0.8 ml (10.5 mmol) methanesulphonyl chloride was metered in and the mixture was stirred for 2 hours at ambient temperature. Then the reaction solution was evaporated to dryness i. vac., the residue was mixed with ethyl acetate, filtered off and dried in the vacuum drying cupboard.

Yield 2.5 g (91%) white crystals 1-a.
ES-MS (M+H)$^+$=288 b) Preparation of 1-b:

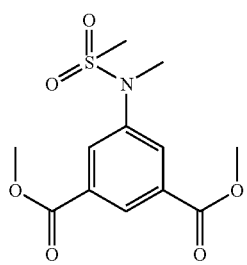

1-b

First of all 2.5 g (8.7 mmol) mmol) methyl iodide were added to a solution of 0.7 g (17.4 mmol) sodium hydride (60% in mineral oil) in 10 ml DMF. The reaction solution was stirred for 1 h at ambient temperature, combined with 100 ml of water and extracted with ethyl acetate. The combined organic phases were dried and evaporated to dryness using the rotary evaporator. Quantitative yield of 1-b as a yellow oil.

ES-MS (M+NH$_4$)$^+$=319 c) Preparation of 1-c:

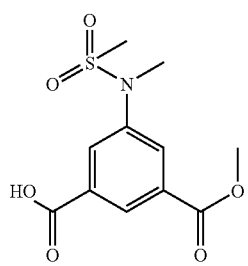

1-c 2.9 g (8.7 mmol) 1-b were dissolved in 25 ml of methanol and 25 ml THF, at 0° C. 8.7 ml (8.7 mmol) 1 N NaOH were added and the reaction solution was stirred for 7 hours at ambient temperature. Then the solvent was eliminated using the rotary evaporator, the residue was dissolved in 30 ml 1 N HCl and extracted with ethyl acetate. The combined organic phases were dried and purified by chromatography on silica gel with the eluant (dichloromethane/methanol 95:5).

Yield 1.2 g (46%) white crystals 1-c.
ES-MS (M+H)$^+$=288 d) Preparation of 1-d:

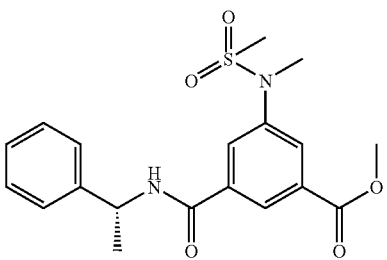

1-d 500 mg (1.7 mmol) 1-c in 10 ml dichloromethane were combined with 615 mg (1.9 mmol) TBTU and 1.2 ml (7.0 mmol) DIPEA, then 226 µl (1.7 mmol) (R)-1-phenyl-ethylamine was added and the mixture was stirred for 1 hour at ambient temperature. The reaction solution was extracted with 20% KHCO$_3$ solution and water. The organic phases were separated using a phase separator cartridge and evaporated to dryness i. vac. The residue was purified by chromatography on silica gel with the eluant (ethyl acetate/heptane 9:1). Yield 580 mg (85%) beige crystals 1-d.

ES-MS (M+H)$^+$=391 e) Preparation of 1-e:

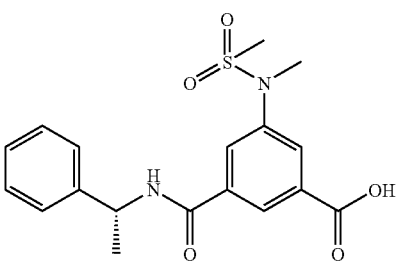

1-e 580 mg (1.5 mmol) 1-d were dissolved in 5 ml of methanol and 5 ml THF, 1.5 ml (3.0 mmol) 2N NaOH was added and the reaction solution was stirred for 1 hour at 50° C. Then the solvent was eliminated i. vac., the residue was combined with 20 ml 1N HCl, the precipitate was filtered off and dried at 50° C. in the vacuum drying cupboard.

Yield 270.0 mg (48%) white crystals 1-e.
ES-MS (M+H)$^+$=377 f) Preparation of 1-f:

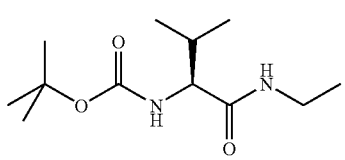

1-f 25.9 g (119.2 mmol) Boc-L-valine in 250 ml dichloromethane were combined with 38.3 g (119 mmol) TBTU and 63.0 ml (371 mmol) DIPEA, while cooling with an ice bath, then 10.7 g (131 mmol) ethylamine-hydrochloride was added. The reaction solution was stirred for 5 hours at ambient temperature and then extracted with 20% KHCO$_3$ solution and water. The organic phases were separated using a phase separator cartridge and evaporated to dryness i. vac. The residue was purified by chromatography on silica gel with the eluant (ethyl acetate/heptane 7:3). Quantitative yield of 1-f as white crystals.

ES-MS (M+H)$^+$=245 g) Preparation of 1-g:

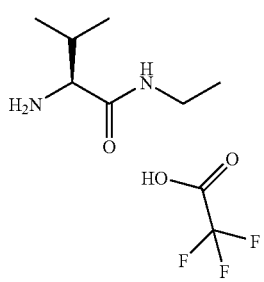

29.0 g (0.1 mol) 1-f was dissolved in 130 ml dichloromethane and combined with 100 ml (1.3 mol) trifluoroacetic acid. The reaction solution was stirred for 1 h at ambient temperature, then evaporated to dryness using the rotary evaporator. Quantitative yield of 1-g as a yellow oil.

h) Preparation of 1-h:

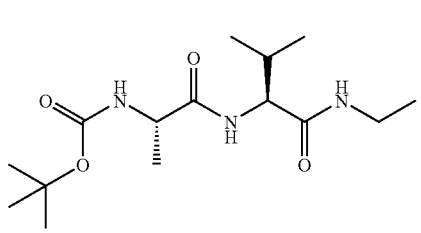

1-h was prepared analogously to 1-d from Boc-Ala-OH and 1-g.

ES-MS (M+H)$^+$=316 i) Preparation of 1-i:

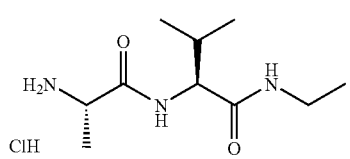

40.0 g (0.1 mol) 1-h were suspended in 800 ml of ethyl acetate and combined with 100 ml (0.4 mol) 4N HCl in dioxane. The reaction solution was stirred overnight at ambient temperature. The precipitate was suction filtered, suspended in diethyl ether, suction filtered again and then dried at 50° C. in the vacuum drying cupboard.

Yield 27.1 g (85%) white crystals 1-i.

ES(−)-MS (M−H)$^−$=250 j) Preparation of 1-j:

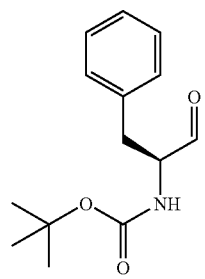

29.7 g (70.0 mmol) of Dess-Martin periodinane were suspended in 150 ml dichloromethane, then within 40 minutes a solution of 16.0 g (63.7 mmol) Boc-phenyl-alaninol in 150 ml dichloromethane was metered in. The reaction solution was stirred for 2 hours at ambient temperature, then combined with 200 ml 20% KHCO$_3$ solution and 200 ml 10% Na$_2$S$_2$O$_3$ solution. The mixture was stirred for 20 min at ambient temperature, the phases were separated and the organic phase was washed with 20% KHCO$_3$ solution and water. The organic phase was dried and evaporated to dryness using the rotary evaporator. Quantitative yield of 1-j as white crystals.

k) Preparation of 1-k:

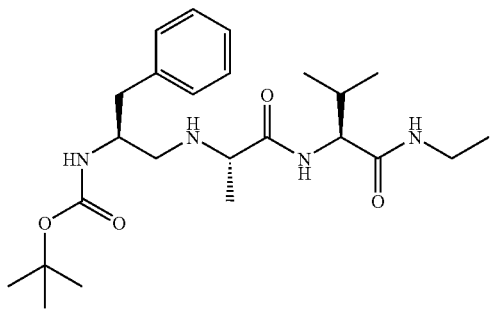

15.4 g (61.2 mmol) 1-i were dissolved in 200 ml acetonitrile and combined with 10.5 ml (61.2 mmol) DIPEA. The mixture was stirred for 10 min at ambient temperature, 15.3 g (61.2 mmol) 1-j was added and the mixture was cooled to 0° C. Then the reaction solution was combined with 7.0 ml (122 mmol) acetic acid and 20.5 g (91.8 mmol) sodium triacetoxyborohydride and stirred overnight at ambient temperature. The reaction solution was evaporated to dryness using the rotary evaporator and the residue was combined with dichloromethane and 1N NaHCO$_3$ solution. The phases were separated, the organic phase was dried and evaporated to dryness i. vac. The residue was purified by chromatography on silica gel with the eluant (ethyl acetate/heptane 7:3 to ethyl acetate/heptane 1:0). Yield 13.1 g (43%) bright yellow crystals 1-k.

ES-MS (M+H)$^+$=449 l) Preparation of 1-l:

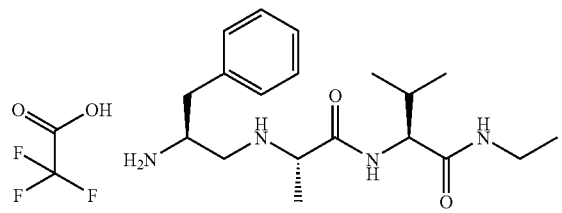

1-l was prepared analogously to Example 1-g from 1-k.
ES-MS (M+H)⁺=349 m) Preparation of 1-m:

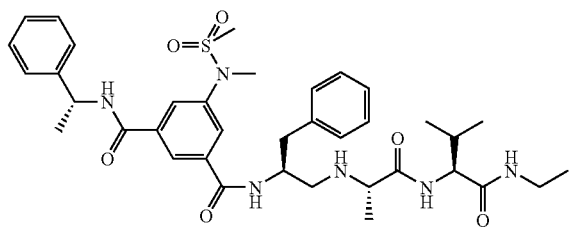

1-m was prepared analogously to 1-d from 1-e and 1-l.
ES-MS (M+H)⁺=707

Analogously to Example 1 the following compounds were prepared from 1-c and the corresponding amount of amine:

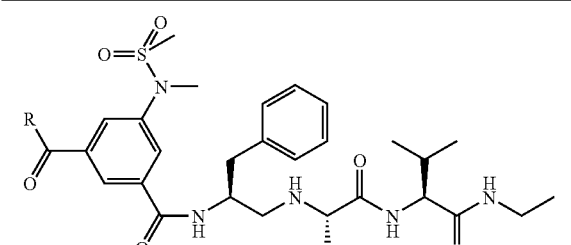

| Example | R | Mass spectrum |
|---|---|---|
| 1.2 | 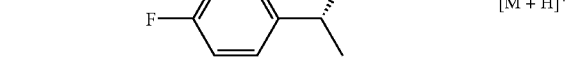 | 725 [M + H]⁺ |
| 1.3 | 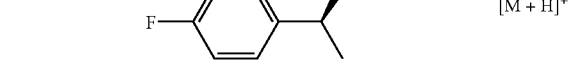 | 725 [M + H]⁺ |
| 1.4 |  ClH | 721 [M + H]⁺ |

-continued

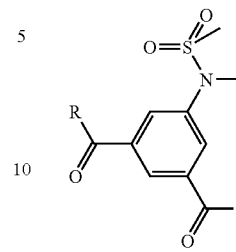

| Example | R | Mass spectrum |
|---|---|---|
| 1.5 | 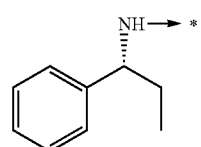 | 721 [M + H]⁺ |
| 1.6 | 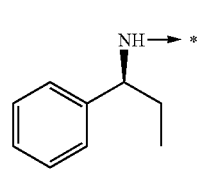 | 721 [M + H]⁺ |
| 1.7 | 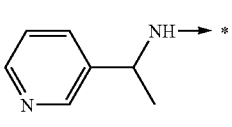 | 708 [M + H]⁺ |
| 1.8 | 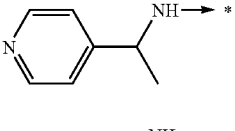 | 708 [M + H]⁺ |
| 1.9 | 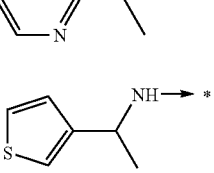 | 708 [M + H]⁺ |
| 1.10 | 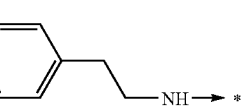 | 713 [M + H]⁺ |
| 1.11 | 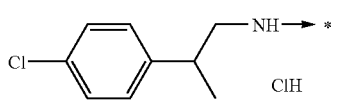 | 707 [M + H]⁺ |
| 1.12 | 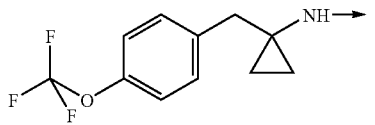 ClH | 755/757 (chlorine isotopes) [M + H]+ |
| 1.13 | 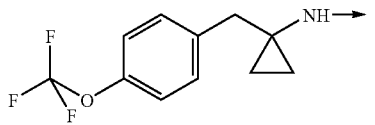 | 817 [M + H]⁺ |

-continued
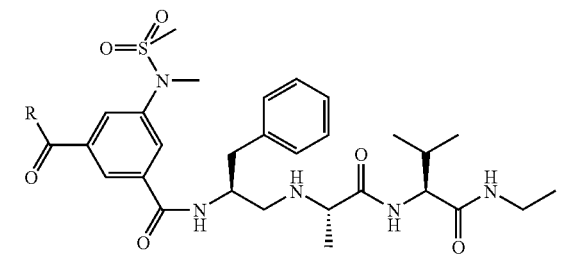
| Example | R | Mass spectrum |
|---|---|---|
| 1.14 | 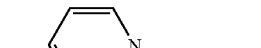 ClH | 784 [M + H]+ |
| 1.15 | 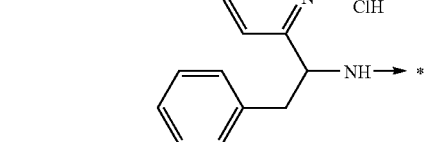 | 735 [M + H]+ |
| 1.16 |  | 790 [M + H]+ |
| 1.17 | 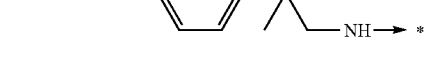 | 782 [M + H]+ |
| 1.18 | 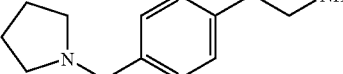 | 737 [M + H]+ |
| 1.19 | 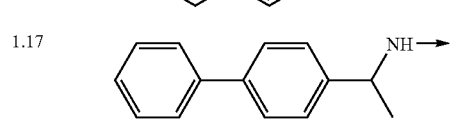 | 785/787 (bromine isotopes) [M + H]+ |
| 1.20 | 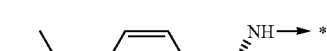 | 757 [M + H]+ |
| 1.21 | 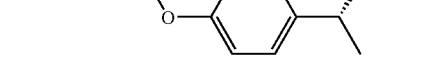 | 721 [M + H]+ |
| 1.22 | 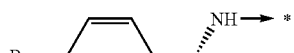 | 721 [M + H]+ |
| 1.23 |  | 719 [M + H]+ |
-continued
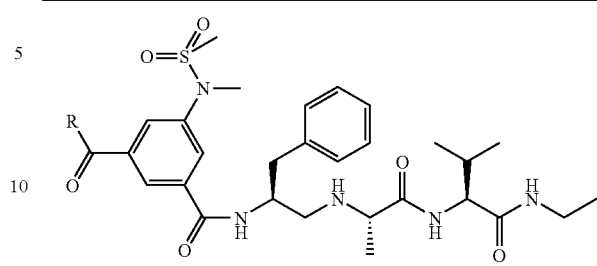
| Example | R | Mass spectrum |
|---|---|---|
| 1.24 | 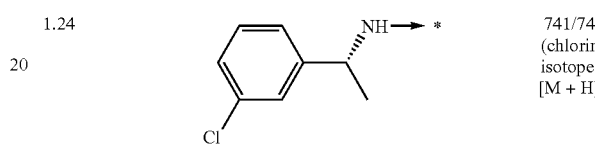 | 741/743 (chlorine isotopes) [M + H]+ |
| 1.25 | 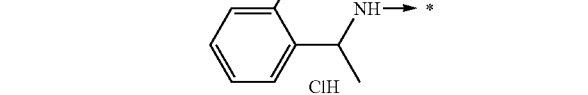 ClH | 737 [M + H]+ |
| 1.26 |  | 735 [M + H]+ |
| 1.27 | 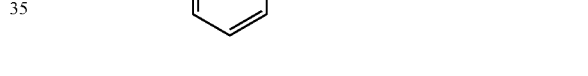 | 721 [M + H]+ |
| 1.27-b | 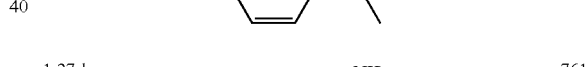 | 761 [M + H]+ |
| 1.27-c | 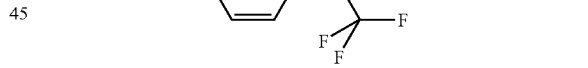 | 694 [M + H]+ |
| 1.27-d | 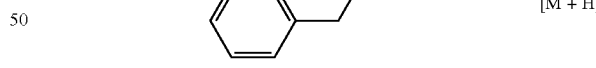 | 738 [M + H]+ |
| 1.27-e | 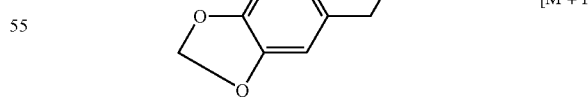 | 730 [M + H]+ |

-continued

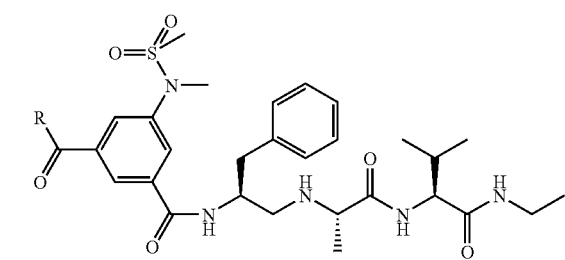

| Example | R | Mass spectrum |
|---|---|---|
| 1.27-f | 2-fluorobenzyl-NH— | 712 [M + H]+ |
| 1.27-g | 3-methylbenzyl-NH— | 708 [M + H]+ |
| 1.27-h | N-benzyl-N-propyl— | 736 [M + H]+ |
| 1.27-i | 3-chlorophenethyl-NH— | 743 [M + H]+ |
| 1.27-j | 3-(trifluoromethyl)phenethyl-NH— | 776 [M + H]+ |
| 1.27-k | 1-(1-methyl-1H-pyrazol-4-yl)ethyl-NH— | 712 [M + H]+ |
| 1.27-l | 1-(1-ethyl-1H-pyrazol-3-yl)ethyl-NH— | 726 [M + H]+ |

-continued

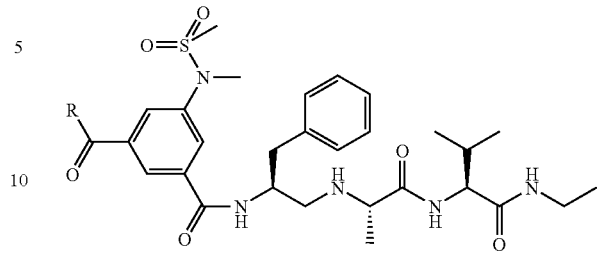

| Example | R | Mass spectrum |
|---|---|---|
| 1.27-m | 3-hydroxybenzyl-NH— | 710 [M + H]+ |
| 1.27-n | 3-hydroxy-4-methoxybenzyl-NH— | 740 [M + H]+ |
| 1.27-o | (5-cyclopropyl-1H-pyrazol-3-yl)methyl-NH— | 724 [M + H]+ |
| 1.27-p | (1H-pyrazol-3-yl)methyl-NH— | 684 [M + H]+ |
| 1.27-q | (5-methyl-1H-1,2,4-triazol-3-yl)methyl-NH— | 700 [M + H]+ |
| 1.27-r | 3,4-difluorophenethyl-NH— | 744 [M + H]+ |
| 1.27-s | N-methyl-N-phenethyl— | 722 [M + H]+ |
| 1.27-t | N-benzyl-N-ethyl— | 722 [M + H]+ |

-continued
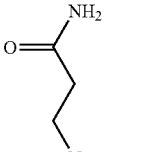
| Example | R | Mass spectrum |
|---|---|---|
| 1.27-u | 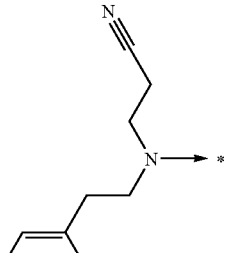 | 765 [M + H]+ |
| 1.27-v | 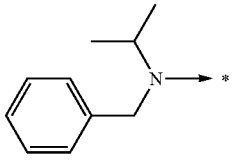 | 736 [M + H]+ |
| 1.27-w | 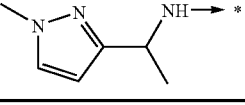 | 787 [M + H]+ |
| 1.27-x | 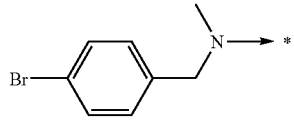 | 709 [M + H]+ |
| 1.27-y | 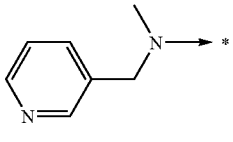 | 747 [M + H]+ |
| 1.27-z | 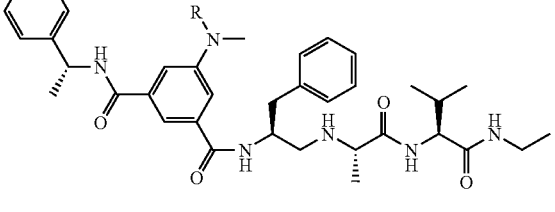 | 750 [M + H]+ |
-continued
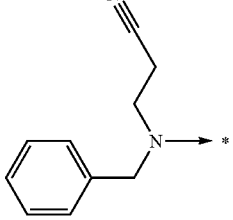
| Example | R | Mass spectrum |
|---|---|---|
| 1.27-za | 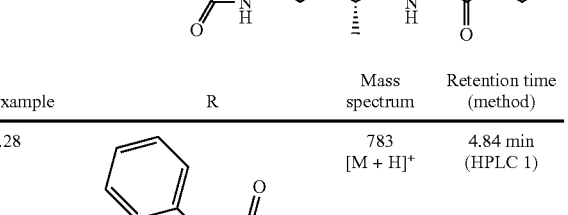 | 761 [M + H]+ |
| 1.27-zb | 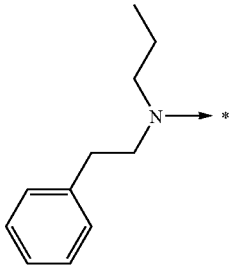 | 712 [M + H]+ |
Analogously to Example 1 the following compounds were prepared from dimethyl 5-amino-isophthalate and the corresponding amount of sulphonyl chlorides:
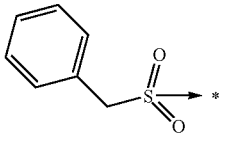
| Example | R | Mass spectrum | Retention time (method) |
|---|---|---|---|
| 1.28 | 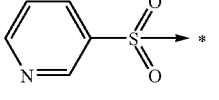 | 783 [M + H]+ | 4.84 min (HPLC 1) |
| 1.29 | 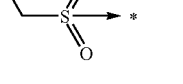 | 770 [M + H]+ | 4.57 min (HPLC 1) |
| 1.30 |  | 721 [M + H]+ | 4.54 min (HPLC 1) |

-continued

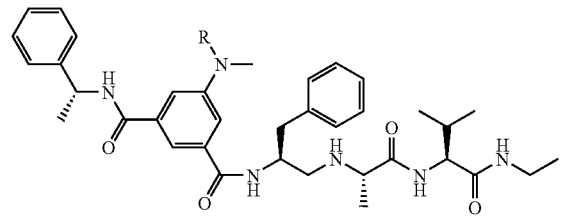

| Example | R | Mass spectrum | Retention time (method) |
|---|---|---|---|
| 1.31 | (dimethylsulfamoyl) | 736 [M + H]+ | 4.64 min (HPLC 1) |
| 1.32 | (morpholinosulfonyl) | 778 [M + H]+ | 4.53 min (HPLC 1) |

-continued

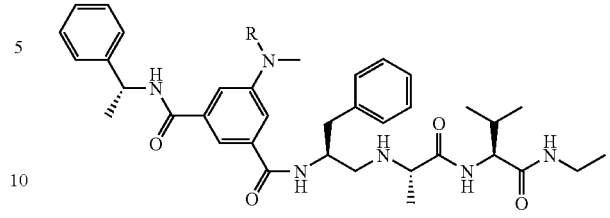

| Example | R | Mass spectrum | Retention time (method) |
|---|---|---|---|
| 1.33 | (phenylsulfonyl) | 769 [M + H]+ | 4.79 min (HPLC 1) |
| 1.34 | (isopropylsulfonyl) | 735 [M + H]+ | |

Analogously to 1 the following compounds were prepared from corresponding educts:

| Example | | Mass spectrum | Retention time (method) |
|---|---|---|---|
| 1.34-a | | 788 [M + H]+ | |
| 1.34-b | | 774 [M + H]+ | |

-continued

| Example | Mass spectrum | Retention time (method) |
|---|---|---|
| 1.34-c | 746 [M + H]+ | 2.58 min (HPLC-MS) |
| 1.34-d | 805 [M + H]+ | |
| 1.34-e | 788 [M + H]+ | 3.03 min (HPLC-MS) |

-continued
| Example | | Mass spectrum | Retention time (method) |
|---|---|---|---|
| 1.34-f | 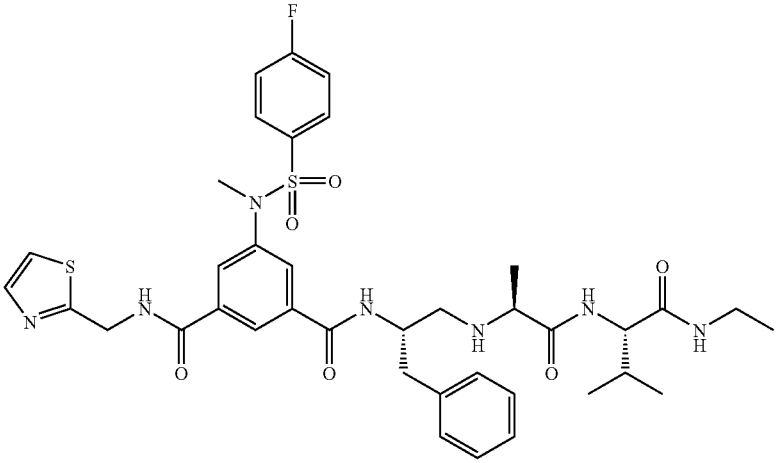 | 781 [M + H]+ | 2.75 min (HPLC-MS) |
| 1.34-g | 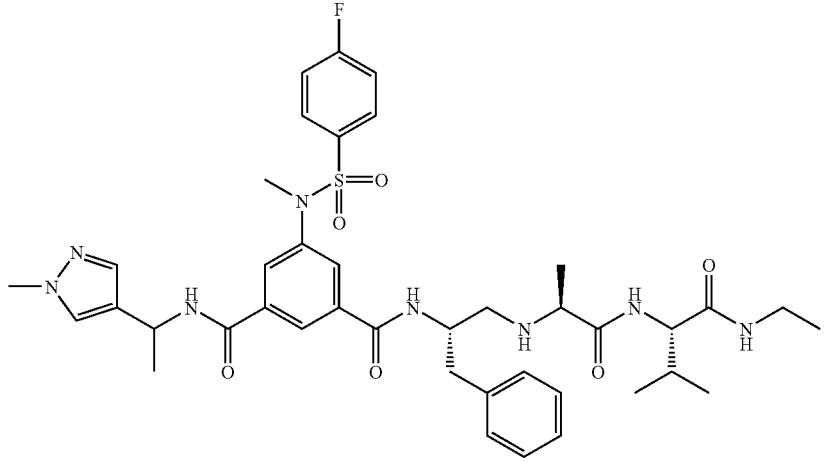 | 773 [M + H]+ | 2.70 min (HPLC-MS) |
| 1.34-h | 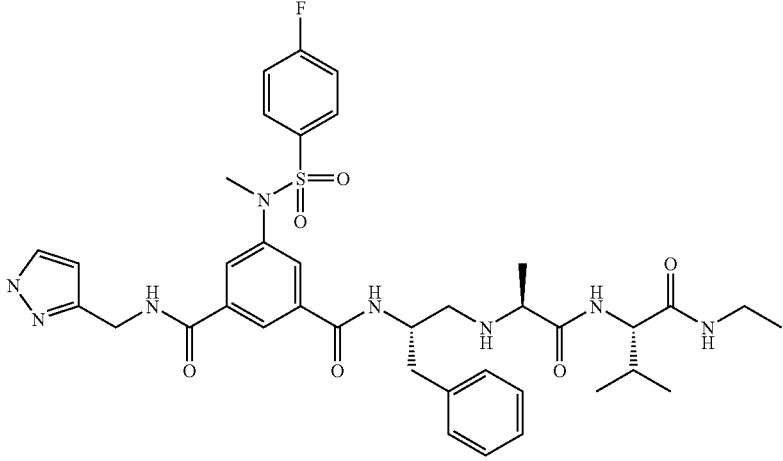 | 764 [M + H]+ | |

| Example | Mass spectrum | Retention time (method) |
|---|---|---|
| 1.34-i | 786 [M + H]+ | 2.14 min (HPLC-MS) |
| 1.34-j | 864 [M + H]+ | 2.71 min (HPLC-MS) |
| 1.34-k | 785 [M + H]+ | 4.17 min (HPLC 1) |

| Example | Mass spectrum | Retention time (method) |
|---|---|---|
| 1.34-l | 863 [M + H]⁺ | 5.01 min (HPLC 1) |
| 1.34-m | 865 [M + H]⁺ | 3.84 min (HPLC 1) |
| 1.34-n | 943 [M + H]⁺ | 4.75 min (HPLC 1) |

293   294
-continued
| Example | | Mass spectrum | Retention time (method) |
|---|---|---|---|
| 1.34-o | | 864 [M + H]⁺ | 4.39 min (HPLC 1) |
| 1.34-p | | 942 [M + H]⁺ | 5.27 min (HPLC 1) |
Example 1.35
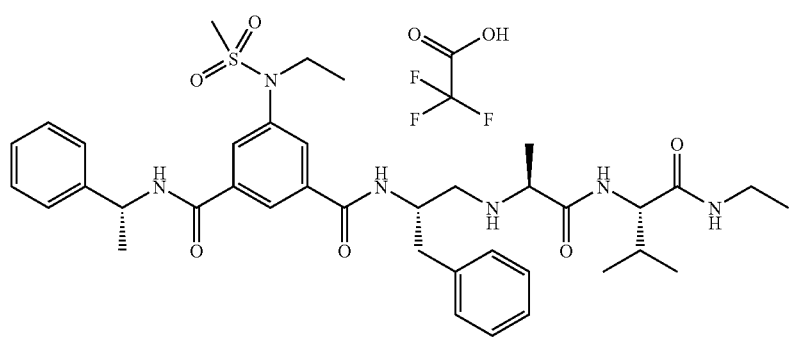
Example 1.35 was prepared analogously to Example 1, except that iodoethane was used instead of methyl iodide.
ES-MS (M+H)⁺=721
RT(HPLC 1)=4.57 min Example 1.36

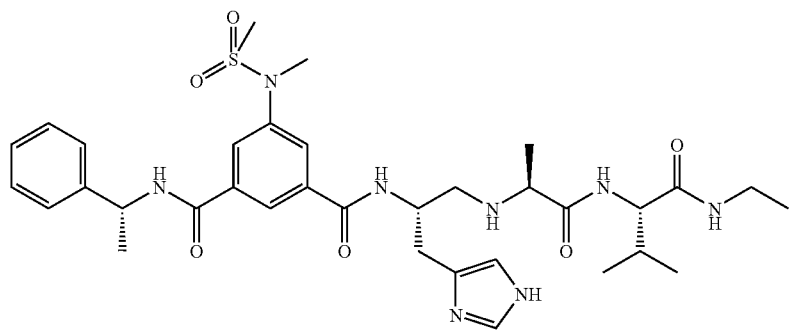

Example 1.36 was prepared analogously to Example 1 from 1-e and (S)-2-{(S)-2-[(S)-2-amino-3-(1H-imidazol-4-yl)-propylamino]-propionylamino}-N-ethyl-3-methyl-butyramide.
ES-MS (M+H)+=697

Example 1.37

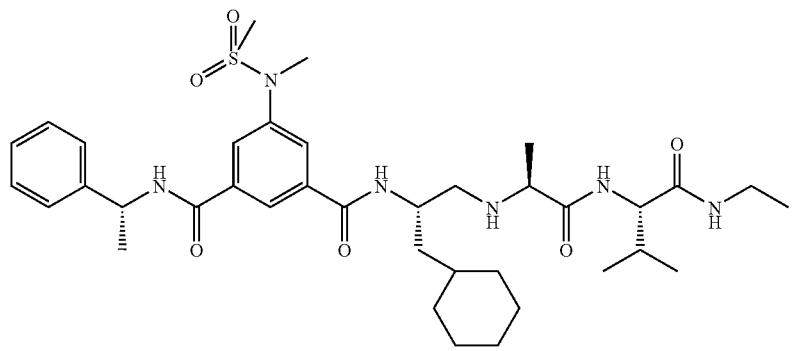

Example 1.37 was prepared analogously to Example 1 from 1-e and the corresponding amine component, by using Boc-(S)-cyclohexylalaninal in step 1k) instead of Boc-(S)-phenylalaninal.
ES-MS (M+H)$^+$=713
RT(HPLC 1)=4.90 min
RT(HPLC-MS)=2.87 min Example 1.38

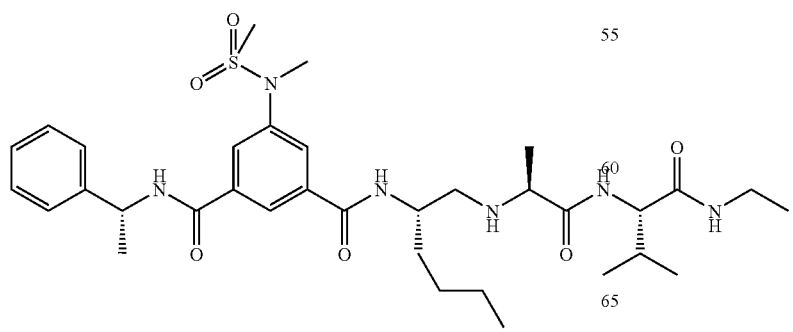

Example 1.38 was prepared analogously to Example 1 from 1-e and the corresponding amine component, by using Boc-(S)-norleucinal in step 1k) instead of Boc-(S)-phenylalaninal.

ES-MS (M+H)$^+$=673
RT(HPLC 1)=5.55 min
RT(HPLC-MS)=2.76 min

Example 1.39

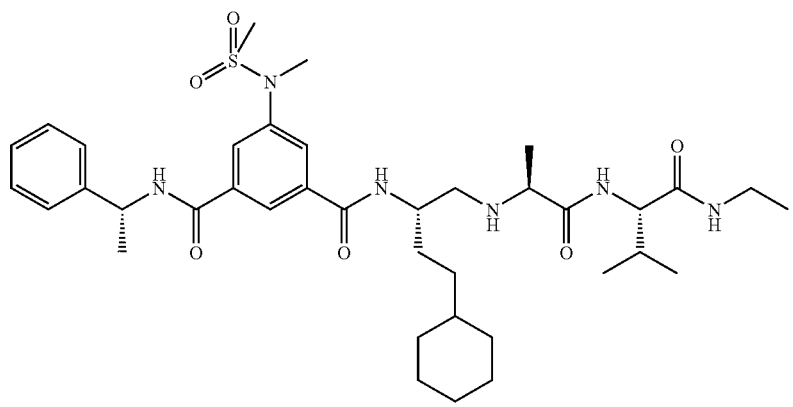

Example 1.39 was prepared analogously to Example 1 from 1-e and the corresponding amine component, by using Boc-(S)-2-amino-4-cyclohexyl-butyraldehyde in step 1k) instead of Boc-(S)-phenylalaninal.

ES-MS (M+H)$^+$=727
RT(HPLC 1)=5.06 min
RT(HPLC-MS)=2.97 min

Example 1.40

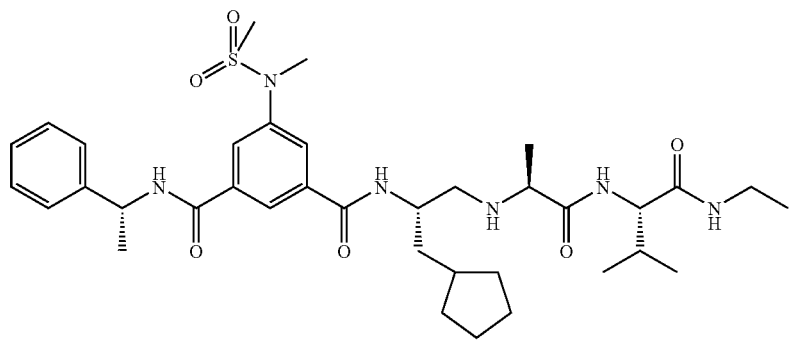

Example 1.40 was prepared analogously to Example 1 from 1-e and the corresponding amine component, by using Boc-(S)-cyclopentylalaninal in step 1k) instead of Boc-(S)-phenylalaninal.
ES-MS (M+H)$^+$=699
RT(HPLC 1)=4.74 min
RT(HPLC-MS)=2.88 min Example 1.41

Example 1.42 was prepared analogously to Example 1 from 1-e and the corresponding amine component, by using Boc-(S)-2-amino-3-(4-trifluoromethylphenyl)-propionaldehyde in step 1k) instead of Boc-(S)-phenylalaninal.
ES-MS (M+H)$^+$=775
RT(HPLC 1)=4.81 min
RT(HPLC-MS)=2.95 min

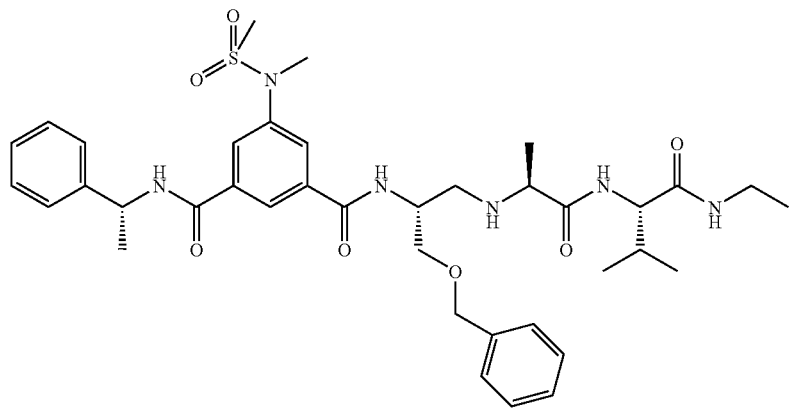

Example 1.41 was prepared analogously to Example 1 from 1-e and the corresponding amine component, by using Boc-(S)-2-amino-3-benzyloxy-propionaldehyde in step 1k) instead of Boc-(S)-phenylalaninal.
ES-MS (M+H)$^+$=737
RT(HPLC 1)=4.67 min
RT(HPLC-MS)=2.83 min Example 1.42

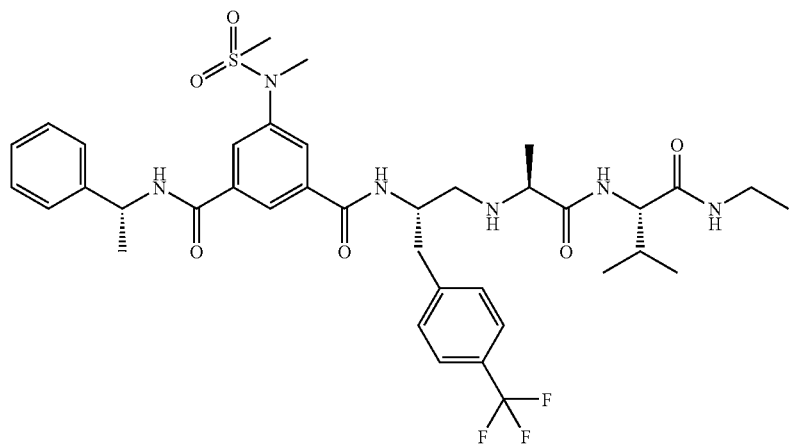

Analogously to Example 1 the following compounds were prepared, using the corresponding amine instead of ethylamine analogously to the preparation of 1f:

| Example | R | Mass spectrum | Retention time (method) |
|---|---|---|---|
| 1.43 | *⟋⟍⟋ | 719 [M + H]⁺ | 4.64 min (HPLC 1), 2.82 min (HPLC-MS) |

-continued

| Example | R | Mass spectrum | Retention time (method) |
|---|---|---|---|
| 1.44 | *—CH₃ | 693 [M + H]⁺ | 4.39 min (HPLC 1) |
| 1.44b | *—CH₂CF₃ (with extra F) | 761 [M + H]⁺ | 4.76 min (HPLC 1), 3.03 min (HPLC-MS) |

Example 1.45

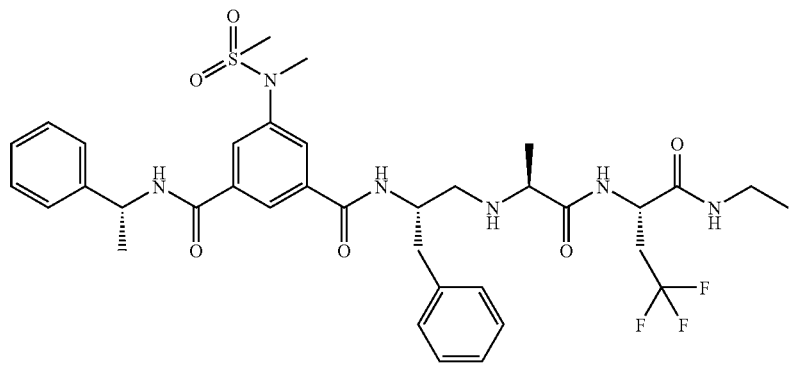

Example 1.45 was prepared analogously to Example 1 from 1-e and the corresponding amine component, by using 2-tert-butoxycarbonylamino-4,4,4-trifluoro-butyric acid in step 1f) instead of Boc-L-valine.
ES-MS (M+H)⁺=747
RT(HPLC-MS)=2.86 min Example 1.46

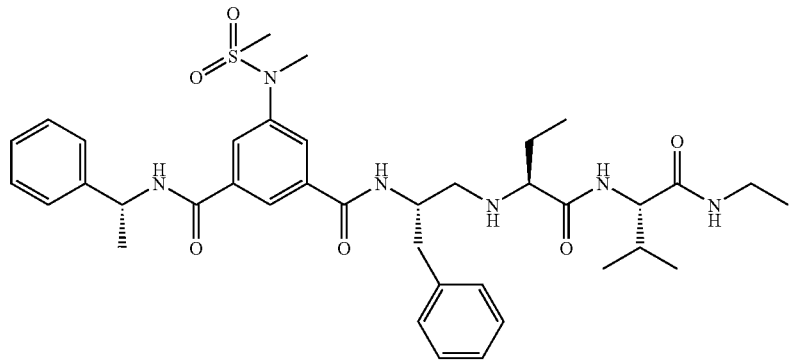

Example 1.46 was prepared analogously to Example 1 from 1-e and the corresponding amine component, by using Boc-(S)-2-aminobutyric acid in step 1 h) instead of Boc-alanine.

ES-MS (M+H)+=747

RT(HPLC-MS)=2.86 min

Example 1.47

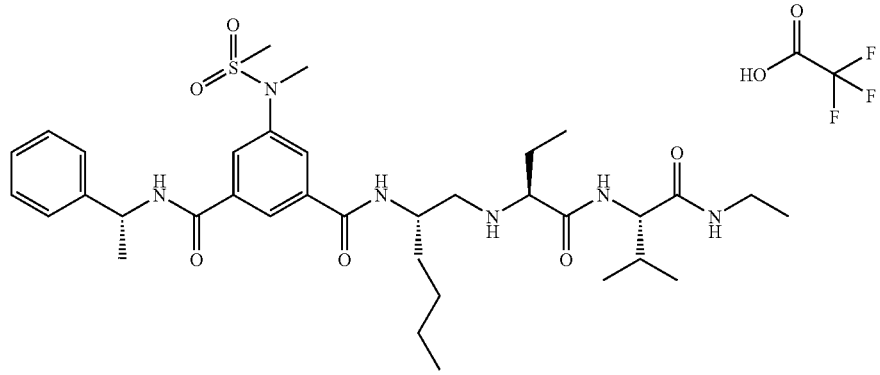

Example 1.47 was prepared analogously to Example 1.46, by using Boc-(S)-2-aminohexanal instead of Boc-(S)-phenylalaninal analogously to step 1 k). The crude product was purified by RP-HPLC.

ES-MS (M+H)+=687

RT(HPLC 1)=4.61 min

Example 1.48

Example 1.48 was prepared analogously to Example 1.38 from 1-e, by using Ala-Val-amide (Bachem AG) in step 1-h) instead of 1 i. The crude product was purified by RP-HPLC.

ES-MS (M+H)+=645

RT(HPLC 1)=4.34 min

RT(HPLC-MS)=2.71 min

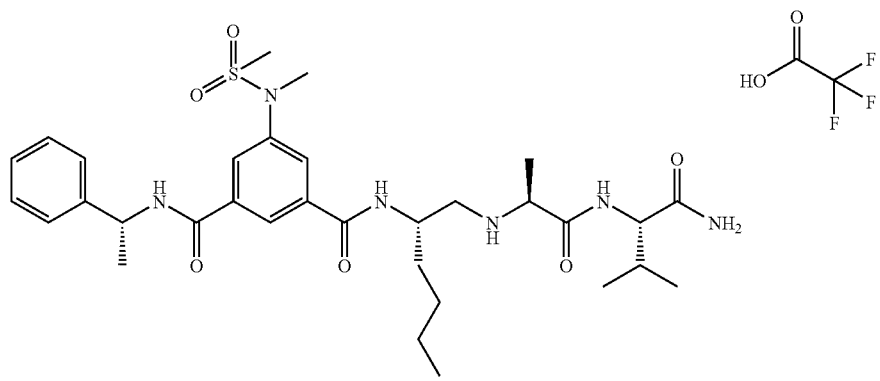

Example 1.49

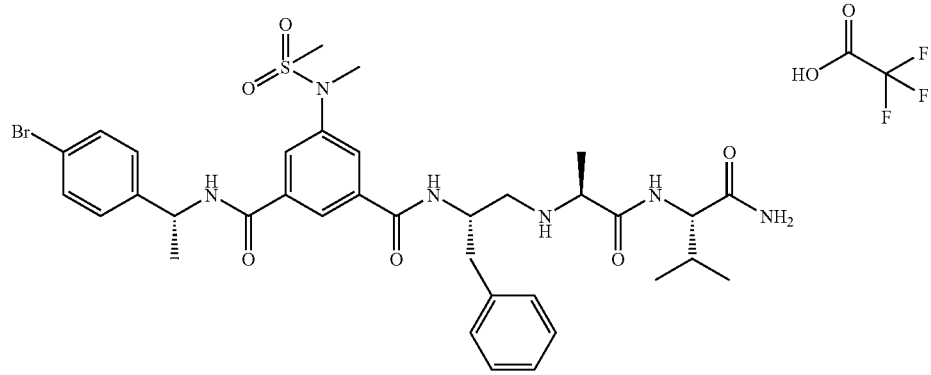

Example 1.49 was prepared analogously to Example 1.19, by using Ala-Val-amide (Bachem AG) in step 1-h) instead of 1i. The crude product was purified by RP-HPLC.
ES-MS (M+H)$^+$=757/759 (Br)
RT(HPLC 1)=4.67 min
RT(HPLC-MS)=1.93 min

Example 1.50

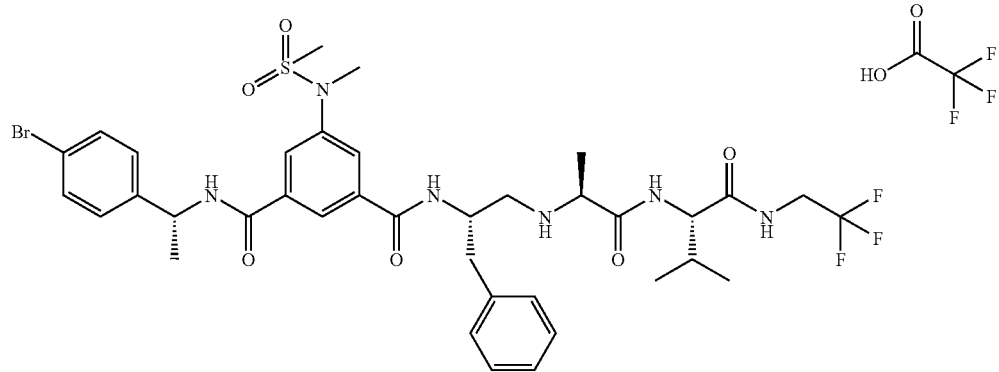

Example 1.50 was prepared analogously to Example 1.19, by using 2,2,2-trifluorethylamine instead of ethylamine in step 1-f). The crude product was purified by RP-HPLC.
ES-MS (M+H)$^+$=839/841 (Br)
RT(HPLC 1)=5.00 min

Example 1.51

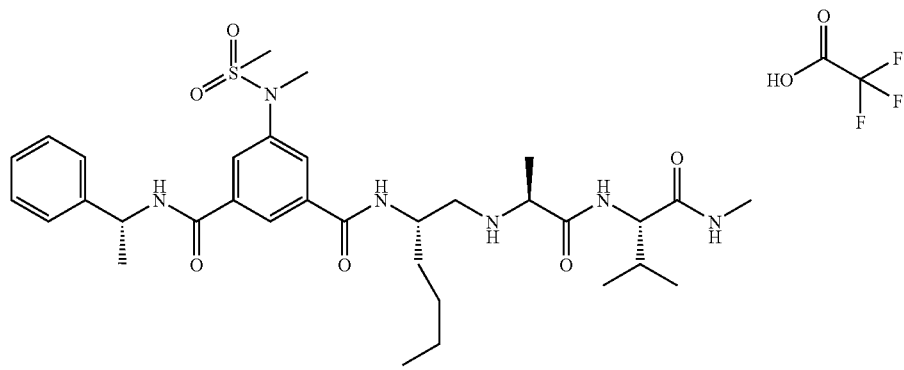

Example 1.51 was prepared analogously to Example 1.38, by using methylamine in step 1-f) instead of ethylamine. The crude product was purified by RP-HPLC.
ES-MS (M+H)$^+$=659
RT(HPLC 1)=4.26 min
RT(HPLC-MS)=2.69 min Example 1.52

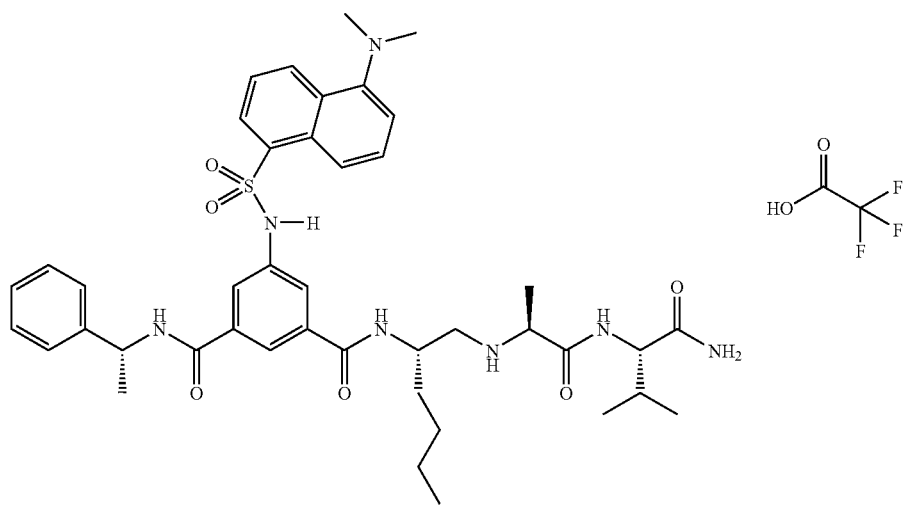

a) Preparation of 1.52-a:

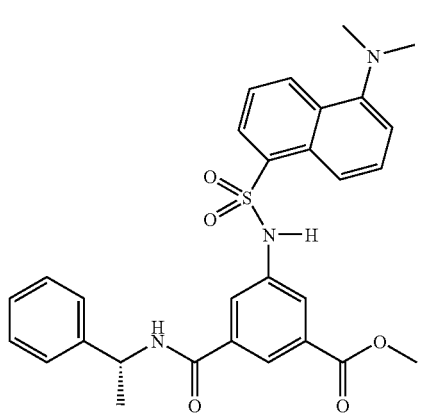
1.52-a 101 mg (0.34 mmol) 18.6-b dissolved in 5 ml of pyridine were combined batchwise with 92 mg (0.34 mmol) dansyl chloride and the mixture was stirred for 14 h at ambient temperature. Then it was poured onto water, mixed with hydrochloric acid, extracted with ethyl acetate, the organic phase was dried and evaporated down. By trituration with ether 132 mg 1.52-a were obtained as a beige solid.

ES-MS (M+H)$^+$=532 b) Preparation of 1.52-b:

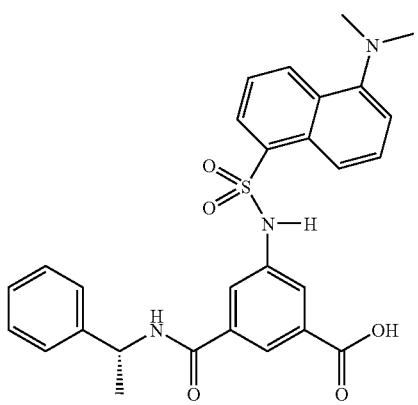
1.52-b

The saponification von 1.52-a to 1.52-b was carried out analogously to step 18.6-d with sodium hydroxide solution in methanol.

ES-MS (M+H)$^+$=518 c) Preparation of 1.52

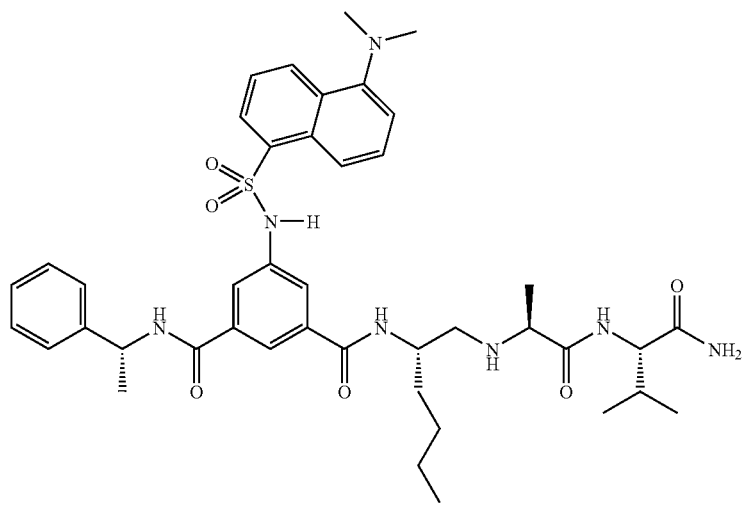

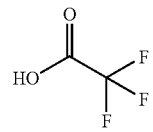

1.52

1.52 was prepared analogously to Example 1.38 from 1.52-b, by using Ala-Val-amide (Bachem AG) in step 1-h) instead of 1 i. The crude product was first of all chromatographed on silica gel (dichloromethane/methanol 95:5) and then purified by RP-HPLC.

ES-MS (M+H)$^+$=786
RT(HPLC 1)=4.55 min

Example 1.53

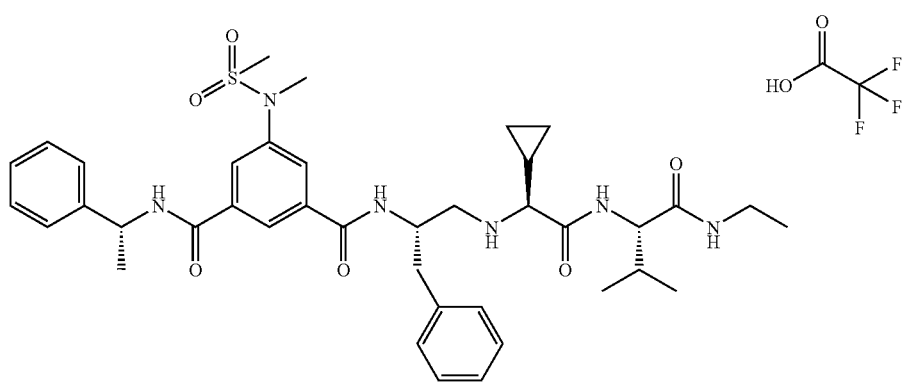

Example 1.53 was prepared analogously to Example 1 from 1-e and the corresponding amine component, by using Boc-L-cyclopropylglycine in step 1 h) instead of Boc-alanine.
ES-MS (M+H)$^+$=733
RT(HPLC-1)=4.66 min Example 1.54

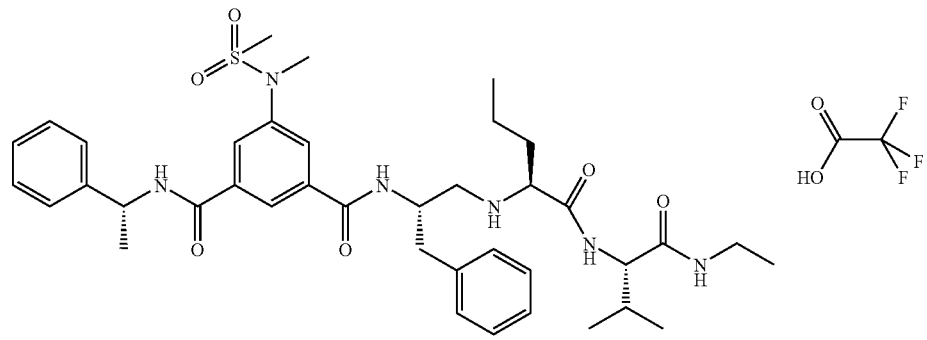

Example 1.54 was prepared analogously to Example 1 from 1-e and the corresponding amine component, by using Boc-L-norvaline in step 1 h) instead of Boc-alanine.

ES-MS (M+H)⁺=735
RT(HPLC-MS)=2.91 min

The following Examples were prepared analogously to Example 1 using the corresponding educts:

| Example | | Mass spectrum | Retention time (method) |
|---|---|---|---|
| 1.55 | | 732 [M + H]⁺ | |
| 1.56 | | 776 [M + H]⁺ | |
| 1.57 | | 798 [M + H]⁺ | 4.99 min (HPLC 1) |
| 1.58 | | 777 [M + H]⁺ | 2.96 min (HPLC-MS) |

| Example | | Mass spectrum | Retention time (method) |
|---|---|---|---|
| 1.59 | 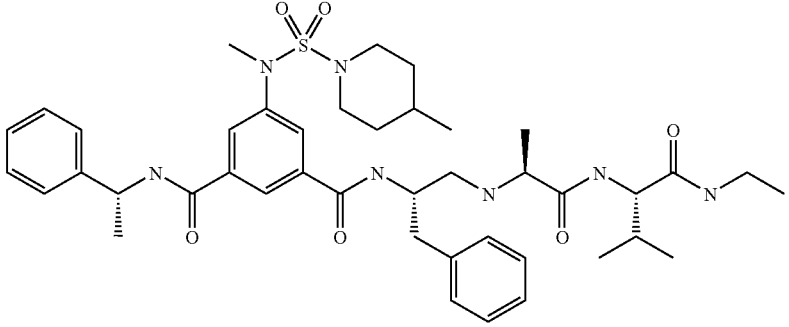 | 791 [M + H]⁺ | 3.04 min (HPLC-MS) |
| 1.60 | 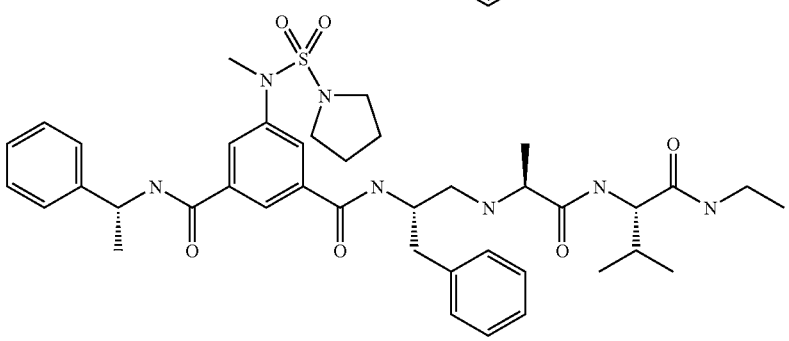 | 763 [M + H]⁺ | 2.87 min (HPLC-MS) |

The following Examples were prepared analogously to Example 1 using 1.61-a and the corresponding educts:

Preparation of 1.61-a 1.61-a

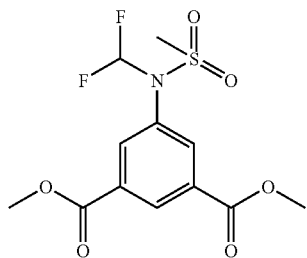

2.00 g (6.96 mmol) 1-a were placed in 50 ml DMF in the autoclave and 1.2 g KOH powder was added. Then 5 bar of chlorodifluoromethane were added under pressure. The reaction mixture was heated to 80° C. and stirred for 14 h. A further 1.0 g KOH powder was added, chlorodifluoromethane was added under pressure and the mixture was stirred for 14 h at 80° C. The solution was cooled, water was slowly added (vigorous foaming) and the mixture was extracted with ethyl acetate. After evaporation brown crystals were formed which were stirred out with MeOH and suction filtered.

Yield: 400 mg (17%) 1.61-a as brown crystals

RT (HPLC-MS)=3.04 min

ES-MS (M) ⁺=337

| Example | | Mass spectrum | Retention time (method) |
|---|---|---|---|
| 1.61 | 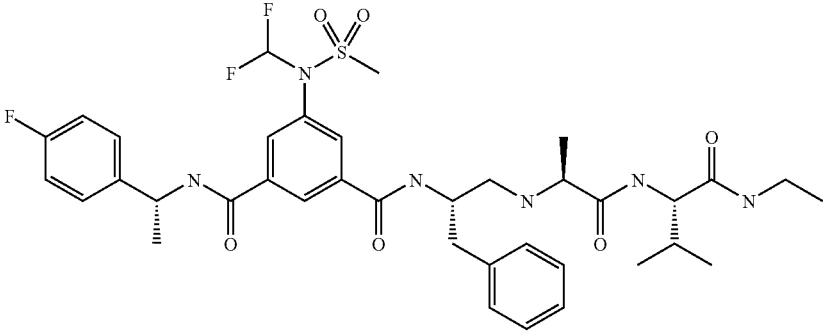 | 762 [M + H]⁺ | 4.77 min (HPLC 1) |

| Example | Mass spectrum | Retention time (method) |
|---|---|---|
| 1.62 | 778 [M + H]⁺ | 4.93 min (HPLC 1) |
| 1.63 | 737 [M + H]⁺ | 4.28 min (HPLC 1) |
Example 2
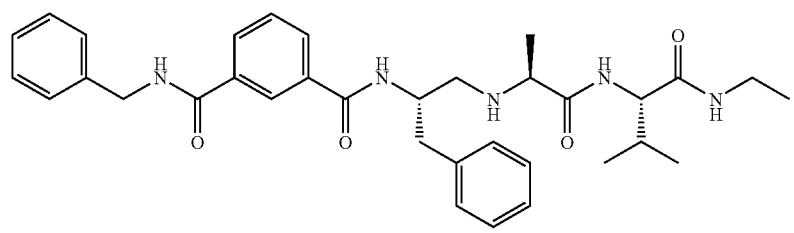
a) Preparation of 2-a:
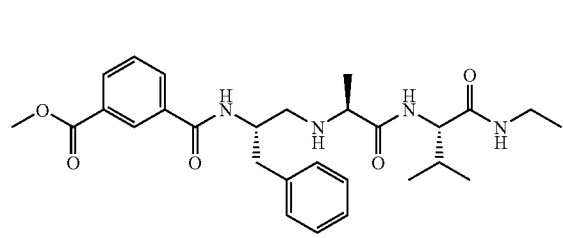
2-a was prepared analogously to 1-d from monomethyl isophthalate and 1-l.
b) Preparation of 2-b:
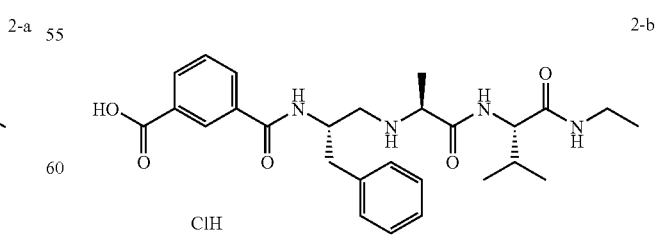
450 mg (0.88 mmol) 2-a were dissolved in 5 ml of methanol, then 5.0 ml (10.0 mmol) 2N NaOH was added and the reaction solution was stirred for 5 hours at ambient temperature. The solvent was eliminated using the rotary evaporator and the residue was combined with 2N HCl. Then the aqueous phase was decanted off, the organic phase was combined with diethyl ether and the precipitate was filtered off.

Yield 320.0 mg (68%) white crystals 2-b.

ES-MS (M+H)$^+$=497 c) Preparation of 2-c:

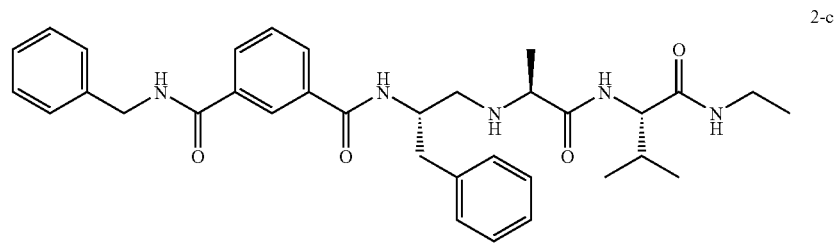

2-c 2-c was prepared analogously to 1-d from 2-b and benzylamine. The purification was carried out by chromatography on silica gel with the eluant (dichloromethane/methanol 9:1).

ES-MS (M+H)$^+$=586

Analogously to Example 2 the following compounds were prepared from 2-b and the corresponding amount of amines:

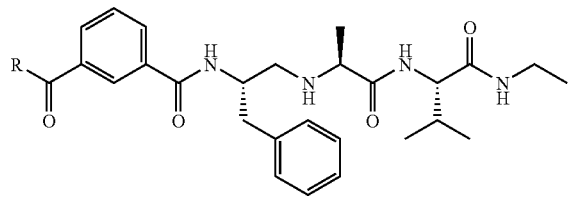

| Example | R | Mass spectrum | Retention time (method) |
|---|---|---|---|
| 2.2 | ![benzyl-N-methyl] | 600 [M + H]$^+$ | |
| 2.3 | ![benzyl-N-propyl] | 628 [M + H]$^+$ | 2.97 min (HPLC-MS) |
| 2.4 | ![phenyl-CH(CH3)-N-methyl] | 614 [M + H]$^+$ | 2.81 min (HPLC-MS) |
| 2.5 | ![4-Br-phenyl-CH(CH3)-NH] | 680 [M + H]$^+$ | 4.20 min (HPLC 2) |

-continued
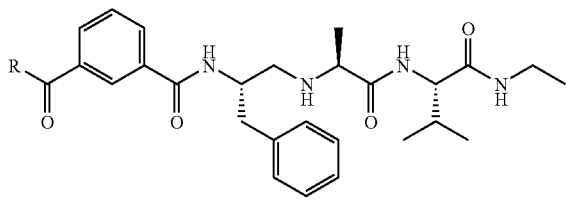
| Example | R | Mass spectrum | Retention time (method) |
|---|---|---|---|
| 2.6 | HO-(3-hydroxy-4-methylphenyl)-CH2-CH(Et)-NH→* | 658 [M + H]+ | 3.91 min (HPLC 2) |
| 2.7 | (PhCH2)(PhCH2)CH-NH→* | 690 [M + H]+ | 4.30 min (HPLC 2) |
| 2.8 | (S)-1-(4-methylphenyl)ethyl-NH→* | 614 [M + H]+ | 3.98 min (HPLC 2) |
| 2.9 | 1-phenylpropyl-NH→* | 614 [M + H]+ | 3.95 min (HPLC 2) |
| 2.10 | (S)-1-(naphthalen-2-yl)ethyl-NH→* | 650 [M + H]+ | 4.25 min (HPLC 2) |
| 2.11 | 3,4-dihydroxyphenethyl-NH→* | 632 [M + H]+ | 3.62 min (HPLC 2) |
| 2.12 | 2-(1H-indol-3-yl)ethyl-NH→* | 639 [M + H]+ | 4.03 min (HPLC 2) |
| 2.13 | 2-(pyridin-2-yl)ethyl-NH→* | 601 [M + H]+ | 3.27 min (HPLC 2) |

-continued
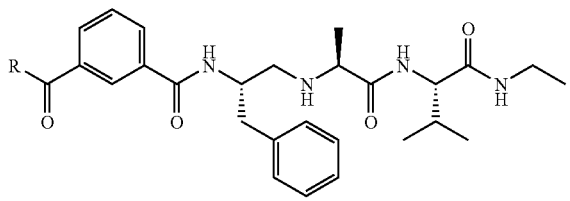
| Example | R | Mass spectrum | Retention time (method) |
|---|---|---|---|
| 2.14 | 2-Cl-C6H4-CH2CH2-NH— | 634 [M + H]+ | 4.19 min (HPLC 2) |
| 2.15 | 2-MeO-C6H4-CH2CH2-NH— | 630 [M + H]+ | 4.09 min (HPLC 2) |
| 2.16 | 3-MeO-C6H4-CH2CH2-NH— | 630 [M + H]+ | 4.05 min (HPLC 2) |
| 2.17 | 3,4-(MeO)2-C6H3-CH2CH2-NH— | 660 [M + H]+ | 3.87 min (HPLC 2) |
| 2.18 | 4-Br-C6H4-CH2CH2-NH— | 680 [M + H]+ | 4.26 min (HPLC 2) |
| 2.19 | 4-Cl-C6H4-CH2CH2-NH— | 634 [M + H]+ | 4.23 min (HPLC 2) |
| 2.20 | 4-HO-C6H4-CH2CH2-NH— | 616 [M + H]+ | 3.74 min (HPLC 2) |
| 2.21 | 4-Me-C6H4-CH2CH2-NH— | 614 [M + H]+ | 4.18 min (HPLC 2) |
| 2.22 | 4-H2NSO2-C6H4-CH2CH2-NH— | 679 [M + H]+ | 3.65 min (HPLC 2) |
| 2.23 | 4-O2N-C6H4-CH2CH2-NH— | 645 [M + H]+ | 4.06 min (HPLC 2) |

-continued
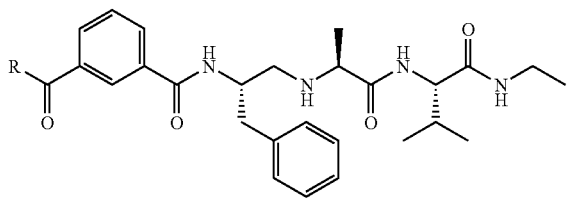
| Example | R | Mass spectrum | Retention time (method) |
|---|---|---|---|
| 2.24 | 3-(trifluoromethyl)phenethyl-NH—* | 668 [M + H]⁺ | 4.27 min (HPLC 2) |
| 2.25 | 3-chlorophenethyl-NH—* | 634 [M + H]⁺ | 4.20 min (HPLC 2) |
| 2.26 | 2-thienylethyl-NH—* | 606 [M + H]⁺ | 4.00 min (HPLC 2) |
| 2.27 | 2-chloro-6-fluorophenethyl-NH—* | 652 [M + H]⁺ | 4.21 min (HPLC 2) |
| 2.28 | 2,6-dichlorophenethyl-NH—* | 668 [M + H]⁺ | 4.31 min (HPLC 2) |
| 2.29 | 2-ethoxyphenethyl-NH—* | 643 [M + H]⁺ | 4.24 min (HPLC 2) |
| 2.30 | 3,5-dimethoxyphenethyl-NH—* | 660 [M + H]⁺ | 4.05 min (HPLC 2) |
| 2.31 | 4-ethoxyphenethyl-NH—* | 644 [M + H]⁺ | 4.19 min (HPLC 2) |

-continued
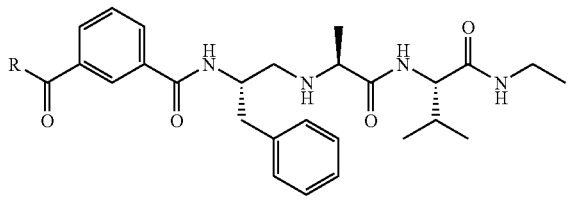
| Example | R | Mass spectrum | Retention time (method) |
|---|---|---|---|
| 2.32 | 7-methyl-1H-indol-3-yl-CH₂CH₂-NH—* | 653 [M + H]⁺ | 4.15 min (HPLC 2) |
| 2.33 | 3-F-C₆H₄-CH₂CH₂-NH—* | 618 [M + H]⁺ | 4.09 min (HPLC 2) |
| 2.34 | 4-F-C₆H₄-CH₂CH₂-NH—* | 618 [M + H]⁺ | 4.07 min (HPLC 2) |
| 2.35 | 3-Br-4-MeO-C₆H₃-CH₂CH₂-NH—* | 710 [M + H]⁺ | 4.20 min (HPLC 2) |
| 2.36 | pyridin-3-yl-CH₂CH₂-NH—* | 601 [M + H]⁺ | 3.27 min (HPLC 2) |
| 2.37 | 2,4-dimethyl-C₆H₃-CH₂CH₂-NH—* | 628 [M + H]⁺ | 4.29 min (HPLC 2) |
| 2.38 | naphthalen-2-yl-CH₂CH₂-NH—* | 650 [M + H]⁺ | 4.32 min (HPLC 2) |
| 2.39 | 4-CF₃-C₆H₄-CH₂CH₂-NH—* | 668 [M + H]⁺ | 4.28 min (HPLC 2) |
| 2.40 | 3,4-diF-C₆H₃-CH₂CH₂-NH—* | 636 [M + H]⁺ | 4.11 min (HPLC 2) |

-continued

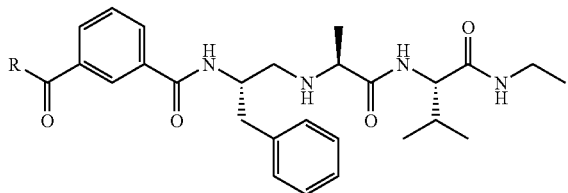

| Example | R | Mass spectrum | Retention time (method) |
|---|---|---|---|
| 2.41 | 2,4-difluorophenyl-CH₂CH₂-NH→* | 636 [M + H]⁺ | 4.12 min (HPLC 2) |
| 2.42 | 2,5-difluorophenyl-CH₂CH₂-NH→* | 636 [M + H]⁺ | 4.10 min (HPLC 2) |
| 2.43 | 3,5-difluorophenyl-CH₂CH₂-NH→* | 636 [M + H]⁺ | 4.14 min (HPLC 2) |
| 2.44 | 2,6-difluorophenyl-CH₂CH₂-NH→* | 636 [M + H]⁺ | 4.09 min (HPLC 2) |
| 2.45 | 3,5-dimethylisoxazol-4-yl-CH₂CH₂-NH→* | 619 [M + H]⁺ | 3.75 min (HPLC 2) |
| 2.46 | 3,5-dimethylpyrazol-4-yl-CH₂CH₂-NH→* | 618 [M + H]⁺ | 3.37 min (HPLC 2) |
| 2.47 | 4-(diethylamino)phenyl-CH₂CH₂-NH→* | 671 [M + H]⁺ | 3.46 min (HPLC 2) |
| 2.48 | furan-2-yl-CH₂CH₂-NH→* | 590 [M + H]⁺ | 3.87 min (HPLC 2) |

-continued

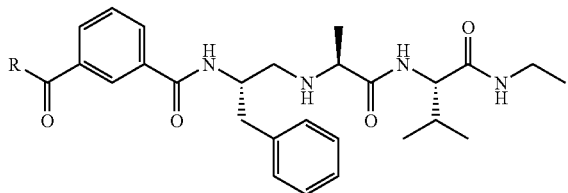

| Example | R | Mass spectrum | Retention time (method) |
|---|---|---|---|
| 2.49 | (2-trifluoromethoxyphenethyl)NH—* | 684 [M + H]+ | 4.32 min (HPLC 2) |
| 2.50 | 1-(1,3-dimethyl-1H-pyrazol-4-yl)ethyl-NH—* | 618 [M + H]+ | 3.55 min (HPLC 2) |
| 2.51 | 1-(3-trifluoromethylphenyl)ethyl-NH—* | 668 [M + H]+ | 4.28 min (HPLC 2) |
| 2.52 | 1-(1-methyl-1H-pyrazol-5-yl)ethyl-NH—* | 604 [M + H]+ | 3.62 min (HPLC 2) |
| 2.53 | 1-(1-methyl-1H-pyrazol-3-yl)ethyl-NH—* | 604 [M + H]+ | 3.61 min (HPLC 2) |
| 2.54 | 1-(1-ethyl-1H-pyrazol-3-yl)ethyl-NH—* | 618 [M + H]+ | 3.73 min (HPLC 2) |
| 2.55 | (naphthalen-1-ylmethyl)NH—* | 636 [M + H]+ | 4.21 min (HPLC 2) |
| 2.56 | (benzo[1,3]dioxol-5-ylmethyl)NH—* | 630 [M + H]+ | 3.87 min (HPLC 2) |

-continued
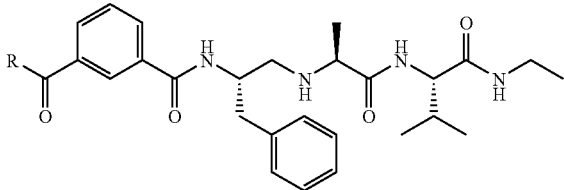
| Example | R | Mass spectrum | Retention time (method) |
|---|---|---|---|
| 2.57 | 2-F-C6H4-CH2-NH—* | 604 [M + H]+ | 3.97 min (HPLC 2) |
| 2.58 | 2-Cl-C6H4-CH2-NH—* | 620 [M + H]+ | 4.07 min (HPLC 2) |
| 2.59 | 2,4-Cl2-C6H3-CH2-NH—* | 656 [M + H]+ | 4.29 min (HPLC 2) |
| 2.60 | 2-Me-C6H4-CH2-NH—* | 600 [M + H]+ | 4.06 min (HPLC 2) |
| 2.61 | 3-F-C6H4-CH2-NH—* | 604 [M + H]+ | 4.00 min (HPLC 2) |
| 2.62 | 3-MeO-C6H4-CH2-NH—* | 616 [M + H]+ | 3.94 min (HPLC 2) |
| 2.63 | 3-Me-C6H4-CH2-NH—* | 600 [M + H]+ | 4.07 min (HPLC 2) |
| 2.64 | 2,6-F2-C6H3-CH2-NH—* | 622 [M + H]+ | 3.95 min (HPLC 2) |
| 2.65 | 3,5-Me2-C6H3-CH2-NH—* | 614 [M + H]+ | 4.21 min (HPLC 2) |
| 2.66 | 2,3-dihydrobenzofuran-5-yl-CH2-NH—* | 628 [M + H]+ | 3.95 min (HPLC 2) |

-continued

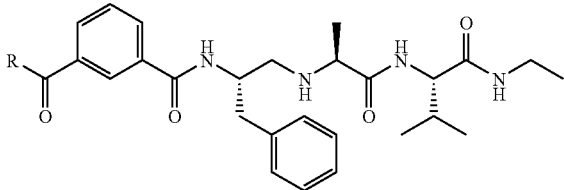

| Example | R | Mass spectrum | Retention time (method) |
|---|---|---|---|
| 2.67 | 2,3-dihydro-1,4-benzodioxin-6-ylmethyl-NH—* | 644 [M + H]+ | 3.88 min (HPLC 2) |
| 2.68 | 4-(1H-pyrazol-1-yl)benzyl-NH—* | 652 [M + H]+ | 3.91 min (HPLC 2) |
| 2.69 | 2-(1H-imidazol-4-yl)ethyl-NH—* | 590 [M + H]+ | 3.26 min (HPLC 2) |
| 2.70 | 1-[2-(trifluoromethyl)phenyl]ethyl-NH—* | 668 [M + H]+ | 4.27 min (HPLC 2) |
| 2.71 | 1-[4-(trifluoromethyl)phenyl]ethyl-NH—* | 668 [M + H]+ | 4.26 min (HPLC 2) |
| 2.72 | 3,4-dichlorobenzyl-NH—* | 654 [M + H]+ | 4.28 min (HPLC 2) |
| 2.73 | 4-chlorobenzyl-NH—* | 620 [M + H]+ | 4.10 min (HPLC 2) |
| 2.74 | 4-isopropylbenzyl-NH—* | 628 [M + H]+ | 4.32 min (HPLC 2) |
| 2.75 | 3,5-difluorobenzyl-NH—* | 622 [M + H]+ | 4.05 min (HPLC 2) |
| 2.76 | 4-(dimethylamino)benzyl-NH—* | 629 [M + H]+ | 3.34 min (HPLC 2) |

-continued

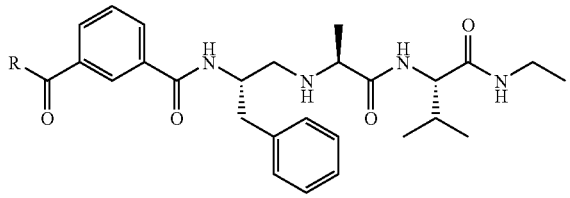

| Example | R | Mass spectrum | Retention time (method) |
|---|---|---|---|
| 2.77 | [benzofuran-5-yl-CH2-NH—*] | 626 [M + H]+ | 4.03 min (HPLC 2) |
| 2.78 | [3,4-difluorobenzyl-NH—*] | 622 [M + H]+ | 4.05 min (HPLC 2) |
| 2.79 | [2,5-difluorobenzyl-NH—*] | 622 [M + H]+ | 4.02 min (HPLC 2) |

Example 2.80

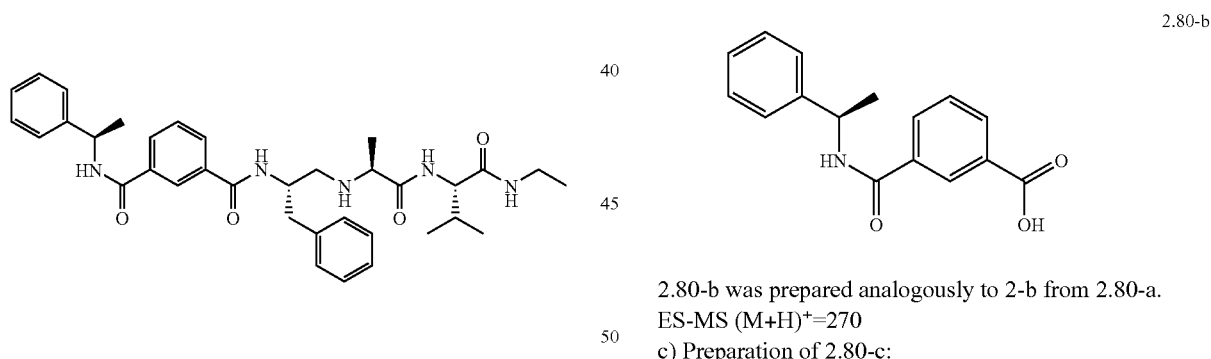

a) Preparation of 2.80-a:

2.80-a was prepared analogously to 1-d from monomethyl isophthalate and (R)-1-phenyl-ethylamine.

b) Preparation of 2.80-b:

2.80-b was prepared analogously to 2-b from 2.80-a.
ES-MS (M+H)+=270 c) Preparation of 2.80-c:

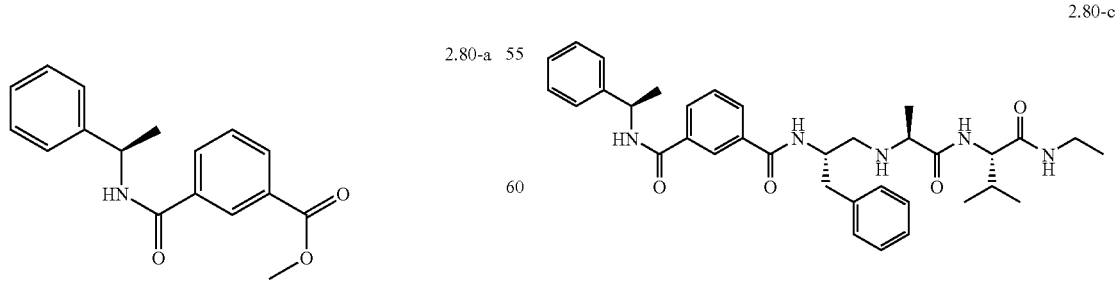

2.80-c was prepared analogously to 1-d from 2.80-b and 1-l.
ES-MS (M+H)+=600

Example 2.81

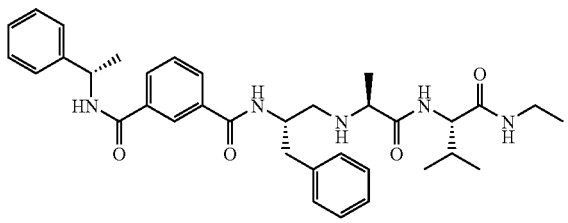

Example 2.81 was prepared analogously to Example 2.80, except that (S)-1-phenyl-ethylamine was used instead of (R)-1-phenyl-ethylamine.
ES-MS (M+H)$^+$=600

Example 2.82

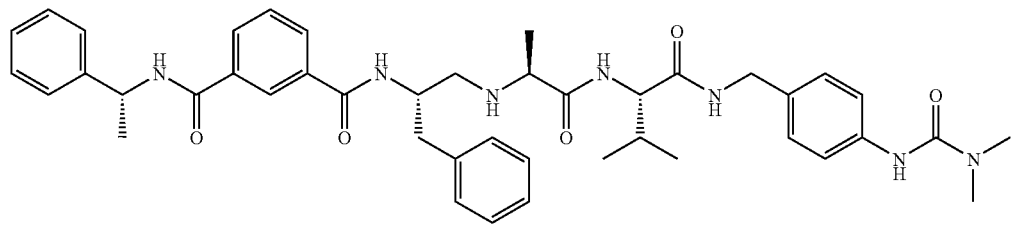

Example 2.82 was prepared analogously to Example 2.80, except that in the synthesis of the precursor analogous to 1-1 the corresponding benzylamine was used in step 1-f.
ES-MS (M+H)$^+$=748
RT(HPLC-MS)=2.75 min

Example 3

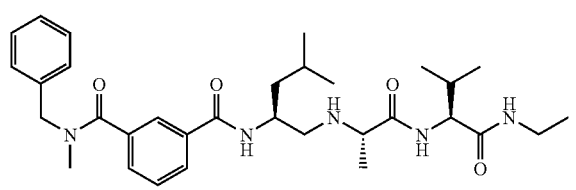

a) Preparation of 3-a:

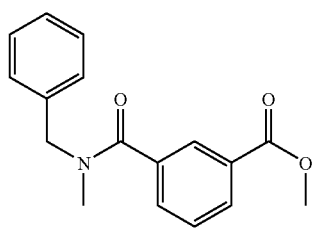

1.0 g (5.6 mmol) monomethyl isophthalate were combined in 30 ml THF with 1.8 g (5.6 mmol) TBTU and 781.0 µl (5.6 mmol) triethylamine, then 723 µl (5.6 mmol) benzylmethylamine was added and the mixture was stirred overnight at ambient temperature. The reaction solution was extracted with sat. NaCl solution and ethyl acetate. The organic phases were dried and evaporated to dryness i. vac. Quantitative yield of 3-a.
RF=0.64 (silica gel; petroleum ether/ethyl acetate 1:1)

b) Preparation of 3-b:

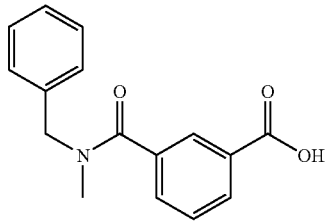

1.6 g (5.6 mmol) 3-a were dissolved in 40 ml THF and 50 ml of water, then 1.2 g (27.8 mmol) lithium hydroxide was added and the reaction solution was stirred for 3 hours at ambient temperature. The solvent was eliminated using the rotary evaporator, the residue was combined with 30 ml 1 N HCl and extracted with ethyl acetate. The combined organic phases were dried, evaporated down i. vac. and combined with petroleum ether/ethyl acetate. The precipitate was suction filtered and dried.
Yield 1.3 g (83%) 3-b.
RF=0.13 (silica gel; petroleum ether/ethyl acetate 1:1)

c) Preparation of 3-c:

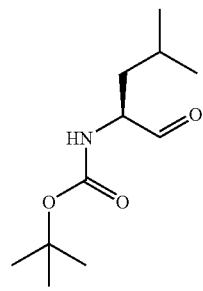

3-c was prepared analogously to 1-j from BOC-L-leucinol.

d) Preparation of 3-d:

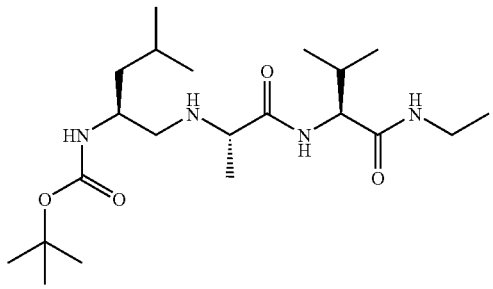

3-d was prepared analogously to 1-k from 3-c and 1-i.
ES-MS (M+H)$^+$=415 e) Preparation of 3-e:
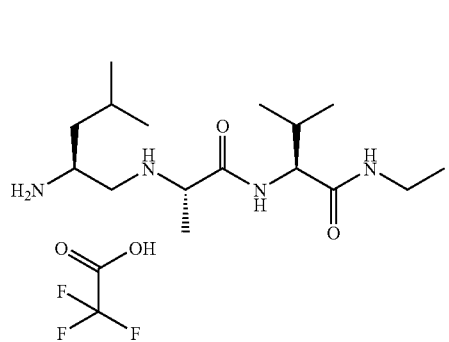
3-e was prepared analogously to 1-g from 3-d.
f) Preparation of 3-f:
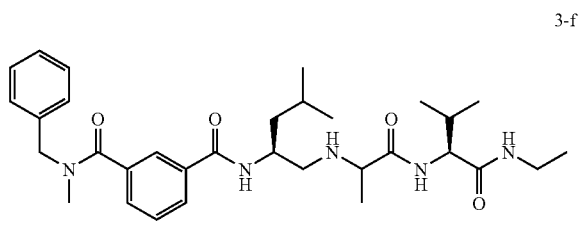
3-f was prepared analogously to 1-d from 3-b and 3-e.
RT(HPLC 3)=1.87 min
Example 4
a) Preparation of 4-a:
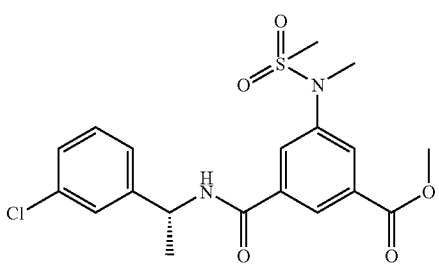
4-a was prepared analogously to 1-d from 1-c and R-1-(3-chlorophenyl)-ethylamine.
b) Preparation of 4-b:
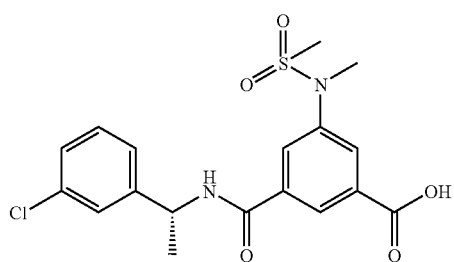
4-b was prepared analogously to 2-b from 4-a.
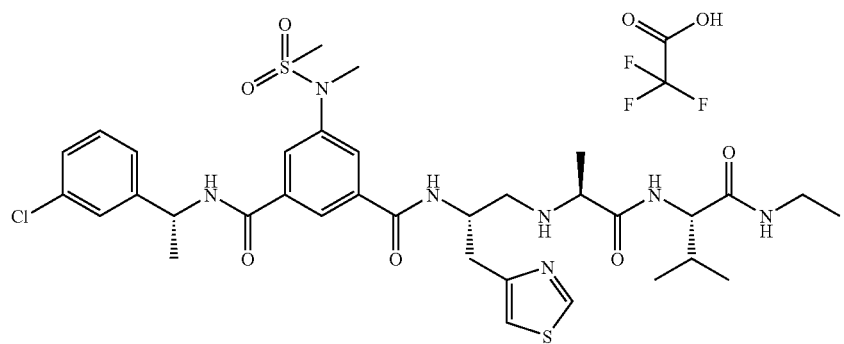

c) Preparation of 4-c:

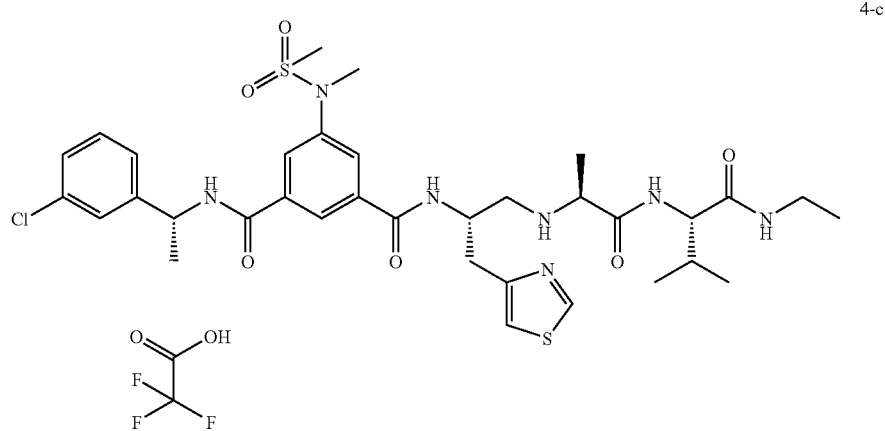

4-c was prepared analogously to 1-d from 4-b and (S)-2-[(S)-2-((S)-2-amino-3-thiazol-4-yl-propylamino)-propionylamino]-N-ethyl-3-methyl-butyramide.

ES-MS (M+H)$^+$=748/750 (chlorine isotopes)

RT(HPLC 1)=4.35 min

Analogously to Example 4 the following compounds were prepared from 1-c and the corresponding amount of amines:

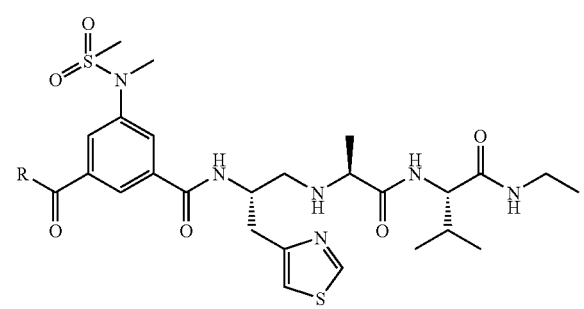

| Example | R | Mass spectrum | Retention time (method) |
|---|---|---|---|
| 4.2 | 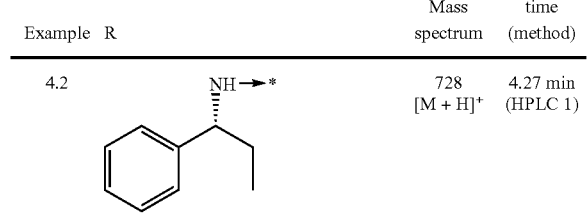 | 728 [M + H]$^+$ | 4.27 min (HPLC 1) |
| 4.3 |  | 720 [M + H]$^+$ | 4.09 min (HPLC 1) |

-continued

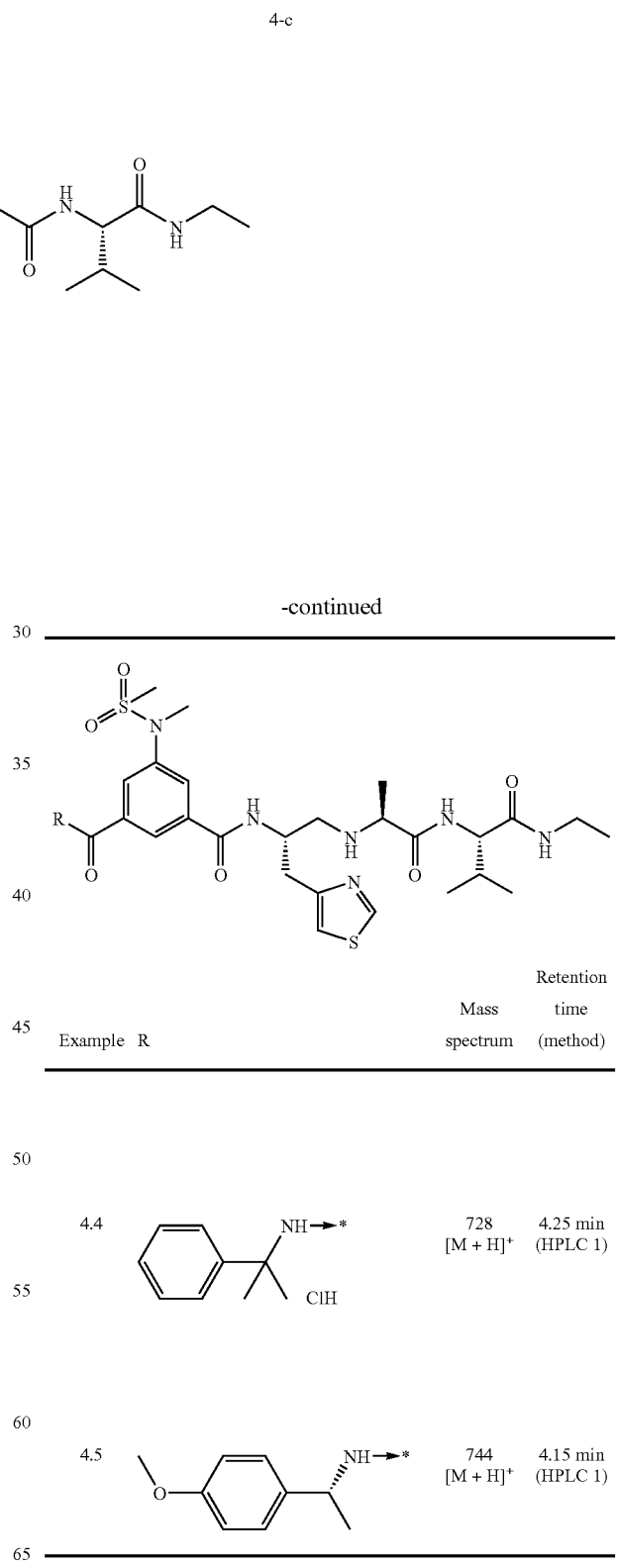

| Example | R | Mass spectrum | Retention time (method) |
|---|---|---|---|
| 4.4 | | 728 [M + H]$^+$ | 4.25 min (HPLC 1) |
| 4.5 | | 744 [M + H]$^+$ | 4.15 min (HPLC 1) |

Example 5

a) Preparation of 5-a:

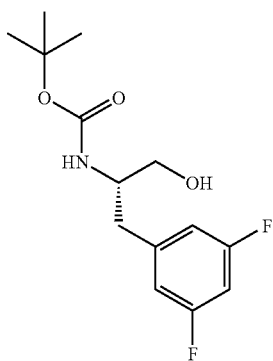

5-a 945 mg (24.9 mmol) lithium aluminium hydride were suspended in 10 ml THF, cooled to 0° C. and then 5.0 g (16.6 mmol) Boc-L-3,5-difluorophenylalanine dissolved in 15 ml THF was slowly metered in. The reaction solution was stirred overnight at ambient temperature, then combined with 10 ml sat. diammonium tartrate solution and magnesium sulphate, stirred for 30 minutes at ambient temperature and filtered through silica gel. The filtrate was evaporated to dryness i. vac. and separated by chromatography by MPLC using the eluant (ethyl acetate/heptane 0:100 to 70:30).

Yield 2.8 g (58%) white crystals 5-a.
RT(HPLC-MS)=2.92 min b) Preparation of 5-b:

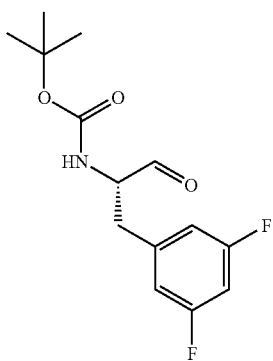

5-b 5-b was prepared analogously to 1-j from 5-a.
RF=0.7 (ethyl acetate/heptane 70:30)

c) Preparation of 5-c:

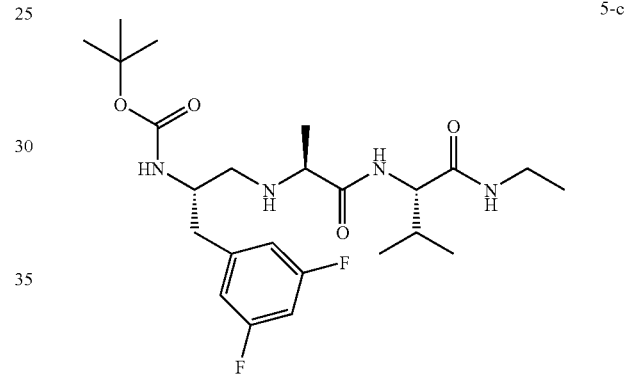

5-c 5-c was prepared analogously to 1-k from 1-i and 5-b.
RT(HPLC-MS)=2.65 min d) Preparation of 5-d:

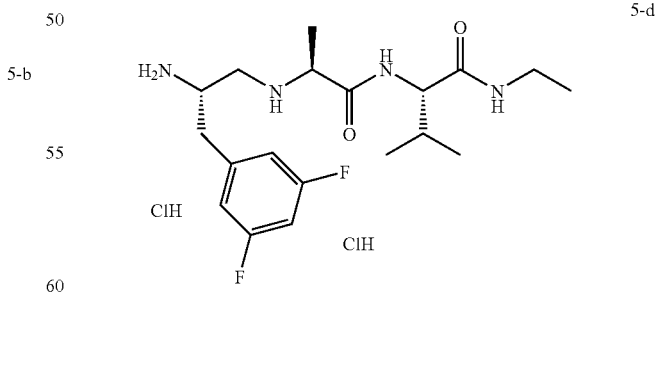

5-d 5-d was prepared analogously to 1-i from 5-c.
ES-MS (M+H)$^+$=385
RT(HPLC-MS)=2.12 min e) Preparation of 5-e:
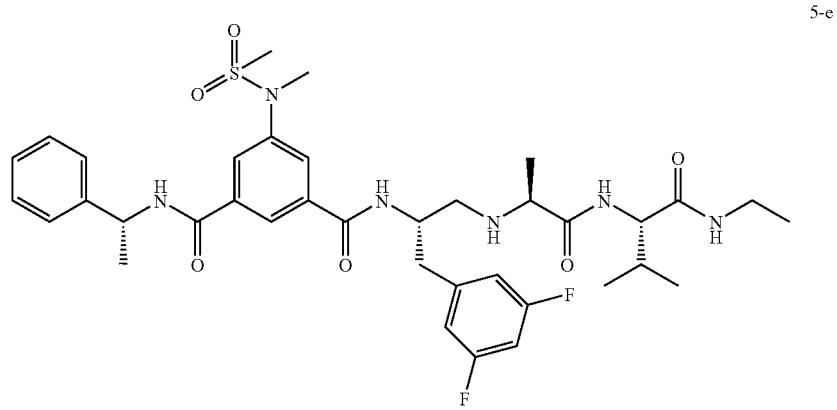
5-e
5-e was prepared analogously to 1-d from 1-e and 5-d.
ES-MS (M+H)$^+$=743
RT(HPLC 1)=4.58 min
Analogously to 5-e the following compounds were prepared from 1-e and the corresponding amount of amines:
| Example | R | Mass spectrum |
|---|---|---|
| 5.2 | (structure with phenethyl group, Ala, Val, NHEt, 2 ClH) | 721 [M + H]$^+$ |
| 5.3 | (structure with indane group, Ala, Val, NHEt, 2 ClH) | 719 [M + H]$^+$ |

| Example | R | Mass spectrum |
|---|---|---|
| 5.4 | (3-thienylmethyl substituted diamine-Ala-Val-NHEt, 2 ClH) | 713 [M + H]+ |
| 5.5 | (3-pyridylmethyl substituted diamine-Ala-Val-NHEt, 3 ClH) | 708 [M + H]+ |
| 5.6 | (2-pyridylmethyl substituted diamine-Ala-Val-NHEt, 3 ClH) | 708 [M + H]+ |
| 5.7 | (4-thiazolylmethyl substituted diamine-Ala-Val-NHEt, 3 ClH) | 714 [M + H]+ |
| 5.8 | (propargyl substituted diamine-Ala-Val-NHEt) | 655 [M + H]+ |
| 5.9 | (3-furylmethyl substituted diamine-Ala-Val-NHEt) | 697 [M + H]+ |

-continued
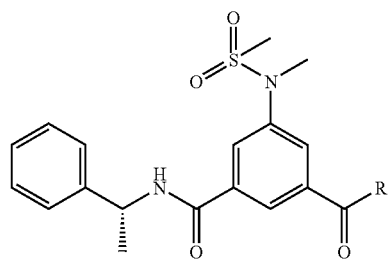
| Example | R | Mass spectrum |
|---|---|---|
| 5.10 | 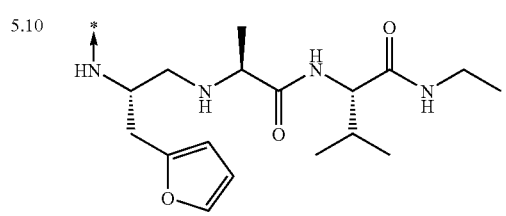 | 697 [M + H]+ |
| 5.11 | 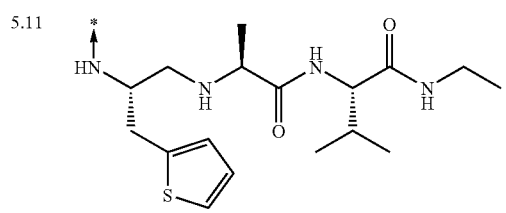 | 713 [M + H]+ |
| 5.12 | 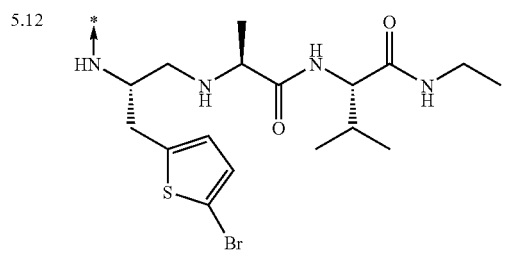 | 791/793 (Br) [M + H]+ |
| 5.13 | 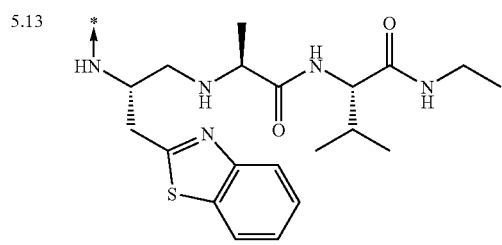 | 764 [M + H]+ |
| 5.14 | 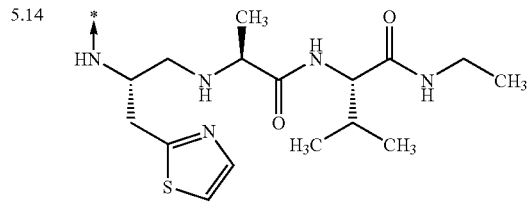 | 714 [M + H]+ |

-continued
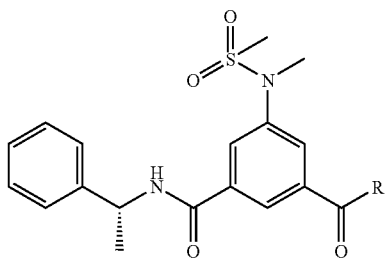
| Example | R | Mass spectrum |
|---|---|---|
| 5.15 | | 670 [M + H]+ |
| 5.16 | | 752 [M + H]+ |
| 5.17 | | 785/787 (Br) [M + H]+ |
| 5.18 | | 722 [M + H]+ |
| 5.19 | | 741/743 (Cl) [M + H]+ |

-continued
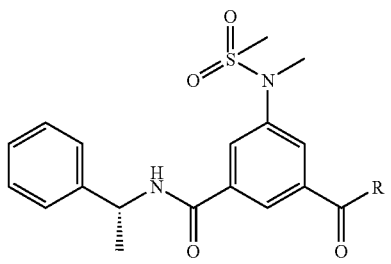
| Example | R | Mass spectrum |
|---|---|---|
| 5.20 | | 747/749 (Cl) [M + H]+ |
| 5.21 | | 727 [M + H]+ |
| 5.22 | | 725 [M + H]+ |
| 5.23 | | 669 [M + H]+ |
| 5.24 | | 712 [M + H]+ |

-continued
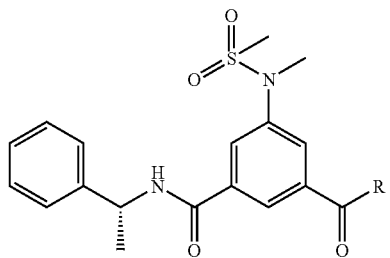
| Example | R | Mass spectrum |
|---|---|---|
| 5.25 | 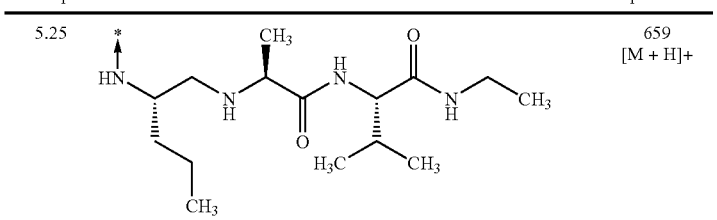 | 659 [M + H]+ |
Analogously to 5-e the following compounds were prepared from the corresponding acids analogous to 1-e and amines analogous to 5-d:
| Example | structure | Mass spectrum [M + H]+ | Retention time [method] |
|---|---|---|---|
| 5.26 | 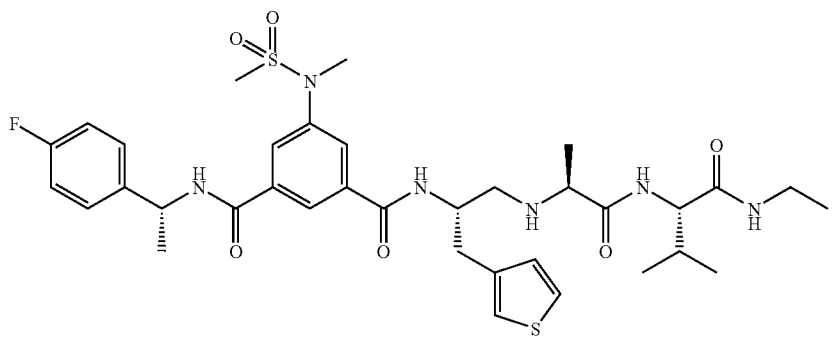 | 731 | 2.78 min [HPLC-MS] |
| 5.27 | 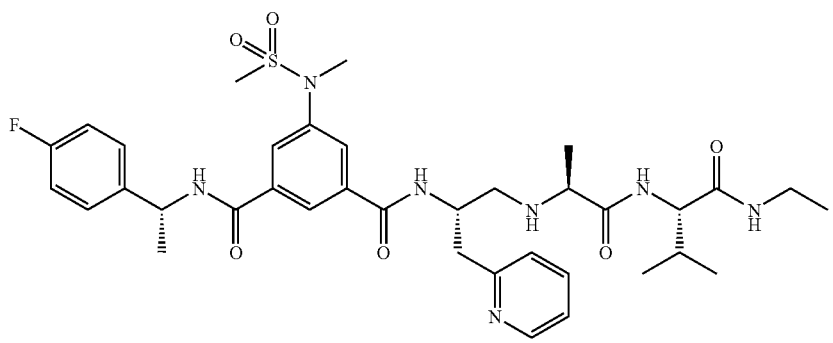 | 726 | 2.46 min [HPLC-MS] |

-continued

| Example | structure | Mass spectrum [M + H]⁺ | Retention time [method] |
|---|---|---|---|
| 5.28 | 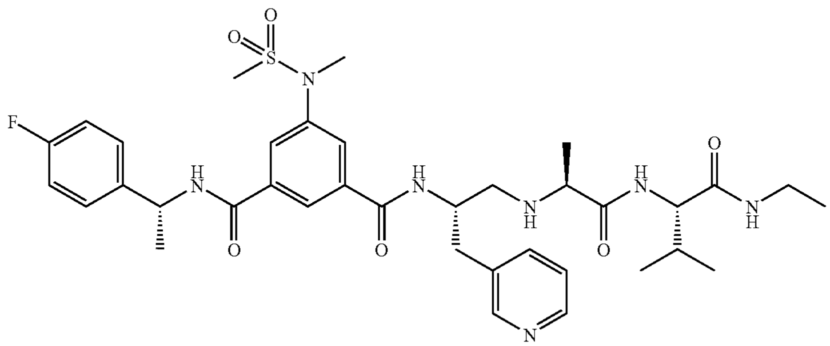 | 726 | 2.40 min [HPLC-MS] |
| 5.29 | 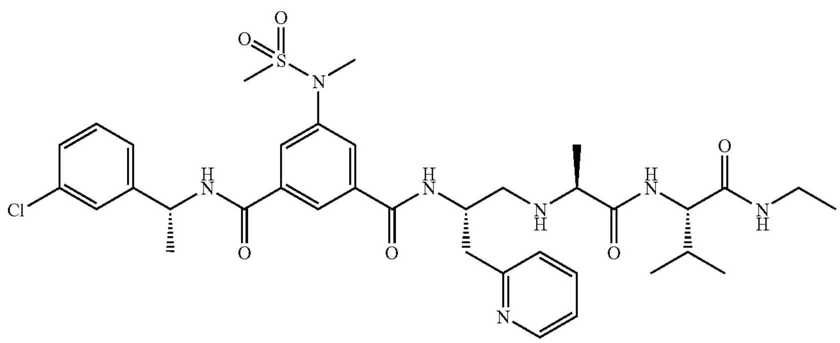 | 742/744 (Cl) | 2.53 min [HPLC-MS] |
| 5.30 | 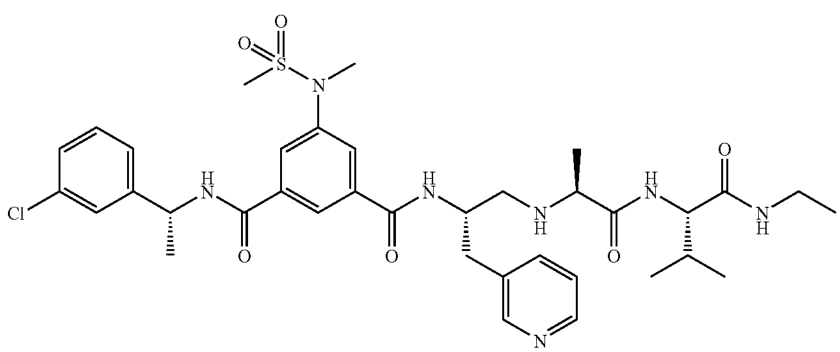 | 742/744 (Cl) | 2.49 min [HPLC-MS] |
| 5.31 | 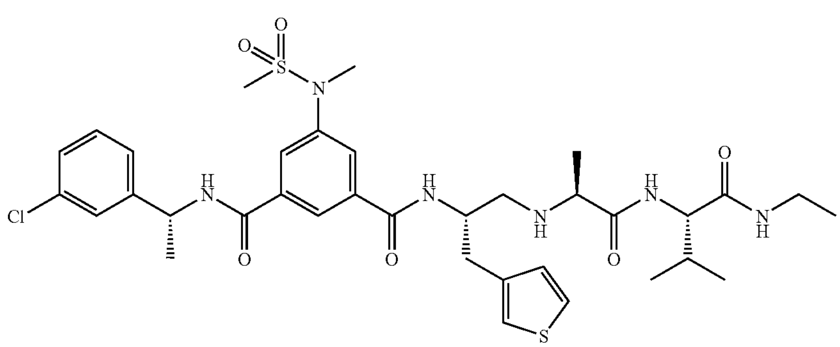 | 747/749 (Cl) | 2.87 min [HPLC-MS] |

-continued
| Example | structure | Mass spectrum [M + H]+ | Retention time [method] |
|---|---|---|---|
| 5.32 | 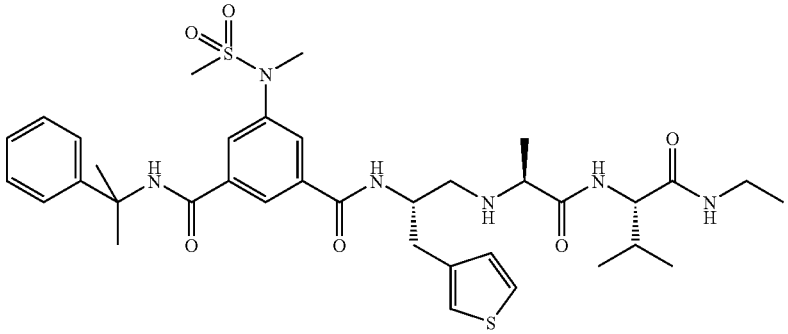 | 727 | 2.83 min [HPLC-MS] |
| 5.33 | 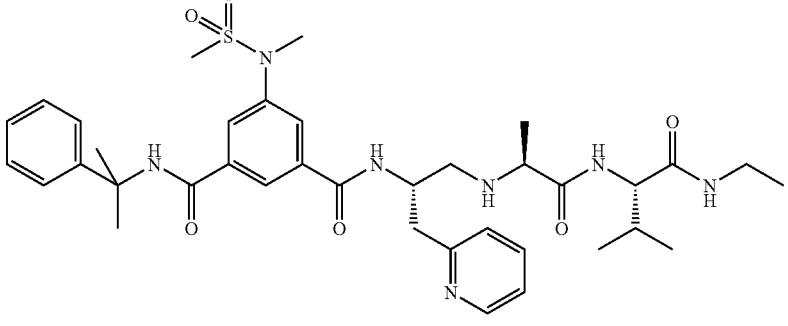 | 722 | 4.00 min [HPLC-1] |
| 5.34 | 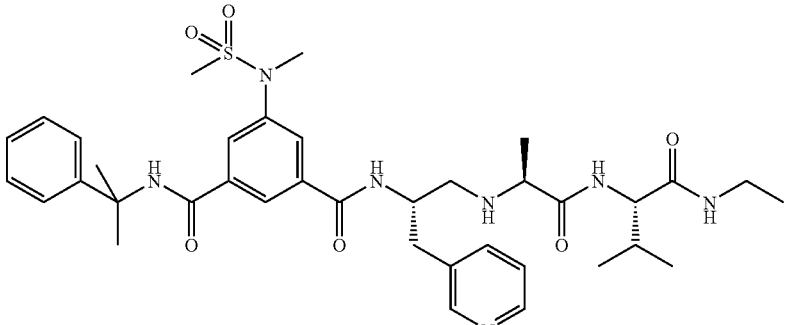 | 722 | 2.42 min [HPLC-MS] |
| 5.35 | 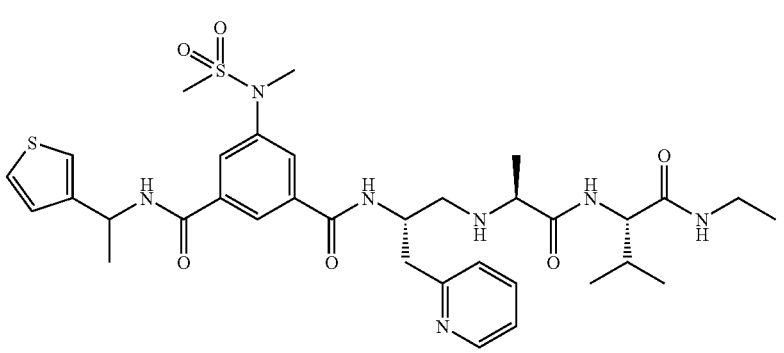 | 714 | 3.86 min [HPLC-1] |

-continued

| Example | structure | Mass spectrum [M + H]+ | Retention time [method] |
|---|---|---|---|
| 5.36 | 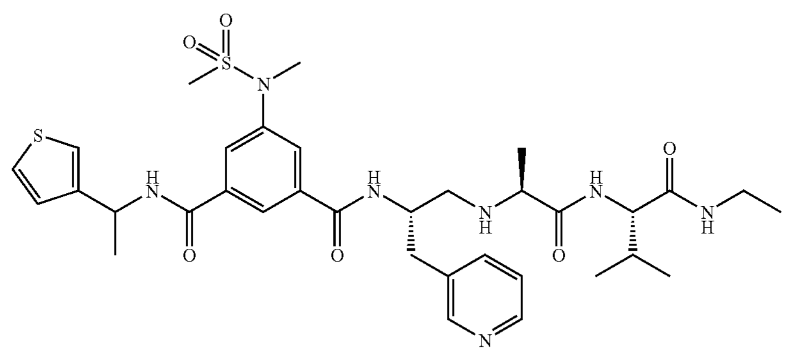 | 714 | 2.33 min [HPLC-MS] |
| 5.37 | 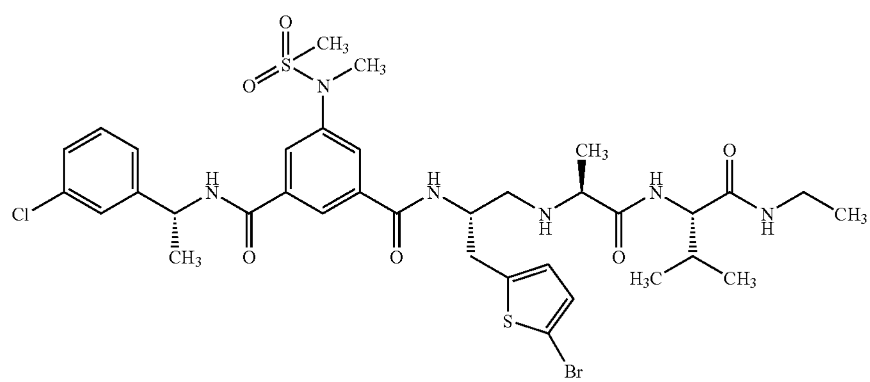 | 825/827/ 829 (Br/Cl) | |
| 5.38 | 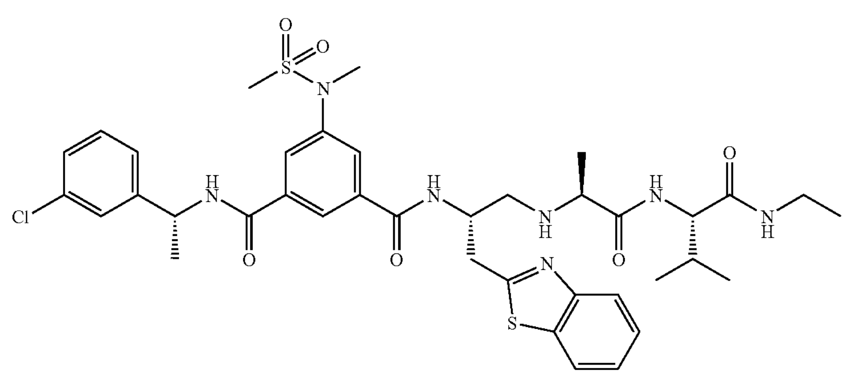 | 798/800 (Cl) | 2.85 min [HPLC-MS] |
| 5.39 | 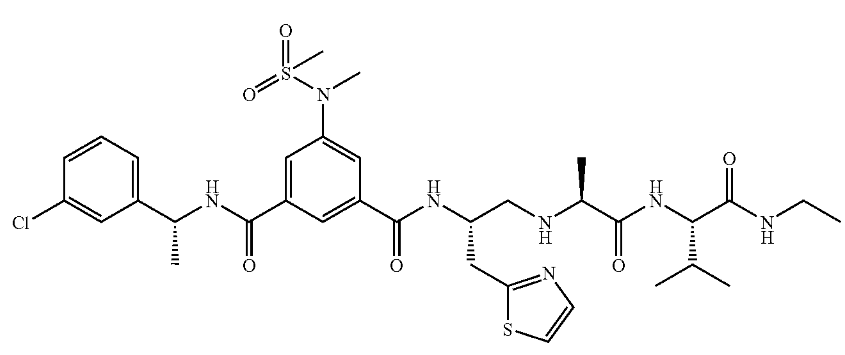 | 748/750 (Cl) | 2.65 min [HPLC-MS] |

| Example | structure | Mass spectrum [M + H]+ | Retention time [method] |
|---|---|---|---|
| 5.40 | 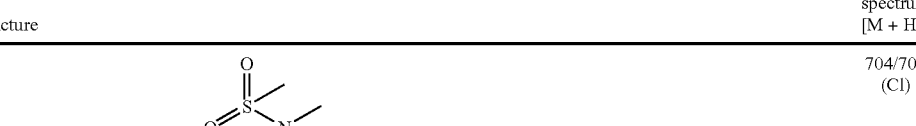 | 704/706 (Cl) | 2.68 min [HPLC-MS] |

Example 6

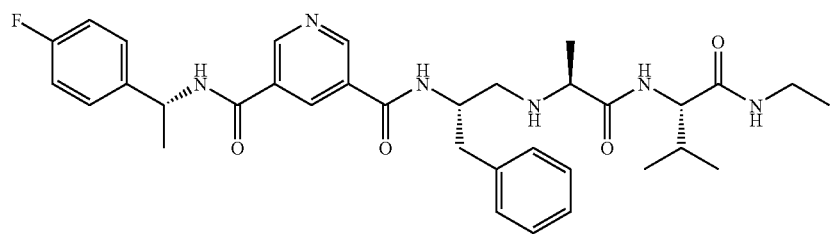

a) Preparation of 6-a:

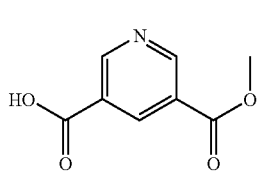
6-a 2.0 g (12.0 mmol) 3,5-pyridinedicarboxylic acid were combined with 0.9 ml (12.0 mmol) thionyl chloride in 40 ml of methanol while cooling with an ice bath. The reaction solution was stirred first at ambient temperature, then at 50° C. overnight. Then the reaction solution was combined with water at ambient temperature and 20% KHCO$_3$ solution and extracted with ethyl acetate. The aqueous phase was adjusted to pH 3 with 4N HCl and extracted with ethyl acetate. The organic phase was dried and evaporated to dryness using the rotary evaporator. The residue was purified by chromatography on silica gel with the eluant (dichloromethane/methanol/ CH$_3$COOH 95:5:0.1). Yield 1.0 g (46%) white crystals 6-a.

ES-MS (M+H)+=182 b) Preparation of 6-b:

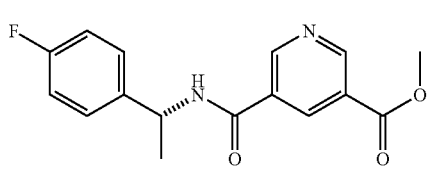
6-b 6-b was prepared analogously to 1-d from 6-a and (R)-1-(4-fluoro-phenyl)-ethylamine.

c) Preparation of 6-c:

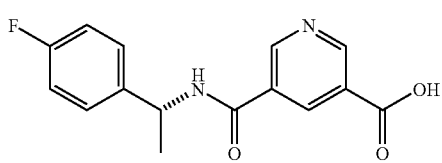
6-c 6-c was prepared analogously to 2-b from 6-b.

d) Preparation of 6-d:

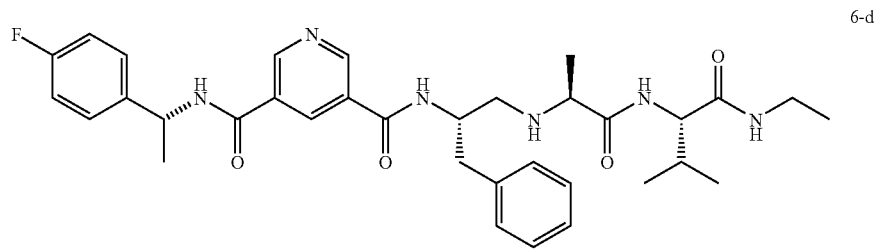

6-d was prepared analogously to 1-d from 1-l and 6-c.
ES-MS (M+H)⁺=619

Example 6.2

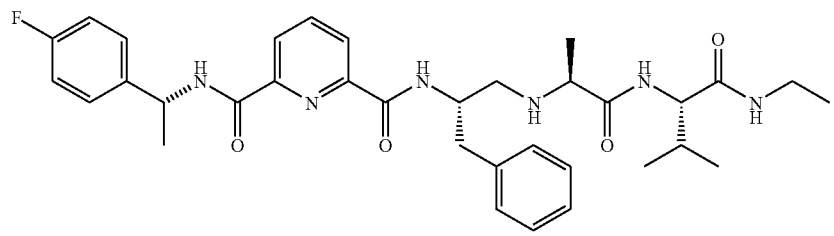

Example 6.2 was prepared analogously to Example 6, except that pyridine-2,6-dicarboxylic acid was used instead of 3,5-pyridinedicarboxylic acid.
ES-MS (M+H)⁺=619

Example 6.3

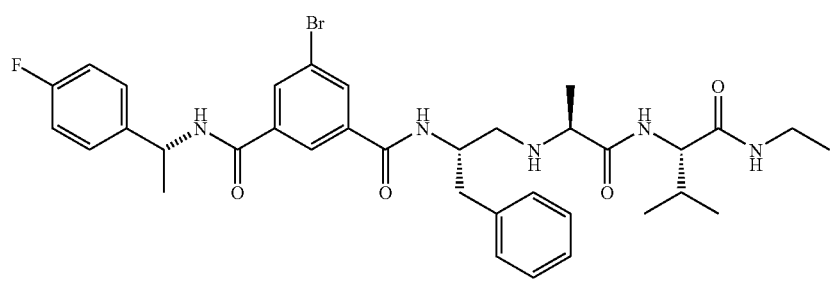

a) Preparation of 6.3-a:

30.0 g (133.2 mmol) monomethyl 5-nitro-isophthalate were dissolved in 200 ml of methanol and combined with 3.0 g Pd/C (5%). The mixture was hydrogenated for 2.5 hours in a Parr apparatus at ambient temperature under a hydrogen pressure of 50 psi. Then the catalyst was filtered off and the filtrate was evaporated down i. vac.

Yield 18.4 g (71%) 6.3-a.
RT(HPLC 1)=2.88 min b) Preparation of 6.3-b:

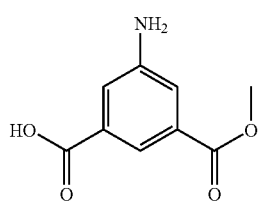

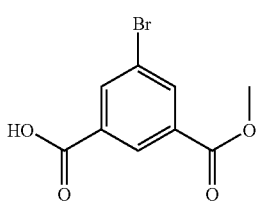

14.0 g (62.7 mmol) copper-(II)-bromide and 12.0 ml (102.6 mmol) n-butylnitrite in 300 ml acetonitrile were combined with 10.0 g (51.2 mmol) 6.3-a, suspended in 300 ml acetonitrile, while cooling with an ice bath. The reaction solution was stirred for 1.5 hours at 30° C., then evaporated to dryness i. vac. Then the residue was combined with dichloromethane and washed with 3N HCl and water. The organic phase was dried and evaporated to dryness using the rotary evaporator. The residue was combined with diethyl ether and the precipitate was filtered off.

Yield 4.5 g (34%) 6.3-b.
ES-MS (M+H)⁺=257/259 (bromine isotopes)
RT(HPLC-MS)=2.87 min c) Preparation of 6.3-c:

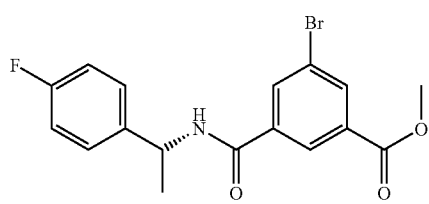

6.3-c 6.3-c was prepared analogously to 1-d from 6.3-b and (R)-1-(4-fluoro-phenyl)-ethylamine.

d) Preparation of 6.3-d:

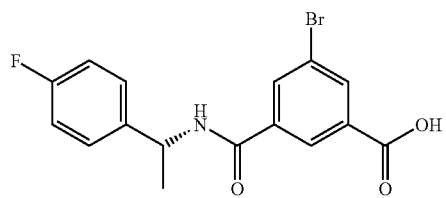

6.3-d 6.3-d was prepared analogously to 2-b from 6.3-c.

e) Preparation of 6.3-e:

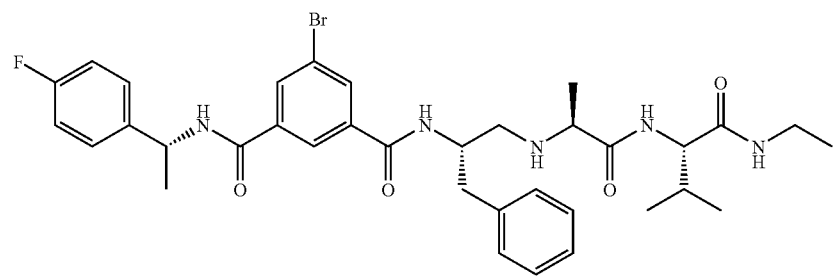

6.3-e 6.3-e was prepared analogously to Example 1-d from 1-l and 6.3-d.
ES-MS (M+H)⁺=696/698 (bromine isotopes)

Analogously to 6.3-e the following compounds were prepared from corresponding educts:

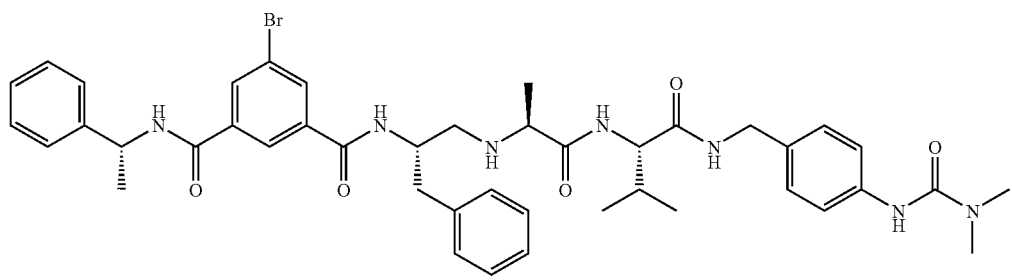

6.3-f

ES-MS (M+H)$^+$=826/828 (Br)
RT(HPLC-MS)=2.84 min
Example 6.4
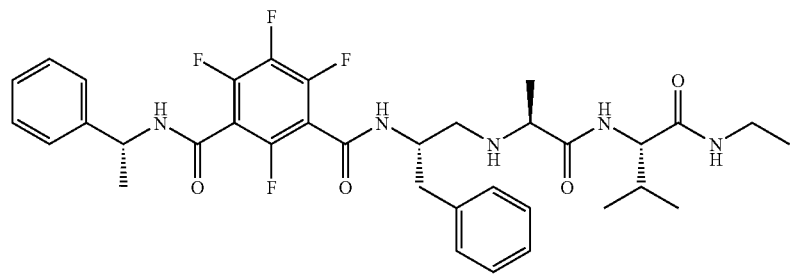
a) Preparation of 6.4-a:
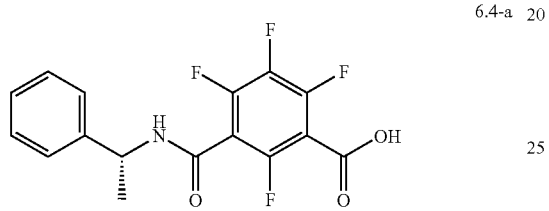
6.4-a
6.4-a was prepared analogously to 1-d from 2,4,5,6-tetrafluoro-isophthalic acid and (R)-1-phenyl-ethylamine.
ES-MS (M+H)$^+$=342
RT(HPLC 1)=4.53 min
b) Preparation of 6.4-b:
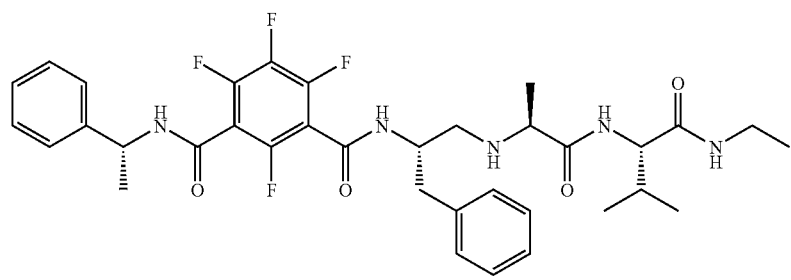
6.4-b
6.4-b was prepared analogously to 1-d from 1-l and 6.4-a.
ES-MS (M+H)$^+$=672
Example 7
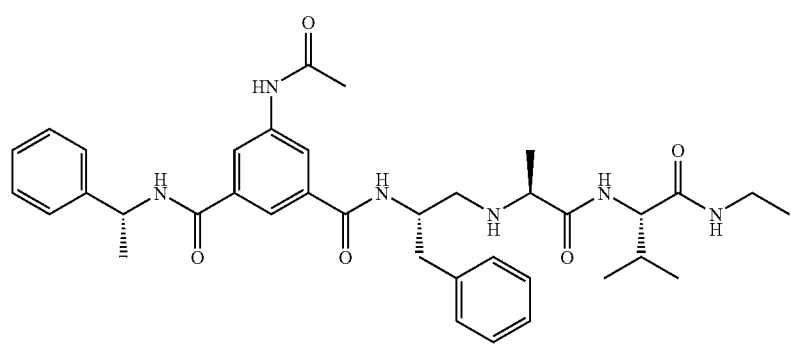

a) Preparation of 7-a:

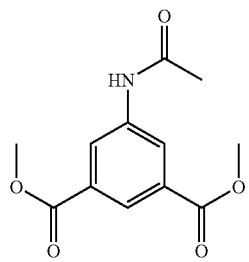

7-a 0.5 g (2.4 mmol) dimethyl 5-amino-isophthalate were refluxed in 10.0 ml (127 mmol) acetyl chloride for 2 hours. The reaction was evaporated to dryness i. vac. and combined with water. The precipitate was filtered off and dried.

Yield 0.6 g (100%) white crystals 7-a.

b) Preparation of 7-b:

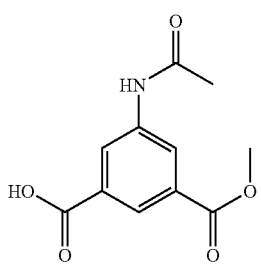

7-b 7-b was prepared analogously to 1-e from 7-a.

c) Preparation of 7-c:

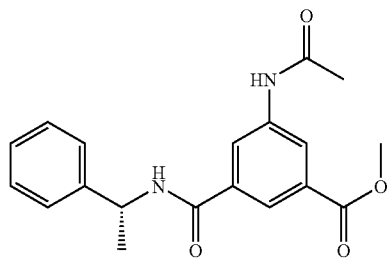

7-c 7-c was prepared analogously to 1-d from 7-b and (R)-1-phenyl-ethylamine.

d) Preparation of 7-d:

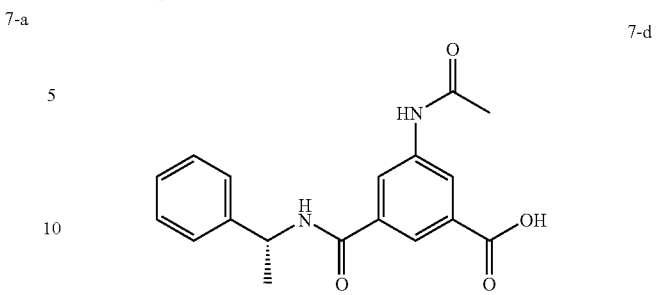

7-d 7-d was prepared analogously to 2-b from 7-c.

e) Preparation of 7-e:

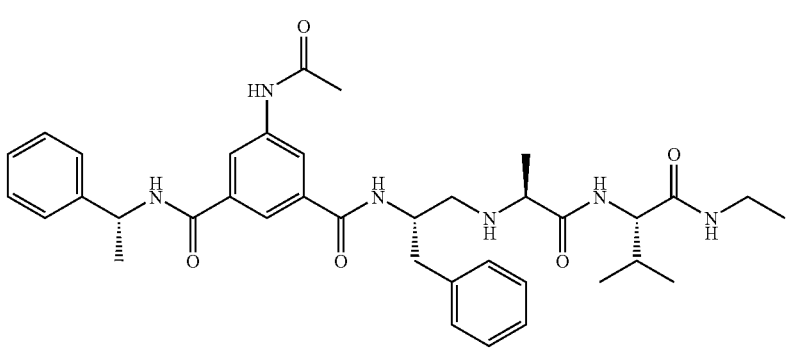

7-e 7-e was prepared analogously to 1-d from 1-l and 7-d.
ES-MS $(M+H)^+$=657

Analogously to Example 7 the following compounds were prepared from dimethyl 5-amino-isophthalate and the corresponding amount of acid chlorides:

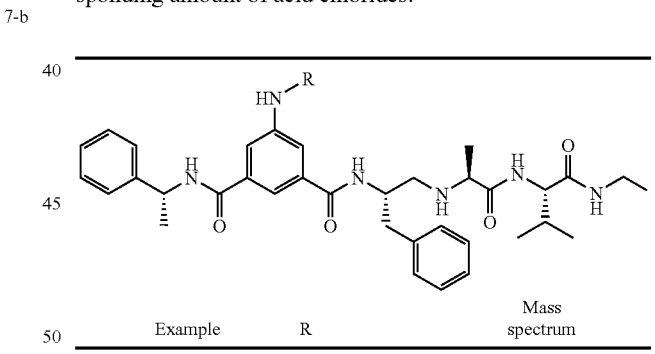

| Example | R | Mass spectrum |
|---------|---|---------------|
| 7.2 | * ![benzoyl] | 719 $[M + H]^+$ |
| 7.3 | * ![phenylacetyl] | 733 $[M + H]^+$ |

Analogously to Example 7 the following compounds were prepared from dimethyl 5-methylamino-isophthalate and the corresponding educts:
| Example | | Mass spectrum |
|---|---|---|
| 7.4 | 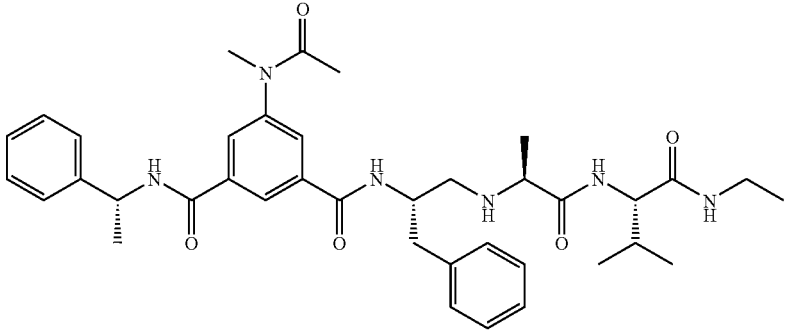 | 672 [M + H]+ |
| 7.5 | 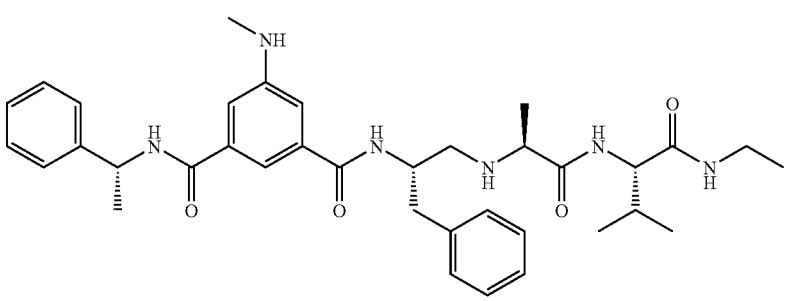 | 630 [M + H]+ |
| 7.6 | 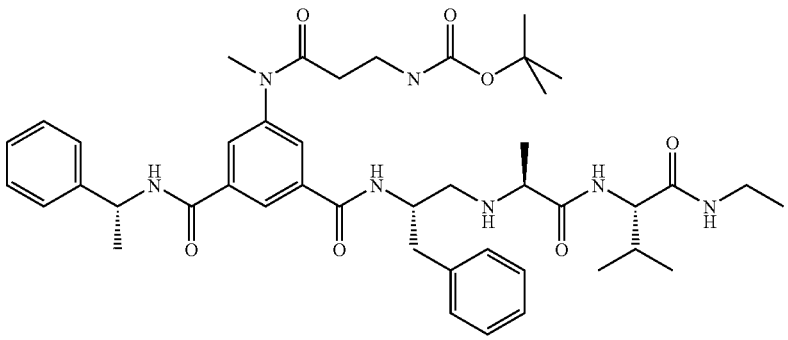 | 880 [M + H]+ |
| 7.7 | 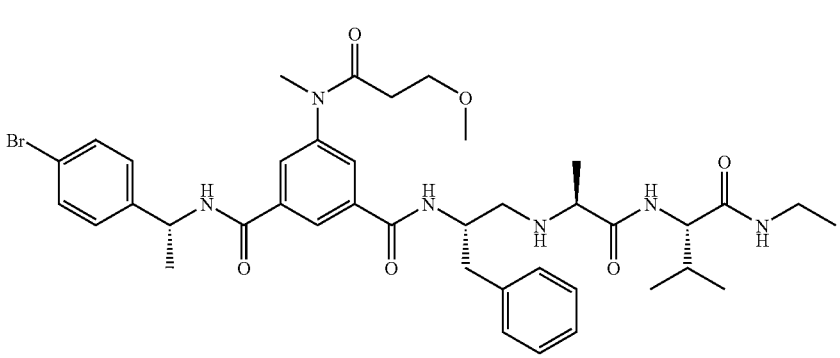 | 794 [M + H]+ |

-continued
| Example | | Mass spectrum |
|---|---|---|
| 7.8 | | 709 [M + H]+ |
| 7.9 | | 822 [M + H]+ |
| 7.10 | | 881 [M + H]+ |
Example 8
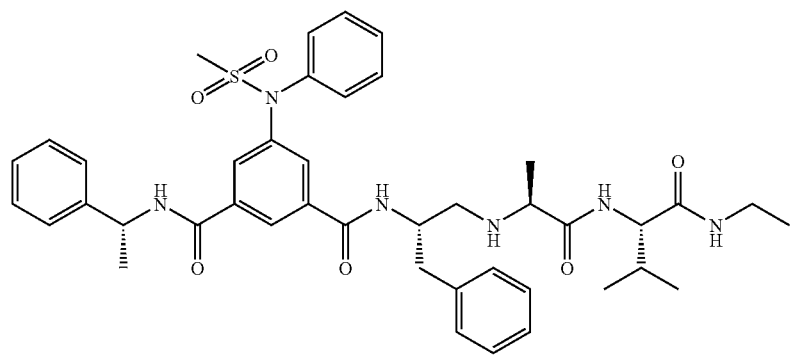

a) Preparation of 8-a:

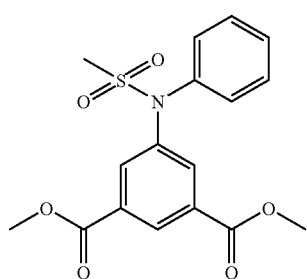

8-a 300 mg (1.0 mmol) 1-a and 255 mg (2.1 mmol) phenylboric acid in 10 ml dichloromethane were combined with 220 mg (1.2 mmol) copper-(II)-acetate, 290 μl (2.1 mmol) triethylamine and 150 mg molecular sieve 4Å. The reaction solution was stirred overnight at ambient temperature and filtered through silica gel. The filtrate was washed first with 2N HCl and then with sat. NaHCO$_3$ solution. The organic phases were separated through phase separation cartridges and evaporated to dryness. The residue was purified by HPLC. Yield 60 mg (16%) 8-a.

ES-MS (M+NH$_4$)$^+$=381
RT(HPLC 1)=4.84 min b) Preparation of 8-b:

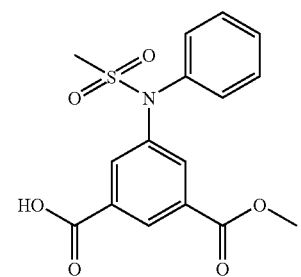

8-b 8-b was prepared analogously to 1-c from 8-a.
RT(HPLC 1)=4.67 min c) Preparation of 8-c:

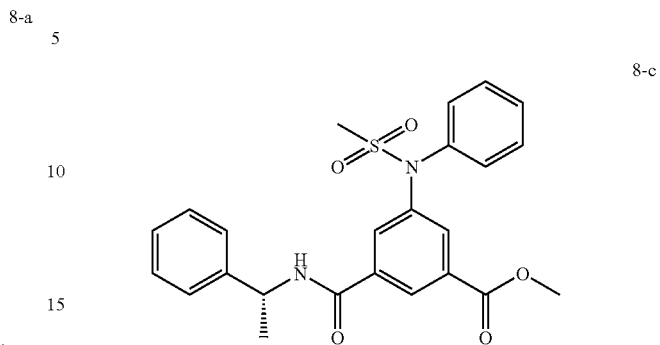

8-c 8-c was prepared analogously to 1-d from 8-b and (R)-1-phenyl-ethylamine.
RT(HPLC 1)=5.03 min d) Preparation of 8-d:

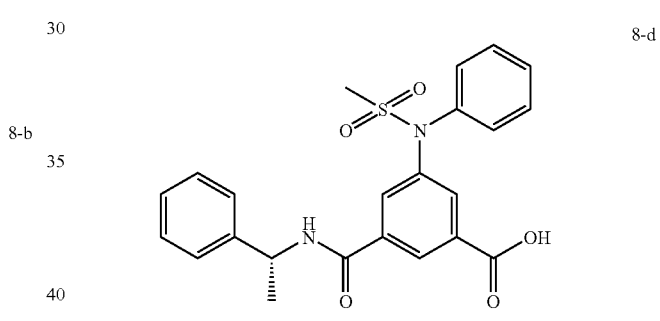

8-d 8-d was prepared analogously to 2-b from 8-c.
RT(HPLC 1)=4.57 min e) Preparation of 8-e:

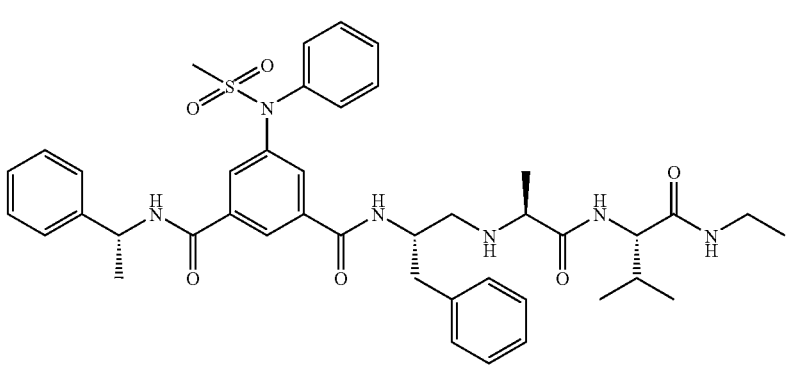

8-e 8-e was prepared analogously to 1-d from 8-d and 1-l.
ES-MS (M+H)⁺=769
RT(HPLC 1)=4.73 min
Example 8.2
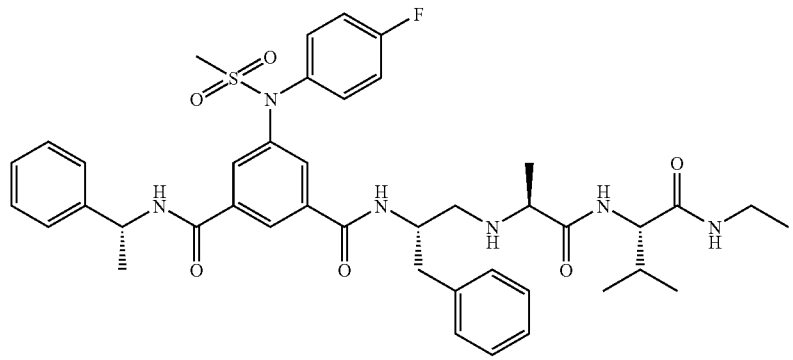
Example 8.2 was prepared analogously to Example 8, except that 4-fluorophenylboric acid was used instead of phenylboric acid.
ES-MS (M+H)⁺=787
RT(HPLC 1)=4.87 min
Example 8.3
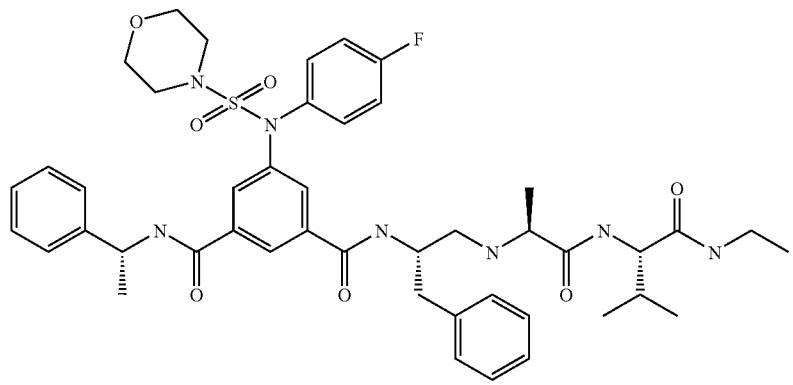
Example 8.3 was prepared analogously to Example 8.2 using the corresponding educts.
ES-MS (M+H)⁺=859
Example 9
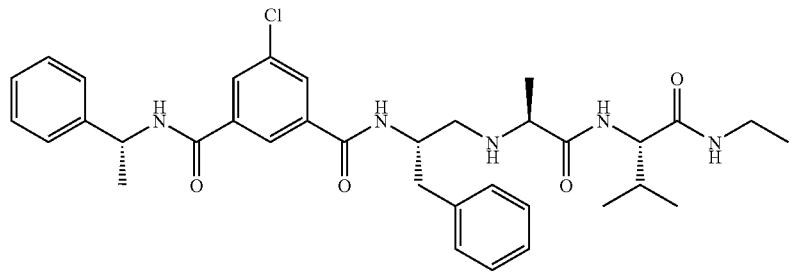

b) Preparation of 9-a:

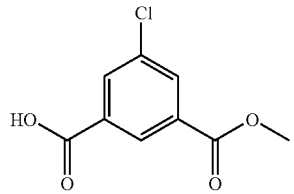

9-a 2.5 g (18.6 mmol) copper-(II)-chloride and 3.6 ml (30.8 mmol) n-butylnitrite were dissolved in 50 ml acetonitrile. While cooling with the ice bath a suspension of 3.0 g (15.4 mmol) 6.3-a in 150 ml acetonitrile was slowly metered in and the reaction solution was stirred for 2 hours at ambient temperature. After the reaction had ended the mixture was evaporated down i. vac., the residue was combined with dichloromethane and washed with 3N HCl and water. The organic phase was evaporated to dryness using the rotary evaporator, the residue was combined with diethyl ether, the precipitate was filtered off and dried. Yield 1.6 g (47%) beige crystals 9-a.

ES-MS (M+H)$^+$=215 c) Preparation of 9-b:

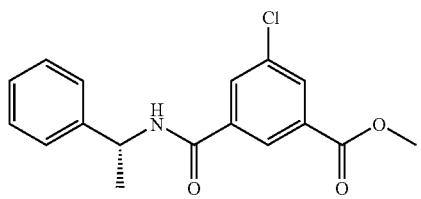

9-b 9-b was prepared analogously to 1-d from 9-a and (R)-1-phenyl-ethylamine.
RT(HPLC 1)=5.17 min d) Preparation of 9-c:

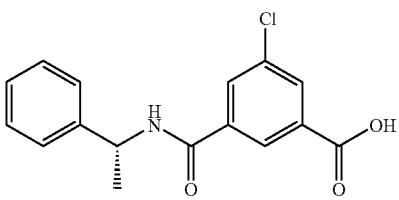

9-c 9-c was prepared analogously to 2-b from 9-b.
RT(HPLC 1)=4.62 min e) Preparation of 9-d:

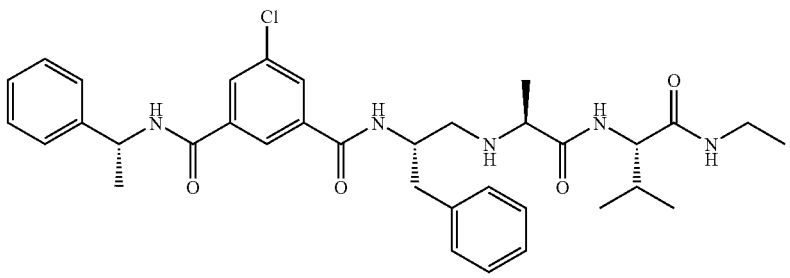

9-d 9-d was prepared analogously to 1-d from 9-c and 1-l.
ES-MS (M+H)$^+$=634/636 (chlorine isotopes)
RT(HPLC 1)=4.71 min Example 9.2

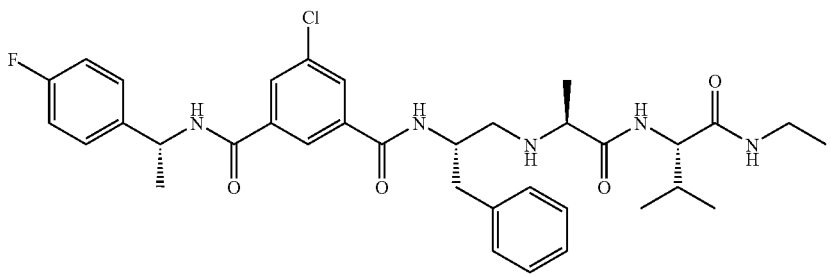

a) Preparation of 9.2-a:

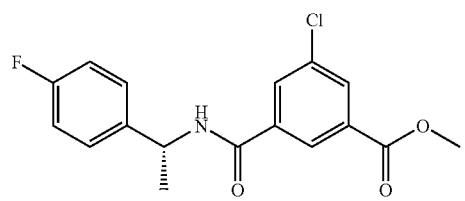

9.2-a 9.2-a was prepared analogously to 1-d from 9-a and (R)-1-(4-fluoro-phenyl)-ethylamine.

RT(HPLC 1)=5.16 min b) Preparation of 9.2-b:

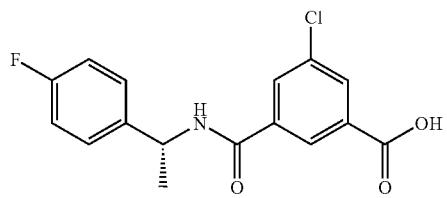

9.2-b 9.2-b was prepared analogously to 2-b from 9.2-a.

RT(HPLC 1)=4.61 min c) Preparation of 9.2-c:

9.2-c was prepared analogously to 1-d from 9.2-b and 1-l.

ES-MS (M+H)$^+$=652/654 (chlorine isotopes)

RT(HPLC 1)=4.71 min

Analogously to Example 9.2 the following compounds were prepared from 9-a and the corresponding amount of amines:

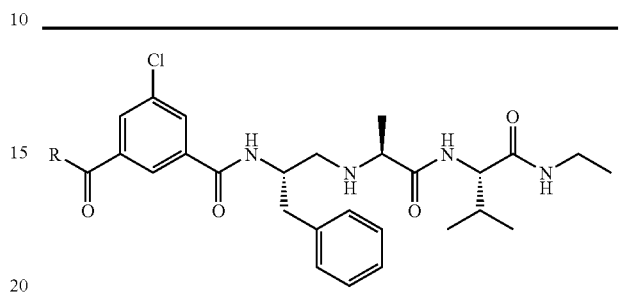

| Example | R | Mass spectrum | Retention time (method) |
|---|---|---|---|
| 9.3 | 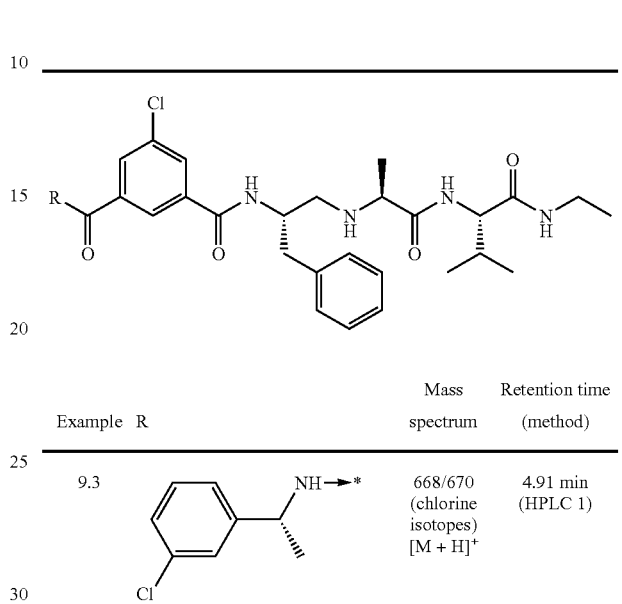 | 668/670 (chlorine isotopes) [M + H]$^+$ | 4.91 min (HPLC 1) |
| 9.4 | 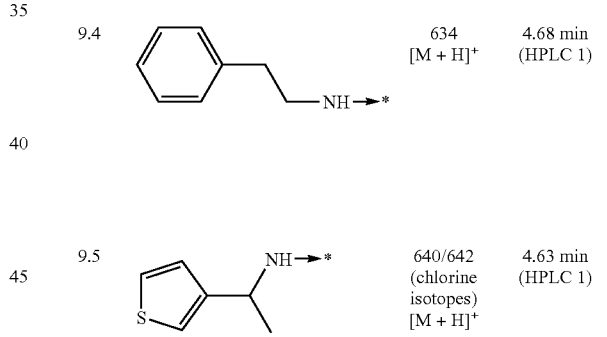 | 634 [M + H]$^+$ | 4.68 min (HPLC 1) |
| 9.5 | | 640/642 (chlorine isotopes) [M + H]$^+$ | 4.63 min (HPLC 1) |

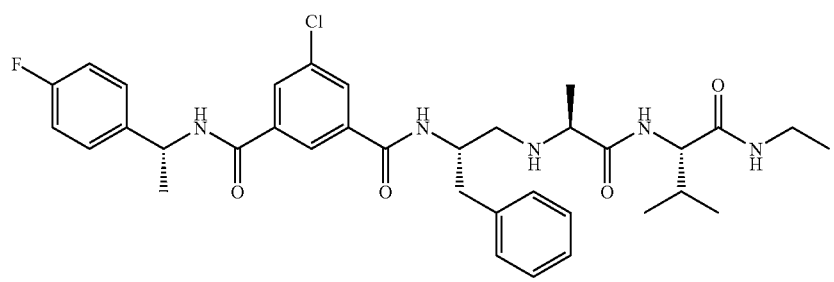

9.2-c

Example 9.6

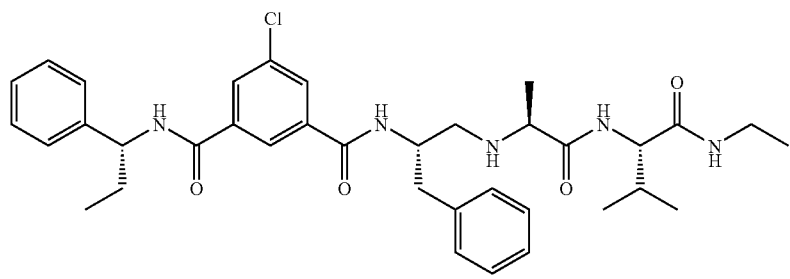

a) Preparation of 9.6-a:

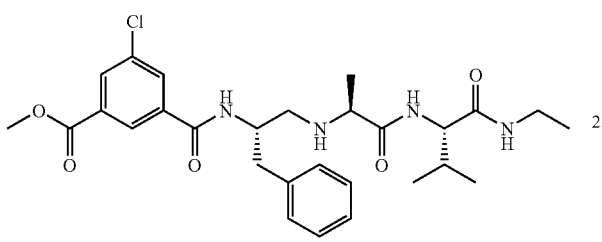

9.6-a 9.6-a was prepared analogously to 1-d from 9-a and 1-l.
RT(HPLC 1)=4.44 min b) Preparation of 9.6-b:

9.6-b

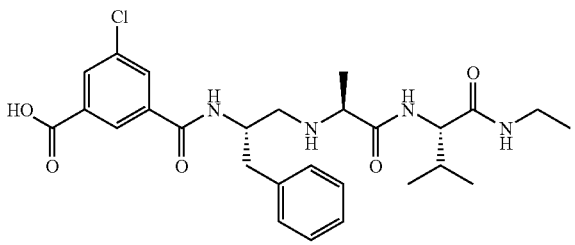

9.6-b was prepared analogously to 2-b from 9.6-a.
ES-MS (M+H)$^+$=531/533 (chlorine isotopes)
RT(HPLC 1)=4.14 min c) Preparation of 9.6-c:

9.6-c

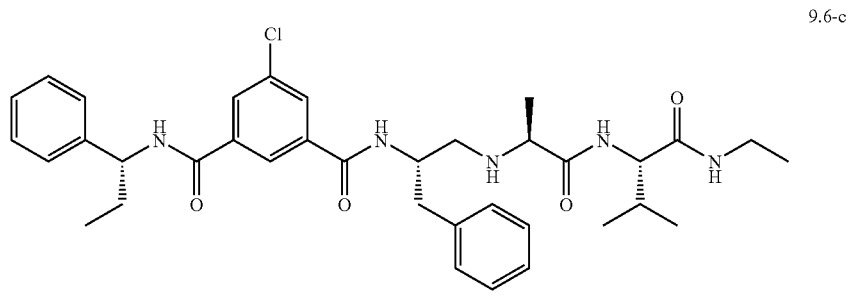

9.6-c was prepared analogously to 1-d from 9.6-b and (R)-1-phenyl-propylamine.

ES-MS (M+H)$^+$=648/650 (chlorine isotopes)
RT(HPLC 1)=4.84 min

Analogously to 9.6-c the following compounds were prepared from 9.6-b and the corresponding amount of amines:

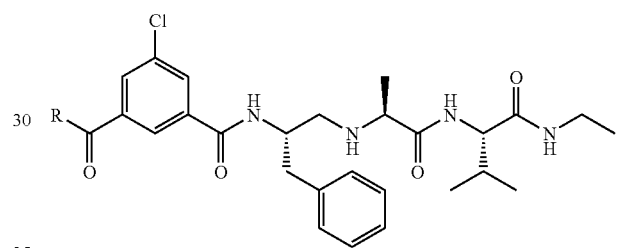

| Example | R | Mass spectrum | Retention time (method) |
|---|---|---|---|
| 9.7 | pyridin-3-yl-CH(CH₃)-NH—* | 635/637 (chlorine isotopes) [M + H]$^+$ | 3.81 min (HPLC 1) |
| 9.8 | 4-methoxyphenyl-CH(CH₃)-NH—* | 664/666 (chlorine isotopes) [M + H]$^+$ | 4.63 min (HPLC 1) |

-continued

| Example | R | Mass spectrum | Retention time (method) |
|---|---|---|---|
| 9.9 | 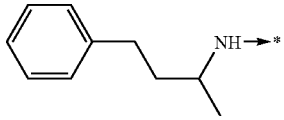 | 662/664 (chlorine isotopes) [M + H]⁺ | 4.93 min (HPLC 1) |
| 9.10 | 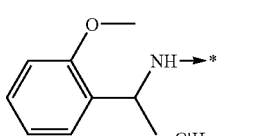 | 664 [M + H]⁺ | 4.79 min (HPLC 1) |

Example 10

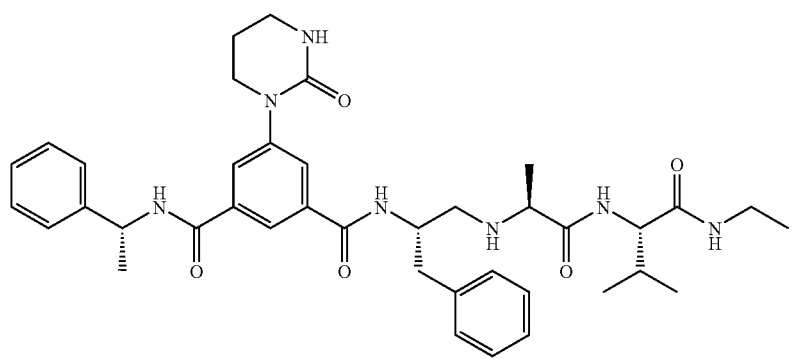

a) Preparation of 10-a:

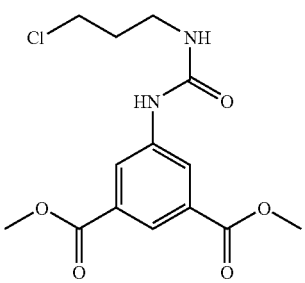

1.8 g (8.4 mmol) dimethyl 5-amino-isophthalate were dissolved in 15 ml THF and combined with 1.0 g (8.4 mmol) 1-chloro-3-isocyanate-propane and refluxed overnight with stirring. Then the reaction solution was evaporated down i. vac. Yield 2.7 g (69%) white crystals 10-a.

RT(HPLC 1)=4.49 min b) Preparation of 10-b:

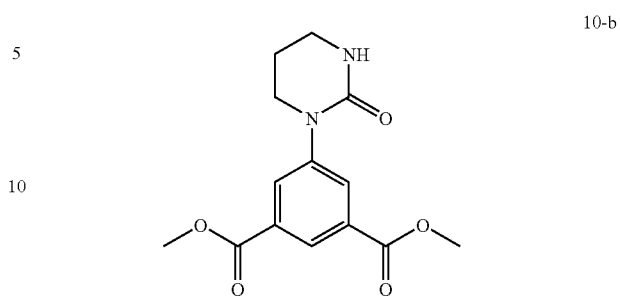

2.7 g (5.8 mmol) 10-a were dissolved in 25 ml DMF, combined with 1.3 g (11.6 mmol) potassium tert-butoxide and stirred overnight at 60° C. Then the reaction solution was combined with water and extracted with dichloromethane. The combined organic phases were dried over MgSO₄, filtered and the filtrate was evaporated to dryness i. vac. The residue was purified by MPLC with the eluant (ethyl acetate/heptane 7:3 up to pure methanol). Yield 870 mg (52%) 10-b as white crystals.

ES-MS (M+H)⁺=293/294
RT(HPLC 1)=3.91 min c) Preparation of 10-c:

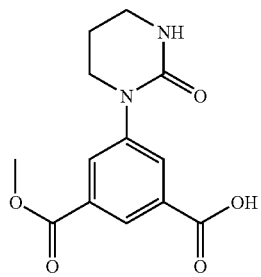

10-c was prepared analogously to 1-c from 10-b.
RT(HPLC 1)=3.44 min d) Preparation of 10-d:

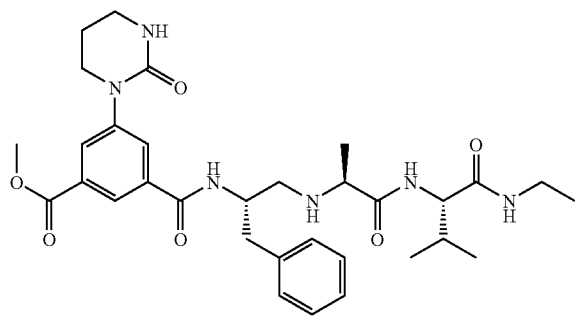

10-d was prepared analogously to 1-d from 10-c and 1-l.
RT(HPLC 1)=3.96 min e) Preparation of 10-e:

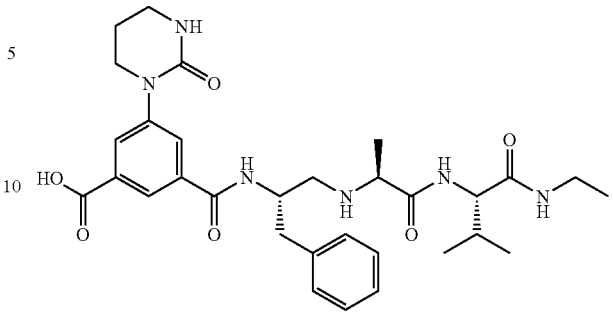

10-e was prepared analogously to 2-b from 10-d.
ES(−)-MS (M−H)⁻=593
RT(HPLC 1)=3.74 min f) Preparation of 10-f:

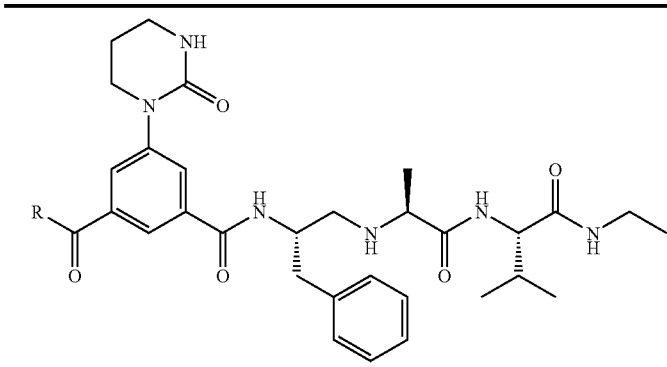

10-f was prepared analogously to 1-d from 10-e and (R)-1-phenyl-ethylamine.
ES-MS (M+H)⁺=698
RT(HPLC 1)=4.27 min Analogously to 10-f the following compounds were prepared from 10-e and the corresponding amount of amines:

| Example | R | Mass spectrum | Retention time (method) |
|---|---|---|---|
| 10.2 | (3-chlorophenyl)-CH(CH₃)-NH—* | 732/734 (chlorine isotopes) [M + H]⁺ | 4.50 min (HPLC 1) |

-continued

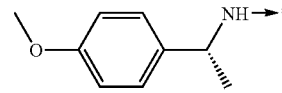

| Example | R | Mass spectrum | Retention time (method) |
|---|---|---|---|
| 10.3 | 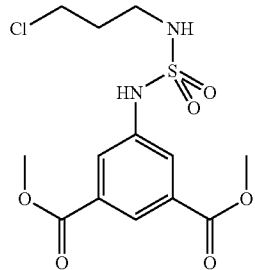 | 728 [M + H]⁺ | 4.31 min (HPLC 1) |

Example 11

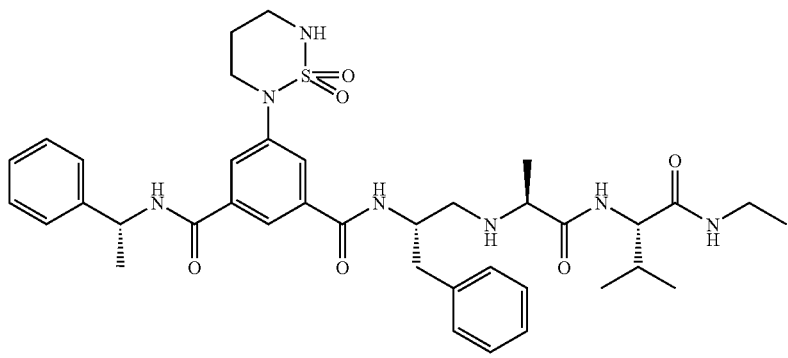

a) Preparation of 11-a:

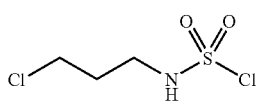

1.3 ml (15.4 mmol) sulphuryl chloride were metered into a solution of 1.0 g (7.7 mmol) 3-chloro-propylamine-hydrochloride in 10 ml acetonitrile while cooling with an ice bath and stirred overnight at 85° C. Then the reaction solution was evaporated down i. vac. Quantitative yield of 11-a.

b) Preparation of 11-b:

11-b 1.0 g (4.8 mmol) dimethyl 5-amino-isophthalate were suspended in 10 ml of pyridine and slowly combined with 1.5 g (7.8 mmol) 11-a and stirred overnight at ambient temperature. Then the reaction solution was combined with dichloromethane and washed with 1 N HCl and water, the organic phase was separated using a phase separation cartridge and evaporated down i. vac.

Yield 1.1 g (41%) brown crystals 11-a.

RT(HPLC 1)=4.51 min c) Preparation of 11-c:

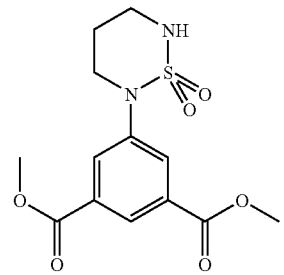

11-c was prepared analogously to 10-b from 11-b.

ES-MS (M+H)⁺=329

RT(HPLC 1)=4.29 min d) Preparation of 11-d:

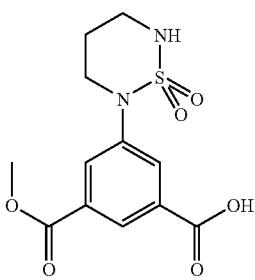

11-d was prepared analogously to 1-c from 11-c.
RT(HPLC 1)=3.79 min e) Preparation of 11-e:

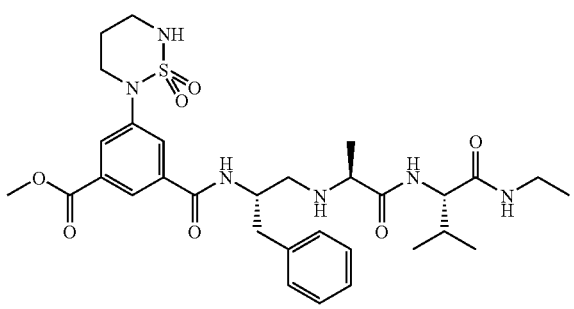

11-e was prepared analogously to 1-d from 11-d and 1-l.
RT(HPLC 1)=4.16 min f) Preparation of 11-f:

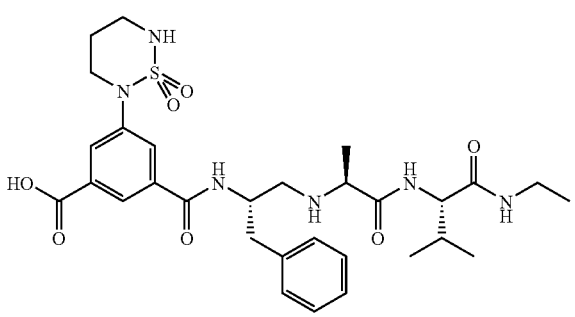

11-f was prepared analogously to 2-b from 11-e.
ES(−)-MS (M−H)⁻=629
RT(HPLC 1)=3.86 min g) Preparation of 11-g:

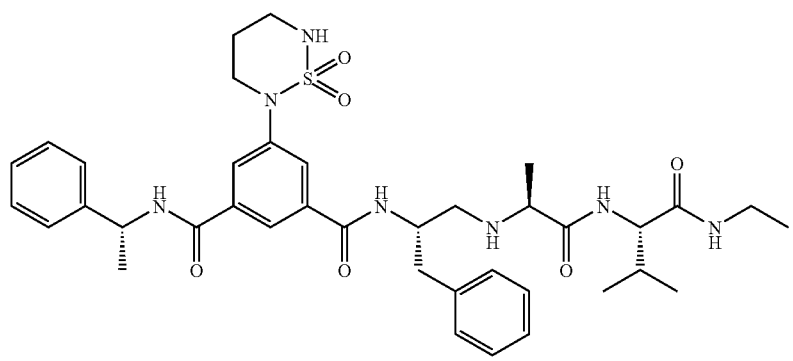

11-g was prepared analogously to 1-d from 11-f and (R)-1-phenyl-ethylamine.
ES-MS (M+H)⁺=734
RT(HPLC 1)=4.46 min Analogously to 11-g the following compounds were prepared from 11-f and the corresponding amount of amines:

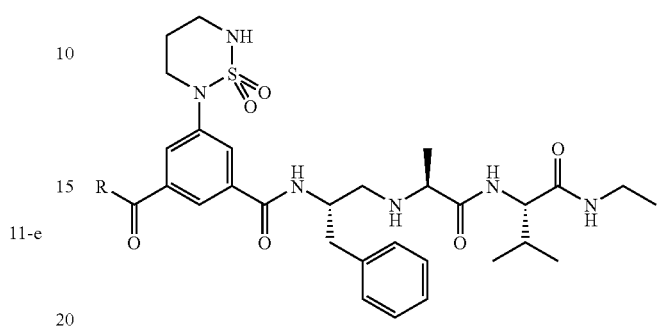

| Example | R | Mass spectrum | Retention time (method) |
|---|---|---|---|
| 11.2 | 3-chlorophenyl-CH(CH₃)-NH–* | 768/770 (chlorine isotopes) [M + H]⁺ | 4.64 min (HPLC 1) |
| 11.3 | 4-methoxyphenyl-CH(CH₃)-NH–* | 764 [M + H]⁺ | 4.39 min (HPLC 1) |
| 11.4 | 4-fluorophenyl-CH(CH₃)-NH–* | 753 [M + H]⁺ | 4.59 min (HPLC 1) |
| 11.5 | phenyl-C(CH₃)₂-NH–* | 749 [M + H]⁺ | 2.79 min (HPLC-MS) |
| 11.6 | 1-methylpyrazol-4-yl-CH(CH₃)-NH–* | 739 [M + H]⁺ | 4.08 min (HPLC 1) |

-continued
| Example | R | Mass spectrum | Retention time (method) |
|---|---|---|---|
| 11.7 | 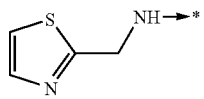 | 714 [M + H]⁺ | 3.99 min (HPLC 1) |
| 11.8 |  | 815 [M + H]⁺ | 4.80 min (HPLC 1) |
-continued
| Example | R | Mass spectrum | Retention time (method) |
|---|---|---|---|
| 11.9 | 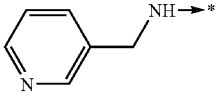 | 735 [M + H]⁺ | 2.26 min (HPLC-MS) |
Analogously to 11-9 the following compounds were prepared from corresponding educts:
| Example | | Mass spectrum | Retention time (method) |
|---|---|---|---|
| 11.10 | 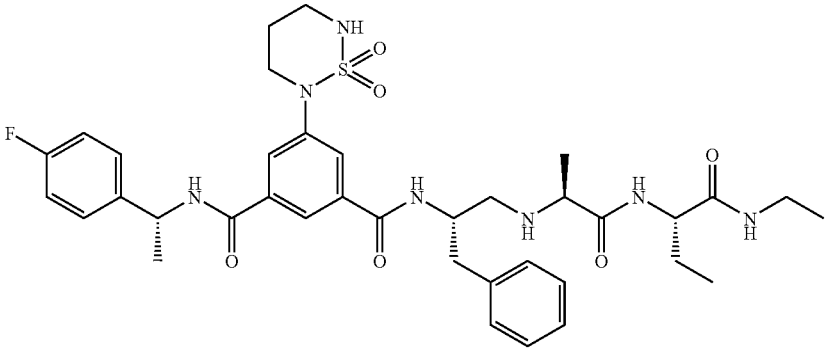 | 739 [M + H]⁺ | 4.54 min (HPLC 1) |
| 11.11 | 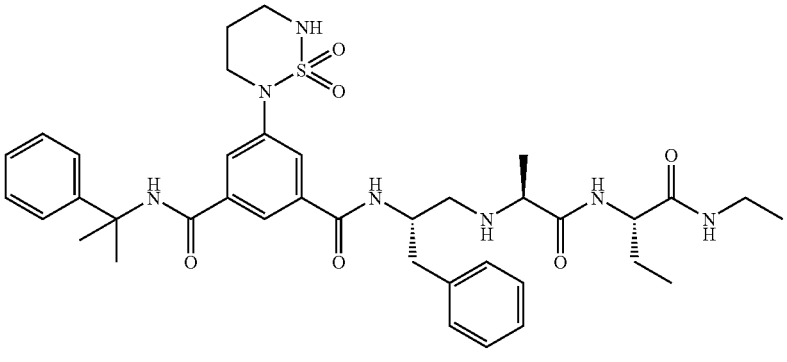 | 735 [M + H]⁺ | 2.71 min (HPLC-MS) |
| 11.12 | 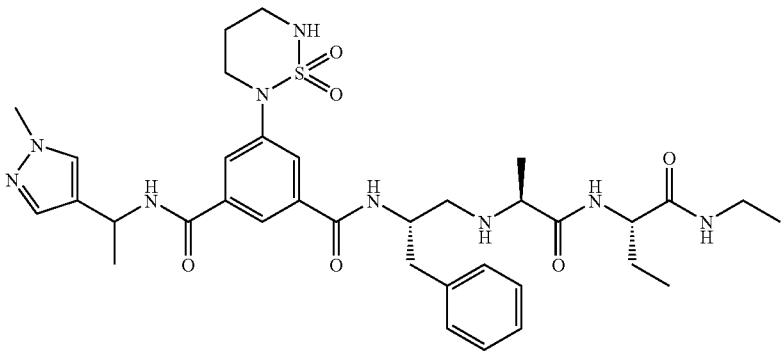 | 725 [M + H]⁺ | 3.95 min (HPLC 1) |

-continued

| Example | Mass spectrum | Retention time (method) |
|---|---|---|
| 11.13 | 714 [M + H]⁺ | 3.99 min (HPLC 1) |
| 11.14 | 736 [M + H]⁺ | 2.38 min (HPLC-MS) |
| 11.15 | 816 [M + H]⁺ | 2.52 min (HPLC-MS) |
| 11.16 | 742 [M + H]⁺ | 4.26 min (HPLC 1) |

-continued

| Example | | Mass spectrum | Retention time (method) |
|---|---|---|---|
| 11.17 | | 821 [M + H]⁺ | 4.51 min (HPLC 1) |
| 11.18 | | 743 [M + H]⁺ | 1.99 min (HPLC-MS) |

Example 12

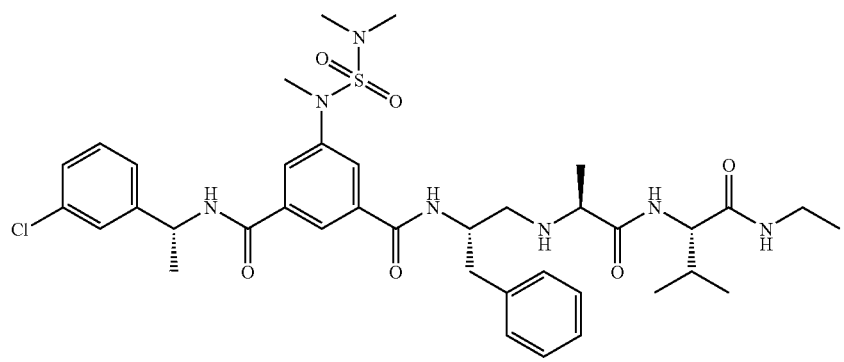

a) Preparation of 12-a:

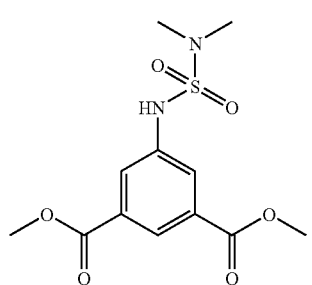

12-a 15.0 g (70.3 mmol) dimethyl 5-amino-isophthalate were dissolved in 150 ml of pyridine and slowly combined with 12.0 ml (111.7 mmol) N,N-dimethylamidosulphonic acid chloride and stirred overnight at 90° C. Then the reaction solution was combined at ambient temperature with 200 ml 4N HCl and the precipitate was filtered off. The crystals were combined with diethyl ether, filtered off again and dried at 40° C. in the vacuum drying cupboard. Yield 17.9 g (64%) beige crystals 12-a.

RT(HPLC 1)=4.14 min b) Preparation of 12-b:

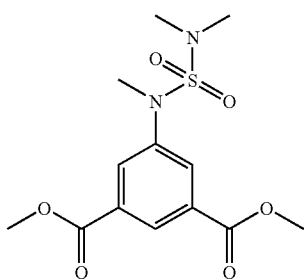
12-b

First 17.9 g (56.6 mmol) 12-a in 250 ml DMF and then 9.3 ml (124.5 mmol) methyl iodide were added to a solution of 5.0 g (125.1 mmol) sodium hydride (60% in mineral oil) in 250 ml DMF while cooling with dry ice. The reaction solution was stirred for 3 h at ambient temperature, combined with 500 ml of water and extracted with ethyl acetate. The combined organic phases were dried over MgSO$_4$ and evaporated to dryness using the rotary evaporator. The residue was combined with diethyl ether, the precipitate was filtered off and dried.

Yield 12.5 g (57%) brown crystals 12-b.
RT(HPLC 1)=4.67 min c) Preparation of 12-c:

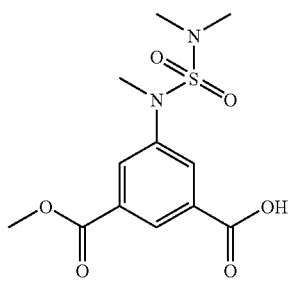
12-c 12-c was prepared analogously to 1-c from 12-b.
RT(HPLC-MS)=2.58 min d) Preparation of 12-d:

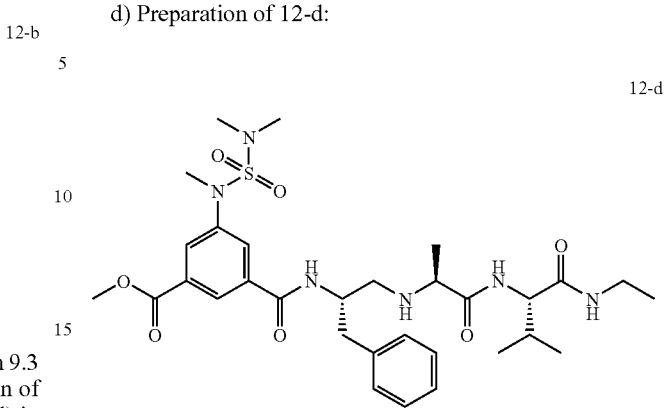
12-d 12-d was prepared analogously to 1-d from 12-c and 1-l.
RT(HPLC 1)=4.37 min e) Preparation of 12-e:

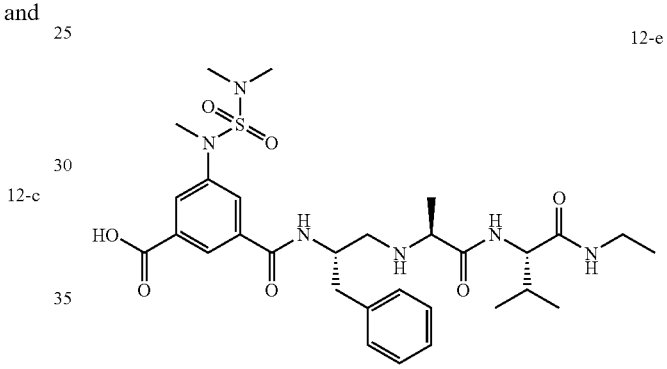
12-e 12-e was prepared analogously to 2-b from 12-d.
ES-MS (M+H)$^+$=633
RT(HPLC-MS)=2.50 min f) Preparation of 12-f:

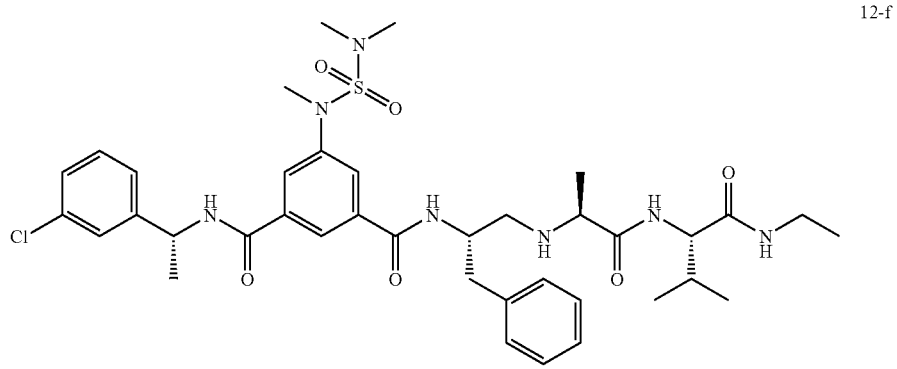
12-f 12-f was prepared analogously to 1-d from 12-e and (R)-1-(3-chloro-phenyl)-ethylamine.
ES-MS (M+H)⁺=770/772 (chlorine isotopes)
RT(HPLC 1)=4.77 min Analogously to 12-f the following compounds were prepared from 12-e and the corresponding amount of amines:

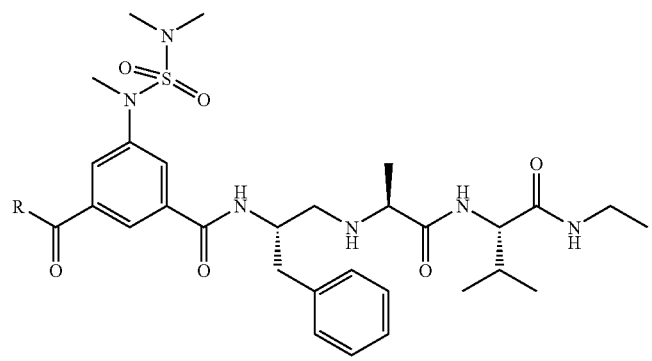

| Example | R | Mass spectrum | Retention time (method) |
|---|---|---|---|
| 12.2 | 4-F-C₆H₄-CH(CH₃)-NH—* | 745 [M + H]⁺ | 4.67 min (HPLC 1) |
| 12.3 | 4-MeO-C₆H₄-CH(CH₃)-NH—* | 766 [M + H]⁺ | 4.58 min (HPLC 1) |
| 12.4 | C₆H₅-CH(Et)-NH—* | 750 [M + H]+ | 4.68 min (HPLC 1) |
| 12.5 | C₆H₅-C(CH₃)₂-NH—* | 750 [M + H]+ | 4.66 min (HPLC 1) |
| 12.6 | 2-pyridyl-CH(CH₃)-NH—* | 737 [M + H]+ | 3.83 min (HPLC 1) |
| 12.7 | 3-pyridyl-CH(CH₃)-NH—* | 737 [M + H]+ | 3.89 min (HPLC 1) |
| 12.8 | 3-thienyl-CH(CH₃)-NH—* | 742 [M + H]+ | 4.55 min (HPLC 1) |

Analogously to 12-f the following compounds were prepared from corresponding educts:

| Example | structure | Mass spectrum [M + H]+ | Retention time [method] |
|---|---|---|---|
| 12.9 | 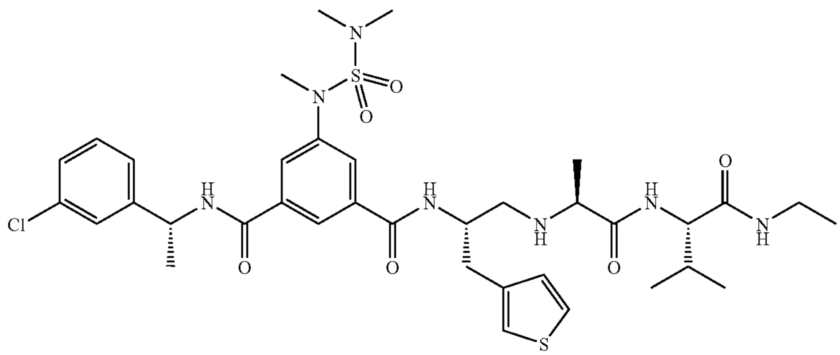 | 776/778 (Cl) | 4.88 min [HPLC-1] |
| 12.10 | 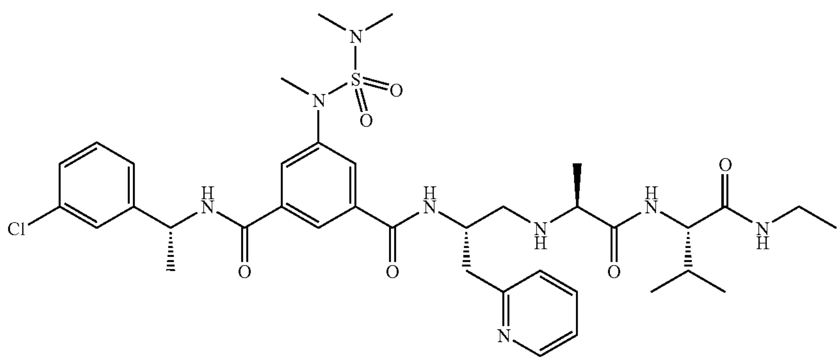 | 771/773 (Cl) | 4.29 min [HPLC-1] |
| 12.11 | 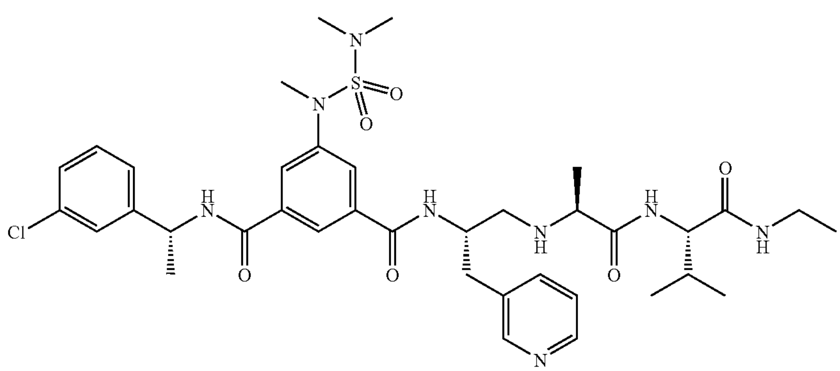 | 771/773 (Cl) | 4.22 min [HPLC-1] |
| 12.12 | 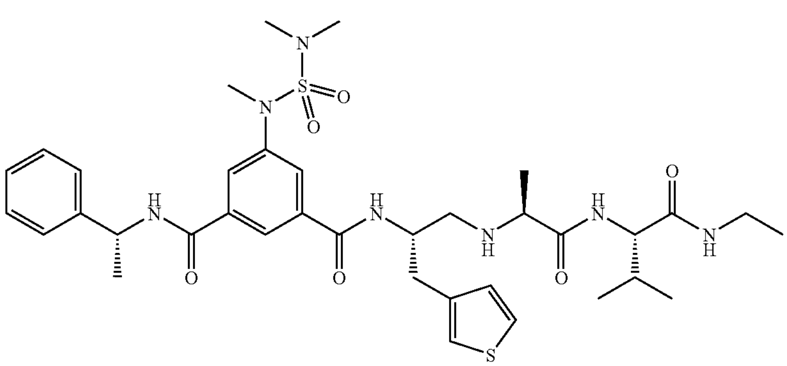 | 742 | 4.67 min [HPLC-1] |

-continued

| Example | structure | Mass spectrum [M + H]+ | Retention time [method] |
|---|---|---|---|
| 12.13 | 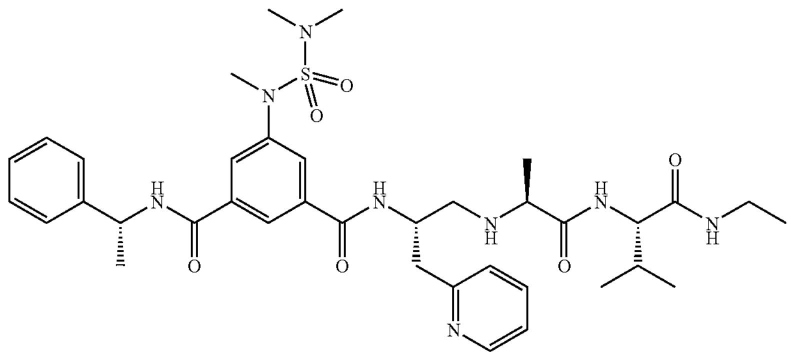 | 737 | 4.11 min [HPLC-1] |
| 12.14 | 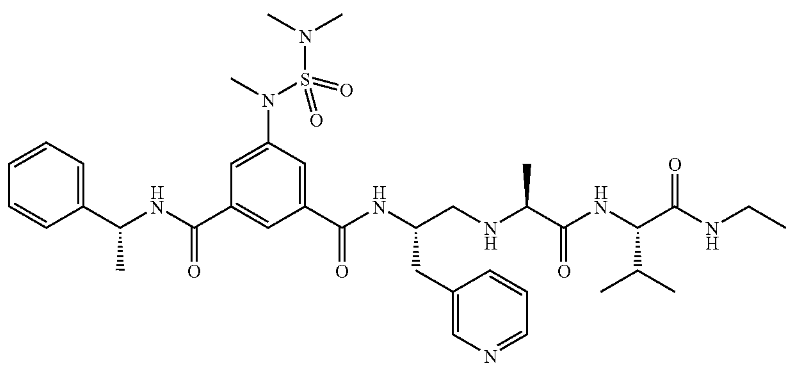 | 737 | 4.03 min [HPLC-1] |
| 12.15 | 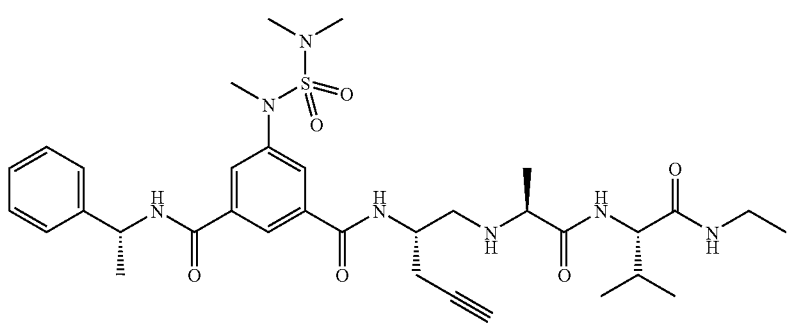 | 684 | 2.70 min [MPLC-MS] |
| 12.16 | 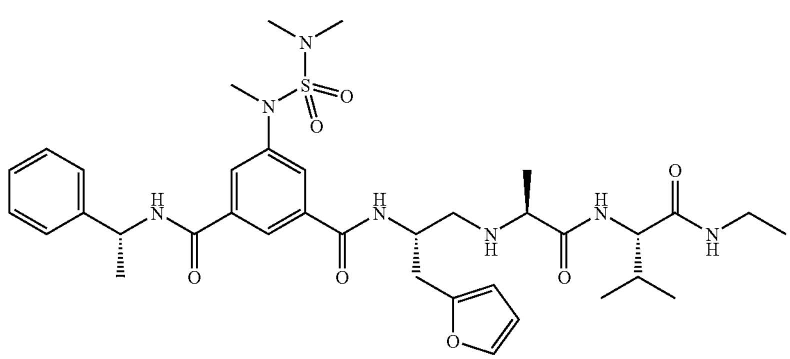 | 726 | 2.73 min [MPLC-MS] |

-continued

| Example | structure | Mass spectrum [M + H]+ | Retention time [method] |
|---|---|---|---|
| 12.17 | 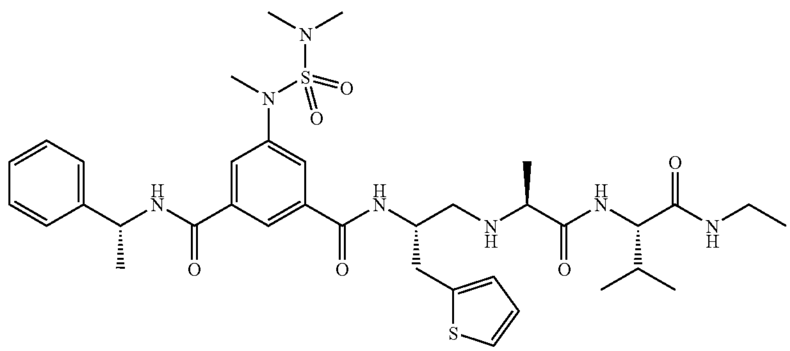 | 742 | 2.81 min [MPLC-MS] |
| 12.18 | 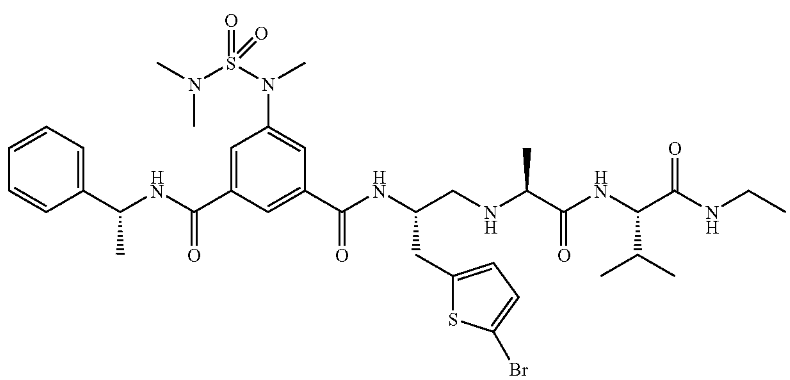 | 820/822 (Br) | |
| 12.19 | 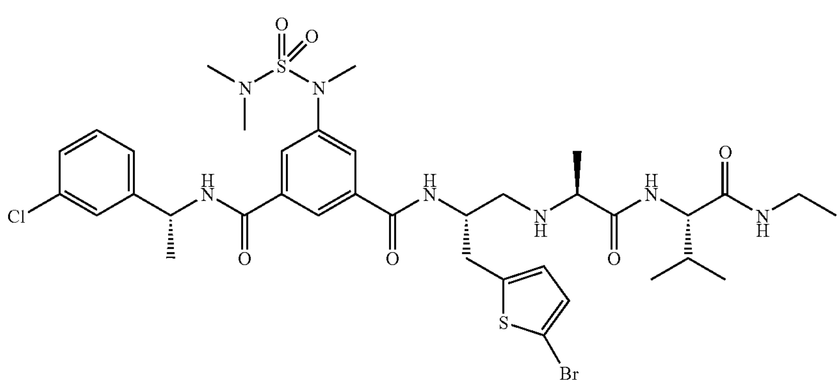 | 854/856/ 858 (Br/Cl) | 5.07 min [HPLC-1] |
| 12.20 | 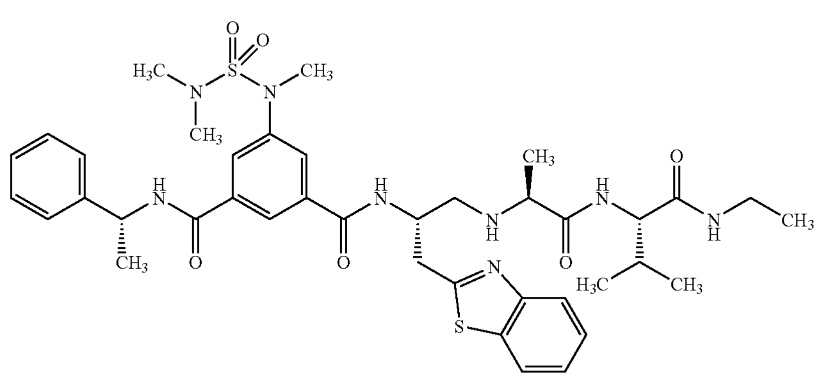 | 793 | 2.82 min [HPLC-MS] |

Example 13

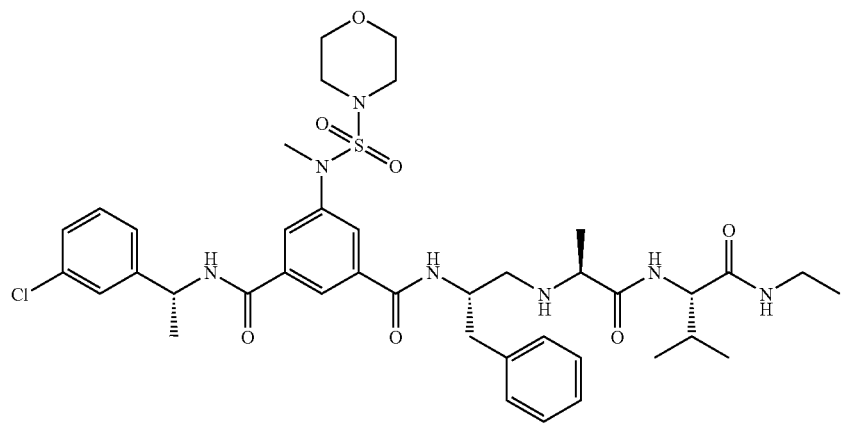

a) Preparation of 13-a:

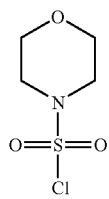
13-a 8.4 ml (96.4 mmol) morpholine in 12 ml acetonitrile were metered into a solution of 4.0 ml (49.3 mmol) sulphuryl chloride in 12 ml acetonitrile while cooling with an ice bath and the mixture was stirred overnight at 85° C. Then the reaction solution was evaporated down i. vac., the residue was combined with diethyl ether, the precipitate was filtered off and the filtrate was distilled under a pressure of 1 mbar and a head temperature of 95-98° C. Yield 3.7 g (40%) colourless oil 13-a.

b) Preparation of 13-b:

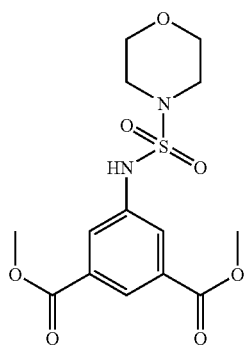
13-b 2.5 g (11.7 mmol) dimethyl 5-amino-isophthalate were suspended in 40 ml of pyridine, slowly combined with 3.3 g (17.8 mmol) 13-a and stirred overnight at 90° C. Then the reaction solution was combined with 50 ml 4N HCl while cooling with an ice bath and the precipitate was filtered off. The crystals were dissolved in dichloromethane, filtered through a phase separation cartridge and the filtrate was evaporated down i. vac.

Yield 2.7 g (64%) brown crystals 13-b.
RT(HPLC 1)=4.30 min c) Preparation of 13-c:

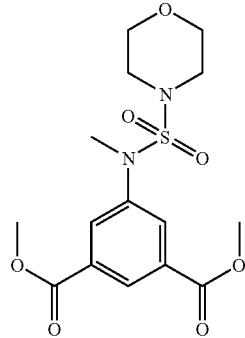
13-c 13-c was prepared analogously to 1-b from 13-b.
RT(HPLC-MS)=2.90 min d) Preparation of 13-d:

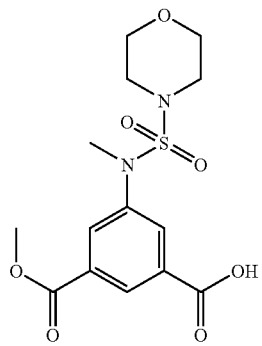
13-d 13-d was prepared analogously to 1-c from 13-c.
RT(HPLC 1)=4.01 min e) Preparation of 13-e:
f) Preparation of 13-f:
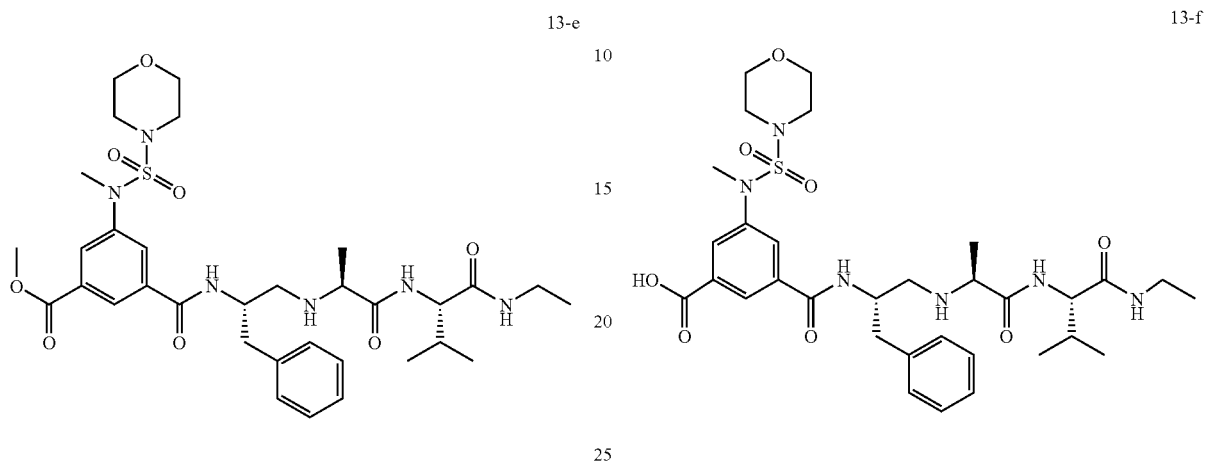
13-e was prepared analogously to 1-d from 13-d and 1-l.
RT(HPLC 1)=4.30 min
13-f was prepared analogously to 2-b from 13-e.
ES(−)-MS (M−H)⁻=675
RT(HPLC 1)=4.05 min
f) Preparation of 13-g:
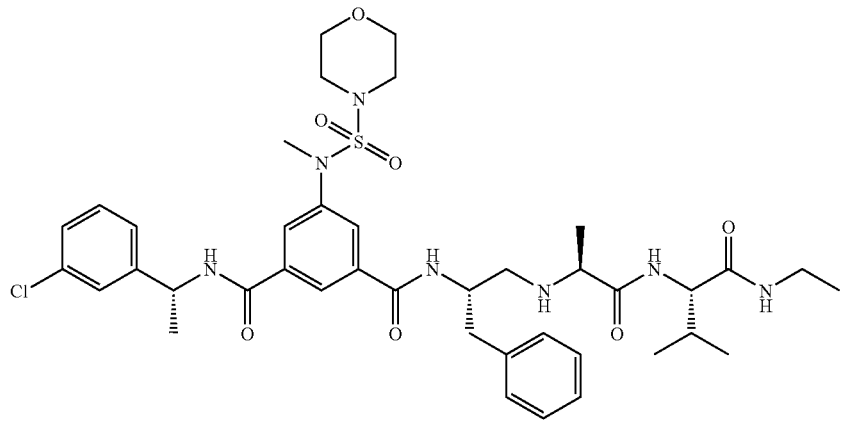

13-g was prepared analogously to 1-d from 13-f and (R)-1-(3-chloro-phenyl)-ethylamine.
ES-MS (M+H)⁺=812/814 (chlorine isotopes)
RT(HPLC-MS)=2.94 min Analogously to 13-g the following compounds were prepared from 13-f and the corresponding amount of amines:

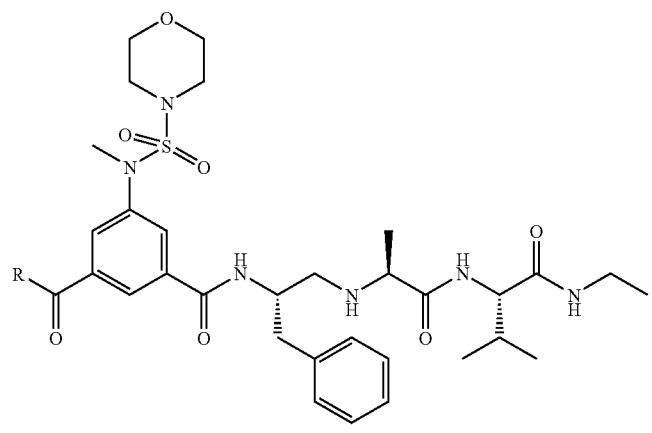

| Example | R | Mass spectrum | Retention time (method) |
|---------|---|---------------|-------------------------|
| 13.2 | 4-F-C₆H₄-CH(CH₃)-NH-* | 796 [M + H]⁺ | 2.84 min (HPLC-MS) |
| 13.3 | 4-MeO-C₆H₄-CH(CH₃)-NH-* | 808 [M + H]⁺ | 2.81 min (HPLC-MS) |
| 13.4 | C₆H₅-CH(Et)-NH-* | 792 [M + H]⁺ | 2.88 min (HPLC-MS) |
| 13.5 | C₆H₅-C(CH₃)₂-NH-* | 792 [M + H]⁺ | 2.90 min (HPLC-MS) |
| 13.6 | 2-pyridyl-CH(CH₃)-NH-* | 779 (chlorine isotopes) [M + H]⁺ | 2.40 min (HPLC-MS) |
| 13.7 | 3-pyridyl-CH(CH₃)-NH-* | 779 [M + H]⁺ | 2.33 min (HPLC-MS) |
| 13.8 | 3-thienyl-CH(CH₃)-NH-* | 784 [M + H]+ | 2.81 min (HPLC-MS) |

Example 14

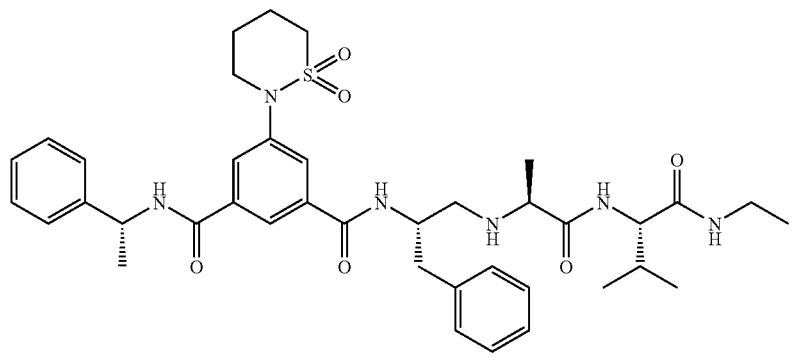

a) Preparation of 14-a:

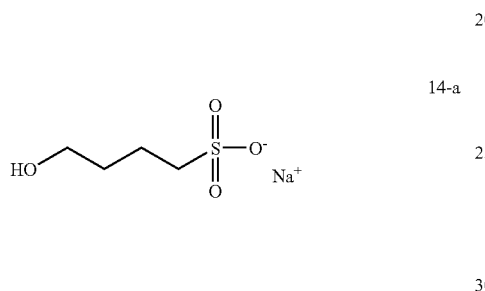

14-a 25.1 ml (120.0 mmol) 4-chlorobutyl acetate and 15.9 g (120 mmol) sodium sulphite were combined in 40 ml of water, then refluxed for 20 hours with stirring. Then the reaction solution was evaporated to dryness i. vac., the residue was combined with 30 ml (conc.) hydrochloric acid and refluxed for a further 2 hours with stirring. The mixture was cooled to ambient temperature, filtered to remove the insoluble matter, the filtrate was neutralised with 4N NaOH and evaporated to dryness using the rotary evaporator. Quantitative yield of 14-a.

ES(−)-MS (M−H)⁻=153 b) Preparation of 14-b:

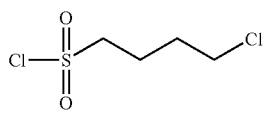

14-b 6.0 g (66%, 22.5 mmol) 14-a were added batchwise to 6 ml phosphorus oxychloride while cooling with an ice bath. Then 9.3 g (45.0 mmol) phosphorus pentachloride was also added batchwise and the mixture was stirred for 24 hours at reflux temperature. It was evaporated to dryness i. vac., the residue was combined with diethyl ether and filtered to remove the insoluble matter. The filtrate was distilled off under 1 mbar pressure at a bottom temperature of 130-170° C.

Yield 2.4 g (31%) 14-b (purity approx. 54%).

c) Preparation of 14-c:

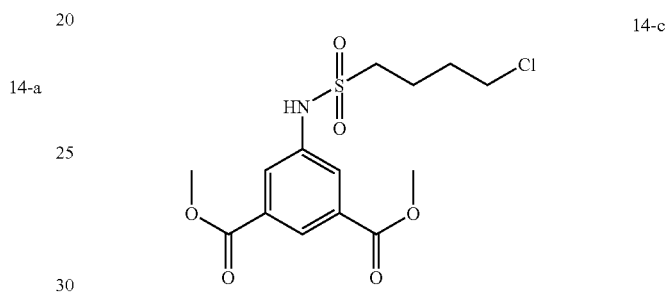

14-c 14-c was prepared analogously to 11-b from 14-a and dimethyl 5-amino-isophthalate.

ES(−)-MS (M−H)⁻=362/364 (chlorine isotopes)

d) Preparation of 14-d:

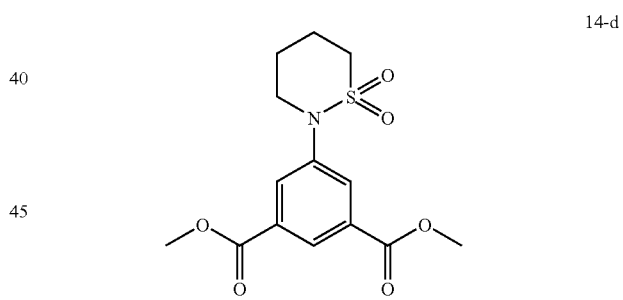

14-d 14-d was prepared analogously to 10-b from 14-c.
ES-MS (M+H)⁺=328
RT(HPLC-MS)=2.86 min e) Preparation of 14-e:

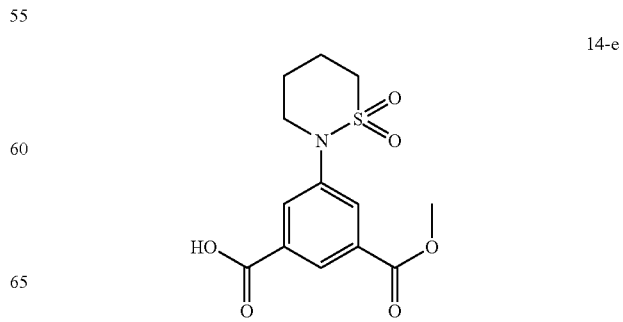

14-e 14-e was prepared analogously to 1-c from 14-d.
ES-MS (M+H)$^+$=314
f) Preparation of 14-f:
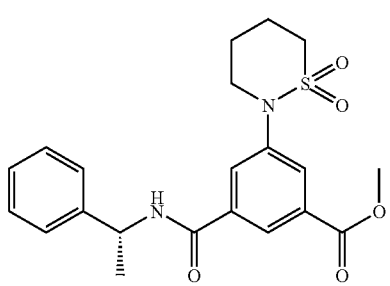
14-f was prepared analogously to 1-d from 14-e and (R)-1-phenyl-ethylamine.
ES-MS (M+H)$^+$=417
g) Preparation of 14-g:
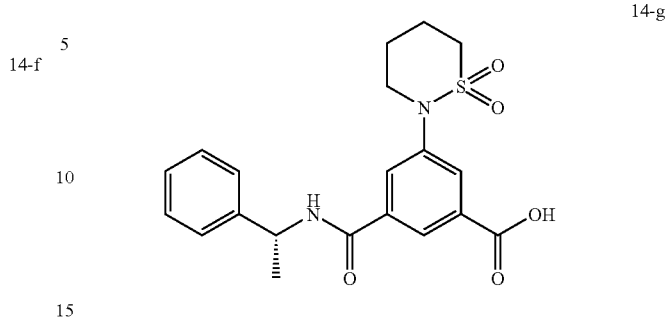
14-g was prepared analogously to 1-c from 14-f.
ES(−)-MS (M−H)$^-$=401
RT(HPLC-MS)=2.76 min
h) Preparation of 14-h:
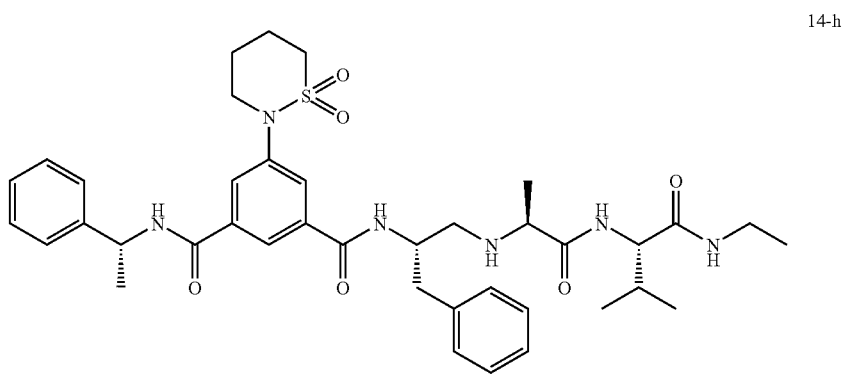
14-h was prepared analogously to 1-d from 14-g and 1-l.
ES-MS (M+H)$^+$=733
Example 14.2
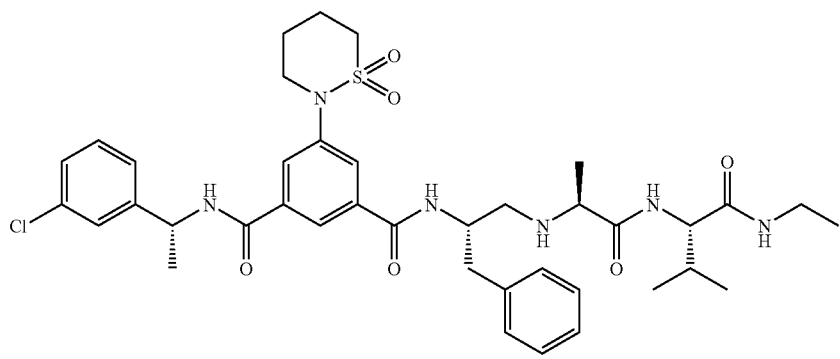

Example 14.2 was prepared analogously to Example 14, except that (R)-1-(3-chloro-phenyl)-ethylamine was used instead of (R)-1-phenyl-ethylamine.
ES-MS (M+NH$_4$)$^+$=468/470

Example 15

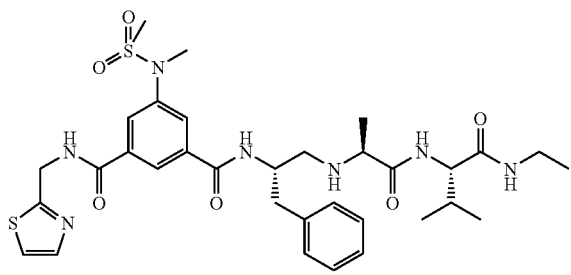

a) Preparation of 15-a:

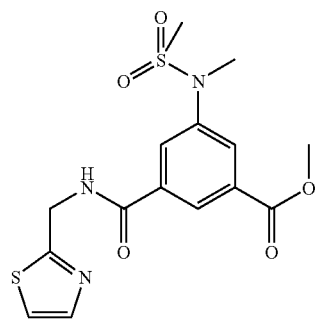

15-a was prepared analogously to 1-d from 1-c and C-thiazol-2-yl-methylamine-hydrochloride.

b) Preparation of 15-b:

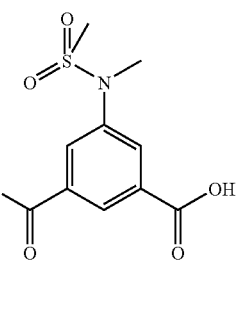

15-b 15-b was prepared analogously to 2-b from 15-a.

c) Preparation of 15-c:

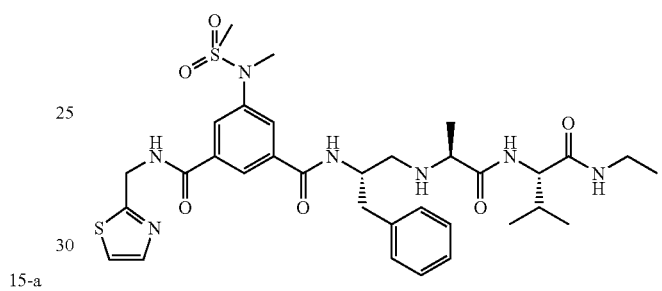

15-c 15-c was prepared analogously to 1-d from 15-b and 1-l.
ES-MS (M+H)$^+$=700

Analogously to Example 15 the following compounds were prepared from 1-c and the corresponding amount of amines:

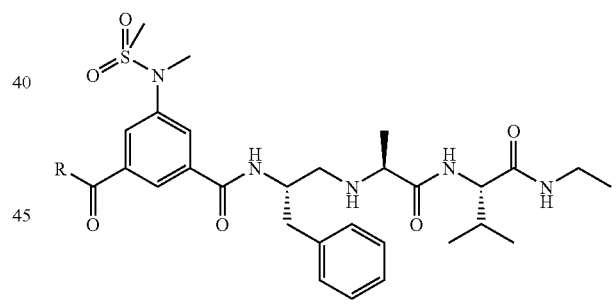

| Example | R | Mass spectrum |
|---|---|---|
| 15.2 | (phenyl-O-CH2-CH(CH3)-NH—*) | 737 [M + H]$^+$ |
| 15.3 | (2-methylphenyl-O-CH2-C(CH3)2-NH—*) | 765 [M + H]$^+$ |

-continued
| Example | R | Mass spectrum |
|---|---|---|
| 15.4 | 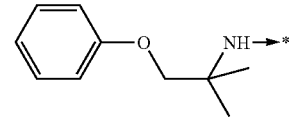 | 751 [M + H]+ |
| 15.5 | 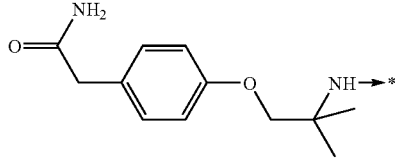 | 808 [M + H]+ |
| 15.6 | 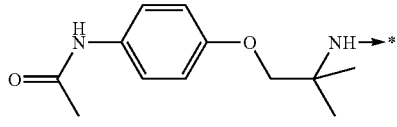 | 808 [M + H]+ |
| 15.7 | 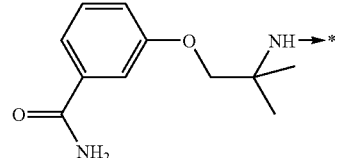 | 794 [M + H]+ |
Example 16
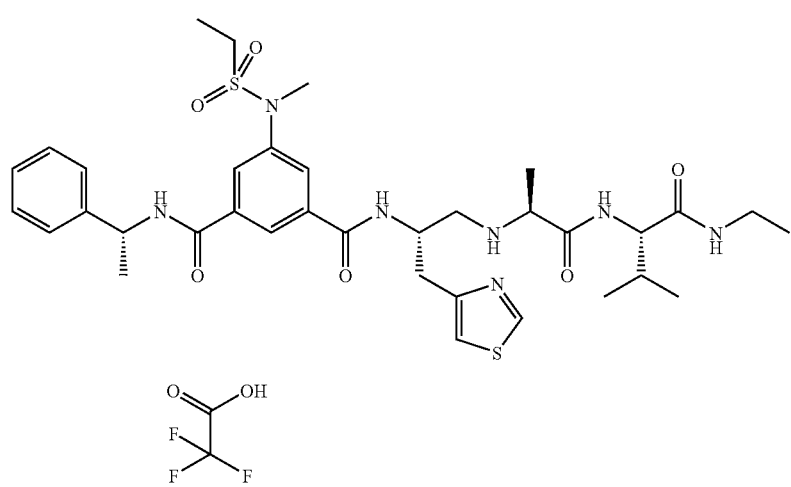

a) Preparation of 16-a:

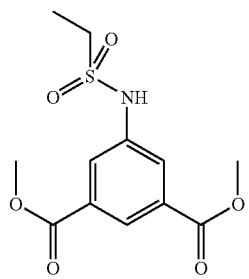
16-a 16-a was prepared analogously to 1-a from dimethyl 5-amino-isophthalate and ethanesulphonyl chloride.
ES(−)-MS (M−H)⁻=300 c) Preparation of 16-b:

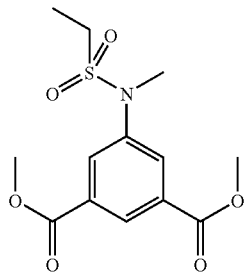
16-b 16-b was prepared analogously to 1-b from 16-a and methyl iodide.
ES-MS (M+H)⁺=316
RT(HPLC 1)=4.56 min c) Preparation of 16-c:

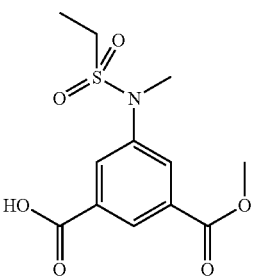
16-c 16-c was prepared analogously to 1-c from 16-b.

RT(HPLC-MS)=2.50 min d) Preparation of 16-d:

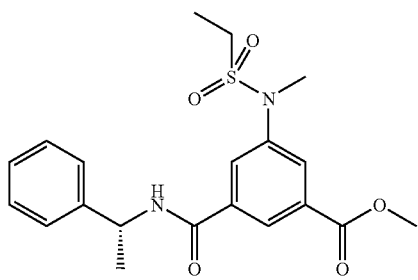
16-d 16-d was prepared analogously to 1-d from 16-c and (R)-1-phenyl-ethylamine.

RT(HPLC 1)=4.79 min e) Preparation of 16-e:

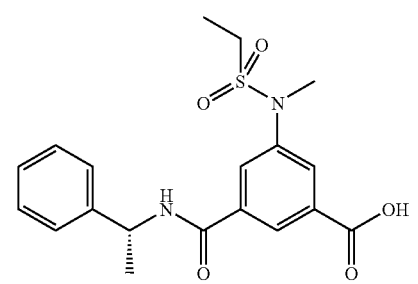
16-e 16-e was prepared analogously to 2-b from 16-d.

ES-MS (M+H)⁺=391

RT(HPLC 1)=4.33 min f) Preparation of 16-f:

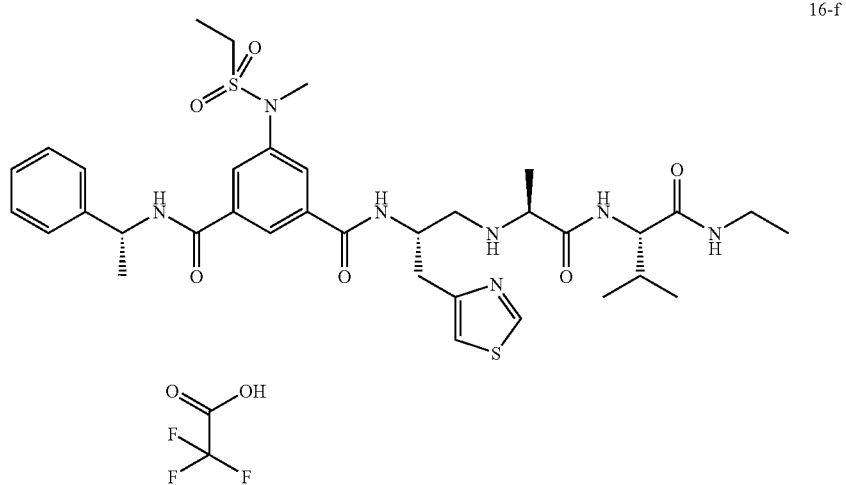

16-f 16-f was prepared analogously to 1-d from 16-e and (S)-2-[(S)-2-((S)-2-amino-3-thiazol-4-yl-propylamino)-propionylamino]-N-ethyl-3-methyl-butyramide.

ES-MS (M+H)$^+$=728

RT(HPLC 1)=4.22 min

Example 16.2

Example 16.2 was prepared analogously to Example 16, except that benzenesulphonyl chloride was used instead of ethanesulphonyl chloride.

ES(−)-MS (M−H)$^-$=776

RT(HPLC 1)=4.52 min

Analogously to 16-2 the following compounds were prepared from corresponding educts:

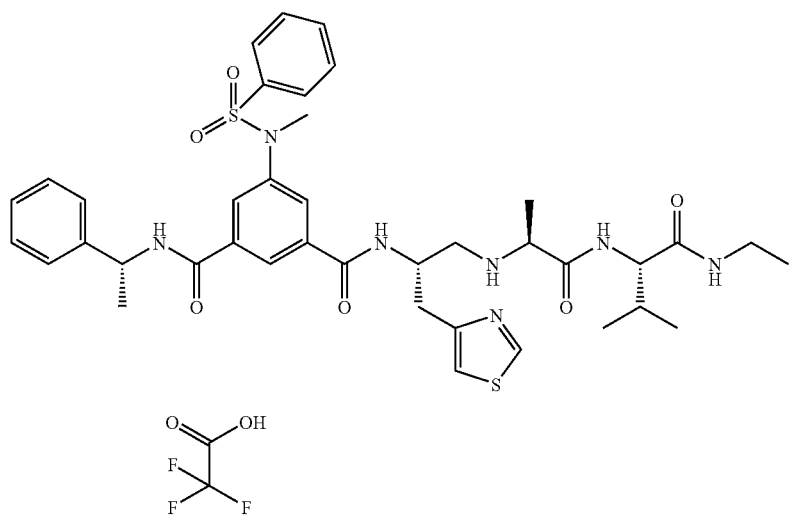

| Example | | Mass spectrum | Retention time (method) |
|---|---|---|---|
| 16.3 | 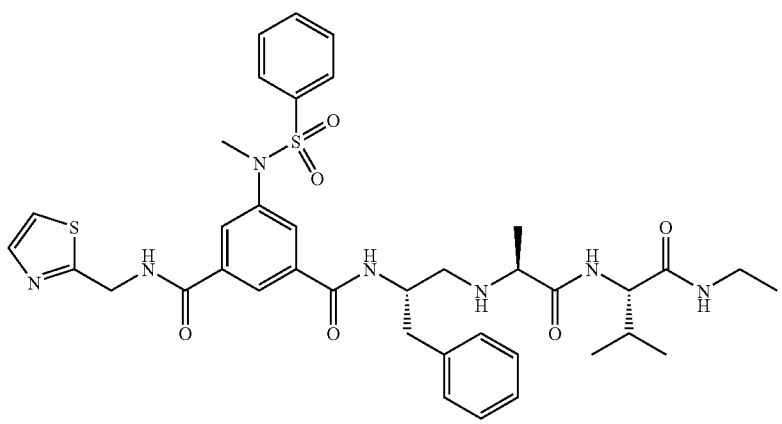 | 736 [M + H]+ | |
| 16.4 | 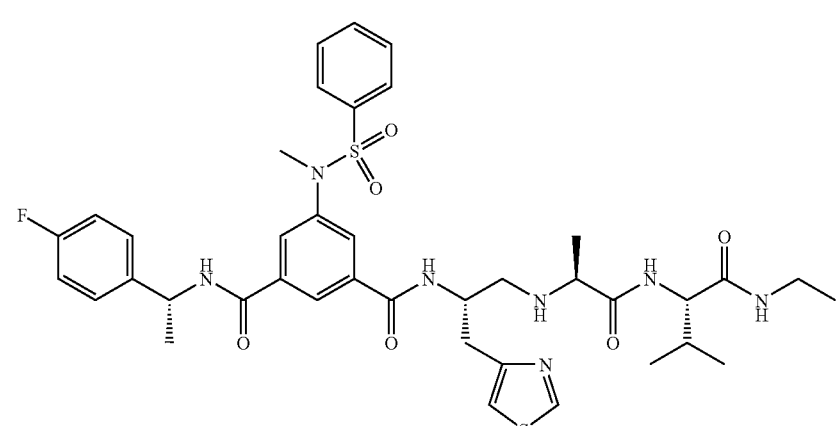 | 795 [M + H]+ | |
| 16.5 | 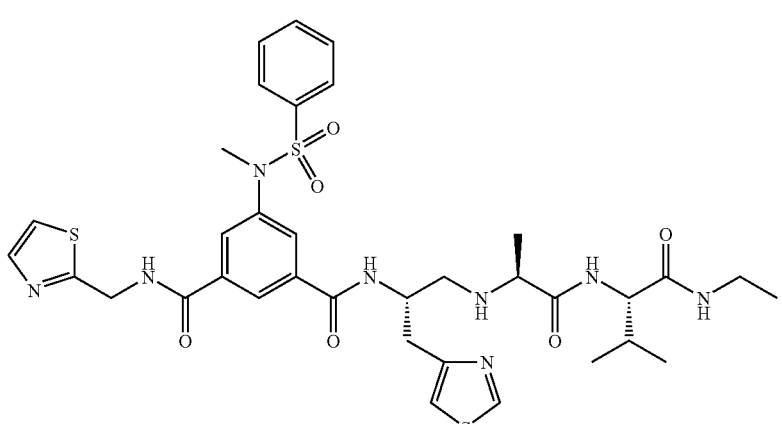 | 770 [M + H]+ | |

-continued

| Example | Mass spectrum | Retention time (method) |
|---|---|---|
| 16.6 | 870 [M + H]+ | 2.90 min (HPLC-MS) |
| 16.7 | 792 [M + H]+ | 2.32 min (HPLC-MS) |
| 16.8 | 871 [M + H]+ | 4.11 min (HPLC 1) |

| Example | | Mass spectrum | Retention time (method) |
|---|---|---|---|
| 16.9 | 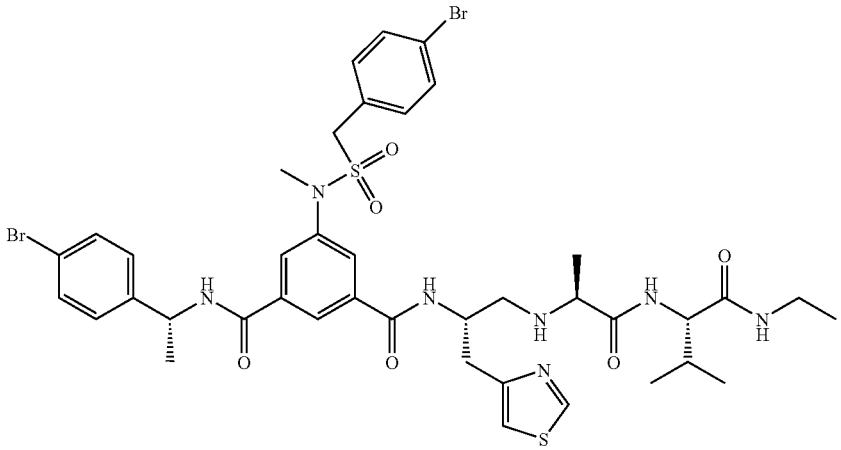 | 948 [M + H]+ | 5.06 min (HPLC 1) |

Example 17

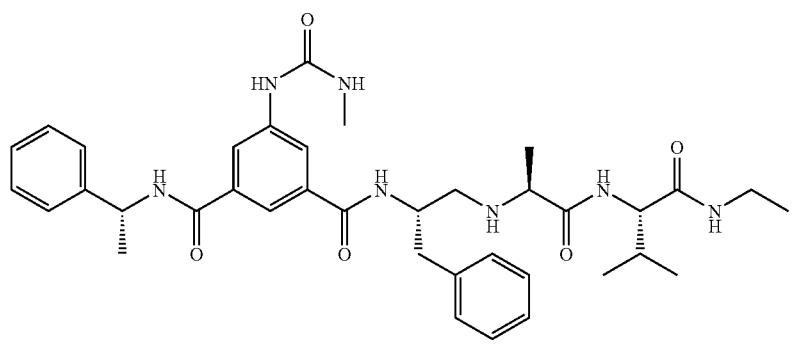

a) Preparation of 17-a:

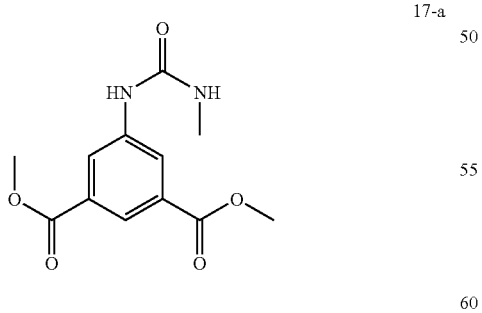

17-a

A solution of 400 mg (1.9 mmol) dimethyl 5-amino-isophthalate in 5 ml THF was combined with 680 μl (3.8 mmol) DIPEA and 164 mg (2.9 mmol) methyl isocyanate. The reaction solution was stirred overnight at ambient temperature and evaporated to dryness i. vac. The residue was combined with water and dichloromethane, the phases were separated through a phase separation cartridge and the organic phase was evaporated to dryness i. vac. The residue was purified by MPLC with the eluant (ethyl acetate/hexane 4:6 to ethyl acetate/hexane 1:0).

Yield 310 mg (61%) white crystals 17-a.

b) Preparation of 17-b:

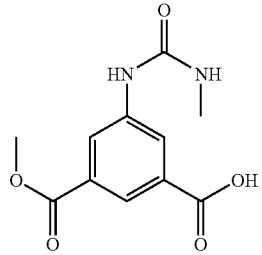

17-b 17-b was prepared analogously to 1-e from 17-a.

c) Preparation of 17-c:

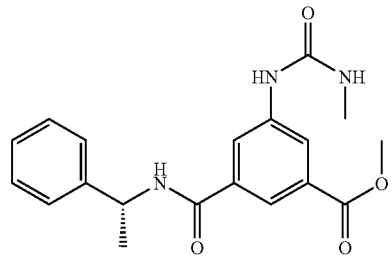

17-c 17-c was prepared analogously to 1-d from 17-b and (R)-1-phenyl-ethylamine.

d) Preparation of 17-d:

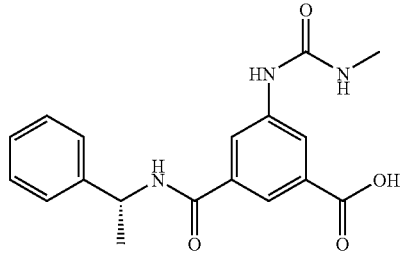

17-d 17-d was prepared analogously to 1-e from 17-c.

e) Preparation of 17-e:

17-e was prepared analogously to 1-d from 17-d and 1-l.
ES-MS (M−H)+=672

Analogously to Example 17 the following compounds were prepared from dimethyl 5-amino-isophthalate and the corresponding amount of isocyanates:

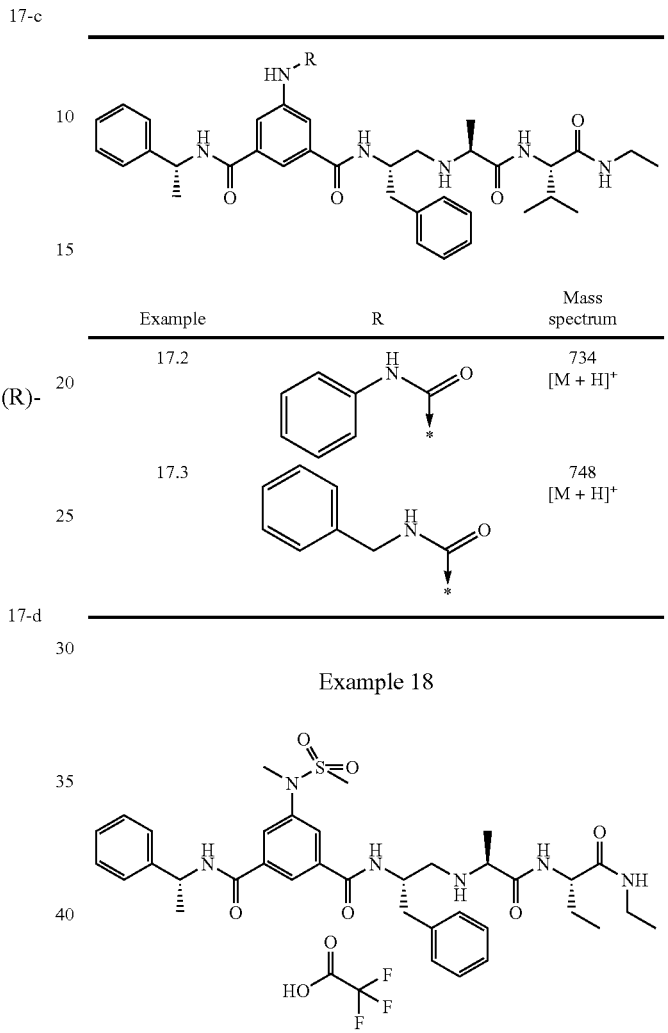

| Example | R | Mass spectrum |
|---|---|---|
| 17.2 | (phenyl-NH-C(=O)-*) | 734 [M + H]+ |
| 17.3 | (benzyl-NH-C(=O)-*) | 748 [M + H]+ |

Example 18

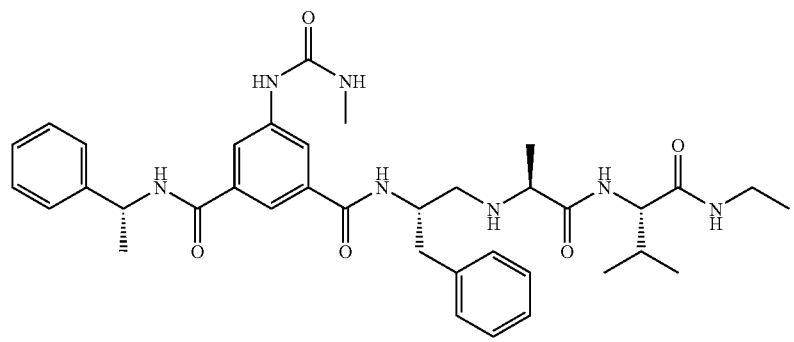

17-e a) Preparation of 18-a:

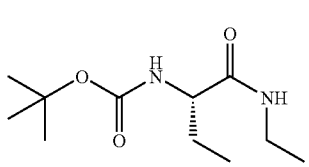

18-a 24.8 ml (49.5 mmol) ethylamine, 8.6 ml (50.0 mmol) DIPEA were metered at 5° C. into a solution of 10.0 g (49.2 mmol) (S)-2-tert-butoxycarbonylamino-butyric acid in 100 ml THF and then 16.1 g (50.0 mmol) TBTU and 6.8 g (50.0 mmol) HOBT were added batchwise. The reaction solution was stirred overnight at ambient temperature, evaporated to dryness i. vac., combined with ethyl acetate and washed with NaHCO$_3$ solution and NaCl solution. The organic phase was dried and evaporated to dryness i. vac. Quantitative yield of 18-a.

ES-MS (M+H)$^+$=118
RT(HPLC 1)=2.8 min b) Preparation of 18-b:

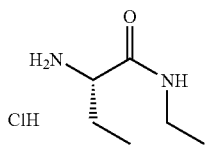

18-b 18-b was prepared analogously to 1-i from 18-a.
ES-MS (M+H)$^+$=131
RT(HPLC-MS)=2.38 min c) Preparation of 18-c:

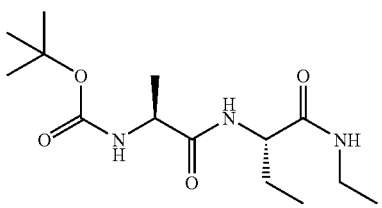

18-c 18-c was prepared analogously to 1-d from 18-b and Boc-L-alanine.
ES-MS (M+H)$^+$=302
RT(HPLC-MS)=2.34 min d) Preparation of 18-d:

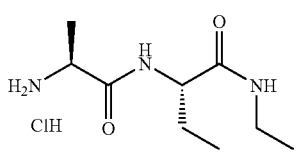

18-d 18-d was prepared analogously to 1-i from 18-c.
ES-MS (M+H)$^+$=202
RT(HPLC-MS)=2.33 min e) Preparation of 18-e:

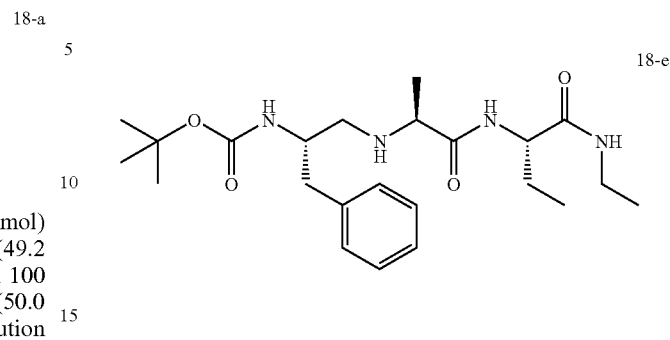

18-e 18-e was prepared analogously to 1-k from 18-d and tert-butyl ((S)-1-benzyl-2-oxo-ethyl)-carbamate.
RT(HPLC-MS)=2.48 min f) Preparation of 18-f:

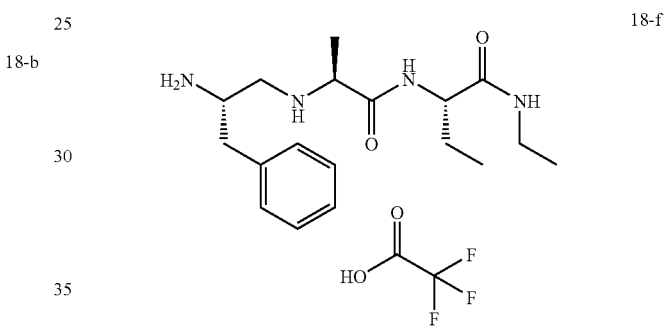

18-f 18-f was prepared analogously to 1-g from 18-e.
ES-MS (M+H)$^+$=335
RT(HPLC-MS)=1.93 min g) Preparation of 18-g:

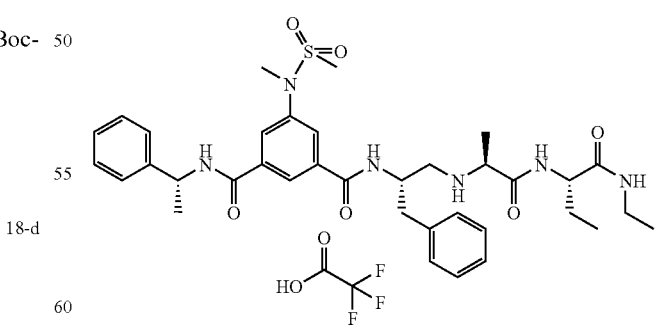

18-g 18-g was prepared analogously to 1-d from 18-f and 1-e.
ES-MS (M+H)$^+$=693
RT(HPLC 4)=19.6 min Example 18.1

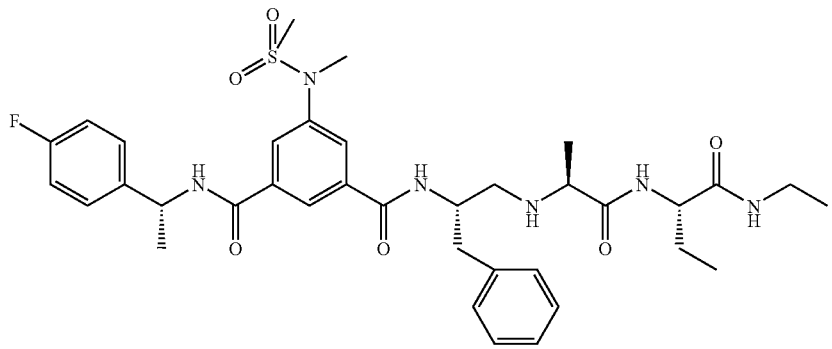

Example 18.1 was prepared analogously to Example 18 from 18-f and (R)-N-[1-(4-fluorophenyl)-ethyl]-5-(methane-sulphonylmethylamino)-isophthalic acid, which was obtained analogously to 1-e using (R)-1-(4-fluorophenyl)-ethylamine.
ES-MS (M+H)$^+$=710
RT(HPLC 1)=4.48 min
RT(HPLC-MS)=2.79 min anesulphonylmethylamino)-isophthalic acid, which was obtained analogously to 1-e using (R)-1-(3-chlorophenyl)-ethylamine.
ES-MS (M+H)$^+$=727
RT(HPLC-MS)=2.86 min Example 18.2

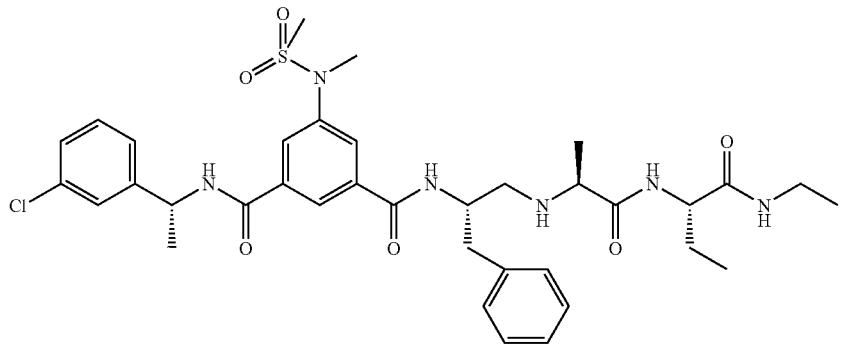

Example 18.2 was prepared analogously to Example 18 from 18-f and (R)-N-[1-(3-chlorophenyl)-ethyl]-5-(meth- Example 18.3

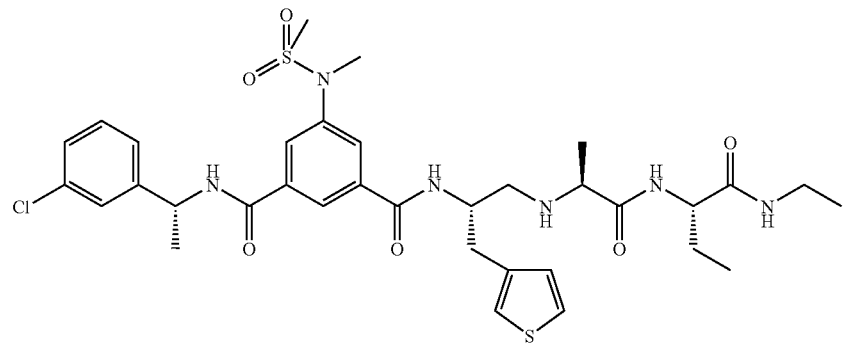

Example 18.3 was prepared analogously to Example 18 from the amine component, which was obtained using 18-d as well as tert-butyl (S)-(2-oxo-1-thiophen-3-ylmethyl-ethyl)-carbamate, and (R)-N-[1-(3-chlorophenyl)-ethyl]-5-(methanesulphonylmethylamino)-isophthalic acid, which was obtained analogously to 1-e using (R)-1-(3-chlorophenyl)-ethylamine.
ES-MS (M+H)$^+$=733/735 (Cl)
RT(HPLC-MS)=3.20 min Example 18.4

Example 18.5 was prepared analogously to Example 18 using 18-d, by using (S)-Boc-2-aminohexanal in step 18-e) instead of tert-butyl ((S)-1-benzyl-2-oxo-ethyl)-carbamate.

ES-MS (M+H)$^+$=659

RT(HPLC 1)=4.27 min

RT(HPLC-MS)=2.65 min

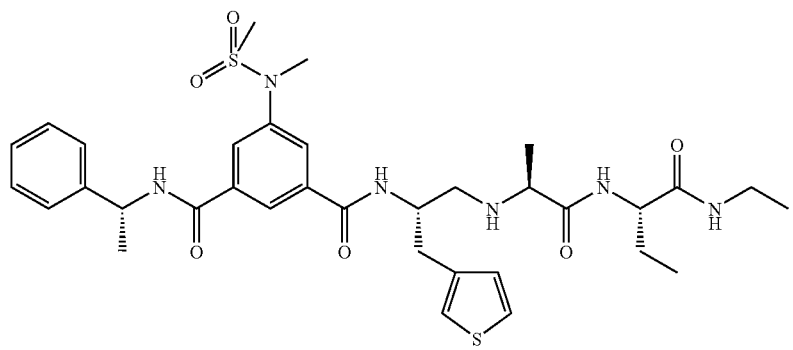

Example 18.4 was prepared analogously to Example 18.3 from the amine component, which was obtained using 18-d and tert-butyl (S)-(2-oxo-1-thiophen-3-ylmethyl-ethyl)-carbamate, as well as 1-e.
ES-MS (M+H)$^+$=699
RT(HPLC 1)=4.44 min
RT(HPLC-MS)=2.90 min Example 18.5

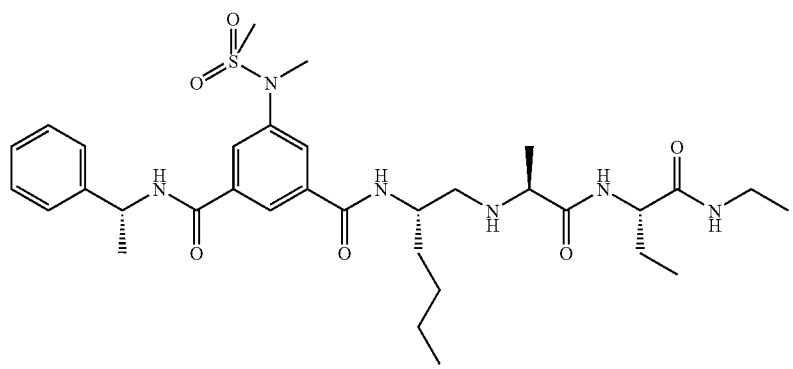

Example 18.6

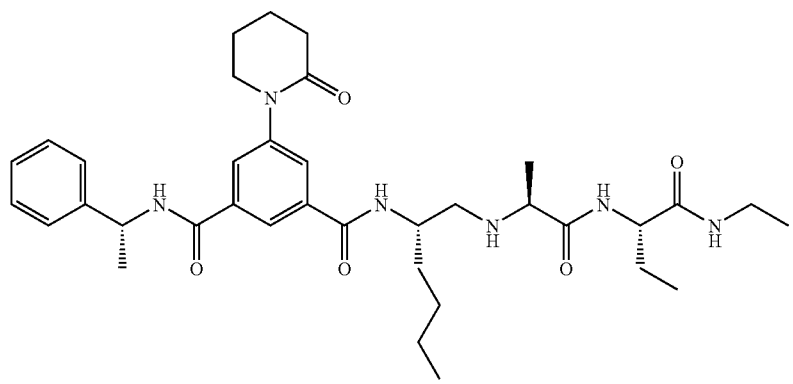

a) Preparation of 18.6-a:

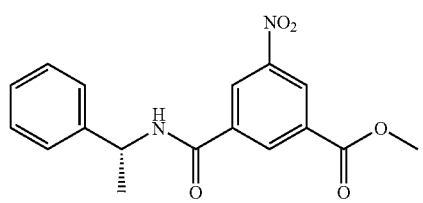
18.6-a 10 g (44.0 mmol) monomethyl 5-nitro-isophthalate were suspended in 100 ml dichloromethane, combined with 14.1 g (44.0 mmol) TBTU and 15 ml (88.0 mmol) DIPEA while cooling with ice and stirred for 30 min at ambient temperature. Then 5.6 ml (44.0 mmol) R-(+)-1-phenylethylamine were added and the mixture was stirred for 14 h. It was washed with water, potassium hydrogen carbonate solution, the organic phase was dried and evaporated down. 14.1 g of 18.6-a was obtained which was used in the next step without any purification.

ES(−)-MS (M−H)⁻=327 b) Preparation of 18.6-b:

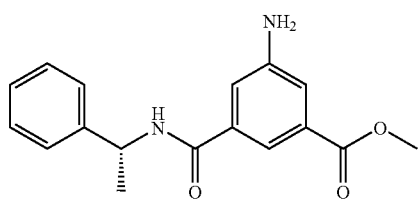
18.6-b 14.1 g (43.0 mmol) 18.6-a were hydrogenated at 50 psi and ambient temperature on palladium charcoal (5%) for 5 h. The catalyst was separated off and the crude product was purified by flash chromatography (dichloromethane/methanol 100:1). 6.86 g of 18.6-b was obtained by trituration with diethyl ether and tert-butylmethylether.

ES-MS (M+H)⁺=299 c) Preparation of 18.6-c:

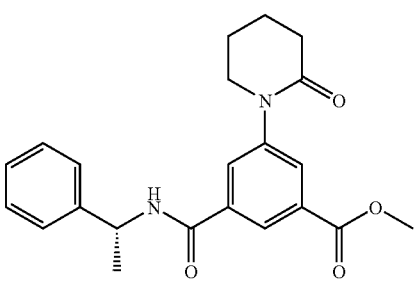
18.6-c 500 mg (1.68 mmol) 18.6-b were dissolved in 14 ml acetonitrile, combined with 2.36 g potassium carbonate and 2 mg dimethylaminopyridine and stirred for 3 min at ambient temperature. Then 0.25 ml (1.84 mmol) 5-bromovaleryl chloride dissolved in 3 ml acetonitrile was added dropwise while being cooled and the mixture was stirred for 4 h at ambient temperature. The solids were separated off, the solution was evaporated down, and the residue was taken up in ethyl acetate. The mixture was washed with water, dried and evaporated down. 496 mg of colourless 18.6-c was obtained which was used in the next step without any further purification.

ES-MS (M+H)⁺=381 d) Preparation of 18.6-d:

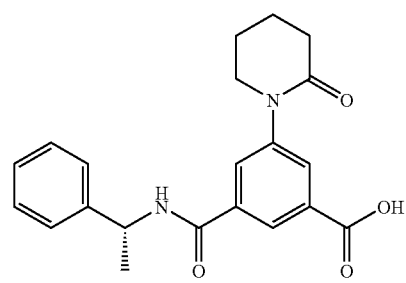
18.6-d 496 mg (1.30 mmol) of 18.6-c dissolved in 10 ml of methanol were combined with 5 ml of 4 N sodium hydroxide solution and stirred for 14 h at ambient temperature. The mixture was combined with 5 ml hydrochloric acid. It was stirred out with dichloromethane and ethyl acetate, dried and after evaporation 150 mg of 18.6-d was obtained as a solid, which was used in the next step without any further purification.

ES-MS (M+H)⁺=367

RT(HPLC-MS)=2.70 min e) Preparation of 18.6:

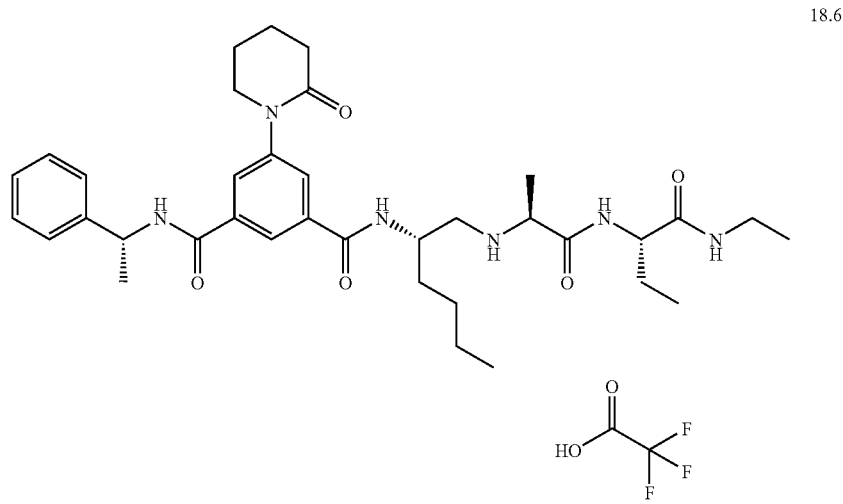

18.6

54.2 mg (0.148 mmol) 18.6-d were dissolved in 5 ml THF and combined with 52 mg TBTU (0.163 mmol) and 77.3 μl (0.444 mmol) DIPEA. After 10 min, 61.4 mg (0.148 mmol) (S)-2-((S)-2-((S)-2-aminohexylamino)-propanamido)-N-ethylbutanamide was added, which was prepared as described in Example 18.5. The mixture was stirred for 14 h, evaporated down, the residue was purified by RP-HPLC and in this way 5 mg of 18.6 was obtained as a TFA salt.

ES-MS (M+H)$^+$=649
RT(HPLC 1)=4.32 min
RT(HPLC-MS)=2.62 min

Example 18.7

Example 18.7 was prepared analogously to Example 18 using 18-d, by using (S)-Boc-2-aminohexanal in step 18-e) instead of tert-butyl ((S)-1-benzyl-2-oxo-ethyl)-carbamate.

ES-MS (M+H)$^+$=659

RT(HPLC 1)=4.27 min

RT(HPLC-MS)=2.65 min

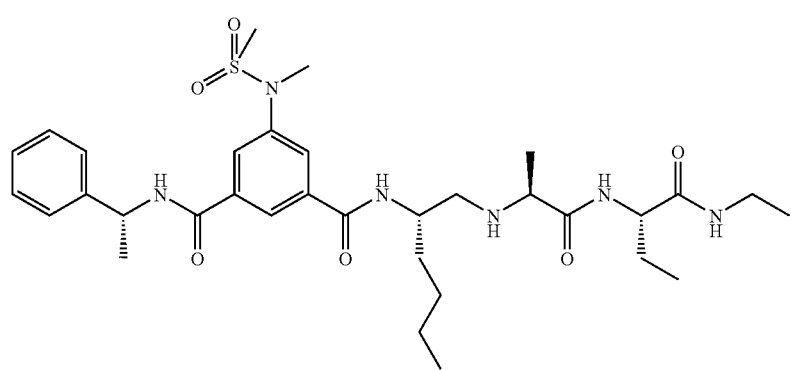

Example 18.8

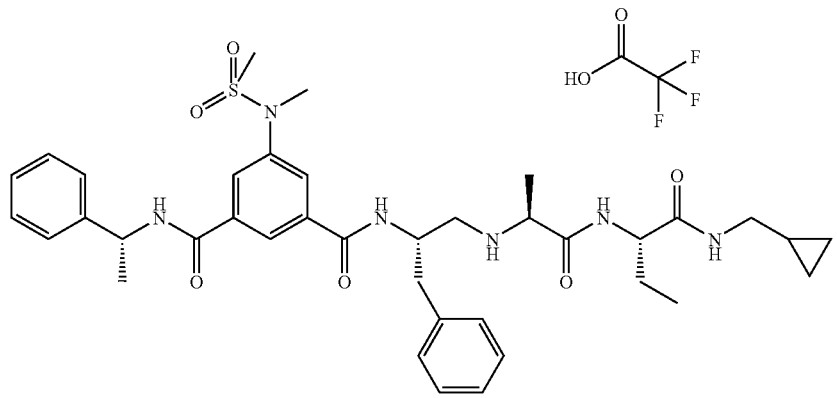

Example 18.8 was prepared analogously to Example 18, by using cyclopropylmethylamine in step 18-a) instead of ethylamine. The product was purified by RP-HPLC.
ES-MS (M+H)$^+$=719
RT(HPLC-MS)=3.00 min

Example 18.9

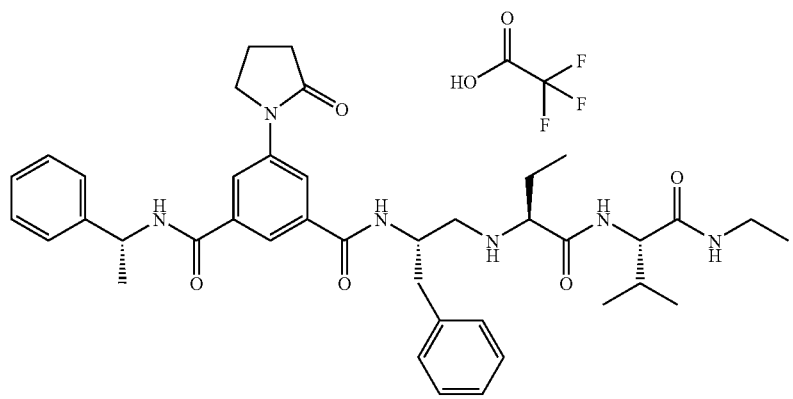

18.9-a was obtained analogously to 18.6-d as a white solid, by using 4-bromobutyric acid chloride instead of 5-bromovaleryl chloride analogously to step 18.6-c. The crude product was purified by flash chromatography (dichloromethane/methanol/acetic acid 95:5:0.1).
ES-MS (M+NH$_4$)$^+$=370
RT(HPLC-1)=4.19 min a) Preparation of 18.9-a:

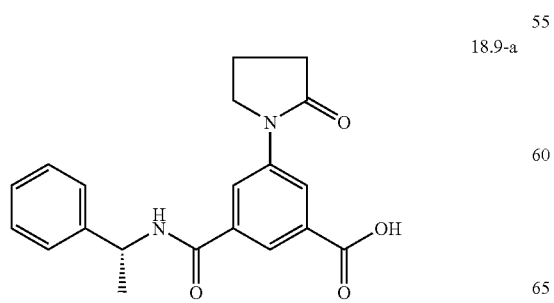

18.9-a b) Preparation of 18.9

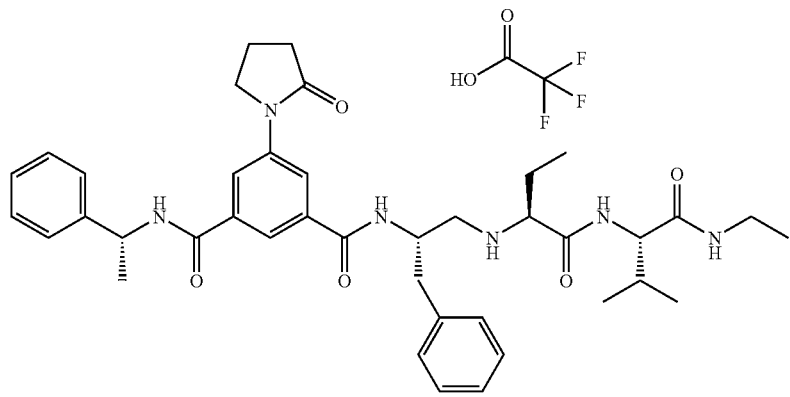

18.9

18.9 was prepared analogously to Example 18.6, by using 18.9-a in step 18.6-e) instead of 18.d. The product was purified by RP-HPLC. 17 mg (16%) were obtained as a white solid.
ES-MS (M+H)$^+$=297
RT(HPLC-1)=4.58 min Example 19.4

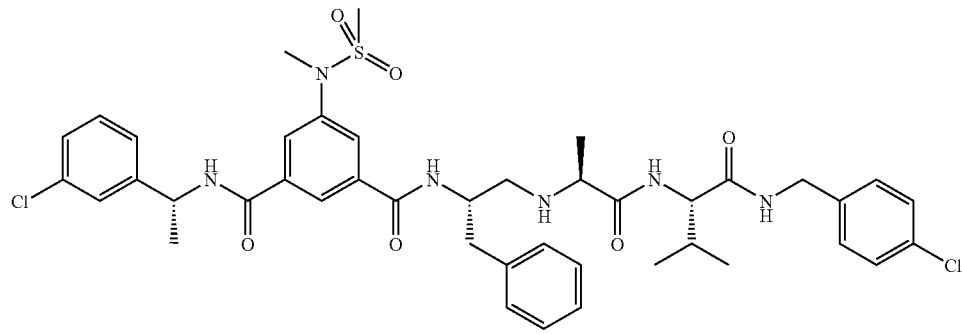

Example 19.4 was synthesised by standard solid phase peptide synthesis on a 3-(formylindolyl)acetamidomethylpolystyrene resin (100 mg, 0.1 mmol; load 1 mmol/g) (Novabiochem).

For the first reductive alkylation the resin was suspended in DMF/TMOF (2:1, 2 ml) and reacted with a solution of 4-chlorobenzylamine (10 equiv.) in DMF/TMOF (2:1, 2 ml) and Na(OAc)$_3$BH (10 Equiv.) in DMF (1 M solution, 1 ml) overnight at ambient temperature. Then the resin was carefully washed with DMF and MeOH.

Fmoc cleavings were carried out by reacting the resin twice (2 minutes and 20 minutes) with 30% piperidine/DMF solution. Then the resin was carefully washed with DMF. The coupling of the first amino acid was carried out overnight with HATU (5 equiv.), HOBt (5 equiv.), Dipea (15 equiv.) and Fmoc-valine (5 equiv.) in DMF as solvent. The coupling of the second Fmoc-amino acid was carried out with TBTU (5 equiv.), HOBt (5 equiv.), Dipea (15 equiv.) and Fmoc-alanine (5 equiv.) in DMF.

After the coupling of the first two amino acids and the cleaving of the Fmoc group reductive alkylation of the amino group was carried out with a solution of freshly prepared Fmoc-phenylalaninal (3.5 equiv.) and NaCNBH$_3$ (10.5 equiv.) in DMF/HOAc (99:1 ml) for 2.25 hours. The resin was then carefully washed with DMF/HOAc (99:1), DMF, 5% Dipea in DMF and DMF. It was then reacted for 16 hours with Boc$_2$O (10 equiv.) and Dipea (10 equiv.) in DMF.

After a repeat cleaving of the Fmoc group and thorough washing with DMF the resin was reacted with a solution of the corresponding acid (prepared analogously to 1-e from 1-c and (R)-1-(3-chlorophenyl)-ethylamine) (3 equiv.), TBTU (3 equiv.) and Dipea (9 equiv.) in DMF.

In order to cleave the product from the resin and also cleave any protective groups the resin was washed with DMF and dichloromethane and dried and then mixed with TFA/water (95:5, 2 ml) for 1 hour at ambient temperature. The solution was filtered off and the resin was washed twice more with dichloromethane (1 ml). The combined filtrates were evaporated down in vacuo and the product was purified by preparative reversed phase HPLC.

The following Examples were obtained analogously to Example 19.4:

| Example | structure | Mass spectrum [M + H]+ | Retention time method HPLC 5 |
|---|---|---|---|
| 19 | 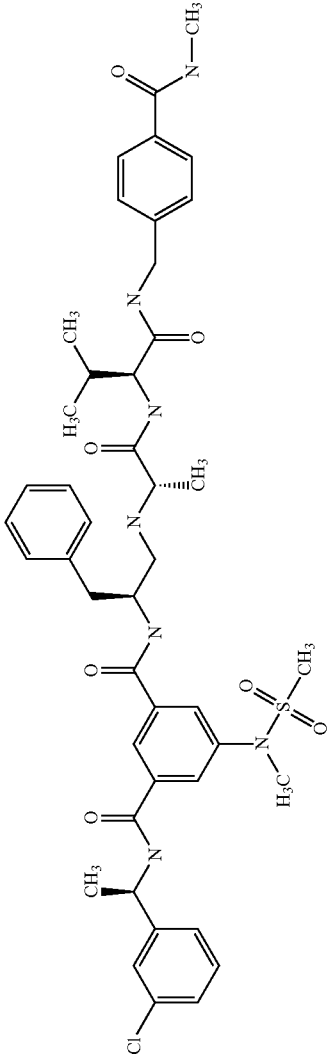 Chiral | 860.4 | RT = 3.67 min |
| 19.1 | 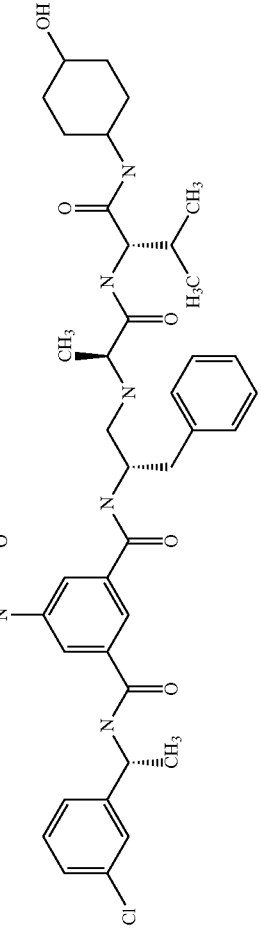 Chiral | 811.4 | RT = 3.63 min |

-continued
| Example | structure | Mass spectrum [M + H]+ | Retention time method HPLC 5 |
|---|---|---|---|
| 19.2 | Chiral 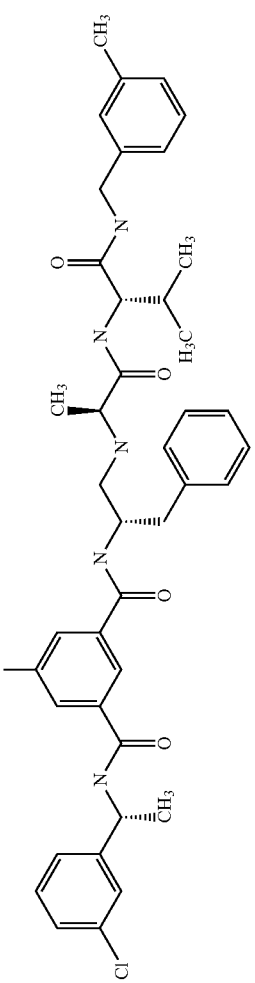 | 817.4 | RT = 3.97 min |
| 19.3 | 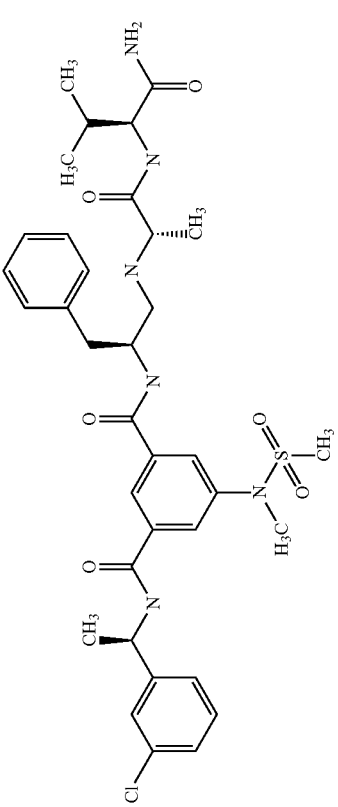 | 713.3 | RT = 3.62 min |

-continued
| Example | structure | Mass spectrum [M + H]+ | Retention time method HPLC 5 |
|---|---|---|---|
| 19.4 | 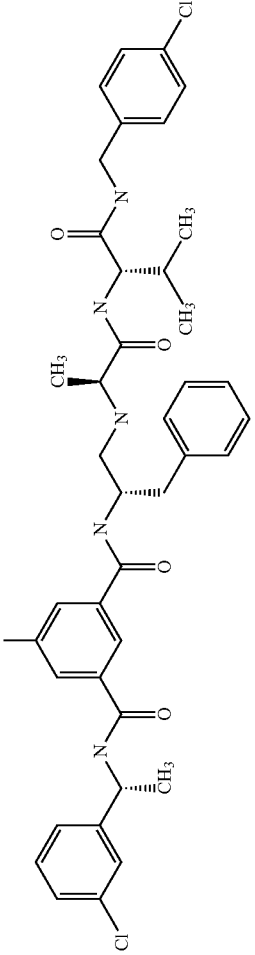 Chiral | 837.4 | RT = 3.99 min |
| 19.5 | 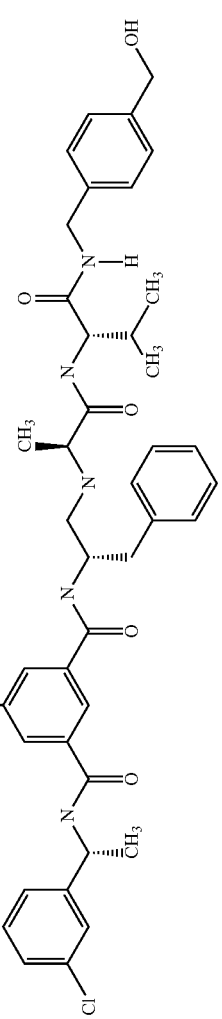 Chiral | 833.4 | RT = 4.33 min |

-continued
| Example | structure | Mass spectrum [M + H]+ | Retention time method HPLC 5 |
|---|---|---|---|
| 19.6 | 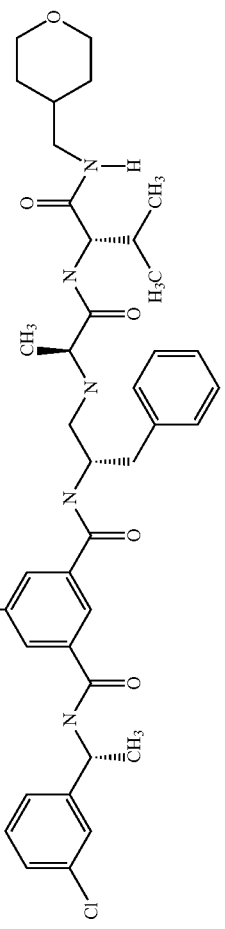 Chiral | 811.4 | RT = 3.70 min |
| 19.7 | 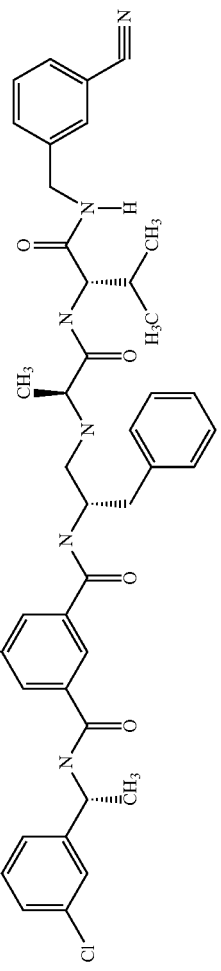 Chiral | 828.4 | RT = 3.86 min |

| Example | structure | Mass spectrum [M + H]+ | Retention time method HPLC 5 |
|---|---|---|---|
| 19.8 | Chiral 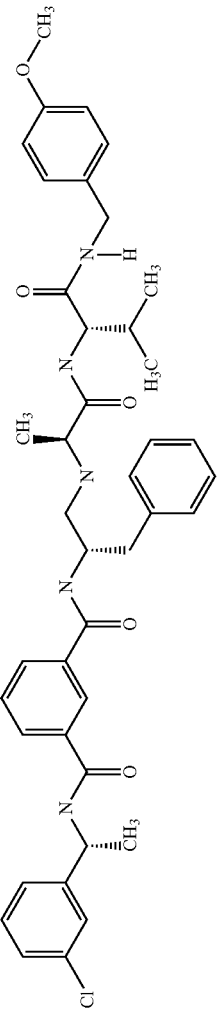 | 833.0 | RT = 3.90 min |
| 19.9 | Chiral 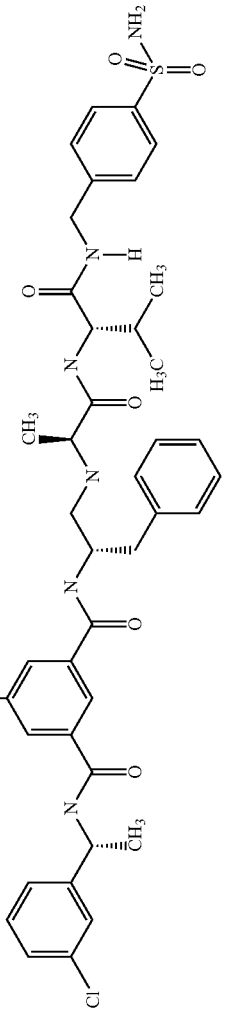 | 882.4 | RT = 3.70 min |

-continued
| Example | structure | Mass spectrum [M + H]+ | Retention time method HPLC 5 |
|---|---|---|---|
| 19.10 | 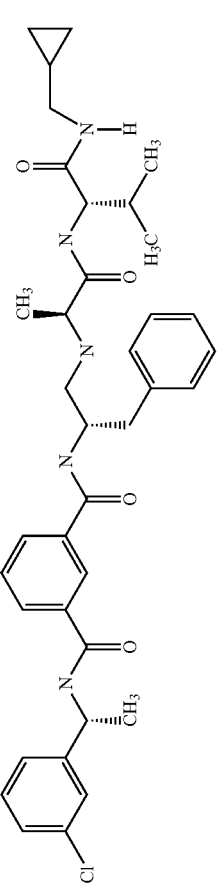 | 767.4 | RT = 3.81 min |
| 19.11 | 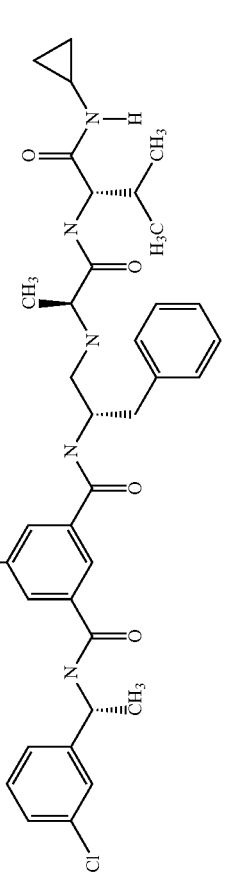 | 753.4 | RT = 3.73 min |

-continued
| Example | structure | Mass spectrum [M + H]+ | Retention time method HPLC 5 |
|---|---|---|---|
| 19.12 | 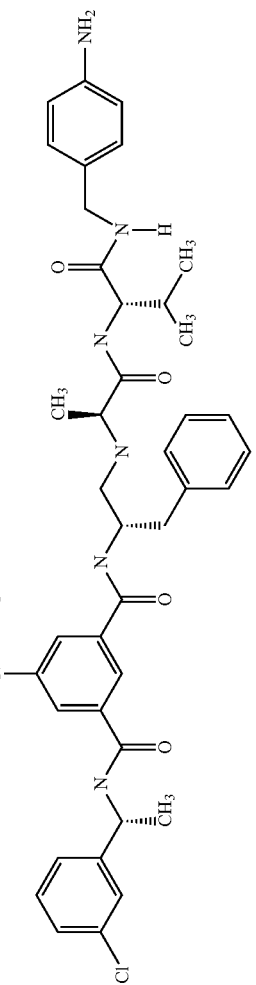 Chiral | 818.4 | RT = 3.44 min |
| 19.13 | 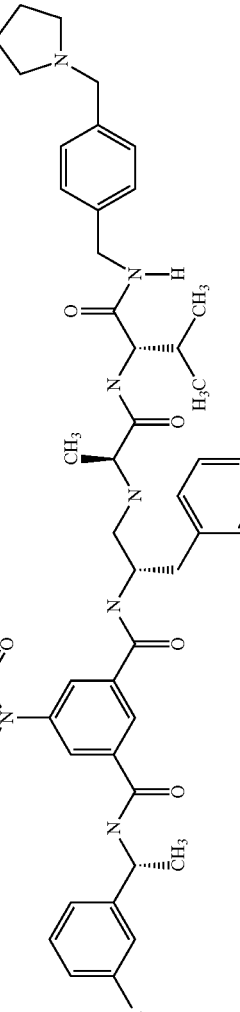 Chiral | 444.0 [1/2M + 1] | RT = 3.49 min |

-continued

| Example | structure | Mass spectrum [M + H]+ | Retention time method HPLC 5 |
|---|---|---|---|
| 19.14 | (structure) | 889.5 | RT = 3.73 min |

Example 20

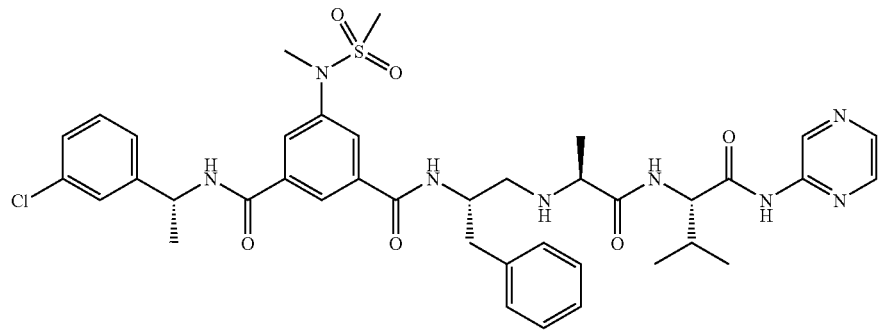

a) Preparation of 20-a:

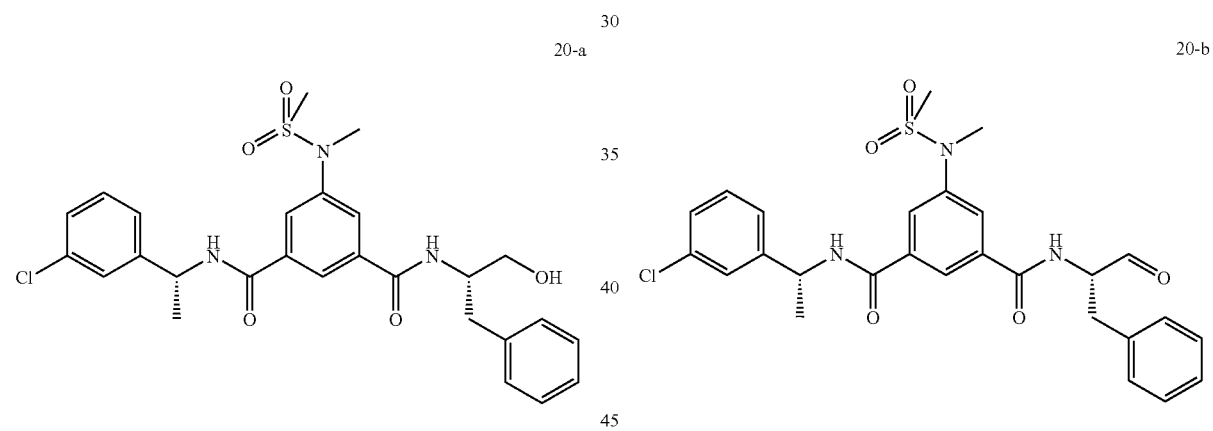

Compound 4-b (6.0 g; 14.6 mmol) was dissolved in DMF (60 ml) and combined with TBTU (4.67 g; 14.6 mmol), HOBt (2.23 g; 14.6 mmol) and Dipea (7.5 ml; 43.6 mmol). After 5 minutes stirring S-phenylalaninol (2.0 g; 13.2 mmol) was added and the mixture was stirred overnight at RT. Then the solvent was eliminated i. vac. and the remainder was taken up in ethyl acetate (200 ml). The org. phase was extracted twice each with water, 0.5 M HCl, water, sat. sodium carbonate solution, water and sat. NaCl solution and dried over sodium sulphate. The org. phase was filtered through silica gel and distilled off i. vac. The residue was triturated with diethyl ether.

Yield 6.2 g (86% white crystals)
ES-MS $(M+H)^+$=544.6 b) Preparation of 20-b:

The alcohol 20-a (6.2 g; 11.3 mmol) was dissolved in dichloromethane and combined with Dess-Martin periodinane (10.1 g; 23.8 mmol) in two batches, with stirring. Then water (0.43 ml; 23.8 mmol) was added and the mixture was stirred for a further two hours. It was combined with a solution of sodium hydrogen carbonate (11.6 g; 138 mmol) and sodium thiosulphate-5-hydrate (14.1 g; 56.7 mmol) dissolved in water (200 ml) and stirred overnight. Then the insoluble residue was filtered off and extracted with dichloromethane. The organic phase was washed with sat. sodium hydrogen carbonate solution and water, dried over sodium sulphate and evaporated down i. vac. The residue was taken up in acetonitrile and freeze-dried.

Yield 5.4 g
ES-MS $(M+H)^+$=542.5 c) Preparation of 20-c:

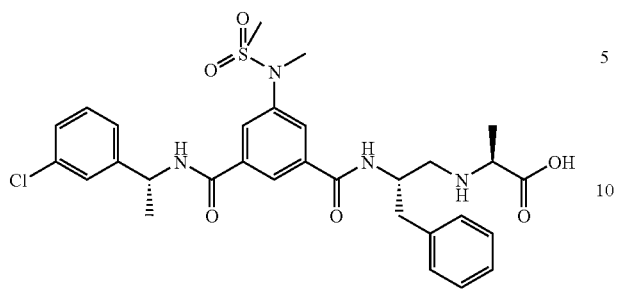

20-c (S)-alanine-tert.-butylester hydrochloride (1.44 g; 8 mmol) was dissolved in dimethylacetamide (20 ml) and combined with glacial acetic acid (0.62 ml; 10.3 mmol) and aldehyde 20-b (5.6 g; 10.3 mmol), dissolved in dimethylacetamide (10 ml). Then sodium triacetoxyborohydride (10.1 g; 47.7 mmol) was added and the mixture was stirred overnight at ambient temperature. The mixture was evaporated down i. vac., taken up in dichloromethane (200 ml), the organic phase was washed with sodium hydrogen carbonate solution and water, dried with sodium sulphate and evaporated down i. vac. The purification was carried out by chromatography on basic Alox (eluant ethyl acetate/petroleum ether 1:1). The combined product fractions were evaporated down i. vac. and combined with ethereal hydrochloric acid. After 2 hours' stirring the crystals were filtered off and washed with diethyl ether.

Yield 4.2 g (72%)

ES-MS (M+H)$^+$=615.6 d) Preparation of compound 20-d:

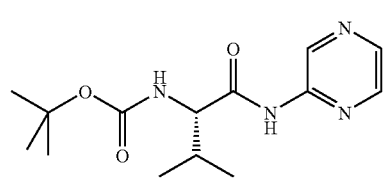

20-d

Aminopyrazine (190 mg; 2.0 mmol) was combined with a solution of Boc-L-valine (434.5 mg; 2.0 mmol), HATU (380.2 mg; 2.0 mmol) and Dipea (685 µl; 4.0 mmol) in DMF (4 ml) and shaken overnight at ambient temperature. The mixture was evaporated down i. vac. and purified by reversed phase HPLC.

Yield 87 mg (15%)

ES-MS (M+H)$^+$=294.4 e) Preparation of compound 20-e:

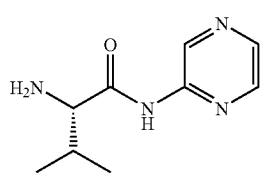

20-e

The Boc compound 20-d (37.8 mg; 0.1 mmol) was dissolved in trifluoroacetic acid/water 95:5 (3 ml) and shaken for 2 hours at ambient temperature. Then the solvent was eliminated i. vac. and co-distilled with toluene. The crude product was further reacted directly without purification.

f) Preparation of compound 20

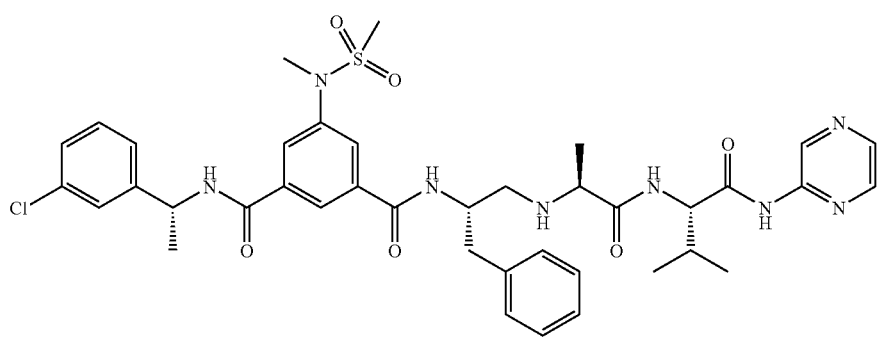

20

The amine compound 20-e (0.1 mmol) was dissolved in DMF (1 ml) and combined with a solution of compound 20-c (61.5 mg; 0.1 mmol), TBTU (32.1 mg; 0.1 mmol), HOBt× H$_2$O (15.3 mg; 0.1 mmol) and Dipea (85.6 µl; 0.5 mmol) in DMF (1.0 ml). After the addition of Dipea (200 µl) the mixture was shaken for 72 hours at ambient temperature. It was evaporated down i. vac. and purified by preparative reversed phase HPLC.

Yield 13.5 mg (13.6%)

ES-MS (M+H)$^+$=791.4

RT=3.76 min (HPLC 6)

Analogously to Example 20 the following compounds were prepared from 20-c and different amines 20-e, using different amine components in step 20-d:

| Example | structure | Mass spectrum [M + H]+ | Retention time method HPLC 6 |
|---|---|---|---|
| 20.2 | 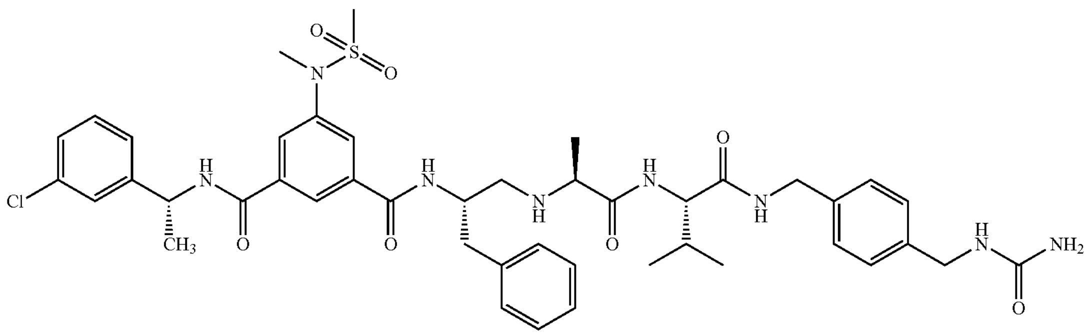 | 875.7 | 3.65 min |
| 20.3 | 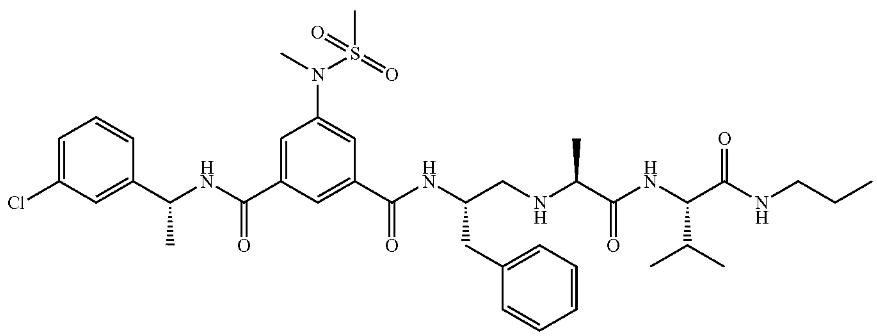 | 755.7 | 3.82 min |

-continued

| Example | structure | Mass spectrum [M + H]+ | Retention time method HPLC 6 |
|---|---|---|---|
| 20.4 | 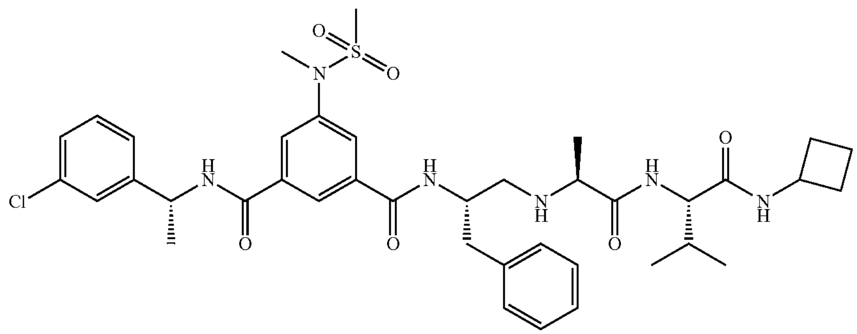 | 767.7 | 3.88 min |
| 20.5 | 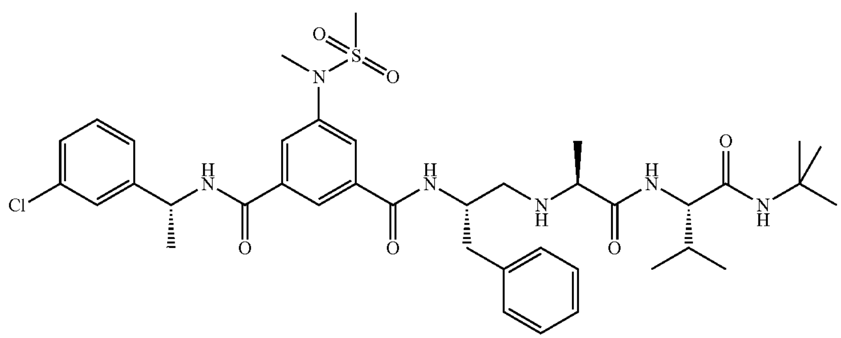 | 769.7 | 3.95 min |
| 20.6 | 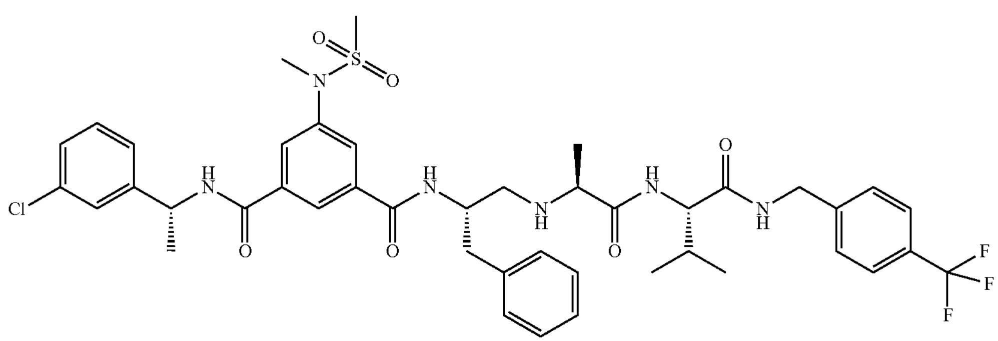 | 871.7 | 4.10 min |

-continued

| Example | structure | Mass spectrum [M + H]+ | Retention time method HPLC 6 |
|---|---|---|---|
| 20.7 | 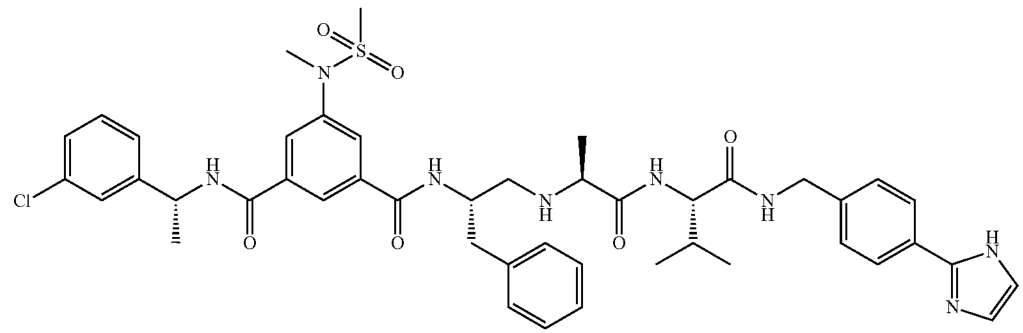 | 869.8 | 3.53 min |
| 20.8 | 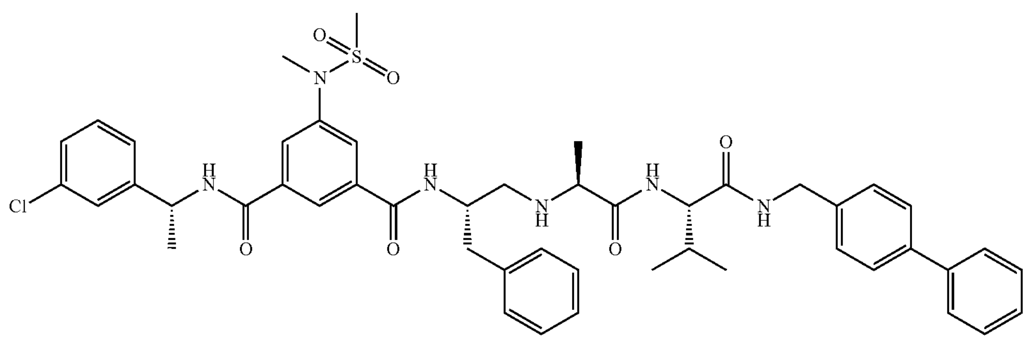 | 879.8 | 4.17 min |

-continued

| Example | structure | Mass spectrum [M + H]⁺ | Retention time method HPLC 6 |
|---|---|---|---|
| 20.9 | 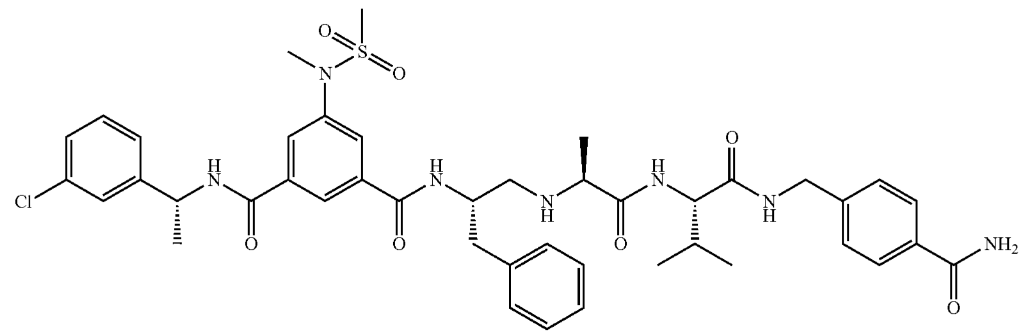 | 846.8 | 3.67 min |
| 20.10 | 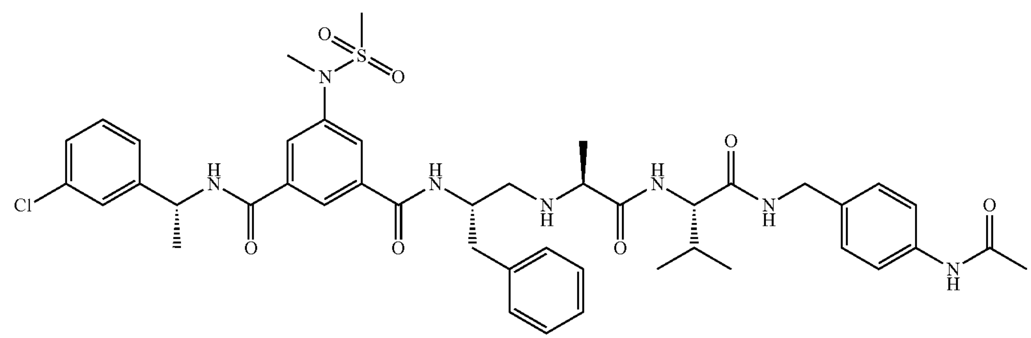 | 860.7 | 3.76 min |
| 20.11 | 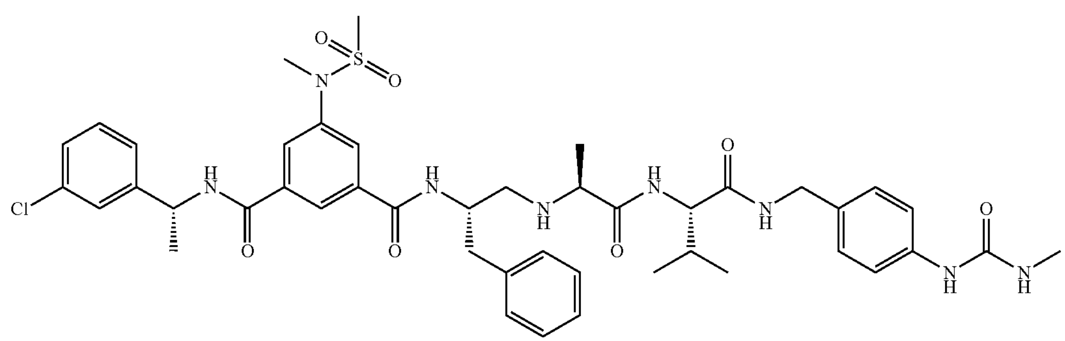 | 875.8 | 3.75 min |

| Example | structure | Mass spectrum [M + H]+ | Retention time method HPLC 6 |
|---|---|---|---|
| 20.12 | 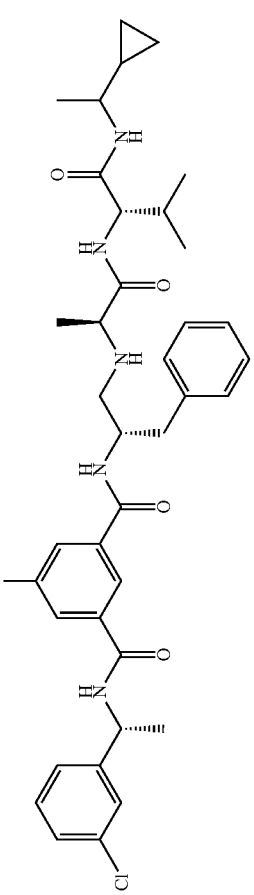 | 781.7 | 3.93 min |
| 20.13 | 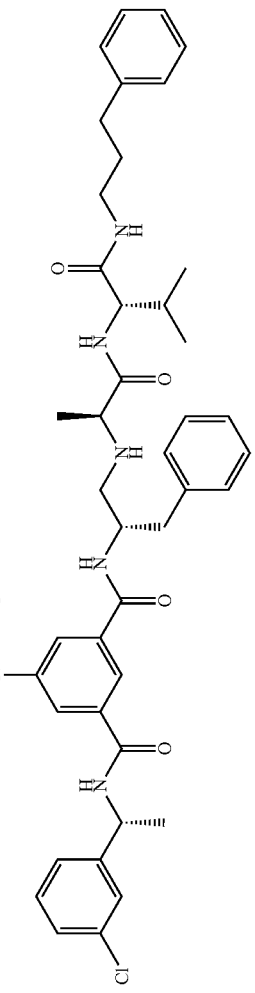 | 831.7 | 4.06 min |

| Example | structure | Mass spectrum [M + H]+ | Retention time method HPLC 6 |
|---|---|---|---|
| 20.14 | 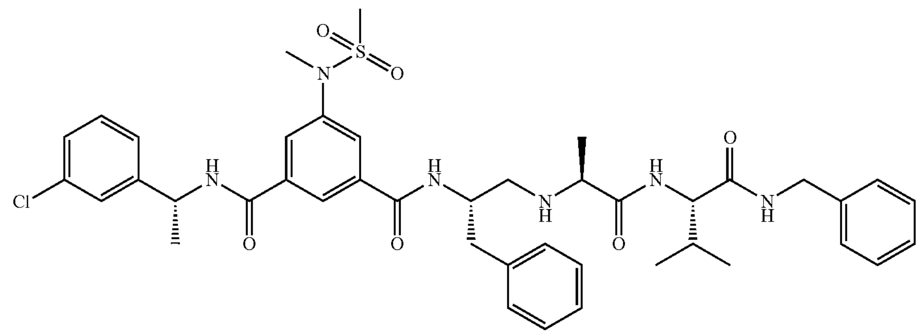 | 803.7 | 3.96 min |
| 20.15 | 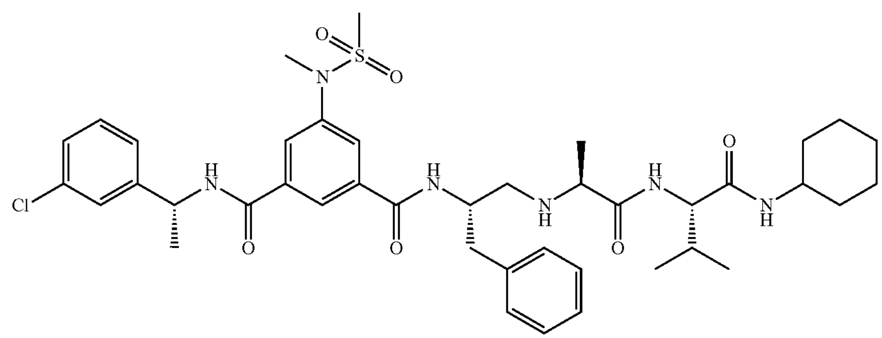 | 795.8 | 4.00 min |
| 20.16 | 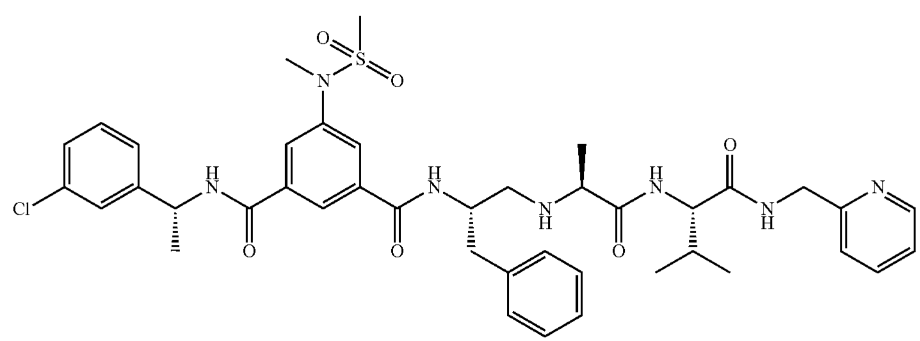 | 804.7 | 3.49 min |

-continued

| Example | structure | Mass spectrum [M + H]+ | Retention time method HPLC 6 |
|---|---|---|---|
| 20.17 | 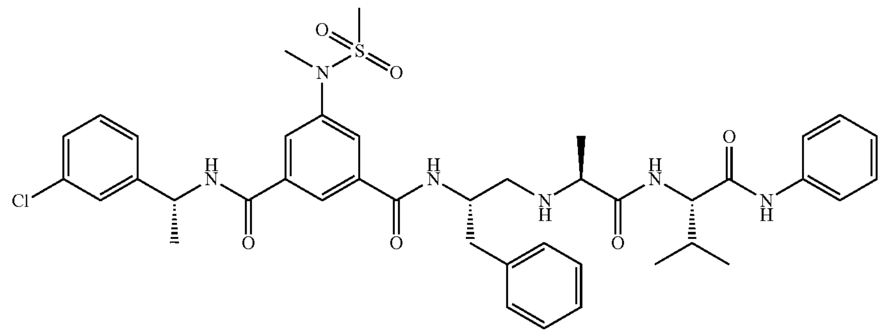 | 789.7 | 3.98 min |
| 20.18 | 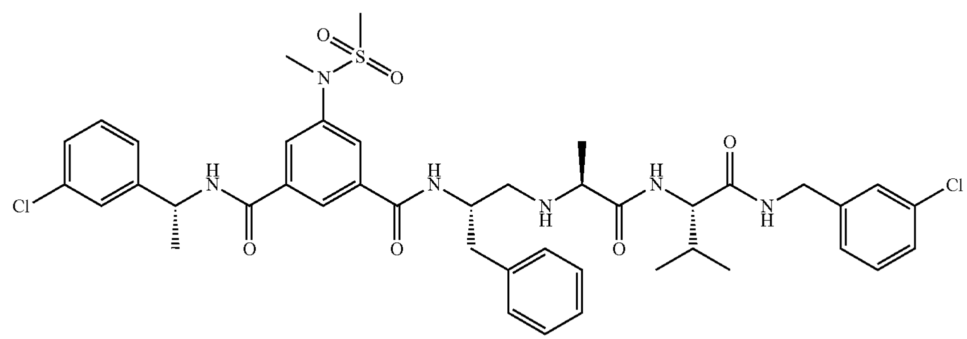 | 837.7 | 4.04 min |

-continued

| Example | structure | Mass spectrum [M + H]+ | Retention time method HPLC 6 |
|---|---|---|---|
| 20.19 | 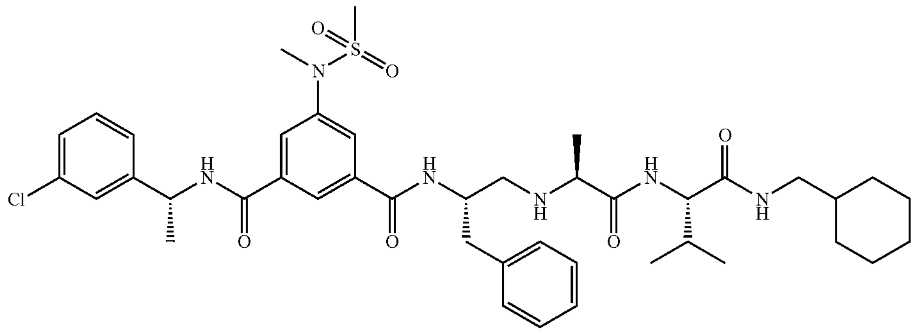 | 809.8 | 4.08 min |
| 20.20 | 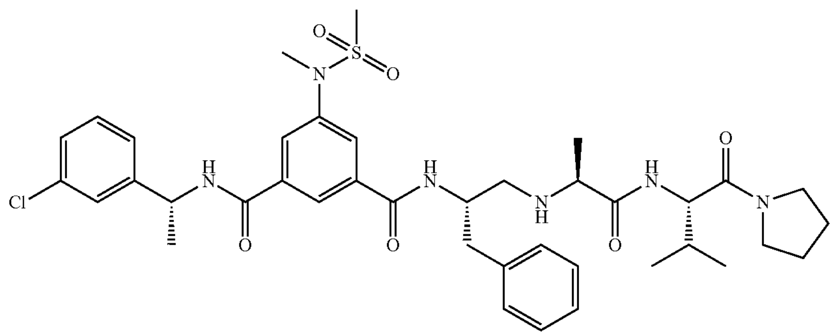 | 767.7 | 3.84 min |
| 20.21 | 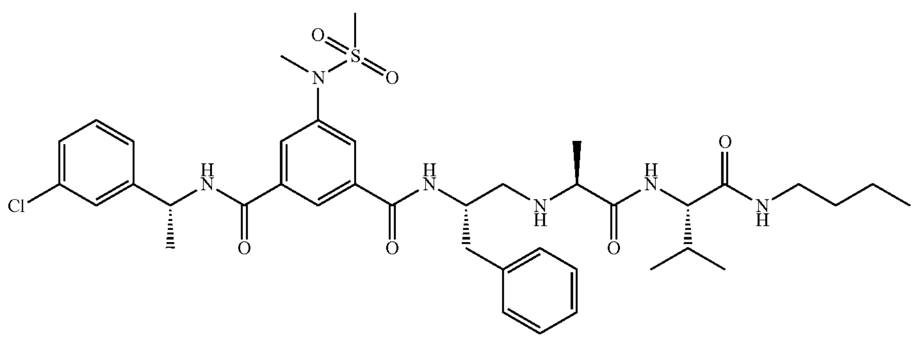 | 769.8 | 3.93 min |

-continued

| Example | structure | Mass spectrum [M + H]⁺ | Retention time method HPLC 6 |
|---|---|---|---|
| 20.22 | 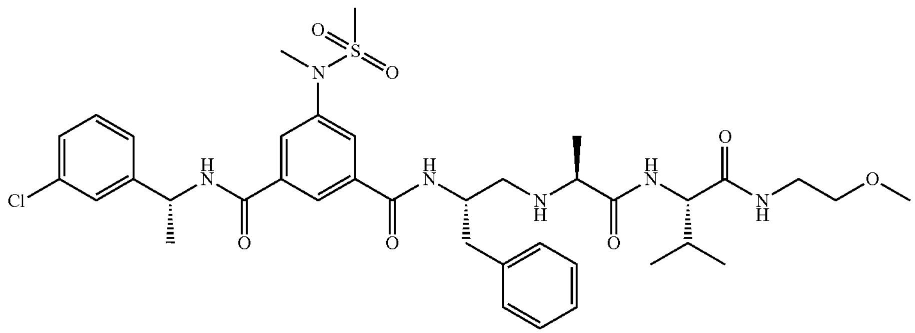 | 771.4 | 3.75 min |
| 20.23 | 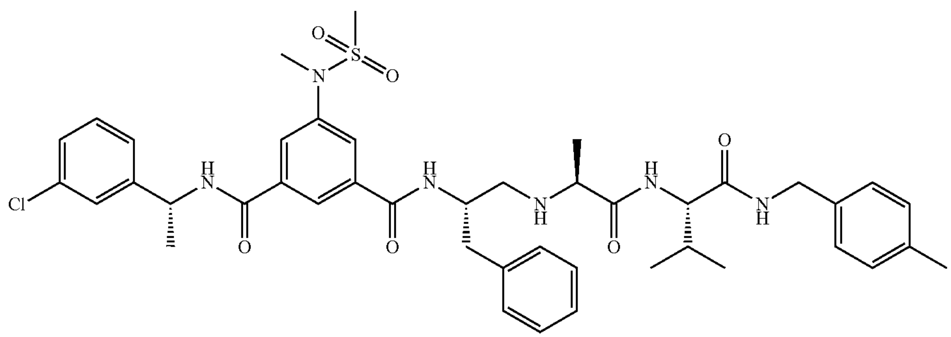 | 817.7 | 4.03 min |

-continued

| Example | structure | Mass spectrum [M + H]+ | Retention time method HPLC 6 |
|---|---|---|---|
| 20.24 | 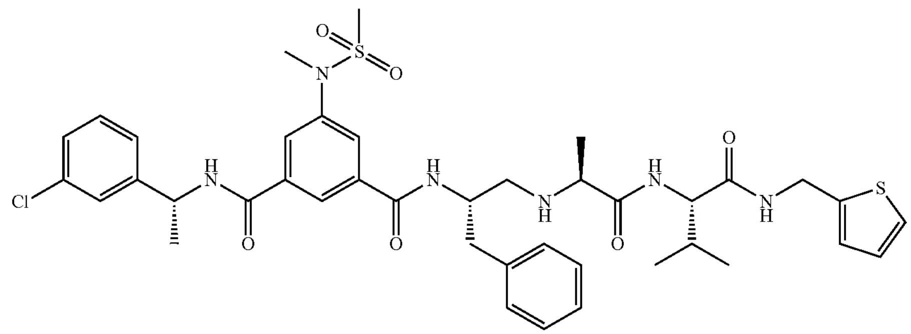 | 809.7 | 3.93 min |
| 20.25 | 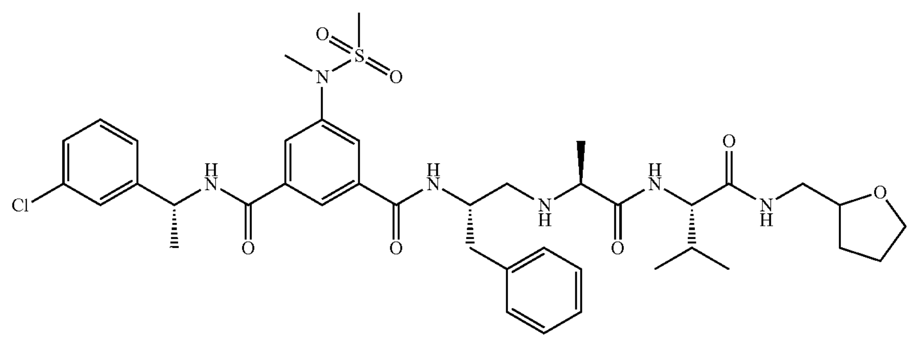 | 797.7 | 3.79 min |
| 20.26 | 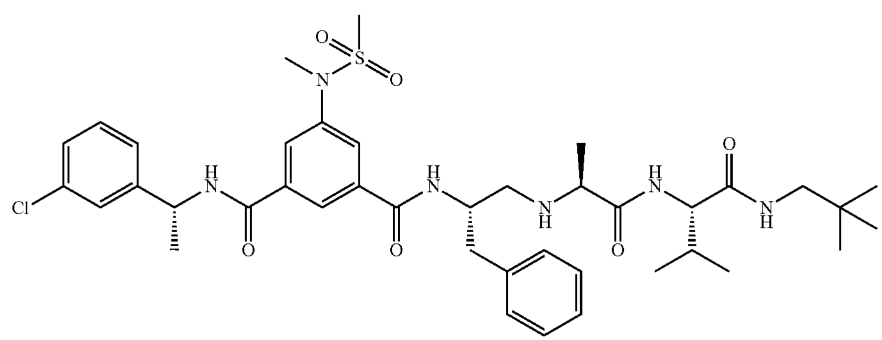 | 783.8 | 3.98 min |

| Example | structure | Mass spectrum [M + H]+ | Retention time method HPLC 6 |
|---|---|---|---|
| 20.27 | 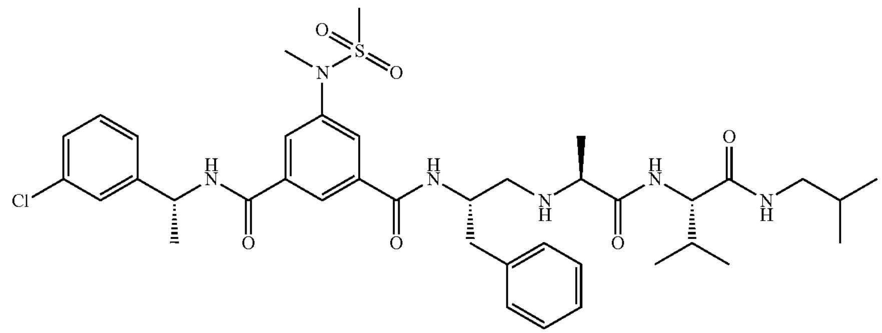 | 769.7 | 3.92 min |
| 20.28 | 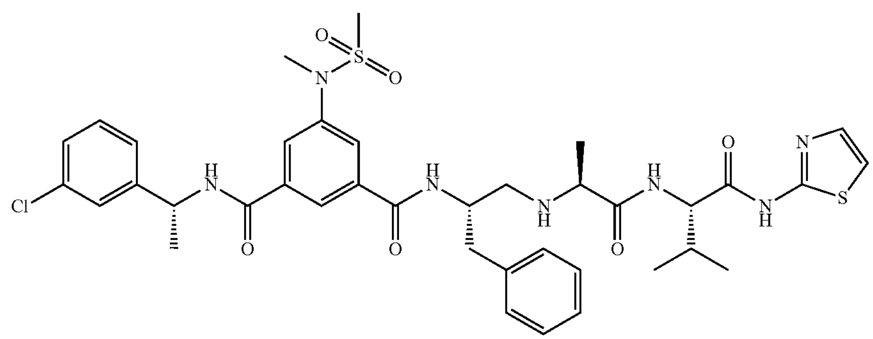 | 796.7 | 3.84 min |

| Example | structure | Mass spectrum [M + H]⁺ | Retention time method HPLC 6 |
|---|---|---|---|
| 20.29 | 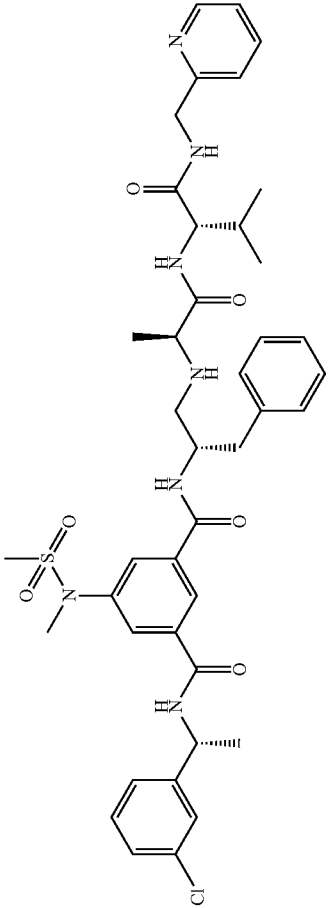 | 804.7 | 3.51 min |
| 20.30 | 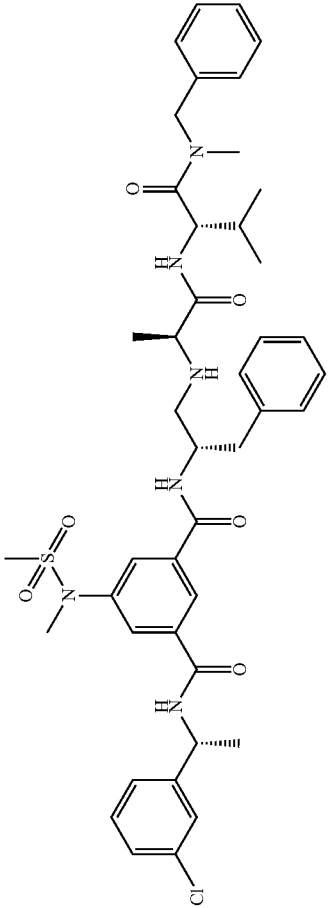 | 817.7 | 4.00 min |
| 20.31 | 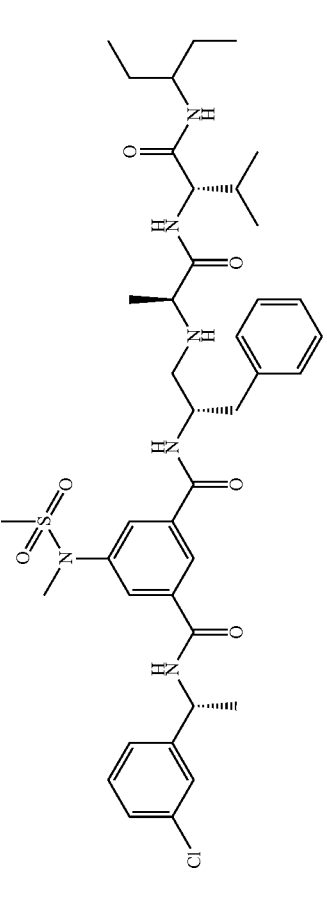 | 783.8 | 3.97 min |

-continued
| Example | structure | Mass spectrum [M + H]+ | Retention time method HPLC 6 |
|---|---|---|---|
| 20.32 | 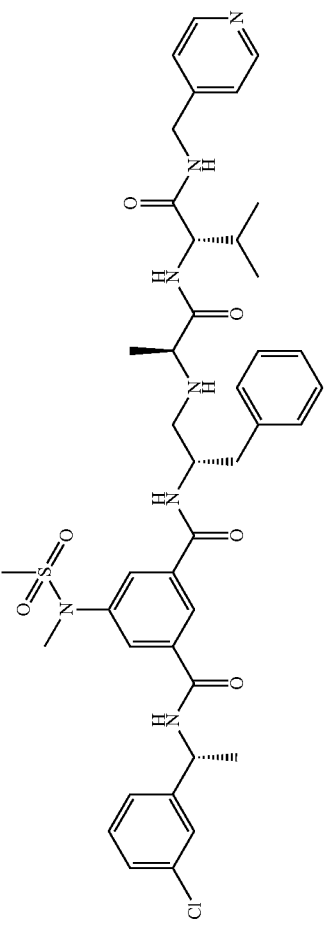 | 804.7 | 3.48 min |
| 20.33 | 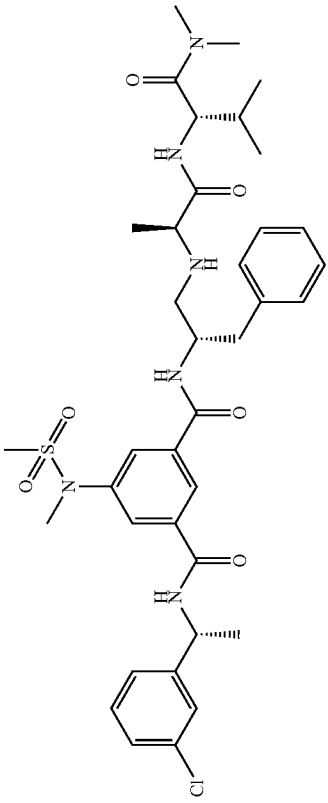 | 741.7 | 3.78 min |

-continued

| Example | structure | Mass spectrum [M + H]+ | Retention time method HPLC 6 |
|---|---|---|---|
| 20.34 | 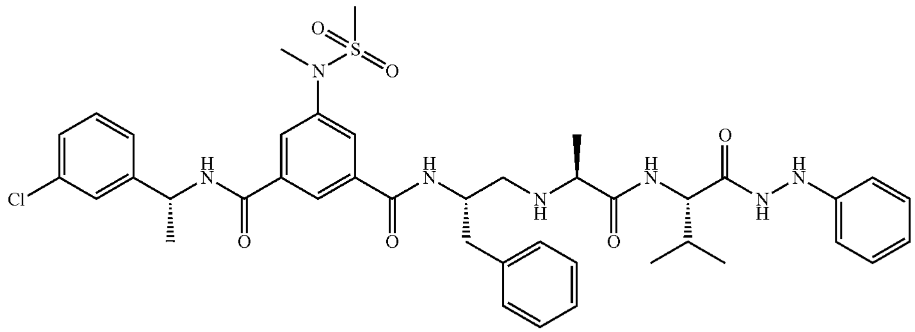 | 804.7 | 3.90 min |
| 20.35 | 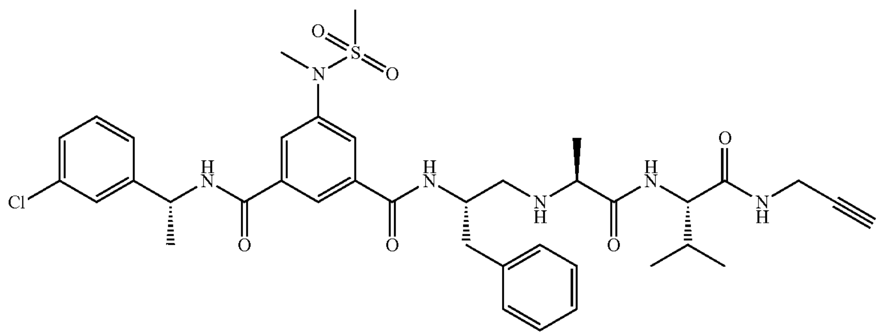 | 751.7 | 3.80 min |
| 20.36 | 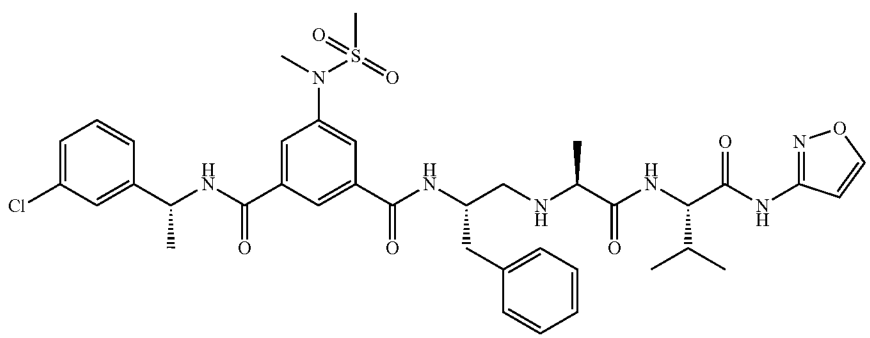 | 780.7 | 3.82 min |

-continued

| Example | structure | Mass spectrum [M + H]+ | Retention time method HPLC 6 |
|---|---|---|---|
| 20.37 | 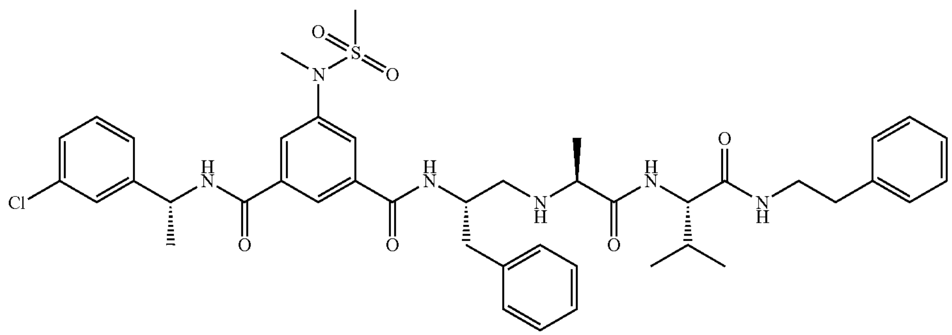 | 817.7 | 4.00 min |

Example 21

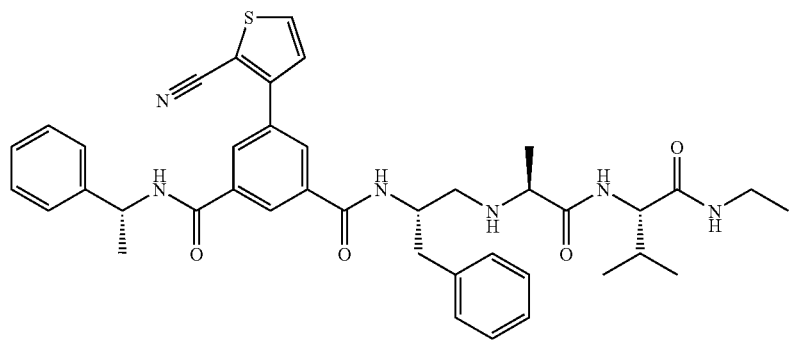

a) Preparation of 21-a:

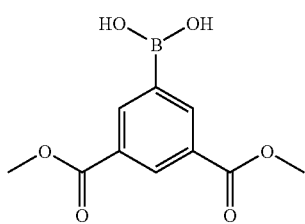

50 g (153 mmol) dimethyl 5-iodo-isophthalate were dissolved in 300 ml THF under a nitrogen atmosphere. At −10° C., 7.14 g (168 mmol) lithium chloride and 168 ml isopropylmagnesium chloride (2.0 M in THF) were added. After 15 min. the mixture was cooled to −60° C., 79.5 ml (765 mmol) trimethylborate was added and the mixture was slowly heated to 25° C. After 12 h, 70 ml aqueous HCl (2.0 M) were added. The suspension is evaporated down to ¼ of the volume. The precipitate was suction filtered and washed with water and cold dichloromethane. 34.0 g (93%) of 21-a were obtained as a colourless solid.

RT (HPLC-MS)=2.39 min.
ES-MS (M+H)$^+$=239.1 b) Preparation of 21-b:

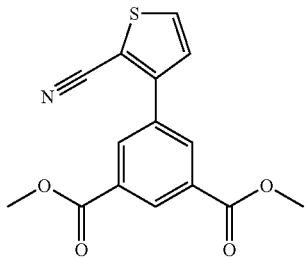

3.00 g (15.5 mmol) 3-bromothiophene-2-carbonitrile were dissolved in 50 ml of toluene under a nitrogen atmosphere. 0.54 g (0.46 mmol) tetrakistriphenylphosphine-palladium(0), a solution of 5.53 g (23.2 mmol) 21-a in 25 ml of methanol and a solution of 1.80 g (17.0 mmol) sodium carbonate in 25 ml of water were added successively. After 8 h at 100° C. the mixture was cooled to 25° C., the precipitate formed was filtered off and washed with toluene, water and cold methanol. 4.00 g (86%) of 21-b were obtained as a colourless solid.

RT (HPLC-MS)=3.26 min.
ES-MS (M+H)$^+$=302.1 c) Preparation of 21-c:

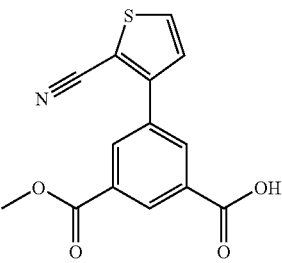

21-c was prepared analogously to 1-c from 21-b.
RT (HPLC-MS)=2.82 min.

d) Preparation of 21-d:

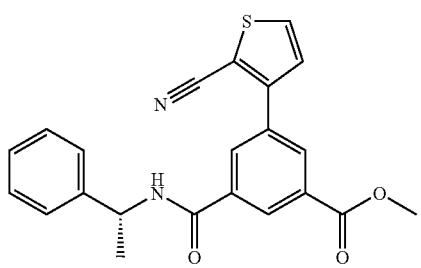

21-d was prepared analogously to 1-d from 21-c and (R)-1-phenyl-ethylamine.
RT (HPLC-MS)=3.35 min.
ES-MS (M+H)$^+$=391.1 e) Preparation of 21-e:

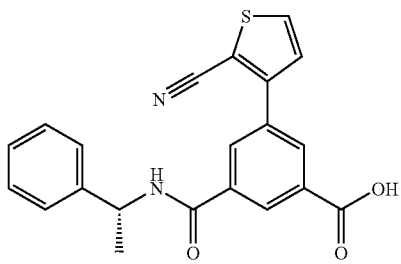

21-e was prepared analogously to 1-e from 21-d.

f) Preparation of 21-f:

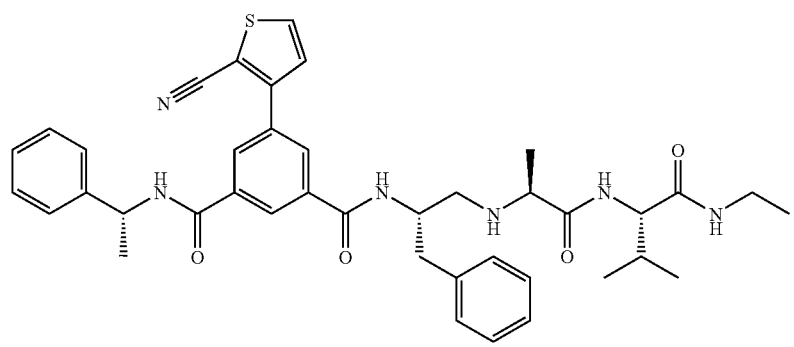

21-f was prepared analogously to 1-d from 21-e and 1-l.
RT (HPLC-MS)=2.90 min.
ES-MS (M+H)$^+$=707.1 g) Preparation of 21-g:

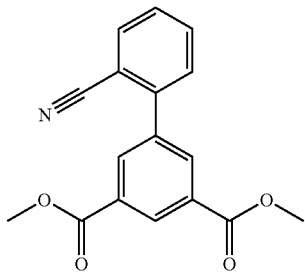

5.29 g (16.5 mmol) dimethyl 5-iodo-isophthalate was dissolved in 80 ml DMF under a nitrogen atmosphere. 4.50 g (23.3 mmol) 2-[1,3,2]-dioxaborinan-2-yl-benzonitrile, 3.90 ml (28.0 mmol) triethylamine, 3.0 ml of water, 0.10 mg (0.45 mmol) palladium acetate as well as 0.13 g (0.43 mmol) tri-o-tolylphosphine were added successively. After 2.5 h at 100° C. the mixture was cooled to 25° C. The solvent was distilled off and the residue was purified by preparative MPLC (SiO$_2$, gradient: cyclohexane to cyclohexane/ethyl acetate 5:95). 2.60 g (45%) 21-g was obtained as a colourless solid.
RT (HPLC-MS)=3.19 min.
ES-MS (M-MeOH+H)$^+$=264.1 h) Preparation of 21-h:

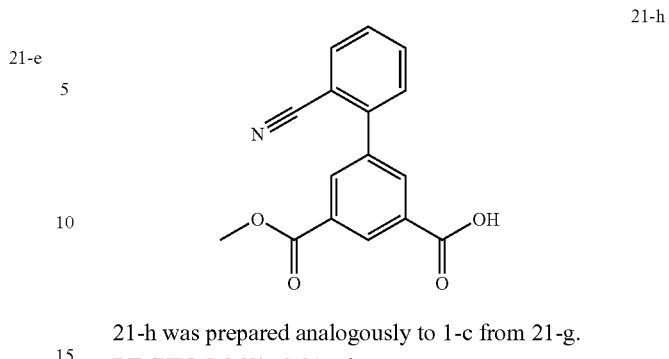

21-h was prepared analogously to 1-c from 21-g.
RT (HPLC-MS)=2.81 min.
ES-MS (M-H$_2$O+H)$^+$=264.1 i) Preparation of 21-i:

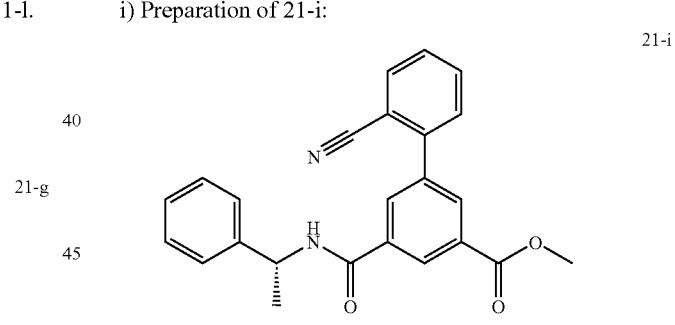

21-i was prepared analogously to 1-d from 21-h and (R)-1-phenyl-ethylamine.

j) Preparation of 21-j:

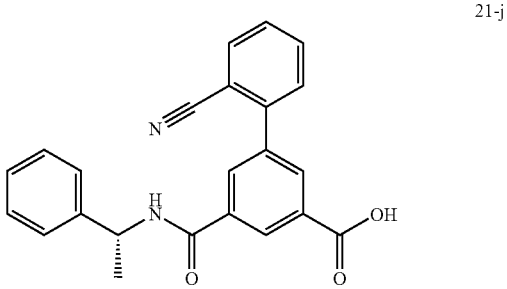

21-j was prepared analogously to 1-e from 21-i.

Analogously to Example 21 the following compounds were prepared from 1-l and 21-j or from acids which had been obtained analogously to 21-e starting from corresponding arylhalides (step 21-b) and suitable amines (step 21-d):

| Example | structure | Mass spectrum [M + H]+ | Retention time method HPLC-MS |
|---|---|---|---|
| 21.2 | 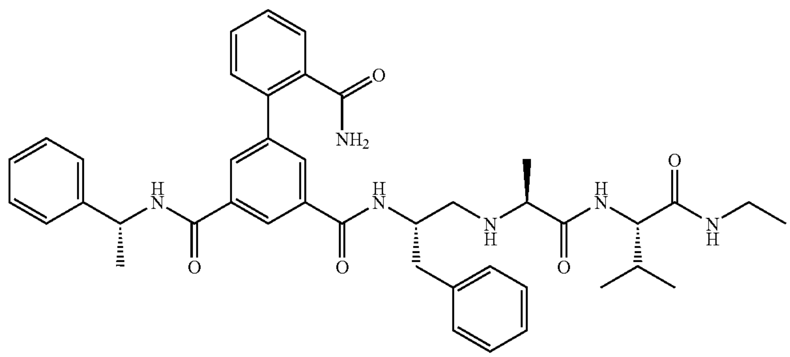 | 719 | 2.70 min |
| 21.3 | 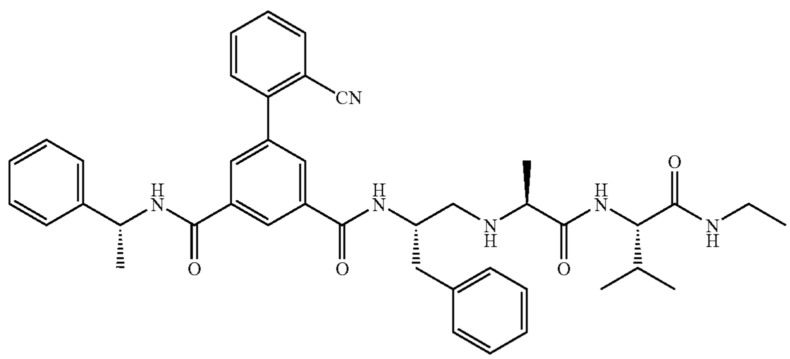 | 701.1 | 2.96 min |
| 21.4 | 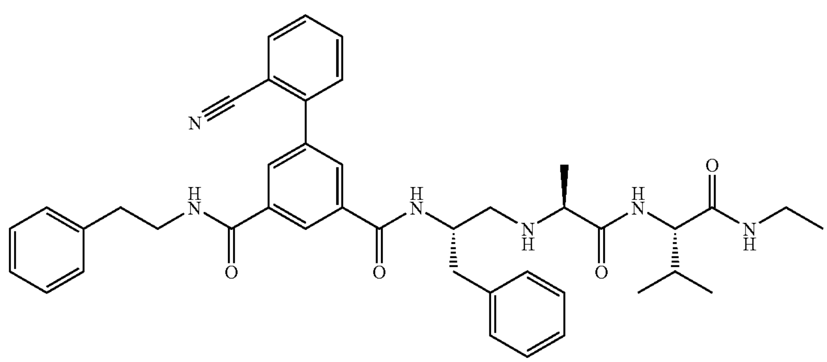 | 701.2 | 2.94 min |
| 21.5 | 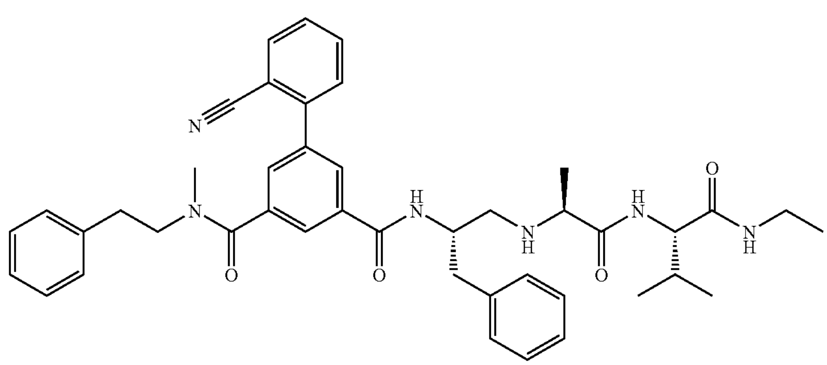 | 715.1 | 2.84 min |

-continued

| Example | structure | Mass spectrum [M + H]+ | Retention time method HPLC-MS |
|---|---|---|---|
| 21.6 | 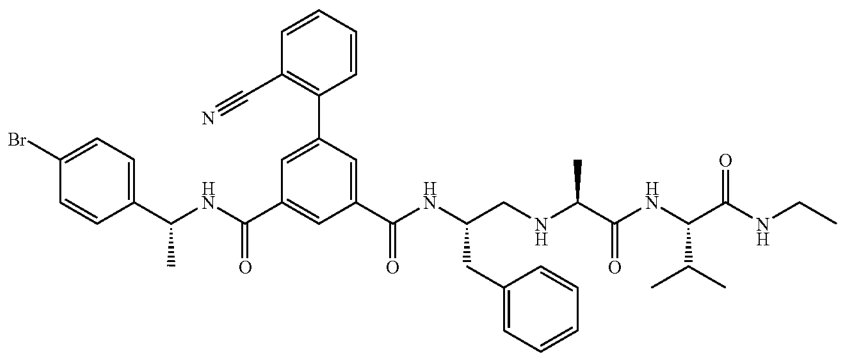 | 779/781 (Br) | 3.12 min |
| 21.7 | 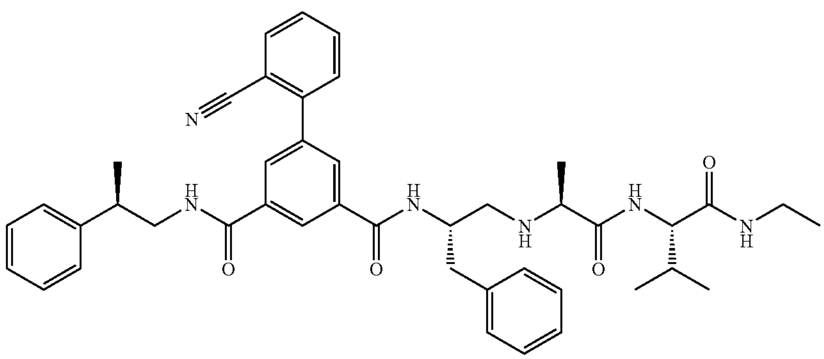 | 715.1 | 3.01 min |
| 21.8 | 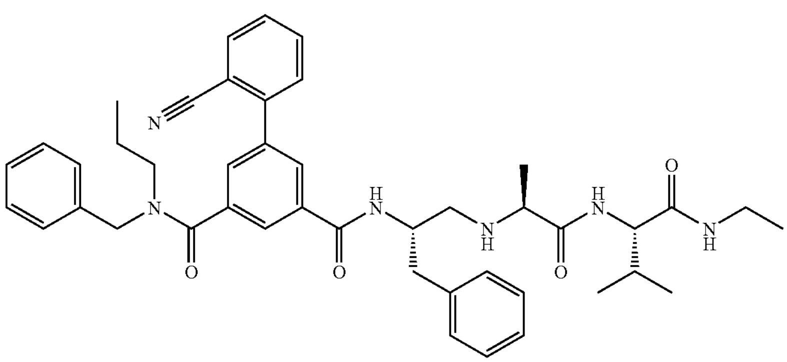 | 729.1 | 2.98 min |
| 21.9 | 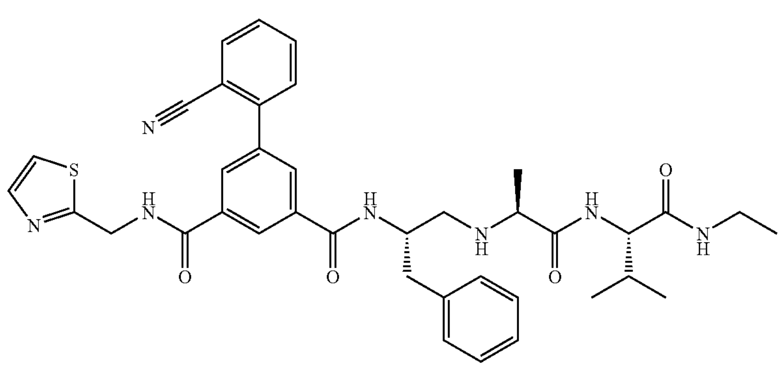 | 694.1 | 2.65 min |

-continued
| Example | structure | Mass spectrum [M + H]+ | Retention time method HPLC-MS |
|---|---|---|---|
| 21.10 | 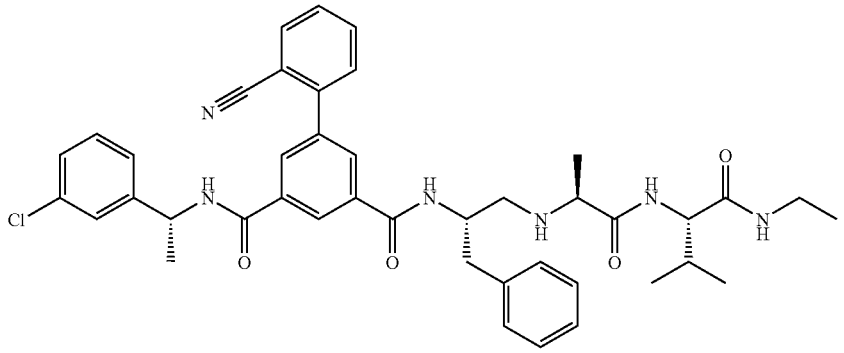 | 735/737 (Cl) | 3.08 min |
| 21.11 | 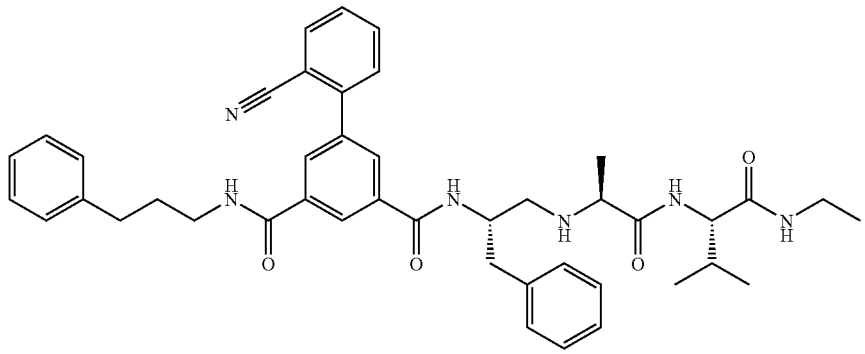 | 715.2 | 2.93 min |
| 21.12 | 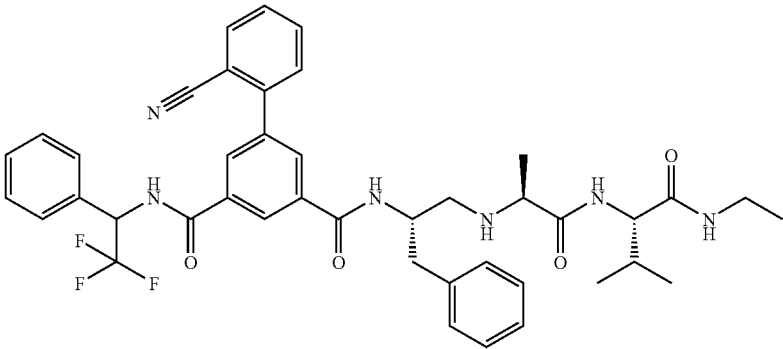 | 755.1 | 2.99 min |
| 21.13 | 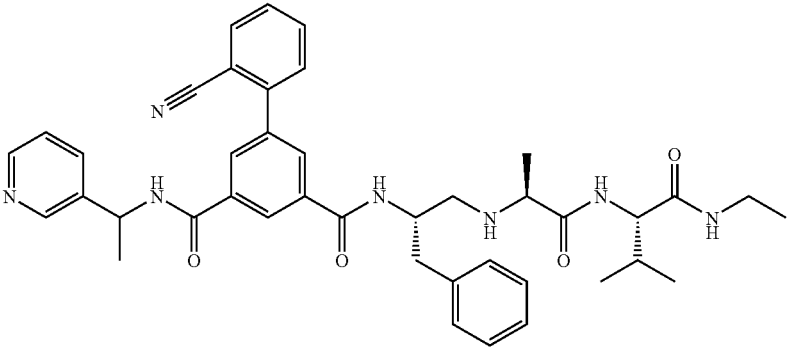 | 702.1 | 2.39 min |

-continued

| Example | structure | Mass spectrum [M + H]+ | Retention time method HPLC-MS |
|---|---|---|---|
| 21.14 | 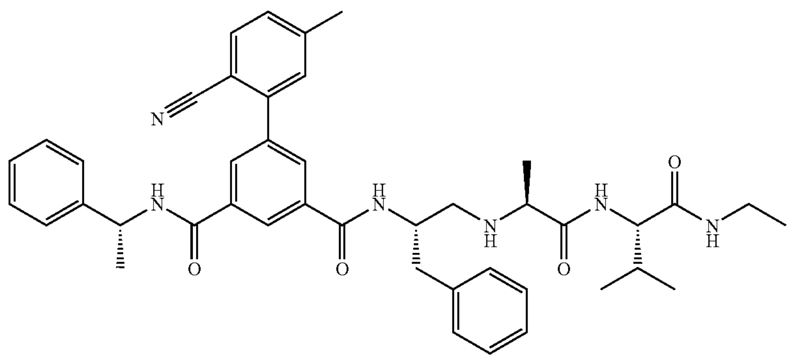 | 715.1 | 2.94 min |
| 21.15 | 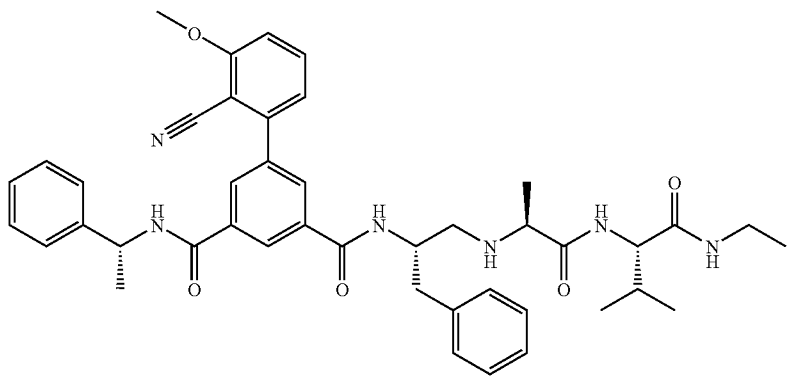 | 731.1 | 2.88 min |
| 21.16 | 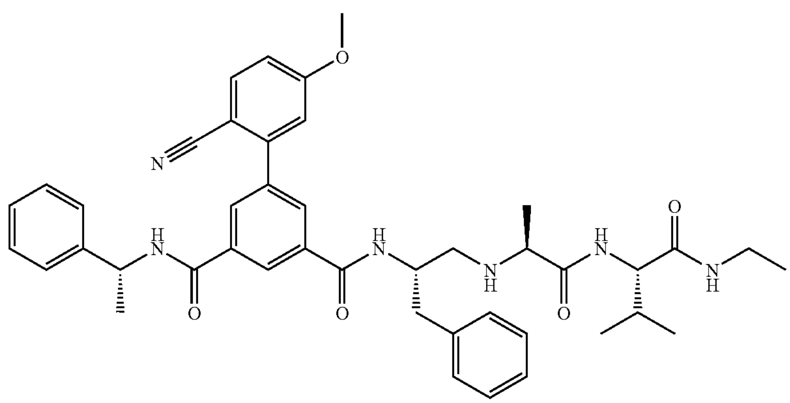 | 731.1 | 2.90 min |
| 21.17 | 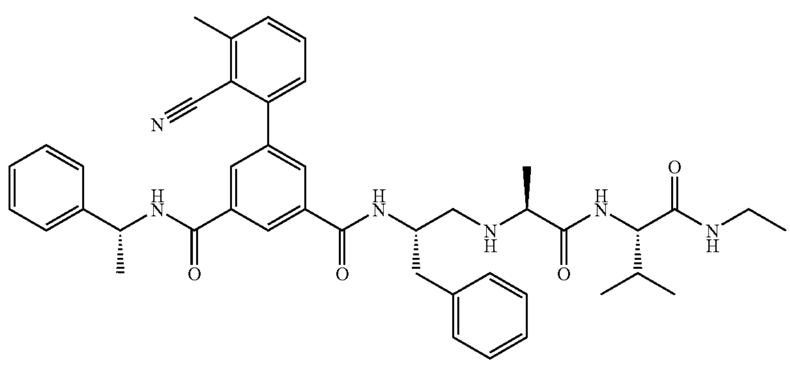 | 715.1 | 3.00 min |

-continued

| Example | structure | Mass spectrum [M + H]+ | Retention time method HPLC-MS |
|---|---|---|---|
| 21.18 | 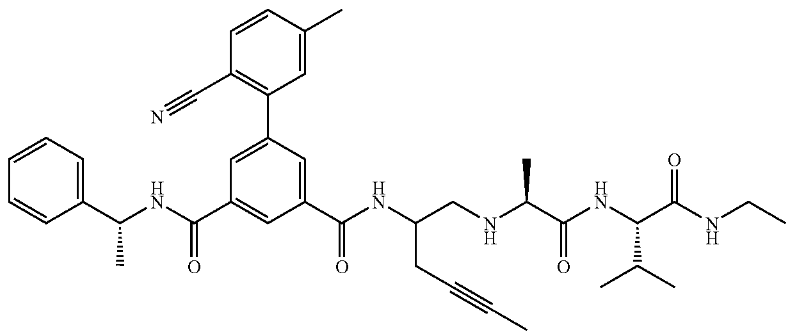 | 677.1 | 2.95 min |

Analogously to Example 21, the following compounds were prepared from acids obtained analagously to 21-e starting from corresponding aryl halides (step 21-b) and amines obtained analagously to 1-l from suitable educts:

| Example | structure | Mass spectrum [M + H]+ | Retention time method HPLC-MS |
|---|---|---|---|
| 21.19 | 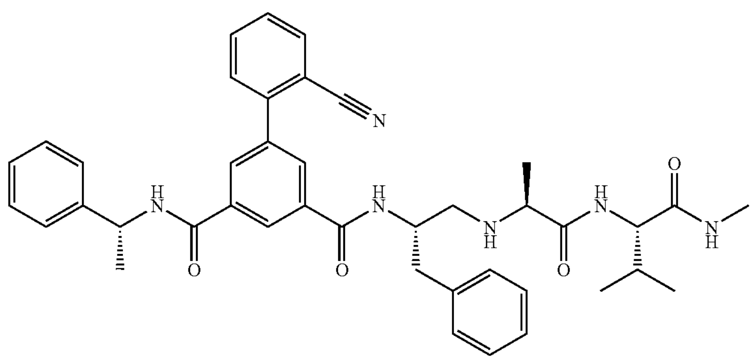 | 687.1 | 1.99 min |
| 21.20 | 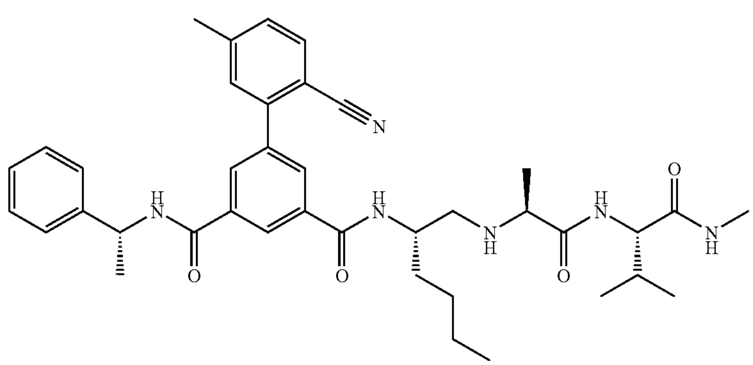 | 667.1 | 3.01 min |

| Example | structure | Mass spectrum [M + H]+ | Retention time method HPLC-MS |
|---|---|---|---|
| 21.21 | 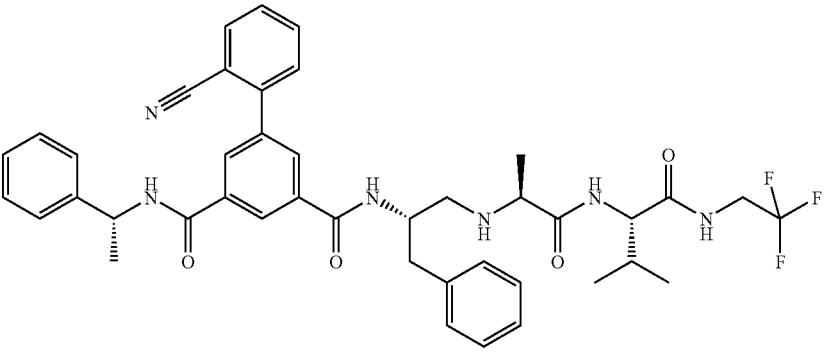 | 755 | 2.14 min |

Example 22

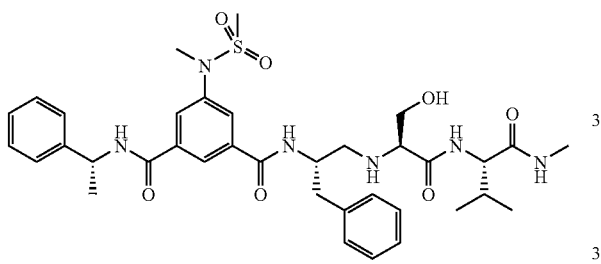

Example 22 was synthesised by standard solid phase peptide synthesis on a [3-((methyl-fmoc-amino)-methyl)-1-indol-1-yl]-acetyl AM resin (367 mg, 0.25 mmol) (Novabiochem).

Fmoc cleavings were carried out by reacting the resin twice (2 minutes and 20 minutes) with 30% piperidine/DMF solution. Then the resin was washed ten times with DMF. The coupling of the first amino acid was carried out with HATU (380 mg, 1.0 mmol), HOAt (0.5 molar solution, 2 ml, 1.0 mmol), Dipea (513 µl, 3 mmol) and Fmoc-valine (339 mg, 1 mmol) in DMF as solvent over 5 hours. The coupling of the second Fmoc-amino acid was carried out analogously with Fmoc-serine-tert.butyl ester (383 mg, 1 mmol).

After the coupling of the first two amino acids and the cleaving of the Fmoc group reductive alkylation of the amino group was carried out with a solution of freshly prepared Fmoc-phenylalaninal (310 mg, 0.75 mmol) and NaBH(OAc)$_3$ (530 mg, 2.5 mmol) in DMF/HOAc (99:1, 2 ml) for 2.5 hours. Then the resin was carefully washed with DMF/HOAc (99:1), DMF, 5% Dipea in DMF and DMF. The resin was then reacted for 16 hours with Boc$_2$O (10 equiv.) and Dipea (10 equiv.) in DMF.

After a repeat cleaving of the Fmoc group and thorough washing with DMF the resin was reacted with a solution of the corresponding acid 4-b (376 mg, 1 mmol), HATU (380 mg, 1.0 mmol), HOAt (0.5 molar solution, 2 ml, 1.0 mmol), Dipea (513 µl, 3 mmol) in DMF.

In order to cleave the product from the resin and also cleave any protective groups the resin was washed with DMF and dichloromethane and dried and then mixed with TFA/water (95:5, 2 ml) for 1 hour at ambient temperature. The solution was filtered off and the resin was washed twice more with dichloromethane (1 ml). The combined filtrates were evaporated down in vacuo and the product was purified by preparative reversed phase HPLC.

Yield 35.1 mg
ES-MS (M+H)$^+$=709.5
RT=3.71 min (HPLC 6)

Example 23

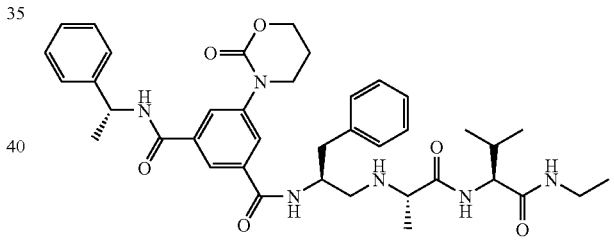

Example 23 was prepared analogously to Example 1 from 23-c and the corresponding precursors.

ES-MS (M+H)$^+$=700
RT (HPLC-MS): 2.70 min a) Preparation of 23-a:

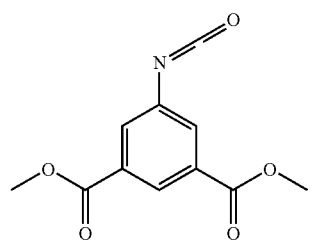

23-a 10.46 g (50 mmol) dimethyl 5-amino-isophthalate were dissolved in 200 ml of toluene and combined with 7.3 ml (60 mmol) diphosgene. The reaction solution was refluxed for 1 h. Then the reaction solution was evaporated down i. vac., twice combined with toluene and distilled off again. The residue (10.6 g) was used in 23-b without being purified.

b) Preparation of 23-b:

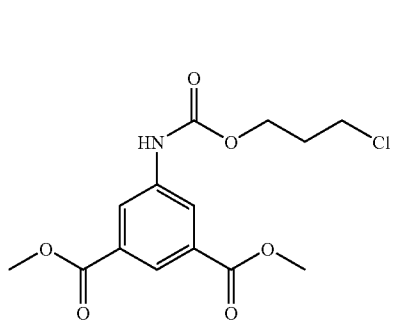

10.6 g (45 mmol) 23-a were dissolved in 450 ml of toluene and combined with 3.88 ml (45 mmol) 3-chloro-1-propanol. The reaction solution was heated to 75° C. for 1 h. Then the reaction solution was evaporated down i. vac. The residue was purified by chromatography on silica gel with the eluant (ethyl acetate/heptane 7:3).

Yield 8.5 g of 23-a (57%)
ES-MS (M+H)$^+$=330 c) Preparation of 23-c:

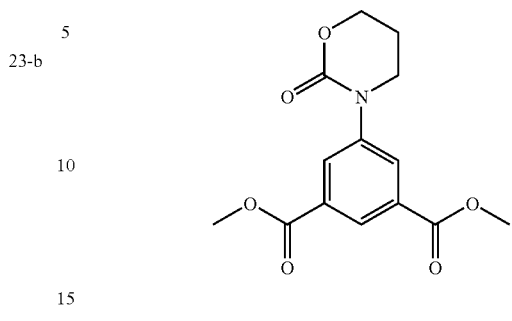

8.49 g (25.8 mmol) 23-b were dissolved in 140 ml acetonitrile, combined with 4.27 g (30.9 mmol) potassium carbonate and refluxed for 2 h. Then the insoluble constituents were filtered off, the reaction solution was evaporated down i. vac. and stirred with ether. The crystals formed were filtered off and washed with ether.

Yield 6.5 g 23-c (77%)
ES-MS (M+H)$^+$=294

Analogously to 23 the following compounds were prepared from corresponding educts:

| Example | | Mass spectrum | Retention time (method) |
|---|---|---|---|
| 23.2 | | 821 [M + H]$^+$ | 2.39 min (HPLC-MS) |
| 23.3 | | 701 [M + H]$^+$ | 2.12 min (HPLC-MS) |

-continued
| Example | | Mass spectrum | Retention time (method) |
|---|---|---|---|
| 23.4 | 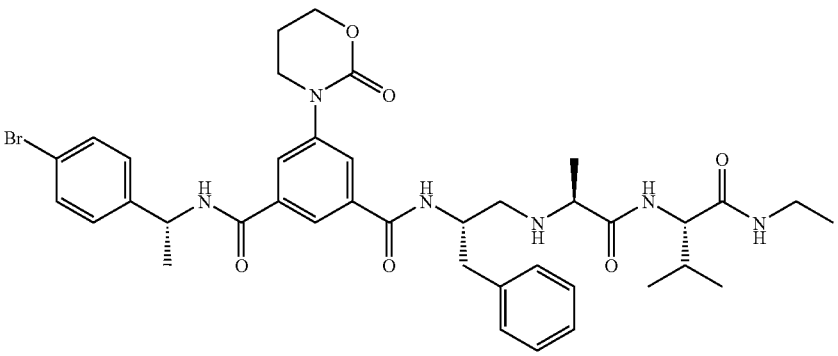 | 779 [M + H]+ | 2.70 min (HPLC-MS) |
| 23.5 | 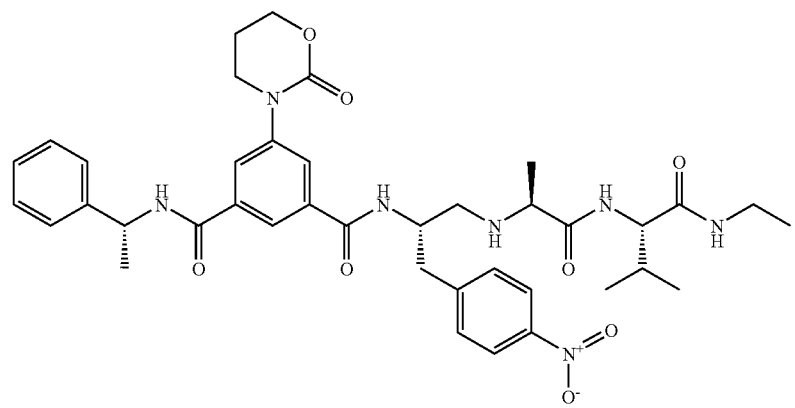 | 745 [M + H]+ | 2.64 min (HPLC-MS) |
| 23.6 | 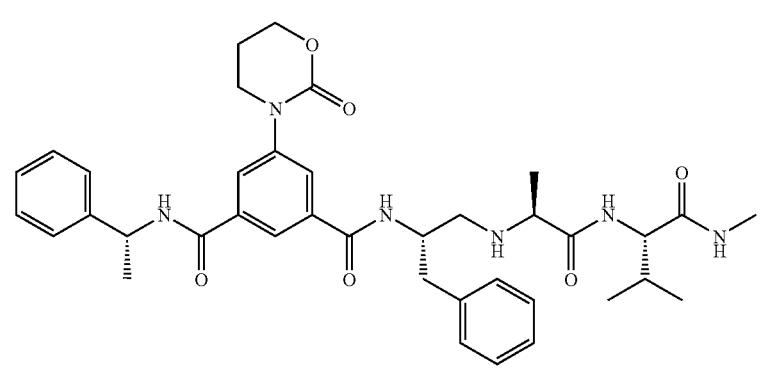 | 686 [M + H]+ | 2.54 min (HPLC-MS) |
| 23.7 | 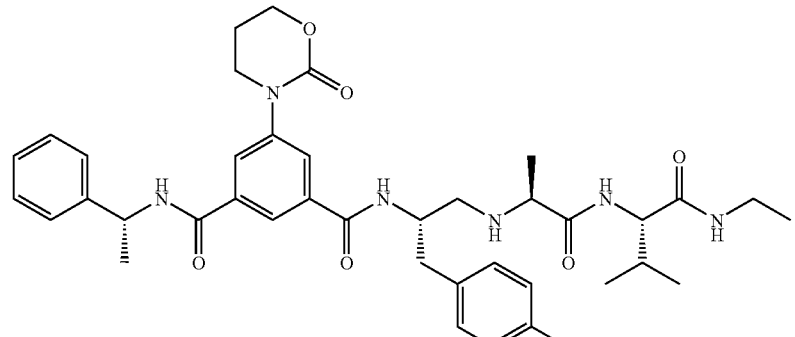 | 715 [M + H]+ | 2.24 min (HPLC-MS) |

-continued
| Example | | Mass spectrum | Retention time (method) |
|---|---|---|---|
| 23.8 | 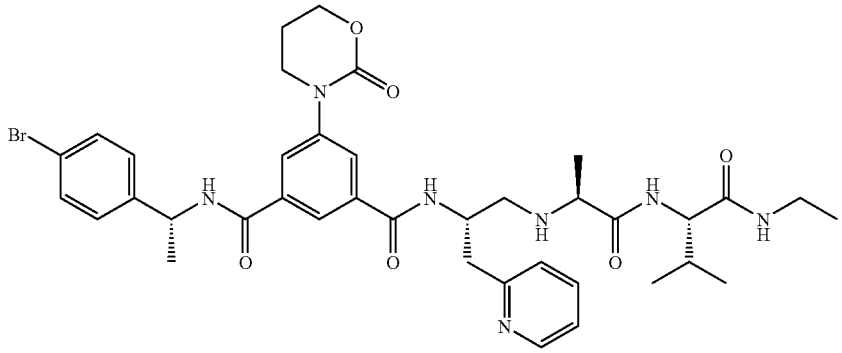 | 780 [M + H]+ | 2.36 min (HPLC-MS) |
| 23.9 | 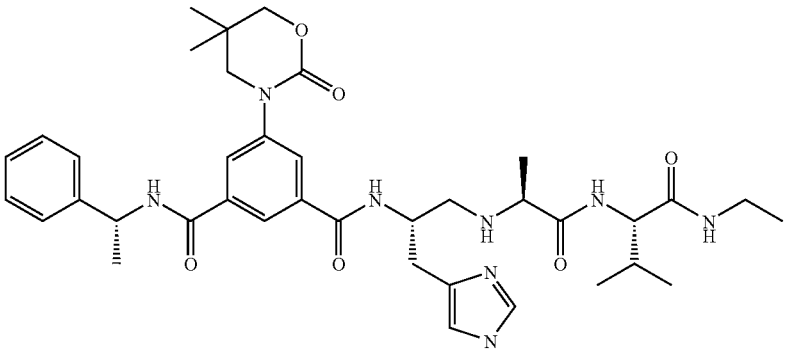 | 735 [M + H]+ | 2.58 min (HPLC-MS) |
| 23.10 | 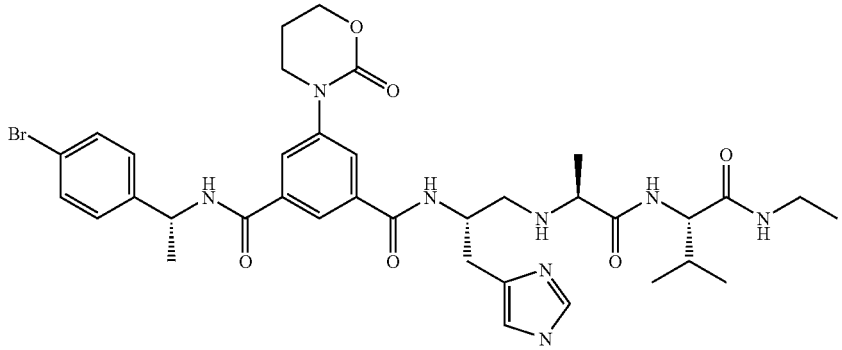 | 786 [M + H]+ | 2.62 min (HPLC-MS) |
| 23.11 | 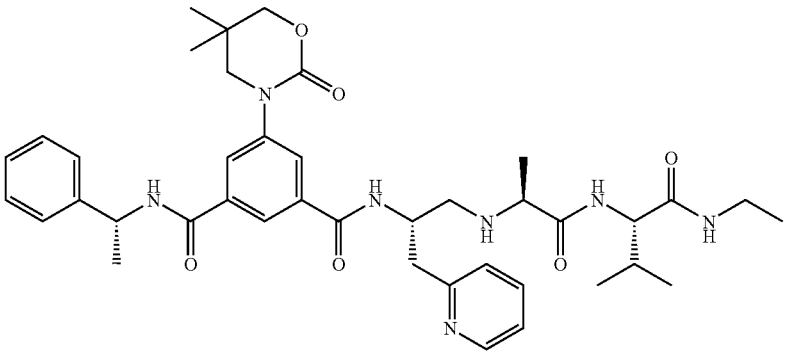 | 729 [M + H]+ | 2.40 min (HPLC-MS) |

-continued
| Example | | Mass spectrum | Retention time (method) |
|---|---|---|---|
| 23.12 | 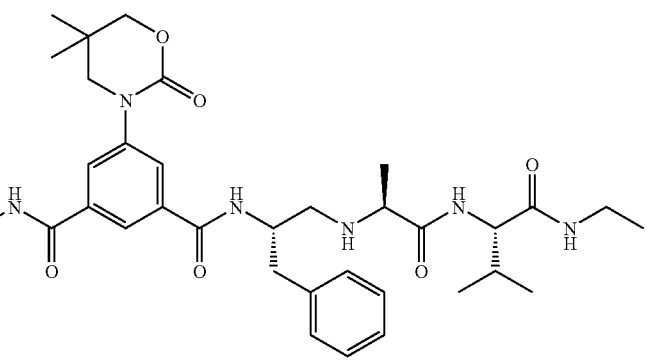 | 728 [M + H]+ | 2.75 min (HPLC-MS) |
| 23.13 | 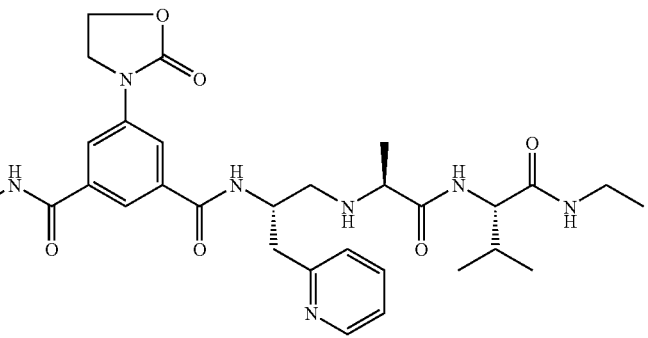 | 687 [M + H]+ | 2.21 min (HPLC-MS) |
| 23.14 | 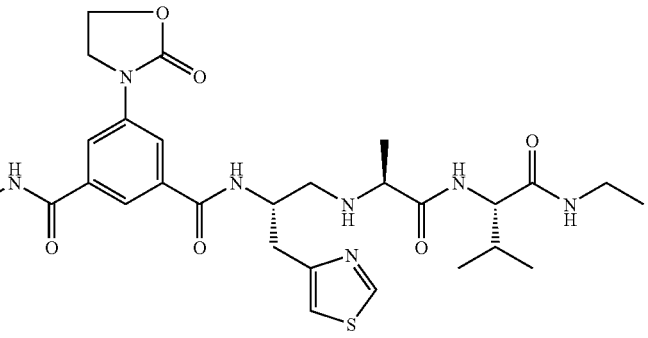 | 693 [M + H]+ | 2.42 min (HPLC-MS) |
| 23.15 | 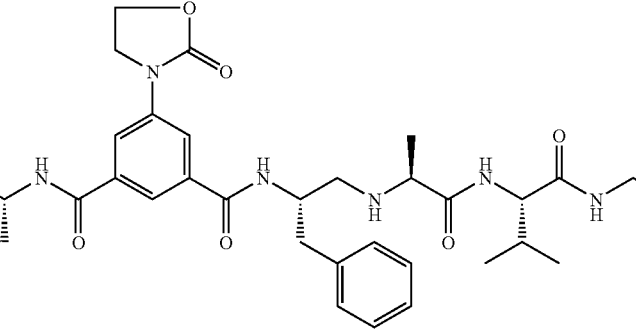 | 765 [M + H]+ | 4.72 min (HPLC 1) |

-continued
| Example | | Mass spectrum | Retention time (method) |
|---|---|---|---|
| 23.16 | 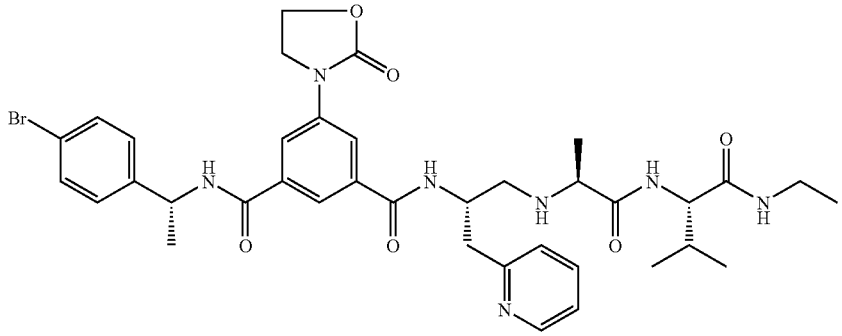 | 766 [M + H]+ | |
| 23.17 | 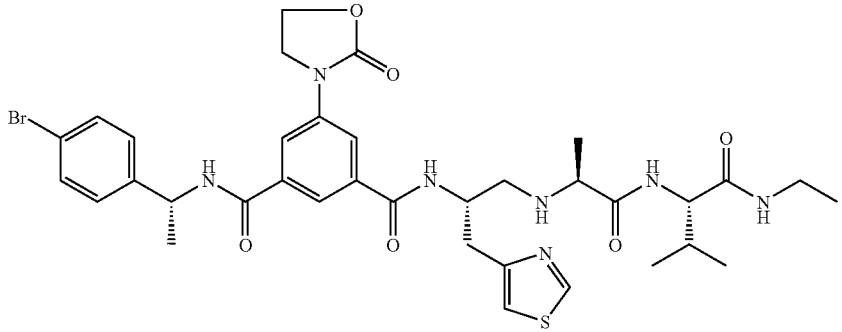 | 772 [M + H]+ | |
| 23.18 | 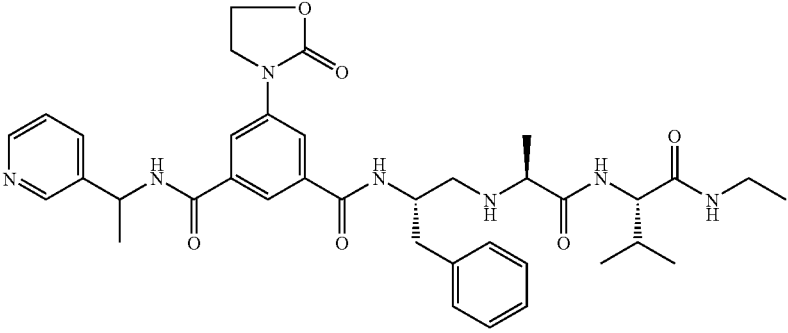 | 687 [M + H]+ | 1.45 min (HPLC-MS) |
| 23.19 | 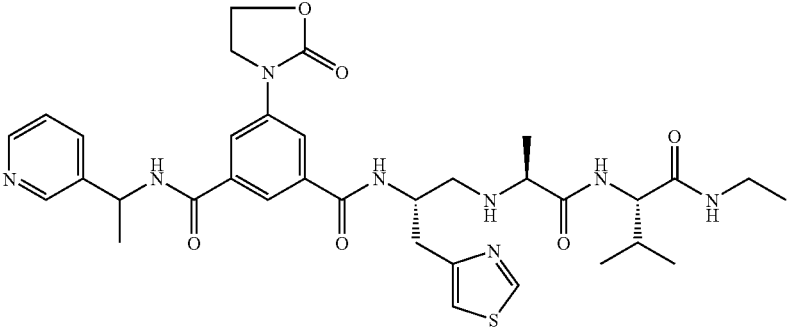 | 694 [M + H]+ | 2.03 min (HPLC-MS) |

-continued
| Example | | Mass spectrum | Retention time (method) |
|---|---|---|---|
| 23.20 | 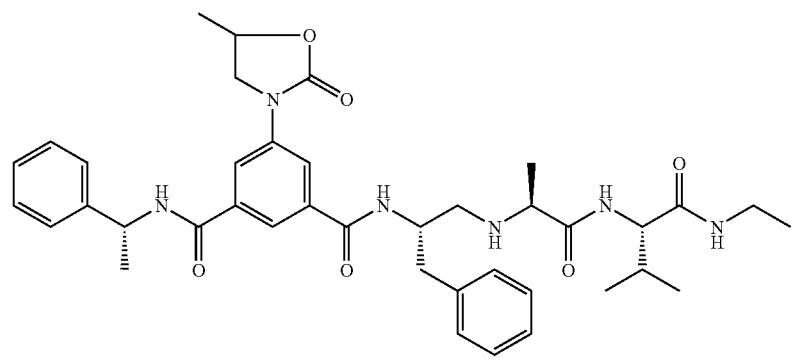 | 700 [M + H]+ | 4.59 min (HPLC 1) |
| 23.21 | 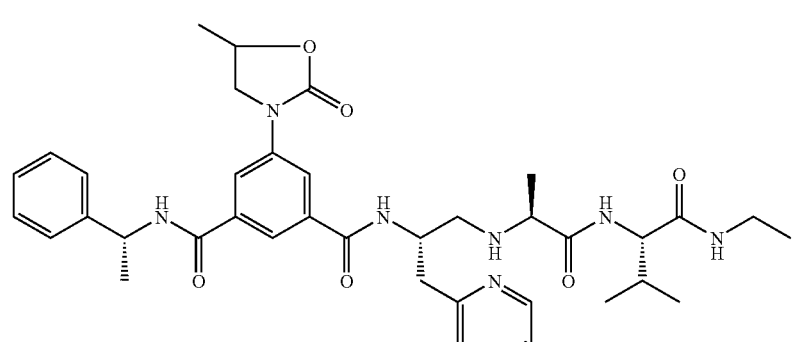 | 701 [M + H]+ | 4.10 min (HPLC 1) |
| 23.22 | 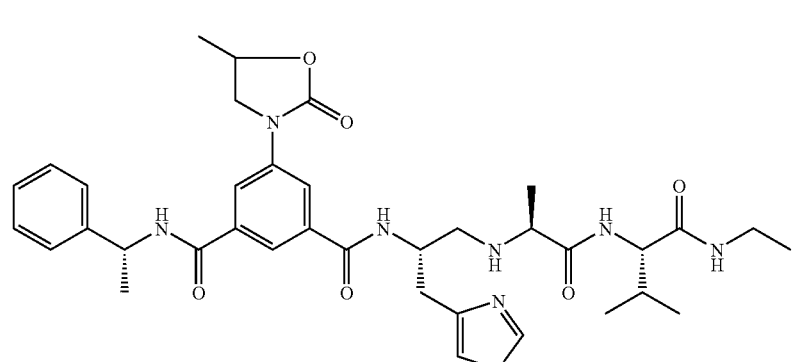 | 707 [M + H]+ | 2.58 min (HPLC-MS) |
| 23.23 | 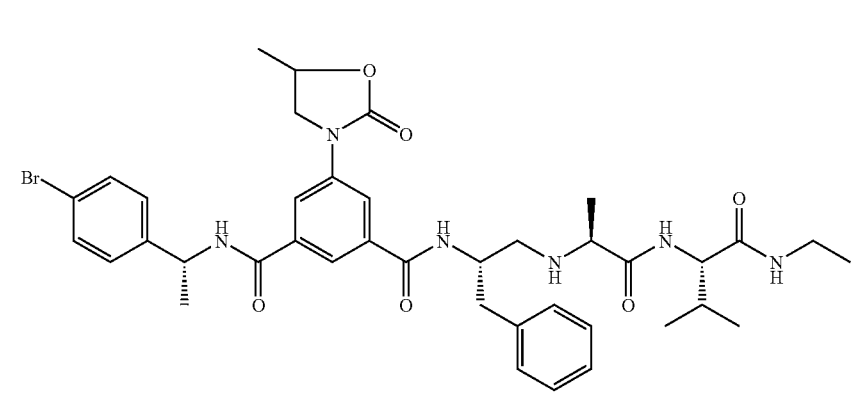 | 779 [M + H]+ | 2.93 min (HPLC-MS) |

-continued
| Example | | Mass spectrum | Retention time (method) |
|---|---|---|---|
| 23.24 | 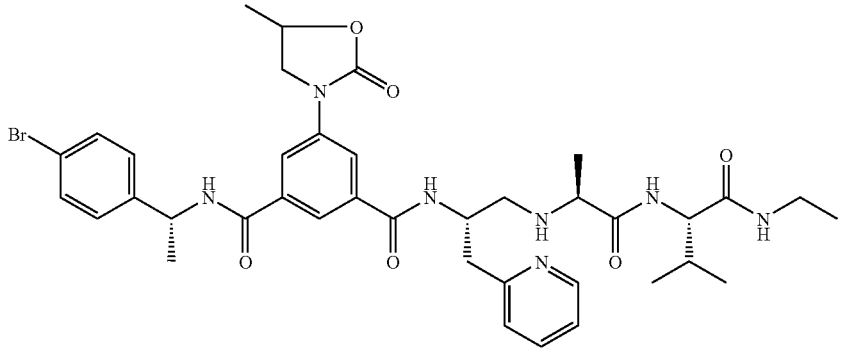 | 780 [M + H]+ | 4.33 min (HPLC 1) |
| 23.25 | 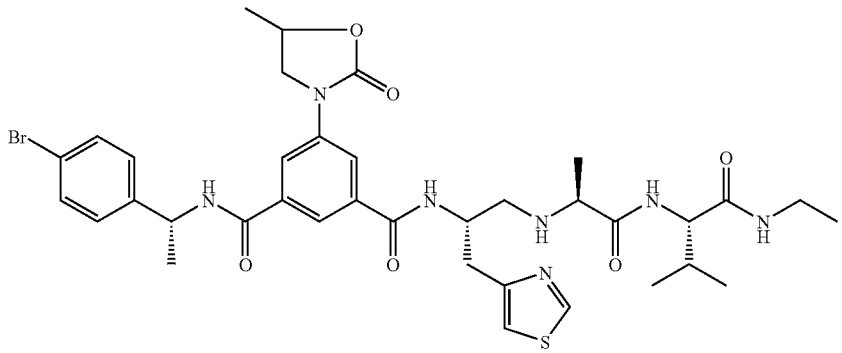 | 786 [M + H]+ | 4.59 min (HPLC 1) |
| 23.26 | 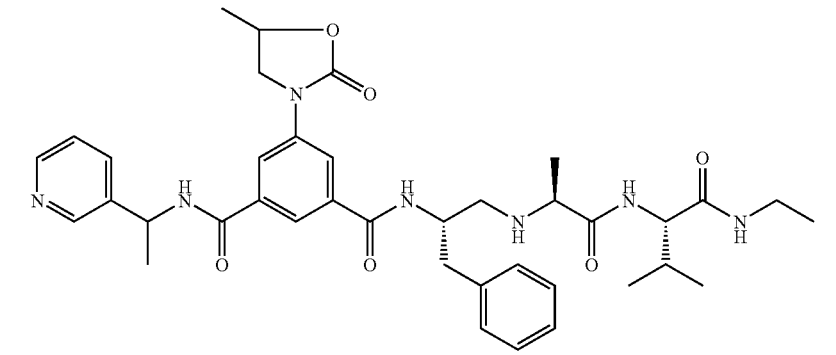 | 702 [M + 2 H]+ | 2.27 min (HPLC-MS) |
| 23.27 | 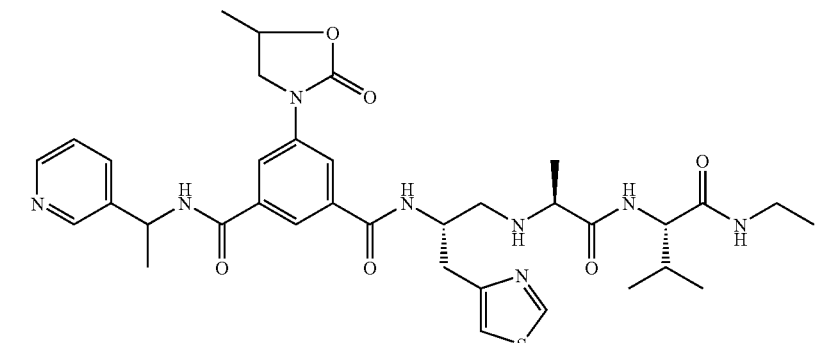 | 708 [M + H]+ | 3.59 min (HPLC 1) |

-continued
| Example | | Mass spectrum | Retention time (method) |
|---|---|---|---|
| 23.28 | 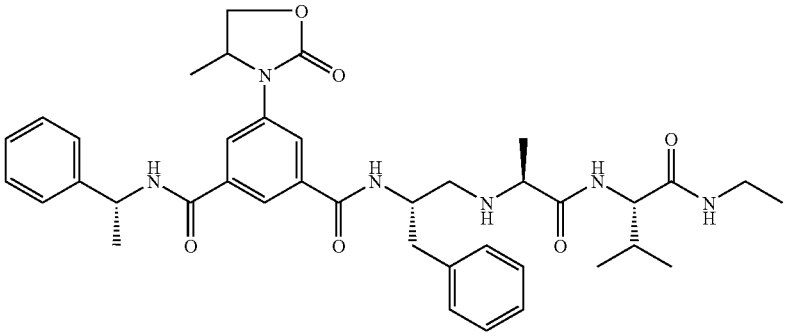 | 700 [M + H]+ | 4.62 min (HPLC 1) |
| 23.29 | 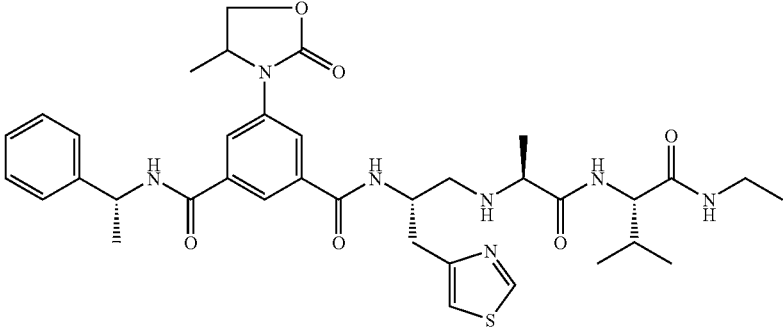 | 707 [M + H]+ | 4.29 min (HPLC 1) |
| 23.30 | 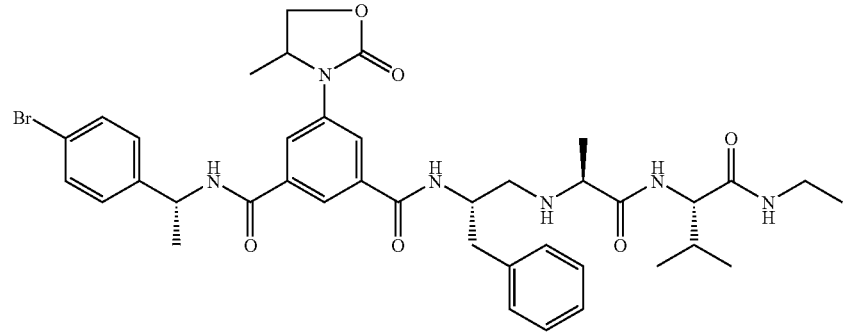 | 779 [M + H]+ | 4.80 min (HPLC 1) |
| 23.31 | 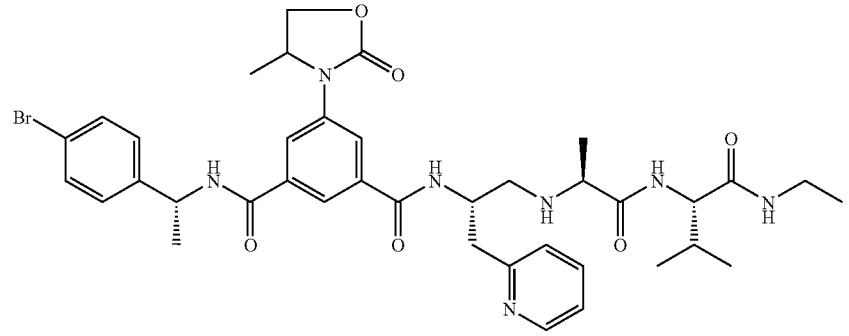 | 780 [M + H]+ | 4.28 min (HPLC 1) |

-continued
| Example | | Mass spectrum | Retention time (method) |
|---|---|---|---|
| 23.32 | 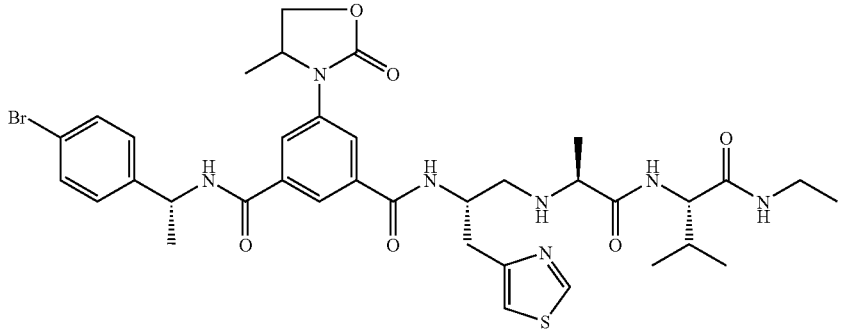 | 786 [M + H]+ | 4.58 min (HPLC 1) |
| 23.33 | 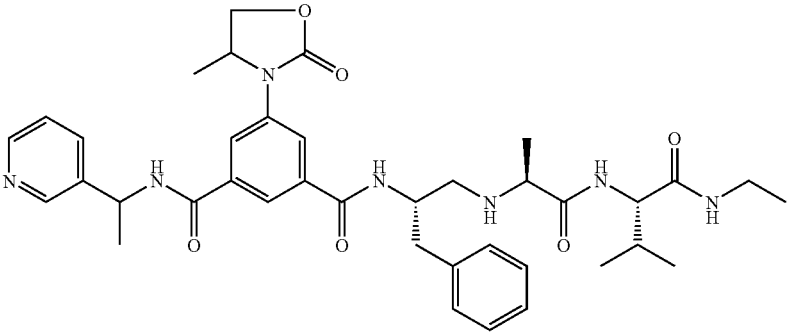 | 701 [M + H]+ | 3.87 min (HPLC 1) |
| 23.34 | 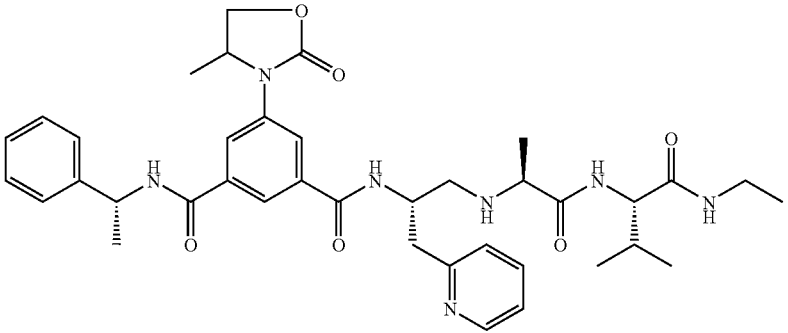 | 701 [M + H]+ | 4.05 min (HPLC 1) |
| 23.35 | 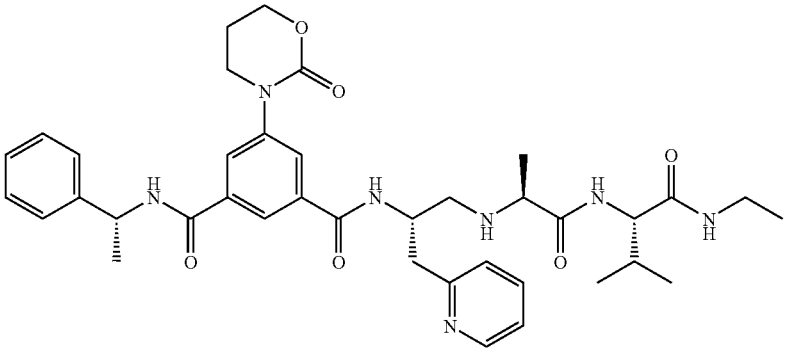 | 701 [M + H]+ | |

-continued

| Example | | Mass spectrum | Retention time (method) |
|---|---|---|---|
| 23.36 | 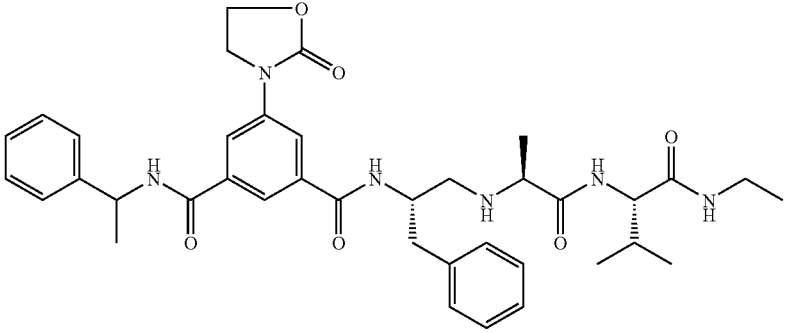 | 686 [M + H]+ | 4.53 min (HPLC 1) |

Example 24

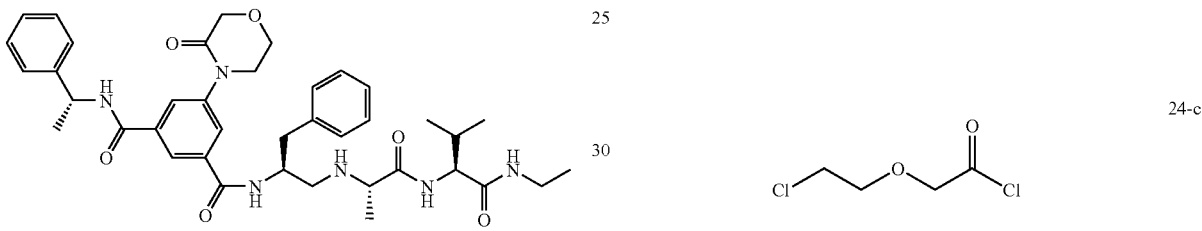

Example 24 was prepared analogously to Example 1 from 24-e and the corresponding precursors.
ES-MS (M+H)+=700
RT (HPLC-MS): 2.70 min
a) Preparation of 24-a:

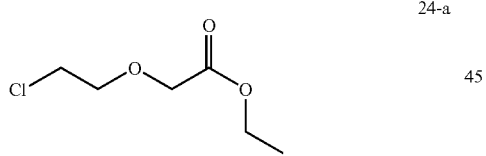

24-a 10.22 g (100 mmol) 2-dioxane were dissolved in 50 ml of ethanol and combined with 14.5 ml (41.4 mmol) thionyl chloride, while the temperature was kept below 30° C. The reaction solution was refluxed for 4 h and then evaporated down i. vac.

Yield 9.2 g of colourless liquid which was used further in its crude state.
b) Preparation of 24-b:

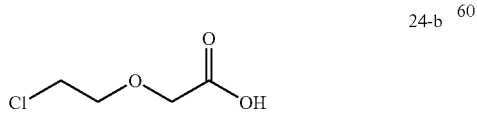

24-b 9.2 g (41.4 mmol) 24-a were dissolved in 50 ml THF and combined with 30 ml of 2N NaOH solution. The reaction solution was stirred for 4 h at ambient temperature. Standard working up yielded 6.7 g of colourless oil.
c) Preparation of 24-c:

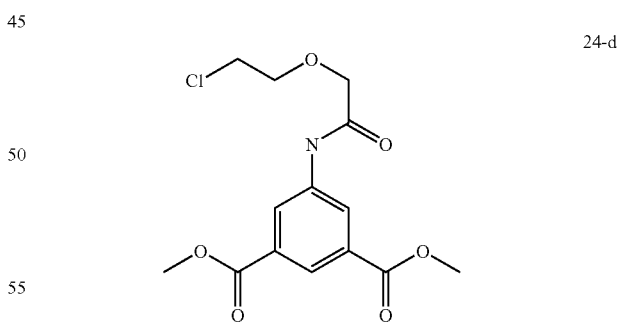

6.7 g (48.4 mmol) 23-c were combined with 25 ml of thionyl chloride and stirred for 2 h at 60° C. The mixture was then evaporated down in vacuo and further reacted immediately in 24-d.
d) Preparation of 24-d:

9.3 g (44.6 mmol) dimethyl 5-amino-isophthalate were dissolved in 30 ml of ethanol and combined with 18.5 ml (133.4 mmol) triethylamine. Subsequently 7.7 g (448.9 mmol) of 24-c dissolved in 30 ml THF were slowly added dropwise while cooling with ice. The reaction solution was refluxed for 2 h. Standard working up yielded 12.6 g of 24-d as a beige solid (86%).

e) Preparation of 24-e:

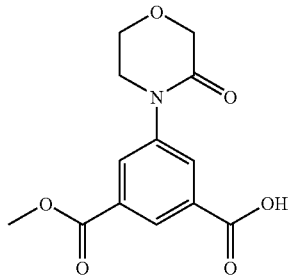

7 g (21.2 mmol) 24-d and 7.15 g potassium-tert-butoxide were dissolved in 40 ml DMF and stirred for 2 h at 60° C. The reaction solution was evaporated down in vacuo, combined with water and extracted three times with ethyl acetate. After acidification of the aqueous phase with 4N HCL solution the mixture was again extracted three times with ethyl acetate. The combined organic phases were dried over magnesium sulphate and distilled off in vacuo. The residue was purified by MPLC (silica gel, methylene chloride:methanol=10:1). Yield 1.6 g of 24-d as an orange oil (27%).

RT (HPLC-MS)=2.16 min

Some examples of formulations will now be described, wherein the term "active substance" denotes one or more compounds according to the invention including the salts thereof. In the case of one of the aforementioned combinations with one or more other active substances the term "active substance" also includes the additional active substances.

Example A

Tablets containing 100 mg of active substance
Composition:
1 tablet contains:

| | |
|---|---|
| active substance | 100.0 mg |
| lactose | 80.0 mg |
| corn starch | 34.0 mg |
| polyvinylpyrrolidone | 4.0 mg |
| magnesium stearate | 2.0 mg |
| | 220.0 mg |

Method of Preparation:

The active substance, lactose and starch are mixed together and uniformly moistened with an aqueous solution of the polyvinylpyrrolidone. After the moist composition has been screened (2.0 mm mesh size) and dried in a rack-type drier at 50° C. it is screened again (1.5 mm mesh size) and the lubricant is added. The finished mixture is compressed to form tablets.

Weight of tablet: 220 mg

Diameter: 10 mm, biplanar, facetted on both sides and notched on one side.

Example B

Tablets containing 150 mg of active substance
Composition:
1 tablet contains:

| | |
|---|---|
| active substance | 50.0 mg |
| powdered lactose | 89.0 mg |
| corn starch | 40.0 mg |
| colloidal silica | 10.0 mg |
| polyvinylpyrrolidone | 10.0 mg |
| magnesium stearate | 1.0 mg |
| | 300.0 mg |

Preparation:

The active substance mixed with lactose, corn starch and silica is moistened with a 20% aqueous polyvinylpyrrolidone solution and passed through a screen with a mesh size of 1.5 mm. The granules, dried at 45° C., are passed through the same screen again and mixed with the specified amount of magnesium stearate. Tablets are pressed from the mixture.

| | |
|---|---|
| Weight of tablet: | 300 mg |
| die: | 10 mm, flat |

Example C

Hard gelatine capsules containing 150 mg of active substance
1 capsule contains:

| | |
|---|---|
| active substance | 50.0 mg |
| corn starch (dried) | approx. 80.0 mg |
| lactose (powdered) | approx. 87.0 mg |
| magnesium stearate | 3.0 mg |
| | approx. 420.0 mg |

Preparation:

The active substance is mixed with the excipients, passed through a screen with a mesh size of 0.75 mm and homogeneously mixed using a suitable apparatus. The finished mixture is packed into size 1 hard gelatine capsules.

Capsule filling: approx. 320 mg

Capsule shell: size 1 hard gelatine capsule.

Example D

Suppositories containing 150 mg of active substance
1 suppository contains:

| | |
|---|---|
| active substance | 150.0 mg |
| polyethyleneglycol 1500 | 550.0 mg |
| polyethyleneglycol 6000 | 460.0 mg |
| polyoxyethylene sorbitan monostearate | 840.0 mg |
| | 2,000.0 mg |

Preparation:

After the suppository mass has been melted the active substance is homogeneously distributed therein and the melt is poured into chilled moulds.

Example E

| Ampoules containing 10 mg active substance Composition: | |
|---|---|
| active substance | 10.0 mg |
| 0.01N hydrochloric acid q.s. | |
| double-distilled water ad | 2.0 ml |

Preparation:

The active substance is dissolved in the necessary amount of 0.01 N HCl, made isotonic with common salt, filtered sterile and transferred into 2 ml ampoules.

Example F

| Ampoules containing 50 mg of active substance Composition: | |
|---|---|
| active substance | 50.0 mg |
| 0.01N hydrochloric acid q.s. | |
| double-distilled water ad | 10.0 ml |

Preparation:

The active substance is dissolved in the necessary amount of 0.01 N HCl, made isotonic with common salt, filtered sterile and transferred into 10 ml ampoules.

We claim:

1. A compound of formula (I):—

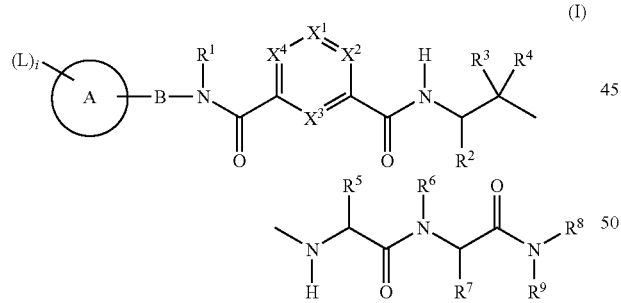

wherein:

A is selected from the group consisting of:

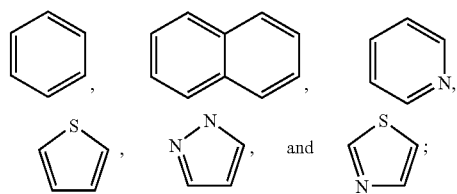

L each independently is hydrogen, fluorine, chlorine, bromine, iodine, cyano, hydroxy, $F_3C$, $HF_2C$, $FH_2C$, $C_{1-6}$-alkyl, $C_{1-6}$-alkoxy, $C_{3-7}$-cycloalkyl, $C_{3-7}$-cycloalkyl-$C_{1-3}$-alkyl, phenyl, $(R^{14})_2N$, $(R^{14})_2N$—CO, $R^{14}$—CO—$(R^{14})_2N$—CO—$(R^{14})N$, $R^{14}$—$SO_2$—$(R^{14})N$ or $(R^{14})_2N$—$SO_2$—, wherein the above-mentioned groups are optionally substituted by one or more fluorine atoms, and i is 0, 1 or 2;

B is selected from the group consisting of:

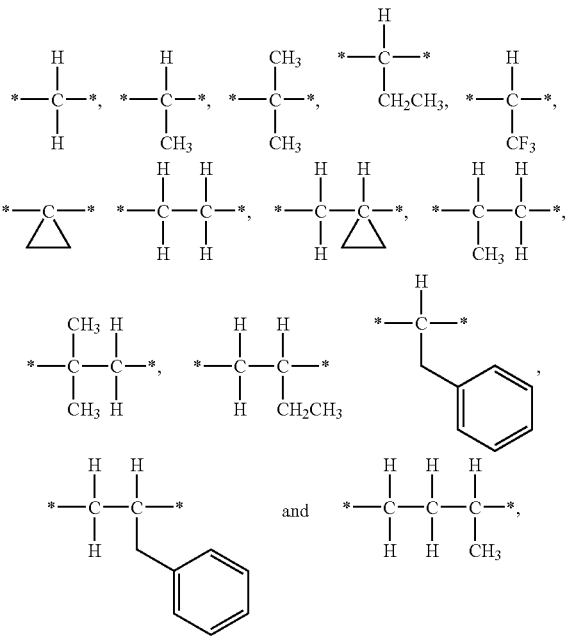

wherein one or more hydrogen atoms are optionally replaced by fluorine;

$R^1$ is hydrogen, $C_{1-6}$-alkyl, $C_{2-6}$-alkenyl, $C_{2-6}$-alkynyl, $C_{3-7}$-cycloalkyl, $C_{3-7}$-cycloalkyl-$C_{1-3}$-alkyl, heterocyclyl, heterocyclyl-$C_{1-3}$-alkyl, aryl, aryl-$C_{1-3}$-alkyl, heteroaryl or heteroaryl-$C_{1-3}$-alkyl, wherein the above-mentioned groups are optionally substituted independently of one another by one or more groups selected from fluorine, chlorine, bromine, hydroxy, carboxy, cyano, nitro, $F_3C$, $HF_2C$, $FH_2C$, $C_{1-3}$-alkyl, $C_{1-3}$-alkoxy and hydroxy-$C_{1-3}$-alkyl;

$X^1$ is $C(R^{10})$;

$X^2$, $X^3$, and $X^4$ each independently is $C(R^{11})$;

$R^2$ is n-propyl, 2-propynyl, n-butyl, benzyl, imidazolo-4-ylmethyl, cyclohexylmethyl, cyclohexylethyl, cyclobutylmethyl, cyclopentylmethyl, benzyloxymethyl, benzyloxyethyl, p-trifluorobenzyl, thiazolylmethyl, 3,5-difluorobenzyl, 2-bromothienylmethyl, cyanoethyl, cyanomethyl, furanylmethyl, phenylethyl, pyridylmethyl, pyridylethyl or thienylmethyl, wherein the above-mentioned groups are optionally substituted independently of one another by one or more groups selected from among fluorine, chlorine, bromine, cyano, $F_3C$, $HF_2C$, and $FH_2C$, $R^3$, $R^4$ each independently is hydrogen, $C_{1-6}$-alkyl, fluorine, $F_3C$, $HF_2C$ or $FH_2C$;

$R^5$ is $C_{1-6}$-alkyl, $C_{3-6}$-cycloalkyl, $C_{3-6}$-cycloalkyl-$C_{1-3}$-alkyl, heterocyclyl, heterocyclyl-$C_{1-3}$-alkyl or phenyl-$C_{1-3}$-alkyl, wherein the above-mentioned groups are optionally substituted independently of one another by one or more groups selected from fluorine, chlorine, bromine, iodine, cyano, hydroxy, carboxy, $C_{1-3}$-alkyl, $C_{1-3}$-alkoxy and $(R^{14})_2N$; and $R^7$ is $C_{1-6}$-alkyl, $C_{3-6}$ cycloalkyl, $C_{3-6}$ cycloalkyl-$C_{1-3}$-alkyl, phenyl or phenyl-$C_{1-3}$-alkyl, wherein the above-mentioned groups are optionally substituted independently of one another by one or more groups selected from fluorine, chlorine, bromine, iodine, cyano, hydroxy, carboxy, $C_{1-3}$-alkyl, $C_{1-3}$-alkoxy and $(R^{14})_2N$;

$R^6$, $R^9$ each independently is hydrogen, $C_{1-6}$-alkyl, $C_{1-6}$-alkoxy-$C_{1-3}$-alkyl, $C_{3-7}$-cycloalkyl, $C_{3-7}$-cycloalkyl-$C_{1-3}$-alkyl, $C_{2-6}$-alkenyl, heterocyclyl-$C_{1-3}$-alkyl, heteroaryl, heteroaryl-$C_{1-3}$-alkyl or $C_{2-6}$-alkynyl, wherein the above-mentioned groups are optionally substituted independently of one another by one or more groups selected from among fluorine, chlorine, bromine, iodine, cyano, $C_{1-3}$-alkyl, $C_{1-6}$-alkoxy- and $(R^{14})_2N$;

$R^8$ is hydrogen, $C_{1-6}$-alkyl, $C_{2-6}$-alkenyl, $C_{2-6}$-alkynyl, $C_{3-7}$-cycloalkyl, $C_{3-7}$-cycloalkyl-$C_{1-3}$-alkyl, $C_{3-7}$-cycloalkyl-$C_{2-4}$-alkenyl, $C_{3-7}$-cycloalkyl-$C_{2-4}$-alkynyl, $C_{3-7}$-cycloalkenyl, $C_{3-7}$-cycloalkenyl-$C_{1-6}$-alkyl, $C_{3-7}$-cycloalkenyl-$C_{2-6}$-alkenyl, $C_{3-7}$-cycloalkenyl-$C_{2-6}$-alkynyl, heterocyclyl, heterocyclyl-$C_{1-3}$-alkyl, heterocyclyl-$C_{2-4}$-alkenyl, heterocyclyl-$C_{2-4}$-alkynyl, aryl, aryl-$C_{1-3}$-alkyl, aryl-$C_{2-4}$-alkenyl, aryl-$C_{2-4}$-alkynyl, heteroaryl, heteroaryl-$C_{1-3}$-alkyl, heteroaryl-$C_{2-4}$-alkenyl or heteroaryl-$C_{2-4}$-alkynyl, wherein the above-mentioned groups are optionally substituted independently of one another by one or more groups selected from fluorine, chlorine, bromine, iodine, hydroxy, oxo, carboxy, formyl, cyano, nitro, $C_{1-3}$-alkyl, heterocyclyl, heterocyclyl-$C_{1-3}$-alkyl, $R^{15}$—O, $R^{15}$—O—$C_{1-3}$-alkyl, $R^{15}$—S, $R^{15}$—S—$C_{1-3}$-alkyl, aryl, heteroaryl, heteroaryl-$C_{1-3}$-alkyl, aryl-$C_{1-6}$-alkyl, $(R^{14})_2N$, $(R^{14})_2N$—$C_{1-3}$-alkyl, $(R^{14})_2N$—CO, $(R^{14})_2N$—CO—$N(R^{14})$—, $(R^{14})_2N$—$SO_2$— and $HOSO_2$—;

$R^{10}$ is hydrogen, fluorine, chlorine, bromine, cyano, $C_{1-4}$-alkyl, $C_{1-4}$-alkoxy, $C_{3-6}$-cycloalkyl, $C_{3-6}$-cycloalkyloxy, $C_{3-6}$-cycloalkyl-$C_{1-3}$-alkoxy, 1,3-diazacyclohexan-2-on-1-yl, 2-oxo-1,3-oxazinan-3-yl, 3-oxomorpholino, 1,1-dioxo-[1,2,6]thiadiazinan-2-yl, phenyl, pyridyl, thienyl, furyl, $(R^{14})_2N$—, $R^{12}$—CO—$(R^{13})N$— or $R^{12}$—$SO_2$—$(R^{13})N$—, wherein the above-mentioned groups are optionally substituted independently of one another by one or more groups selected from fluorine, chlorine, bromine, carboxy, cyano, $C_{1-4}$-alkyl, $C_{1-4}$-alkoxy, $C_{1-4}$-alkyl-S, $R^{15}$—CO, $R^{15}$—O—CO, $R^{14}$—$SO_2$—, $F_3C$, $HF_2C$, $FH_2C$, $F_3C$—O, $HF_2C$—O, $FH_2C$—O and $(R^{14})_2N$—CO; and $R^{11}$ each independently is hydrogen, fluorine, chlorine, bromine, iodine, $C_{1-6}$-alkyl-O, $(R^{14})_2N$ or $C_{1-3}$-alkyl, wherein the $C_{1-3}$-alkyl group is optionally substituted by one or more fluorine atoms;

$R^{12}$ is $C_{1-6}$-alkyl, $C_{2-6}$-alkenyl, $C_{2-6}$-alkynyl, $C_{3-7}$-cycloalkyl-$C_{2-6}$-alkenyl, aryl-$C_{2-3}$-alkenyl, heteroaryl-$C_{2-4}$-alkenyl, heterocyclyl-$C_{2-4}$-alkenyl, aryl-$C_{2-3}$-alkynyl, $C_{3-7}$-cycloalkyl-$C_{2-4}$-alkynyl, heterocyclyl-$C_{2-4}$-alkynyl- heteroaryl-$C_{2-3}$-alkynyl, $C_{3-7}$-cycloalkyl, $C_{3-7}$-cycloalkyl-$C_{1-6}$-alkyl, heterocyclyl, heterocyclyl-$C_{1-4}$-alkyl, $C_{3-7}$-cycloalkenyl, $C_{3-7}$-cycloalkenyl-$C_{1-6}$-alkyl, $C_{3-7}$-cycloalkenyl-$C_{2-6}$-alkenyl, $C_{3-7}$-cycloalkenyl-$C_{2-6}$-alkynyl, aryl, aryl-$C_{1-4}$-alkyl, heteroaryl, heteroaryl-$C_{1-3}$-alkyl or $(R^{14})_2N$, wherein the above-mentioned groups are optionally substituted independently of one another by one or more groups selected from among fluorine, chlorine, bromine, hydroxy, oxo, carboxy, formyl, cyano, nitro, $C_{1-3}$-alkyl, heterocyclyl, heterocyclyl-$C_{1-3}$-alkyl, $R^{15}$—O, $R^{15}$—O—$C_{1-3}$-alkyl, $R^{14}$—$CO(R^{14})N$, $R^{14}$—$SO_2(R^{14})N$, $(R^{14})_2N$—$SO_2$—, $R^{14}$—$SO_2$—, $R^{14}$—SO, $R^{14}$—S, $(R^{14})_2N$, $(R^{14})_2N$—$C_{1-3}$-alkyl and $(R^{14})_2N$—CO;

$R^{13}$ is hydrogen, $C_{1-6}$-alkyl, $C_{2-6}$-alkenyl, $C_{2-6}$-alkynyl, $C_{3-7}$-cycloalkyl, $C_{3-7}$-cycloalkyl-$C_{1-3}$-alkyl, aryl, aryl-$C_{1-3}$-alkyl, heterocyclyl, heterocyclyl-$C_{1-3}$-alkyl, heterocyclyl-$C_{2-3}$-alkenyl, heterocyclyl-$C_{2-3}$-alkynyl, heteroaryl, heteroaryl-$C_{2-3}$-alkenyl, heteroaryl-$C_{2-3}$-alkynyl or heteroaryl-$C_{1-3}$-alkyl, wherein the above-mentioned groups are optionally substituted independently of one another by one or more groups selected from among fluorine, chlorine, bromine, hydroxy, oxo, carboxy, formyl, cyano, nitro, $C_{1-3}$-alkyl, heterocyclyl, heterocyclyl-$C_{1-3}$-alkyl, $R^{15}$—O, $R^{15}$—O—$C_{1-3}$-alkyl, $(R^{14})_2N$, $(R^{14})_2N$—$C_{1-3}$-alkyl and $R^{14}$ CO;

or $R^{12}$ and $R^{13}$ together form a $C_{2-6}$-alkylene bridge, so that with the inclusion of the nitrogen atom linked to $R^{13}$ and the $SO_2$— or CO group linked to $R^{12}$, a heterocyclic ring is formed, wherein one or two $CH_2$ groups of the $C_{2-6}$-alkylene bridge may be replaced independently of one another by O, S, SO, $SO_2$ or $N(R^{14})$ in such a way that in each case two O or S atoms or an O and an S atom are not joined together directly, and the C atoms of the above-mentioned $C_{2-6}$-alkylene bridge are optionally substituted by one or more groups selected from fluorine, chlorine, bromine, hydroxy, carboxy, formyl, cyano, $F_3C$, $HF_2C$, $FH_2C$, $C_{1-6}$-alkyl, $C_{1-6}$-alkoxy, oxo and nitro;

$R^{14}$ each independently is hydrogen, $C_{1-6}$-alkyl, $C_{1-6}$-alkoxy-$C_{1-3}$-alkyl, $C_{3-6}$-cyclyoalkyl, $C_{3-6}$-cyclyoalkyl-$C_{1-3}$-alkyl, aryl or aryl-$C_{1-3}$-alkyl, heterocyclyl, heterocyclyl-$C_{1-3}$-alkyl, heteroaryl or heteroaryl-$C_{1-3}$-alkyl, wherein two $C_{1-6}$-alkyl groups bound to the same nitrogen atom together may form a $C_{2-6}$-alkylene bridge, so that with the inclusion of the nitrogen atom bound to the groups $R^{14}$ a heterocyclic ring is formed, wherein a $CH_2$ group of the $C_{2-6}$-alkylene bridge may be replaced by O, S or $N(R^{14})$, and the above-mentioned groups and the heterocyclic ring are optionally substituted independently of one another by one or more groups selected from among fluorine, chlorine, bromine, iodine, hydroxy, oxo, carboxy, formyl, cyano, nitro, $C_{1-3}$-alkyl, hydroxy-$C_{1-3}$-alkyl, $C_{1-3}$-alkoxy, $(R^{15})_2N$—CO or $(R^{15})_2N$, and $R^{15}$ each independently is hydrogen, $C_{1-6}$-alkyl, $C_{2-6}$-alkenyl, $C_{2-6}$-alkynyl, $C_{3-7}$-cycloalkyl, $C_{3-7}$-cyclyoalkyl-$C_{1-3}$-alkyl, aryl, aryl-$C_{1-3}$-alkyl, heterocyclyl, heterocyclyl-$C_{1-3}$-alkyl, heteroaryl or heteroaryl-$C_{1-3}$-alkyl, wherein the above-mentioned groups are optionally substituted independently of one another by one or more groups selected from fluorine, chlorine, bromine, iodine, hydroxy, oxo, carboxy, formyl, cyano, nitro, $C_{1-3}$-alkyl- and $C_{1-3}$-alkoxy;

or a tautomer, diastereomer, or enantiomer thereof, or a salt thereof.

2. A compound according to claim 1, wherein
A is phenyl, thienyl, thiazolyl or pyridyl.

3. A compound according to claim 1, wherein
L each independently is hydrogen, fluorine, chlorine, bromine, hydroxy, $C_{1-4}$-alkyl or $C_{1-4}$-alkoxy,
   wherein the above-mentioned groups are optionally substituted by one or more fluorine atoms, and
i is 0, 1 or 2.

4. A compound according to claim 1, wherein
B is a $C_{1-2}$-alkylene bridge,
   wherein the $C_{1-2}$-alkylene bridge is optionally substituted by one or more $C_{1-4}$-alkyl groups, and
   wherein two $C_{1-4}$-alkyl groups bound to the same carbon atom of the $C_{1-2}$-alkylene bridge may be joined together forming a cyclopropyl group, and
   wherein one or more hydrogen atoms of the above-mentioned $C_{1-2}$-alkylene bridge and/or the $C_{1-4}$-alkyl groups and/or the cyclopropyl group formed therefrom are optionally replaced by one or more fluorine atoms.

5. A compound according to claim 1, wherein the part of the compound of formula (I) having partial formula (II)

is selected from the group consisting of the following groups:

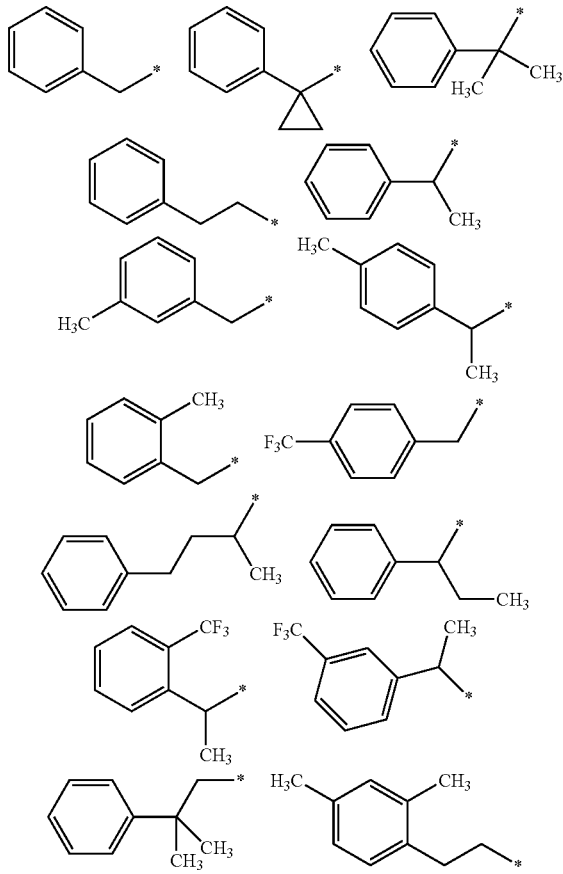

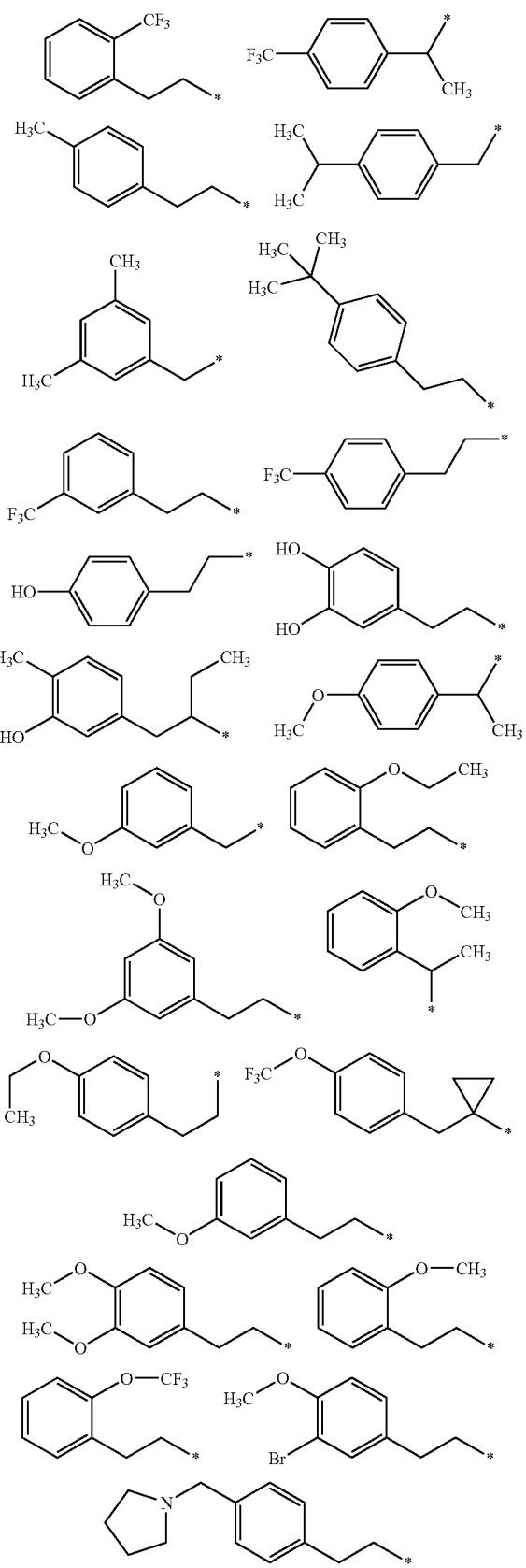

-continued
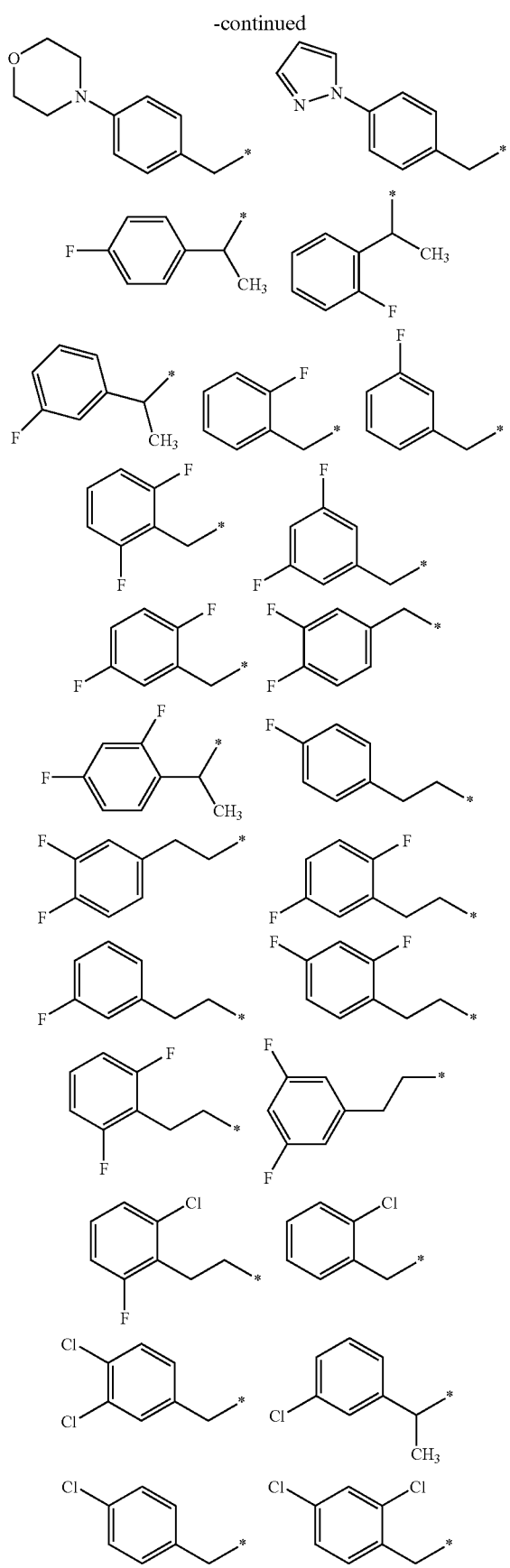
-continued
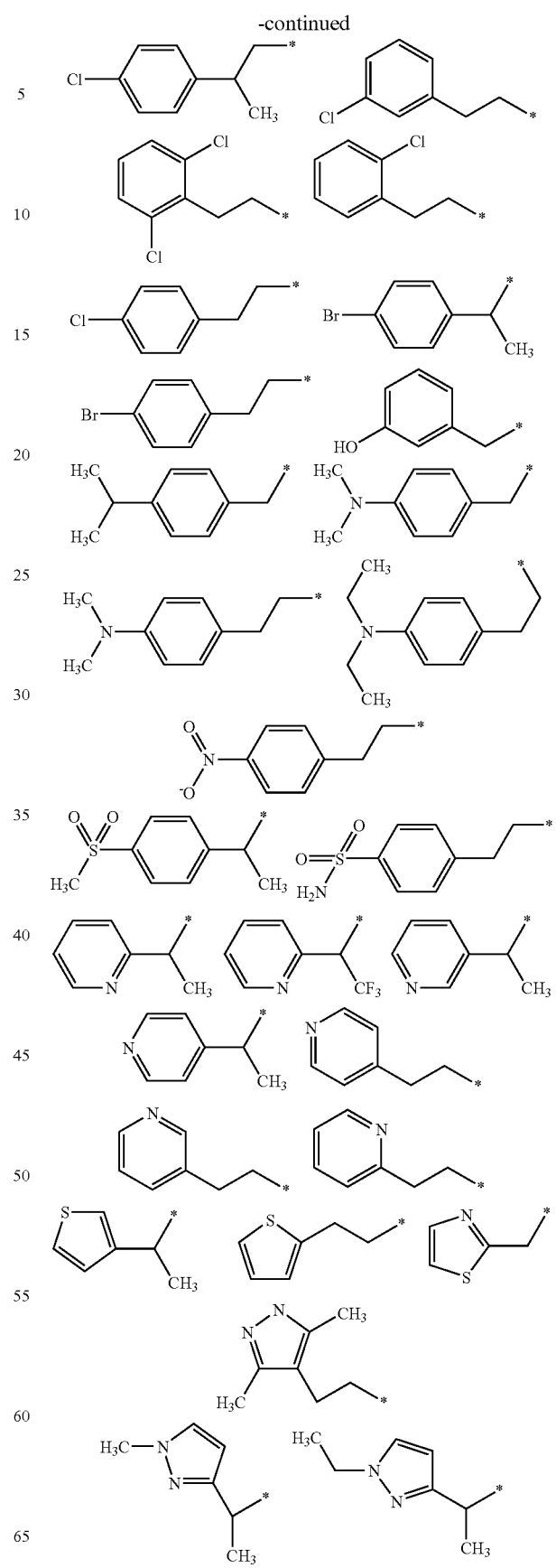

-continued

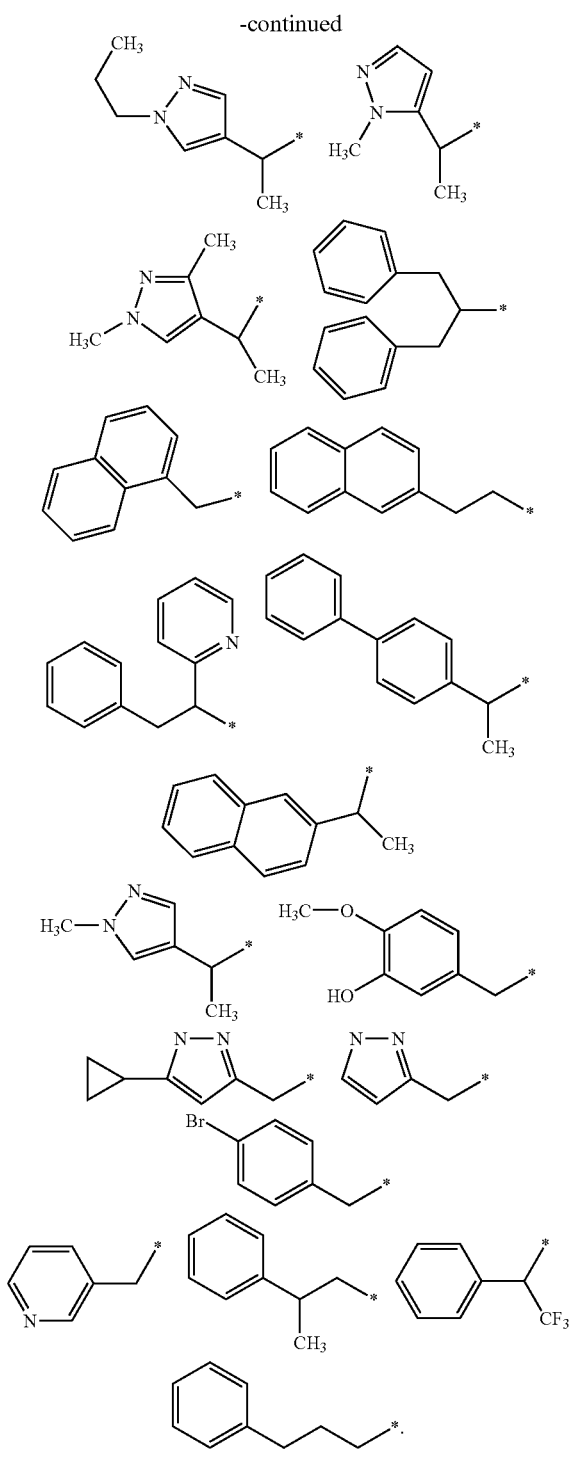

6. A compound according to claim 1, wherein $R^1$ is hydrogen, $C_{1-4}$-alkyl, $C_{3-4}$-alkenyl, $C_{3-6}$-cycloalkyl, $C_{3-6}$-cycloalkyl-$C_{1-3}$-alkyl, wherein the above-mentioned groups are optionally substituted independently of one another by one or more groups selected from among fluorine, hydroxy and $C_{1-3}$-alkoxy.

7. A compound according to claim 1, wherein
$R^2$ is n-propyl, n-butyl, 2-propynyl, benzyl, 2-phenylethyl, pyridylmethyl, furanylmethyl, thienylmethyl or thiazolylmethyl, wherein the above-mentioned n-propyl, n-butyl, and propynyl groups are optionally substituted by one or more fluorine atoms and the benzyl, and 2-phenylethyl, furanylmethyl, thienylmethyl or thiazolylmethyl groups are optionally substituted independently of one another by one or more groups selected from fluorine, chlorine, bromine, methyl, $F_3C$, $HF_2C$, $FH_2C$ and $H_2N$.

8. A compound according to claim 1, wherein
$R^3$ is hydrogen, $C_{1-6}$-alkyl, fluorine, $F_3C$, $HF_2C$ or $FH_2C$; and
$R^4$ is hydrogen.

9. A compound according to claim 1, wherein
$R^8$ is hydrogen, $C_{1-6}$-alkyl, $C_{2-6}$-alkenyl, $C_{2-6}$-alkynyl, $C_{3-7}$-cycloalkyl, $C_{3-7}$-cycloalkyl-$C_{1-3}$-alkyl, $C_{3-7}$-cycloalkenyl, $C_{3-7}$-cycloalkenyl-$C_{1-3}$-alkyl, heterocyclyl, heterocyclyl-$C_{1-3}$-alkyl, aryl, aryl-$C_{1-3}$-alkyl, heteroaryl or heteroaryl-$C_{1-3}$-alkyl,
wherein the above-mentioned groups are optionally substituted independently of one another by one or more groups selected from fluorine, chlorine, bromine, iodine, hydroxy, carboxy, cyano, nitro, $C_{1-3}$-alkyl, heterocyclyl, heterocyclyl-$C_{1-3}$-alkyl, aryl, aryl-$C_{1-3}$-alkyl, heteroaryl, heteroaryl-$C_{1-3}$-alkyl, $(R^{14})_2N$, $(R^{14})_2N$—$C_{1-3}$-alkyl, $(R^{14})_2N$—CO, $(R^{14})_2N$—CO—$N(R^{14})$—, $(R^{14})_2N$—$SO_2$—, $R^{15}$—O, $R^{15}$—O—$C_{1-3}$-alkyl, $R^{15}$—S and $R^{15}$—S—$C_{1-3}$-alkyl.

10. A compound according to claim 1, wherein
$R^8$ is hydrogen, $C_{1-6}$-alkyl, $C_{2-6}$-alkenyl, $C_{2-6}$-alkynyl, $C_{3-6}$-cycloalkyl, $C_{3-6}$-cycloalkyl-$C_{1-3}$-alkyl, heterocyclyl, heterocyclyl-$C_{1-3}$-alkyl, phenyl, phenyl-$C_{1-3}$-alkyl, heteroaryl or heteroaryl-$C_{1-3}$-alkyl,
wherein the heteroaryl groups are 5- or 6-membered aromatic heteroaryl groups which contain 1, 2 or 3 heteroatoms selected from the group consisting of N, O and S, and
wherein the above-mentioned groups are optionally substituted independently of one another by one or more groups selected from fluorine, chlorine, bromine, carboxy, hydroxy, cyano, $C_{1-3}$-alkyl, $C_{1-3}$-alkoxy, $C_{1-3}$-alkoxy-$C_{1-3}$-alkyl, $C_{1-3}$-alkyl-S, $C_{1-3}$-alkyl-S—$C_{1-3}$-alkyl, hydroxy-$C_{1-3}$-alkyl, heterocyclyl, heterocyclyl-$C_{1-3}$-alkyl, $(R^{14})_2N$, $(R^{14})_2N$—$C_{1-3}$-alkyl, $(R^{14})_2N$—CO—$N(R^{14})$— and $(R^{14})_2N$—$SO_2$—.

11. A compound according to claim 1, wherein
$R^8$ is hydrogen, $C_{1-6}$-alkyl, $C_{3-6}$-cycloalkyl, $C_{3-6}$-cycloalkyl-$C_{1-3}$-alkyl, phenyl-$C_{1-3}$-alkyl or tetrahydropyranyl-$C_{1-3}$-alkyl,
wherein the above-mentioned groups are optionally substituted independently of one another by one or more groups selected from fluorine, chlorine, bromine, pyrrolidin-1-ylmethyl, hydroxy, cyano, $C_{1-3}$-alkyl, $C_{1-3}$-alkoxy, $C_{1-3}$-alkyl-S, hydroxy-$C_{1-3}$-alkyl, $(R^{14})_2N$, $(R^{14})_2N$—$C_{1-3}$-alkyl, $(R^{14})_2N$—CO—$N(R^{14})$— and $(R^{14})_2N$—$SO_2$—.

12. A compound according to claim 1, wherein
$R^5$ is $C_{1-6}$-alkyl, cyclopropyl, $C_{3-6}$-cycloalkyl-$C_{1-3}$-alkyl or phenyl-$C_{1-3}$-alkyl,
wherein the above-mentioned groups are optionally substituted independently of one another by one or more groups selected from fluorine, chlorine, bromine, iodine, cyano, hydroxy, carboxy, $C_{1-3}$-alkyl, $C_{1-3}$-alkoxy and $(R^{14})_2N$, and
$R^7$ is $C_{1-6}$-alkyl, $C_{3-6}$-cycloalkyl, $C_{3-6}$-cycloalkyl-$C_{1-3}$-alkyl, phenyl or phenyl-$C_{1-3}$-alkyl, wherein the above-mentioned groups are optionally substituted independently of one another by one or more groups selected from fluorine, chlorine, bromine, iodine, cyano, hydroxy, carboxy, $C_{1-3}$-alkyl, $C_{1-3}$-alkoxy and $(R^{14})_2N$.

13. A compound according to claim 1, wherein
$R^5$, $R^7$ each independently is $C_{1-4}$-alkyl or cyclopropyl,
wherein one or more hydrogen atoms of the above-mentioned groups are optionally replaced by fluorine atoms.

14. A compound according to claim 1, wherein
$R^6$ is hydrogen, and
$R^9$ is hydrogen or $C_{1-4}$-alkyl,
wherein one or more hydrogen atoms of the $C_{1-4}$-alkyl group may be replaced by fluorine.

15. A compound according to claim 1, wherein
$R^{10}$ is hydrogen, fluorine, chlorine, bromine, cyano, $C_{1-4}$-alkyl, $C_{1-4}$-alkoxy, $C_{3-6}$-cycloalkyl, $C_{3-6}$-cycloalkyloxy, $C_{3-6}$-cycloalkyl-$C_{1-3}$-alkoxy, 1,3-diazacyclohexan-2-on-1-yl, 2-oxo-1,3-oxazinan-3-yl, 3-oxomorpholino, 1,1-dioxo-[1,2,6]thiadiazinan-2-yl, phenyl, pyridyl, thienyl, furyl, $R^{12}$—CO—$(R^{13})$N or $R^{12}$—SO$_2$—$(R^{13})$N,
wherein the above-mentioned groups are optionally substituted independently of one another by one or more groups selected from fluorine, chlorine, bromine, carboxy, cyano, $C_{1-4}$-alkyl, $C_{1-4}$-alkoxy, $C_{1-4}$-alkyl-S, $R^{15}$—CO, $R^{15}$—O—CO, $R^{14}$—SO$_2$—, F$_3$C, HF$_2$C, FH$_2$C, F$_3$C—O, HF$_2$C—O, FH$_2$C—O and $(R^{14})_2$N—CO; and
$R^{11}$ each independently is hydrogen, fluorine, chlorine, or bromine.

16. A compound according to claim 1, wherein
$R^{10}$ is $R^{12}$—CO—$(R^{13})$N, $R^{12}$—SO$_2$—$(R^{13})$N, cyanophenyl or cyanothienyl,
wherein the above-mentioned cyanophenyl and cyanothienyl groups are optionally substituted independently of one another by one or more groups selected from fluorine, chlorine, bromine, $C_{1-4}$-alkyl, $C_{1-4}$-alkoxy, F$_3$C, HF$_2$C, FH$_2$C, F$_3$C—O, HF$_2$C—O and FH$_2$C—O; and $R^{11}$ each independently is hydrogen, fluorine, chlorine, or bromine.

17. A compound according to claim 1, wherein
$R^{12}$ is $C_{1-6}$-alkyl, $C_{2-6}$-alkenyl, $C_{2-6}$-alkynyl, $C_{3-7}$-cycloalkyl, $C_{3-7}$-cycloalkyl-$C_{1-3}$-alkyl, heterocyclyl, heterocyclyl-$C_{1-3}$-alkyl, $C_{3-7}$-cycloalkenyl, $C_{3-7}$-cycloalkenyl-$C_{1-3}$-alkyl, aryl, aryl-$C_{1-3}$-alkyl, heteroaryl, heteroaryl-$C_{1-3}$-alkyl or $(R^{14})_2N$,
wherein the above-mentioned groups are optionally substituted by one or more groups selected from fluorine, chlorine, bromine, hydroxy, carboxy, cyano, nitro, $C_{1-3}$-alkyl, heterocyclyl, heterocyclyl-$C_{1-3}$-alkyl, $C_{1-3}$-alkoxy, hydroxy-$C_{1-3}$-alkyl, $R^{14}$—CO($R^{14}$)N, $R^{14}$—SO$_2$($R^{14}$)N, $(R^{14})_2$N—SO$_2$—, $R^{14}$—SO$_2$—, $R^{14}$—SO, $R^{14}$—S, $(R^{14})_2$N, $(R^{14})_2$N—$C_{1-3}$-alkyl and $(R^{14})_2$N—CO; and
$R^{13}$ is hydrogen, $C_{1-6}$-alkyl, $C_{2-6}$-alkenyl, $C_{2-6}$-alkynyl, $C_{3-7}$-cycloalkyl, $C_{3-7}$-cycloalkyl-$C_{1-3}$-alkyl, aryl, aryl-$C_{1-3}$-alkyl, heterocyclyl, heterocyclyl-$C_{1-3}$-alkyl, heteroaryl or heteroaryl-$C_{1-3}$-alkyl,
wherein the above-mentioned groups are optionally substituted independently of one another by one or more groups selected from fluorine, chlorine, bromine, hydroxy, cyano, $C_{1-3}$-alkyl, $C_{1-3}$-alkoxy, hydroxy-$C_{1-3}$-alkyl, heterocyclyl, heterocyclyl-$C_{1-3}$-alkyl, $(R^{14})_2$N— and $(R^{14})_2$N—$C_{1-3}$-alkyl, or
$R^{12}$ and $R^{13}$ together form a $C_{2-6}$-alkylene bridge, so that with the inclusion of the nitrogen atom attached to $R^{13}$ and the SO$_2$ or CO group attached to $R^{12}$ a heterocyclic ring is formed,
wherein one or two CH$_2$ groups of the $C_{2-6}$-alkylene bridge may be replaced independently of one another by O, S, SO, SO$_2$ or N($R^{14}$) in such a way that in each case two O or S atoms or one O atom and an S atom are not directly joined together, and
wherein the C atoms of the above-mentioned $C_{2-6}$-alkylene bridge are optionally substituted independently of one another by one or more groups selected from among fluorine, hydroxy, carboxy, F$_3$C, HF$_2$C, FH$_2$C, $C_{1-3}$-alkyl and $C_{1-3}$-alkoxy.

18. A compound according to claim 1, wherein
$R^{12}$ is $C_{1-6}$-alkyl, heterocyclyl, phenyl, phenyl-$C_{1-3}$-alkyl, heteroaryl, heteroaryl-$C_{1-3}$-alkyl or $(R^{14})_2N$,
wherein the heteroaryl groups are 5- or 6-membered aromatic heteroaryl groups which contain 1 or 2 heteroatoms selected from the group consisting of N, O and S, wherein a maximum of one O or S atom may be present, and
wherein the above-mentioned groups are optionally substituted independently of one another by one or more groups selected from fluorine, chlorine, bromine, hydroxy, cyano, $C_{1-3}$-alkyl, $C_{1-3}$-alkoxy, heterocyclyl, heterocyclyl-$C_{1-3}$-alkyl, hydroxy-$C_{1-3}$-alkyl, $(R^{14})_2$N and $(R^{14})_2$N—$C_{1-3}$-alkyl; and
$R^{13}$ is hydrogen, $C_{1-6}$-alkyl, heterocyclyl, heterocyclyl-$C_{1-3}$-alkyl, $C_{3-6}$-cycloalkyl, $C_{3-6}$-cycloalkyl-$C_{1-3}$-alkyl, phenyl, phenyl-$C_{1-3}$-alkyl, heteroaryl or heteroaryl-$C_{1-3}$-alkyl, wherein the heteroaryl groups are 5- or 6-membered aromatic heteroaryl groups which contain 1 or 2 heteroatoms selected from the group consisting of N, O and S, wherein a maximum of one O or S atom may be present, and
wherein the above-mentioned groups are optionally substituted independently of one another by one or more groups selected from a fluorine, chlorine, bromine, hydroxy, cyano, $C_{1-3}$-alkyl, $C_{1-3}$-alkoxy, hydroxy-$C_{1-3}$-alkyl, heterocyclyl, heterocyclyl-$C_{1-3}$-alkyl, $(R^{14})_2$N— and $(R^{14})_2$N—$C_{1-3}$-alkyl;

or
$R^{12}$ and $R^{13}$ together form a $C_{2-6}$-alkylene bridge, so that with the inclusion of the nitrogen atom attached to $R^{13}$ and the SO$_2$ or CO group attached to a $R^{12}$ a heterocyclic ring is formed,
wherein one or two CH$_2$ groups of the $C_{2-6}$-alkylene bridge may be replaced independently of one another by O, S, SO, SO$_2$ or N($R^{14}$) in such a way that in each case two O or S atoms or an O atom and an S atom are not directly joined together, and
wherein the C atoms of the above-mentioned $C_{2-6}$-alkylene bridge are optionally substituted independently of one another by one or more groups selected from among fluorine, hydroxy, carboxy, F$_3$C, HF$_2$C, FH$_2$C, $C_{1-3}$-alkyl and $C_{1-3}$-alkoxy.

19. A compound according to claim 1, wherein
$R^{12}$ is $C_{1-4}$-alkyl, morpholinyl, phenyl, benzyl, pyridyl or $(CH_3)_2N$,
wherein the above-mentioned groups are optionally substituted independently of one another by one or more groups selected from fluorine, chlorine and bromine;
$R^{13}$ is hydrogen, methyl, ethyl, phenyl or 4-fluorophenyl wherein the above-mentioned groups are optionally substituted independently of one another by one or more groups selected from fluorine, chlorine and bromine;

or $R^{12}$ and $R^{13}$ with the inclusion of the nitrogen atom attached to $R^{13}$ and the $SO_2$ or CO group attached to $R^{12}$ together form a heterocyclic ring of formulae (IIa), (IIb), (IIc) or (IId)

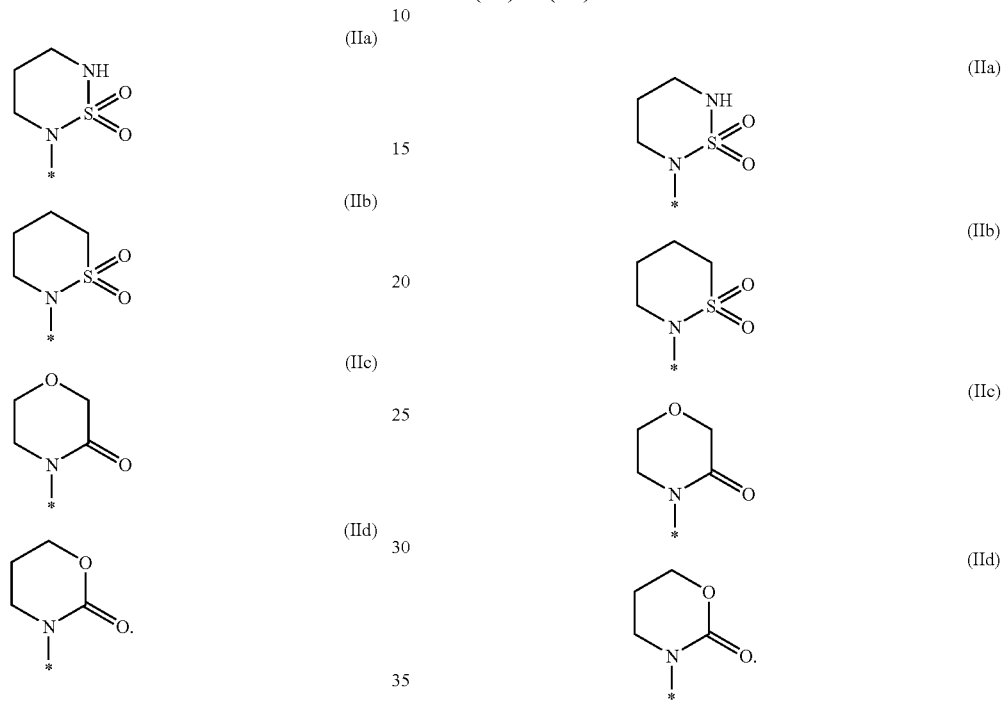

20. A compound according to claim 1, wherein $R^{12}$ and $R^{13}$ together form a $C_{2-6}$-alkylene bridge, so that with the inclusion of the nitrogen atom attached to $R^{13}$ and the $SO_2$ or CO group attached to $R^{12}$ a heterocyclic ring is formed, wherein one or two $CH_2$ groups of the $C_{2-6}$-alkylene bridge may be replaced independently of one another by O, S, SO, $SO_2$ or $N(R^{14})$ in such a way that in each case two O or S atoms or an O atom and an S atom are not directly joined together, and wherein the C atoms of the above-mentioned $C_{2-6}$-alkylene bridge are optionally substituted independently of one another by one or more groups selected from fluorine, hydroxy, carboxy, $F_3C$, $HF_2C$, $FH_2C$, $C_{1-3}$-alkyl and $C_{1-3}$-alkoxy.

21. A compound according to claim 1, wherein $R^{12}$ and $R^{13}$ with the inclusion of the nitrogen atom attached to $R^{13}$ and the $SO_2$ or CO group attached to $R^{12}$ together form a heterocyclic ring of formulae (IIa), (IIb), (IIc) or (IId)

22. A compound according to claim 1, wherein $R^{14}$ is hydrogen or $C_{1-6}$-alkyl, wherein one or more hydrogen atoms of the $C_{1-6}$-alkyl group may be replaced by fluorine.

23. A compound according to claim 1, wherein $R^{15}$ is hydrogen or $C_{1-3}$-alkyl.

24. A compound according to claim 1, which is a compound of one of formulae (Ia), (Ib), (Ic), (Id) or (Ie):

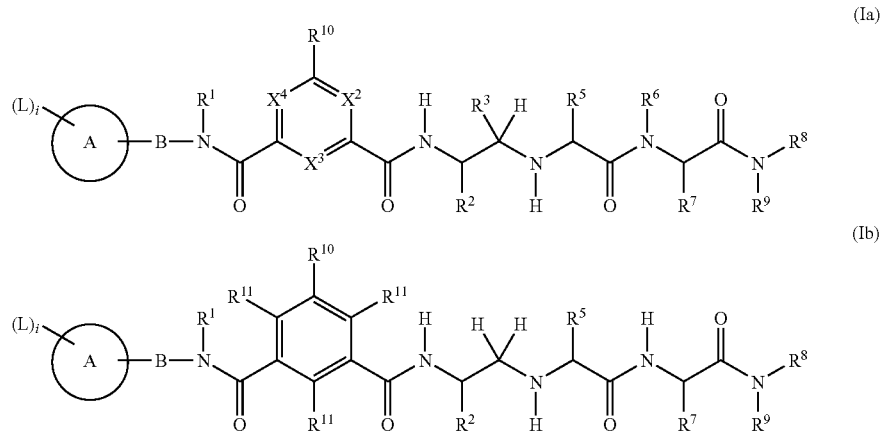

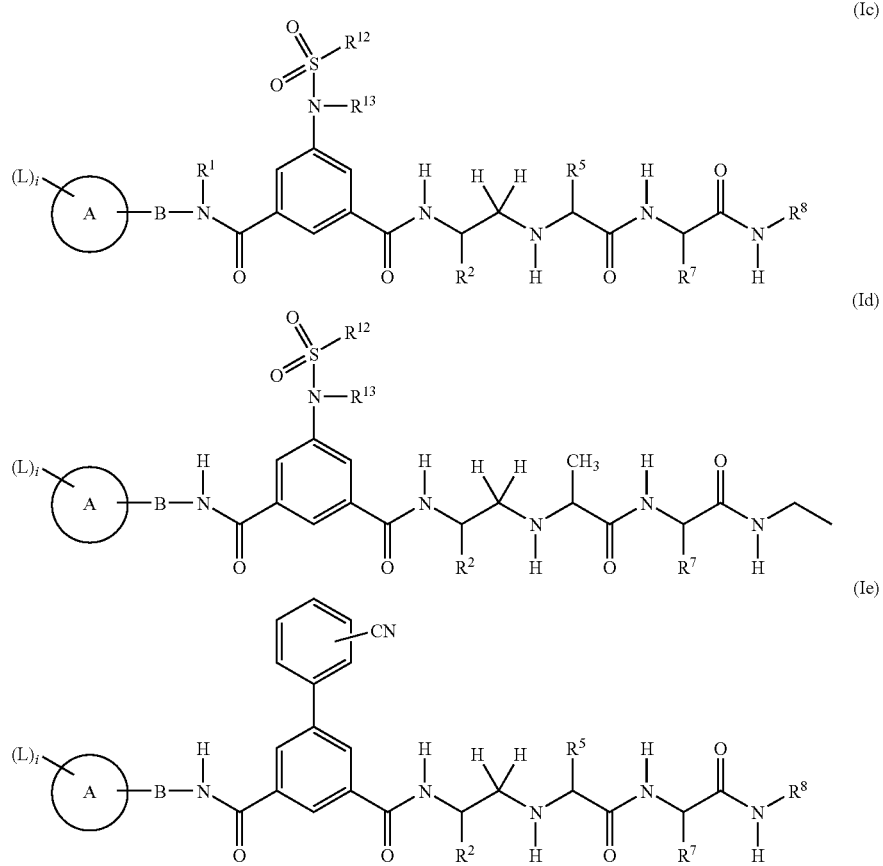

wherein
A, B, L, $x^2$, $x^3$, $x^4$, i, $R^1$, $R^2$, $R^3$, $R^5$, $R^6$, $R^7$, $R^8$, $R^9$, $R^{10}$, $R^{11}$, $R^{12}$, $R^{13}$, $R^{14}$ and $R^{15}$ are as defined in claim 1.

25. A physiologically acceptable salt of a compound according to formula (I) of claim 1.

26. A pharmaceutical composition comprising a compound according to claim 1 and one or more inert carriers and/or diluents.

27. The pharmaceutical composition according to claim 26, further comprising one or more medicinally effective active substances selected from alzhemed, vitamin E, ginkolide, donepezil, rivastigmine, tacrine, galantamine, memantine, NS-2330, ibutamoren mesylate, capromorelin, minocyclin and rifampicin.

* * * * *